US006991904B2

(12) United States Patent
Cole et al.

(10) Patent No.: US 6,991,904 B2
(45) Date of Patent: Jan. 31, 2006

(54) **METHOD FOR ISOLATING A POLYNUCLEOTIDE OF INTEREST FROM THE GENOME OF A *MYCOBACTERIUM* USING A BAC-BASED DNA LIBRARY: APPLICATION TO THE DETECTION OF MYCOBACTERIA**

(75) Inventors: Stewart Cole, Clamart (FR); Roland Buchrieser-Brosch, Paris (FR); Stephen Gordon, Paris (FR); Alain Billault, Roissy-en-Brie (FR)

(73) Assignee: Institut Pasteur, Paris (FR)

( * ) Notice: Subject to any disclaimer, the term of this patent is extended or adjusted under 35 U.S.C. 154(b) by 185 days.

(21) Appl. No.: 10/259,678

(22) Filed: Sep. 30, 2002

(65) Prior Publication Data

US 2003/0198974 A1 Oct. 23, 2003

Related U.S. Application Data

(60) Continuation of application No. 09/670,314, filed on Sep. 26, 2000, now Pat. No. 6,492,506, which is a division of application No. 09/060,756, filed on Apr. 16, 1998, now Pat. No. 6,183,957.

(51) Int. Cl.

| | |
|---|---|
| ***C12Q 1/68*** | (2006.01) |
| ***C12P 19/34*** | (2006.01) |
| ***C07H 21/04*** | (2006.01) |
| ***C07H 21/02*** | (2006.01) |

(52) U.S. Cl. ......................... 435/6; 435/91.2; 536/22.1; 536/23.4; 536/24.33

(58) Field of Classification Search ..................... 435/6, 435/91.2; 536/22.1, 23.4, 24.33

See application file for complete search history.

(56) References Cited

FOREIGN PATENT DOCUMENTS

| | | |
|---|---|---|
| WO | WO93/03187 | 2/1993 |
| WO | WO93/18186 | 9/1993 |
| WO | WO97/23624 | 7/1997 |
| WO | WO99/54487 | 10/1999 |

OTHER PUBLICATIONS

U.S. Appl. No. 09/673,476, filed Nov. 30, 2000, Cole et al.

U.S. Appl. No. 10/802,796, filed Mar. 18, 2004, Cole et al.

GenBank Z79701[1524225] (submitted Sep. 2, 1996; posted Sep. 6, 1996; replaced Jun. 27, 1998) (23 pages).

GenBank Z79701 Revision history (1 page).

"On the Preparation and Utilization of Isolated and Purified Oligonucleotides," Including attached disk of polynucleotides, Mar. 9, 2000.

Brosch et al., "Use of a Mycobacterium Tuberculosis H37Rv Bacterial Artificial Chromosome Library for Genome Mapping Sequencing, and Comparative Genomics," *Infection and Immunity*, vol. 66, No. 5, pp. 2221–2229 (May 1998).

Cole et al., "Deciphering the Biology of Mycobacterium Tuberculosis from the Complete Genome Sequence," *Nature*, vol. 393, pp. 537–545 (Jun. 11, 1998).

Cole et al., Novartis Foundation Symposium, pp. 160–177 (1998).

Kim et al., "Construction and Characterization of a Human Bacterial Artificial Chromosome Library," *Genomics*, vol. 34, pp. 213–218 (Jun. 1, 1996).

International Search Report of PCT/IB99/00740.

Philip et al., "Physical Mapping of *Mycobacterium bovis* BCG Pasteur Reveals Differences from the Genome Map of *Mycobacterium tuberculosis* H37Rv and from *M. bovis*," *Microbiology*, vol. 142:3135–3145 (1996).

Philip et al., "An Integrated Map of the Genome of the Tubercle Bacillus, *Mycobacterium Tuberculosis* H37Rv, and Comparison with *Mycobacterium leprae*," *P.N.A.S.*, vol. 93:3132–3137 (1996).

Zimmer et al., "Construction and Characterization of Large–Fragmented Chicken Bacterial Artificial Chromosome Library", *Genomics*, vol. 42:217–226 (1997).

GenEmbl AD00001 Dec. 3, 1996.

GenEmbl AD000017 Dec. 10, 1996.

GenEmbl 400013 Mar. 1,1994.

GenEmbl X63508 Nov. 20, 1996.

*Primary Examiner*—Kenneth R. Horlick
*Assistant Examiner*—Joyce Tung
(74) *Attorney, Agent, or Firm*—Finnegan, Henderson, Farabow, Garrett & Dunner, LLP

(57) ABSTRACT

A method for isolating a polynucleotide of interest that is present in the genome of a first mycobacterium strain and/or is expressed by the first mycobacterium strain, where the polynucleotide of interest is also absent or altered in the genome of a second mycobacterium strain and/or is not expressed in the second mycobacterium. The method includes (a) contacting the genomic DNA of the first mycobacterium strain under hybridizing conditions with the DNA of a least one clone that belongs to a bacterial artificial chromosome (BAC) genomic DNA library of the second mycobacterium strain, and (b) isolating the polynucleotide of interest that does not form a hybrid with the DNA of the second mycobacterium strain. This invention further pertains to a *Mycobacterium tuberculosis* strain H37Rv genomic DNA library, as well as a *Mycobacterium bovis* BCG strain Pasteur genomic DNA library, and the recombinant BAC vectors that belong to those genomic DNA libraries. This invention also relates to mycobacterial nucleic acids, and methods and kits for using these nucleic acids to detect mycobacteria in a biological sample.

9 Claims, 12 Drawing Sheets

```
(SEQ ID NO. 727) H37Rv ·····PTQTLTGRPLIGNGTPGAVGSGATGAPGGWLLGDGGAGGSGAAGSGAPGGAGGAAGLWGT  837273
                 ·········::::::::::::::::::::::::::::::::::::::::::::::::::::::::::
(SEQ ID NO. 728) BCG   ······PTQTLTGRPLIGNGTPGAVGSGATGAPGGWLLGDGGAGGSGAAGSGAPGGAGGAAGLWGT

                 H37Rv ···GGAGGAGGSSAGGGGAGGAGGAGGWLLGDGGAGGIGGASTVLGGTGGGGGVGGLWGAGGA  837453
                 ·······································:::::::::::::::::::::::::::::
                 BCG   ·····--------------------------------GGAGGIGGASTVLGGTGGGGGVGGLWGAGGA

                 H37Rv ···GGAGGTGLVGGDGGAGGAGGTGGLLAGLIGAGGGHGGTGGLSTNGDGGVGGAGGNAGMLA  837633
                 ·······::::::::::::::::::::::::::::::::::::::::::::::::::::::::::
                 BCG   ·····GGAGGTGLVGGDGGAGGAGGTGGLLAGLIGAGGGHGGTGGLSTNGDGGVGGAGGNAGMLA

                 H37Rv ···GPGGAGGAGGDGENLDTGGDGGAGGSAGLLFGSGGAGGAGGFGFLGGDGGAGGNAGLLLS  837813
                 ·······::::::::::::::::::::::::::::::::::::::::::::::::::::::::::
                 BCG   ·····GPGGAGGAGGDGENLDTGGDGGAGGSAGLLFGSGGAGGAGGFGFLGGDGGAGGNAGLLLS

                                                       837897
                 H37Rv ···SGGAGGFGGFGTAGGVGGAGGNAGWLGF--------------------------------
                 ·······::::::::::::::::::::::::::································
                 BCG   ·····SGGAGGFGGFGTAGGVGGAGGNAGWLGFGAGGIGGIGGNANGGAGGNGGTGGQLWGSGGA

                 H37Rv ···--------------GGAGGVGGSAGLIGTGGNGGNGGTGANAGSPGTGGAGGLLLGQNGLNGLP  838047
                 ·················::::::::::::::::::::::::::::::::::::::::::::::::::
                 BCG   ·····GVEGGAALSVGDTGGAGGVGGSAGLIGTGGNGGNGGTGANAGSPGTGGAGGLLLGQNGLNGLP
```

FIG. 6 pBeloBAC11

(SEQ ID NO. 728) GCGGCCGCAA GGGGTTCGCG TCAGCGGGTG TTGGCGGGTG TCGGGGCTGG

*Not*I restriction site

CTTAACTATG CGGCATCAGA GCAGATTGTA CTGAGAGTGC ACCATATGCG

GTGTGAAATA CCGCACAGAT GCGTAAGGAG AAAATACCGC ATCAGGCGCC

ATTCGCCATT CAGGCTGCGC AACTGTTGGG AAGGGCGATC GGTGCGGGCC

TCTTCGCTAT TACGCCAGCT GGCGAAAGGG GGATGTGCTG CAAGGCGATT primer T7-BAC1

AAGTTGGGTA ACGCCAGGGT TTTCCCAGTC ACGACGTTGT AAAACGACGG

CCAGTGAATT GTAATACGAC TCACTATAGG GCGAATTCGA GCTCGGTACC

T7-promoter sequence

CGGGGATCCT CTAGAGTCGA CCTGCAGGCA TGCAAGCTTG AGTATTCTAT primer T7-Belo2 *Hind*III cloning site SP6-promoter

AGTGTCACCT AAATAGCTTG GCGTAATCAT GGTCATAGCT GTTTCCTGTG sequence (complementary strand) primer SP6-Mid (complementary strand)

TGAAATTGTT ATCCGCTCAC AATTCCACAC AACATACGAG CCGGAAGCAT

AAAGTGTAAA GCCTGGGGTG CCTAATGAGT GAGCTAACTC ACATTAATTG primer SP6-BAC1 (complementary strand)

CGTTGCGCTC ACTGCCCGCT TTCCAGTCGG GAAACCTGTC GTGCCAGCTG

CATTAATGAA TCGGCCAACG CGAACCCCTT GCGGCCGCCC GGGCCGTCGA

*Not*I restriction site

FIG. 7

SEQUENCE LISTING

<160> NUMBER OF SEQ ID NOS: 743

<210> SEQ ID NO 1
<211> LENGTH: 12732
<212> TYPE: DNA
<213> ORGANISM: Mycobacterium tuberculosis

<400> SEQUENCE: 1
acctgcgctt gcagagatca aatagggcgc atgggtcagc atagtacagg tcgtcgcgca 60
tctttgatgc atcggaataa gatgtcaggc aattaaaaga gaagccacgg cgactcgcgg 120
cattcagcat gtcgagcgtc gcttcgatgt gagcgcacca ttccgtgtcc aacgatttca 180
gacgaacatt gaatattcca ctcgcgacgc tatagtccgc ctcccgatct atgcgcgccg 240
cgcagatgaa gtctgcgttc gcccgacctt cgaaacgtag tgcggccgcg cgcaccattt 300
cgggggagac gtcgatgccg gtgtaatcag ttttgaagcc acgcgcatct aggtagtcca 360
gtagagcccc atagccacag cctagatcgt tgatcgaaaa tgggtccgcc gcattgacaa 420
tgcgcaccag ctggtcaaag cgcaacgcct gcccggcttc gccgttccaa tcgacgccgc 480
gcgggtgccg tgtgcttcga gtttcgatgc gtagtaacgg gccacgtcag cgagcatggt 540
cgttgcgtct tccgccatga agctgcctca cgatttgtgt gtgtgggcgt cggtgcgtgg 600
gtccgagact ataccttcaa cagttgcatg ccgaggctgc ggcgggcaat gacccaaaaa 660
cccgccggca cggttcgccg agcaaggaag cgtggagacg atagataatt tcactggcga 720
cagtacctca aatagtccgg agcctcggct ccgacgttaa agagcagatc cagaatcgac 780
acggcgggct cgaaccctcc ccacaattgc ttataatcgc ggtagccgtc ataatcgaac 840
caagttaccc ggatgctaag ttcgtcgaac acgcgctcat cgacatacga acgggctgag 900
gggccagaga catattcggt cgctgcggcc tgttggcaga ggttggccag tctctcggtc 960
ttgccgtcgg ctaattcgta gtcccacgaa tttgccagtc gcgtgctgat accgagataa 1020
ctgcaaatcg cattcaatag acgcctgttg agtaaggaaa gattcgtgtg ctgttcttcg 1080
aggtaaatcg gcgcgagcca gtcagcgatc tccgcaaaat gagcggccgc gctgtagttg 1140

-continued aattctagtg cccgccagtg cgctttcgcc caatcggtgc cgtcgatcag cgtctcacgt 1200
atcttttgat ggaaacgtcc cttcacctgg acgggaacag ttatccactg taacccctgg 1260
ctcgttttga tccgatttct gtttcgccaa tcacgcttgg tatattgcat gtcatcatag 1320
atgatgaatt catcgacgaa tgcaatcagg tcaaaatatc ctcgccaagg tatgtaattt 1380
gattgaacaa tcgcgacttt cttcaacgcg gtgtctccaa tttagaataa caaatacgtc 1440
gcgcccgcga cagctccgct ggagcgagtt caagcgattc tgcgacatat tcaatatggt 1500
gctcgggaag gccaggatgg gccgcgaccc ggggcgtccg gtgcgcgatg aacgtcgcat 1560
cgtctcctgt gagataattg catccgatca tatagggctg gctgcggcta ggttgctggc 1620
aaaaagatat cgcggccgat ccgtttctgg ttttgtcttg atgatcaaat ccgcttccgt 1680
tcacgagatc gattcctggt cttcccccag cgtcgcgatg tcgataggtg tcgcgctttg 1740
ttcgtacccg cactacgcgg cggcgagaac ctcgccaccg aatcgggatt gggggggagga 1800
taccactcgg tcgaggcccg tcaccggcct tctagcgggt tgaccatcag tgtttgcagg 1860
gccctatccc ggtatggcgc accacgggat cggcagcgtt ccggttgctg gcgtggtacc 1920
tcgttgtggc gccgtggtcc atgtcgattg agtgcgtgga tcagtgtaaa ccgttgcgcg 1980
ccatgttctg taggcactgg ttcgggttgt ggttaggctg cacggttggc aggttaccaa 2040
ccactgagcc cctgggcgga tgtgagctcg gactccgcct atggggtgta attttggcag 2100
attgggccgg gtccccgtgg tgaggactcc tcaaccggat tgggtaagca tgaggtggtg 2160
ctggcagcgg tgtcctggtc gctctcccga gtaggcccgt tgtgactgtc atgtgggcga 2220
gcgggtttgc gcgcgtagga gacgatgatt actacgcacg tgaccaacca caagaacggt 2280
gcccatgtca ccgtggtgaa aacgagtggc gtggtaccga ctaccccttt ggctcccagc 2340
tgtccataga gcggcacgta gaacggctgg cccgggaccg cgacgttgac gatgctcagc 2400
gccacggcca aactcacgca gacgccgacc gcgcggcggc ggtctccatg ggctgcgagt 2460
tggtcgaata tcccagcacc aggaggcccg ttggggtctc gggctaccag tgcagcgatt 2520
ggcaagacga aaacgagata gtagaaggcg acgtccgcgg gggagaaggt ggcggtggcg 2580
agcaacacaa tccccaccat gacaggcggg atacggcgtc cgagcgccag cacggcgacc 2640
acgactatga ctaggacagc aaacccgatc tgcgttcgcg gaccagtgag gaaaccctct 2700
gggatcttgc ccgattgata gttcttgatg ctatcgggga tcagcaggag tgccttgcca 2760
aaggacacgt tccgcgggtc tcgaagccct ccgaacgaac tattgaactt gatgatgccg 2820
tggatcgact gtgcgatcgt ccccgggaag cctcgtggcc acaacagaaa ggctgcgata 2880
ttggacacca ccacgccggt gatcccgata ccagcccacc gccattgtcg agccgccaac 2940
aacaccacgc cgagaacgac gaactgcggc tttaccagga cggccaagat caccgtgatg 3000
gtggcgaggc cccaccgctg tcgggacaac gccacgaagt aagccagcgc gatcggtacc 3060
acgaaccctg tcgagttgcc tcgatcgatg accccccacg ccgggatggc cgcggcgccc 3120
agtgtcacga agatgaccac tcgctccaga ccacgtgccc cccgggccgc ccagatggcg 3180
ggagatatga ccgccatcgt tagggcgacc aggtaacaga tcagccccaa gcgcggcgca 3240
cccagccaat ggctgggtag tccgaaaatc gcatacggta tgcgggcggg ggcccatgca 3300
gcaaccgcgg tcggctggta atcggcgggt agcgagatca ggtagtccgc gggattgggt 3360
tgaatcccgg cggcggcgac catggcgtag tcgctgaagc agtgccgacc gatattcatg 3420
ccccaatcaa gccaacagtc cccagggact accaaaagag tggaaaagac gtcgaccgcg 3480
taccactgac tgagggcgta cgccgtcgcc gccgaaatca ccgacgccag caggatggtg 3540

-continued

```
ccgagcatga gggtgcgctc ggattgggag ccgatcgccc agagccgctc ccggctcgcg   3600
gtcacggcac cgcgcaacac ctccggggt cgcttcatct ggattctcct cggttctgcg   3660
cgaaacggta gcagagcgcc atggttgcca acgcggtcgc cgggcagtct agaccggatc   3720
ttcctcgtgg caaccgacaa caggacgtcg ttgccgaaag ggcgctgggc accgacatct   3780
aggatgaacc cacagccacg ccccgacgtt atgccatggc gaagagcgac cggcaggagc   3840
gggaacccag tgaagcgagc gctcatcacc ggaatcacag gaccggacgg ctcgtatctc   3900
gctaagctcc cgctgaaggg atatgtggcc gctggtagcc cggccgaggt ctatttctgc   3960
tgggcgacac ggaattatcg cgaattgtat gggttgctcg cggtcaacag catctggttc   4020
aatcacgaat caccgcgtca cggcgagaca ttcatgactc gtaatcctgc accatatcgc   4080
ggtcggcaac gaggcgctga tcgatgcgca gacgctgatg cgccggccca cccggatagg   4140
tatcagtatt ggggcgttcc ggccagcgta cgaggcgtga tcgaccgcgc aatgggtgtt   4200
tgcgttgagt aataatctga accgtgtgaa cgcatgcatg gatggattcc ttgcccgtat   4260
ccgctcacat gttgatgcgc acgcgccaga attgcgttca ctgttcgata cgatggcggc   4320
cgaggcccga tttgcacgcg actggctgtc cgaggacctc gcgcggttgc ctgtcggtgc   4380
agcattgctg gaagtgggcg ggggggtact tctgctcagc tgtcaactgg cggcggaggg   4440
atttgacatc accgccatcg agccgacggg tgaaggtttt ggcaagttca gacagcttgg   4500
cgacatcgtg ctggaattgg ctgcagcacg acccaccatc gcgccatgca aggcggaaga   4560
ctttatttcc gagaagcggt tcgacttcgc cttctcgctg aatgtgatgg agcacatcga   4620
ccttccggat gaggcagtca ggcgggtatc ggaagtgctg aaaccggggg ccagttacca   4680
cttcctgtgc ccgaattacg tattcccgta cgaaccgcat ttcaatatcc caacattctt   4740
caccaaagag ctgacatgcc gggtgatgcg acatcgcatc gagggcaata cgggcatgga   4800
tgacccgaag ggagtctggc gttcgctcaa ctggattacg gttcccaagg tgaaacgctt   4860
tgcggcgaag gatgcgacgc tgaccttgcg cttccaccgt gcaatgttgg tatggatgct   4920
ggaacgcgcg ctgacggata aggaattcgc tggtcgccgg gcacaatgga tggtcgctgc   4980
tattcgctcg gcggtgaaat tgcgtgtgca tcatctggca ggctatgttc ccgctacgct   5040
gcagcccatc atggatgtgc ggctaacgaa gaggtaatga catggcgcaa gcgacatcgg   5100
gcattcgcgc ggcactttcg caacctgctg tgtatgaggc gtatcagcgg attgcgggcg   5160
ctaaaagcgg gcttgcgtgg atcacaaccg accccatcca gtcgttgcca ggcatgcgta   5220
ctctcgacct cggttgctgg ccagcggtga tacacagctc cccgccagtg gacgtgacat   5280
gtacgagaga cggcatgagc gcggaatgtg cgaccgtgcc gtcgagatga ccgacgtcgg   5340
cgctacggca gcccccaccg gacctatcgc gcggggcagc gtcgctcggg tcggcgcggc   5400
gaccgcgttg gccgttgcct gcgtctacac ggtcatctat ctggcggccc gcgacctacc   5460
cccggcttgt ttttcgatat tcgcggtgtt ttgggggggcg ctcggcattg ccaccggcgc   5520
cacccacggc ctcctgcaag aaacgacccg cgaggtccgc tgggtgcgct ccacccaaat   5580
agttgcgggc catcgtaccc atccgctgcg ggtggccggg atgattggca ccgtcgcggc   5640
cgtcgtaatt gcgggtagct caccgctgtg gagccgacag ctattcgtcg aggggcgctg   5700
gctgtccgtg gggctactca gcgttggggt ggccgggttc tgcgcgcagg cgaccctgct   5760
gggcgcgctg gccggcgtcg accggtggac acagtacggg tcactgatgg tgaccgacgc   5820
ggtcatccgg ttggcggtcg ccgcggcagc ggttgtgatc ggatggggtc tggccgggta   5880
```

-continued

```
cttgtgggcc gccaccgcgg gagcggtggc gtggctgctc atgctgatgg cctcgcccac   5940
cgcgcgcagc gcggccagcc tgctgacgcc cgggggaatc gccacgttcg tgcgcggtgc   6000
cgctcattcg ataaccgccg cgggtgccag cgcgattctg gtaatgggtt tcccagtgtt   6060
gctcaaagtg acctccgacc agttaggggc aaagggcgga gcggtcatcc tggctgtgac   6120
cttgacgcgt gcgccgcttc tggtcccact gagcgcgatg caaggcaacc tgatcgcgca   6180
tttcgtcgac cggcgcaccc aacggcttcg ggcgctgatc gcaccggcgc tggtcgtcgg   6240
cggcatcggt gcggtcggga tgttggccgc agggcttacc ggtccctggt tgctgcgtgt   6300
tggattcggc cccgactacc aaactggcgg ggcgttgctg gcctggttga cggcagcggc   6360
ggtagctatc gccatgctga cgctgaccgg cgccgccgcg gtcgcggccg cactgcaccg   6420
ggcgtatttg ctgggctggg tcagcgcgac ggtggcgtcg acgctgttgc tgctgctgcc   6480
gatgccgctg gagacgcgca ccgtgatcgc gctgttgttc ggtccaacgg tgggaatcgc   6540
catccatgtg gccgcgttgg cgcggcgacc cgactgattt gtgccccagg tcgacaaatc   6600
acgccgtctc gtcagtgagc actccgtcct cgggtccgat ccttccagga gacgttgcaa   6660
cctgatttgg ctcaaattgg tgcgcaccga gggtcgggca catcgtaggg tcgcaacagt   6720
cacatgtgtc actgcaccgg gcgacacccg atgtcccggc tctcagcgac agctgtctga   6780
cctgtggttt tgttcccaag ttggtcgtgg ctgtgcggga ttggaggtgg cgtgggggtc   6840
gcgtcgtatg gattctcctc ctcggttccg cgcgaaacgg ccgcaggcgc aatggtcacc   6900
aacttggccg cggtggagtc tagcctcaca ttttcctggt cgcccccgac aaccaggagg   6960
tcgctgcaga acgggcgttc cctacccaca tctactatga agcgacagcg gcgccccgct   7020
gtgatggctg agcatgaccg acagaggcgg gaagacagtg aagcgagcgc tcatcaccgg   7080
aatcaccggc caggacggct cgtatctcgc cgaactgctg ctggccaagg ggtatgaggt   7140
tcacgggctc atccggcgcg cttcgacgtt caacacctcg cggatcgatc acctctacgt   7200
cgacccgcac caaccgggcg cgcggctgtt tctgcactat ggtgacctga tcgacggaac   7260
ccggttggtg accctgctga gcaccatcga acccgacgag gtgtacaacc tggcggcgca   7320
gtcacacgtg cgggtgagct tcgacgaacc cgtgcacacc ggtgacacca ccggcatggg   7380
atccatgcga ctgctggaag ccgttcggct ctctcgggtg cactgccgct tctatcaggc   7440
gtcctcgtcg gagatgttcg gcgcctcgcc gccaccgcag aacgagctga cgccgttcta   7500
cccgcggtca ccgtatggcg ccgccaaggt ctattcgtac tgggcgaccc gcaattatcg   7560
cgaagcgtac ggattgttcg ccgttaacgg catcttgttc aatcacgaat caccgcggcg   7620
cggtgagacg ttcgtgaccc gaaagatcac cagggccgtg gcacgcatca aggccggtat   7680
ccagtccgag gtctatatgg gcaatctgga tgcggtccgc gactggggt acgcgcccga   7740
atacgtcgaa ggcatgtggc ggatgctgca gaccgacgag cccgacgact tcgttttggc   7800
gaccgggcgc ggtttcaccg tgcgtgagtt cgcgcgggcc gcgttcgagc atgccggttt   7860
ggactggcag cagtacgtga aattcgacca acgctatctg cggcccaccg aggtggattc   7920
gctgatcggc gacgcgacca aggctgccga attgctgggc tggagggctt cggtgcacac   7980
tgacgagttg gctcggatca tggtcgacgc ggacatggcg gcgctggagt gcgaaggcaa   8040
gccgtggatc gacaagccga tgatcgccgg ccggacatga acgcgcacac ctcggtcggc   8100
ccgcttgacc gcgcggcccg ggtctacatc gccgggcatc gcggcctggt cgggtccgcg   8160
ctgctacgca cgtttgcggg cgcggggttc accaacctgc tggtgcggtc acgcgccgag   8220
cttgatctga cggatcgggc cgcgacgttc gacttcgttc tcgagtcgag gccgcaggtc   8280
```

-continued

```
gtcatcgacg cggcggcccg ggtcggcggc atcctggcca acgacaccta cccggccgat   8340
ttcctgtcgg aaaacctcca gatccaggtc aacctgctgg atgccgccgt ggcggcgcgg   8400
gtgccgcggc tgctgttcct gggctcgtcg tgcatctacc cgaaactcgc cccgcagccg   8460
atcccggaga gcgcgctgct caccggtccg ttggagccga ccaacgacgc gtacgcgatc   8520
gccaaaatcg ccggcatcct tgcggtccag gcggtgcgcc gccaacatgg cctgccgtgg   8580
atctcggcga tgcccaccaa cctgtacggg ccaggcgaca acttttcgcc gtccggctcg   8640
catctgctgc cggcactcat ccgccgctat gacgaggcca aagccagtgg cgcgcccaac   8700
gtgaccaact ggggcaccgg cacgccccga cgggagttgc tgcacgtcga cgacctggcg   8760
agcgcatgcc tgtatctgct ggaacatttc gacgggccga cccatgtcaa cgtgggaacc   8820
ggcatcgacc acaccatcgg cgagatcgcc gagatggtcg cctcggcggt aggctatagc   8880
ggcgaaaccc gctgggatcc aagcaaaccg gacggaacac cacgcaaact gctggatgtt   8940
tcggtgctac gggaggcggg atggcggcct tcgatcgcgc tgcgcgacgg catcgaggcg   9000
acggtggcgt ggtatcgcga gcacgcggga acggttcggc aatgaggctg gcccgtcgcg   9060
ctcggaacat cttgcgtcgc aacggcatcg aggtgtcgcg ctactttgcc gaactggact   9120
gggaacgcaa tttcttgcgc caactgcaat cgcatcgggt cagtgccgtg ctcgatgtcg   9180
gggccaattc ggggcagtac gccaggggtc tgcgcggcgc gggcttcgcg ggccgcatcg   9240
tctcgttcga gccgctgccc gggccctttg ccgtcttgca gcgcagcgcc tccacggacc   9300
cgttgtggga atgccggcgc tgtgcgctgg gcgatgtcga tggaaccatc tcgatcaacg   9360
tcgccggcaa cgagggcgcc agcagttccg tcttgccgat gttgaaacga catcaggacg   9420
cctttccacc agccaactac gtgggcgccc aacgggtgcc gatacatcga ctcgattccg   9480
tggctgcaga cgttctgcgg cccaacgata ttgcgttctt gaagatcgac gttcaaggat   9540
tcgagaagca ggtgatcgcg ggtggcgatt caacggtgca cgaccgatgc gtcggcatgc   9600
agctcgagct gtctttccag ccgttgtacg agggtggcat gctcatccgc gaggcgctcg   9660
atctcgtgga ttcgttgggc tttacgctct cgggattgca acccggtttc accgaccccc   9720
gcaacggtcg aatgctgcag gccgatggca tcttcttccg ggcagcgat tgacgcgccg    9780
gcgcgtcaat ctatttcgac attcgcgtga agacgttttc ccagaatcga ctgttgtagg   9840
cgtagaactc ccggccgcgt aggtaggcat gtgatattcg ccttcccccg aacgggtagc   9900
ggcgatgaag gtcgcccatg cggcgcagat caccgaagac cgcgcttggt tcccggtgcg   9960
agccgacgcc cgtggtgtcg aactcgcaca gcacacaccg aatcgtgacc ggctcgcata  10020
ccagcgcggc ccgcaatatg aattcctggt cggcggcgat cccgaaatca aggtcgtagc  10080
caccgatctt ggccaccagc gatgatccga agaacgatgc ttgatgcgga acaacctgct  10140
tgccggccag gaatttgcgc aggctgaaag gtatcgggcc gcgcacccga tcgagcccga  10200
cgagacgatc catcccgaag ccccacaatt cggacaccgg tcccttgccg gatagcgcct  10260
ccacggcctg ggctaccacg tcgggcccgg aaaaacgatc ggcggagtgc aagaaccaca  10320
acagatcacc cgatgcgtgc gcgatgccct ggttcatcgc gtcgtaccgc ccgccgtcgg  10380
gctcggactg ccaatacgcg aagcctggtt cacacccgga caggtatgcc accacgtcgt  10440
cgccgctgcc accgtcgatt acgatgtgct cgatgcgtcc ccggtagcgt tgcgcccgca  10500
cacttttcac cgtgcgctgc aacccgtcga ggtcgttgaa cgagatcgtt atcaccgaga  10560
cggtcggagc agacgtcacc gagttcccct aggttgctgg cggcgattgt ggatcaccgg  10620
```

-continued

```
gtcttgatac cgatgaaggt gcctcgaaga ttcgccgcat aggaacctcc gagcaacgac  10680
tcggcgatgc ttggttccaa gttgtcgtac tcctccatca ccaggtcgac gccgacgtct  10740
ttgatggcct gaagtaggtg ctcgcgttga atccagaatg accggcgatt gtcccaggac  10800
gcccattttg cggtgtcgcg ctggccaaac gagcggtcgt cggaaaactc ggtaaaccac  10860
ctaccgggaa gtccctcatg ttcggtgggc gccgagagca tgaacttcac cggcgccggc  10920
cgccgcagca accgatcggt caattgtcgt gccgtcgtgg gcaaccggag ccatttatcg  10980
ctccggttga tgatcgagaa gtgcgtctgg agaatcagca gcttgttcgt taccgacgag  11040
agggtttcca ggtattgctt cggattctcc aggtggtaga agaggccgca gcagaagacg  11100
gtatcgaaga gcccgtggtt ggcgatgttg agggcgttgt cgtggacgaa ccggagattc  11160
ggcaggttgg tcttcgattt gatgtagttg caggccgcca tgttcagctc gcgaacctcg  11220
atcccgagga cctgaaatcc catgcgcgcg aacccgaccg cgtacccgcc ttccaagcag  11280
ccgacatcgg ccaggcgtag gtggctcttg tccccgggaa agacggtttc cagaatcccg  11340
cgcgccgaga tgaaccagga cgattcgtct aacgtgcgcg aggactccgg tatcgtcaag  11400
gttccgtcgt cgaggcgaac gttgtgggcg gtgaattgta ccgcgccggc cgaatgttcc  11460
tgtgccatca cttggttagc cccttcggct ggtcctgggt ttgtcgacat ggtcaggctc  11520
gacagccgcg tcggagccgg gagggccaca catccacgag ccccctgcgg ctcggcgtcg  11580
cggcggcgag cttgcgccac tgggtcttga gccgccgcgc gggtgtcgcc ccgcggtgct  11640
gcagcgccag catggcgatc cggggatggc gcgcgatggt ttcctgcagc gcggcgcgcc  11700
cctccgggcc tggaacgttg gcgatctggc gaaggatcca gtcggccatg acggcgatga  11760
gctcctcgcg cgcggggtct cccgggaaca ggtcgagcat cgcgtcaaac gtcgccgcat  11820
gccccggacc ctgcgtcaac cagaactttg gcgggtccac cacctggttg tgccacatgc  11880
cttgggcgtg gcggcgatac acggccatgg tgtcgggcaa catggcgatg tcgccatgca  11940
ccgcgtgccg gacgtgcaga taccagtcca ggggcatgac gtcggcagga atgtcgtcgt  12000
agcgctcgag gcgacggtac acggccgagt tggtctggat gaagttcatc aagatcaacg  12060
catccaggct caagttgccc cgcacccgaa ccggggggaa cttcgagtcc ttggcatggc  12120
cgtcctccca tatcactcgg acgggatgga agcacaccgt cgtcttgggg tgccggtcga  12180
ggaatgcgac ctgtttgctt agcttcagcg gatcgatcca gtagtcgtcc gcctcgcaca  12240
acgcgacgta ctcgccgcga gcggccgaca gggcgccggt caggttccca ttgaggccga  12300
ggttttcggt cctgaagatc ggccggaaca cgtgcgggta ccgctcggcg tactcacgga  12360
tgatcgccgg ggtggcatcg gtcgacgcgt cgtcggcgac gatgatctcc accgggaagt  12420
cggtttgctg gtcgagaaag ctgtcgaagg cctgacgggc gtagcccgcc tggttgtgag  12480
tggtcgagac gatgctcacc ttggggcaaa gctggggact caccgtcggc ccttttcctg  12540
cgcggccgca agggtattgc gatggcgaac gtgaatcgcc tgtgcccgcc ggccgtcggc  12600
cgtcgtggcc tggtggtcgg cggacgtacg gcacacgctg gcgaagtata gcgagggtgc  12660
actgacgttg ggctcgaacc gcgtggcgcg cggtgtgggc gcaccgtctc gagtcggtgc  12720
tggttggctc gc                                                       12732
```

<210> SEQ ID NO 2
<211> LENGTH: 289
<212> TYPE: DNA
<213> ORGANISM: Mycobacterium tuberculosis

<400> SEQUENCE: 2

-continued

```
atactcaagc ttgccgcaat cgaaaccaac ctgtttgtgc cgcaagaaat tacgccgtgg     60

cccggcgccg atcaagaaac gccccggcgc gcggcggtgt cgtcgtatgg catgacgggc    120

accaatgtgc acgccattgt cgagcaggca ccggtgccag cccccgaatc cggtgcacca    180

ggcgacaccc cggccacacc cggtatcgac ggcgcgctgc tgttcgcgct gtcggccagc    240

tcgcaggacg cgctgcggca aaccgccgcg cggctggccg attgggtct                289
```

<210> SEQ ID NO 3
<211> LENGTH: 278
<212> TYPE: DNA
<213> ORGANISM: Mycobacterium tuberculosis

<400> SEQUENCE: 3

```
ttggcgggtt ggccacacac ccgccggtga cggcgacgat gctgggctgg ttgcggccct     60

gcgccaccgc ggcttgcatg ctggttggct gtcttgggac gatcccgaaa tagtccacgc    120

ggatctggtg attttgcggg ctacccgcga ttaccccgcg cggctcgacg agtttttggc    180

ctggactacc cgcgtggcca atctgctgaa ctcgcggccg gtggtggcct ggaatgtcca    240

cgccgttcac ctacgtgacc ttgatgggat ccgggggt                            278
```

<210> SEQ ID NO 4
<211> LENGTH: 1280
<212> TYPE: DNA
<213> ORGANISM: Mycobacterium tuberculosis

<400> SEQUENCE: 4

```
ccgacccaga cactgaccgg gcgaccgctg atcggcaacg gcacccccgg ggcggtcggc     60

agcggggcca ccggggcccc cggtgggtgg ctgctcggcg acggcggggc cggcgggtcc    120

ggcgcggcgg gctcgggcgc gcccggcggg gcgggcgggg ctgccgggct gtggggtacc    180

ggcggggccg gcgggatcgg cggagccagc accgtactcg gcggcaccgg cgggggaggc    240

ggggtcggtg ggctgtgggg cgccggtggg gccggcgggg ccggtggaac cggccttgtt    300

ggtggcgacg gcggggccgg tggggccggc gggaccggcg gactgctggc cgggctgatc    360

ggtgccggcg gaggtcacgg cgggaccggc gggctcagca ctaatggcga cggcggggtt    420

ggcggggccg gcgggaatgc cggaatgctc gccgggccgg gcggcgccgg cggagccggc    480

ggtgacggcg aaaacctgga caccggtggg gacggcgggg ccggcggtag cgcagggctg    540

ctgttcggca gcggcggcgc cggcggcgcc ggcggatttg gtttcctcgg tggggacggc    600

ggggccggtg gcaacgccgg gctgctgttg tccagcggcg gggccggcgg gttcggcggg    660

ttcggcaccg ccggtggggt cggtggggcc ggcggcaatg ccggctggct gggcttcggc    720

ggggccgggg gcatcggcgg aatcggcggt aacgctaacg gggcgccgg tgggaacggc    780

ggcaccggcg gtcagttatg ggtagcggc ggcgccggcg tcgaaggcgg cgcagcctta    840

agcgtcggcg acaccggcgg ggccggtggc gtcggcggca gcgccgggct gatcggcacc    900

ggcggcaacg gcggcaacgg cggcaccggc gccaacgccg gcagccccgg aaccggcggc    960

gccggcgggt tgctgctggg ccaaaacggg ctcaacgggt tgccgtagcc gggcggcacg   1020

gcatggcttc cgggcgtcaa ccactcgccg gtgatgcaga tcggctgcgg agcgggccgc   1080

caaaatgggg gccgccgcgc caggtatctc ggcgaagatc cccggcgctc gagcgctttg   1140

tcagaggccc gtcgcgggtc gtcgtgacga cggctatccg ggcggtgcgg gtttcgcggc   1200

gcgccctgtg cccggcaccg ccgcccgttt gtcggcaacg ccgccgcgac ccgtgagccg   1260
```

-continued

```
tccagcagct ggcgcctgcg                                              1280

<210> SEQ ID NO 5
<211> LENGTH: 127
<212> TYPE: DNA
<213> ORGANISM: Mycobacterium tuberculosis

<400> SEQUENCE: 5

gggcatcggc ggaatcggcg gtaacgctaa cgggggcgcc ggtgggaacg gcggcaccgg     60

cggtcagtta tggggtagcg gcggcgccgg cgtcgaaggc ggcgcagcct taagcgtcgg    120

cgacacc                                                              127

<210> SEQ ID NO 6
<211> LENGTH: 434
<212> TYPE: DNA
<213> ORGANISM: Mycobacterium tuberculosis

<400> SEQUENCE: 6

aatactcaag cttgcccagc cgtcgatgac aagaaatatg tccgcaaaag actcagcggc     60

cgactttgct cgcagctggc ggtaccgcgc caccgattct atgccgtggt cgcggaaaaa    120

tgcctcccga aatcgcacgg ccgactccag ttcggcgagc atccgcgatg ccagctgcgg    180

ctgcgccctg ccggccacgg cacccacatg cggcagttcg tccacctggg ccagcgcccc    240

gccgccgaat tccaaacaat agaactgcac ccggcccgca tcgtgggtaa cagccaacgc    300

catgatcagc gtccgcagcg cggttgactt gcccgtttgc ggtgcaccta cgaacgcgac    360

attgcctgcg gccccggaca agtcgatcgt gcgcggcacc cgtgactgct ctaacgggcg    420

attgaaattc cgat                                                      434

<210> SEQ ID NO 7
<211> LENGTH: 332
<212> TYPE: DNA
<213> ORGANISM: Mycobacterium tuberculosis

<400> SEQUENCE: 7

ccacccgtgt aatttgggat gggcaaaaag gcgaagcacc gcgtggccac gaacgccggg     60

agggacaatc tcgggcggtt agggcttctc gcgggaaggc ccgaacgtac ggcgtttcaa    120

cacctcgcgt cgccctccga ccgcgaacat tcggggatgg cagcaacctg ctggcaccct    180

ggccgggcga tgatctgcag cgtcgccgcg ggtagtcgcc gcccgggcgg ctacactctg    240

aaacgcgatg accatcgatg tgtggatgca gcatcccgac gcaacggttc ctacaccgcg    300

atatgttcgc ctcgctgccc cggtggaccg gt                                  332

<210> SEQ ID NO 8
<211> LENGTH: 354
<212> TYPE: DNA
<213> ORGANISM: Mycobacterium tuberculosis

<400> SEQUENCE: 8

aatactcaag ctttccgccg atacccgcca tgtcgcgcac atccaggact tctgggggga     60

tccgctgaca gcggcgggat cccaaagtgc ggatgatcgg gccgcctacg tcgtggtgta    120

cctcgtcggt aacaacgaaa ccgaagcgta tgactcggtc cacgcggtgc ggcacatggt    180

ggacaccaca ccgccaccgc acggggtgaa ggcctatgtc accggtccgg cagcactcaa    240

tgccgaccag gccgagggcg gagacaaaag tatcgctaag gtcaccgcga tcaccaacat    300

ggtgatcgca gcaatgttgc tagtgatcta tcgctccgta attaccgcgg ttct          354
```

-continued

<210> SEQ ID NO 9
<211> LENGTH: 353
<212> TYPE: DNA
<213> ORGANISM: Mycobacterium tuberculosis

<400> SEQUENCE: 9
gtgccgttcc aacccgaatt ggctttcggc gccatcggtg aggacggcgt gcgggtgctc 60
aacgacgacg tcgtccgcgg gacacacctc gatgctgccg ccatggacgc ggtcgaacgc 120
aagcagctga tcgagctaca acgccgcgcg gaacgcttcc gccgcgggcg tgaccgcatc 180
ccgttgaccg ggcggatcgc ggtgatcgtc gatgacggca tcgccaccgg agcgacggcc 240
aaggcggcgt gccaggtcgc ccgggcgcac ggtgcggaca aggtggtgct ggcggtcccg 300
atcggcccag acgacatcgt ggcgagattc gccgggtacg ccgatgaggt ggt 353

<210> SEQ ID NO 10
<211> LENGTH: 279
<212> TYPE: DNA
<213> ORGANISM: Mycobacterium tuberculosis

<400> SEQUENCE: 10
aatactcaag ctttcggcgg aaacggacac attgcgaata ttgatgacaa aataaaaatc 60
attgatggtt tgagtcacca ggccgatcaa gccttcgccg agccaaattc caatcaagag 120
gcccaagccc gtaccaatca gcccggcaac gagggattcc gtcattatca gccaaaataa 180
ctgctctcgg gttacaccca aacagcgcaa tatggcgaaa aacggtcgcc gttgcacgac 240
attaaatgtc acggtattgt agattaaaaa gatacccac 279

<210> SEQ ID NO 11
<211> LENGTH: 376
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 11
tgctcccgaa acctgggggt gtgcctgctc tgtatgcacg gcatacggac atccttcccc 60
tgagacccgc ggtcgaacca gccacgtgtc catcatagng ggtcaacccc ggccaagggc 120
gacggcacgc caagttcgcc gaccgttaac ctagtgctgt tagcttcatt tgctgcgatc 180
aaaacagctg gtcggccgtt aggaactgaa ttgaaactca accgatttgg tgccgccgta 240
ggtgtcctgg ctgcgggtgc gctggtgttg tccgcgtgtg gtaacgacga caatgtgacc 300
gggggaggtg caaccactgg ccaggcgtcg gcaaaggtcg attgcggggg gaagaagaca 360
ctcaaagcca gtgggt 376

<210> SEQ ID NO 12
<211> LENGTH: 393
<212> TYPE: DNA
<213> ORGANISM: Mycobacterium tuberculosis

<400> SEQUENCE: 12
atactcaagc tttgccgacg agcgggcgat gttgatgacg ggaaacccca gcgcacaacc 60
gacgattttg gcgtagccgg cggacgtctg ctcgattccg atcacgtcgg cgctcgcatc 120
gagcatggcg ccggcgacgg ctagcagcga tccgccgtcg tcgaggagca cgacacgagc 180

-continued

```
cgtacgcccg gccgtaagcc gcgcccagga ttcggcgaaa aaccgttcta cgtggcgggt    240

gtactgggtg tcgaatgatt cgtggggtgc gtaggcgtcg ctgcaatcgt cgacatagat    300

gccgtcgggc cgcatcgcgt cgacaactcc gggtgagtgg aatagcactt gccgatcacc    360

gcgacgttgc gcggatgagg ccgaacccga ata                                 393
```

<210> SEQ ID NO 13
<211> LENGTH: 272
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 13

```
tcctatgtcc ctgccgagca ngtgatcgaa cgcggtgaca gatttgtcta tcctggacct     60

gacggtgagg tcgaagtttt ccaggaattc ggcaaaatcg gtaagagcct gaagaattcg    120

gtatcgccgg acgaaatctg cgacgcatac gggggcatat acgcttcggg tttacgagat    180

gtcgatgggg ccgctggagg cttcacgtcc atgggccaca aaggatgttg tcggcgcgta    240

ccgttttctg cagcgggtgt ggcgcttggt cg                                  272
```

<210> SEQ ID NO 14
<211> LENGTH: 286
<212> TYPE: DNA
<213> ORGANISM: Mycobacterium tuberculosis

<400> SEQUENCE: 14

```
atactcaagc ttgattccgc cgaaaccgac cgtgagcacc ccgccagcca ccacgctcgg     60

gtcgggcgcc gggcccgggc cgccaggctg ctccgctcgg tgatggcacg ccaccgcgac    120

accacccggc tgcgctacgt ctaaccattc caggcggagc tacatcagct cggccgccca    180

gtgttcgggc cctctttcca ggtcgaagtc tataccgata tgcgcatccg cagccgccac    240

cctggagaac agaacgatgc cctactaatg cttgtctggc ggggcc                   286
```

<210> SEQ ID NO 15
<211> LENGTH: 357
<212> TYPE: DNA
<213> ORGANISM: Mycobacterium tuberculosis

<400> SEQUENCE: 15

```
ggtacgcttc ggtcgcagtc tgcgagtgat gcatgacgac cgggacctcg tcggcatctt     60

ccatagcccg ccacaccttc agttgctcac cggaatccaa ccggtagaag gtcggcgagc    120

gctcggcatt ggtcatcggg atatgccgct cgggacggtc agagccctcg ggtccggcca    180

gcactccgca ggcttcgtcg gggtggtcgc gacgcgcatg ggccaccatc gcattcacca    240

ggtctgcgcg aatcaccagc acgtagacgg ttcctttcct aagcaacacc gaagtttcag    300

gacccgaatg ctccgggaaa catgtcacgg taggtcggta ttccggctac cggctga       357
```

<210> SEQ ID NO 16
<211> LENGTH: 83
<212> TYPE: DNA
<213> ORGANISM: Mycobacterium tuberculosis

<400> SEQUENCE: 16

```
ggcgtcaacg gtgtcggaac ccgcgtcaag caattggtag gcctgcagtc tgtgaatcag     60
```

-continued

```
gccgacgctg tggccgccgc ggc                                            83


<210> SEQ ID NO 17
<211> LENGTH: 383
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 17

ggctngcgta cccggtaccg gccgcgggcc taccacgtgc cggaactgga agcgcagtaa     60

gccctcaacg cgccaccgct ttggcccgcg cgcccggcgt aggcgcatcg gcggtggccg    120

tggggcggcg cactgcgacc tcaccagcgg ctttcgagct ttgttcgatc aaccggccag    180

catggtcgan gatgcattcg agaccatatt cgaaattggt ttcatcgggg gccccgatcc    240

gatgcccccct cccagttgcg tgagcaanca gcggagtcnt cgcgggatcg atggccacgg   300

ggtgttcaat ggcggatggt ccgctgcccg ccgactggct cttgcgggag aaccgatcta    360

gcaccaccga tccgcgcacg tng                                           383


<210> SEQ ID NO 18
<211> LENGTH: 603
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 18

cgtaatntcg cgcacancca ngacttctgg ggggatcngc tgacagtggt nggatcccaa     60

attgcggatg atcgggccgc cnacgtcgtt gtgtacctcn tcngtcacaa cnaanccgaa    120

ncgtatgact cggtccacgc ggtgcggcac atggtggaca ccacaccgcc accgcncggg    180

gtgaaggcct atgtcaccgg tccggcaaca ctcaatgccg accaggccga ngccggacac    240

nanagtatcn ctaacgtcac cgcgatcacg agcatggtga tcgnncaatg ttnctantga    300

tctatcgctc cgtaattacc gcggttctcg tcttgatcat ggtcgcancg aactccggcg    360

caatccgcgg attcatcgnc ttgctcgccg atcacatatt ttcagccttt cacattgcaa    420

cnaacctgct cgtctcatgg ngatgcggcg acacggacta ccgatatcat gctcgccgtt    480

acacaatcnc gccacgccgc gaagacngga aacgcttcta cacaatnttc ncgggacgcc    540

actnaacttg gttcnggttt gacattgccg cgcatgtntg cccagctttg ccggctcccc    600

tta                                                                 603


<210> SEQ ID NO 19
<211> LENGTH: 190
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 19

tgaatttccc gatcccacaa tctcggttca gatacaggtc gccatacccc ttacttcggc     60
```

-continued aacgctgggc ggattggccc tgcngctgca gcanaccatc gacgccatcg aattgccggc 120
aatctcgttc agccaatcca tacccatcga cattccgccg atcgacatcc cggccttcnc 180
cctttaacgg 190

<210> SEQ ID NO 20
<211> LENGTH: 506
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 20
aacagctatg accatgntta cgccaagcta tttaggtaac actatanaat actcaagctt 60
ttacggtgat cgcgcatcac ctggttcatg aactggaagc agcgcancgc ttccttttcg 120
gccgcaacat gagccagcct ctcgtccgcg gtcnggtgca ggtgctcggg cagctcggcc 180
gcgacagccg cctgaccctg aaaccagctt ccatatcccg cgacnaacna cnccagtccg 240
ctacgtaacc cctccgcgac tgtccatgga caacagcgcg ttctccaccg accgggcccg 300
ggtgtggggt gtttcggcga ccggcagcca ggtggtccac actgccgacg ggcgccgcga 360
gccgttcacc gaccaagccg ccgaacaagt ccgcccgatc gcatactcca accggttgcg 420
gtactgcagg tcagctggcg tacctcctcn tcncgctcgg cgaagtcttg ctccancacg 480
tcgcagaacg gcaaggaaca cgttca 506

<210> SEQ ID NO 21
<211> LENGTH: 388
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 21
gaccgnncca tgtttccaca atgtggtgcc agtncggngg ctacgtgcca tcnanacact 60
ggcgcaggct atcgcacccg ttatcngcta cgaacaaatc ncggtatgcg ttctttanca 120
tgagtcggcg accgncgatc atggtcgaca cccacgacng aaatacgcag atcgccntcn 180
agcntgtgtg ccgcggatta tcangactga cctcctggct gaccggnntg tntggtcgcg 240
atgcctggcg cccggccggc gtgntcgtgg tcggctcgga tagcgaagtc agctaattct 300
cgtggcagct cgaaagggtc ctgccggtgc cggtctttgc gcaaaccatg cncatgttac 360
ggtccctcgg gtgcggcctg gcggcggc 388

<210> SEQ ID NO 22
<211> LENGTH: 138
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 22
gggatgggcg ggcccgctaa actcttcgtg ttccactaac tccgggaggg ncaatctcgg 60

-continued

```
gccgttatgg ctcacgtcgc gtcgccctcc gaccgcgaac attcggagtt ggcagcaacc    120

tggtagcacc ctggccgg                                                  138


<210> SEQ ID NO 23
<211> LENGTH: 142
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 23

nccgtcgttg acaagtaaat atgtccgcaa aagtctcagc ggccgacttt gctcgcaggt     60

ggcggtaccg cgccaccgag tcgatgccgt ggtcgcggaa gaatgcctcc cgaaatcgca    120

cggccttccc nntttaaacg ga                                             142


<210> SEQ ID NO 24
<211> LENGTH: 441
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 24

tttaggtgac actatagaat actcaagctt ttggtctagc cggccgagca cgatacgggt     60

gtcattggcc accggcggcg gctgtccggg aaatggcggg tccccggtgg ttttgctgat    120

gagtgctgaa ccgtantcga agtgggcggc gtcagactcc acccanccag caggcagcgc    180

gaagctgaat cctccaaccg ggttgtcnat ccggacaagt tggggtgcgt ttggggcaat    240

gacaggtggc ngcggtgcgt tcgggtccgc cggcggaagt gctgcgttgg gatcncccgc    300

tgggcattcg gcntttttgc ggcggccggt ggtngggggg caacaggtnt cccngtgcgg    360

gtggcgctca acggtcnacg gcgcaagccg ccgttgttgg taccnggggc gctggctccg    420

gatcgcgttg gcggtcnccg g                                              441


<210> SEQ ID NO 25
<211> LENGTH: 453
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 25

ctacaccatc gaatacgacg gcgtcgccna ctttccgcgg tacccgctca actttgtgtc     60

gaccctcaac gccattgccg gcacctacta cgtgcactcc aactacttca tcctgacgcc    120

ggaacaaatt gacgcagcgg ttccgctgac caatacggtc ggtcccacga tgacccagta    180

ctacatcatt cgcacggana acctgccgct gctagagcca ctgcgatcgg tgccgatcgt    240

ggggaaccca ctggcgaacc tggttcaacc aaacttgaan gtgattgtta acctgggcta    300

cngcgacccg gcctatggtt attcnacctc nccgcccaat gttgcgactc cgttcgggtt    360

gttcccanaa gtcnncccgg tcgtcatcgc cgaanctctc ntcccgggac ccacagggaa    420
```

-continued tcngcnattt cncctacaaa tcanccacct cca 453

<210> SEQ ID NO 26
<211> LENGTH: 228
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 26
gcatgatcgg ccacctttcg ggccgcccgg catacggcgg cgtaccgatc tccgcgtcat 60
acacccgcgg gtaatcgccg acggtgccgg ttcgcgagcc gaaggtgacg actctgattg 120
aatcgagttc caggtccagc gggtggcgca ccaacggcgc gagctcaacg acgtcaatcn 180
cgttgtcgct ttctacggtc accgaccctg gtgaccgtag ttcncccg 228

<210> SEQ ID NO 27
<211> LENGTH: 357
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 27
gacactatag aatactcaag cttgccaacc gccagcctgc atccggcggc gancactgct 60
ccgccgacca gtacgaacca acctgcggtg cccaggccat tgacgatgtg ctggtcggcg 120
cccgcgagtc cgcgcaccat caacgccgcg ggcaccacca nggcggcccc accctgcacg 180
gcgacgatca ttccggcgcc gctcacggcg ggcggggctc gaacangcac agcatcaacg 240
tngtcacccg gccgtgaccg gcccgcatcg tcacaccacc caagcccatt gccgtcctcc 300
tcaacngggc gacccggccc gcatcgtcac acggnctaag gccattgccg tcctcct 357

<210> SEQ ID NO 28
<211> LENGTH: 384
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 28
tcggcgccat cggcaccttc gaggacctgt atttcgacgc cgtggccnac ctgaggttgg 60
cggtggacna agtgtgcacc cggttgattc gctcggcctt gccggatgcc acccngcgcc 120
tggtggtcga tccgcnaana gacaanttgt ggtggangct tctgctgcct gcgacaccca 180
cnacgtggtg gcaccgggca gctttagctg gcatgtcctg accgcgctgg ccgacnactc 240
cagacnttcc acnaanggtc gccnncccaa tgtnccgnan tgtctccggn tccctttacc 300
ncccaatggg cngnttccac nggttacggg ccccntnccg gcgggtctnc ctcccaanct 360
accaaatacg cccgacnttc cgga 384

<210> SEQ ID NO 29
<211> LENGTH: 266

-continued

<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 29
atactcaagc ttttatggtg atcgcgcatc acctggttca tgaactggaa gcagcgcagc 60
gcttcctttt cggccgcaac atgagccagc ctctcgtcgg cggtcgggtg caggtgctcg 120
ggcagctcgg ccgcgaacag cccggcttga accctgaaaa ccngctttcc atatcccgcg 180
acgaaagaac gccagttccg ctacttaacc cctccgcgaa ccgtccatgg acaacagcgc 240
gttctccacc aaccgggccc gggtgt 266

<210> SEQ ID NO 30
<211> LENGTH: 423
<212> TYPE: DNA
<213> ORGANISM: Mycobacterium tuberculosis

<400> SEQUENCE: 30
tcggctcagg ccgcgctgct ggtagagtcg ctgaccggtg caggtttcga caatgtggtg 60
ccggttcggc ggctacgtgc catcgagaca ctggcgcagg ctatcgcacc cgttatcggc 120
tacgaagcaa atcgcggtat gcgttcttga gcatgagtcg gcgaccgtcg tcatggtcga 180
cacccacgac ggaaagacgc agatcgccgt caagcatgtg tgccgcggat tatcaggact 240
gacctcctgg ctgaccggca tgtttggtcg cgatgcctgg cgcccggccg gcgtggtcgt 300
ggtcggctcg gatagcgagg tcagcgaatt ctcgtggcag ctcgaaaggg tcctgccggt 360
gccggtcttt gcgcaaacaa tagcgcaggt tacggtcgcg cggggtgcgg cctggcggcg 420
gcc 423

<210> SEQ ID NO 31
<211> LENGTH: 455
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 31
caagctattt aggtgacact atagaatact caagcttcgc gtctacgccg gcccggagca 60
tccgcacagc gctcagcagc cggttccgta cganctcaag caggtggcgc aatgaccgaa 120
accaccccag ccccgcaaac cccggcggcc ccggccgggc ccgcacaatc gttcgtgttg 180
gagcggccca tccanaccgt tgggcgccgt aaggangccg tggtacgaat gcggctggtg 240
cccggcaccg gcaagttcga cctcaacggc cgcagcttgg angactactt cccaaacaag 300
gtgcaccagc agttgatcaa ggcacccctg gtcaccgtgg atcgggtgga aagtttcgac 360
atctttgccc acctgggcgg cggcggccgt ccggtcaggc cgggcctgcc ctgggtatcg 420
cccgggcatt gattctggta tccccngaag aaccg 455

<210> SEQ ID NO 32
<211> LENGTH: 371
<212> TYPE: DNA
<213> ORGANISM: Mycobacterium tuberculosis
<220> FEATURE:

-continued

<221> NAME/KEY: unsure
<222> LOCATION: (various positions within the sequence)
<223> OTHER INFORMATION: applicants are uncertain of bases designated as "n"

<400> SEQUENCE: 32

```
cggttggcca ccgcttctgc ggtgccgccg ccgtcgacaa tgaccgtgtc gtccttgctg     60

accaccacgc gtcgggccga gcccagcacc tccaagccca cctcgcgcag caccatgccg    120

gcgtcggggt tgaccacctg gccacccgtc accaccgcca ggtcctcaag gaaacgcctt    180

acggcggtca ccgaagtacg gccccttgac cgcgaccgct ttcaacgtct tgcgaatcgc    240

gttgacgacc agcgtcgcca acgcttcgcc ctccacgtct tcagccacga tcagtagtgg    300

cttacccgtt cctgcaacct tttccagcaa tggcaacaga tcgggaagcg anctgatctt    360

gtcttggtgc n                                                         371
```

<210> SEQ ID NO 33
<211> LENGTH: 320
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 33

```
ccaagctatt taggtgacac tatagaatac tcaagctttt ggctgggtcg ccttcgaatt     60

cngcgtgcac cgctatgggt tgcancagcg gctggcgccg cacaccccac tggcccgggt    120

gttttcgccc cgaacccgga tcatggtgag cgaaaaggan attcncctgt tcgatgctgg    180

gattcgccac gccaaggcat ctancgatta ctctccncgg ggtgggaaaa gtgcccaatc    240

cccctccctc caactttccn aacaatcatt ccggttccnc cntccggttg gnggtaaccn    300

nccaataaaa cccctgcccg                                                320
```

<210> SEQ ID NO 34
<211> LENGTH: 383
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 34

```
gcccgcncat ggccaatccc cgaagacatc attggccagt ggccgggcgc taacaggttc     60

cagcccccca ccantgccgc tcgaacatgc ggtgcaaccc attcgcaggc cggcagggaa    120

agcaccgcgg aagccgcaaa gggctgcagt tccgcgccca ataatgtcgt ccgcaaccag    180

atgcgctcna aaaccncncc ggcagtcagc gcacccgacg cgangtcgaa agacgtcntc    240

agcgcgccca catggggtgc caatcggcac ggcaggtatg ccgcgcgcaa cccgagcgcg    300

tggtgcatgc ccacggtccg cangangcgc ancacccgcc aatgccgaan cccacgaaac    360

atcgggcgca tccaccttca acc                                            383
```

<210> SEQ ID NO 35
<211> LENGTH: 275
<212> TYPE: DNA
<213> ORGANISM: Mycobacterium tuberculosis -continued

<400> SEQUENCE: 35
atactcaagc ttgcccagcc gtcgatgaca agaaatatgt ccgcaaaaga ctcagcggcc 60
gactttgctc gcagctggcg gtaccgcgcc accgagtcga tgccgtggtc gcggaagaat 120
gcctcccgaa ttcgcacggc caattccatt ccgggaagca tccgcaatgc cagctgcggt 180
tgccccctgc cggccacggc acccacttgc ggcattgcgt ccacctgggc cagcgccccg 240
ccgccaaatt ccaaacaata aaaattgcac ccggc 275

<210> SEQ ID NO 36
<211> LENGTH: 322
<212> TYPE: DNA
<213> ORGANISM: Mycobacterium tuberculosis

<400> SEQUENCE: 36
ccacccgtgt attttgggat gggcaaaaag gcgaagcacc gcgtggccac gaacgccggg 60
agggacaatc tcgggcggct agggcttctc gcgggaaggc ccgaacgtac ggcgtttcaa 120
cacgtcgcgt cgccctccga ccgcgaacat tcggggatgg cagcaacctg gtagcaccct 180
ggccgggcga tgatctgcag cgtcgccgcg ggtagtcgcc gcccgggcgg ctacagtctg 240
aaacgcgatg accatcgatg tgtggatgca gcatccgacg caacggttcc tacacggcga 300
tatgttcgcc tccctgcccc gt 322

<210> SEQ ID NO 37
<211> LENGTH: 167
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 37
ctgcccatgt ttggggacgc ccgaccagcc gatgctggag gcctacacgg cccttggtgc 60
gctggccacg gcgaccgagc ggctgcaact gggcgcgttg gtgaccggca atacctaccg 120
cagccngacc cctntcncaa naggatnttg ttcgccggac cccnctc 167

<210> SEQ ID NO 38
<211> LENGTH: 287
<212> TYPE: DNA
<213> ORGANISM: Mycobacterium tuberculosis

<400> SEQUENCE: 38
ccgactttcc gcggtacccg ctcaactttg tgtcgaccct caacgccatt gccggcacct 60
actacgtgca ctccaactac ttcatcctga cgccggaaca aattgacgca gcggttccgc 120
tgaccaatac ggtcggtccc acgatgaccc agtactacat cattcgcacg gagaacctgc 180
cgctgctaga gccactgcga tcggtgccga tcgtggggaa cccactggcg aacctggttc 240
aaccaaactt gaaggtgatt gttaacctgg gctacgcgac cgccttt 287

<210> SEQ ID NO 39
<211> LENGTH: 322
<212> TYPE: DNA
<213> ORGANISM: Mycobacterium tuberculosis

<400> SEQUENCE: 39
atactcaagc tttgtcacac caagtgtttc gaccaggcgc tccatccggc gagtggatac 60

-continued

```
tcccagcagg tagcaggtcg ccaccacgct ggtcagtgcg cgttcagctc gcttgcggcg    120

ctgcagcagc cattcgggga aatacctgcc ctggcgcagc tgggggatcc caacttcaat    180

ggttgcggca cgggtgtcaa attcacggtg gcggtagccg ttgccctaat tggaccgctc    240

atcgctgctt tcgcggtacc ccgccccgca cagggcttcg gcttcagccc ccatcagggc    300

ggcaataaac ttcaagagca cc                                             322
```

<210> SEQ ID NO 40
<211> LENGTH: 471
<212> TYPE: DNA
<213> ORGANISM: Mycobacterium tuberculosis

<400> SEQUENCE: 40

```
gaggcagctt cgccggcaat tctactagcg agaagtctgg cccgatacgg atctgaccga     60

agtcgctgcg gtgcagccca ccctcattgg cgatggcgcc gacgatggcg cctggaccga    120

tcttgtgccg cttgccgacg gcgacgcggt aggtggtcaa gtccggtcta cgcttgggcc    180

tttgcggacg gtcccgacgc tggtcgcggt tgcgccgcga aagcggcggg tcgggtgcca    240

tcaggaatgc ctcaccgccg cggcactgca cggccagtgc cgcggcgatg tcagccatcg    300

ggacatcatg ctcgcgttca tactcctcga ccagtcggcg gaacagctcg attcccggac    360

cgcccagcgc attggtgatg gaatcggcga acttggccac ccgctgggtg ttgacatcct    420

cgacggtggg caattgcgcc tcggtaagct ttgccgcgta gccttttcat c             471
```

<210> SEQ ID NO 41
<211> LENGTH: 247
<212> TYPE: DNA
<213> ORGANISM: Mycobacterium tuberculosis

<400> SEQUENCE: 41

```
atactcaagc ttcactgaca agggacgaat tcgtcggccg cctgttcgac tgggtggtgg     60

ccgagctggt cgccaccact caggccgcgg tcacggcggt accggcgcgg gagcaaactc    120

gcgcgggcat ggccaacttc ttgcggacca tcaccgcaga cgcccgcttc ggacccctgc    180

tgtccaccac acagttggcc aacgcattaa tcacccgcaa gcttgcggaa tccaccgccc    240

tgttcgc                                                              247
```

<210> SEQ ID NO 42
<211> LENGTH: 325
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 42

```
tccatcaccc gatgtggcng gagcactgcc atgtcgatct caactaccac ctccggccgt     60

ggcggttgcg cgccccgggg ggtccgcgcg aactcgacga ggcggtcgga gaaatcgcca    120

ncaccccgct gaaccgcgac cacccgctgt gggagatgta cttcgttgag ggcttgccca    180

accaccggat cgcggtggtt gccaaaattc accatgcgtt ggctgacggt gttgcctcgg    240

caaacatgat ggcacggggg atggatctgc cgccgggacc ggaggtcggc cgctatgtgc    300

ctgaccccgc tcctaccaag cggca                                          325
```

<210> SEQ ID NO 43

-continued

<211> LENGTH: 221
<212> TYPE: DNA
<213> ORGANISM: Mycobacterium tuberculosis

<400> SEQUENCE: 43
agctttgcag ttgctgagta atgtcggcca acgtcaccac aaccgcgatg aattcaatca 60
tgccgcccag ggcggccaac ccaatggtgg ccgcgagcgg cagctcgatc gcagcgcgga 120
ggttgccggc cgccagttga ttcacgaaca gggtgaggtc ataggcgggc aggatagtga 180
cgaaggcaag acctccatct gccgtcggaa gaagtatcga g 221

<210> SEQ ID NO 44
<211> LENGTH: 285
<212> TYPE: DNA
<213> ORGANISM: Mycobacterium tuberculosis

<400> SEQUENCE: 44
agcttcagaa caggcctgtt gtgggcgcac ccggctcgcc gagttctgca cgcaccgcct 60
caagtgcggc ccgcaccgcc ggcatctccc ggtcacgcag ggccgcggcc cgcgccgcag 120
cgacggcgtg ttcgcgcagt tcgccgtcaa tgatgctgac ctgatcggcc acccgggcgt 180
tctcggcgtc gtcgcgttca ctaatcgcgg tgctcagcag cgtctcgaca gccaccaccc 240
gagtggcgac cagctgctcc accacggacc gcagcgatgc ccgtc 285

<210> SEQ ID NO 45
<211> LENGTH: 179
<212> TYPE: DNA
<213> ORGANISM: Mycobacterium tuberculosis

<400> SEQUENCE: 45
atactcaagc ttcagttcct ccacgacgcg ttcccaaatg aatttcccga tcccacaatc 60
tcggttcaga tacaggtcgc catacccctt acttcggcaa cgctgggcgg attggccctg 120
ccgctgcacc aaaccatcaa cgccttcaaa ttgccggcaa tctcgttcag ccaatccat 179

<210> SEQ ID NO 46
<211> LENGTH: 315
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 46
gctctacgcc gcctacgggt cgaacatgca tcccgagcag atgctcgagc gcgcacccca 60
ctcgccgatg gccggaaccg gctggttacc cgggtggcgg ctgacgttcg gcggcgagga 120
catcngctgg gaaggggcgc ttgccaccgt cgtcnaagac ccaaattcga aggtgttcgt 180
cgtgctctac gacatgaccc cggcggacga gaagaacctt gaccggtggg aaggctccga 240
gttcggtatc caccagaaga tccgatgccg cgtggagcgc atttcctcgg acaccacaac 300 ccgt cctcg 315

SEQ ID NO 47
LENGTH: 285
TYPE: DNA
<213> ORGANISM: Mycobacterium tuberculosis

<400> SEQUENCE: 47

-continued

```
atactcaagc ttgccaaaga gacctcgtcc accaagcagg acgcgaccgt cgaggtggcg     60

atccggcttg gcgtcgaccc gcgtaaggca aaccagatgg ttcgcggcac ggtcaacctg    120

cccacaccgg cactggttaa gaactgcccg cgtcgcggtt ttcgcggttg gtgaaaaggc    180

caatgcctgc gtttgccgtg gggcggatg ttgtcgggag tgacaatctg atcaaaagga    240

ttcagggcgg ttggctggaa ttcaatgccg caatcgcgac accgg                    285
```

<210> SEQ ID NO 48
<211> LENGTH: 369
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 48

```
ccacggcgtg gatcaaggta ccggccggga tgttgcgcaa tggcaggttg ttgcccggct     60

tgatgtcggc gttagcgccg gattccacca catccccttg cgaaagtccg ttgggtgcaa    120

tgatgtagcg cttctcccca tcgagatagt ggagcaacgc aatccgtgcg gtacggttcg    180

ggtcgtactc gatgtgcgcg accttggcgt tgacaccatc tttgtcattg cggcgaaagt    240

cgatcatccg gtaagcgcgc ttatgaccgc cgcctttgtg ccgggtggta atccggccat    300

gcgcgttgcg tccaccgcga cgtgcagcgg gcgcaccagc gacttctccg gggttgaccg    360

ggtnatctc                                                            369
```

<210> SEQ ID NO 49
<211> LENGTH: 461
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 49

```
gcagcatgac ggcggtagcg aacaccgccg gatgcagcgc aagtagcgtc gatgtgctca     60

cggaatcgcc ccggcaccgc gatctcgang atcaccagtg ccaccccctg cagcgcnaca    120

ccgacgattc cgtacaccgc cacgccgatc aggccctggg ccatctgatt ggagctggcg    180

tanatggcgg cgatggtgac gatggccagc gccacataca ttgtggcggc cagaaccacg    240

gcgttggggc ggcggtcgat gaacactagg cgacgcagat cgcccggggt caacaggttg    300

accatcagaa agcctgcgac tagcacggcg gcgccactag gaagtacaag aangtggcca    360

ccaccccatg caggatcggg gtaaggctga tggtcccgaa atcgactccg gcctaataca    420

tgactctctc ctttgcgtca tcgccttact tgtgcgcgga a                        461
```

<210> SEQ ID NO 50
<211> LENGTH: 127
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 50

-continued

```
gggacacacc tcgatgctgc cgcnatggac gcggtcgaac gcaagcagct gatcgagcta     60

caacgccgcg cggaacgctt ccgccgcggg cgtgacgcat cccgttgacc ggccggancn    120

ctctcta                                                              127


<210> SEQ ID NO 51
<211> LENGTH: 305
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 51

tgggcgcctc tttcggcctt cccnntttaa acgnagcang acattctggg tatcgagttg     60

tactggatgg tgttggcgat gtcggtgatc ctgctcctgg cggtgggatc cgactacaat    120

ctgctgctga tttcccggtt gaaagaggaa attggggccg gattgaacac cggaattatc    180

cgtgccatgg ctggtaccgg gggagtggtg acggctgccg gcatggtgtt cgccgttacc    240

atgtcgttgt ttgtgttcag cgatttgcga attattggtc agatcggtac caccatcgcc    300

ttccc                                                                305


<210> SEQ ID NO 52
<211> LENGTH: 449
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 52

ccgatcggcg ccgcanctgg ttggtgttnc ggatgaatcc gcagcgaaaa tgtagctgcg     60

gtggcgtgtc gtgactcgtn ggcgtcgacg ctcgtggcag ccaccgancg gttggtccag    120

gatctggatg ggcaaagttg tgcggcccgg ccggtgacgg ccgatgagct gaccgaggtc    180

gacagcgccg tgttggctga cttggaaccg acatggagtc gccccggttg gcgtcacctc    240

aagcatttca atggttatgc gaccagtttt tgggttacgc cgtcagacat cacgtcggag    300

acttggatga gctgtgtctg ccagatagcc ccgaatcggg acgaccgtgg tcacggtgcg    360

tctgaccact cgggtcgggt cgcccgcgct atcggcatgg gtgcgtnatc acagcgacac    420

gcgcctgccc aaggangtnc ggncggacc                                      449


<210> SEQ ID NO 53
<211> LENGTH: 160
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 53

cgggttgcgg atccacgcgt gcgggttgtc agcagctacg gcactgaacc gcgcccacag     60

ctcgccgatc cgctttcggt ggttctcgat cgactcgccg taggcgatgc gcagcgcctg    120

ctcgaatatc gggtacacgt aggccggcct tcccncttta                          160
```

-continued

<210> SEQ ID NO 54
<211> LENGTH: 308
<212> TYPE: DNA
<213> ORGANISM: Mycobacterium tuberculosis

<400> SEQUENCE: 54
cttgattttg atcatcatga cgatcatcac cctaattttg ctacccgcac tggttatcgt 60
gggtaccgtc gtgctttcca tgggcgcctc tttcgggctt tccgtattgg tctggcagga 120
cattctgggt atcgatttgt actggatggt gttggcgatg tcggtgatcc tgctcctggc 180
ggtgggatcc gactacaatc tgctgctgat ttcccggttg aaaaaggaaa ttggggccgg 240
attgaacacc ggaattatcc gtgccatggc tggtaccggg ggagtggtga cggctgccgg 300
catggtgt 308

<210> SEQ ID NO 55
<211> LENGTH: 460
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 55
ggggatccct agatcgacct gcaggcatgc aagcttggcg tgtcgttcca acccgaattg 60
gctttcggcg ccatcggtga ggcgggacac acctcgatgc tgccgccatg gacgcggtcg 120
aacgcaagca gctgatcgag ctacaacgcc gcgcggaacg cttccgccgc gggcgtgacc 180
gcatcccgtt gaccgggcgg atcgcggtga tcgtcgatga cggcatcgcc accggagcna 240
ctgtcaaggc ggcgtgccag gtcgcccggg cgcacggtgc ggacaaggtg gtgctggcgg 300
tcccgatcgg cccagacgac atcgtggcga gattcgncgg gtacgccgat gaggtggtgt 360
gtttggcgac gccggcgtng ttcttcgccg ncgggcangg ttaccgcaac ttcacccaga 420
cctccgacga cgaggtggtg gcgtctcctg gatcgtgctc 460

<210> SEQ ID NO 56
<211> LENGTH: 299
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 56
aaggctgcag gtcgaagcgg ntggttacga ctccctgtgt gtgatggacc agttctacta 60
tctgcgtcta cacggccctt ggtgcgctgg ccacggcgac cgagcggctg caactgggcg 120
cgttggtgac cggcaatacc taccgcagcc ccgaccctgc tggcaaagat natcaccacg 180
ctcgacgtgg ttagcgccgg tcgagcgatc ctcggcattg gagccggcgg gtttgaactg 240
gaacaccgcc agctcggctt cgagtccggc acttccagtg accggttcaa ccggctcga 299

<210> SEQ ID NO 57
<211> LENGTH: 373
<212> TYPE: DNA
<213> ORGANISM: Mycobacterium tuberculosis
<220> FEATURE:
<221> NAME/KEY: unsure -continued
<222> LOCATION: (various positions within the sequence)
<223> OTHER INFORMATION: applicants are uncertain of bases designated as "n"

<400> SEQUENCE: 57
ctttccgcgg tacccgctca actttgtgtc gaccctcaac gccattgccg gcacctacta 60
cgtgcactcc aactacttca tcctgacgcc ggaacaaatt gacgcngcgg ttccgctgac 120
caatacggtc ggtcccacga tgacccagta ctacatcatt cgcacggaga acctgccgct 180
gctacagcca ctgcgatcgg tgccgatcgt ggggaaccca ctggcgaacc tggttcaacc 240
aaacttgaag gtgattgtta acctgggcta cggcgacccg gcctatggtt attcgacctc 300
gccgnccaat gttgcgactc cgttcgggtt gttccagang tcagcccggt cgtcatcgcc 360
gacgctctcg tcn 373

<210> SEQ ID NO 58
<211> LENGTH: 338
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 58
cggtcatagc cctcgggtcc ggccagcact ccgcaggctt cgtcggggtg gtcgcgacgc 60
gcatgggcca ccatcgcatt caccaggtct gcgcgaatca ccagcacgta gacggttcct 120
ttcctaagca acaccgaagt ttcacgaccc gaatgctccg ggaaacatgt cacggtaggt 180
cggtattccg gctaccggct gagcattgag cacgccggcc agcaccgcac gagccaggca 240
atcagccgcc gccgcaccga tcgcggtgac cagctgagtc tccggagaca atgcggccgg 300
cacgccggnc tccggcggca ccgctacngc gcccgtgg 338

<210> SEQ ID NO 59
<211> LENGTH: 374
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 59
gtgatggcac gccaccgcga caccacccgg ctgcgctacn tcgagccata ccgggcggag 60
ctacatcggc tcggccgccc agtgttcggg ccctctttcg aggtcgaggt cgataccgat 120
ttgcgcatcc gcanccgcnc cctggacgac agaaccgtgc cctacgagtg cttgtcgggc 180
ggggccaaag aacagcttgg catcctggcg cgattggccg gcgcggcgct ggtcgccaag 240
gacgacgccg ttccggtgct gatcgacgac gcgctggggt tcaccgatcc ggagcgacta 300
tcaagatggg ggaggtctct gacaccatcg gccccnacgg acatgtgatc gtgccgacgt 360
gcagtcccac cccg 374

<210> SEQ ID NO 60
<211> LENGTH: 448
<212> TYPE: DNA
<213> ORGANISM: Mycobacterium tuberculosis
<220> FEATURE:
<221> NAME/KEY: unsure -continued
<222> LOCATION: (various positions within the sequence)
<223> OTHER INFORMATION: applicants are uncertain of bases designated as "n"

<400> SEQUENCE: 60
gcgaaagtcc gttgggtgca atgatgtagc gcttctcccc atcgagatag tggagcaacg 60
caatccgtgc ggtacggttc gggtcgtact cgatgtgcgc gaccttggcg ttgacaccat 120
ctttgtcatt gcggcgaaag tcgatcatcc ggtnngcgcg cttatgaccg ccgcctttgt 180
gccgggtggt aatccggcca tgcgcgttgc gtccaccgcg accgtgcagc gggcgcacca 240
gcgacttctc cggggttgac cgggtgatct cggcgaaatc agatacgctg gcgccgcgac 300
gaccaggcgt cgtgggcttg tncttgcgaa ttgncatgtc taatcangtc tttctctcac 360
gctctcgtcg ccgggctagg ccgcattgcc ctgctcctcc tcatcgcttc gctctgcatc 420
gtccccgggc taagcccgtg ccccgaaa 448

<210> SEQ ID NO 61
<211> LENGTH: 356
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 61
gatggttcgc ggcacggtca acctgccaca cggcactggt aagactgccc gcgtcgcggt 60
attcgcggtt ggtgaaaagg ccgatgctgc cgttgccgcg ggggcggatg ttgtcgggag 120
tgacgatctg atcgagagga ttcagggcgg ctggctggaa ttcgatgccg cgatcgcgaa 180
caccggatca gaatggccaa agtcggtcgc atcgctcggg tgctgggtcc gcgcggcctg 240
atgcccaacc cgaaaaccgg caccgtcacc gccgactccc catggcgtcc cggatatcaa 300
gggccggcaa atcaacttcc cggttgatca gcaaggcaac ctgcctccnc ctccgg 356

<210> SEQ ID NO 62
<211> LENGTH: 336
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 62
atactcaagc ttcgtcataa gaccatggtg cgctttcttt cacccgtcca gagtcggggg 60
catccgcacc ggctcgcatc gcatcatcct cccacgacgg gccgctcatc agcttgggcc 120
atttcaatgt acttgatacc ccgcgctgcg ggtaggccac tgcgacaatt caaacacggt 180
gtcacacggt gaatagtgtc gagatgggct ctgatcaacc gtcgcaaacc cggtttcgca 240
tcaatagcgg aatcccaccg ggttgcatgg aggctgctga ccttggaaaa caaaattttt 300
tcattacaac aaaacaaccg ccncggaaac tttgca 336

<210> SEQ ID NO 63
<211> LENGTH: 489
<212> TYPE: DNA
<213> ORGANISM: Mycobacterium tuberculosis

<400> SEQUENCE: 63

-continued

```
cgaattcggc gtgcaccgct atgggttgca gcagcggctg gcgccgcaca ccccactggc     60

ccgggtgttt tcgccccgaa cccggatcat ggtgagcgaa aaggagattc gcctgttcga    120

tgctgggatt cgccaccgcg aggccatcga ccgattactc gccaccgggg tgcgagaggt    180

gccgcagtcc cgctccgtcg acgtctccga cgatccatcc ggcttccgcc gtcgggtggc    240

ggtagccgtc gatgaaatcg ctgccggccg ctacctgcaa ggtgattctg tcccgttgtg    300

tcgaagtgcc tttcgcgatc gactttccgt tgacctaccg gctggggcgt cggcacaaca    360

ccccggtgag gtcgtttttg ttgcagttgg gcggaatccg tgctctgggt tacagccccg    420

aactcgtcac ggcggtgcgc gccgacggag ttgttatcac cgatccgttg gccgtaccgc    480

gccttgggc                                                            489
```

<210> SEQ ID NO 64
<211> LENGTH: 448
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 64

```
tcagactcca cccagccagc aggcagcgcg aagctgaatc ctccaaccgg gttgtcgatc     60

cggacaggtt ggggtgcgtt tggggcaatg acaggtggcg gcggtgcgtt cgggtcggcc    120

ggcggaggtg ctgcgttggg atcgcccggc tgggcattcn gcgtgttggc ggcggccggt    180

ggtggggggg caacaggtgt cgccggtgcg ggtggcgctg cagcggtcga cggcggcgaa    240

gcggccgttg tgggtaccgg gggcgctggc tccggatcgg cgttggcggt cgcgggcacc    300

gcaacggtca ccaagctggc gctggccatc gccgcgatag ccagtgccgc caatcgtccc    360

ttgcgacgtg tcaagtnggg gtccacctga tgcatggcca aagaacctac cgtgttaacg    420

gcncaacnca aggaccgcgc cggtcgcn                                       448
```

<210> SEQ ID NO 65
<211> LENGTH: 346
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 65

```
tttccgcggt acccgctcaa ctttgtgtcn accctcaacg ccattgccgg cacctactac     60

gtncactcca actacttcat cctgacgccg gaacaaattg acgcagcggg tccgctgaac    120

aattcggtcc gtcccacgaa agaaccagtt ttncntcttt cncacggaga acctgccgct    180

gctagagcca ctgcgatcgg tgccgatcgt ggggaaccca ctggcgaacc tgtgtttcaa    240

ccaacactta gagtgtaatt gtaaacctgg gctaggggaa accggctcta gtttttccac    300

cntctccgcc ccntgtttcg aatactccgt tcgggttgtc cccaaa                   346
```

<210> SEQ ID NO 66
<211> LENGTH: 277
<212> TYPE: DNA
<213> ORGANISM: Mycobacterium tuberculosis -continued

<400> SEQUENCE: 66
gcttccggct cgtatgttgt gtggaattgt gaccggatac caatttcaca caggaaacag 60
ctatgaccat gattacgcca agctagttag gtgacactat acaatactca agcttgccgg 120
ctggtgggcc gaccacttcg atggcacgac ccgtgaactg ctgcccggcc aattcttctt 180
ggtcgcccgg accgatggac cgcggctggg attccagaag gtgcccgatc ccgcccctgg 240
gaaaaaccgc gtgcacctct acttcacgac caacgac 277

<210> SEQ ID NO 67
<211> LENGTH: 434
<212> TYPE: DNA
<213> ORGANISM: Mycobacterium tuberculosis

<400> SEQUENCE: 67
ccgatcgact gatgcgccga caaccacgcc ccaacaactg gaatgaaccg tcgtgaccat 60
catcagcacg cggttgtagg cgacttgcga catgttcaac ccgccgtact cggacggaat 120
cttcaaaccg aaacagccca gctcggccag gcctttcacg tactcgtcgg ggatctgggc 180
accacgctcg aggacgctgc cgtccacggt gtctaggaat tcccgcagtt tgaccagaaa 240
cgcctcggtt cgggcctcct cggcgtccga cggcttggga aatgggtgta tgagccctac 300
gggaaaccgg cccacaaaga gttctttggc gaaggacggt ttatcccaac cactttcgcg 360
agattcctcg gcaagggccc gcgcttgctc ctcggtgacc tgagtttgct gtgccatcgc 420
cgcctcctcc ctga 434

<210> SEQ ID NO 68
<211> LENGTH: 465
<212> TYPE: DNA
<213> ORGANISM: Mycobacterium tuberculosis

<400> SEQUENCE: 68
tgcatccggc tcgtatgttg tgtggaattg tgagcggata acaatttcac acaggaaaca 60
gctatgacca tgattacgcc aagctattta ggtgacacta tagaatactc aagcttttac 120
ggtgatcgcg catcacctgg ttcatgaact ggaagcagcg cagcgcttcc ttttcggccg 180
caacatgagc cagcctctcg tcggcggtcg ggtgcaggtg ctcgggcagc tcggccgcga 240
cagccgcctg accctgaaac cagcttccat atcccgcgac gaacgacgcc agtccgctac 300
gtaacccctc cgcgactgtc catggacaac agcgcgttct ccaccgaccg ggcccgggtg 360
tggggtgttt cggcgaccgg cagccaggtg gtccacactg ccgacgggcg ccgcgagccg 420
ttcaccgacc aggccgccga gcaagtccgc ccgatcgcat actcc 465

<210> SEQ ID NO 69
<211> LENGTH: 463
<212> TYPE: DNA
<213> ORGANISM: Mycobacterium tuberculosis

<400> SEQUENCE: 69
gggggcgctg ctggtatagt cgctgaccgg tgcaggtttc gacaatgtgg tgccggttcg 60
gcggctacgt gccatcgaga cactggcgca ggctatcgca cccgttatcg gctacgagca 120
aatcgcggta tgcgttcttg agcatgagtc ggcgaccgtc gtcatggtcg acacccacga 180
cggaaagacg cagatcgccg tcaagcatgt gtgccgcgga ttatcaggac tgacctcctg 240
gctgaccggc atgtttggtc gcgatgcctg gcgcccggcc ggcgtggtcg tggtcggctc 300
ggatagcgag gtcagcgaat tctcgtggca gctcgaaagg gtcctgccgg tgccggtctt 360

-continued

```
tgcgcaaacg atggcgcagg ttacggtcgc gcggggtgcg gcctggcggc ggccagagca    420

cgagttcacc gatgcgcagc tagtggcgac agcgtcagcc aac                      463


<210> SEQ ID NO 70
<211> LENGTH: 447
<212> TYPE: DNA
<213> ORGANISM: Mycobacterium tuberculosis

<400> SEQUENCE: 70

tgcttccggc tcgtatgttg tgtggaattg tgagcggata acaatttcac acaggaaaca     60

gctatgacca tgattacgcc aagctattta ggtgacacta tagaatactc aagcttccgt    120

acaggtcgcc tccaacacgg cggggaagcg acaccagcct accgagcttg gagtccagga    180

cgccagcggc ggcgtcggtc tgcgtcgtgg tgccgccggg gtggcgttgg ctggcaacga    240

tctccaccca gccggtcggg ttacccacga tctcggcata gacgcgggcc gaggccggtg    300

cgataccgta ttgcgtcaat tgggacgcgg ttgtgcattc ggctagctcg gttgccacac    360

ccgtcagggg ttcgacgttg gcgggttcgg cgggccccag caccgctgtc accatgcccg    420

ccaagccgac ctgcggcgcc accaact                                        447


<210> SEQ ID NO 71
<211> LENGTH: 460
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 71

cggcatgacc accgacaggc ccgactggtc gtaccactcg aacgccgggg tgttgatgtc     60

ccagccgctg aagtcgtcct gcgcgcgcag gccgtcgagc aggtacaggg cgggcgagtt    120

ggcaccacca ctttggaatt ggaccttgat gtcacggccc atcgacggcg acggcacctg    180

caggtactcc accggcaagc ccggccggga aaatgccccc gcggtcgccg tgccaccgac    240

ggcgccgacc agacccgaca ctagggccgc gccgacggcc ccgaccacga gtcgacgcga    300

catacccgtg acggcgccac gaaccctgtc aacaagctgc attcttgctt ccctcatcct    360

catctcaacg catccatgca tgtttgggcg catcctgaat tangtcagac tgcaggcgct    420

gggccggcag tgctcgtgta tcaaccacaa cttcgggcgt                          460


<210> SEQ ID NO 72
<211> LENGTH: 404
<212> TYPE: DNA
<213> ORGANISM: Mycobacterium tuberculosis

<400> SEQUENCE: 72

ttccaaccct aattggcttt cggccccatc cgtgaggacg gggtgcgggt gctcaacaac     60

aacgtcgtcc gcgggacaca cctctatgct gccgccatgg acgcggtcca acgcaagcag    120

ctgatcgagc tacaaccccg cgcggaacgc ttccgccgcg ggcgtgaccg catcccgttg    180

accgggcgga tcgcggtgat cgtcgatgac ggcatcgcca ccggagcgac ggccaaggcg    240

gcgtgccacg tcgcccgggc gcacggtgcg gacaaggtgg tgctggcggt cccgatcggc    300

ccaaacgaca tcgtggcgag attcgccggg tacgccgatg aggtggtgtg tctggcgacg    360

ccggcgttgt tcttcgccct cgggcagggt taccgcaact tcac                     404
```

-continued

<210> SEQ ID NO 73
<211> LENGTH: 465
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 73
caggcatgca agctttccgc cgatacccgc catgtcgcgc acatccagga cttctggggg 60
gatccgctga cagcggcggg atcccaaagt gcggatgatc gggccgccta cgtcgtggtg 120
tacctcgtcg gtaacaacga aaccgaagcg tatgactcgg tccacgcggt gcggcacatg 180
gtggacacca caccgccacc gcacggggtg aaggcctatg tcaccggtcc ggcagcactc 240
aatgccgacc aggccgaggc cggagacaaa agtatcgcta aggtcaccgc cgatcacnag 300
catggtgatc gcagcaatgt tgctagtgat ctatcgctcc gtaattaccg cggttctcgt 360
cttgatcatg gtcggcatcg actcggccaa tccgcggatt catcgccttg ctcgccgaac 420
acaacatttt cacctttcac atttgcacca acctgctctt ctcat 465

<210> SEQ ID NO 74
<211> LENGTH: 387
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 74
cactactcaa gctctctcnt cattaccacc cctgtaattt gggatgggca aaaaggcgaa 60
gcaccgcttg gccacnaacg ccgggaggga caatctcggg cggctatggc ttctcccggg 120
aaggccccaa cgtacggcgt ttcaacacgt cgcgtcgccc tccgaccgcg aacattcggg 180
gattggcacc aacctgntac caccctggcc gggcgatgat ctgcagcgtc gccgcgggta 240
gtccccgccc gggcggctac agtctgaaac cccgatgacc atcgatgtgt ggatgcagca 300
tccgacgcaa cggttcctac acggcggata tgttctcctc gctgcgccgg tggaccggtg 360
ggtctatccc ctgaaaccga catcccn 387

<210> SEQ ID NO 75
<211> LENGTH: 445
<212> TYPE: DNA
<213> ORGANISM: Mycobacterium tuberculosis

<400> SEQUENCE: 75
caggcatgca agctttcgtc agttcattgc gccagcagac caacaagagc atcgggacat 60
acggagtcaa ctacccggcc aacggtgatt tcttggccgc cgctgacggc gcgaacgacg 120
ccagcgacca cattcagcag atggccagcg cgtgccgggc cacgaggttg gtgctcggcg 180
gctactccca gggtgcggcc gtgatcgaca tcgtcaccgc cgcaccactg cccggcctcg 240
ggttcacgca gccgttgccg cccgcagcgg acgatcacat cgccgcgatc gccctgttcg 300
ggaatccctc gggccgcgct ggcgggctga tgagcgccct gacccctcaa ttcgggtcca 360
agaacatcaa cctctgcaac aacggcgacc catttgttcg gacggcaacc ggtggcaacg 420

-continued

```
cacctaagct acttgcccgg gatga                                           445


<210> SEQ ID NO 76
<211> LENGTH: 345
<212> TYPE: DNA
<213> ORGANISM: Mycobacterium tuberculosis

<400> SEQUENCE: 76

gtttatgcac tggttaggtg tttccatgag tttcattctg aacatccttt aatcattgct      60

ttgcgttttt ttattaaatc ttgcaattta ctgcaaagca acaacaaaat cgcaaagtca     120

tcaaaaaacc gcaaagttgt ttaaaataag agcaacacgt acacaaggag ataagaagag     180

cacatacctc agtcacttat tatcactagc gcccgccgca gccgtgtaac cgagcatagc     240

gagcgaactg gcgaggaagc aaagaagaac tgttctgtca gatagctctt acgctcagcg     300

caagaagaaa tatccaccgt ggggaaaaac tccaggtaga ggtac                     345


<210> SEQ ID NO 77
<211> LENGTH: 139
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 77

atactcaagc ttgggtgtag ccgatcaccg gaagtcncat gatcagccac gttccgcgcc      60

gcccggcata cggtggtgta ccgatctccg cgtcatacac ccgcgggtaa tcgccgacgg     120

tgccggttcg cgagccgaa                                                  139


<210> SEQ ID NO 78
<211> LENGTH: 298
<212> TYPE: DNA
<213> ORGANISM: Mycobacterium tuberculosis

<400> SEQUENCE: 78

agctttatcg aaagcgcgaa cagctcgcgg cggcccacga cgtgctgcgt cggattgccg      60

gcggcgagat caattccagg cagctcccgg acaatgcggc tctgctggcc cgcaacgaag     120

gactcgaggt caccccggtg cccggggtcg tggtgcacct gccgatcgca caggttggcc     180

cacaaccggc cgcttgatgc ccggtcggca agcccggcag ttgccaaacc catcgtgatc     240

aggctcggct cgcgagttcg gcgaagaaat ggttcgcctg atcacctacc atcggcca       298


<210> SEQ ID NO 79
<211> LENGTH: 300
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 79

tcaacacgcc gccagccacc acgcgcgggt cgggcgccgg gcccgggcct ccaggctnct      60

ccgctcggtg atggcacgcc accgcgacac cacccggctg cgctacgtcg agccataccg     120

ggcggagcta catcggcccg gccgcccagt gttcgggccc tctcgcccag gtcgaggtcg     180

acaccgattt gcgcatccgc agccgcaccc tgcgacgaca gaaccgcggc cctacccact     240
```

gcttgtcggg cgggggccaa agaaccagct tgncatcctg ccacaattgg ccggcgcccg 300

<210> SEQ ID NO 80
<211> LENGTH: 321
<212> TYPE: DNA
<213> ORGANISM: Mycobacterium tuberculosis

<400> SEQUENCE: 80
caggcatgca agcttcacgt ccgtacggct cgggtacgct tcggtcgcag tgtgcgagtg 60
atagatgacg accgggacct cgtcggcatc ttccatagcc cgccacacct tcagttgctc 120
accggaatcc aaccggtaga aggtcggcca gcgctcggca ttggtcatcg ggatatgccg 180
ctcgggacgg tcagagccct cgggtccggc cagcactccg caggcttcgt cggggtggtc 240
gcgacgcgca tgggccacca tcgcattcac caggtctgcg cgaatcacca gcacgtagac 300
ggttcctttc ctaagcaaca c 321

<210> SEQ ID NO 81
<211> LENGTH: 340
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 81
aatattcaag ctttcggcgg aaacggacnc cttgcgaaca ttgataacaa aatagaaatc 60
attgatggtt tgagtcacca ggccgatcaa gccttcgccg agccaaattc caatcaagag 120
gcccaagccc gtaccaatca gcccggcaac gagggattcc gtcnttatca gccnaaataa 180
ctgctctcgg gtaccaccca aacagcgcaa tatggcgaaa aacggtcgcc gttgcacaac 240
attaaatgtc tcggtattgt tgattaaaaa gatacccacc accagggcaa tccaactgag 300
agcggttaaa ttgaccgtaa aaacctcccg tcatctgttt 340

<210> SEQ ID NO 82
<211> LENGTH: 394
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 82
caggcatgca agcttgctgc atcttcctgt gactgctccc gaaacctggg ggtgtgcctg 60
ctgtgtatgc acggcatacg gacatccttc ccctgatacc cgcggtcgaa ccagccacgt 120
gtccatcatc aggggtcaac cccggccaag ggcgacggca cgccaagttc gccgaccgtt 180
aacctagtgc tgttagcttc atttgctgcg agcaaaacag ctggtcggcc gttaggaact 240
gaattgaaac tcaaccgatt tggtgccgcc gtaagtgtcc tgtctgcggg tgcgctggtg 300
ttgtccgcgt gtggtaacga cgacaatgtg accgggggag gtgcaaccac tggccaggcg 360
tccgcgaaag tccattgcng ggggaagaag acac 394

<210> SEQ ID NO 83
<211> LENGTH: 487
<212> TYPE: DNA

-continued

<213> ORGANISM: Mycobacterium tuberculosis

<400> SEQUENCE: 83
gaaagtgccc caaggtgttg gtgaaactcg ctggacggtc cccaggatgt tggcagcaca 60
ttcaccggac atgaccggag caagaccgga catcctccca taccgtcgtc gccgtgtaca 120
tccgtagccc gtcctggcag gtgctgggtt gaacaaaatc agcccaacac ctgccacgac 180
gaagaagcgg gttgcgctgg catgtcttgt cggctcggcg atcgaattct acgaattcct 240
tatctacggg accgctgcgg cgctggtgtt tcccaccgtg ttcttcccac acctggatcc 300
cacggtggcc gccgtggcct ccaaggggac atttgctgtg gcgttcctat cccggccgtt 360
cggcgcggcc gtctttggat actttggaga ccgcctcggc cgccagaaga ccctggtcgc 420
cacactgttg atcatgggcc tggcaaccgt gactgttggg ctggttccac gacagtggcc 480
atcgcgc 487

<210> SEQ ID NO 84
<211> LENGTH: 418
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 84
atattcaagc tttgtcacac caagtgttcc gaccaancgc tccatccggc gagtggatac 60
tcccagcagg tagcaggtcg ccaccacgct ggtcagtgcg cgttcatctc gcttgcggcg 120
ctgcagcagc cagtccggga aatagctgcc ctggcgcagc ttggggatcg cgacgtcgat 180
ggttgcggca cgggtgtcga aatcacggtg gcggtagccg ttgcgctgat tggaccgctc 240
atcgctgcgt tcgcggtagc ccnccccgca cagggcgtcg gcttcagccc ccatccaagg 300
cggcgatgaa cgtcgagagc agcccgcgca gcaaatccgg gctcgcctgt gcgagttggt 360
cagccagaag ctgctcggtg tcataagatg agaagaggtc agtgcgtcct ttccttcg 418

<210> SEQ ID NO 85
<211> LENGTH: 399
<212> TYPE: DNA
<213> ORGANISM: Mycobacterium tuberculosis

<400> SEQUENCE: 85
caggcatgca agctttttga gcgtctcgcg gggcagcttc gccggcaatt ctactagcga 60
gaagtctggc ccgatacgga tctgaccgaa gtcgctgcgg tgcagcccac cctcattggc 120
gatggcgccg acgatggcgc ctggaccgat cttgtgccgc ttgccgacgg cgacgcggta 180
ggtggtcaag tccggtctac gcttgggcct ttgcggacgg tcccgacgct ggtcgcggtt 240
gcgccgccaa agcggcgggt cgggtgccat catgaatgcc tcaccgccgc cgcactgcac 300
ggccagtgcc ccggcgatgt cagccatcgg gacatcatgc tcgcgttcat actcctcgac 360
cagtccgcgg aacagctcca ttcccggacc gcccaacgc 399

<210> SEQ ID NO 86
<211> LENGTH: 474
<212> TYPE: DNA
<213> ORGANISM: Mycobacterium tuberculosis
<220> FEATURE:
<221> NAME/KEY: unsure
<222> LOCATION: (various positions within the sequence)

-continued

<223> OTHER INFORMATION: applicants are uncertain of bases designated as "n"

<400> SEQUENCE: 86
atactcaagc ttttggctgg gtcgccttcc aattcagcgt gcaccgctat gggttgcagc 60
agcggctggc nccgcacacc ccactggccc gggtgttttc gccccgaacc cggatcatgg 120
tgagcgaaaa ggagattcnc ctgttcgatg ctgggattcg ccaccgcgag gccatcgacc 180
gattactcgc caccggggtg cgagaggtgc cgcagtcccg ctccgtcgac gtctccgacg 240
atccatccgg cttccgccgt cgggtggcgg tagccgtcga tgaaatcgct gccggccgct 300
accacaaggt gattctgtcc cgttgtgtcc aagtgccttt cgcgatcgac tttccgttga 360
cctaccggct ggggcgtcgg cacaacaccc cggtgaggtc gtttttgttg cagttgggcg 420
gaatccgtgc tctgggttac agccccgaac tcgtcacggc ggtgcgccgc cgac 474

<210> SEQ ID NO 87
<211> LENGTH: 383
<212> TYPE: DNA
<213> ORGANISM: Mycobacterium tuberculosis

<400> SEQUENCE: 87
caggcatgca agcttcaacc tattgacgca ttgtgcgaac tgacggcgcc cgcgcatggc 60
caatccggaa gaccatcatt ggccagtggc cgggcgctaa caggttccag ccccccacca 120
gtgccgctcg aacatgcggt gcaacccatt cgcaggccgg cagggaaagc accgcggaag 180
ccgcaaaggg ctgcagttcc gcgcccaata gtgtcgtccg caaccagatg cgctcgaaaa 240
ccgccgccgg cagtcagcgc acccgacgcg aggtcgagag acgtcgtcag cgcgcccaca 300
tggggtgcca atcggcacgg caggtaggcc gcgcgcaacc ccaacgcgtg gtgcatgcca 360
cggtccgcag gaggccacca ccc 383

<210> SEQ ID NO 88
<211> LENGTH: 455
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 88
atactcaagc ttcccggccg caggtgacgg cgcggcctag cgccacttga tgccgcaccc 60
gatcgacggn cgttggtcgg ggttgactgg ccgcccggcg agcagggcgt caaccgcggc 120
ccggacgtcg gcggccgtca ccggtcggcc attgcccggg cgggagtcgt cgagctgacc 180
acggtagaca agtcggcgct ggccgtcgaa gacaaacgtg tcgggtgtgc aggccgcgga 240
gaaggcgcng gcgacgtctc gggtttcgtc gtagagatac gggaacgtcc agccgtggcg 300
gcgggcctcg gcgaccatct gatcgggccc gtcctgcggg taggtgacca cgtccttact 360
ggagataccg accatcggga ccctttgatc ggcgaggtcc cggccgaccg tggccaatcc 420
ggcggcgacg tgtcgcccgt accggccagt ggttc 455

<210> SEQ ID NO 89
<211> LENGTH: 429
<212> TYPE: DNA
<213> ORGANISM: Mycobacterium tuberculosis
<220> FEATURE:
<221> NAME/KEY: unsure -continued
<222> LOCATION: (various positions within the sequence)
<223> OTHER INFORMATION: applicants are uncertain of bases designated as "n"

<400> SEQUENCE: 89
caggcatgca agctttanca ncatcaaccc cgccccgcac cagcaccgac acgatgtcga 60
tgccatcgag gtgaatgtcg aactggcnca aaccatctgg cgaccgcgac caccggcaac 120
atgggtaccg gcgatttccg gtgccaatgc cgacccgacg ggccgctctc accgcaggtg 180
acctcgatca ccgagaccag ccggccgtta tactcacgca cccctaccgt gtcacgccca 240
aaacggcgct ggtggtcgat tgccggagtg caccccgcac ccagtgtcgt gcccggatcc 300
gccgaccaat cccgcaccca cgtcgccaaa cccgaaatca ccgtgatgcc gtggtaactg 360
accaccgaca gtaacgtcac tacggccgcc acgccgacgc cgaaccacca cgcacatgat 420
gatcggctg 429

<210> SEQ ID NO 90
<211> LENGTH: 321
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 90
atattcaacc ttgcacacat tgacgatacc ttggtcacga gaccccaaaa gctggcctcc 60
accgcgcgcc ggggaccacg gtcatacctt gannc ngctt tcgatcgttg atgctgcgtc 120
ttggtccgcg gaaaccgcag gctggcatat gcacgtgggc gcactggcga tctgcgatcc 180
ccaccgattc gcccgaatac agctttcagc ggctccccaa gttgatcatc gaccggctgc 240
cggatatccc gcacttgcgg tggcgggtca ccggcgcccc gctcggactg gaccggccgt 300
ggttcgtcga ggaccacgaa c 321

<210> SEQ ID NO 91
<211> LENGTH: 134
<212> TYPE: DNA
<213> ORGANISM: Mycobacterium tuberculosis

<400> SEQUENCE: 91
caggcatgca agcttcatgc ccgcggcatg atagccacat gcacgcaatc gaactcagcg 60
aaaccggcgg gccaggcgtc ttacgccacc tcaccagcgc gcaacctcaa cccggccacg 120
gagacctcct gatc 134

<210> SEQ ID NO 92
<211> LENGTH: 513
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 92
atactcaagc ttgattttga tcatcatgat gatcatcacc cgaattgtgg tagccgcagt 60
ggttatcgtg ggtaccgtcg tgctttccat gggcgcctct ttcgggcttt ccgtattggt 120
ctggcaggac attctgggta tcgagttgta ctggatggtg ttggcgatgt cggtgatcct 180

-continued

```
gctcntggcg gtgggatccg actacaatct gctgctgatt tcccggttga aagaggaaat    240

tggggccgga ttgaacaccg gaattatccg tgccatggct ggtaccgggg gagtggtgac    300

ggctgccggc atggtgttcg ccgttaccat gtcgttgttt gtgttcagcg atttgcgaat    360

tattggtcag atcggtacca ccatcggcct gggcttgctg ttcgacaccc tcgtcgtgcc    420

tcgttcatga aaccgtccat tgctgccctg ctgggacctg gttctggtgg ccgctacggg    480

tgcgcccgcg cccggcagtc aaatcttccg ccg                                 513
```

<210> SEQ ID NO 93
<211> LENGTH: 345
<212> TYPE: DNA
<213> ORGANISM: Mycobacterium tuberculosis

<400> SEQUENCE: 93

```
caggcatgca agcttggcgt gccgttccaa cccgaattgg ctttcggcgc catcggtgag     60

gacggcgtgc gggtgctcaa cgacgacgtc gtccgcggga cacacctcga tgctgccgcc    120

atggacgcgg tcgaacgcaa gcagctgatc gagctacaac gccgcgcgga acgcttccgc    180

cgcgggcgtg accgcatccc gttgaccggg cggatcgcgg tgatcgtcga tgacggcatc    240

gccaccggag cgacggccaa ggcggcgtgc caggtcgccc gggcgcacgg tgcggacaac    300

gtggtgctgg cggtccccat cggcccagac gacatcgtgg cgaga                    345
```

<210> SEQ ID NO 94
<211> LENGTH: 302
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 94

```
atactcaagc ttttacggtg atcgcgcatc acctggttca tgaactggaa gcagcgcagc     60

gcttcctttt cggccgcaac atgagccagc ctctcgtcgg cggtcgggtg caggtgctcg    120

ggcagctcgg ccgcgacagc cgcctgaccc tgaaaccagc ttccatatcc cgcgacgaac    180

gacgccagtc cgctacgtaa cccctccgcg actgtccatg gacaacagcg cgttctccac    240

cgaccgggcc cgggtgtggg gtgtttcggc gaccggcagc cangtggtcc acactgccga    300

ag                                                                   302
```

<210> SEQ ID NO 95
<211> LENGTH: 286
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 95

```
tagtcgctga ccggtgcagg tttcgacnat gtggtgccgg ttcggcggct acgtgccatc     60

gagacactgg cgcaggctat cgcacccgtt atcggctacg agcaaatcgc ggtatgcgtt    120

cttgagcatg agtcggcgac cgtcgtcatg gtcgacaccc acgacggaaa gacgcagatc    180

gccgtctanc ntgtgtgccg cggattatca ggactgacct cctggctgac cggcatgttt    240
```

-continued ggtcgcgatg cctggcgccc ggccggcgtg gtcgtggtcg gctcgg 286

<210> SEQ ID NO 96
<211> LENGTH: 482
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 96
atactcaagc tttccgccga tacccgccat gtcgcgcaca tccagaactt ctggggggat 60
ccgctgacag cggcgggatc ccaaagtgcg gatgatcggg ccgcctacgt cgtggtgtac 120
ctcgtcggta acaacgaaac cgaagcgtat gactcggtcc acgcggtgcg gcacatggtg 180
gacaccacac cgccaccgca cggggtgaag gcctatgtca ccggtccggc agcactcaat 240
gccgaccagg ccgaggccgg agacaaaagt atcgctaagg tcaccgcgat cacgagcatg 300
gtgatcgcag caatgttgct agtgatctat cgccccgtaa ttaccgcggt tctcgtcttg 360
atcatggtcg gcatcgacct cggcgcaatc cgcggattcn tcgccttgct cgccgaccac 420
aacattttca gcctttcaac atttgcgaca acctgctcgt tctcatggcg attgcngcga 480
ac 482

<210> SEQ ID NO 97
<211> LENGTH: 395
<212> TYPE: DNA
<213> ORGANISM: Mycobacterium tuberculosis

<400> SEQUENCE: 97
caggcatgca agcttggcgt gccgttccaa cccgaattgg ctttcggcgc catcggtgag 60
gacggcgtgc gggtgctcaa cgacgacgtc gtccgctgga cacacctcga tgctgccgcc 120
atggacgcgg tcgaacgcaa gcagctgatc gagctacaac gccgcgcgga acgcttccgc 180
cgcgggcgtg accgcatccc gttgaccggg cggatcgcgg tgatcgtcga tgacggcatc 240
gccaccggag cgacggccaa ggcggcgtgc caggtcgccc gggcgcacgg tgcggacaag 300
gtggtgctgg cggtcccgat cggcccagac gacatcgtgg cgagattcgc cgggtacgcc 360
gatgaagtgg tgttgtttgg cgacccggcg ttgtt 395

<210> SEQ ID NO 98
<211> LENGTH: 439
<212> TYPE: DNA
<213> ORGANISM: Mycobacterium tuberculosis

<400> SEQUENCE: 98
atactcaagc tttggcattg tgcacatttt ccacccgtgc tctattaatg ctgagccgct 60
aattgtgacc ccagtcggga aacacgcgga gcaccaaatt caccgcagcg gccggggcgg 120
ttcaactcac catggatcgc tctcgtcgtc tggtgctgga caatcgtcgc tgtagcgcgt 180
cgcgaacacc tcagcttctg ctgccgcggc ttcttccggc gatggtaacc cccaggtttc 240
gcccacggtc ttacgtagca gtgcgacgcg gtgttcatct gcatcgacct gttgactcat 300
cctgtcaagg atgaaggcgt actgggccga ctgcgccttc tgccgcgcca ggtcggcaat 360
caccaggatc tcagaaacga gctgcgactc actcttccag gccaccctgg ccgaaagctc 420
gacatggtca atccggccg 439

-continued

<210> SEQ ID NO 99
<211> LENGTH: 348
<212> TYPE: DNA
<213> ORGANISM: Mycobacterium tuberculosis

<400> SEQUENCE: 99
caggcatgca agcttgcggg ccggagtggt ttcgacggcc gctcgcttct cggcatcggt 60
ttgggctgtc accagcagtt ggtagttctt cacgtactgt tgttcgagcg tcgagccgcc 120
gcgcgtgtcg aggtcgccgg acgcgtatcc cgccaggccg gtcagggtgc ccttccagtc 180
cacgccgctg tggtcggcga accgcttatc ttcaatcgag acgatcgcca gcttcatcgt 240
gttggcgatc ttgtccgagg gcacctcgaa ccggcgctgc gagtacagcc acgcgatcgt 300
gttgcccttc gcgtcgacca tcgtcgatac cgcaggcact tgcccctc 348

<210> SEQ ID NO 100
<211> LENGTH: 436
<212> TYPE: DNA
<213> ORGANISM: Mycobacterium tuberculosis

<400> SEQUENCE: 100
atactcaagc ttcccggcgg ccagtaccga aagcgcgaac agctcgcggc agcccacgac 60
gtgctgcgtc ggattgccgg cggcgaaatc aattccaggc agctcccgga caatgcggct 120
ctgctggccc gcaacgaagg actcgaggtc accccggtgc ccggggtcgt ggtgcacctg 180
ccgatcgcac aggttggccc acaaccggcc gcttgatgcc cggtcggcaa gcccggcagt 240
tgccaaaccc agcgtgatca ggctcggctc gcgagttcgg cgaagaagtg gctcgcctga 300
tcacctacca tcggccagga tctgcgtgtc atcacaacgc tcgccaagga ggttgttgtg 360
gtgctatcga cggcctttag ccagatgttc ggaatcgact atccgatagt gtccgcgcca 420
atggacttga tcgccg 436

<210> SEQ ID NO 101
<211> LENGTH: 445
<212> TYPE: DNA
<213> ORGANISM: Mycobacterium tuberculosis

<400> SEQUENCE: 101
agcttcggtg tagccgatca ccggaagccg catgatcagc cacgtttcgc gccgcccggc 60
atacggcggc gtaccgatct ccgcgtcata cacccgcggg taatcgccga cggtgccggt 120
tcgcgagccg aaggtgacga cgctgattga atcgagttcc aggtccagcg ggtggcgcag 180
caacggcgcg agctcaacga cgtcaatcac gttgtcgctt tctacggtca ccgacccggt 240
gaccgtagtc gcccggtgcg ctcggccgag aagttgcacc gccaccaccg cgacaccgtc 300
ttgcacgcgg acgccacccc cggatcggtt gttggccaag gtaattgggt cattccattt 360
gacgggacgc cgaccccgca gccccagtac cgcccacgac cacgccggct gacccaccac 420
tgtacgaaca ccaaggcgac gccga 445

<210> SEQ ID NO 102
<211> LENGTH: 261
<212> TYPE: DNA
<213> ORGANISM: Mycobacterium tuberculosis

<400> SEQUENCE: 102
atactcaagc ttcggtggct tcgcccgccc tgccgggtgg acttcatgac aacgcggggg 60
cgattacccc cgctaccgcc agcagcatga cggcggtacc taacaccgcc cggatgcctc 120

-continued

```
gcacgtgcct cgatgtgctc acggaatcgc cccggcaccg cgatctcgag gatcaccagc    180

gttacccccg gcagcgcgac accgacaatt ccgtacaccg ccacgccgat ccggccctgg    240

gccagctgat tggagctggc g                                              261
```

<210> SEQ ID NO 103
<211> LENGTH: 244
<212> TYPE: DNA
<213> ORGANISM: Mycobacterium tuberculosis

<400> SEQUENCE: 103

```
caggcatgca agcttccaca tgtacggatc cacgaacatc ccgttgaact gacaggtgcg     60

gcccggctcg atcaggccgg ccacttgttc tacgcggtta ccgaagatct cttcggtgac    120

ctgcccgccg ccggccagct cggcccagtg cccggcgttg gccgccgcgg cgacgatctt    180

ggcgtccacg gtggtccggg tcttgcccgc tagcacgatc cgcgagtcgg ccggtcaccc    240

gggt                                                                 244
```

<210> SEQ ID NO 104
<211> LENGTH: 376
<212> TYPE: DNA
<213> ORGANISM: Mycobacterium tuberculosis

<400> SEQUENCE: 104

```
atactcaagc tttccaagtc ccaagtgtcg atcatggcca aagagctcga caaagccgta     60

gaggcgtttc ggacccgccc gctcgatgcc ggcccgtata ccttcctcgc cgccgacgcc    120

ctggtgctca aggtgcgcga ggcaggccgc gtcgtcgggg tgcacacctt gatcgccacc    180

ggcgtcaacg ccgagggcta ccgaaagatc ctgggcatcc aggtcacctc cgccgaagac    240

ggggccggct ggctggcgtt cttccgcgac ctggtcgccc gcggcctgtc cggggtcgcg    300

ctggtcacca gcgacgccca cgccggcctg gtggccgcga tcggggccac cctgcccgca    360

gcggcctggc agcgct                                                    376
```

<210> SEQ ID NO 105
<211> LENGTH: 284
<212> TYPE: DNA
<213> ORGANISM: Mycobacterium tuberculosis

<400> SEQUENCE: 105

```
caggcatgca agcttcacac gtaggcgccg tcgataaatg actccgccgc gcttcgcaca     60

tcctcgtagc gatccttggc gagcaggtca accgggcgct gcccgtcgag gagccggttt    120

ttggcgtgca gccactggcc gacacctcgg ggggtaagcg aatccgagag caggaggacg    180

aggtcacgaa gctgcgccag ccggtcgtac cgctcagggc ggatgtcgcc ggtccgccac    240

ccgcgtaccg cccgatcgga cacctgtatg accgcggcga cgtc                     284
```

<210> SEQ ID NO 106
<211> LENGTH: 140
<212> TYPE: DNA
<213> ORGANISM: Mycobacterium tuberculosis

<400> SEQUENCE: 106

```
cgcggcggcg cattaccccc gctaccgtca gcagcttgac ggcggtagcg aacaccgccg     60

gatgcagcgc aggtgcgtct atgtgcacac ggaatcgccc cggcaccgcg atctcgagga    120

tcaccagtgc ccgccccctg                                                140
```

-continued

<210> SEQ ID NO 107
<211> LENGTH: 491
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 107
gggatcgagg aacagcgcgt tgaactgata ggtgcggccc ggctcgagca ggccggccat 60
ttgttcgatg cggttaccga agatctcttc ggtgacctgc ccgccgccgg ccagctcggc 120
ccagtgcccg gcgttggccg ccgcggcgac gatcttggcg tccacggtgg tcggggtcat 180
gcccgcgagc aggatcggcg agcggccggt cagccgggtg aacttcgtcg agagcttgac 240
cctgccgtcg gggaggcgaa ccacggtcgg tgcgtatctc gaccaggccc gggcaacctc 300
gggggtggcg ccgacggtga acaggttgcg ctggccaccg cgggtagccg ccggcactat 360
gccgatgccc aggccgcgga tcaccggtgc ggtcagtcgg gtcaggatgt cgcccggccc 420
caggtcgaag atccagcggg cgccggccgc gtggacacng gtgatctcgt ccaccatcga 480
ctttctgatc a 491

<210> SEQ ID NO 108
<211> LENGTH: 364
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 108
taactcaagg cttgcgttga ggccccaggc ccatcgacgg tttggcggcc ttaaatgcac 60
tgaggtcgtc aattgacccc acagcggaaa tgccgactat tcgcaggcct ccttcgcctt 120
ggctgccgga gaggggctcc gcgggaaccg catgcaggta tatgacctcg gtttctcggg 180
tgctaccgcg tgccttgtcg aggatgaact cggcgttgga attgtccagc cggcccaatt 240
catcgagcgc agattcgtac acatggccgg cggcgacata cgcttcaccg tggatctgct 300
ccacacggac cgccctgtcg ggatcctgct cacgggtaaa ggaacttacn tggcnctcgg 360
tgcc 364

<210> SEQ ID NO 109
<211> LENGTH: 453
<212> TYPE: DNA
<213> ORGANISM: Mycobacterium tuberculosis

<400> SEQUENCE: 109
ccttctgcgc cacccacacc gtcaacgccc gcgaagtcga cgtcgtccag gccatcggcg 60
gcctcacgga tggattcggc gcggacgtgg tgatcgacgc cgtcggccga ccggaaacct 120
accagcaggc cttctacgcc cgcgatctcg ccggaaccgt tgtgctggtg ggtgtgccga 180
cgcccgacat gcgcctggac atgccgctgg tcgacttctt ctctcacggc ggtgcgctga 240
agtcgtcgtg gtacggcgat tgcctgcccg aaagcgactt ccccacgctg atcgaccttg 300
acctgcatgg ccggctgccg ctgcagcggt tcgtttccga acgcatcggg ctcgaagacg 360
tcgaggaggc gttccacaag atgcatggcg gcaaggtatt gcgttcggtg gtgatgttgt 420

-continued

```
gatggccgcc atcgagcgcg tcatcaccca cgg                                453


<210> SEQ ID NO 110
<211> LENGTH: 329
<212> TYPE: DNA
<213> ORGANISM: Mycobacterium tuberculosis

<400> SEQUENCE: 110

atactcaagc ttgattttga tcatcatgat gatcatcacc cgaagtgtgg tagccgcagt     60

ggttatcgtg ggtaccgtcg tgctttccat gggcgcctct ttcgggcttt ccgtattggt    120

ctggcaggac attctgggta tcgagttgta ctggatggtg ttggcgatgt cggtgatcct    180

gctcctggcg gtgggatccg actacaatct gctgctgatt tcccggttga aaaaagaaat    240

tggggccgga ttgaacaccg gaattatccg tgccatggct ggtaccgggg gagtggttac    300

cgctgccggc atggtgttcg ccgttacca                                      329


<210> SEQ ID NO 111
<211> LENGTH: 438
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 111

attgnctttc ggcgccatcg gtgaggacgg cgtgcgggtg ctcaacgacg acgtcgtccg     60

cgggacacac ctcgatgctg ccgccatgga cgcggtcgaa cgcaagcagc tgatcgagct    120

acaacgccgc gcggaacgct tccgccgcgg gcgtgaccgc atcccgttga ccgggcggat    180

cgcggtgatc gtcgatgacg gcatcgccac cggagcgacg gccaaggcgg cgtgccaggt    240

cgcccgggcg cacggtgcgg acaaggtggt gctggcggtc ccgatcggcc cagacgacat    300

cgtggcgaga ttcgccgggt acgccgatga ggtggtgtgt ttggcgacgc cggcgttgtt    360

cttcgccgtc gggcagggtt accgcaactt cacccagacc tccgacgaag aagtggtggc    420

gttttctgga tcgtgctc                                                  438


<210> SEQ ID NO 112
<211> LENGTH: 438
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 112

atactcaagc ttttcccgtc cgtcatcgcc caagcgcgtg aggccgaagc ggctggttac     60

gactccctgt ttgtgatgga ccacttctac caactgccca tgttggggac gcccgaccag    120

ccgatgctgg aggcctacac ggcccttggt gcgctggcca cggcgaccga gcggctgcaa    180

ctgggcgcgt tggtgaccgg caatacctac cgcagcccga ccctgctggc aaagatcatc    240

accacgctcg acgtggttag cgccggtcga gcgatcctcg gcattggagc cggttggttt    300

gagctggaac accgccagct cggcttcgag ttcggcactt tcagtgaccg gttcaaccgg    360

ctcgaanagg cgctacagat cctcgagcca atggtcaagg gtgagcgcca acgtttttcg    420
```

-continued

```
gcgattggta cccaccga                                                438

<210> SEQ ID NO 113
<211> LENGTH: 482
<212> TYPE: DNA
<213> ORGANISM: Mycobacterium tuberculosis

<400> SEQUENCE: 113

cggccaccgg ggccactccg cacaatctgt acccgaccaa gatctacacc atcgaatacg     60

acggcgtcgc cgactttccg cggtacccgc tcaactttgt gtcgaccctc aacgccattg    120

ccggcaccta ctacgtgcac tccaactact tcatcctgac gccggaacaa attgacgcag    180

cggttccgct gaccaatacg gtcggtccca cgatgaccca gtactacatc attcgcacgg    240

agaacctgcc gctgctagag ccactgcgat cggtgccgat cgtggggaac ccactggcga    300

acctggttca accaaacttg aaggtgattg ttaacctggg ctacggcgac ccggcctatg    360

gttattcgac ctcgccgccc aatgttgcga ctccgttcgg gttgttccca gaggtcagcc    420

cggtcgtcat cgccgacgct ctcgtcgccg ggaccagcag ggaatcggcg atttcgccta    480

ca                                                                   482

<210> SEQ ID NO 114
<211> LENGTH: 388
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 114

atactcaagc ttggggtggc gctgtcggtc ggtgtgcttg gcggcgtcgg tatcaacacc     60

gcccacgaaa tggggcacaa gaaggattcg ctggagcggt ggctgtccaa aatcaccctc    120

gcccagacct gctacgggca cttctacatc gagcacaacc gtggccatca cntccgggtg    180

tccacaccgg aggacccggc gtcggcgcgg ttcggcgaaa cgttgtggga gttcctgccc    240

cgcagtgtta tcggcggctt gcgctcggcc gttcatttgg aggcccaacg gctgcgtcgg    300

ctcggcgtca gcccctggaa tcccatgacg tatctgcgca acgacgtgcn caacncgtgg    360

ctgatgtcng tggtgttgtg gggtgggc                                       388

<210> SEQ ID NO 115
<211> LENGTH: 455
<212> TYPE: DNA
<213> ORGANISM: Mycobacterium tuberculosis

<400> SEQUENCE: 115

tcgccaccgc accgcggcga acgctcaaag gcacctactg gcaccaaggc cccacacgtc     60

accctgtgac ctcctgcgcc gaccccgccc gaggtcctgg ccgttaccac cgaacgggcg    120

agccgggagt ctggtacgca tcgaacaaag agcaaggtgc atgggcggag ttgttccgcc    180

acttcgtcga tgacggggtc gatccattcg aggtccgtcg ccgcgtcggt cgagtggcgg    240

tcacactcca ggtactcgac ctcacagacg agaggactcg atcccatcta ggtgtggacg    300

aaacagatct tctgtccgac gactacacca ccacccaggc catcgccgcc gcccgcgatg    360

ccaacttcga cgccgtactg gccccggcgg cggcgctccc cggttgtcaa acactttgcc    420

gtgttcgttc acgcactgcc caacatcgag cccga                               455
```

-continued

<210> SEQ ID NO 116
<211> LENGTH: 328
<212> TYPE: DNA
<213> ORGANISM: Mycobacterium tuberculosis

<400> SEQUENCE: 116
atgaaataag aagagcacat ccctcagtcg gttatcatca ctagcgctcg ccgcacccgt 60
gtaaccgatc atagcgagcg aactggcgag gaagcaaaga atatctgttc tgtcagatag 120
ctcttacgct cagcgcaaga agaaatatcc cccgcgggaa caactccagg tagaggtaca 180
cacgcggata gccaattcag agtaataaac tgtgacactc acaccctcat caatgatgac 240
gaactacacc ccgatatccg gtcacatgac gaagggaaag agaaggatat catctgtgac 300
aaactgccct caaatttggc ttccttaa 328

<210> SEQ ID NO 117
<211> LENGTH: 318
<212> TYPE: DNA
<213> ORGANISM: Mycobacterium tuberculosis

<400> SEQUENCE: 117
atactcaagc ttgtcgaact ccttcttgaa taccggccgg ccatccacag atgcccggaa 60
gaacttccag gtacccatgg cggctggatc agggggcggc acagttggtc ttgtcctgcc 120
tcgagtggcg tcgttgtccg gcttggacgg ggctccgacg gtaccggagg gcagcgacaa 180
aacacttatg cacttgggcg acccgccgag acggtgcgac acccatcccg acggcacaag 240
ctcagccgcg gccgctcttg ttcttcgtcg gatcgacatt cacccacttc tgaccgggct 300
tgggcgaagg aagcagaa 318

<210> SEQ ID NO 118
<211> LENGTH: 405
<212> TYPE: DNA
<213> ORGANISM: Mycobacterium tuberculosis

<400> SEQUENCE: 118
ggtatagtcg ctgaccggtg caggtttcga caatgtggtg ccggttcggc ggctacgtgc 60
catcgagaca ctggcgcagg ctatcgcacc cgttatcggc tacgagcaaa tcgcggtatg 120
cgttcttgag catgagtcgg cgaccgtcgt catggtcgac acccacgacg gaaagacgca 180
gatcgccgtc aagcatgtgt gccgcggatt atcaggactg acctcctggc tgaccggcat 240
gtttggtcgc gatgcctggc gcccggccgg cgtggtcgtg gtcggctcgg atagcgaggt 300
cagcgaattc tcgtggcagc tcgaaagggt cctgccggtg ccggtctttg cgcaaacgat 360
ggcgcaggtt acggtcgcgc ggggtgcggc cctggcggcg gccca 405

<210> SEQ ID NO 119
<211> LENGTH: 89
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 119
gacactatat natactcaag cttcaggtca atgtgcgcca agccctgacg ctggccgacc 60
aggccaccgc cgccggancc ctntctaga 89

-continued

<210> SEQ ID NO 120
<211> LENGTH: 354
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 120
ctgtagccac ctgttgccat ccccgtcatg cccgactctg gtcatctcgg atccgctgac 60
accccgctaa ggctgctcct ctcggtgcat tacctcaccg acggcgaacn cccccagctt 120
tacgactatc cggatgacgg cacctggttg ccggctaact tcaccgtcag cttggacggc 180
ggcgctaccg tcgatggcgc cagcggggcg atggccgggc ccggcgaccg attcgtcntc 240
ancctgtcgc gtgaacttgc cgacgtcatc gtggtcggtg tgggcaccgt gcgcattgag 300
ggctactccg gcgtccggat gggtgtcgtc aagcgcccgc accggcaggc ccga 354

<210> SEQ ID NO 121
<211> LENGTH: 379
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 121
atactcaagc ttcgcacgct cggcgcgcgc ggtaccgccc aggtcgccca acagatcgtc 60
gatgttcgcg tcgtccgcct cgcgcacgtg gtctgtcacc agtcaacgtt aacgccgccg 120
cacatgtcct gcggccgggc aaaaacgtga aaaacgagcg ggcgactgcn atgtcatgac 180
accgacggcc gccgatgggc ccagggtctg gcaaattcga tctgtgcggc cagtgccagc 240
agcgtcgcct cgtcatacgg ccggccgacg agttgaaccg acatgggcag gccgtcgccg 300
tcgaagtccc acggcaccac gggcgcgggc tggccggtca gattccaaaa ttgaaagtac 360
ggaaccgctg caccaccaa 379

<210> SEQ ID NO 122
<211> LENGTH: 393
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 122
atcgtttcga ccaggcgctc catccggcga gtggatactc ccagcaggta gcaggtcgcc 60
accacgctgg tcagtgcgcg ttcagctcgc ttgcggcgct gcagcagcca gtccgggaaa 120
tagctgccct ggcgcagctt ggggatcgcg acgtcgatgg ttgcggcacg ggtgtcgaaa 180
tcacggtggc ggtagccgtt gcgctgattg gaccgctcat cgctgcgttc gcggtagccc 240
gccccgcaca gggcgtcggc ttcagccccc atcaaggcgg cgatgaacgt cgagagcagc 300
ccgcgcagca gatccgggct cgcctgtgcg agttggtcag ccagaagctg ctcggtgtcg 360
ataagatgan aagaagtcat tgcgttattt cct 393

-continued

<210> SEQ ID NO 123
<211> LENGTH: 333
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 123
atactcaagc ttgggtgttg ccgatcaccg gaagccgcat gatcagccac gtttcgcgcc 60
gcccggcata cggcggcgta ccgatctccg cgtcatacac ccgcgggtaa tcgccgacgg 120
tgccggttcg cgagccgaag gtgacgacgc tgattgaatc gagttccagg tccagcgggt 180
ggcgcagcaa cggcgcgagc tcaacnacgt caatcacgtt gtcgctttct acggtcaccg 240
acccggtgac cgtagtcgcc cggtgcgctc ggccgagaag ttgcaccgcc accaccgcga 300
caacgtcttg cacgcggacg ccaccccccg gat 333

<210> SEQ ID NO 124
<211> LENGTH: 426
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 124
gcgcnaacag ctcgcggcag cccacgacgt gctgcgtcgg attgccggcg gcgagatcaa 60
ttccaggcag ctcccggaca atgcggctct gctggcccgc aacgaaggac tcgaggtcac 120
cccggtgccc ggggtcgtgg tgcacctgcc gatcgcacag gttggcccac aaccggccgc 180
ttgatgcccg gtcggcaagc ccggcagttg ccaaacccag cgtgatcagg ctcggctcgc 240
gagttcggcg aaaaagtggc tcgcctgatc acctaccatc ggccaggatc tgcgtgtcat 300
cacgacgctc gccaaggagg ttgttgtggt gctatcgacg gcctttagcc agatgttcgg 360
aatcgactat ccgatagtgt ccgcgccaat ggacttgatc gccggcggtg agctggctgc 420 cgcngt 426

<210> SEQ ID NO 125
<211> LENGTH: 336
<212> TYPE: DNA
<213> ORGANISM: Mycobacterium tuberculosis

<400> SEQUENCE: 125
atactcaagc tttctccgat acccgccatg tcgcgcacat ccaggacttc tgggggggatc 60 cgctgacagc ggcgggatcc caaagtgcgg atgatcgggc cgcctacgtc gtggtgtacc 120
tcgtcggtaa caacgaaacc gaagcgtatg actcggtcca cgcggtgcgg cacatggtgg 180
acaccacacc gccaccgcac ggggtgaagg cctatgtcac cggtccggca gcactcaatg 240
ccgaccaggc cgaggccgga aacaaaagta tcgctaaggt caccgcgatc acgaacatgg 300
tgatcgcagc aatgttgcta gtgatctatc gctccg 336

<210> SEQ ID NO 126
<211> LENGTH: 347
<212> TYPE: DNA
<213> ORGANISM: Mycobacterium tuberculosis -continued

<400> SEQUENCE: 126
ccatgagcac cgccagccga gcacgaggcc aaactccgcc gacgcaggcc ggttggactt 60
gtcgtgctgg acaaggggtt tagccgccga agcagtgacg tacatcggcg aagagcagtt 120
cgcctgtcga ccgacggcgc aaaccgtgag gctagggaag cgaggagcac atggccgccg 180
acccgcaatg tacacgctgc aagcaaacca tcgaacccgg atggctatac atcaccgccc 240
atcgccgcgg tcaagccggg atcgtcgatg acggcgcagt actgattcac gtgcccggtg 300
aatgccgcac cccggggagc actttccgcc aaaactaacc cggttgg 347

<210> SEQ ID NO 127
<211> LENGTH: 315
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 127
cgggtgtcat tggccaccgg cggcggctgt ccgggaaatg gcgggtcccc ggtggttttg 60
ctgaggagtg ctgaaccgta gtcgaagtgg gcggcgtcag actccaccca gccagcaggc 120
agcgcgaanc tgaatcctcc aaccgggttg tcnatccgga caggttgggg tgcgtttggg 180
gcaatnacag gtggcggcgg tgcgttcggg tcggccggcg gaggtgctgc nttgggatcc 240
ccggctgggc attcggcntg ttggcggcgg ccggtggtgg ggggggcaac acgtgtcncc 300
ggtgcgggtg gccct 315

<210> SEQ ID NO 128
<211> LENGTH: 354
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 128
ccaagatcta caccatcgaa tacgacggcg tcgccgactt tccgcggtac ccgctcaact 60
ttgtgtcgac cctcaacgcc attgccggca cctactacgt gcactccaac tacttcatcc 120
tgacgccgga acaanttgac gcagcggttc cgctgaccaa tacggtcggt cccacgatga 180
cccagtacta catcattcgc acggagaacc tgccgctgct agagccactg cgatcggtgc 240
cgatcgtggg ganacccact ggcgaacctg ggttcaacca aacttgaagg tgattgttaa 300
cctgggctac ggcgacccgg cctatggtta ttcgacctcg ccgcccaaat gttg 354

<210> SEQ ID NO 129
<211> LENGTH: 360
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 129
agcttcccga gttcggcttt ggatcaagac cccagtccgc gggcgcgatc cggcngctcg 60

-continued

```
gtgactacat caagccacaa atcgacggct ttcggggtgc cgataccgat gacgtggcgg    120

atgtcgagtg ttgagttctc ggcggggcgg atgctcacct ggcgatcacc tgcctctcgt    180

tgacgatcga tcgtctatgc cgccgtctct gcgggaacag gccnccagta catcgccaca    240

gacgggatcc acccgcattt cggctacggt tgctcgtttc ggtgttcgga ctagtcggtc    300

ctggtgacgt gccggtgatg cggaccggtc ctagcactga ccaatggcca aaatgcgggc    360
```

<210> SEQ ID NO 130
<211> LENGTH: 483
<212> TYPE: DNA
<213> ORGANISM: Mycobacterium tuberculosis

<400> SEQUENCE: 130

```
cggggggcct cttaatagtg taggaaagaa gctctacata ttcaggagga ttcaccatgg     60

ctcgtgcggt cgggatcgac ctcgggacca ccaactccgt cgtctcggtt ctggaaggtg    120

gcgacccggt cgtcgtcgcc aactccgagg gctccaggac caccccgtca attgtcgcgt    180

tcgcccgcaa cggtgaggtg ctggtctgcc agcccgccaa gaaccaggca gtgaccaacg    240

tcgatcgcac cgtgcgctcg gtcaagcgac acatgggcag cgactggtcc atagagattg    300

acggcaagaa atacaccgcg ccggagatca gcgcccgcat tctgatgaag ctgaagcgcg    360

acgccgaggc ctacctcggt gaggacatta ccgacgcggt tatcacgacg cccgcctact    420

tcaatgacgc ccagcgtcag gccaccaagg acccggccag atcgccggtc tcacgtgctg    480

cgg                                                                  483
```

<210> SEQ ID NO 131
<211> LENGTH: 423
<212> TYPE: DNA
<213> ORGANISM: Mycobacterium tuberculosis

<400> SEQUENCE: 131

```
atactcaagc ttcataacag gcctgttgtg ggcgcacccg gctcgccgag ttctgcacgc     60

accgcctcaa gtgcggcccg caccgccggc atctcccggt cacgcagggc cgcggcccgc    120

gccgcagcga cggcgtgttc gcgcagttcg ccgtcaatga tgctgacctg atcggccacc    180

cgggcgttct cggcgtcttc gcgttcacta atcgcggtgc tcagcagcgt ctcgacagcc    240

accacccgag tggcgaccag ctgctccacc acggaccgca gcgatgccgt cacctcaccc    300

gtccagcggt ccaccacgac acggtcgtgc accagcgcgc gggcattcac cacccaggcg    360

gtcaccgcca ggccgatcgc cacacccgcc accatccccg atgcagccag gccgggagta    420

aga                                                                  423
```

<210> SEQ ID NO 132
<211> LENGTH: 338
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 132

```
ctggtgctgg acggagccta gtacaacttc ctctccaatg ctcttgcccc gatcgcggcg     60

accaggatga cccaggacat cctgccgccc gaagtactgg aaaagctcac acccgagttc    120

gtcgcaccgg tggtggccta cctgtgcacc gaggagtgtg ccgacaaccc atcggtgtac    180
```

-continued gtcgtcagtg gtggttaggt gcagcgagtt gcgctgtttg gcaacgacgg cgccaacttc 240
gacaaaccgc cgtcngtaca agatgttgcg gcgcggtggg ccgagatcnc cgatctgtcc 300
ggtgcgaaaa ttgctggatt caagttgtag aactaaat 338

<210> SEQ ID NO 133
<211> LENGTH: 173
<212> TYPE: DNA
<213> ORGANISM: Mycobacterium tuberculosis

<400> SEQUENCE: 133
atactcaagc ttttccggcg tcgtccacct gacccaaaaa gcgcaggtgc gccgccaaac 60
ggcccgcctg gccgcgcaac tggtcggcgt cgccgtggcc gacaatcagt agctggacat 120
ccggaaaccg ctgcaccacc ttcggcagcg cgtcaagcaa aaacggccat tcc 173

<210> SEQ ID NO 134
<211> LENGTH: 255
<212> TYPE: DNA
<213> ORGANISM: Mycobacterium tuberculosis

<400> SEQUENCE: 134
tttcagatct catttttatg acatgactgg agatctgtct agattgcagc tcctgtgagc 60
gtgggtaccg gattcaagcc ggtcggtcac gccgcggtgg taccggcttt gcggcagtgc 120
tcggcctcga gttcggcgat cgcgcgcgaa gtgcgtttcg cgcaccaaga tcgcggccta 180
atggccggcg atgaccgcga tgaccagcgc gatccaggaa aaaccgttcc aaccagtgct 240
gggcggccat ccccg 255

<210> SEQ ID NO 135
<211> LENGTH: 285
<212> TYPE: DNA
<213> ORGANISM: Mycobacterium tuberculosis

<400> SEQUENCE: 135
atactcaagc ttcccgacca caagttgaac agcaccgatt tcggcgagca cttcgtcaac 60
ttccagggtg cccgcaccaa gtatttcgac aagtatttcc gtcgggccgc cgccgccggc 120
gcgcggcagg tggtcatcct ggcggcgggg ctggactccc gcgcgtaccg gctgccttgg 180
cccgacggga ccacggtttt tgagctggac cgcccgcagg tccttgattt caagcgcgag 240
gtgctcgcca gccacggtgc ccaaccgcgc gccctgcgcc cgcga 285

<210> SEQ ID NO 136
<211> LENGTH: 494
<212> TYPE: DNA
<213> ORGANISM: Mycobacterium tuberculosis

<400> SEQUENCE: 136
gtgtgctgtc aattcagagc tgagcctgat gcactcaact tactgagcat gctaacgctg 60
gtcgtgcggg tcttgttccc gcgtgtcggc agggcacacg ctcggggcgt agctgggaga 120
ggccccggtc aagcccggag agcagtgctc agtccgccag cttgaccgac tttcgatgag 180
aacgcgcttc tcgccgtatt gaactggcgt gctgacggtc gctgagcagc gctcgccgag 240
tgcggccgct gattctttca tcgagccagg aggcgcattc gtgttcggcc gcctgcgggt 300
cggccccatc gtcgacgcga tccgtcaccc actcctcgat caggtctgcc tcatcgaacg 360
ggccaacggt gctgtcggag tatgtgtgcg tgggcacggc gagccgggtg ctgtggtaca 420

-continued

```
cccaccgttg catgaccaag ttgacgcctg actggctgag caccgcgatc cgctcacagg    480

tcggaacgtt ggtg                                                      494


<210> SEQ ID NO 137
<211> LENGTH: 357
<212> TYPE: DNA
<213> ORGANISM: Mycobacterium tuberculosis

<400> SEQUENCE: 137

atactcaagc ttttggtcta gccggccgag cccgatacag gtgtcattgg ccaccggcgg     60

cggctgtccg ggaaatggcg ggtccccggt ggttttgctg aggagtgctg aaccgtatgc    120

gaagtgggcg gcgtcagact ccacccagcc agcaggcagc gcgaaactga atcctccaac    180

cgggttgtcg atccggacag gttggggtgc gtttggggca atgacaggtg gcggcggtgc    240

gtccgggtcg gccggcggaa gtgctgcgtt gggatcgccc ggctgggcat tctgcgtgtt    300

ggcggcggcc ggtggtgggg gggcaacagg tgtctccggt gcgggtggcg ctgcacc       357


<210> SEQ ID NO 138
<211> LENGTH: 458
<212> TYPE: DNA
<213> ORGANISM: Mycobacterium tuberculosis

<400> SEQUENCE: 138

ggggccactc cgcacaatct gtacccgacc aagatctaca ccatcgaata cgacggcgtc     60

gccgactttc cgcggtaccc gctcaacttt gtgtcgaccc tcaacgccat tgccggcacc    120

tactacgtgc actccaacta cttcatcctg acgccggaac aaattgacgc agcggttccg    180

ctgaccaata cggtcggtcc cacgatgacc cagtactaca tcattcgcac ggagaacctg    240

ccgctgctag agccactgcg atcggtgccg atcgtgggga acccactggc gaacctggtt    300

caaccaaact tgaaggtgat tgttaacctg ggctacggcg acccggccta tggttattcg    360

acctcgccgc ccaatgttgc gactccgttc gggttgttcc cagaggtcag cccggtcgtc    420

atcgccgacg ctctcgtcgc cgggacccag cacggaat                            458


<210> SEQ ID NO 139
<211> LENGTH: 595
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as “n”

<400> SEQUENCE: 139

ttctntcttc ccnnattcgt nnntctcnta ctaccngggc cncaaaacac cttggcnaac     60

gctcaaaggc gntacnggca ccaaggcccc acacgtcacc ctgtgacctc ctgcgccgac    120

cccgcccgag gtcctggccg ttaccactga acgggcgagc cgggagtctg gtacgcatcg    180

aacaaagagc aaggtgcatg ggcggagttg ttccgccnct ttttttatga cggggtcgat    240

ccattcgagg tccgtcgccg cgtcggtcga gtggcggtca cactccaggt actcgacctc    300

ncagacgaga ggactcgatc ccatctangt gtggacnaaa cagatcttct gtccgacgac    360

tacacaccac ccaggccatc gccgccgccc gcgatgccaa cttcnacncc gtnctggccc    420

cggcggcggc gctccccggt tgtcaaacac ctgccgtgtt cgttcacnca ctgcccaaca    480

tcnagcccga ncnatccnag gtccgtccaa cgcctccgcg gctcnccaac ctnctcccnc    540
```

-continued

```
tgatcntccg caccaaacac atgcccgact ccntgcnccn attgcttgna tccct        595


<210> SEQ ID NO 140
<211> LENGTH: 434
<212> TYPE: DNA
<213> ORGANISM: Mycobacterium tuberculosis

<400> SEQUENCE: 140

ccgctatcgg tcggtgtgct tggcggcgtc ggtatcaaca ccgcccacga aatggggcac     60

aagaaggatt cgctggagcg gtggctgtcc aagatcaccc tcgcccagac ctgctacggg    120

cacttctaca tcgagcacaa ccgtggccat cacgtccggg tgtccacacc ggaggacccg    180

gcgtcggcgc ggttcggcga gacgttgtgg gagttcctgc cccgcagtgt tatcggcggc    240

ttgcgctcgg ccgttcattt ggaggcccaa cggctgcgtc ggctcggcgt cagcccctgg    300

aatcccatga cgtatctgcg caacgacgtg ctcaacgcgt ggctgatgtc ggtggtgttg    360

tggggtgggc tgatcgcggt cttcggcccg gcgctgatcc cgttcgtcat catccaggca    420

gtcttcggct tcag                                                      434


<210> SEQ ID NO 141
<211> LENGTH: 321
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 141

atactcatgc ttgccgaagt tccgatgggt cgcgccggcg ancccagcga agtcgctagc     60

gtggccgtgt tcttggcttc ggatctatcc tcgtacatga ccggcaccgt gttggacgtg    120

actggcggcc ggttcatatg acaccgagat cattgccacg gtacggcaat tcgtcaagaa    180

ggaaatcttt cccaatgcac cggccctcga acgtggcaac agctacccgc aagaaatcgt    240

cgatcggctg ggtgttattg gcttgctcgg tcgccggctg caagggtatc gacaccaccg    300

agttcattct ccgggcgtgc c                                              321


<210> SEQ ID NO 142
<211> LENGTH: 348
<212> TYPE: DNA
<213> ORGANISM: Mycobacterium tuberculosis

<400> SEQUENCE: 142

ggcgtcaacg gtgtcggcac cggcgtcctg cagttggtag gcctgcagtt tgtgcatcag     60

gccgatgccg cggccctcgt ggccacgcat gtacagcacc acgccgcgcc cctcacgggc    120

gaccatcgcc agcgcggcgt ccagctgagg cccgcaatcg cagcggcgtg acccaaacac    180

atcgccggtc aagcactccg aatgcacccg gaccagcacg tcgtcaccgt cggcgttggg    240

cccggcgatc tcgccgcgga ccagcgcgac atgttccacg tcctcgtaga tgctggtgta    300

gccgatggcg cgaatctccc atgacgagtc ggaatccgcg cctcggcg                 348


<210> SEQ ID NO 143
<211> LENGTH: 339
<212> TYPE: DNA
<213> ORGANISM: Mycobacterium tuberculosis

<400> SEQUENCE: 143
```

-continued

```
atactcaagc ttcggcctcg ctgcaggagt gggagccgca gggctggaaa tccgaaaaac     60

gagccggtga tcgcactgtc gccgatcggg gccgcacctg gttggtgtta ccgatgaatc    120

cgcacccaaa atgtggctgc ggtggcgttt cttgactcct tggcgtcgac tcttgtggca    180

gccaccgagc ggttggtcca ggatctggat gggcaaagtt gtgcggcccg gccggtgacg    240

gccgatgagc tgaccgaggt cgacagcgcc gtgttggctg acttggaacc gacatggatt    300

cgccccggtt ggcgtcacct caagcatttc aatggttat                           339
```

```
<210> SEQ ID NO 144
<211> LENGTH: 269
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as “n”

<400> SEQUENCE: 144

atgcgtcacc ccgatgcgcc cagatcgggg cttcgcaaat aaagcacgaa caggcgggca     60

aaacgtctat ctcggagccg gaagggcaat cagccgaccg tcgacgaacg acaccggcga    120

taaccactta ggcgttgaac ggccggccca aacattacgc ctccgttgat aaggctttcg    180

gtctcttccc cggtcatccc aagcaccttg cggcaaattt gaacgctttc ctgtccgggc    240

accggccccg ggctttgggg tccntccga                                      269
```

```
<210> SEQ ID NO 145
<211> LENGTH: 285
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as “n”

<400> SEQUENCE: 145

atactcaagc ttcaatcgcg ccgccacaat ccaaatatgc gtctagcgtc tcgatgagcg     60

tcggtccggc atcggctagg ggccgcatca cgtcggtatg cagggccacg atcgcccaag    120

gcgtcgccca tcaagggcgc gttcgggcaa aaattcccct atccagcacg ggccgcggcg    180

ctccgcncca gccggcgacg gcgttcatcc cggagatcgc ctcgctagcg ctgcggtgcg    240

ccgcggtcag catgggcgcc gtggggccga tgaccaccgg ggcgt                    285
```

```
<210> SEQ ID NO 146
<211> LENGTH: 75
<212> TYPE: DNA
<213> ORGANISM: Mycobacterium tuberculosis

<400> SEQUENCE: 146

ttcggcgggt ctgtagattg cggtcggcca ccccacaggc actcatgaac cgcagcccac     60

gatcgatctc ggtgg                                                      75
```

```
<210> SEQ ID NO 147
<211> LENGTH: 164
<212> TYPE: DNA
<213> ORGANISM: Mycobacterium tuberculosis

<400> SEQUENCE: 147

gcgcaccatc gccagtaggt gcccgtggtc gggcgcgtcg agccacccga gcggaaacgc     60
```

gagtccgaac agcaacagca ggacgggcgc aaccagggcg gtgaccatgc ccccggcgct 120
gaacatcaac cacaggaagg gctccgccga gcgtccgcgc gacc 164

<210> SEQ ID NO 148
<211> LENGTH: 228
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 148
catcgtcgaa cttcggtccg ggttgntagn accgcagcac caaacgcacc caccgacccc 60
cacgcttcac gccaaccctt tagttcattg gcgtgaacag cagcgtagcc ggttgccccg 120
atatatgtgg aaaaatcgtt cggacgtaca aaaaaagttc ctgacgctgg cgtcaactcg 180
aaactgcctc ggaagtcaat gatgatccat cagtcaatat taaagtcg 228

<210> SEQ ID NO 149
<211> LENGTH: 238
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 149
atactcaagc ttgtctgctg cctcagcgta tgcatccaac agcgcatcgc gatcaacgat 60
caggcgcgcc gatttcgggc cgcgggcagt ggcactggcc agatggccgt ttttttcgag 120
aaacttcaac gcctgagcgc tgcttcccat cgagagaccg gtggcctcta caaccgatgc 180
gacagttgga ccggcgatgt tcgccagcag cgcttcacat acggcaagtn tggcgcgg 238

<210> SEQ ID NO 150
<211> LENGTH: 162
<212> TYPE: DNA
<213> ORGANISM: Mycobacterium tuberculosis

<400> SEQUENCE: 150
ttgtccaggc ggggaatcgg gcagggagac gacaccttcg ttcggttcga tcgtcgcgaa 60
cgggtagttg gccgcgacca cgttgtttcg ggtcagcgcg ttgaaaagtg tcgacttgcc 120
gacgttgggc aggcccacga tccccaggct caagctcaca ga 162

<210> SEQ ID NO 151
<211> LENGTH: 377
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 151
atactcatgc ttggcgcctg ggtggcagcc cacctgccca ccacacggac cgcggtgcgg 60
acgcggctga cgcgcctggt ggtcagcatc gtggccggtc tgctgttgta tgccaacttc 120
ccgccgcgca actgctggtg ggcggcggtg gttgcgctcg cattgctggc ctgggtgctg 180

-continued acccnccgcn cnacaacacc ggtgggtggg ctgggctacg gcctgctatt cggcctggtg 240
ttctacgtct cgttgttgcc gtggatcggc gagctggtgg gccccgggcc ctggttggca 300
ctggcgacga cgtncgcgct gttccccggc atcttcggtc tgttcgccgt cgtggtaccc 360
tgttgccggg ttggccc 377

<210> SEQ ID NO 152
<211> LENGTH: 308
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 152
cgccaattca cgatatcgtt aaccgatatc ccgagccgat agctggcggg ctcgggtggt 60
ggccagcggc gctgcgacga aaggtgtgac cgtcatgaaa cagacaccac cggcggccgt 120
cggccgtcgt cacctgctcg agatctcagc atccgcagcc ggtgtgatcg cgctttcggc 180
gtgtagtggg tcgccgcccg accccggcaa aggccggccc gacacaaccc cggaacagga 240
agtcccggtc accgcgcccg aagnacttga tgcgcgaacn cggagtgctc caaacgcatc 300
ctgctgat 308

<210> SEQ ID NO 153
<211> LENGTH: 377
<212> TYPE: DNA
<213> ORGANISM: Mycobacterium tuberculosis

<400> SEQUENCE: 153
atactcaagc ttgggcactg acttcggtac cccctccgcc tttggccagc agcagccaca 60
gcgcggttcg cggaccgaac gtggacatca atagcccgga atcggtgtgt gcaagttggt 120
aaacggtgtt gatcccaagc tttgccagcc ttttcgtagt cttgggcccc acaccccaca 180
gtgcttcgac ggtacggtca cccatgatgg ccatccagtt ggcatcggtg agctgataaa 240
tgccagctgg tttcgccaac ccggtagcga tcttggcgcg ctgcttgttg tcactgatac 300
ctatcgagca agacagcccg gtttgcgaca aaatgacttt tcggatctct tcggcgactt 360
cgatggggtc gtcggga 377

<210> SEQ ID NO 154
<211> LENGTH: 259
<212> TYPE: DNA
<213> ORGANISM: Mycobacterium tuberculosis

<400> SEQUENCE: 154
aaagtcctgt gccggttcgc taaacacccg gcggacactc agacggtgct ggtggtgcgg 60
catggcaccg cgggcagcaa agcgcacttc tccgggggac gacagcaagc gaccgctaga 120
caagaggggt cgtgcgcagg cagaaacgtt ggtacacagc tgctggcgtt cggcgccacc 180
gatgtttatg ccgccgaccg ggtgcgctgc caccagacga tggagccact cgccgcggaa 240
ctgaacgtga ccatacaca 259

<210> SEQ ID NO 155
<211> LENGTH: 372
<212> TYPE: DNA
<213> ORGANISM: Mycobacterium tuberculosis -continued
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 155
atactcaagc ttgggttcca cgcccgcgca gccacgccgt cacctttcca cgagacctca 60
cctgccgatc cgaaatggaa tcggccgtga cggaattggc gcaccgaaca cccaacgagg 120
tggtggcttc gtcgcgaacc gtcacccgag tcgcggccac cgtgcgcacg gcgacgttct 180
acacccgcac caagatccga aagctgcaag ctcccagcac cgatcccgac gtcatcaccg 240
ctgccgcccg gcacgtcctt gacctattcg agctggatcg gcccgtccgg ttgctgggag 300
tgcggttaga actggcctag aaccggcggg cacaccgcnc ctgggcgggg cgaattcttg 360
accgcnccgg cc 372

<210> SEQ ID NO 156
<211> LENGTH: 290
<212> TYPE: DNA
<213> ORGANISM: Mycobacterium tuberculosis

<400> SEQUENCE: 156
cgcggttggc gtagttggac gggtcgccct ccgaggccaa tgatgacgat gaccacgccg 60
atcacgatgg ccaccgagag ggacaacaac agaaagctga cgaatccctc cttggcggcc 120
ggggctttgt ggtcgccggt cgcgatgggc gcgaatttac ggcccgctcc cccaggccgc 180
cgcgaagcag ggtccccagc cagttggcgt aggcggaatt aacgatcagc gccaccgcga 240
taacctgcca tgcctcgggc atatcgatgt gcggccagaa caggccgaac 290

<210> SEQ ID NO 157
<211> LENGTH: 470
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 157
ccaacaagag catcgggaca tacggagtca actacccggc caacggtgat ttcttggccg 60
ccgctgacgg cgcgaacgac gccagcgacc acattcagca gatggccagc gcgtgccggg 120
ccacgaggtt ggtgctcggc ggctactccc agggtgcggc cgtgatcgac atcgtcaccg 180
ccgcaccact gcccggcctc gggttcacgc agccgttgcc gcccgcagcg gacgatcaca 240
tcgccgcgat cgccctgttc gggaatccct cgggccgcgc tggcgggctg atgagcgccc 300
tgacccctca attcgggtcc aagaccatca ncctctgcaa caacggcgac ccgatttgtt 360
cngacggcaa ccggtggcga gcgcacctag gctacgtgcc cgggatgacc aaccaggcgg 420
cgcgtttcgt cgcgagcagg atctaaccgc gagccgccca tagattcccg 470

<210> SEQ ID NO 158
<211> LENGTH: 434
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

-continued

<400> SEQUENCE: 158
taanacccgt gtaatttggg atgggcaaaa aggccaagca ccgcgtggcc acgaacgccg 60
ggagggacaa tctcgggcgg ctagggcttc tcgcgggaag gcccgaacgt acggcgtttc 120
aacacgtcgc gtcnccctcc gaccgcgaac attcggggat ggcagcaacc tggtagcncc 180
ctggccgggc gatgatctgc agcgtcgccg cgggtagtcg ccgcccgggc ggctacagtc 240
tgaaacgcga tgaccatcga tgtgtggatg cagcatccga cgcaacggtt cctacacggc 300
gatatgttcg cctcgctgcg ccggtggacc ggtgggtcta tcccggagac cgacntcccg 360
atcgaagcga ccgtctcctc gatggacgcc ggcggcgtca ccctgggttt gctcaccgcc 420
tggcgtggcc ccaa 434

<210> SEQ ID NO 159
<211> LENGTH: 363
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 159
gtccgcaaaa gactcagcgg ccgactttgc tcgcagctgg cggtaccgcg ccaccgattc 60
gatgccgtgg tcgcggaaga atgcctcccg aaatcgcacg gccgactcca gttcggcgag 120
catccgcgat gccagctgcg gctgcgccct gccggccacg gcacccacat gcggcagttc 180
gtccacctgg gccagcgccc cgccgccgaa gtccaaacaa tagaactgca cccggcccgc 240
atcgtgggta gcagccaacg ccatgatcag cgtccgcagc gcggttgact tgcccgtttg 300
cggtgcacct acgaccgcga cattgcctgc ggccccggac aagtcgatcg tcagcggcac 360 ccn 363

<210> SEQ ID NO 160
<211> LENGTH: 301
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 160
cgtggccacg aacgccggga gggacantct cgggcggcta gggcttctcg cgggaaggcc 60
cgaacgtacg gcgtttcaac acgtcgcgtc gccctccgac cgcgaacatt cggggatggc 120
agcaacctgg cagctacctg gccgggcgat gatctgcagc gtcgccgcgg gtagtcgccg 180
cccgggcggc tacagtctga aacgcgatga ccatcgatgt gtggatgcat catccgacgc 240
aacggttcct acacggcgat atgttcncct cgctgcgccg gtggaccggt gggtctatcc 300
c 301

<210> SEQ ID NO 161
<211> LENGTH: 436
<212> TYPE: DNA
<213> ORGANISM: Mycobacterium tuberculosis
<220> FEATURE:
<221> NAME/KEY: unsure
<222> LOCATION: (various positions within the sequence)

-continued

<223> OTHER INFORMATION: applicants are uncertain of bases designated as "n"

<400> SEQUENCE: 161
atactcaagc tttgcggcgg gcgccgaaat gtgaacgcac caaacccgcc cgctgcgggt 60
cggcgggcca ctcgacctcg aatttcgccg ccgtgaccat ccagcccgac ggcagttggg 120
cacccggccc cccggtcgcg gcataactgt tggcgtcgcc gtcataaagc tcgaacagca 180
ccgaaaccga ctccaccacc ggccggtgcg cctcaaaatc cacgccgatc tccacatacc 240
gggaaaacgt cggtgtccca tcgggtttcg gcttgcccgc cagctgcaca ccaccggtgg 300
cctcggccac cttcgcggcc tgagcgcagc tacncatcct gacgatcatc accccgcccc 360
cggctcacgc ttggcctccg tgaccgcacg catcgcccgg ttgcgcgcac cgcgacgccc 420
gtacagccgc gcgcac 436

<210> SEQ ID NO 162
<211> LENGTH: 390
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 162
agcttgccgg gactgcggaa cagaagcggc ggttcctacc gcggtgtgcg gccggcgcga 60
tatcggcctt tttactaacc gaacccgatg tgggctccga tccggcgcgc atggcatcga 120
cggcgacgcc gatcgatgac ggccaggctt acgagcttga gggtgtgaag ttgtggacca 180
ccaacggtgt ggtagcggac ctgctagtgg ttatggcgcg ggtaccgcgc agtgaagggc 240
accgaggggg aatcagcgcc tttgtcgtcg aggctgattc gcccgggatc accgtggagc 300
ggcgcaacaa gttcatggga ctgcgtggca tcnaaaacgg cgtgacccgg cttcatcgcg 360
tcngggtgcc caaagacaac ttgatcggca 390

<210> SEQ ID NO 163
<211> LENGTH: 75
<212> TYPE: DNA
<213> ORGANISM: Mycobacterium tuberculosis

<400> SEQUENCE: 163
ctcaagcttg gcgatgcggg ctggccaaaa ctggccgggc gggggttggc ttgttcaatc 60
aagggtgggt tgccg 75

<210> SEQ ID NO 164
<211> LENGTH: 110
<212> TYPE: DNA
<213> ORGANISM: Mycobacterium tuberculosis

<400> SEQUENCE: 164
ccgaaggccc gttcccgggc gttcagcaag cgatcgtcgg ttggcccact gcgggtcgaa 60
tcttgcggcc gcgccggtcg tggaacgccc aggtcacccg gcggcgtacc 110

<210> SEQ ID NO 165
<211> LENGTH: 455
<212> TYPE: DNA
<213> ORGANISM: Mycobacterium tuberculosis

<400> SEQUENCE: 165

```
atactcaagc tttttctgc tcatgaaggt tagatgcctg ctgcttaagt aattcctctt     60
tatctgtaaa ggctttttga agtgcatcac ctgaccgggc aaatagttca ccggggtgag    120
aaaaaagagc aacaactgat ttaggcaatt tggcggtgtt gatacagcgg gtaataatct    180
tacgtgaaat attttccgca tcagccagcg cagaaatatt tccagcaaat tcattctgca    240
atcggcttgc ataacgctga ccacgttcat aagcacttgt tgggcgataa tcgttaccca    300
atctggataa tgcagccatc tgctcatcat ccagctcgcc aaccagaaca cgataatcac    360
tttcggtaag tgcagcagct ttacgacggc gactcccatc ggcaatttct atgacaccag    420
atactcttcg accgaacgcc ggtgtctgtt gacca                               455
```

<210> SEQ ID NO 166
<211> LENGTH: 309
<212> TYPE: DNA
<213> ORGANISM: Mycobacterium tuberculosis

<400> SEQUENCE: 166

```
ctcaagcttg gtgccgacat ggccgggctg gagcccgcgt atggcaaggt tccgctcaat     60
gtggttgtga tgcagcagga ctacgttcgc ctcaatcagc tcaaacgtca cccccgtggc    120
gtgctgcgca gcatgaaggt cggcgcccgc acgatgtggg cgaaggcaac aggtaaaaac    180
ctggtcggca tgggtcgagc cctcattggg ccgttgcgga tcgggttgca ccgcgccgga    240
gtgccggtcg aactcaacac cgccttcacc gatcttttcg tcaaaaatgg cgtcgtgtcc    300
ggggtatac                                                            309
```

<210> SEQ ID NO 167
<211> LENGTH: 232
<212> TYPE: DNA
<213> ORGANISM: Mycobacterium tuberculosis

<400> SEQUENCE: 167

```
ccgaagcgtg ggaaatcctg accgaatacc gcgacgtgct ggacactttg gccggcgagc     60
tgctggaaaa ggagaccctg caccgacccg agctggaaag catcttcgct gacgtctaaa    120
agcggccgcg gctcaccatg ttcgacgact tcggtggccg gatcccgtcg gacaaaccgc    180
ccatcaagac acccggggga gatcgcgatc gaaacgcggc gaaacttggg cc            232
```

<210> SEQ ID NO 168
<211> LENGTH: 455
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 168

```
cgactcgaca agcattcttg acagttgttt tggctcggca tggttagcca aggttctgcg     60
gtcccaccag atcatcttgg tccggtagcg ctcgtccggg tatgctgccg ccgggattct    120
cgctgctatt actccccccg aaaaacgcca ccggtccagc gcgtgggccg ccgcggtccc    180
catcacaaac tgaaccccca acaggggaca tgcttagcgg tagggcgcgc gccaaggcgg    240
cagcaatcgc atcactgcgc tgcgcgtcac tattaaccca cccggacttc acttccacga    300
ccccgaatgg cgcccggtca ttgatcatct tgcgcaccgc ggataatccg ggattgccag    360
cccattcgac taccgcatgc gagtcatcgg ctgaccgcag cggtccgatt acccgagcgc    420
```

-continued cccgantaca tctcctccaa tatcaatggg cgcaa 455

<210> SEQ ID NO 169
<211> LENGTH: 428
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 169
gcggtntagc ttcccgtcgt accggcgacc gccagccgag aagctcgttt tcccagtgtt 60
gctggggatt ctcacgctgc tgctgagtgc gtgccagacc gcttccgctt cgggttacaa 120
cgagccgcgg ggctacgatc gtgcgacgct gaagttggtg ttctccatgg acttggggat 180
gtgcctgaac cggttcacct acgactccaa gctggcgccg tctcgtccgc aggtcgttgc 240
ttgcgatagc cgggaggccc ggatccgcaa tgacggattc catgccaacg ctccgagttg 300
catgcggatc gactacgaat tgatcaccca gaaccatcgg gcgtattact gcctgaagta 360
cctggtgcgg gtcggatact gctatccggc ggtgacgacc cccggcaagc cgccatccgt 420
gctgctgt 428

<210> SEQ ID NO 170
<211> LENGTH: 385
<212> TYPE: DNA
<213> ORGANISM: Mycobacterium tuberculosis

<400> SEQUENCE: 170
ctcaagcttg ggcgtgacgg ccaccggggc cactccgcac aatctgtacc cgaccaagat 60
ctacaccatc gaatacgacg gcgtcgccga ctttccgcgg tacccgctca actttgtgtc 120
gaccctcaac gccattgccg gcacctacta cgtgcactcc aactacttca tcctgacgcc 180
ggaacaaatt gacgcagcgg ttccgctgac caatacggtc ggtcccacga tgacccagta 240
ctacatcatt cgcacggaga acctgccgct gctaaagcca ctgcgatcgg tgccgatcgt 300
ggggaaccca ctggcgaacc tggttcaacc aaacttgaag gtgattgtta acctgggcta 360
cggcgacccg gcctatggtt attcc 385

<210> SEQ ID NO 171
<211> LENGTH: 318
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 171
cgggtgtcat tggccaccgg cggcggctgt ccgggaaatg gcgggtcccc ggtggttttg 60
ctgaggagtg ctgaaccgta gtcgaagtgg gcggcgtcag actccaccca gccagcaggc 120
agcgcgaagc tgaatcctcc aaccgggttg tcgatccgga caggttgggg tgcgtttggg 180
gcaatgacag gtggcggcgg tgcgttcggg tcggccggcg gaggtgctgc gttgggatcg 240
cccggctggg cattcggcgt gttggcggcg gccggtggtg ggggggcaac angtgtcgcc 300
ggtgcgggtg gcgctgca 318

-continued

<210> SEQ ID NO 172
<211> LENGTH: 443
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 172
ncttgatatt ggcgtcaacg gtgtcggcac cggcgtcctg cagttggtag gcctgcagtt 60
tgtgcatcag gccgatgccg cggccctcgt ggccacgcat gtacagcacc acgccgcgcc 120
cctcacgggc gaccatcgcc agcgcggcgt ccagctgagg cccgcaatcg cagcggcgtg 180
acccaaacac atcgccggtc aagcactccg aatgcacccg gaccagcacg tcgtcaccgt 240
cggcgttggg cccggcgatc tcgccgcgga ccagcgcgac atgttccacg tcctcgtaga 300
tgctggtgta gccgatggcg cgaaactccc catgacgagt cggaatccgc gcctcggcga 360
cccgctcaat gtgcttctcg tgcttgcgcc gccattcgat caagtcagca atggtgatca 420
gcgccagacc gtgctcntcg gcg 443

<210> SEQ ID NO 173
<211> LENGTH: 420
<212> TYPE: DNA
<213> ORGANISM: Mycobacterium tuberculosis

<400> SEQUENCE: 173
cataagggcc ggcgtacccg gtaccggccg cgggcctacc acgtgccgga actggaagcg 60
cagtaagccc tcaacgcgcc accgctttgg cccgcgcgcc cggcgtaggc gcatcggcgg 120
tggccgtggg gcggcgcact gcgacctcac cagcggcttt cgagctttgt tcgatcaacc 180
ggccagcatg gtcgaggatg cattcgagac catattcgaa attggtttca tcgggggccc 240
cgatccgatg ccccctccca gttgcgtgag caagcagcgg agtcgtcgcg ggatcgatgg 300
ccacggggtg ttcaatggcg gatggtccgc tgcccgccga ctggctcttg cgggagagcc 360
gatctagcac caccgatccg cgcacgtgga ccgaaaccgc cgagtagatg tcgaaagcgt 420

<210> SEQ ID NO 174
<211> LENGTH: 336
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 174
cgtccttttc cccaagatag aaaggcagga gagtgtcttc tgcatgaata tgaagatctg 60
gtacccatcc gtgatacatt gaggctgttc cctgggggtc gttaccttcc acnagcaaaa 120
cacgtagccc cttcagagcc nnatcctgag caanatgaac agaaactgag gttttgtaaa 180
cgccaccttt atgggcagca accccgatca ccggtggaaa tacgtcttca gcacgtcgca 240
atcgcgtacc aaacacatca cgcatatgat taatttgttc aattgtataa ccaacacgtt 300
gctcaacccg tcctcgaatt tccatatccg ggtgcg 336

<210> SEQ ID NO 175
<211> LENGTH: 264

-continued

<212> TYPE: DNA
<213> ORGANISM: Mycobacterium tuberculosis

<400> SEQUENCE: 175
ctcaagcttc atgtccgtac ggctcgggta cgcttccgtc gcagtgtgcg agtgataaat 60
gacgaccggg acctcgtcgg catcttccat agcccgccac accttcagtt gctcaccgga 120
atccaaccgg tagaaggtcg gcgagcgctc ggcattggtc atcgggatat gccgctcggg 180
acggtcagag ccctcgggtc cggccagcac tccgcaggct tcgtcggggt ggtcgcgaca 240
cgcatgggcc accatcgcat tcac 264

<210> SEQ ID NO 176
<211> LENGTH: 325
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 176
ncgccgccag ccaccacgcg cgggtcgggc gccgggcccg ggccgccagg ctgctccgct 60
cggtgatggc acgccaccgc gacaccaccc ggctgcgcta cgtcgagcca taccgggcgg 120
agctacatcg gctcggccgc ccagtgttcg ggccctcttt cgaggtcgag gtcgataccg 180
atttgcgcat ccgcagccgc accctggacg acagaaccgt gccctacgan tgcttgtcgg 240
gcggggccaa agaacagctt ggcatcctgg cgcgattggc cggcgcggcg ctggtctcca 300
aagaagacgc ccttccggtg ctgat 325

<210> SEQ ID NO 177
<211> LENGTH: 243
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 177
cgccacgttc atgggcaaca accccgatca ccggtggaaa tacgtcttca gcacgtcgca 60
atcgcgtacc aaacacatca cgcatatgat taattcgtcc aattgtataa ccaacacgtt 120
gctcaacccg tcctcgaatt tccatatccg ggtgcggtag tcgccctgct ttctcggcat 180
ctctgatagc ctgagaagaa accccaacta aatccgctgc ttcncctatt ctccagcgcc 240
ggg 243

<210> SEQ ID NO 178
<211> LENGTH: 430
<212> TYPE: DNA
<213> ORGANISM: Mycobacterium tuberculosis

<400> SEQUENCE: 178
atactcaagc ttcaaccgat tgacgcattg tgcgaactga cggcgcccgc gcatggccaa 60
tccggaagac catcattggc cagtggccgg gcgctaacag gttccagccc cccaccagtg 120
ccgctcgaac atgcggtgca acccattcgc aggccggcag ggaaagcacc gcggaagccg 180
caaagggctg cagttccgcg cccaatagtg tcgtccgcaa ccagatgcgc tcgaaaaccg 240

-continued

```
cgccggcagt cagcgcaccc gacgcgaggt cgagagacgt cgtcagcgcg cccacatggg    300

gtgccaatcg gcacggcagg taggccgcgc gcaacccgaa cgcgtggtgc atgcccacgg    360

tccgcaggag gcgcagcacc cgccaatgcc gaagcccacg aaacatcggg cgcatccacg    420

cttcaacctc                                                            430
```

<210> SEQ ID NO 179
<211> LENGTH: 448
<212> TYPE: DNA
<213> ORGANISM: Mycobacterium tuberculosis

<400> SEQUENCE: 179

```
agcttttggc agggtctcct tcgaattcgg cgtgcaccgc tatgggttgc agcagcggct     60

ggcgccgcac accccactgg cccgggtgtt ttcgccccga acccggatca tggtgagcga    120

aaaggagatt cgcctgttcg atgctgggat tcgccaccgc gaggccatcg accgattact    180

cgccaccggg gtgcgagagg tgccgcagtc ccgctccgtc gacgtctccg acgatccatc    240

cggcttccgc cgtcgggtgg cggtagccgt cgatgaaatc gctgccggcc gctaccacaa    300

ggtgattctg tcccgttgtg tcgaagtgcc tttcgcgatc gactttccgt tgacctaccg    360

gctggggcgt cggcacaaca ccccggtgag gtcgtttttg ttgcagttgg gcggaatccg    420

tgctctgggt tacagcccga atcgtcac                                        448
```

<210> SEQ ID NO 180
<211> LENGTH: 380
<212> TYPE: DNA
<213> ORGANISM: Mycobacterium tuberculosis

<400> SEQUENCE: 180

```
atactcaagc tttgtcacac caactgtttc caccaggcgc tccatccggc gagtggatac     60

tcccagcagg tagcaggtcg ccaccacgct ggtcagtgcg cgttcagctc gcttgcggcg    120

ctgcagcagc cagtccggga aatagctgcc ctggcgcagc ttggggatcg cgacttctat    180

ggttgcggca cgggtgtcga aatcacggtg gcggtagccg ttgcgctgat tggaccgctc    240

atcgctgcgt tcgcggtagc ccgccccgca cagggcgtcg gcttcagccc ccatcaaggc    300

ggcgatgaac gtcgagagca gcccgcgcag cagatccggg ctcgcctgtg cgagttggtc    360

agccagaacc tgctcggtgt                                                 380
```

<210> SEQ ID NO 181
<211> LENGTH: 532
<212> TYPE: DNA
<213> ORGANISM: Mycobacterium tuberculosis

<400> SEQUENCE: 181

```
ccttaagccc cgcagggccc ggcacgcgcg gtaccgccca ggtcgcccaa cagatcgtcg     60

atgttcgcgt cgtccgcctc gcgcacgtgg tctgtcacca gtcaacgtta acgccgccgc    120

acatgtcctg cggccgggca aaaacgtgaa aaacgagcgg gcgactgcaa tgtcatgaca    180

ccgacggccg ccgatgggcc cagggtctgg cagattcgat ctgtgcggcc agtgccagca    240

gcgtcgcctc gtcatacggc cggccgacga gttgaaccga catgggcagg ccgtcgccgt    300

cgaagtccca cggcaccacg gccgcgggct ggccggtcag attccagact tgaaagtacg    360

gaacccgctg caccaccagc agcaacgtcg aaactgcacc ccggcgttgg taggcgccga    420

tgcgggacgg gccggtcgcg gcgcctggcg tcacaactac gtcgacatcg tcgaagatcg    480

actggatcgg ctgctcacac cactcggcgg ccgcaggccg ccatccgccg tc             532
```

-continued

<210> SEQ ID NO 182
<211> LENGTH: 477
<212> TYPE: DNA
<213> ORGANISM: Mycobacterium tuberculosis

<400> SEQUENCE: 182
agctttttga gcgtcgcgcg gggcagcttc gccggcaatt ctactagcga gaagtctggc 60
ccgatacgga tctgaccgaa gtcgctgcgg tgcagcccac cctcattggc gatggcgccg 120
acgatggcgc ctggaccgat cttgtgccgc ttgccgacgg cgacgcggtg ggtggtcaag 180
tccggtctac gcttgggcct ttgcggacgg tcccgacgct ggtcgcggtt gcgccgcgaa 240
agcggcgggt cgggtgccat caggaatgcc tcaccgccgc ggcactgcac ggccagtgcc 300
gcggcgatgt cagccatcgg gacatcatgc tcgcgttcat actcctcgac cagtcggcgg 360
aacagctcga ttcccggacc gcccagcgca ttggtgatgg aatcggcgaa cttggccacc 420
cgctgggtgt tgacatcctc gacggtgggc aattgccccc ggtaacgttt gccgcct 477

<210> SEQ ID NO 183
<211> LENGTH: 461
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 183
cggtccgacc ctgttcgacg gctacctgaa tcaacccgat gccaccgccg cggcgttcga 60
cgccgacagc tggtaccgca ccggcgacgt cgcggtggtc gacggcagtg ggatgcaccg 120
catcgtggga cgcgagtcgg tcgacttgat caagtcgggt ggataccggg tcggcgccgg 180
tgaaattgaa acggtgctgc tcgggcatcc ggacgtggcg gaggcggcag tcgtcggggt 240
gcccgacgat gatctaggcc agcggatcgt tgcctacgta gtcggctcag cgaatgtcga 300
tgcggacggg cttatcaact ttgttgccca acaactttcg gtgcacaagc gcccgcgcga 360
ggtgcgtatc gtanatgcgc tgccgcgcaa cgccttgggg aaagtgctcc agaacattgc 420
tgtcagaagc tganctacgc gaattatcgt gttacgctgg a 461

<210> SEQ ID NO 184
<211> LENGTH: 440
<212> TYPE: DNA
<213> ORGANISM: Mycobacterium tuberculosis

<400> SEQUENCE: 184
atactcaagc ttgccgaagt tccgatgggt cgcgccggcg agcccagcga agtcgctacc 60
gtggccgtgt tcttggcttc ggatctatcc tcgttcatga ccggcaccgt gttggacgtg 120
actggcggcc ggtccatatg acaccgagat cattgccacg gtacggcaat tcgtcaagaa 180
ggaaatcttt cccaatgcac cggccctcga acgtggcaac agctacccgc aagaaatcgt 240
cgatcggctg ggtgttattg gcttgctcgg tcgccggctg caagggtatc gacaccaccg 300
agttcattct cgggcgtgcc ggcgcattcg agctggcggt gcgcgctgcc cagcaccgtc 360
ataggtactt gacgatggtc cacgtcggac gagcgcctcc acgtcgctgc cgaacggtat 420
gcatggcggc tacgattctc 440

-continued

<210> SEQ ID NO 185
<211> LENGTH: 515
<212> TYPE: DNA
<213> ORGANISM: Mycobacterium tuberculosis

<400> SEQUENCE: 185
cggtgtcggc accggcgtcc tgcagttggt aggcctgcag tttgtgcatc aggccgatgc 60
cgcggccctc gtggccacgc atgtacagca ccacgccgcg cccctcacgg gcgaccatcg 120
ccagcgcggc gtccagctga ggcccgcaat cgcagcggcg tgacccaaac acatcgccgg 180
tcaagcactc cgaatgcacc cggaccagca cgtcgtcacc gtcggcgttg ggcccggcga 240
tctcgccgcg gaccagcgcg acatgttcca cgtcctcgta gatgctggtg tagccgatgg 300
cgcgaaactc cccatgacga gtcggaatcc gcgcctcggc gacccgctca atgtgcttct 360
cgtgcttgcg ccgccattcg atcaagtcag caatggtgat cagcgccaga ccgtgctcat 420
cggcgaacac cgcaattcat cggtgttgcg ccatcgagcc ctcatctttt tggctgacga 480
tctcgcaaat cgcccccgcg ggttgcagcc ggcat 515

<210> SEQ ID NO 186
<211> LENGTH: 345
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 186
atactcaagc tttgggtgaa agccgatcac cggaagccgc atgatcagcc acgtttcgcg 60
ccgcccggca tacggcggcg taccgatctc cgcgtcatac acccgcgggt aatcgccgac 120
ggtgccggtt cgcgagccga aggtgacgac gctgattgaa tcgagttcca ggtccagcgg 180
gtggcgcagc aacggcgcga gctcaacgac gtcaatcacg ttgtcgcttt ctacggtcac 240
cgacccggtg accgtnctcg cccggtgcgc tcggccgata agttgcaccg ccaccaccgc 300
gacaccgtct tgcacgcgga cccacccccg gatccgttgt tggcc 345

<210> SEQ ID NO 187
<211> LENGTH: 366
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 187
agcttgctgg catccgctcc agtagcgccc cgcgcgtggc ttccagcgcc cgcagatgct 60
ccatgagccg gccggtcgag tcggcgccgg cgttcaccgc cacccgccag gagctggcgg 120
ccagcatctc cgccttcacg cattgcgcga tcacagagag aatatacgtc tcatattcgt 180
tggaggtcgt cgcaggcaat cggtcgatga cggatttgat ggcatcgagc tgtgcttcgg 240
cgtagccctc cagcacgtcg gtatcgctgt ggcggtccac gacgaccgca ccggcgcggc 300
ggacagccgt cgggttggac gntgtgcggc gatcagtccg gccagctccg cctcgggatc 360
agcggc 366

<210> SEQ ID NO 188

-continued

<211> LENGTH: 423
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 188
atactcaagc ttgctgcagc ttcctatgac tgctcccgaa acctgggggt gtgcctgctg 60
tgtatgcacg gcatacggac atccttcccc tgagacccgc ggtcgaacca gccacgtgtc 120
catcatcagg ggtcaacccc ggccaagggc gacggcacgc caagttcgcc gaccgttaac 180
ctagtgctgt tagcttcatt tgctgcgagc aaaacagctg gtcggccgtt aggaactgaa 240
ttgaaactca accgatttgg tgccgccgta ggtgtcctgg ctgcgggtgc gctggtgttg 300
tccgcgtgtg gtaacnacna caatgtgacc gggggaggtg caaccactgg ccaggcgtcg 360
gcgaaggtcg attgcggggg gaagaagaac tcaaagccag tgggtcgacg cgcaggccaa 420
cgc 423

<210> SEQ ID NO 189
<211> LENGTH: 453
<212> TYPE: DNA
<213> ORGANISM: Mycobacterium tuberculosis

<400> SEQUENCE: 189
agcttgacgc ggagacggac acattgcgaa cattgatgac aaaatagaaa tcattgatgg 60
tttgagtcac caggccgatc aagccttcgc cgagccaaat tccaatcaag aggcccaagc 120
ccgtaccaat cagcccggca acgagggatt ccgtcattat cagccaaaat aactgctctc 180
gggttacacc caaacagcgc aatatggcga aaaacggtcg ccgttgcacg acattaaatg 240
tcacggtatt gtagattaaa aagataccca ccaacaaggc aatcaaactg agagcggtta 300
aattgaccgt aaaagcgtcc gtcatctgtt tgacggtgtc ccgttgggta tccgacgttt 360
ccatacgcac accggccggc agtctttgtt ggatgcgtgt tgcagtggcc tcatctttga 420
tgatcaaatc gatgtggctc agtcttccgg gca 453

<210> SEQ ID NO 190
<211> LENGTH: 402
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 190
atactcaagc ttcggctcag gcggcgctgc tggtaaagtc gctgaccggt gcaggtttcg 60
acaatgtggt gccggttcgg cggctacgtg ccatcgagac actggcgcag gctatcgcac 120
ccgttatcgg ctacgagcaa atcgcggtat gcgttcttga gcatgagtcg gcgaccgtcg 180
tcatggtcga cacccacgac ggaaagacgc agatcgccgt caagcatgtg tgccgcggat 240
tatcaggact gacctcctgg ctgaccggca tgtttggtcg cgatgcctgg cgcccggccg 300
gcgtggtcgt ggtccgctcg gatagcgagg tcagcgaatt cncntggcag ctccaaaggg 360
tcctgccggt gccggtcttt gcgcaaacna aggcncaggt ta 402

-continued

<210> SEQ ID NO 191
<211> LENGTH: 427
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 191
tgatcgcgca tcacctgctt cataaactgg aagcagcgca gcgcttcctt ttcggccgca 60
acatgagcca gcctctcgtc ggcggtcggg tgcaggtgct cgggcagctc ggccgcgaca 120
gccgcctgac cctgaaacca gcttccatat cccgcgacga acgacgccag tccgctacgt 180
aacccctccg cgactgtcca tggacaacag cgcgttctcc accgaccggg cccgggtgtg 240
gggtgtttcg gcgaccggca gccaggtggt ccacactgcc gacgggcgcc gcgagccgtt 300
caccgaccag gccgccgagc aagtccgccc gatcgcatac tccaaccggt tgcggtactg 360
caggttcagc tggcgtactc ctcgtcgcgc tcggcgaggt cttgctccag cacgtcgcan 420
acggcag 427

<210> SEQ ID NO 192
<211> LENGTH: 347
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 192
caaagcgcga actgctcgcg gcagcccacg acgtgctgcg tcggattgcc ggcggcgaaa 60
tcaattccag gcagctcccg gacaatgcgg ctctgctggc ccgcaacgaa ggactcgagg 120
tcaccccggt gcccggggtc gtggtgcacc tgccgatcgc acaggttggc ccacaaccgg 180
ccgcttgatg cccggtcggc aagcccggca gttgccaaac ccagcgtgat caggctcggc 240
tcgcgagttc cgggaagaag tggctccgcc tgatcaccta ccatccgcca ggatctgcgt 300
gtcttcacca cgcccgccaa ggaggttgtt gtggtgctat cgaccgn 347

<210> SEQ ID NO 193
<211> LENGTH: 330
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 193
ccggaagccg catgatcagc caagtttcgc gccgcccggc atacggcggc gtaccgatct 60
ccgcgtcata cacccgcggg taatcgccga cggtgccggt tcgcgagccg aaggtgacga 120
cgctgattga atcgagttcc aggtccagcg ggtggcgcag caacggcgcg agctcaacga 180
cgtcaatcac gttgtcgctt tctacggtca ccgacccggt gaccgtngtc gcccggtgcg 240
ctcggccgaa aanttgcacc gccaccaccg cgaaaccgtc ttgcacnccg gaagccaccc 300
ccgatccgtt gttgggccag gttattgggt 330

-continued

<210> SEQ ID NO 194
<211> LENGTH: 215
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 194
ccggaaccgc cgacggcacg gtataacgcc tccgcatatg ggtcgacaac cagcgggtcg 60
gacttctggg cttctagcgt tcgcgcngtc gcgacaaaca gcgcggtcga accgacactc 120
gttgtgatgt cctagctatc acgttcggta cgcacccaat cgagtctagc gcgggtagnt 180
cagccccgat ctccangctc cgccgagcca ggcgc 215

<210> SEQ ID NO 195
<211> LENGTH: 225
<212> TYPE: DNA
<213> ORGANISM: Mycobacterium tuberculosis

<400> SEQUENCE: 195
ctggtttatg tcccgttgaa gttccatcac ccgatgtggc gggagcactg ccaggtcgat 60
ctcaactacc acatccggcc gtggcggttg cgcgccccgg ggggtcggcg cgaactcgac 120
gaggcggtcg gagaaatcgc cagcaccccg ctgaaccgcg accacccgct gtgggagatg 180
tacttcgttg aggggcttgc caaccaccgg atcgcggtgg ttgcc 225

<210> SEQ ID NO 196
<211> LENGTH: 161
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 196
ccgagcagtt gggaatcgct ctgcancaaa ccaatattct gcgcgacgtc gcgcgacgag 60
ctggaccgat taggcgtacg cctccgnctg gacgacaccg gggcactcga tgaccccgac 120
gcctacgctc gcaggatatt gttcgccgga cccctctcta g 161

<210> SEQ ID NO 197
<211> LENGTH: 240
<212> TYPE: DNA
<213> ORGANISM: Mycobacterium tuberculosis

<400> SEQUENCE: 197
tatataatac tcaagcttgc cgacgccaac gctcgcgcga tgttgttagc ccgacccggc 60
tcttacatgg caccggtgcc ccacacgtca gcctgtgacg tcctgcaccg cgactcttta 120
catagaatgt ggattgccgg attggggatg tccggcatcg ctcaatctgt agtccgcgtt 180
gtcccgcgag ggccatgtgg atggggggaa ggatccgtgg cgtccgggat caccatgggg 240

<210> SEQ ID NO 198
<211> LENGTH: 348
<212> TYPE: DNA
<213> ORGANISM: Mycobacterium tuberculosis

<400> SEQUENCE: 198

-continued

```
atactcaagc ttgccgaagt tccgatgggt cgcgccggcg agcccaacga aatcgctagc     60

gtggccgtgt tcttggcttc ggatctatcc tcgtacatga ccggcaccgt gttggacgtg    120

actggcggcc ggttcatatg acaccgagat cattgccacg gtacggaaat tcgtccagaa    180

ggaaatcttt cccaatgcac cggccctcga acgtggcaac agctacccgc aagaaatcgt    240

caatcggctg ggtgttattg gcttgctcgg tcgccggctg cgagggtttc tacaccaccg    300

agttcattct cgggcgtgcc ggcgcattcg aactggcggt gcgcgctg                 348
```

```
<210> SEQ ID NO 199
<211> LENGTH: 371
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 199

gcaccggcgt cctgcagttg gtaggcctgc agtttgtgca tcaggccgat gccgcggccc     60

tcgtggccac gcatgtacag caccacgccg cgcccctcac gggcgaccat cgccagcgcg    120

gcgtccagct gaggcccgca atcgcagcgg cgtgacccaa acacatcgcc ggtcaagcac    180

tccgaatgca cccggaccag cacgtcttca ccgtcggcgt tgggcccggc gatctcgccg    240

cggaccaacg cgacatgttc cacgtcctcg tagatgctgg tgtagccgat ggcgcgaaac    300

tccccangac aagtcggaat ccgcgcctcg gcgaaccgct caatgtgcct ctcgtgcttg    360

cgccgccatt c                                                         371
```

```
<210> SEQ ID NO 200
<211> LENGTH: 165
<212> TYPE: DNA
<213> ORGANISM: Mycobacterium tuberculosis

<400> SEQUENCE: 200

tggtccgtgt gcgcatacca atacaacgcg ccgggcacct gacgcggcgg ccgcaaccaa     60

tcggtggcca tcgccatctt ctgctacccg gtcaacggac gcaccttctc ctggccgacg    120

tagtgcgccc acccgccgcc gttgcgtccc atcgatccgg tcaac                    165
```

```
<210> SEQ ID NO 201
<211> LENGTH: 390
<212> TYPE: DNA
<213> ORGANISM: Mycobacterium tuberculosis

<400> SEQUENCE: 201

ggcgtgttgg ccaccggggc cactccgcac aatctgtacc cgaccaagat ctacaccatc     60

gaatacgacg gcgtcgccga ctttccgcgg tacccgctca actttgtgtc gaccctcaac    120

gccattgccg gcacctacta cgtgcactcc aactacttca tcctgacgcc ggaacaaatt    180

gacgcagcgg ttccgctgac caatacggtc ggtcccacga tgacccagta ctacatcatt    240

cgcacggaga acctgccgct gctaaagcca ctggcgatcg gtgccgatcg tggggaaccc    300

actggcgaac ctggttcaac caaacttgaa ggtgattgtt tacctgggct acggcgaccc    360

ggcctatggt tattcgacct ccccgcccaa                                     390
```

```
<210> SEQ ID NO 202
<211> LENGTH: 427
<212> TYPE: DNA
```

-continued

<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 202
cgtccgtgnc ccctcaancg cgtgnngccg aagcggctgg ttacgactcc ctgtttgtga 60
tggacacttc taccaactgc ccatgttggg gacgcccgac cagccgatgc tggaggccta 120
cacggccctt ggtgcgctgg ccacggcgac cgancggctg caactgggcg cgttggtgac 180
cggcaatacc taccgcagcc cgaccctgct ggcaaagatc atcaccacgc tcgacgtggt 240
tagcgccggt cgagcgatcc tcggcattgg agccggttgg tttgagctgg aaacaccgcc 300
agctcggctt cgagttcggc actttcagtg accggttcaa ccggctcgaa gaggcgctac 360
agatcctcca gccaatggtc aagggtgagc gcccaacgtt tttcggcgat tggtacacca 420
ccgaatc 427

<210> SEQ ID NO 203
<211> LENGTH: 498
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 203
ccgcttccgt gtaaccgagc anngcgagcg anctggcgag gaagcaaaga agaactgttc 60
tgtcagatag ctcttacgct cagcgcaaga agaaatatcc accgtgggaa aaactccagg 120
tagaggtaca cacgcggata gccaattcag agtaataaac tgtgataatc aaccctcatc 180
aatgatgacg aactatcccc cgatatcagg tcacatgacg aagggaaaga gaaggaaatc 240
aactgtgaca aactgccctc aaatttggct tccttaaaaa ttacagttca aaaagtatga 300
gaaaatccat gcaggctgaa ggaaacagca aaactgtgac aaattaccct cagtaggtca 360
gaacaaatgt gacgaaccnc cctcaaatct gtgacagata accctcagac tatcctgtcg 420
tcatggaagt gatatcgcgg aaggaaaata cgatntgagt cgtctggcgg cctttctttt 480
tctcaatgta tgagagcg 498

<210> SEQ ID NO 204
<211> LENGTH: 265
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 204
tgacacccaa cagagggcac ttaagatggc aatgcggccg cctacctgca cgttttcgcg 60
atgtcagagg atgccgaggg agaacaatgc gagcacggcc gctgacnttg ctcaccgctt 120
tggcggcggt gacattggtg gtggttgcgg gctgcnaggc ccgantcnag gccgaagcat 180
atagcgcggc cgaccgcatt tcgtctcgac cgcaagcgcg acctcagccg cagccggtgg 240
agctactgct gcgcgccatc acgcc 265

-continued

<210> SEQ ID NO 205
<211> LENGTH: 369
<212> TYPE: DNA
<213> ORGANISM: Mycobacterium tuberculosis

<400> SEQUENCE: 205
acgggcgacg ctgaggtggg cccgcggcta ttcatgctgt cgtccacgtc cagcgacgca 60
ctgcgccaga cggcccgcca actagccacc tgggtggaag aacaccagga ctgcgtggcg 120
gcctcggatc tggcctacac gctggcgcgt ggccgcgcgc accggccggt gcgcaccgcg 180
gtggttgccg ccaacctgcc ggagctcgtc gagggtttgc gcgaggtggc cgacggtgac 240
ccctctatga cgcggcggtg ggacactgtg atctaagacc ggtctgggtc ttctccgggc 300
aagggtctca gtgggcggcg atgggcaccc aattgctcgc cagcgaacca gtgttcgcgg 360
ccaccatcg 369

<210> SEQ ID NO 206
<211> LENGTH: 428
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 206
atactcaagc ttcgcgagat ccggatggca ctcacgctgg acaagacctt cacaaaatct 60
gaaatcctga cccgatactt gaacctggtc tcgttcggca ataactcgtt cggcgtgcag 120
gacgcggcgc aaacgtactt cggcatcaac gcgtccgacc tgaattggca gcaagcggcg 180
ctgctggccg gcatggtgca atcgaccagc acgctcaacc cgtacaccaa ccccgacggc 240
gcgctggccc ggcggaacgt ggtcctcgac accatgatcn aaaacttccc ggggaggcgg 300
aggcgttgcg tgccgcccag ggcgaaccgc tgggggttct gccgcagccc aatgattgcc 360
gcgcggctgc atcgcgggcg gcgaccgcca ttcttctgcg aatacgtcca ggagtactgt 420
ctcggggc 428

<210> SEQ ID NO 207
<211> LENGTH: 378
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 207
agcttatgtg gccgcccacc taccttatct agcctagcta actaaatcca gtgccgacag 60
tgcgcggctg gccacccagc atgaggttat gaccacggca tatgccagcg cgctggcggc 120
gatgccgacg ctgaccgagt tggccgctaa tcacaccagc catgcggtgt tgctgggaac 180
gaatttcttt ggaatcaata cgatcccgat cgcgctcaat gaggccgact atgcgcggat 240
gtggattcag gcggccacca cgatgagtat ctatgagggc acctccgatg cggcgctggc 300
gtcngcaccg caaaccacac cggctccggt actgttcaac ggcggtgctg gcgtttgcca 360
gcgcctgccg gcgatctc 378

-continued

<210> SEQ ID NO 208
<211> LENGTH: 284
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 208

```
atactcaagc ttgccaccca tgccgagcaa ggtcgactca gcgatgacga attgttcttc     60
ttcgcggtgt tgctgctggt tgcgggctat gagagcactg ctcatatgat tagcacnttg    120
tttctgacgc tggccgacta tccagatcag ctgacactcc ttgcgcagca accagacctg    180
atcccgtcgg cgatcgagga gcacctccgc tttatatcgc aatccaaaac atctgccgca    240
caacgcgcgt cgactattcg gtcggtcaag cggtcatccc ggga                     284
```

<210> SEQ ID NO 209
<211> LENGTH: 236
<212> TYPE: DNA
<213> ORGANISM: Mycobacterium tuberculosis

<400> SEQUENCE: 209

```
ccggggtaga acgatgcgat ctgggccatg tcgacatcgg tggtacaggt aaaccgcgcc     60
gtgtgcgcgg tctcggagat cagaacgtgg tcgcagttga caccgcgggc tttcagccag    120
tcgcgataat cggcgaagtc ggcgcctgcc gccccaacta gcgcgacctc gccacctagc    180
acaccgatgg cgaaggccat gtttccggcc acgccgccgc ggtgcatcat caactc        236
```

<210> SEQ ID NO 210
<211> LENGTH: 278
<212> TYPE: DNA
<213> ORGANISM: Mycobacterium tuberculosis

<400> SEQUENCE: 210

```
atactcaagc ttggcggcaa cgccactacc gggctcacca ggtcctgtgc cgccaccgcc     60
ggcgccgaaa gcaccatcag gtcgtagttg tctggacgtt cgacaccgta agcgaacaca    120
atgccgccgc ccatgctgtg cccgagcacg atgcgcttgc acccgggata ttcccgggtg    180
gcgatcccaa cgagggtgtc gaagtcagcg gtgtatctga gatgtctctc actatcatcc    240
gtttggcacc cgagcgggca tgcccgcggg gggtcaac                           278
```

<210> SEQ ID NO 211
<211> LENGTH: 360
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 211

```
gtcgacggca tcaaggtccg cagtgatggt gttcatctca cccaggaagg cgtgaagtgg     60
ctgataccgt ggcttgagga ttcggtgcgg gtcgccagtt aatccgccgt gtgctccgga    120
tgagcgcgac ggtaaccctg gaattgtgct gtgtgctggc tgtgtcgttg tgatgagcct    180
gtctaagtgg tgcgtaaccg tttgacgagc cgcggcctcg ctgcaaacat tgaagcccgc    240
acgtctgggt ttgtatttac acaacgaggg cgctccccga tctggcgcgc gcaacgaggt    300
```

-continued

```
gcncactatc cattcgaggt gaactggact ccttgatgct catgccggtg cggttttgtc    360


<210> SEQ ID NO 212
<211> LENGTH: 256
<212> TYPE: DNA
<213> ORGANISM: Mycobacterium tuberculosis

<400> SEQUENCE: 212

atactcaagc ttgcgttcga tgaagtagtc gtcggtcagc gccgcctctt cgagctcctt     60

ggcgatgccc agcaaggagt catcgccgcc gagcttggcc aggatcttgt cggcctgttc    120

cttgacgatg cgggcccgcg gatcgtagtt cttgtagaca cgatgaccga aacccatcaa    180

tttgaccccg gcctcgcggt tcttgacctt gcgttacaaa ctcgctgacg tcgtcgccgc    240

tgtcgcgaat gccctc                                                     256


<210> SEQ ID NO 213
<211> LENGTH: 262
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 213

ngtcaagccg agcatgcgcg aggnaacgac gaacccaaca agccatggtg gttggcgccg     60

tcgagaggtc ggcggtcgcc acaacgggaa gatcgccttg agcgtcgctc gaccgccgcc    120

tcgagttggg tcataacgaa gtagctgatg ccgatcatgt cgacgtttcc gtcgcatcag    180

cgtgcagcgg cgacccactc gacgaggtct cggtgccgcc gcggccaggg caccagcagt    240

gacgattcca ggcgccgtcg gg                                              262


<210> SEQ ID NO 214
<211> LENGTH: 336
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 214

cgataatcgc ttccggtaag tgcagcagct ttacgacggc gactcccatc ggcaatttct     60

atgacaccag atactcttcg accgaacgcc ggtgtctgtt gaccagtcag tagaaaagaa    120

gggatgagat ctccccgtgc gtcctcagta agcagctcct ggtcgcgttc attacctgac    180

catacccgag aggtcttctc aacactatca ccccggagca cttctagagt aaacttccca    240

tcccgaccac atataggcta aggtaatggg cattaccgcg agccattact cctacgcgcg    300

caattaacga atccaccatc ggggccgctg gtgtcn                               336


<210> SEQ ID NO 215
<211> LENGTH: 259
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"
```

-continued

<400> SEQUENCE: 215
naatactcaa gctttctcgt gattaccacc cgtgtaattt gggatgggca aaaaggcgaa 60
tcaccgcgtg gccacaaacg ccgggaggga caatctcggg cggctagggc ttctcgcggg 120
aaggcccgaa cgtacggcgt ttcaacacgt cgcgtcgccc tccgaccgcg aacattcggg 180
gatggcagca acctggtatc accctggccg ggcaatgatc tgcagcgtcg ccgcgggtag 240
tgnccgcccg ggcggctac 259

<210> SEQ ID NO 216
<211> LENGTH: 325
<212> TYPE: DNA
<213> ORGANISM: Mycobacterium tuberculosis

<400> SEQUENCE: 216
ccaactagag catcgggaca tacggagtca actacccggc caacggtgat ttcttggccg 60
ccgctgacgg cgcgaacgac gccagcgacc acattcagca gatggccagc gcgtgccggg 120
ccacgatgtt ggtgctcggc ggctactccc agggtgcggc cgtgatcgac atcgtcaccg 180
ccgcaccact gcccggtctc gggttcacgc agccgttgcc gcccgcagcg gacgatcaca 240
tcgccgcgat cgccctgttc gggaatccct cggggccgcg ctggcgggct gatgatcgcc 300
ctgacccctc aattcgggtc caaga 325

<210> SEQ ID NO 217
<211> LENGTH: 300
<212> TYPE: DNA
<213> ORGANISM: Mycobacterium tuberculosis

<400> SEQUENCE: 217
atactcaagc ttgctgcagc ttcctgtgac tgctcccgaa acctgggggt gtgcctgctg 60
tgtatgcacg gcatacggac atccttcccc tgagacccgc ggtcgaacca gccacgtgtc 120
catcatcagg ggtcaacccc ggccaagggc gacggcacgc caagttcgcc gaccgttaac 180
ctagtgctgt tagcttcatt tgctgcgagc aaaacagctg gtcggccgtt aggaactgaa 240
ttgaaactca accgatttgg tgccgcccgt aagtgtcctg gctgccggtg cgctggtgtt 300

<210> SEQ ID NO 218
<211> LENGTH: 265
<212> TYPE: DNA
<213> ORGANISM: Mycobacterium tuberculosis

<400> SEQUENCE: 218
agcttgcgcg gcgtggcgat cgcggttcaa ggcgcgctct tcgagcacaa cgagcgaaga 60
cagctcggcg acggagcctt tatcgacatc cgttcgggct ggctgaccgg cggcgaagaa 120
ctgctggacg cgttgttgtc gacggtgccg tggcgagccg agcgccgtca gatgtacgac 180
cgggtggtcg atgtgccgcg gctggtgagt tttcacgacc tgaccatcga agatccgccg 240
catccgcagc tggcgcggat gcgcc 265

<210> SEQ ID NO 219
<211> LENGTH: 362
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

-continued

<400> SEQUENCE: 219
aatactcaag cttgcgcacg accaggacgt cgagtggcgc ttgcagtgac ttggcgacct 60
caaaggccac cggtaccccg ccgcgcggca agccaaggac nacnacggcc ttgccggata 120
gctgcgccag gcgttgcgcc aactggcgtc cagcgtcgcc acgatcgtca aagagcttca 180
tctgccgagt gtgtcgccat ctcatggctc caaatatgga attaggtccc tgggccgact 240
gacgacagtc cctcagcgac cggattgcgc atcccgcctt gtacgctgct ccgcaaatcc 300
cgggcttgcg tccgcggaag cgaactcggc ggcgctacgg tggtggctca cttcggccgt 360
gc 362

<210> SEQ ID NO 220
<211> LENGTH: 486
<212> TYPE: DNA
<213> ORGANISM: Mycobacterium tuberculosis

<400> SEQUENCE: 220
ggttggtgcg gtccaccttc gcggcggcgg cgcgatatgc cttgctggtc ttgctcattt 60
gatatccaat ctatgggtcg tggttactca gcgggccgaa gctggccctc ccacgggtag 120
ggccctattc gacggtgatg cccatcgacc gagcggtacc ggcgatgatc ttggccgcag 180
cgtcgacgtc gttggcgttg aggtccgtct tcttggtctc ggcgatttcg cggacttgat 240
cccaggtgac tttggcgacc ttggtcttgt gcggctccgc cgaacccttc gccacaccag 300
cggccttaag cagcagcttg gcggcgggcg gcgtcttcag cgtgaaagtg aagctacggt 360
cttcataaac ggtgatctcc accgggatga cgttgccgcg ctggttctcc gtcgcggcgt 420
tgtacgcctt gcagaactcc atgatgttga cccgtgctga ccgaacgcgg ggcccactgg 480
cggggc 486

<210> SEQ ID NO 221
<211> LENGTH: 373
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 221
atactcaagc ttttcgaccc gcaagccggc ggtgcccctc ctcgttccgc tgcccggtct 60
gctcgatcgg ttcggggtcg ccgcgctagg cccaattgcc cggctcctcc tcgggccgtt 120
ccacaacccg catcgtcgcc gggctaggtt caagccatgc cggtaaaccc caggacgcca 180
gtgctgatcg gctatggaca ggtcaaccac cgaggcgaca tcgacgccna aaatcagtcc 240
atcgaacccg tcgacctgat ggccnccgcg gcccggaaag ccgccgagtc caccgtgctc 300
gaagcggtgg attccatccg tgtggtgcac atgctgtcgg cgcattaccg gaattcccgg 360
gcgtctcctc ggc 373

<210> SEQ ID NO 222
<211> LENGTH: 331
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

-continued

<400> SEQUENCE: 222
ncctggttca tgaactggaa gcagcgcagc gcttcctttt cggccgcaac atgagccagc 60
ctctcgtcgg cggtcgggtg caggtgctcg ggcagctcgg ccgcgacagc cgcctgaccc 120
tgaaaccagc ttccatatcc cgcgacgaac gacgccagtc cgctacgtaa cccctccgcg 180
actgtccatg gacaacagcg cgttctccac cgaccggggc cgggtgttgg ggtgttcggc 240
aacggcaacc aagttggtcc acactgccga cgggcgccgc aaatccgttc accgaaccag 300
gccgccnaaa caattccgcc cgatcccata t 331

<210> SEQ ID NO 223
<211> LENGTH: 377
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 223
atactcaagc ttgtcgggat caatctcgag ggcatccacg cacgaaaagt aaactctatc 60
aagcttttttg acgacaccca cggacgcccc atatatgttc gggtgggcaa gaacggtccc 120
tacctggaac gtttggtggc cggcgacacc ggtgagccca cgccgcagcg ggccaacctc 180
agcgactcga ttaccccgga cgaactgact ctacaggtgg ccgaagagct ctttgccaca 240
ccgcaacagg gacggacttt gggcttggac ccagaaaccg gccacgaaat ctttgccagg 300
ggaaggccgg tttgggcctt atgttaccta tatcctgccg gaacctgcgg ctgatgcggc 360
cgcggccgct cagggan 377

<210> SEQ ID NO 224
<211> LENGTH: 436
<212> TYPE: DNA
<213> ORGANISM: Mycobacterium tuberculosis

<400> SEQUENCE: 224
agcagctagc cgcgctcgcc gcgctggtcg gtgcgtgcat gctcgcagcc ggatgcacca 60
acgtggtcga cgggaccgcc gtggctgccg acaaatccgg accactgcat caggatccga 120
taccggtttc agcgcttgaa gggctgcttc tcgacttgag ccagatcaat gccgcgctgg 180
gtgcgacatc gatgaaggtg tggttcaacg ccaaggcaat gtgggactgg agcaagagcg 240
tggccgacaa gaattgcctg ggctatcgac ggtccagcac aggaaaaggt ctatgccggc 300
accgggtgga ccgctatgcg cggccaacgg ctggatgaca gcatcgatga ctccaagaaa 360
cgcgaccact acgccattca agcggtcgtc ggcttcccga ccgcacatga tgccgaagaa 420
ttctacagct cctccg 436

<210> SEQ ID NO 225
<211> LENGTH: 539
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 225

-continued

```
cgcgactggc tccccggncg gctgctcggg tccgccgata gagaccggga tgtcgcccga     60

cgacgggcag ccgggttgcg tgggacgggg cgggggtcgg gcagcccaag caacgggcta    120

gtccccgaat cctacggagc cgtcacctac gcctacgtaa tagtagctat caataacagt    180

tgacatacgc aacgatctgt gagatcaata ttgcctgacg catgtcaaga caggcgtcaa    240

gacaggtgtc aataattcgc tccgctggtg acggtaaccg gtcgtgcggg tgtgtgacgc    300

ctaaggaagg agtgtgggtg gtgacgctga gagtggttcc tgagggtttg gcggccgcca    360

gtgcggcggt ggaggcgttg accgcacggc tggccgccgc acacgctggc gcggcgccgg    420

cgattacggc ggtggtggcg cccgcggcgg atccggtgtc gttgcagaat gcggtggggt    480

ttagcgcctt aagtagccag catgccgcga tcgccggcga aagggtccaa gaactgggt     539
```

<210> SEQ ID NO 226
<211> LENGTH: 517
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 226

```
atactcaagc ttattgaacc gcgggtcgca ggcaaagtgg acctcataac gactcgggtc     60

cagcgaccgc gccaacacga acggccggac gacgtgggcc agggtcgcgg cctcccctac    120

aaacaggatc cgttgcctgc gaacgacagg ctccggtgcg gcgttgggcg ccgtgctcgt    180

cccagcgtcc ggtcccgggt cgccggcgac gcttgtttcc tccatactcg ccccctaatc    240

tcgaggcagc ccgtacccgc aggcaacctc ccaaaaatgc aatcccgcaa aatgcaatgc    300

gtcnagctat ttctcacacc gaccgctagt tgcggatcag aaatccgttg ggcgcggaag    360

tccagccgaa tttgttctcc cgctccgcat catgcttgta atcgtttgga aattcatcct    420

catatgcctc gatcgcttca tagggtccag gcccaaaccc gggcaggact gggtggccgt    480

tgatgttgga atcctccact actaggtatt caccggc                             517
```

<210> SEQ ID NO 227
<211> LENGTH: 488
<212> TYPE: DNA
<213> ORGANISM: Mycobacterium tuberculosis

<400> SEQUENCE: 227

```
gtctcgatca tggccaaaga gctcgacgaa gccgtagagg cgtttcggac ccgcccgctc     60

gatgccggcc cgtatacctt cctcgccgcc gacgccctgg tgctcaaggt gcgcgaggca    120

ggccgcgtcg tcggggtgca caccttgatc gccaccggcg tcaacgccga gggctaccga    180

gagatcctgg gcatccaggt cacctccgcc gaggacgggg ccggctggct ggcgttcttc    240

cgcgacctgg tcgcccgcgg cctgtccggg gtcgcgctgg tcaccggcga cgcccacgcc    300

ggcctggtgg ccgcgatcgg cgccaccctg cccgcagcgg cctggcagcg ctgcagaacc    360

cactacgcag ccaatctgat ggcagccacc ccgaagccct cctggccgtg ggtgcgcacc    420

ctgctgcact ccatctacga ccagcccgac gccgaatcag ttgttgccaa tatgatcggg    480

ttctcgac                                                             488
```

<210> SEQ ID NO 228
<211> LENGTH: 264
<212> TYPE: DNA

-continued

<213> ORGANISM: Mycobacterium tuberculosis

<400> SEQUENCE: 228
atactcaagc tttcgtcagt tcatggcgcc agcagaccaa caagagcatc gggacatacg 60
gagtcaacta cccggccaac ggtgatttct tggccgccgc tgacggcgcg aacgacgcca 120
gcgaccacat tcagcaaatg gccagcgcgt gccgggccac gaggttggtg ctcggcggct 180
actcccaggg tgcggccgtg atcaagatct tcaccgccgc accactgccc ggcctcgggt 240
tcacgcatcc gtttggccgc cgcc 264

<210> SEQ ID NO 229
<211> LENGTH: 229
<212> TYPE: DNA
<213> ORGANISM: Mycobacterium tuberculosis

<400> SEQUENCE: 229
gccccgtgta atttgggatg ggcaaaaagc gaagcaccgc gtggccacga acgccgggag 60
ggacaatctc gggcggctag ggcttctcgc gggaaggccc gaacgtacgg cgtttcaaca 120
cgtcgcgtcg ccctccgacc gcgaacattc ggggatggca gcaacctggt agcaccctgg 180
ccgggcgatg atctgcagcg tcgccgcggg tagtctccgc ccgggccgc 229

<210> SEQ ID NO 230
<211> LENGTH: 266
<212> TYPE: DNA
<213> ORGANISM: Mycobacterium tuberculosis

<400> SEQUENCE: 230
atactcaagc ttcctttgac cgaacgcgtc caccgcaccg tgagattggt ggcgccattc 60
gtcgtggtgt agctgctgtt ggcggcgtcg ccgtattgtg cgggccagcc ttgtgcgggg 120
gccgcttcta cccacaagtc ggcacttccg caaccgccca gctcgaccgc gaattacggc 180
ggccgcaacg gccgccggaa ggcgtcacgc aatcgcttat cctttccagg ttcccaaatc 240
ctccgcttac ttgggtcctt catcgg 266

<210> SEQ ID NO 231
<211> LENGTH: 258
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 231
ggcagcggcg acaaccggaa cgtccgcacg gtgctcaatc acgggtgcac ggtgtgcatc 60
agaatggcgg gggttcgttg tcgcggtgag gcgttcggcg aggaggtagt gtctacccct 120
tgcccgcggg ttcgtgcgga ctgaaaggga tttcattggg aacccacggc tgcgtatcgc 180
agggcctcgg tgacgtctgc ttcctcnagc tcaggaagtt cggcgagaat ctcggtggat 240
gttatttggt ccgcctac 258

<210> SEQ ID NO 232
<211> LENGTH: 224
<212> TYPE: DNA
<213> ORGANISM: Mycobacterium tuberculosis

<400> SEQUENCE: 232

-continued

```
atactcaagc tttctcggct tctctgatag cctgagaaga aaccccaagt taatccgctg     60

cttcacctat tctccagcgc cgggttattt tcctcgcttc cgggctgtca tcattaaact    120

gtgcaatggc gatagccttc gtcatttcat gaccagcgtt tatgcactgg ttaagtgttt    180

ccatgagttt cattctgaac atcctttatt cattgttttg cgtt                     224


<210> SEQ ID NO 233
<211> LENGTH: 333
<212> TYPE: DNA
<213> ORGANISM: Mycobacterium tuberculosis

<400> SEQUENCE: 233

atactcaagc ttggtgaccg gcaccgcgat acgttgcggc aggcatctgg gctggcggtg     60

gttcgccgct ccgaagccgt cgaacaccat cgccagcgcg gcttccacat caacgaccat    120

ttcggccagc ttgcggcgca tcagcggctt gtcgatgagc gccccaccga atgcccgccg    180

ctgcccggcg tatcacatcg attcgaccat cgcgcggcgc gcgttgccga gggcgaacga    240

ggcggtgccc aaccgcaatc tgtttggtca gctccctcat gcgggttgat tccttgccgt    300

ccggacgggc ccgcgtcatg cgctcggttc gcc                                 333


<210> SEQ ID NO 234
<211> LENGTH: 407
<212> TYPE: DNA
<213> ORGANISM: Mycobacterium tuberculosis

<400> SEQUENCE: 234

ccgttgcgca gcgtgagccg atagttgaca tccggctcgg tgaaggtgaa atcgatggcc     60

aggtcgaggt cccatgcgcg tgggccattg atgctgatcg ccaggacgtc aaagatttgg    120

tccggcgtca gctgggcgaa aaacgtgggc gccgggactt gcccggagct gcccgggttc    180

ccgtcgcgca gctcggcggc cccggtcaga aagaaattgc gccaggtcgc acactccgcg    240

ccgtaggcca gctgctccag ggtgtcggca tagagcccgc gggccgcagc gtgctcgctg    300

tcggcgaaca ccgcatggtc gagaagcgtt gccgcccaac gggaaatcac ctgcgtcgaa    360

agcttcgcgg gccagctcca gcactcggtc gatgccaccc aacgcgt                  407


<210> SEQ ID NO 235
<211> LENGTH: 389
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 235

atactcaagc ttgcggatgt taccccctgac agcgtgaact atgtcnaaac acacggcacc     60

ggaacggtgt tgggggaccc catcgagttc gagtcgctgg cggccactta tggcctgggt    120

aaaggccagg gcgagagccc gtgcgcattg gggtcggtca aaaccaacat cggccacctg    180

gaggcggccg ccggtgtggc tggattcatc aaggcggtgc tggcggtgca acgtgggcac    240

attccccgca acttgcactt cacccggtgg aacccggcca tcaacacgtc ggcgacgcgg    300

ctgttcgtgc cgaccgaaag cgccccgtgg ccggcggctg ccggtccacg cagggctgcg    360

gtgtcatcgt tcggcctcag cgggaccaa                                      389


<210> SEQ ID NO 236
```

-continued

<211> LENGTH: 432
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 236
ccggtaacca gatcagctcg tcgacctcac tgccgggggt gaattcccca ccggtgctgc 60
gcgctgccca gtagtgcacc ttcttgacgc ctcgaaaagg ggagtcggtc gggtaggtca 120
ccgtcaggag ccgcctaccc aggttggcgc ggtgaccggt ctcctcgagt atctcccgca 180
ccgcccccac cggtgcggtc tcgcccggat ccactttgcc cttgggcagc gaccagtcgt 240
cgtaacgggg gcggtgaatg acagcgatct cgaccggccc ttccgaatcg gcactgccgg 300
gtcgccagaa caccgcaccg gcggcgtaca caatccggcc cgccgagcgc cggcgggcgg 360
acganttctg gatcgacacc tcaactcctg caggtcaatt cggccaagct gctcgcggtc 420
gtggatgtgg tc 432

<210> SEQ ID NO 237
<211> LENGTH: 287
<212> TYPE: DNA
<213> ORGANISM: Mycobacterium tuberculosis

<400> SEQUENCE: 237
atactcaagc ttgatgccgc cgaaaccgag cgtgagcacg ccgccaccca ccacgcgcgg 60
gtcgggcgcc gggcccgggc cgccaggctg ctccgctcgg tgatggcacg ccaccgcgac 120
accacccggc tgcgctacgt cgagccatac cgggcggagc tacatcggct cggccgccca 180
gtgttcgggc cctctttcga ggtcgaggtc tataccgatt tgcgcatccg cagccgcacc 240
ctggtcgtct cgtaccgtgc cctacctctg cttgtcgggc ggggcca 287

<210> SEQ ID NO 238
<211> LENGTH: 272
<212> TYPE: DNA
<213> ORGANISM: Mycobacterium tuberculosis

<400> SEQUENCE: 238
tccgtacggc ccgggtacgc ttcggtcgca gtgtgcgagt gatagatgac gaccgggacc 60
tcgtcggcat cttccatagc ccgccacacc ttcagttgct caccggaatc caaccggtag 120
aaggtcggcg agcgctcggc attggtcatc gggatatgcc gctcgggacg gtcagagccc 180
tcgggtccgg ccagcactcc gcaggcttcg tcggggtggt cgcgacgcgc atgggccacc 240
atccatccac caggtctgcg cgaatcaccc gc 272

<210> SEQ ID NO 239
<211> LENGTH: 410
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 239
ggacacattg cgaacattga tgacaaaata gaaatcattg atggtttgag tcaccaggcc 60
gatcaagcct tcgccgagcc aaattccaat caagaggccc aagcccgtac caatcagccc 120

-continued ggcaacgagg gattccgtca ttatcagcca aaataactgc tctcgggtta cacccaaaca 180
gcgcaatatg gcgaaaaacg gtcgccgttg cacgacatta aatgtcacgg tattgtaaat 240
taaaaagata cccaccaaca aggcaatcaa actgagagcg gttaaattga ccgtaaaagc 300
gtccgtcatc tgtttgacgg tgtcccgttg ggtntccgac gtttccatac gcacaccggc 360
cggcagtctt tgttggatgc gtgttgcagt ggcctcatct ttgatgatca 410

<210> SEQ ID NO 240
<211> LENGTH: 439
<212> TYPE: DNA
<213> ORGANISM: Mycobacterium tuberculosis

<400> SEQUENCE: 240
gcctggccca ggtgaaggcc gacctcgacg ccaaagccgc tgatccggca catgagtcgg 60
tggactggga cttgaagtcg ctgcgatggg cgtggaaccg agccaaagat gacgtggcgc 120
cgtggtgggc cgagaattcc aaggagtgct actcgtcggg gttggccgat ctggcccagg 180
gcctggctaa ttggaaagct ggcaagaacg ggacccgcaa aggccggcgg gtgggcttcc 240
cgcgattcaa atccgggcgg cgtgatcctg gcagggtgcg gttcaccacc ggcaccatgc 300
gcatagagga tgaccggcgc acgatcacgg tcccggtgat cgggccgctg cgggccaagg 360
agaacacccg ccgggtgcaa cgccacctcg tgagcgggcg cgcgcagatc ctgaacatga 420
ccttgtcgca gcggtgggg 439

<210> SEQ ID NO 241
<211> LENGTH: 356
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 241
taactcaagc ttcaagtccg cngtccgacc ctgttcgacg gctacctgaa tcaacccgat 60
gccccgccgc ggcgttcgac ccgacagctg gtaccgcacc ggcgacgtcg cggtggtcga 120
cggcagtggg atgcaccgca tcgtgggacg cgagtcggtc gacttgatca agtcgggtgg 180
ataccgggtc ggcgccggtg aaattgaaac ggtgctgctc gggcatccgg acgtggcgga 240
ngcggcagtc gtcggggtgc tcgactatta tctaggccag cggatcgttg cctacgtagt 300
cggctcagcg aatgtcgatg cggacgggct tatcaacttt gttgcccaac aacttt 356

<210> SEQ ID NO 242
<211> LENGTH: 341
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 242
ccatgtcgcc caacatatcg tcgatgttcg cgtcgtccgc ctcgcgcacg tggtctgtca 60
ccagtcaacg ttaacgccgc cgcacatgtc ctgcggccgg gcaaaaacgt gaaaaacgag 120
cgggcgactg caatgtcatg acaccgacgc cgccgatggg cccagggtct ggcagattcg 180

-continued

```
atctgtgcgg ccagtgccag cagcgtcgcc tcgtcatacg gccggccgac gagttgaacc    240

gacatgggca tgccgtcgcc gtcgaagtcc cacggcacca cggccgcggg ctggccggtc    300

agattccana cttgaaagta ctgaagccgc tgcaccacca g                        341
```

<210> SEQ ID NO 243
<211> LENGTH: 336
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 243

```
cgaaagcgtg aaacagctcg cggcagcccc cgacgtgctg cgtcggatag ccggcgggcg     60

aagatcaatt ccaggcagct cccggacaat gcggctctgc tggcccgcaa cgaaggactc    120

gaggtcaccc cggtgcccgg ggtcgtggtg cacctgccga tcgcacaggt tggcccacaa    180

ccggccgctt gatgcccggt cggcaagccc ggcagttgcc aaacccagcg tgatcntgct    240

cngctctnta nttcggcgaa gaagtggctc gcctgatcac ctaccatcgg ccaggatctg    300

cgtgtcatca caacgctcgc caaggaggtt gttgtg                              336
```

<210> SEQ ID NO 244
<211> LENGTH: 337
<212> TYPE: DNA
<213> ORGANISM: Mycobacterium tuberculosis

<400> SEQUENCE: 244

```
tccgccacgc ttcgcgccgc ccggcatacg gcgcgtaccg atctccgcgt catacaccgc     60

gggtaatcgc cgacggtgcc ggttcgcgag ccgaaggtga cgacgctgat tgaatcgagt    120

tccaggtcca gcgggtggcg cagcaacggc gcgagctcaa cgacgtcaat cacgttgtcg    180

ctttctacgg tcaccgaccc ggtgaccgta gtcgcccggt gcgctcggcc gagaagctgc    240

accgccacca ccgcgacacc gtcttgcacg cggacccacc ccggatcggt tgttggccaa    300

ggtaattggg tcattccatt tgacgggacg ccgaccc                             337
```

<210> SEQ ID NO 245
<211> LENGTH: 337
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 245

```
cattctttaa cagttgtttt gggctcggca tggttagcca acgttctgcg gtccaccata     60

tcatcttggt ccggtagcgc tcgtccgggg tatgctgccg ccgggattct cgctgctatt    120

actccccccg aagaaccgcc accggtccag cgcgtgggcc gncgcggtcc catcacaaac    180

tgaaccccca acagggacat gcttatcggt agggcgcgcg ccaaggcggc agcaatcgca    240

tcactgcgct ctgcgcgtca ctattaaccc acccggactt cacttccacc accccgaatg    300

gcgcccggtc attgatcatc tggcgcaccg cggataa                             337
```

<210> SEQ ID NO 246
<211> LENGTH: 343

-continued

<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 246
cggtgtcctg cagttggtag gcctgcagtt tgtgcatcat gccgatgccg cggcctcgtg 60
gccacgcatg tacagcacca cgccgcgccc ctcacgggcg aacatcgcca gcgcggcgtc 120
cagctgaagc ccgcaatcgc agcggcgtga ccaaacacat cgccggtcaa gcactccgaa 180
tgcaccggac cagcacgtcg tcaccgtcgg cgttgggccc ggcgatctcg ccgcggacca 240
tgcgcgacat gttccacgtc ctcgtanatg ctggtgtagc cgatggcgcg aaactcccca 300
tgacgagtcg gaatccgcgc ctcggcgacc cgctcaatgt gct 343

<210> SEQ ID NO 247
<211> LENGTH: 340
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 247
cggcatctgg cggctgaacc tgttcttggg caacatgccg aggatcgcct cttccaccac 60
gcggtcgggg tggcgttgca ttacctcacc gatggtgcgc ttgtgcaggc cgccgggata 120
ccccgagtgc cggtaaacca tcttgtgctg cagtttgtcg ccgctgatgg cgaccttgtc 180
ggcgttgatc acgatnacna atcaccgcca ncgacattgg gggcgaacgt cggctcgtgc 240
ttgccgcgca gcaggctggc cgccgcgacg caaggcgcca accaccacgt ccgtggcgtc 300
gatgacgtac caccatcgcg tggtgtcacc cgccttgggc 340

<210> SEQ ID NO 248
<211> LENGTH: 322
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 248
gcggcaaaaa ttgaagcact cntggccact nccgccggga gggacaatct cgggcggcta 60
gggcttctcg cgggaaggcc cgaacgtact gcgtttcaac acgtcgcgtc gccctccgac 120
cgcgaacatt ctgggatggc agcaacctgt tagcaccctg gccgggcgat gatctgcagc 180
gtcgccgcgg gtagtcgccc ccgggcggct acagtctgaa acgcgatgac catcgatgtg 240
tggacgccgc atccgacnca acggttccta cactgtgata tgttcgcctc gctgcgccgg 300
tggacggtgg gtctatcccg ga 322

<210> SEQ ID NO 249
<211> LENGTH: 278
<212> TYPE: DNA
<213> ORGANISM: Mycobacterium tuberculosis
<220> FEATURE:
<221> NAME/KEY: unsure -continued
<222> LOCATION: (various positions within the sequence)
<223> OTHER INFORMATION: applicants are uncertain of bases designated as "n"

<400> SEQUENCE: 249
cgcgttgaac tgaaggggtg ccgcccggct cgagcaggca agccatttgt tcgatgcggt 60
taccgaagat ctcttcggtg actgcccgcc gccggccagc tcggctcagt gtccggcgtt 120
ggtcgccgcg gcgacaatct tggcgtccac ggtggtcggg gtcatgcccg cgagcaggat 180
tggcgagcgg ncggtcagcc gggtgaactt cgtcaagagc tgacgctgcg gttggggagg 240
cgaatcatgg tcggtgcgta gcctcgacta ggcccggg 278

<210> SEQ ID NO 250
<211> LENGTH: 336
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 250
tgacaacgcg gcggcgatta ccccgctacc gcagcagcat gacgcggtag cgaacaccgc 60
cggatgcagc gcaggtgcgt cgatgtgctc acggaatcgc cccggcaccg cgatctcgag 120
gatcaccagt gccacccccct gcagcgcgac accgacgatt ccgtacaccg ccacgccgat 180
caggccctgg gccagctgat tggagctggc gtatatggcg gcgatggtga cgatggtcat 240
cgcctcttac attgtggcgg ccagaaccac ggcgttgggg cggcggtcga tgaacactag 300
gcgaccanat ccccggggtc aacaggttga ccatcc 336

<210> SEQ ID NO 251
<211> LENGTH: 95
<212> TYPE: DNA
<213> ORGANISM: Mycobacterium tuberculosis

<400> SEQUENCE: 251
cgcggacatc ccgaacgagg acacgcgacc gcttcggtgt gtgatctatc agggctcgca 60
ccacgcgcaa ccgcttccgg ctacctagac gcggt 95

<210> SEQ ID NO 252
<211> LENGTH: 94
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 252
gcatgcgggt gatgccgttc tcagtgcgca acagcgttcg acgcggcata cccagccgca 60
catgccgtgc acgccggngc cggggcggga atct 94

<210> SEQ ID NO 253
<211> LENGTH: 302
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated -continued as “n”

<400> SEQUENCE: 253
ctcaagcttc agnccntcta agcggtctgc gcggcgatcg caaagatcgc cctttgccgg 60
cgttgggggc ttctgctcgg gggtgttgta caccttctcg aacacctcgg caccgacacc 120
accaccgtcg gcttgaacac cgccaacatc ggcagcanat cttgatgtcc tggtgaatcc 180
acggtgactt tggagtggaa ggcggccata ctgatcgcgc gcgccaccac atgagctagc 240
ggcaggaaaa ccagcagccg ctcacccttg cgcagcagcg tcgggtgata tgcctggcgc 300
cc 302

<210> SEQ ID NO 254
<211> LENGTH: 291
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 254
agtcgaangt cagtccggtc tcctctccga ctacggccaa gaactggggc gacggtgtca 60
gtgcagaaca gcggaaactg gtggcgccct aggcgagcga acgctcacaa acggcggtga 120
ccgcttctgg tcgtgcacca tcgagccgtg cccagcccgg ccgcgtgccg tcagccgcat 180
ccactggatg cccttctcgg cggtttcaat cangtacagg cgacgttcgc caccatcgtg 240
ccggggcacg gttagcgaga aacgccgact tcaccgattg cctcggtgat g 291

<210> SEQ ID NO 255
<211> LENGTH: 454
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 255
agcttcgcgg cgtggcgatc gcggttcaag gcgcgctctt cgagcacaac gagcgaagac 60
agctcggcga cggagccttt atcgacatcc gttcgggctg gctgaccggc ggcgaagaac 120
tgctggacgc gttgttgtcg acggtgccgt ggcgagccga gcgccgtcag atgtncgacc 180
gggtggtcga tgtgccgcgg ctggtgagtt ttcacgacct gaccatcgaa gatccgccgc 240
atccgcagct ggcgcggatg cgccggcggc tcaacgacat ctacggcggc gaactgggtg 300
agcccttcac caccgccggg ctgtgctact accgcgacgg ctctgacagc gtcgcctggc 360
atggcgacac cattggtcgc ggcagcactg aggacactat ggtggcgatc gtcagcctcg 420
gcgccacccg cgtcttcgcg ctgcggccgc gtgg 454

<210> SEQ ID NO 256
<211> LENGTH: 346
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

-continued

<400> SEQUENCE: 256
agcttcagct gatactcgac cagccccact cgggccaata cgtgaatgtc tagcatcttc 60
acccgttcac gggctantcg agtagtagac attgattagc ctgaacgtac ctccgacgcc 120
agctgacgaa cgggtatgac ggatggattt cgtggtgtcg cgcccgaggt caattcgtta 180
cggatgtatc tcggggccgg atcggggccg atgttggcgg ccgcggcggc ctgggacgga 240
ctatccgacg aactggcggt ggcggcgtcg tggtttgggt cggtgacctc gggcctggcg 300
gatgcggcgt ggcgcggccc gcggcggttg cgatggcncg cgcggt 346

<210> SEQ ID NO 257
<211> LENGTH: 339
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 257
ctggtcatgg acgttgctcc ggtagtggct cactgccgat cctcctcgtt gagagtgcca 60
cctcagggtt gggtagggtt gggtactcga aaccaagtta cccaccagta acaccgtcaa 120
aatatatccg ttgcataggt caatgcaagt tgatgtgagc tacattgcac caactaacta 180
accaaccggt tgggttagcg gtgatcctgg ccgtgtcggt cctctcacct gcggtgatag 240
cgatcaaatg aagaatatgc ggagtctagg gcggcagcgc ctggcancgt agatcatcgg 300
ctcacgcgga tgcggcctct tggtacggac atgcgcgcg 339

<210> SEQ ID NO 258
<211> LENGTH: 182
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 258
ctcgtgagta gcacccctgt aatttgggat cggcaaaaag gcgaatcacc gcgtggccac 60
gacacgccgg gagggacnat ctcgggcggc tagggcttct cgcgggaagg cccgaacgta 120
cggcgtttca acacgtcgcg tcgccctccg accgcgaaca ttcggggatg gcagcaacct 180
gg 182

<210> SEQ ID NO 259
<211> LENGTH: 213
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 259
ggatcaacta ccggccaacg gtgattcttg ggcgccgctg acgcgcgaac gacccagcga 60
cacattcagc agatggccag cgcgtgccgg gccacgatgt tggtgctcgg cggctactcc 120
catggtgcgg cncgtgatcg acatcgtcac cgccgcacca ctgccggcct cgggttcacg 180

-continued cagccgttgc cgcccgcagc ggacgatcac atc 213

<210> SEQ ID NO 260
<211> LENGTH: 321
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 260
aggaccgtca gcacggcgac gtgctactcg ccgagcagtg ggaatcgctc tgcagcaaac 60
cattactctg cgcgacgttc gagatgacct tctgaatgga cggatctacc tgccgcgcga 120
cgacctggac cgcgtatgcg tccgcctccg cctggacgac accggggcac tctatgaccc 180
cgacggacgg ctcgcggtac tgctgcggtt caccgccgac gcccgcacgg tacgcgtcgg 240
gactgcgctg agtccancct cgacgccgta gcgctgctgc tgtgcggcca tgtctggcat 300
ctaccgccgt cgctcccttg a 321

<210> SEQ ID NO 261
<211> LENGTH: 334
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 261
cgactctgtt ggccactgcg ggtcgatctt gcggccgccc cggtcgtgga acgcccaggt 60
cacccggcgg cgcaccgcgg tcagcgcgtc gttggccagc gtggtcacat ggaagtggtc 120
gacgacgagc ttggcgttgg gcagcagccc gggcgtgcgg atcgccgagg cgtatgcagc 180
ggcggggtcg atggccaccg tactggatgc tctcccggaa ctgcggtgtg cgcgcttgca 240
gccatgccag caccgccgcg ccgccgcggc cttcatgctg cccataaacc ctgataccgg 300
ccaggtcgac naaccngtat cccacggtca accc 334

<210> SEQ ID NO 262
<211> LENGTH: 208
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 262
cacacggacg gcggtgcgga cgcagctgac gcgcatggtg gtcagcatcg cggccggtct 60
gctgttgtat gcctacttcg cgccgcgcaa atgctggtgg gcggcggtgg tggcgctcgc 120
atggctgggc tgggtgctga cccaactctc gaaccacacc ggtgggtggg ctgggctatg 180
gcctgccata tcggcctggt gttctacn 208

<210> SEQ ID NO 263
<211> LENGTH: 233
<212> TYPE: DNA
<213> ORGANISM: Mycobacterium tuberculosis
<220> FEATURE:

-continued

```
<221> NAME/KEY: unsure
<222> LOCATION: (various positions within the sequence)
<223> OTHER INFORMATION: applicants are uncertain of bases designated
      as "n"

<400> SEQUENCE: 263

ccgatatccg agccgatagc tggcgggctc gggtggtngc cagcggcgct gcgacgaaag     60

tgtgaccgtc atgaaacaga caccaccggc ggccgtcggc cgtcgtcacc tgctcgagat    120

ctcagcatcc gcagccggtg tgatcgcgct ttcggcgtgt agtgggtcgc cgcccgagcc    180

cggcaaacgc cggcccgaca caaccccgga acaggaagtc cggtcaccgc gcc           233


<210> SEQ ID NO 264
<211> LENGTH: 320
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 264

gcttcaggac aaattgnatc cctatgcacc cgttgtcacg ccgatgagtg aagactgcac     60

gcaatcgccg gaatccggca aaaccctgca caagcgaaat caaccggagg ctgacaaggc    120

aacgtcggtg atccgtaccg cctggttgga caaacggcag aaggcgcctc gtccggtcca    180

tctacgccga gcacactggt gatagcgcca tcggcatcgg tgcggccacg gtggagacga    240

acgtccgcng gcgtctgggt cagtaacccg ccgaccagtt ctcgggcaag ctggtcaaca    300

tcgggcgcca cgtctccaac                                                320


<210> SEQ ID NO 265
<211> LENGTH: 304
<212> TYPE: DNA
<213> ORGANISM: Mycobacterium tuberculosis

<400> SEQUENCE: 265

gtttggcggc cttattgcac tgaggtcgtc aattgaccca cagcggaaat gccgactatt     60

cgcaggcctc cttcgccttg gctgccggag atgggctccg cgggaaccgc atgcaggtat    120

atgacctcgg tttctcgggt gctaccgcgt gccttgtcga ggatgaactc ggcgttggaa    180

ttgtccagcc ggcccaattc atcgagcgca gattcgtaca catggccggc ggcgacatac    240

cttcaccgtg gatctgctcc acacggaccg ccctgtcggg atctgctcac gggtaaagga    300

atta                                                                 304


<210> SEQ ID NO 266
<211> LENGTH: 217
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 266

gcgcactcct ccttatcgct ccgctctgca tcgtcgcggc gcggtcaggt gcaaacgcct     60

tcgggggtgg gggtcctgcg gagcacaccg gatacggagc gcaacgcgtc gcgttgtgcg    120

ggcaaacaag tgtgcaggnn ccaatgccat gtccagcagc ttatcagtgt cgaacgtgcg    180
```

-continued

```
aacgtcgcgc cttcgccggt gcctgaatct ctacaag                          217


<210> SEQ ID NO 267
<211> LENGTH: 174
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 267

cgctgaaagc caccattcgc gggtcgggcg ccgggctcgg gccgccaggc tgctccgctc     60

ggtgatggca cgccaccgcg acaccacccg gctgcgctac gtcgagccat accgggcgga    120

gctacatcgg ctcggccgcc tagtgttcgg gncctctttc gaggtcgagg tcga          174


<210> SEQ ID NO 268
<211> LENGTH: 144
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 268

tgtaatttgg gatgggcaaa aagcaaanca ccgcgtggcc acaaacgcgg ggagggacaa     60

tctcgggcgg ctagggcttc tcgcgggaag cccgaaacgt acggcgtttc aacacgtcgc    120

gtcgcctccg acgcgaaatt cggg                                           144


<210> SEQ ID NO 269
<211> LENGTH: 216
<212> TYPE: DNA
<213> ORGANISM: Mycobacterium tuberculosis

<400> SEQUENCE: 269

cttgggcaac atgctgagga tcgccttttc accacgcggt cggggtggcg ttgcattagc     60

tcaccgatgg tgcgcttgtt gcaggccgcc gggataccg agtgccggta aaccatcttg    120

tgctgcagtt tgtcccgctg atggcgacct tgtcgcgttg atcacgatga cgaagtcacc    180

gccatcgaca ttgggggcga actcggcttg tgcttg                              216


<210> SEQ ID NO 270
<211> LENGTH: 199
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 270

gcatgcttca ttatctaatc tccagccgtg gtttaatcag acgatcgaaa attcatgcag     60

acggtcccaa atagaaagac attctccagg caccagttga agaggttgat caatggtctg    120

ttcaaaaaca agttctcatc cggattgaac tttaccaact tcatccgttt catgtacaac    180

atttttagaa ncatgcttc                                                 199


<210> SEQ ID NO 271
```

-continued

<211> LENGTH: 230
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 271
atactcaagc ttgatgccgc cgaaaccgag cgtgagcacg ccgccagcca ccacgcgcgg 60
gtcgggcgcc gggcccgggc cgccaggctg ctccgctcgg tgatggcacg ccaccgcgac 120
accacccggc tgcgctacgt ctatccatac cgggcggagc tacatcggct cggccgccca 180
ttgttcnggc cctctttcga ggtcgaggtc tataccgatt tgcgcatccg 230

<210> SEQ ID NO 272
<211> LENGTH: 188
<212> TYPE: DNA
<213> ORGANISM: Mycobacterium tuberculosis

<400> SEQUENCE: 272
tccgtactgg tcgggtacgc ttcggtcgca gtgtgcgagt gatagatgac gaccgggacc 60
tcgtcggcat cttccatagc ccgccacacc ttcagttgct caccggaatc caaccggtag 120
aaggtcggcg agcgctcggc attggtcatc gggatatgcc gctcgggacg gtcagaacct 180
cgggtccg 188

<210> SEQ ID NO 273
<211> LENGTH: 158
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 273
gttctcgcac gatttcggat tagcgggatg gtctcaattg ggtatgcggg gaaggcgctg 60
acattcgccg cgattagctg tttgatggac cgggggtgat ttttgatcac ggaaatgggt 120
gtttatncag gtcgcacgct ttcatccggg gcggaacg 158

<210> SEQ ID NO 274
<211> LENGTH: 237
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 274
gggtgtgcct gctgtgtatg cacggcatac ggacatcctt cccctgaaga cccgcggtcg 60
aacagccacg tgtccatcat canggggtca accccggcca agggcgacgg cacgccaagt 120
tcgccgaccg ttaacctagt gctgttagct tcatttgctg cgagcaaaac agctggtcgg 180
ncgttaggaa tgaattgaaa ctcaaccgat ttggtgccgc cgtaggtgtc ctggctg 237

<210> SEQ ID NO 275
<211> LENGTH: 262
<212> TYPE: DNA

-continued

<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 275
actacccggc caacggtgat ntcttggccg ccgctgacng cgcgaacgac gccagcgacc 60
acattcagca gatggccagc gcgtgccggg ccacgangtt ggtgctcggc ggctactccc 120
anggtgcggn cgtgatcgac atcntcaccg ccgcaccact gcccggcctc gggttcacca 180
gccgttgccg cccgcagcgg acgatcacat cgcttttatt tnntnttcng gaatccctcg 240
ggccgcgctg gcgggctgat ga 262

<210> SEQ ID NO 276
<211> LENGTH: 222
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 276
acgtcgggan actgttcgcg ttcatcctcg tctcggcgga ttggtctgct gcgccggacc 60
gaccgatctt cagcgggggg tcacgctccg tggggtgccg ttacttccga tcgcccagtg 120
tgcgcgtgct gtggctgatg ctgaacctca ccgcgttgan ttggatcggt tcgggatctg 180
gctggtggcc ggaacgcnat ttatgtcgct acgggcgccg gc 222

<210> SEQ ID NO 277
<211> LENGTH: 166
<212> TYPE: DNA
<213> ORGANISM: Mycobacterium tuberculosis

<400> SEQUENCE: 277
gctcaaaggc actactggca ccaaggccca cacgtcacct gtgactcctg cgccgacccg 60
cccgaggtct ggccgttaca ccgaacgggc gagccgggag ttggtaccat cgaacaagac 120
aaggtgcatg ggcggagttg ttccgccact tcgtcgatga cgggtc 166

<210> SEQ ID NO 278
<211> LENGTH: 330
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 278
cgataccggc tgcttaccga gacatccacc atgccacccg aatcaccgca cgcgccgaaa 60
tcgcacaaca gcttgacgcc ttgcaggttc cgcgattgga attgccgacg gtctctgacg 120
gcgtcgacct tggcagcctc tacgagctct cggaatcact tgcccagcag ggggttcgat 180
gagtgtcaca ccgaagacct cgatatgggc gcaatcctgg ccgacacatc caaccgggtg 240
gttgtgtgct gcggcgccgg tggggtcngc aanacactac cgcggccgcg ctggcgttgc 300
gcgcggccga atatggccgc actgtggtcg 330

-continued

<210> SEQ ID NO 279
<211> LENGTH: 332
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 279
cgtcgtcgtc gtggtatgcg atagccatcc cgtcgggcta ctcgccatca ccgatcagct 60
tcgccccgaa gccgccgcgg cgatttccgc tgcgaccaaa ctgaccgggg ccaaaccggt 120
attgcttacc ggcgacaacc gggccaccgc cgatcggctc ggtgtacang ttggcatcga 180
cgacgtacgg gccgggctac tgccgacgac aangtcgcag ccgtgcngcn gctgcaagct 240
ggaggtgcca gattgaccgt ggtcggtgac ggtatcaacg acctccggcc ttagcggccg 300
cgcatgtcgc atcgccatgg gcagcgcccg ac 332

<210> SEQ ID NO 280
<211> LENGTH: 222
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 280
gcacgcaatc gaagtcaccc aaaccgggcg ggccaggcgt ctnacgccac gtcnaccagc 60
cgcaacctca acccggccac ggcgagctcc tgatcaaggc cgaggccatc ggtgtctact 120
tcatcgacac ctacttccgc tccgggcaat atccgcgcga actcccgttc gtcatctgct 180
ccgaagtatg cggcacggtg gangccgtcg gccaggggtt ac 222

<210> SEQ ID NO 281
<211> LENGTH: 184
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 281
tcgactgtgt ggccacagat cacgccccgc atgccgagca cgagaaatgc gtcgaattcg 60
ccgcgggccg gccggcatgc tcgggttgca gacggcattg tcggtggtgg tgcatacaat 120
ggtggcgccg gcttgttgan ttnggcgcga tatcgcgcgg gtgatgagtg anaaccggcg 180
tgca 184

<210> SEQ ID NO 282
<211> LENGTH: 409
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 282

-continued

```
gaacctgaca ccctggtcac gggtgagcac ggacttgatt tcttcnctat tggtcggcgc     60

tgttgagcac accacgccgc tgacggccgt cgcgtcctcg ctgtgctcgg tctggtggag    120

cgcgctgccc gcggccnaac atcntaaatc aagcgtattc gtcaacagat atcatcaatg    180

tcggcgctgg actattcaaa tcatcgatat actggtgacc tggtccttcg ccatcgatca    240

atggcgatag tcacgcaaat cgtcacggac atcgtcggcg tcccagctgg cccgtgccaa    300

cagatgctgc aacccatcgg ggtggtatca ccgcggtgct cggcgatggt ccacaattct    360

tgcggtccaa gcccnaaaca tcccgggcat gaattcaccg gcatgcgcn                409
```

<210> SEQ ID NO 283
<211> LENGTH: 413
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 283

```
ctatcgtacc cgcgccggtc accttctgga tatcgccggc ctggtcaagg gggcgtccga     60

gggagccggg ctgggtnaca agttcctggc tcatatccgc gaatgcgacg ccatttgtca    120

ggtggtgcgg gtgttcgtcg acgacgacgt gactcatgtc accggacggg tcgatcccca    180

gtccgacatt gaggtcgtcg agaccgagct gatcctggca gatctgcaaa ccctggagcg    240

ggccacgggc cggctggaga atgaagcgcg caccaacaag gcgcgcaagc cggtctacga    300

agcggcactg cgtgcccagc angtgctcga cgccgggcaa gacgctgttc gccgcggggg    360

tggatgccgc cgcgttgcgc gactgaaact gctgaccacc aagcccttcc tgt            413
```

<210> SEQ ID NO 284
<211> LENGTH: 283
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 284

```
tactcaagct tcaggccgcc acgtccgccg tccgtcggcg acgtgacctc gagcgccgag     60

ttcgactcga catcgccgcc ggcgcatgcc gacatgaacg cggcactcac cgcaagcccg    120

tcggacgtca ggtcgatcga ctccgcttca agcaccggat cgtccgggca actcgcggcc    180

tcggcctgtg cgaacggcac acccgtcgtg gcggcncccc gcgcggaact gggctcatca    240

cggtcgttgc gagccggtcg cgtcaccgcg taccgacgcc gtc                      283
```

<210> SEQ ID NO 285
<211> LENGTH: 397
<212> TYPE: DNA
<213> ORGANISM: Mycobacterium tuberculosis

<400> SEQUENCE: 285

```
ccgacatcga gtgggctcgc agtgacttgg cgacctccaa gccaccggta cccgccgcgc     60

ggcaagccaa ggacgacgac ggccttgccg gatagctgcg ccaggcgttg cgccaactgg    120

cgtccagcgt cgccacgatc gtcaaagagc ttcatctgcc gagtgtgtcg ccatctcatg    180
```

-continued gctccaaata tggaattagg tccctgggcc gactgacgac agtccctcag cgaccggatt 240
gcgcatcccg ccttgtacgc tactccgcaa atcccgggct tgcgtccgcg gaagcgaact 300
cggcggcgct acgtggtggt tcacttcggc cgtgcgcact cggatcgacg ggccgatggt 360
ggccgggccc gcgcgcttct tggtcatccg attgagt 397

<210> SEQ ID NO 286
<211> LENGTH: 342
<212> TYPE: DNA
<213> ORGANISM: Mycobacterium tuberculosis

<400> SEQUENCE: 286
atactcaagc ttgtcgcggt aaaccgcacg cagggcggtg ggtgcggtgt caaagacacc 60
cacacttctt tgcggttcgg tgatctcgac accggccgcg agccgaccac catgcgcgcg 120
tagatcggcg atcagcgcgt cggctatcgc ctgggtgccg cccaccggaa tcggccagcc 180
gaccgaatgg gccagcgttg ccagcatcag tccggcgccg gccgacacca gtgacggcaa 240
cggtgaaatc gcgtgggcgg caacgccggt gaacaacgcg cgggcatcct cgcccgccaa 300
cgaccgccag gcagggtgcc tgggccatca tccgcagccc ga 342

<210> SEQ ID NO 287
<211> LENGTH: 430
<212> TYPE: DNA
<213> ORGANISM: Mycobacterium tuberculosis

<400> SEQUENCE: 287
tggactcata acgatcgggt cagcgacgcg ccaacacgaa cggccggacg agtgggccag 60
ggtcgcgcct cccctacaaa caggatccgt tgcctgcgag cgacaggctc cggtgcggcg 120
ttgggcgccg tgctcgtccc agcgtccggt cccgggtcgc cggcgacgct tgtttcctcc 180
atactcgccc cctaatctcg aggcagcccg tacccgcagg caacctccca aaaatgcaat 240
cccccaaaat gcaatgcgtc gagctatttc tcacaccgac cgctagttgc ggatcagaaa 300
tccgttgggc gcggaagtcc agccgaattt gttctcccgc tccgcatcat gcttgtaatc 360
gtttggaaat catcctcata tgcctcgatc gcttcatagg tcaagcccaa acccggcagg 420
atgggtggcc 430

<210> SEQ ID NO 288
<211> LENGTH: 473
<212> TYPE: DNA
<213> ORGANISM: Mycobacterium tuberculosis

<400> SEQUENCE: 288
ctttacactt tatgcttccg gctcgtatgt tgtgtggaat tgtgagcgga taacaatttc 60
acacaggaaa cagctatgac catgattacg ccaagctatt taggtgacac tatagaatac 120
tcaagcttag tggttgcgca cgtaaattcg tcaggtgacc gatcccctgc tgtctcactc 180
gcctcacagc gaccaccacg gctggcgctc aaggcgggca cgtgcggagc agatgaggaa 240
tgtgcgacgt cttgatgcag cctgtcagaa caccgagacc ctcgacgaac ttacgatcga 300
aaccgcttag gccaaccggt gacgggggtg tctttccgcg gctagggcgc cttatcgtcc 360
gaaggccgtg ggtggtgatc gccttctggg tcgcgcttgc gggtctgctt gcgccgacgg 420
tgccgtccct ggaccgatct cccagcggca tccagtggcg attctgccat cgg 473

<210> SEQ ID NO 289
<211> LENGTH: 418

-continued

<212> TYPE: DNA
<213> ORGANISM: Mycobacterium tuberculosis

<400> SEQUENCE: 289
caggcatgca agcttgcgat gtatcaacac gccgttgcgc agcgtgagcc gatagttgac 60
atccggctcg gtgaaggtga aatcgatggc caggtcgagg tcccatgcgc gtgggccatt 120
gatgctgatc gccaggacgt caaagatttg gtccggcgtc agctgggcga aaaacgtggg 180
cgccgggact tgcccggagc tgcccgggtt cccgtcgcgc agctcggcgg ccccggtcag 240
aaagaaattg cgccaggtcg cacactccgc gccgtaggcc agctgctcca cggtgtcggc 300
atatagcccg cgggccgcag cgtgctcgct gtcggcgaac accgcatggt cgagaagcgt 360
tgccgcccaa cggaaatcac tgcgtcaaag cttcgccggg ccactccagc actccgtc 418

<210> SEQ ID NO 290
<211> LENGTH: 194
<212> TYPE: DNA
<213> ORGANISM: Mycobacterium tuberculosis

<400> SEQUENCE: 290
atactcaagc ttgaccgacg ctgatcgcac cgcacgcggg aacctcaagg gcactactgg 60
cacaagggcc cacacgtcaa cctgttaact cctgcgccga ccccggccga agtccttggc 120
gttaacaccg aacgggccaa cccgggaatt tgggttccat caaaacaaat agcaggtgcc 180
tgggcggagt gttc 194

<210> SEQ ID NO 291
<211> LENGTH: 166
<212> TYPE: DNA
<213> ORGANISM: Mycobacterium tuberculosis

<400> SEQUENCE: 291
gtcgtcgtgt gctggggcgt ccgtatcagc acgcccacga aatggggcac aagaaggatt 60
cctggaacgg tggctgtcca agatcaccct cgcccaaaac tgctacgggc acttctacat 120
cgagcacaac cgtggccatc acgtccgcgg tgtccacacc gggagg 166

<210> SEQ ID NO 292
<211> LENGTH: 291
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 292
atatgccttg ctgagctttt cggatcgcag cgagtcgtac ccgcgccggt caccttcgtg 60
gatatcgccg gcctggtcaa gggggcgtcc gagggagccg ggctgggtaa caagttcctg 120
gctcatatcc gcgaatgcga cgccatttgt caggtggtgc gggtgttcgt cgacaacgac 180
gtgactcatg tcaccggacg ggtcgatccc cagtccgaca ttgaggtcgt cgagaccgag 240
ctgatcctgg cagatctgca agccctggag cgggccacgg ggcggctnga a 291

<210> SEQ ID NO 293
<211> LENGTH: 442
<212> TYPE: DNA
<213> ORGANISM: Mycobacterium tuberculosis
<220> FEATURE:
<221> NAME/KEY: unsure -continued
<222> LOCATION: (various positions within the sequence)
<223> OTHER INFORMATION: applicants are uncertain of bases designated as "n"

<400> SEQUENCE: 293
gacaccctgg tcacgggtga gcaggactcg atttcttcgc tattggtcgg cgctgttgag 60
gcacagcacg ccgctgaggc cgtcgcgtcc tcgctgtgct cggtctggtg gagcgcgctg 120
cccgcggccg aacatcgtaa atcaagcgta ttcgtcaaca gatatcatca atgtcggcgc 180
tggactattc aaatcatcga tatactggtg acctggtcct tcgccatcga tcaatggcga 240
tagtcacgca gatcgtcacg gacatcgtct gcgtcccagc tggcccgtgc caacagatgc 300
tgcaacccat cggggtggta tcnccgcggt gctcggcgat ggtccaacaa ttcttgcggt 360
ccaagcccga aaccatccgg ccatgagttc accggcatgg cgcaacggct ggtgccgggc 420
aaaacgcggc gcgatcgaat tc 442

<210> SEQ ID NO 294
<211> LENGTH: 150
<212> TYPE: DNA
<213> ORGANISM: Mycobacterium tuberculosis

<400> SEQUENCE: 294
tgtagaaggt gggtcccgtc caacttcgcg gcggcggcgc gatatgcctt gctggtcttg 60
ctcatttgat atccaatcta tgggtcgtgg ttactcaacg ggccgaagct ggccctccca 120
cgggtagggt cctattcgac ggtgatgtcc 150

<210> SEQ ID NO 295
<211> LENGTH: 321
<212> TYPE: DNA
<213> ORGANISM: Mycobacterium tuberculosis

<400> SEQUENCE: 295
cccgaatccg gtggccggca gggggcctgg cgacgtggac accttctaac ttgtctttac 60
cggtcactgt tgcaccccaa cacctttaac gacgtggacg gacgttacat cggattcgac 120
ggtgtcatcc acagcgttgc cattgggcac acccactacg ccaatttctc cgactgggac 180
acctaccgca gcctcgcccc actgcaggga ctgttgttcc cgcaacgggc catcgacatg 240
atccagtcgt tggtgaccga cgcggagcag actggtgcgt atccgcgttg ggcgctggcg 300
aaattccgcc accggcatga t 321

<210> SEQ ID NO 296
<211> LENGTH: 184
<212> TYPE: DNA
<213> ORGANISM: Mycobacterium tuberculosis

<400> SEQUENCE: 296
ttgagatgct ggtcgggatg ccgatggttg gaacatggtc ccctggcgtc gaatacgcgc 60
gagcgcatga gctcaccggt tcggaacaac gtatcgaaga actcgcactg ctggcagatg 120
gtatctccga tgtggttgta atttgtatcc caactctaac tgtgctatcg gatctgcgtg 180
aata 184

<210> SEQ ID NO 297
<211> LENGTH: 259
<212> TYPE: DNA
<213> ORGANISM: Mycobacterium tuberculosis
<220> FEATURE:
<221> NAME/KEY: unsure -continued
<222> LOCATION: (various positions within the sequence)
<223> OTHER INFORMATION: applicants are uncertain of bases designated
as "n"

<400> SEQUENCE: 297
cgtaatcacg atcccgctga gacacttgac cttacggccg aagtgacttc gctgctgcta 60
tgccgacacc cgatttccat acgctgctgt acacgacggc cgggccggtg gcctccatca 120
cgctcaaccg cccggaacag ctcaacacca tcgtcccgcc catgcccgac gagatcgagg 180
ccgctatcgg gttggtcgaa cgcgaccagg acatcaaggt catcntnctg cgcggtggcg 240
ggcgcgcctt ctccggcgg 259

<210> SEQ ID NO 298
<211> LENGTH: 369
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 298
caagcttaag ctggttccgg ccactccatg agccgtagtg caatggttcg tgcacggcga 60
ggccgaactt gccataaaca tccctgacga aagtctccgg caagccgatt gcttcttcgg 120
gccgcttctt gtggattgtc cgataacccg gtccctcatg ctggaagttg tgcgcactct 180
ttccttccgc gatgtgggct aacgactcgt cattgagcaa gaagtacgtg cacaggcatc 240
gtccgccggg cttcagcacg cgggagatct cgtccagata gtgctccacg tccggnggga 300
aacatgtggg tgaacaccga ggtnagaaac accncatcca acgacgcatc cgggatatgg 360
aaagcgaaa 369

<210> SEQ ID NO 299
<211> LENGTH: 387
<212> TYPE: DNA
<213> ORGANISM: Mycobacterium tuberculosis

<400> SEQUENCE: 299
tatggtcttc gtcgaccagt acgtcgtagg cgccatgagc cagcgactga agccgcgcca 60
tgcctgcacg gcccgctcat ccagcgaggc ggccatctcc cgcagatagc ctgccgcctc 120
ggcgcgcacg ctgtccggat cgcgtccgag ctcgtcggcc agcgcacgca gccgctcgtc 180
ataccatcgg gcatccagca gttgggtaac ctcaacgggg tcggtcgcta gcggcgtcat 240
tgattcagca acaataccga tgcgctgcag caactttcgc agtccgatgc ggcccacctc 300
ccgtgcagtc actggctagc ccccgtcatg ccggttgtgt cgatggcacg gcagcgggct 360
cgtaaacctg cggtctcagc tcgctgg 387

<210> SEQ ID NO 300
<211> LENGTH: 73
<212> TYPE: DNA
<213> ORGANISM: Mycobacterium tuberculosis

<400> SEQUENCE: 300
gcttagcggt cttgctcgaa ccgacattgc gtgccactca tgagcgggtg gcggtcgcgg 60
tgcttacaca tct 73

<210> SEQ ID NO 301

-continued

<211> LENGTH: 156
<212> TYPE: DNA
<213> ORGANISM: Mycobacterium tuberculosis

<400> SEQUENCE: 301
gtatctggcg cctctcgaat atccttgaac gtcccgcggt gccacccaga tagatcgcag 60
cgccctgcaa tggagttccc tttatggcct ctctagcctc ccgcttgatc ggctcgaccc 120
gagagatgcc ctcgggcgtt gcgggatctc cctcca 156

<210> SEQ ID NO 302
<211> LENGTH: 394
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 302
cttcacgccg atccgcgacc gcgaacgcga cggtgacggt gggcgacaag gttcggttgg 60
tcgccgcggc gctgggcgat atcagctcac ccggtttcga ggtgttcggc gaccggacgg 120
tgctgcagac attcttgagc gtcctcgacc ggcccgattc ggccttcaac atcgtgacgc 180
cgtatttcgg cggtaccgct cggcgccgag tcgaaggcgg cctgagctaa agccgggcat 240
tgcgcgagtg gtaaacaagt tcggtgactt cggttgaccg actcgacggg ctcgatctgg 300
gcgcgctgga ccggtatctg cgttcgctgg ggatcgggcc naccgcnant tgcgttgcga 360
nctgattccg gtggagctcc aatctgactt ccgg 394

<210> SEQ ID NO 303
<211> LENGTH: 404
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 303
gcagctaccg accctagcga cgagtgtgtt cgcagcgtcg aatgtgaacg ttcggcgtga 60
ttcggcgcgc gggttcccgc tctcagcgca cgttcggcgc cgaggnggct agtccctggt 120
taagcaatgt ctcggtcgcc gccagcagcg cgcatgtcgc caacccgtcn accgcgttgc 180
gcatgtccgg taccgacgga aacgacggcg cgatccggat gttcttgtcg tccggatcct 240
ttcgatacgg gaacgacccc ccgcctcggt caccgcgata ccaacgtcct tagccaangc 300
tacngtccgg cgcgcggtcc cgggcaacac gtcgaagctg atgaantaac cacccttggg 360
ctcggtccaa gangcgatct tggactcctt aaccgctgat ncaa 404

<210> SEQ ID NO 304
<211> LENGTH: 479
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 304

-continued

```
tccccatcgg cgccggaccg tttgaaagtc caagcacggg tgggatggaa tcgacgacag     60

ttgagcgccg tcggtggccg tggtcagcag ctgttcgcga acgcaccagg tcacatccct    120

tcgacatctc accgacgtgg cacgggcgac atcaacagga agattgacga atccctcgca    180

ggcgcggcac gtccgcaggc caacgccaac tacggggcca ccagcgatcc tccgctcacg    240

caccagccca agccaggctc anccacccaa gtcggcccgc gctctccctc gccccctggt    300

ctccggggcc ttgttaaaca actaccggaa gtccaccaat cctcgctgca tctcgacacc    360

gtccgcctca ctcccttcct cccgcccctc tccacacnac acacctcttg cattaaggtc    420

acggagcggt cacttttcgt cggacgaaat tcgcaatccg gccgctcgcc gccagagat     479
```

<210> SEQ ID NO 305
<211> LENGTH: 260
<212> TYPE: DNA
<213> ORGANISM: Mycobacterium tuberculosis

<400> SEQUENCE: 305

```
cggaaagtgg atactcccag caggtagcag gtcgccacca cgctggtcag tgcgcgttca     60

gctcgcttgc ggcgctgcag cagccagtcc gggaaatagc tgccctggcg cagcttgggg    120

atcgcgacgt cgatggttgc ggcacgggtg tcgcaaatca cggtggcggt agccgttgcg    180

ctgattggac cgctcatcgc tgcgttcgcg gtagcccgcc ccgcacaggg cgtcggcttc    240

agcccccatc aaggcggcga                                                260
```

<210> SEQ ID NO 306
<211> LENGTH: 464
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 306

```
ggccgagtcc agcacttcgc actatgtgca gaccaaanac ccggtggtcg ccgcgctgcg     60

gcagcggctg gcaacggcgc cggtgatcac cgagtggtgc gnagttgccg accggcagtt    120

cgccgcgggc ttactacgag aagggcctgc gcgacgtcat caggtatcac gtgtcgatga    180

cgtcgagcgt taacttcccc gaccagacgg cgacctcgcc gatggacccc gcgttgtacc    240

tggtgtgggc gcaagctaac gccgccgcan gctatcggta ctcggtcgaa gcgcagccgg    300

ggtcgcaagc gctagcgggc aaggtcgcga cgatctcggt cacctggacc aactacggcg    360

ctgctgccgc caccgaatag tgngtgcccg gctaccggct ggtggattcc acgggacatg    420

tggttcggac ctgccggcag cggtggaact gaagangctg gtct                     464
```

<210> SEQ ID NO 307
<211> LENGTH: 315
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 307

```
agcttcaagg acatcgtcat cgcgaccaaa accgcgagct aggtcggcat ccgggaagca     60

tcgcgacacc gtggcgccga gcgccgctgc cggcaggccg attaggcggg cagattagcc    120
```

-continued

```
cgccgcggct cccggctccg attacggcgc cccgaatggc gtcaccggct ggtaaccacg    180

cttgcgcgcc tgggcggcgg cctgccggat caggtggtat atgccgacaa agcctgcgtg    240

atcggtcatc accaacggtg acagcagccg gttgtgcacc atcgcnaacg ccaccccggt    300

ctccgggtct gtcan                                                     315


<210> SEQ ID NO 308
<211> LENGTH: 331
<212> TYPE: DNA
<213> ORGANISM: Mycobacterium tuberculosis

<400> SEQUENCE: 308

gctcgcggtc cagcagcaga cgtgtctgac cccgacgccc ggccgccggt accgaaaccg     60

gatcggcccg ccgatggccg cggccacggc gtctgcctta cccggcccgg ataccagcag    120

ccacacctcg cgggaacgct gaatcgccgg caggtcaag gtgattcggc gtggcggcgg     180

tttcgcgaat cgtccaccgc caccaccatg cgggtgctct cgaagacgcg gggctgtgcg    240

ggaacagcga gttaatgtgg ccctcgggcc ccatgcccag caggtggacg tcgaaattcg    300

gcccgggtca cctggtgcgg cactggcggc c                                   331


<210> SEQ ID NO 309
<211> LENGTH: 286
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 309

agcttgtcga tcgtccggca gcgtccggcg agtcaagtcg aagccagtcc ggtctcctct     60

ccgactacgg ccaagaactg ggcgacggtg tcagtgcata ccagcggana ctggtggcgc    120

cctaggcgag cgaccgcctc acaaacggcg gtgaccgcgt tctggtcgtg caccatcgag    180

ccgtgcccat cccggccgcg tgccgtcagc cgcatccact ggatgccctt ctcggcggtt    240

tcaatcaggt acaggcgacg ttcgccanca tcgtgccggg gcangg                   286


<210> SEQ ID NO 310
<211> LENGTH: 331
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 310

ttggtgatca tcgncccaac gaccccgagg cgatgttctt gcacaccgag gagtgtcgca     60

agctggggct ggccttcgcc gccgatccgt ctcagcagct ggcgaagctg tcggggtgag    120

gaaattcgca ggctcgtcaa cggtgctgct tacttgttca ccaacgacta ctaatgggat    180

ctgctgctgt ccaagaccgg ctggtcagan gccgatgtga tggcgcagat cgacctgcgg    240

gtgaccacat tgggtcctaa gggtgtcgat ttggtagaac ctgacgcacc accatccacg    300

tcggcgttgg tccccgaaac agccagaccg a                                   331


<210> SEQ ID NO 311
```

-continued

<211> LENGTH: 458
<212> TYPE: DNA
<213> ORGANISM: Mycobacterium tuberculosis

<400> SEQUENCE: 311
ggctcgtatg ttgtgtggaa ttgtgagcgg ataacaattt cacacaggaa acagctatga 60
ccatgattac gccaagctat ttaggtgaca ctatagaata ctcaagcttg attttgatca 120
tcatgatgat catcacccga agtgtggtag ccgcagtggt tatcgtgggt accgtcgtgc 180
tttccatggg cgcctctttc gggctttccg tattggtctg gcaggacatt ctgggtatcg 240
agttgtactg gatggtgttg gcgatgtcgg tgatcctgct cctggcggtg ggatccgact 300
acaatctgct gctgatttcc cggttgaaag aggaaattgg ggccggattg aacaccggaa 360
ttatccgtgc catggctggt accgggggag tggtgacggc tgccggcatg gtgttcgccg 420
ttaccatgtc gttgtttgtg ttcagcgatt tgcgaatt 458

<210> SEQ ID NO 312
<211> LENGTH: 289
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 312
caggcatgca agcttggcgt gccgttccaa cccgaattgg ctttcggcgc catcggtgag 60
gacggcgtgc gggtgctcaa cgacgacgtc gtccgcggga cacacctcga tgctgccgcc 120
atggacgcgg tcgaacgcaa gcagctgatc gagctacaac gccgcgcgga acgcttccgc 180
cgcgggcgtg accgcatccc gttgaccggg cggatcgcgg tgatcgtcga tgacggcatc 240
gccaccggag cgacggccaa ggcggcgtgc caggtcnccc gggcgcacg 289

<210> SEQ ID NO 313
<211> LENGTH: 154
<212> TYPE: DNA
<213> ORGANISM: Mycobacterium tuberculosis

<400> SEQUENCE: 313
ggcatcttgg ccgccatgtt agccacactg ccaccggcta tagaagcgat gcgcaccgtc 60
ctgccagcac attgcggcgc tcctccctgg aaagcaagat aaccaagctc atgccgtggt 120
tgtgggtggc gtggtttggt ttgggtaact ttgg 154

<210> SEQ ID NO 314
<211> LENGTH: 324
<212> TYPE: DNA
<213> ORGANISM: Mycobacterium tuberculosis

<400> SEQUENCE: 314
tcggctaata atcgtcgacg ccggcctcct ctgcaatcgc cttggcggtc gccgggttgt 60
caccggtgat catcacggtg cggatgctca ttcggcgcat ttcgtcgaat cgttcccgta 120
tgcccacctt gacgatgtcc ttcagatgga cgacgccgat ggcccgcgcg ctgctgttat 180
cggtccattc cgcaacgact aggggtgtcc cccgccggag ctgatgccgt cgacaatggc 240
acccacctcc tcggtggggt gggcaccgtg atcgcgaacc cacttcatca ccgcagccgc 300
ggcaccttgc ggattcgacg gatg 324

-continued

<210> SEQ ID NO 315
<211> LENGTH: 322
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 315
ctcaagcttg gaggcgtggc gatcgcggtc caaggcgcgc tctccgagca caacgagcga 60
agacngctcg gcgacggagc ctttatcgac ntccgttcgg gctggctgac ggcggcnaaa 120
taatgctgga ctcgttgttg tcgacggtgc cgtggcgagc cgagcgccgt cagatgtacg 180
accgggtggt ctatgtgccg cggttggtga gtttccacga cctgaccatc gaagatccgc 240
cgcatccgct gctggcgcgg atgcgccggt ggctcaacta attctacggc ggcgaactgg 300
gtnatccctt cnccaccgtc gg 322

<210> SEQ ID NO 316
<211> LENGTH: 404
<212> TYPE: DNA
<213> ORGANISM: Mycobacterium tuberculosis

<400> SEQUENCE: 316
cctaggtcaa ccgtaccgtc atcggatcgg ggtcgaccgc acagatggac tggagcttcg 60
gcgaggtcat cgcctatgcc tcgcgggggg tgacgctgac cccgggtgac gtgttcggct 120
cgggcacggt gcccacctgc acgctcgtcg aagcacctca ggccaccgga aatcattccc 180
gggctggctg cacgactgcg acgtggtcac cctccaggtc gaagggctgg gcgagacgat 240
gcagaccgtc cggacgagcg gcactccttt tccgttggct cttcggccga atccggacgc 300
cgaacccgac cggcgcgggg tcaacccggc accgacgcgg gtgccgttta cccgcgggct 360
gcacaaatcc cgacgggtat gggctttgac ctgccgacgg ggga 404

<210> SEQ ID NO 317
<211> LENGTH: 346
<212> TYPE: DNA
<213> ORGANISM: Mycobacterium tuberculosis

<400> SEQUENCE: 317
agcttggcgt gacaccaaca cagggcactt aagatggcaa tgcgccgcct acctgcacgt 60
tttcgcgatg tcagaggatg ccgaggggag aacaatgcga gcacggccgc tgacgttgct 120
caccgctttg gcggcggtga cattggtggt ggttgcgggc tgcgaggccc gagtctaggc 180
cgaagcatat agcgcggccg accgcatttc gtctcgaccg caagcgcgac ctcagccgca 240
gccggtggag ctactgctgc gcgccatcac gccgcctagg gctccggcgg cgtcgccgaa 300
cgtcgggttt ggcgaactgc ctacccgggt ccggcaggca accgat 346

<210> SEQ ID NO 318
<211> LENGTH: 333
<212> TYPE: DNA
<213> ORGANISM: Mycobacterium tuberculosis

<400> SEQUENCE: 318
tcatgccgtt ggaccgacca tcggagttag ttgccgaacc gcgggaccac cgcaagcacc 60
cggtcctggt cgcgcaccgc gtcggccaac cgcttgagca ccaccacgcc gcagccctcg 120

-continued

```
ccgcgcacga atccatccgc gttggcgtcg aagctgttgc atcggccggt cggtgacagc    180

gccgaccact tggacagcgc gatggcggtg aacggtgaca aggtgagctg caccccgccc    240

gccaatgcca cgtcggtttc acgcaggcga agctctgaca cgccaagtga attgccacca    300

gcgacgacga acaagcggta tctacggcga tgg                                 333
```

```
<210> SEQ ID NO 319
<211> LENGTH: 207
<212> TYPE: DNA
<213> ORGANISM: Mycobacterium tuberculosis

<400> SEQUENCE: 319

gggtcgactt tctgcaaggc gaggctacac cgtcgtcgtc gtggtatgcg atagccatcc     60

cgtcgggcta ctcgccatca ccgatcagct tcgccccgaa gccgccgtgg tgatttccgc    120

tgcgaccaaa ctgaacgggg ccaaaccggt attgcttacc ggcgacaacc gggccaccgc    180

cgatcggctc ggtgttcagg ttggcat                                        207
```

```
<210> SEQ ID NO 320
<211> LENGTH: 250
<212> TYPE: DNA
<213> ORGANISM: Mycobacterium tuberculosis

<400> SEQUENCE: 320

aatccgaaat cctgaccgat acttgaacct ggtctcgttc ggcaataact cgtcggcgtg     60

caggacgcgg cgcaaacgta cttcggcatc aacgcgtccg acctgaattg gcagcaagcg    120

gcgctgctgg ccggcatggt gcaatctaac agcacgctct tcccgtacac caaccccgac    180

ggcgcgctgg cccgggcgga acgtggtcct cgacaccatg atcgaaaaac cttcccgggg    240

aggcggatgc                                                           250
```

```
<210> SEQ ID NO 321
<211> LENGTH: 365
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 321

ttccgaattt cgggtccngg tcatatgacc ctcatggaag aagaagcggc cgccccgcgc     60

ccgtgcgacg gcgaatgaaa accctcaccc aggccgcatt gaacgccgac aagacggtgg    120

agcaggtcga agacgtcctg gacggtctgg gtaagaccat ggccgagctg aacagctcgc    180

tgtcacagct gaacagcacc gtggagcgct tggaggacgg tctggaccat ctcgaaggta    240

ccctgcacag cctggacgat ctcgcgaaac ggctcatcgt gttggtcgag ccggtggaag    300

ccatcgtcga tcggatcgac tacatcgtga gcctcggcga aacggtgatg tcaccgctgt    360

cggtc                                                                365
```

```
<210> SEQ ID NO 322
<211> LENGTH: 413
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"
```

-continued

<400> SEQUENCE: 322

```
nctcgatctt ggggtacgtt cgatgaggct gctgaccaac aacccggcca agcgggtggg     60
actggatgga tacggattgc acatcatcga gcgcgtgccg ctgccggtgc gggccaacgc    120
ggaagaacat ccgttacctg atgaccaagc gtgacaaatt ggggcacgac ttggctgggt    180
tggacgattt tcacgaatcc gtgcatctgc ccggagaatt cggcggtgcc ttgtgaaggt    240
ggcgccgggg tgccggatct gccgtcgctg gatcgtctgg tgtgcggctg gcgattgtcg    300
ccagcagctg gcacggaaag atctgcgacg cgctgttgga cggcgcccgc aagtggccgc    360
cgggtgtggc ctcgatgacc gactgtggtt cgggtgctcc gcgcgatcga tat           413
```

<210> SEQ ID NO 323
<211> LENGTH: 364
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 323

```
tcatcccgac caaaacgcga gctaggtcgg catccgggaa gcatcgcgac accgtggcgc     60
cgagcgcgct gccggcaggc cgattaggcg ggcatattat cccgccgcgg ctcccggctc    120
cgagtacggc gccccgaatg gcgtcaccgg ctggtaaccg ctcttgcgcg cctgggcggc    180
ggcctgccgg atcaggtggt agatgccnac aaagcctgcg tgatcggtca tcaccaacgg    240
tgacagcagc cggttgtgca ccaagcgcga acgccacccc ggtctccggg tctgtccaac    300
cgatcgaccg cccaagccca catgaacaaa ccccggcatc acgttgccga tcggcatacc    360
gtga                                                                 364
```

<210> SEQ ID NO 324
<211> LENGTH: 488
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 324

```
ttggcgggtt ggcccagcag cccgccggtg acggcgacga tgctgggctg gttgcggccc     60
tgcgccaccg cggcttgcat gctggttggc tgtcttggga cgatcccgaa atagtccacg    120
cggatctggt gattttgcgg gctacccgcg attaccccgc gcggctcgac gagtttttgg    180
cctggactac ccgcgtggcc aatctgctga actcgcggcc ggtggtggcc tggaatgtcg    240
agcgccgtta cctacgtgac ctgatggatc gggggtgcc gaccgtgccc ggcgatgtgt    300
atgtgccggg anagccggtc cggttgccac gcaaaggcca tgtcttcgtc ggtccgacca    360
tcggtaccgg gacacggcgc tgtattgccc ggttcgctgc cgagttcgtc gcgcaactgc    420
acgcnggcgg gccagcggtg ctcgttcanc ccggaggttc cggtgacgat gatcgtgttg    480
gtctccct                                                             488
```

<210> SEQ ID NO 325
<211> LENGTH: 396
<212> TYPE: DNA

-continued

<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 325
gtaggagaga acaaagaccg tcgataggac acgtgttacg ccggtagctg tcattggtat 60
ggggtgccgc tgccgggggg catctactca cccgatcggt tgtgggaggc gttgctgcgg 120
ggcgacaatc tggtcaccga gatccccgcc gaccgctggg acatctacga gtactacgac 180
cccgaacccg gcgtgcccgg acgcaccgac tgcaaatggg gcgcgtacct cgataacgtc 240
ggcgactttg atcccgagtt cttcgggatc ggggagaaag aaacgatagc gatcgatccg 300
cagcaccgct tgttgctgga aacctcctgg gaagccatgg aacacggcgg gctaacaccg 360
aaccatatgc ctcccgacan gggttttcgt ggggtt 396

<210> SEQ ID NO 326
<211> LENGTH: 394
<212> TYPE: DNA
<213> ORGANISM: Mycobacterium tuberculosis

<400> SEQUENCE: 326
cgaactgagc ccatagaaag gcagcgacta attcgctggg caaataggaa gaccctttgt 60
cctgccacgt atatttgtcg acctcgttgc gaaggaagcg gctgcgattg gtgccctttt 120
ccctggagaa tctctgcccg gagcaggaag tcttatgagt tgacaagcag gggcgccgcc 180
ttcgccggaa atcacattct tggtctcgtg aaatgagagc gctcccaggt cgccgatgct 240
gccgagcgcc cgcccacgat acgacgccat cgcgccttgg gccgcgtctt cgaccaccgc 300
caggttgtgg tgcgtggcga tcttcatgat cgcgtccatc tcgcaggcca cccggcatag 360
tgaacgggga ccatggcctc ggttcgcggg tgaa 394

<210> SEQ ID NO 327
<211> LENGTH: 140
<212> TYPE: DNA
<213> ORGANISM: Mycobacterium tuberculosis

<400> SEQUENCE: 327
cttagacgcc acctccgggc cgagctccac ggggtggata agtacggccg gatgtggccg 60
caatgggaag ttgttgcccg cttgactgtc cgggttaacg ccggattcca ccacatcccc 120
ttgcgaaagg ccgttgggtt 140

<210> SEQ ID NO 328
<211> LENGTH: 242
<212> TYPE: DNA
<213> ORGANISM: Mycobacterium tuberculosis

<400> SEQUENCE: 328
gatcgcgatc gtcgatgtgg ccatccggct tggcgtcgac ccgcgtaagg cagaccagat 60
ggttcgcggc acggtcaacc tgccacacgc actggtaaga ctgcccgcgt cgcggtattc 120
gcggttggtg aaaaggccga tgctgccgtt gccgcggggg ctgatgctgt cggatcgacg 180
atctgatcga gaggatcagg gcggctggct ggaattcgat gccgcgatcg cgataccgga 240
tt 242

<210> SEQ ID NO 329

-continued

<211> LENGTH: 220
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 329
agcttacgcc gctttcgctt cngatttggg acgccgcatc gaaagcgcag ttggaagcgc 60
ggcgcccggc tggtcgagct gctcaagcag ccgcaatccc agcccatgcc cgttgaggag 120
caagtggttt cgatcttcct gggcaccggc ggtcacctgg actcggtgcc cgtcaaggat 180
gtcggcggtt cgaaaccgaa ttactggacc acatgcgggc 220

<210> SEQ ID NO 330
<211> LENGTH: 328
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 330
cgacgggacc tcgtcgcatc ttccatagcc cgccacacct tcagttgctc accggaatcc 60
aaccggtata aggtcggcga agcgctcggc attggtcatc gggatatgcc gctcgggacg 120
gtcagatgcc ctcgggtccn gccagcactc ctcaggcttc gtcggggtgg tcgcgaccgc 180
atgggccaca tcgcattcac caggtctgcg cgaatcacca gcacgtanac ggttcctttc 240
ctaagcaaca ccgaaatttc aggacccgaa tgctccggga aaacatgtca cggtaagtcc 300
ggtattccgg gtaccggttg agcattga 328

<210> SEQ ID NO 331
<211> LENGTH: 366
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 331
cggcatcggt ttgggctgtc accagcagtt ggtagttctt cactactgtt gttcgagcgt 60
cgagccgccg cgcgtgtcga ggtcgccgga cgcgtacccg ccaggccggt cagggtgccc 120
ttccagtcca cgcngctgtg gtcggctaac cgcttatctt caatcgagac natcgccagc 180
ttcatcgtgt tggcgatctt gtccgagggc acctcgaacc ggcgctgcga ntacagccac 240
gcgatcgtgt tgcccttcgc gtcgaccatc gtcgataccg caggcacttg cccctcgagc 300
agctgggccg atccgttggc aacgacctca gaggcacgat tggacatcag ccctagcccg 360
cctgcg 366

<210> SEQ ID NO 332
<211> LENGTH: 407
<212> TYPE: DNA
<213> ORGANISM: Mycobacterium tuberculosis
<220> FEATURE:
<221> NAME/KEY: unsure
<222> LOCATION: (various positions within the sequence)

-continued

<223> OTHER INFORMATION: applicants are uncertain of bases designated as "n"

<400> SEQUENCE: 332
ccgtcgangc cgccgacttg gcttgaccga caccaacatg gcctgagggt gttcaacaag 60
accgtggccg acgggctgaa catcaccatg agcggcatga gccacgccac cgagttcatc 120
atgttgatcg ccgaaaacca ttggcgggta gcggaagaac ggtcgaggtg ctctacaccg 180
agtattcgaa gtcgaaaggc caaccgctgc tcaacggcgt caacatcatt ttcgacgggt 240
ttctgcgagg gaggatgcca cgatgaactg gatccaggtg ctgttgatcg cgtcgatcat 300
cgggttgctg ttctacctgt tgcggtcgcg ccgaagcgcg cggtccgtgc ctgggtcaag 360
gtgggctatg tcttgttcgt gctcccggca tctatgccgt gctgaga 407

<210> SEQ ID NO 333
<211> LENGTH: 473
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 333
ttacacgncc tgcttccggc tcgtatgttg tgtggaattg tgagcggata acaatttcac 60
acaggaaaca gctatgacca tgattacgcc aagctattta ggtgacacta tagaatactc 120
aagctttttg agcgtcgcgc ggggcagctt cgccggcaat tctactagcg agaagtctgg 180
cccgatncgg atctgaccga agtcgctgcg gtgcagccca ccctcattgg cgatggcgcc 240
gacnatggcg cctggaccga tcttgtgccg cttgccgacg gngacgcggt angtggtcaa 300
gtccggtcta cncttgggcc tttgcggacg gtcccgacgc tggtcgcggt tgcgccgcgg 360
aaagcggcgg gtcgggtgcc atcaggaatg cctcaccgcc gcggcactgn acggccagtg 420
ccgcggcgat gtcngccatc gggacatcat gctcgcgttc atactcctcg acc 473

<210> SEQ ID NO 334
<211> LENGTH: 305
<212> TYPE: DNA
<213> ORGANISM: Mycobacterium tuberculosis

<400> SEQUENCE: 334
caggcatgca agctttgtca caccaagtgt ttcgaccagg cgctccatcc ggcgagtgga 60
tactcccagc aggtagcagg tcgccaccac gctggtcagt gcgcgttcag ctcgcttgcg 120
gcgctgcagc agccagtccg ggaaatagct gccctggcgc agcttgggga tcgcgacgtc 180
gatggttgcg gcacgggtgt cgaaatcacg gtggcggtag ccgttgcgct gattggaccg 240
ctcatcgctg cgttcgcggt agcccgcccc gcacagggcg tcggcttcag cccccatcaa 300
ggcgg 305

<210> SEQ ID NO 335
<211> LENGTH: 432
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

-continued

<400> SEQUENCE: 335
agcttagcca gtttttctac tcttgggccc acacccacag tgcttcgacg gtacggtcac 60
ccatgatggc catccagttg gcatcggtga gctgataaat gccagctggt ttcgccaacc 120
cggtagcgat cttggcgcgc tgcttgttgt cactgatacc tatcgagcaa gacagcccgg 180
tttgcgacaa gatgactttt cggatctctt cggcgacttc gatggggtcg tcgggagtcc 240
cgggcgccac cgcgaggtaa gcctcgtccc agccccatac ctcgaccggg tatcccaggt 300
cgcgcaataa cgccaccacc tcctcggacg ccgcgttgta ggcggctggg ttcgacggca 360
agaagtggcc tcagggcatc gtcggcgcgg tcccaacggc ntgccggcgc gcacaccgta 420
ggcgcggggc tc 432

<210> SEQ ID NO 336
<211> LENGTH: 429
<212> TYPE: DNA
<213> ORGANISM: Mycobacterium tuberculosis

<400> SEQUENCE: 336
ccggcggaac tcagacgtgc tggtggtgcg gcatggcacc gcgggcagca aagcgcactt 60
ctccggggac gacagcaagc gaccgctaga caagaggggt cgtgcgcagg cagaagcgtt 120
ggtaccacag ctgctggcgt tcggcgccac cgatgtttat gccgccgacc gggtgcgctg 180
ccaccagacg atggagccac tcgccgcgga actgaacgtg accatacaca acgagcccac 240
cctgaccgaa gagtcctacg ccaacaaccc caaacgcggc cgacaccgag tgctgcagat 300
cgtcgagcaa gtaggcacac ccgtgatctg cacgcagggc aaggtcattc ccgatctgat 360
cacgtggtgg tgcgagcgcg accgtgtgcc cccgacagtc ccgcaatcgc aaaggcagca 420
cgttggtgt 429

<210> SEQ ID NO 337
<211> LENGTH: 94
<212> TYPE: DNA
<213> ORGANISM: Mycobacterium tuberculosis

<400> SEQUENCE: 337
gtatggtcag ctgtccatcc ggcgctgtcg gccgagctgc cagatctcgt cagccgtaac 60
cgggttgcgg gatccacgcg tgcgggttgt ctac 94

<210> SEQ ID NO 338
<211> LENGTH: 351
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 338
ccgactttcc gcgggtaccc gctcaacttt gtgtcnacct caacgccatt gccggcacct 60
actacgtgca ctccaactac ttcatcctga cgccggaaca aattgacgca gcggttccgc 120
tgaccaatac ggtcggtccc acgatgaccc agtactacat cattcgcacg gagaacctgc 180
cgctgctaga gccactgcga tcggtgccga tcgtggggaa cccactggcg aacctggttc 240
aaccaaactt gaaggtgatt gttaacctgg gctacgcgac ccggcctatg gttattcgac 300
ctcgccgccc aatgttgcga ctccgttcgg ttgttccaga angtcagccc g 351

-continued

<210> SEQ ID NO 339
<211> LENGTH: 152
<212> TYPE: DNA
<213> ORGANISM: Mycobacterium tuberculosis

<400> SEQUENCE: 339
gcaccgatgt cggcgagcac ttcgtcaact tccaggggtg cccgcaccaa gtatttcgac 60
gagtatttcc gtcgggccgc cgccgccggt gcgcggcagg tggtcatcct ggcggcgggg 120
ctgggactcg cgcgcgtacc ggctgcctcg gc 152

<210> SEQ ID NO 340
<211> LENGTH: 263
<212> TYPE: DNA
<213> ORGANISM: Mycobacterium tuberculosis

<400> SEQUENCE: 340
tgcacccaac ttactgagca tgctaacgct ggtcgtgcgg gtcttgttcc cgcgtgtcgg 60
cagggcacac gctcggggcg tagctgggag aggccccggt caagcccgga gagcagtgct 120
cagtccgcca gcttgaccga ctttcgatga gaacgcgctt ctcgccgtat tgaactggcg 180
tgctgacggt cgctgagcag cgctcgccga gtgcggccgc tgattctttc atcgagccag 240
gacgcgcatt cgtgttcggc cgc 263

<210> SEQ ID NO 341
<211> LENGTH: 249
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 341
agcttacggc cggtcgacgc gacgagtggt tcatgacacc acaaaccgtc aacgcctact 60
acaacccggg gatgaacgaa atcgtcttcc cgcagcgatt ttacagccac catttttcga 120
tccgcaggcc gacgaggccg ccaactacgg cgggatcggg gcgcgtgatc gggcacgatg 180
atcgggcacg gtttcgacga tagggcgcca aatacgangg cgacgcaatc tggtcnattg 240
gtggatcga 249

<210> SEQ ID NO 342
<211> LENGTH: 269
<212> TYPE: DNA
<213> ORGANISM: Mycobacterium tuberculosis

<400> SEQUENCE: 342
atgtcgtcac gtcaccacaa tcgcgaggac ccaatcatgc cgcccagggc ggccaaccca 60
atggtggccg cgaagcggca gctcgatcgc agcgcggagg tgccggccgc cagttgattc 120
acgaacaggg tgaggtcata ggcgggcagg atagtgacga acgcaagacc tatatctgcc 180
gtcggagtaa gaatcgagta gccggtcgac caacggaagc gaaagtgtcc gcgatgttga 240
tgagcgtcgc cggttgtggc ggcggtggc 269

<210> SEQ ID NO 343
<211> LENGTH: 336
<212> TYPE: DNA
<213> ORGANISM: Mycobacterium tuberculosis
<220> FEATURE:

-continued

<221> NAME/KEY: unsure
<222> LOCATION: (various positions within the sequence)
<223> OTHER INFORMATION: applicants are uncertain of bases designated as "n"

<400> SEQUENCE: 343
agcttcacca gcgtgccgat gctgttcgcn acacctccct actatgcgca attcgccgac 60
acgggtggca tcaacacggg cgataaggtg gacatcgctg gggtgaacgt cgggctggtg 120
cgctcgctgg caatccgcgg caaccgcgtg ttgatcggat tctcgttgcc cggcaagaca 180
atcgggatgc aaagccgggc agcaattcgc accgacacca ttcttggccg taagaacctg 240
gaaatcgaac cccgcggttc ggagccgttg aaacccaacg gtttcctgcc gttggcgcag 300
aacactacgc cataccaaat ctatgacgcg ttcgtc 336

<210> SEQ ID NO 344
<211> LENGTH: 417
<212> TYPE: DNA
<213> ORGANISM: Mycobacterium tuberculosis

<400> SEQUENCE: 344
ctgccgcggt ggcggtcagc gcctggcaag tcaccgcacc gccgtccggt tcatcggcag 60
gctcccccga aaagggccct ggcaacagaa ggtgatcaat gagctcccgc agaccttcgc 120
cgatctggga ccgacatacg tgaagttcgg ccagatcatc gcgtccagcc cgggagcatt 180
cggtgagtcg ctgtcgcggg gaattccgcg gcctgctcga ccgggtgccg cccgcaaaaa 240
ccgacgaggt gcacaagctc ttcgtcgagg aactcggcga cgagccggcc cggctgttcg 300
cctccttcga ggaagaaccg ttcgcgtctg cgtccatcgc ccaagtgcac tacgcgacct 360
gcgcagcggc gaagaagtgt ggtcaagatc cacggccggg catccgccgc cgcgttt 417

<210> SEQ ID NO 345
<211> LENGTH: 405
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 345
gatcgtgccg gccccccggc ggcagtagca gatcagctcg tcgaaatcgc ggcaaccagt 60
ccagtcgatt tccatacggg cgccgtcaat caactctgcg aacatcgcga tcggcaccgg 120
aaaccggcga gccgcgtcag ccagcgcaac cagcaccggg atcggatgaa tcatcaatat 180
tatcaagtga tttcctgatg gcatcgagct cggtgatctt ggtctcgggg gccagctcgc 240
cgtcggcgac gtcgtcgatc cggcggccga gcgcatagac cgcaaatagt gccgctcgct 300
tttcgcgcgg caagagtcgg atgccgtaat atangtttct ggcggccgtg cgcgtgatcn 360
actcggtgat tcgatacgcc tgttcatctc ggtcatgccg tcctc 405

<210> SEQ ID NO 346
<211> LENGTH: 414
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

-continued

<400> SEQUENCE: 346
ggtggcgcaa tgaccgaaac caccccagcc ccgcaaaccc cggcggcccc ggccgggccc 60
gcacaatcgt tcgtgttgga gcggcccatc cagaccgttg ggcgccgtaa ggaggccgtg 120
gtacgagtgc ggctggtgcc cggcaccggc aagttcgacc tcaacggccg cagcttggag 180
gactacttcc caaacaaggt gcaccagcag ttgatcaagg caccccctggt caccgtggat 240 cgggtggaaa gtttcgacat ctttgcccac ctgggcggcg gcggcccgtc gggtcatggc 300
cggcgcgctg cgcctgggta tcgcccgggc attgattctn gtatcgccgg atgaccggcc 360
cgcgctgaat aangccggct tcttgaccgt gatccacgcg ccaccgaacg caaa 414

<210> SEQ ID NO 347
<211> LENGTH: 331
<212> TYPE: DNA
<213> ORGANISM: Mycobacterium tuberculosis

<400> SEQUENCE: 347
cacaatagat tactcaagct tcgaaccagc ggccttatca cgtatccccg ctgagacctt 60
gacccttagg gccgaagtga cttcgctgct gctatgccga cacccgattt ccagacgctg 120
ctgttacacg acggccgggc cggtggccac catcacgctc aaccgcccgg aacagctcaa 180
caccatcgtc ccgcccatgc ccgacgagat cgaggccgct atcgggttgg ccgagcgcga 240
ccaggacatc aaggtcatcg tgctgcgcgg tgccggccgc gccttctccg gcggttacaa 300
cttcggcggc gggttccaac attgggggca t 331

<210> SEQ ID NO 348
<211> LENGTH: 386
<212> TYPE: DNA
<213> ORGANISM: Mycobacterium tuberculosis

<400> SEQUENCE: 348
tcaggacgct tatggttggc agatggtcgc cctggcgtcg aatacgcgcg agcgcatgag 60
ctcaccggtt cggaacaacg tatcgaagaa cgtcgcactg ctggcagatg gtatctccga 120
tgtggttgta atttgtatcc caactctaac tgtgctatcg gatcagcgtg aatatcgaga 180
tattgcgaat gcgatgacag gccgccattc ggtttattcg cttacgcttc ccgggttcga 240
ttcgtctgat gcactgccgc aaaacgcgga tatgattgtt gaaaccgtat ctaacgcaat 300
tattgatgtg gtaggcggca gctgccgttt tgtgctgtcg ggctattcat cgggtggggg 360
tgtttggcta tgccctctgc tcccat 386

<210> SEQ ID NO 349
<211> LENGTH: 187
<212> TYPE: DNA
<213> ORGANISM: Mycobacterium tuberculosis

<400> SEQUENCE: 349
cgcagctgtc gccgatctgg tccggaatac ctagctccag gttctgagtg gagatgagtg 60
cggccatcga agtgttgtca atgtactcca ggatgtcagg tgccaggccg ctggcgagga 120
tcttgggcac cgccgccatg acttggtcga agtcggcgaa cggggcgagc acgctggcgt 180
cgtggtc 187

<210> SEQ ID NO 350
<211> LENGTH: 241
<212> TYPE: DNA
<213> ORGANISM: Mycobacterium tuberculosis -continued

<400> SEQUENCE: 350
gtagttcgtt catccaaaca cagtgcggta ccggctcaag cggatcaccg acttcaccgg 60
gcgcgatccc acccagccac gcgatgccta tgtccttcgg gtggcggcca ccgtgggtca 120
actcaactat ccgacgccgc actgaagcat cgacagcaat gccgtgtcat agattccctc 180
gccggtcaga gggggtccag caggggcccc ggaaaagata ccaggggcgc cgtcggaccg 240
a 241

<210> SEQ ID NO 351
<211> LENGTH: 335
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 351
tccgctcgct tctccgagag gttgagtgcc aacgctctgc cgatgcccga agccggcccc 60
ggtgatgacg gcgaccttgc cttcgaatga gctcatttga ctactccccg tggttgtccc 120
tgcgattggt ggaggtggcc gcgcagcctt gccccgaggt cggcgatcgc gtctcgggct 180
tcggggagca gactgacctg cagatggaag tcgtgccaca tgcccgcgaa ccggcgatgc 240
tcgatgcttg ttttcgaagc ggcgcaggcg gtttcgatct tgtccgcgtc aacacngatc 300
ggatcgtcgc ccgcggtctg catgacgaat gggcg 335

<210> SEQ ID NO 352
<211> LENGTH: 441
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 352
atgggaggcc accgattacc atcttgcaca caccgattcc gggctattga tgtccacgtt 60
cggtccgcga accgcgctgt ggctgctgct ggccaaaggc ggaggcgata ccgaagtcag 120
tgcccaagct tgggttccac gctcgcgcag ccacgccgtc acctttccac gagacctcac 180
ctgccgatcc gaaatggaat cggccgtgac ggaattggcg cagcgaacac tcaacgaggt 240
ggtggcttcg tcgcgaaccg tcacccgagt cgcggtcacc gtgcgcacgg cgacgttcta 300
cacccgcacc aagatccgaa agctgcaagc tcccagcacc gatcccgacg tcatcaccgc 360
tgccgcccgg cacgttcttg aacctattcg agctggaatc ggccgtccgg ttgctgggaa 420
ttgcngttaa gaactgggcc t 441

<210> SEQ ID NO 353
<211> LENGTH: 332
<212> TYPE: DNA
<213> ORGANISM: Mycobacterium tuberculosis

<400> SEQUENCE: 353
gctttgcgcg cttctccgag aggttggagt gccaacgctc tgccgatgcc cgagccggcc 60
ccggtgatga cggcgacctt gccttcgaat gagctcattt gactactccc cgtggttgtc 120

-continued

```
cctgcgattg gtggaggtgg ccgcgcagcc ttgccccgag gtcggcgatc gcgtcgcggg    180

cttcggggag caaactgacc tgcagatgga agtcgtgcca catgcccgcg aaccggcgat    240

gctcgatgct tgttttcgaa gcggcgcagg cggttcgatc ttgtccgcgt caacgcagat    300

cggatcgtcg cccgcgggtc tgcatgaaga at                                  332
```

<210> SEQ ID NO 354
<211> LENGTH: 334
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 354

```
ctcacgcagc cacgccgtca cctttccacg aagacctcac ctgccgatcc gaaatggaat     60

cggccgtgac ggaaattggc gcagcgaaac actcaacgag gtggtggctt cgtcgcgaac    120

cgtcacccga gtcgcggtca ccgtgcgcac ggcgacgttc tacacccgca ccaacatccg    180

aaagctgcaa gctcccagca ccgatcccga cgtcatcacc gctgccgccc ggcacgttct    240

tgacctattc gagctggatc ggcccgtccg gttgctggga gtgcggttag aaactggcct    300

agaaaccggc gggcacaccg cacctgggcg gggn                                334
```

<210> SEQ ID NO 355
<211> LENGTH: 341
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 355

```
tgcttccggc tcgtatgttg tgtggaattg tgagcggata acaatttcac acaggaaaca     60

gctatgacca tgattacgcc aagctattta ggtgacacta tagaatactc aagcttgatg    120

ccgccgaaac cgagcgtgag cacgccgcca gccaccacnc gcgggtcggg cgccgggccc    180

gggtcgccan gctgctccgc tcggtgatgg cacgccaccg cgacaccacc cggctgcgct    240

acgtcgagcc ataccgggcg gagctacatc ggctcggccg cccagtgttc gggccctctt    300

tcgaagtcga agtcgatacc gattgcgcat ccgcngccgc a                        341
```

<210> SEQ ID NO 356
<211> LENGTH: 259
<212> TYPE: DNA
<213> ORGANISM: Mycobacterium tuberculosis

<400> SEQUENCE: 356

```
caggcatgca agcttcacgt ccgtacggct cgggtacgct tcggtcgcag tgtgcgagtg     60

atagatgacg accgggacct cgtctgcatc ttccatagcc cgccacacct tcagttgctc    120

accggaatcc aaccggtaga aggtcggcga gcgctcggca ttggtcatcg ggatatgccg    180

ctcgggacgg tcagaaccct cgggtccggc cagcactccg caggcttcgt cggggtggtc    240

gcgacgcgca tgggccacc                                                 259
```

<210> SEQ ID NO 357
<211> LENGTH: 349

-continued

<212> TYPE: DNA
<213> ORGANISM: Mycobacterium tuberculosis

<400> SEQUENCE: 357
gcttgtctat cgtcccggcc aggtccggcc agtcaaggtc gaaggccagt ccggtctcct 60
ctccgactac ggccaagaac tgggcgacgg tgtcagtgca gaccagcgga aactggtggc 120
gccctaggcg agcgaccgcc tcacaaacgg cggtgaccgc gttctggtcg tgcaccatcg 180
agccgtgccc agcccggccg cgtgccgtca gccgcatcca ctggatgccc ttctcggcgg 240
tttcaatcag gtacaggcga cgttcgccac catcgtgccg gggcacggtt agcgagaaac 300
cgccgacttc acgattgcct cggtgatgcc gtcgaaacag atcgggcct 349

<210> SEQ ID NO 358
<211> LENGTH: 325
<212> TYPE: DNA
<213> ORGANISM: Mycobacterium tuberculosis

<400> SEQUENCE: 358
gcgcgccatg ttgaggttgt ccgacggtga cgacggtgaa ccacaactgt ttgacctgtc 60
cgcacacacc gtgtggatcg gcgagcggac ccgacaaatc gatggcgcgc acatcgcgtt 120
tgcccaggtg attgctaatc cggtcggggt caagttgggc cccaacatga ccccggaact 180
ggccgtggag tacgtcgagc ggctcgaccc gcacaataag ccgggccggc tgacttggtg 240
agcaggatgg gcaaccacaa ggtccgcgat ctgttgccac cgatcgtgga gaacgtccat 300
gccaccgggc atcaggtcat ctggc 325

<210> SEQ ID NO 359
<211> LENGTH: 191
<212> TYPE: DNA
<213> ORGANISM: Mycobacterium tuberculosis

<400> SEQUENCE: 359
ttgccttcca tgccgagcaa ggtcgactca gcgatgacga attgttcttc ttcgcgggtg 60
ttgctgctgg ttgcgggcta tgagagcact gctcatatga ttagcacatt gtttctgacg 120
ctggccgact atccagatca gctgacactc cttgcgcagc aaccagacct gatcccgccg 180
gcgatcgagg a 191

<210> SEQ ID NO 360
<211> LENGTH: 74
<212> TYPE: DNA
<213> ORGANISM: Mycobacterium tuberculosis

<400> SEQUENCE: 360
cgacgctggg cccaactgcg accaccaggt cctggtatgg caggacatgg ccgggttcag 60
cggcgccaat accg 74

<210> SEQ ID NO 361
<211> LENGTH: 312
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 361
taacgactcg ggtccagcga ccgcgccaac acnaacggcc ggacnacgtg ggccagggtc 60

-continued

```
gcggcctccc ctacaaacag gatccgttgc ctgcgaacga caggctccgg tgcggcgttg    120

ggcgccgtgc tcgtcccagc gtccggtccc gggtcgccgg cgacgcttgt ttcctccata    180

ctcgccccct aatctcgagg cagcccgtac ccgcaggcaa cctcccaaaa atgcaatccc    240

ccaaaatgca atgcgtcnag ctatttctca caccgaccgc tagttgcgga tcanaaatcc    300

gttgggcgcg ga                                                        312
```

<210> SEQ ID NO 362
<211> LENGTH: 335
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 362

```
cntggcggtg ggtgcggtgt cgaacacgac cacacttctt tgcggttcgg tgatctcgac     60

accggccgcg agccgaccac catgcgcgcg tagatcggcg atcagcgcgt cggctatcgc    120

ctgggtgccg cccaccggaa tcggccagcc gaccgaatgg gccagcgttg ccatcatcag    180

tccggcgccg gccgacacca gtgacggcaa cggtgaaatc ncgtgggcgg caacgccggt    240

gaacaacgcg cgggcatcct cgcccgccag cgaccgccag gcaggggtgc cctgggccag    300

catccgcagc ccgagacnca ggaccgancc cagtg                               335
```

<210> SEQ ID NO 363
<211> LENGTH: 386
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 363

```
gcttttcnga tcgcagcgag tcgtacccgc gccggtcacc ttcgtggata tcgccggcct     60

ggtcaagggg gcgtccgagg gagccgggct gggtaacaag ttcctggctc atatccgcga    120

atgcnacgcc atttgtcagg tggtgcgggt gttcgtcaac aacnacttga ctcatgtcac    180

cggacgggtc gatccccant ccgacattga ggtcgtcgan accgagctga tcctggcana    240

tctgcaaacc ctggagcggg ccacgggccg gctggagaag gaancgcgca ccaacaaggc    300

gcgcaagccg gtctacgacg cggcactgcg tgcccagcag gtgctcgacg ccggcaanac    360

gctgttcgcc gcgggggtgg atgccg                                         386
```

<210> SEQ ID NO 364
<211> LENGTH: 386
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 364

```
gtcgtacgcc attngtcggt gtgcgcatac cagtacgacg cgccgggcac ctgacgcggc     60

ggccgcgacc agtcggtggc catcgccatc gtctgccacc cggtcaacgg acgcaccttc    120
```

-continued tcctggccga cgtagtgcgc ccacccgccg ccgttgcgtc ccatcnatcc ggtcaacatg 180
agcagcgcca acaccgagcg gtacatgaca tcgctgtgga accagtgaca gattccgccg 240
cccatgatga tcatcgaccg tcctccggat tcggtcgcgt tgcgggcgaa attccttggc 300
aaaccggatt gcctgcgcgg ccggcacacc ggtgatcgac tcctgccagg ccggggtgtt 360
ctgctgggtt cggtcgtggt accggt 386

<210> SEQ ID NO 365
<211> LENGTH: 335
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 365
gcgaggcggt atcgcttccc gtcgtaccgg cgaccgccag ccgagaagct cgttttccca 60
gtgttgctgg ggattctcac gctgctgctg antgcgtgcc anaccgcttc cgcttcgggt 120
tacaacgagc cgcggggcta cgatcgtgcg acgctgaant tggtgttctc catggacttg 180
gggatgtgcc tgaaccggtt cacctacnac tccaagctgg cgccgtctcg tccgcaggtc 240
gttgcttgcg atagccggga ggcccggatc cgcaatgacg gattccatgc caacgctccg 300
agttgcatgc ggatcgaata cnaattgatc accca 335

<210> SEQ ID NO 366
<211> LENGTH: 396
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 366
tgggtcttgc cggcgagccc agcgaagtcg ctagcgtggc cgtgtttctt ggcttcggat 60
ctatcctcgt tacatgaccg gcaccgtgtt ggacgtgact ggcggccggt tcatatgaca 120
ccgagatcat tgccacggta cggcaattcg tcaagaagga aatctttccc natgcaccgg 180
ccctcgaacg tggcaacagc tacccgcaag aaatcgtcga tcggctgggt gttattggct 240
tgctcggtcg ccggctgcaa gggtatcgac accaccgagt tcattctcgg gcgtgccggc 300
gcattcgagc tggcggtgcg cgctgcccag caccgtcata agtacttgan gatggtcaaa 360
cgtcggacga accgccacca cgtcgctgcc gaacgg 396

<210> SEQ ID NO 367
<211> LENGTH: 262
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 367
tagatgccca agcttgccnt tanagacctc gtcgaccaag cacggacgcg accgtcgaag 60
gtggcgaatc cgggcttggc gtcnacccgc gtaaggcaga ccagatggtt cgcggcacgg 120

-continued tcaacctgcc acacggcact ggtaagactg cccgcgtcgc ggtattcgcg gttggtgaaa 180
aggccgatgc tgccgttgcc gcgggggcgg atgttgtcgg gagtgacgat ctgatcgaga 240
ggattcaggg cggctggctg ga 262

<210> SEQ ID NO 368
<211> LENGTH: 303
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 368
tctccacggc gtggatcaag gtaccggccg ggatgttgcg caatggcagg ttgttgcccg 60
gcttgatgtc tgcgttagcg ccggattcca ccacatcccc ttgcgaaaag tccgttgggt 120
gcaatgatgt agcgcttctc cccatcgaga tagtggagca acgcaatccg tgcggtacgg 180
ttcgggtcgt actcgatgtg cgcgaccttg gcgttgacac catctttgtc attgcggcga 240
aagtcgatca tccggtaagc gcgcttatga ccgccgcctt tgtgccgggt nggtaatccg 300
gcc 303

<210> SEQ ID NO 369
<211> LENGTH: 367
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 369
gcccggttcg atcgggcatg tccgcagtcg tcgttaccgg aggcggtcgt ggccgcgcta 60
atcggcgtcg gcgccgacaa gatgtgggat atccgcaatc ggggcgtcat ccctgcgggc 120
gcgctccccc gcgtccgagc cttcgtcgac gcaatcgagg caagtcacga cgcggatgag 180
gggcagcagt gaattacagc gaggtcgagc tgttgagtcg cgctcatcaa ctgttcgccg 240
gaaacagtcg gcgaccgggg ttggatgcgg gcaccacacc ctacgggggga tctgctgtct 300 cgggctgccg acctgaatgt nggtgcgggc ancgccggta tcnactcccg tggaacacag 360
ccggggc 367

<210> SEQ ID NO 370
<211> LENGTH: 366
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 370
ctcggcgtgg atatcggtgt agccggcgcc ggtgaangtc ggctccttac gtccactcga 60
caacagctca tagcgatcca accagtangc aaccgccttc agcagtacaa ccgcgccggc 120
gaacactgcg agttgaacgc gagctgcctg ggtcagcatg cctctgccgg ttgtcagccg 180
aaggccgccg aacaggtaat gcgtcaacag gctcgctaga aacgccagaa ccacggccac 240

-continued gaacagccag ttcagcaccg accggtagaa cggcagatcg aagacgaaaa aacccaatgt 300
catagccgaa ttcggggtcc acgatgccaa aggtgccccc gtgtacaaca actgaacctt 360
caccca 366

<210> SEQ ID NO 371
<211> LENGTH: 455
<212> TYPE: DNA
<213> ORGANISM: Mycobacterium tuberculosis

<400> SEQUENCE: 371
tccggctcgt atgttgtgtg gaattgtgag cggataacaa tttcacacag gaaacagcta 60
tgaccatgat tacgccaagc tatttaggtg acactataga atactcaagc ttcacgtccg 120
tacggctcgg gtacgcttcg gtcgcagtgt gcgagtgata gatgacgacc gggacctcgt 180
cggcatcttc catagcccgc cacaccttca gttgctcacc ggaatccaac cggtagaagg 240
tcggcgagcg ctcggcattg gtcatcggga tatgccgctc gggacggtca gagccctcgg 300
gtccggccag cactccgcag gcttcgtcgg ggtggtcgcg acgcgcatgg gccaccatcg 360
cattcaccag gtctgcgcga atcaccagca cgtagacggt tcctttccta agcaacaccg 420
aagtttcagg accgaatgct ccgggaaaca tgtca 455

<210> SEQ ID NO 372
<211> LENGTH: 196
<212> TYPE: DNA
<213> ORGANISM: Mycobacterium tuberculosis

<400> SEQUENCE: 372
caggcatgca agcttgatgc cgccgaaacc gagcgtgagc acgccgccag ccaccacgcc 60
cgggtcgggc gccgggcccg ggccgccagg ctgctccgct cggtgatggc acgccaccgc 120
gacaccaccc ggctgcgcta cgtcgagcca taccgggcgg agctccatcc gctcggccgc 180
cagtgtccgg gccctc 196

<210> SEQ ID NO 373
<211> LENGTH: 443
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 373
cctgcatccg gctcgtatgt tgtgtggaat tgtgancgga taacaatttc acacaggaaa 60
cagctatgac catgattacg ccaagctatt taggtgacac tatagaatac tcaagcttcc 120
aatccccctg ccctgatacg cgtcggcaac cgtgaacgcg atctcggcga ccgtcggatc 180
ggtttcatcc cgcacaaaac gcgcgtcggc tacggggtcg cttccgtcgg tcaccaccca 240
gacgaagtgg tcgacgtagt cgacttccga caggtagtgc atcaacgccg gactgggaac 300
acnagccgac atgaaccgtc gatacagcgt ctcnccggag aactggatgt gtccgtgcac 360
ggtccgctcg cggtcaccgg gcagcacggg gcgtaacatc agttgagtcc cgtcggcaag 420
ccgtaccgga atcggggaga cga 443

<210> SEQ ID NO 374
<211> LENGTH: 445

-continued

<212> TYPE: DNA
<213> ORGANISM: Mycobacterium tuberculosis

<400> SEQUENCE: 374
caagatgatc gccggtgcca ccccgatccg tgcctcggtc agcgcgaacg tgctttccgg 60
tccggcgacc accatgtcgc acgcaccgac caggccgaac ccgccggccc gcacatgccc 120
gttgatggcg ccgaccaccg gcagcggcga ctcgacgatg gcgcgcaaca gcgccgtcat 180
ttcccgcgcc cgcgccaccg ccatccggta cggatcacca ccaccaccgc cggcctcgct 240
gaggtccgcg ccggcgcaga acgttccgcc ggtatgcccc agcacgacca gccgcaccgc 300
cggatctgct tcggccgcac tcagcccttg atgtagttgg ctgaccagcg tgctcgacag 360
cgcgttgcgg ttgtgcggag agttcagtgt cagcctggcg aaggggccgc cgcaggcggc 420
cgggccagcg tagtcgacgg ggctg 445

<210> SEQ ID NO 375
<211> LENGTH: 308
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 375
ctcaagcttc gatcgacagt actcccgcct tgggtctggt cttcgagctg gtcggtcatg 60
gtcggacctg ctggtagtgg ggatctaacg caacatggtc gggattcatc atggtgtacc 120
cgtgataccc attcgcagct gccggtgaaa ccccgcgatg ccgggatttc cagccgcact 180
aggatgtcta gccggccagc cgctgccgcc ggacttcggg atgttcggta taccaccgat 240
cggcaatctt gcntatccgc cgatgctcga acgctagcca ccccaaacca accactgtga 300 cnacaatc 308

<210> SEQ ID NO 376
<211> LENGTH: 239
<212> TYPE: DNA
<213> ORGANISM: Mycobacterium tuberculosis

<400> SEQUENCE: 376
tgaatttccc gatcccacaa tctcggttca gatacaggtc gccatacccc ttacttcggc 60
aacgctgggc ggattggccc tgccgctgca gcagaccatc gacgccatcg aattgccggc 120
aatctcgttc agccaatcca tacccatcga cattccgccg atcgacatcc cggcctccac 180
tatcaacgga atttcgatgt cggaggtcgt gccgatcgat gtgtccgtcg acattccgg 239

<210> SEQ ID NO 377
<211> LENGTH: 431
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 377
tactcaagct tgaacgctgc gagcgagccc atgtagagcg tttggtacca aaccgatcgg 60
tgggccaact tgccatgggc tcacagcggc tatcgcgagc gtgtagccga tcatcggcca 120

-continued

```
ggcgacggtg gcctgagcgg caggggttgc cttatccatc ctcttgcggc atggttgccg    180

cagggagtgc cggtaagtct ggtcggcaac ctggcccgct gcgggttggg ttcggattcc    240

ctcggctagt aaggtgctcg cctggtgtta caacgaatcg ctagacagct cttatcggga    300

gtggccgtcg cgatcgttgc gctgccgctg gcgatcgcgt tcggcnttac cgccaccgga    360

acgtcccaag gtgcgctcat cgggctctac ggcgccatct tcgccggatt cttcccngcc    420

gtgttcggtg g                                                         431
```

```
<210> SEQ ID NO 378
<211> LENGTH: 334
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 378

gcggtgtctg aacttcgccc gttccctcca gcgcattgag cttcagcccg accggcaggt     60

agggagtcgg catgcggtcc ttcgccccga ccccgctggc taaatagcca cccccgagcg    120

cggtcacggt ctttgcaccg ggacgacggc ataccggcag cgcgaacatc gccgcgggct    180

gcagcgtgaa cgtcgaatac gagtcgaaca gtgtcggcgc gtaaaaaccc gagccggcgg    240

tcgcttcggt aatcaacggc tcctgcgcaa ccagctgcaa ntcnccggtg ccaccggcgt    300

tgacaatctt gatntcggcg acctcgcgca ccan                                334
```

```
<210> SEQ ID NO 379
<211> LENGTH: 302
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 379

tactcagctt cggctcaggt ggtgctgctg gtaaagttcn ctgaacggtg caggtttcga     60

caatgtggtg ccggttcggc gggtactgcc atcgagacac tggcgcaggc tatcgcaccc    120

gttatcggct acaaacaaat cgcggtatgc gttcttgagc atgagtcggc gaccgtcgtc    180

atggtcgaca cccacgacgg aaagacgcag atcgccgtca agcntgtgtg ccgcggatta    240

tcaggactga cctcctggct gaccggcntg tttggtcncg atgcctggcg cccggccggc    300

gt                                                                   302
```

```
<210> SEQ ID NO 380
<211> LENGTH: 240
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 380

catcacctgg ttcatgaaac tggaagcagc gcagcgcttc cttttcggcc gcaacatgag     60

ccagcctctc gtcggcggtc gggtgcaggt gctcgggcag ctcggccgcg acagccgcct    120
```

-continued

```
gaccctgaaa ccagcttcca tatcccgcga cgaacgacgc cagtccgcta cgtaacccct    180

ccgcgactgt ccatggacaa cancgcgttc tccaccgacc gggcccgggt gtggggtgtt    240


<210> SEQ ID NO 381
<211> LENGTH: 362
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 381

ctcaagcttc ccggcggcca gtaccgaaag cgcgaacagc tcgcggcagc ccacaacntg     60

ctgcgtcgga ttgccggcgg cganatcaat tccaggcagc tcccggacaa tgcggctctg    120

ctggcccgca acgaaggact cgaggtcacc ccggtgcccg gggtcgtggt gcacctgccg    180

atcgcacagg ttggcccaca accggccgct tgatgcccgg tcggcaagcc cggcagttgc    240

caaacccagc gtgatcaggc tcggctcgcg agttcggcga agaagtggct cgcctgatca    300

cctaccatcg gccaggatct gcgtgtcatc acnacgctcg ccaaggaggt tgttgtggtg    360

ct                                                                   362


<210> SEQ ID NO 382
<211> LENGTH: 411
<212> TYPE: DNA
<213> ORGANISM: Mycobacterium tuberculosis

<400> SEQUENCE: 382

gccacgtttc gcgccgcccg gcatacggcg gcgtaccgat ctccgcgtca tacacccgcg     60

ggtaatcgcc gacggtgccg gttcgcgagc cgaaggtgac gacgctgatt gaatcgagtt    120

ccaggtccag cgggtggcgc agcaacggcg cgagctcaac gacgtcaatc acgttgtcgc    180

tttctacggt caccgacccg gtgaccgtag tcgcccggtg cgctcggccg agaagttgca    240

ccgccaccac cgcgacaccg tcttgcacgc ggacgccacc cccggatcgg ttgttggcca    300

aggtaattgg gtcattccat ttgacgggac gccgaccccg cagccccagt accgcccacg    360

accacgccgg ctgaccccac cactgtacga acaccaaggc gacgccgacc a             411


<210> SEQ ID NO 383
<211> LENGTH: 331
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 383

ctcaagcttg atgccgccta aaccgaagcg tgagcacgcc gccacccacc acgcgcgggt     60

cgggcgccgg gcccgggccg ccaggctgct ccgctcggtg atggcacgcc accgcgacac    120

cacccggctg cgctacgtca agccataccg ggcggagcta catcggctcg gccgcccagt    180

gttcgggccc tctttcgagg tcnaggtcna taccgatttg cgcatccgca gccgcaccct    240

ggacgacaga accgtgccct acgagtgctt gtcgggcggg gccaaagaac ancttggcat    300

cctggcgcga ttggccggcg cggtcctggt c                                   331
```

-continued

<210> SEQ ID NO 384
<211> LENGTH: 254
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 384

```
ctcgggtacg cttcggtcgc agtgtgcgag tgatagatga cgaccgggac ctcgtcggca     60

tcttccatag cccgccacac cttcagttgc tcaccggaat ccaaccggta naangtcggc    120

gagcgctcgg cattggtcat cgggatatgc cgctcgggac ggtcagagcc ctcgggtccg    180

gccagcactc cgcaggcttc gtcggggtgg tcgcgacncg catgggccac catcgcattc    240

accaggtctg cgcg                                                      254
```

<210> SEQ ID NO 385
<211> LENGTH: 346
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 385

```
ctcaagcttc aattcctcca cgacgcgttc ccaaatgaat ttcccgatcc cacaatctcg     60

gttcagatac aggtcgccat acccccttact tcggcaacgc tgggcggatt ggccctgccg    120

ctgcagcaaa ccatcgacgc catcgaattg ccggcaatct cgttcagcca atccataccc    180

atcgacattc cgccgatcga catcccggcc tccactatca acggaatttc gatgtcggag    240

gtcgtgccga tcgatntntc cgtcnacatt ccggnggtca ccatcaccgg caccagnatc    300

gacccgattc cgctgaactt cgacgttctc agcagcgccg gaacca                   346
```

<210> SEQ ID NO 386
<211> LENGTH: 287
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 386

```
ttaacccccg tggcctctac gccgcctncg ggtcgaacat gcatcccgag canatgctcg     60

agcgcgcacc ccactcgccg atggccggaa ccggctggtt acccgggtgg cggctgacgt    120

tcggcggcga ggacatcggc tgggaagggg cgcttgccac cgtcgtcgaa gacccagatt    180

cgaaggtgtt cgtcgtgctc tacgacatga ccccggcgga cgagaagaac cttgaccggt    240

gggaaggctc cgagttcggc atccaccana agatccgatg ccgcgtt                  287
```

<210> SEQ ID NO 387
<211> LENGTH: 370
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated -continued as “n”

<400> SEQUENCE: 387

```
ctcaagcttg attttgatca tcatggatga tcatcacccg aagtgtggta gccgcagtgg     60

ttatcgtggg taccgtcgtg ctttccatgg gcgcctcttt cgggctttcc gtattggtct    120

ggcaggacat tctgggtatc gagttgtact ggatggtgtt ggcgatgtcg gtgatcctgc    180

tcctggcggt gggatccgac tacaatctgc tgctgatttc ccggttgaaa aangaaattg    240

gggccggatt gaacaccgga attatccgtg ccatggctgg taccggggga gtggtgacgg    300

ctgccggcat ggtgttcgcc gttaccatgt cgttgtttgt gttcagcgat ttgcgaatta    360

ttggtcagat                                                           370
```

<210> SEQ ID NO 388
<211> LENGTH: 330
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 388

```
cgnccaaccc gaattggttt tcggcgccnt cggtgaggac ggcgtgcggg tgctcaacga     60

cgacgtcgtc cgcgggacac acctcgatgc tgccgccatg gacgcggtcg aacgcaagca    120

gctgatcgag ctacaacgcc gcgcggaacg cttccgccnc nggcgttacc gcatcccgtt    180

gaccgggcgg atcgcggtga tcgtcgatga cggcatcgcc accggagcga cggccaaggc    240

ggcgtgccag gtcgcccggg cgcacggtgc ggacaaggtg gtgctggcgg tcccgatcgg    300

cccanacgac atcgtggcga gattcgccgg                                     330
```

<210> SEQ ID NO 389
<211> LENGTH: 346
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 389

```
cgtgactgcc accggggcca ctccgcagaa tctgtacccg accaagatct acaccatcga     60

atacgacggc gtcgccgact ttccgcggta cccgctcaac tttgtgtcna ccctcaacgc    120

cattgccggc acctactacg tgcactccaa ctacttcatc ctgacgccgg aacaaattga    180

cncagcggtt ccnctgacca atacggtcgg tcccacgatg acccantact acntcattcg    240

cacgganaac ctgccgctgc tagagccact gcgatcggtg ccgatcgtgg ggaacccact    300

ggcgaacctg gttcaaccaa acttgaaggt gattgttaac ctgggg                   346
```

<210> SEQ ID NO 390
<211> LENGTH: 355
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

-continued

<400> SEQUENCE: 390
tcgctcaagc gcntgaggcc gaancggctg gttacgactc cctgtttgtg atggaccact 60
tctaccaact gcccatgttg gggacgcccg accagccgat gctggaggcc tacacggccc 120
ttggtgcgct ggccacggcg accgagcggc tgcaactggg cgcgttggtg accggcaata 180
cctaccgcag cccgaccctg ctggcaaaga tcatcaccac gctcgacgtg gttagcgccg 240
gtcgagcgat cctcggcatt ggagccggtt ggtttgagct ggaacaccgc cagctcggct 300
tcgagttcgg cactttcagt gaccggttca accggctcga aaaggcgcta canat 355

<210> SEQ ID NO 391
<211> LENGTH: 403
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 391
atactcaagc ttccgctggg gcctgttcaa ccatggcgat cccgttggtc ccggacatcc 60
cgaacgagga caccgcgacc cncttcggtg tgtgatcatt accgttgggc cactgcgtaa 120
ccgcttgcgg cacaaagagc ccggtctcga cgtcggaaag ctcatcgggc acccgattga 180
aatgcagcag cggcggcacc accccgtgcc gcagtgacag aattgccttg atcagcccga 240
cggtccccgc cgatgccgtg ctgtgcccca tgttgctctt ggccgatcca agcgcgcagg 300
gggtgcccgc gccatacacc cgcgccaggc tgcggtactc aatcgggtcg ccgattggcg 360
taccggtgcc gtgcgcctcc accacaccga ccgtttcggg ctg 403

<210> SEQ ID NO 392
<211> LENGTH: 440
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 392
caacagcgtt ccagcggcat accaccgcac atgccgtgca cccggcgccg ggcggagtcg 60
ccgcataaca cangtacacc ttgggaatcg gtgtgcgcca gggattcnac cgcggggtgg 120
ggccggcgat cgcgcgccag gtcgagttgg cgccgaccgt gatntcaccg ccgacgtagt 180
tggcgttgtg gtccgccatc cgcgcggcgg gcacggcgcg ggccgccacc acgatgtcac 240
ggaagccggg ggcgaacgct cgacgacctg gttaccgtct cngtcgcntc nancgtggac 300
ccgacngcac gtgggcatat gtccanaacg gacgnggccg gtttcntcga tgcngccggg 360
gtccgcgacn tgcggacncn cngncacacc atccgccagt ccgcgtggcg tcccgccgcg 420
actctgcctc ggccgcgcca 440

<210> SEQ ID NO 393
<211> LENGTH: 353
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated -continued as “n”

<400> SEQUENCE: 393
ctcaagcttt gncgacgatc gggcgatgtc gatganagga aaccccagcg cacaaccgac 60
nattttggcg tagccggcgg acntctgctc gattccgatc acgtcggcgc tcgcatcgag 120
catggcgccg gcgacggcta gcagcgatcc gccgtcgtcg aggaacacga cacgagccgt 180
acgcccggcc gtaagccgcg cccaggattc ggcgaaaaac cgttctacgt ggcgggtgta 240
ctgggtgtcc aatgattcgt ggggtgcgta ggcgtcgctg caatcgtcga cataaatgcc 300
gtcggcccgc atcgcgtcaa caactcccgg gtgagtggaa tancacttgc cga 353

<210> SEQ ID NO 394
<211> LENGTH: 340
<212> TYPE: DNA
<213> ORGANISM: Mycobacterium tuberculosis

<400> SEQUENCE: 394
tccaacgcgg tgacagattt gtctatcctg gacctgacgg tgaggtcgaa gttttccagg 60
aattcggcaa aatcggtaag agcctgaaga attcggtatc gccggacgaa atctgcgacg 120
catacggggc agatacgctt cgggtttacg agatgtcgat ggggccgctg gaggcttcac 180
gtccatgggc cacaaaggat gttgtcggcg cgtaccgttt tctgcagcgg gtgtggcgct 240
tggtcgtcga cgagcacacc ggcgaaactc gggtggctga cggcgtggaa ctcgacatcg 300
atacgctacg ggcgttgcac cgcaccatcg tcggcgtgtc 340

<210> SEQ ID NO 395
<211> LENGTH: 362
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 395
ctcgtccttg actacgccca gtatcgaaan cctcctgtgc cggtncgcta aacacccggc 60
ggacactcan acggtgctgg tggtgcggca tggcaccgcg ggcagcaaag cgcacttctc 120
cggggacgac agcaagcgac cgctagacaa gaggggtcgt gcgcaggcag aagcgttggt 180
accacagctg ctggcgttcg gcgccaccga tgtttatgcc gccgaccggg tgcgctgcca 240
ccanacnatg gagccactcg ccgcggaact gaacgtgacc atacacaacg agcccnccct 300
gaccgaagag tcctacgcca acaaccccaa acgcggccga caccgagtgc tgcagatctt 360
cg 362

<210> SEQ ID NO 396
<211> LENGTH: 356
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 396
gtatcgcctc cncctttggc caccagcagc cacagcgcgg ttcgcggacc gaacgtggac 60
atcaatagcc cggaatcggt gtgtgcaagt tggtaaacgg tgttgatccc aagctttgcc 120

-continued agccttttcg tagtcttggg ccccacaccc cacagtgctt cgacggtacg gtcacccatg 180
atggccatcc agttggcatc ggtgagctga tagatgccag ctggtttcgc caacccggta 240
gcgatcttgg cgcgctgctt gttgtcactg atacctatcg agcaagacag cccggtttgc 300
gacaagatga cttttcggat ctcttcngcg aacttccaat gggggtctcc gggant 356

<210> SEQ ID NO 397
<211> LENGTH: 350
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 397
ctcaagcttt tggtctagcc ggccgagcac gatacgggtg tccttggcca ccggcggcgg 60
ctgtccggga aatggcgggt ccccggtggt tttgctgang antgctgaac cgtagtcgaa 120
gtgggcggcg tcagactcca cccagccagc aggcagcgcg aagctgaatc ctccaaccgg 180
gttgtcgatc cggacaggtt ggggtgcgtt tggggcaatg acaggtggcg gcggtgcgtt 240
cgggtcggcc ggcggaggtg ctgcgttggg atcncccggc tgggcattcg gcntnttggc 300
ggcggccggt ggtggggggg caacangtgt cccggtgcgg gtggcgctgc 350

<210> SEQ ID NO 398
<211> LENGTH: 355
<212> TYPE: DNA
<213> ORGANISM: Mycobacterium tuberculosis

<400> SEQUENCE: 398
atctgtaccc gaccaagatc tacaccatcg aatacgacgg cgtcgccgac tttccgcggt 60
acccgctcaa ctttgtgtcg accctcaacg ccattgccgg cacctactac gtgcactcca 120
actacttcat cctgacgccg gaacaaattg acgcagcggt tccgctgacc aatacggtcg 180
gtcccacgat gacccagtac tacatcattc gcacggagaa cctgccgctg ctagagccac 240
tgcgatcggt gccgatcgtg gggaacccac tggcgaacct ggttcaacca aacttgaagg 300
tgattgttaa cctgggctac ggcgacccgg cctatggtta ttcgacctcg ccgcc 355

<210> SEQ ID NO 399
<211> LENGTH: 360
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 399
ctcaagcttg caatgcgggt cgggatgccc atggttggaa natggtcgcc ctggcgtcna 60
atacgcgcga gcgcatgagc tcaccggttc ggaacaacgt atcgaaaaac gtcgcactgc 120
tggcagatgg tatctccgat gtggttgtaa tttgtatccc aactctaact gtgctatcgg 180
atcagcgtga atatcganat attgcgaatg cgatgacagg ccgccattcg gtttattcgc 240
ttacgcttcc cgggttcgat tcgtctgatg cactgccgca aaacgcggat atgattgttg 300
aaaccgtatc taacgcaatt attgatgtgg taggcggcag ctgccgtttt gtgctgtcgg 360

-continued

<210> SEQ ID NO 400
<211> LENGTH: 272
<212> TYPE: DNA
<213> ORGANISM: Mycobacterium tuberculosis

<400> SEQUENCE: 400
caaatacacg ccggacgcac aggcggacat cgccatcccg agcacaccca aaacgggata 60
caggatggag gccaacgcca cggccgcgcc caggatcacc aaccacaccg gcttggtcag 120
cttgtcggcg gcggtatagg catcgggccg ctgcaacgca gcatgcacaa acgcgtacac 180
cgctgtcacc aagacggcga ccagcaatac cagcatgacg gtacccacga ggtggctcac 240
gcattcagac tatgcggttt gcatccaaca cg 272

<210> SEQ ID NO 401
<211> LENGTH: 306
<212> TYPE: DNA
<213> ORGANISM: Mycobacterium tuberculosis

<400> SEQUENCE: 401
ctcgtccttc ggcctcgctg caggagtggg agccgcaggg ctggaaatcc gaaaaacgag 60
ccggtgatcg cactgtcgcc gatcggcgcc gcacctggtt ggtgttacgg atgaatccgc 120
agcgaaatgt ggctgcggtg gcgtgtcgtg actcgttggc gtcgacgctg gtggcagcca 180
ccgagcggtt ggtccaggat ctggatgggc aaagttgtgc ggcccggccg gtgacggccg 240
atgagctgac cgaggtcgac agcgccgtgt tggctgactt ggaaccgaca tggagtcgcc 300
ccggtt 306

<210> SEQ ID NO 402
<211> LENGTH: 300
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 402
gtctagnccg ccgaacacga tacgggtgtc attggccacc ggcggcggct gtccgggaaa 60
tggcgggtcc ccggtggttt tgctgaagan tgctgaaccg tagtcgaagt gggcggcgtc 120
agactccacc cagccagcag gcagcgcgaa gctgaatcct ccaaccgggt tgtcgatccg 180
gacaggttgg ggtgcgtttg gggcaatgac aggtggcggc ggtgcgttcg ggtcggccgg 240
cggaagtgct gcgttgggat cgcccggctg ggcattcggc gtgttggcgg cggccggtgg 300

SEQ ID NO 403
<211> LENGTH: 396
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 403
actcaagctt gagattggcg tcaacgggtg tcggcaccgg cgtcctgcag ttggtaggcc 60
tgcagtttgt gcatcaggcc gatgccgcgg ccctcgtggc cacgcatgta cancaccacg 120
ccgcgcccct cacgggcgac catcgccagc gcggcgtcca gctgaggccc gcaatcgcag 180

-continued cggcgtgacc caaacacatc gccggtcaag cactccgaat gcacccggac cagcacgtcg 240
tcaccgtcgg cgttgggccc ggcgatctcg ccgcggacca gcgcgacatg ttccacgtcc 300
tcgtaaatgc tggtgtancc gatggcgcga aactccccat gacaantcgg aatcccgcgc 360
ctcggcgacc ccgctcaatg ttgcttctcn tgcttg 396

<210> SEQ ID NO 404
<211> LENGTH: 352
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 404
tcgacnagca ttcttgacng ttgttttggc tcggcatggt tagccaaggt tctgcggtcc 60
caccagatca tcttggtccg gtagcgctcg tccgggtatg ctgccgccgg gattctcgct 120
gctattactc cccccgaaga acgccaccgg tccagcgcgt gggccgccgc ggtccccatc 180
acaaactgaa cccccaacag gggacatgct tagcggtagg gcgcgcgcca aggcggcagc 240
aatcgcatca ctgcgctgcg cgtcactatt aacccacccg gacttcactt ccacgacccc 300
gaatggcgcc cggtcattga tcatcttgcg caccgcggat aatccgggat tg 352

<210> SEQ ID NO 405
<211> LENGTH: 420
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 405
accggggcca ctccgcacaa tctgtacccg accaanatct acaccatcga atacgacggc 60
gtcgccgact ttccgcggta cccgctcaac tttgtgtcna ccctcaacgc cattgccggc 120
acctactacg tgcactccaa ctacttcatc ctgacgccgg aacaaattga cgcngcggtt 180
ccgctgacca atacggtcgg tcccacnatg acccantact acatcattcg cacgganaac 240
ctgccgctgc taaagccact gcgatcggtg ccgatcgtgg ggaacccact ggcgaacctg 300
gttcaaccaa acttgaaggt nattgttnac ctgggctacg gcganccggc ctntggttat 360
tccacctcnc cgcccaatgt ttgcnactcc cgttcggggt tgttcccnna aggtcaaccc 420

<210> SEQ ID NO 406
<211> LENGTH: 328
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 406
cgctcaagcg cntgaggccg aancggctgg ttacgactcc ctgtttgtga tggaccactt 60
ctaccaactg cccatgttgg ggacgcccga ccagccgatg ctggaggcct acacggccct 120
tggtgcgctg gccacggcga ccgagcggct gcaactgggc gcgttggtga ccggcaatac 180

-continued

```
ctaccgcagc ccgaccctgc tggcaaagat catcaccacg ctcgacgtgg ttagcgccgg    240

tcgagcgatc ctcggcattg gagccggttg gtttganctg gaacaccgcc agctcggctt    300

cgagttcggc actttcagtg accggttc                                       328
```

<210> SEQ ID NO 407
<211> LENGTH: 315
<212> TYPE: DNA
<213> ORGANISM: Mycobacterium tuberculosis

<400> SEQUENCE: 407

```
ctcaagcttg cgttcgatga agtagtcgtc ggtcagcgcc gcctcttcga gctccttggc     60

gatgcccagc aaggagtcat cgccgccgag cttggccagg atcttgtcgg cctgttcctt    120

gacgatgcgg gcccgcggat cgtagttctt gtagacacga tgaccgaaac ccatcaattt    180

gaccccggcc tcgcggttct tgaccttgcg tacaaactcg ctgacgtcgt cgccgctgtc    240

gcgaatgccc tcgagcatct ccaggacagc ctgattggcg ccgccatgaa gcggacccca    300

tagtgcgttg atgcc                                                     315
```

<210> SEQ ID NO 408
<211> LENGTH: 329
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 408

```
ggtcaggccg agcaggcgcg aggaacgacg aacccaacaa gccatggtgg ttggcgccgt     60

cgagaggtcg gcggtcgcca caacgggaag atcgccttga gcgtcgctcg accgccgcct    120

cgagttgggt cataacgaag tagctgatgc cgatcatgtc gacgtttccg tcgcatcagc    180

gtgcagcggc gacccactcn acgaggtctc ggtgccgccg cggccagggc accagcagtg    240

acgagtccag gcgccgtcgg gccaagcagt cgcggtgcca nccgtggtgg gtcgggcgat    300

ggttgggtgt gctcatttcg ggaacgcca                                      329
```

<210> SEQ ID NO 409
<211> LENGTH: 294
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 409

```
ctcgaagctt taacagcatc aaccccgccc cgcaccagca ccgacacnat gtcgatgcca     60

tcgaggtgaa tgtcgaactg gcgcaaacca tcggcgaccg cgaccaccgg caacatgggt    120

accggcgatt tccggtgcca atgccgaccc gacgggccgc tctcaccgca ggtgacctcg    180

atcaccgaga ccanccggcc gttntnntca cgcaccccta ccgtgtcacg cccaaaacgg    240

cgctggtggt cgattgccgg agtgcacccc ncacccagtg tcgtgcccgg atcc          294
```

<210> SEQ ID NO 410
<211> LENGTH: 288
<212> TYPE: DNA

-continued

<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 410
tgatgccgca cccgatcgac ggtcgttggt cggggttgac tggccgcccg gcgaagcagg 60
gcgtcgaccg cggcccggac gtcggcggcc gtcaccggtc ggccattgcc cgggcgggag 120
tcgtcgagct gaccacggta gacaagtcgg cgctggccgt cgaagacnaa cgtgtcgggt 180
gtgcaggccg cggagaaggc gcgggcgacn tcttgggttt cgtcgtanag atacgggaac 240
gtccagccgt ggcggcgggc ctcggcgacc atctgatcgg gcccgtcc 288

<210> SEQ ID NO 411
<211> LENGTH: 420
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 411
tttcgggcga ggcggtatan cttcccntcg taccggcgac cgccagccga naagctcgtt 60
ttcccagtgt tgctggggat tctcacgctg ctgctgantg cgtgccaaac cgcttccgct 120
tcgggttaca acgagccgcg gggctacnat cgtgcgacgc tgaagttggt gttctccatg 180
gacttgggga tgtgcctgaa ccggttcacc tacnactcca agctggcgcc gtctcgtccg 240
caggtcgttg cttgcgatag ccgggaggcc cggatccgca atgacggatt ccntgccanc 300
gctccgagtt gcntgcggat cgactacnaa ttgatcaccc anaaccatcg ggcgtnttac 360
tgcctgaagt acctggtgcg ggtcggatac tgctatccgg cggtgacaac cccggcaagc 420

<210> SEQ ID NO 412
<211> LENGTH: 378
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 412
gttttggctc ggcatggtta gccaaggttc tgcggtccca ccagatcatc ttggtccggt 60
agcgctcgtc cgggtatgct gccgccggga ttctcgctgc tattactccc cccgaagaac 120
gccaccggtc cagcgcgtgg gccgccgcgg tccccatcac aaactgaacc cccaacaggg 180
acatgcttag cggtagggcg cgcgccaagg cggcagcaat cgcatcactg cgctgcgcgt 240
cactattaac ccacccggac ttcacttcca cgaccccgaa tggcgcccgg tcattgatca 300
tcttgcgcac cgcggataat ccgggattgc cagcccattc nactaccgca tgcgagtcat 360
cggctgaccg cagcggtc 378

<210> SEQ ID NO 413
<211> LENGTH: 347
<212> TYPE: DNA
<213> ORGANISM: Mycobacterium tuberculosis
<220> FEATURE:

-continued

<221> NAME/KEY: unsure
<222> LOCATION: (various positions within the sequence)
<223> OTHER INFORMATION: applicants are uncertain of bases designated
as “n”

<400> SEQUENCE: 413
tcgcctaggc gggcttcccc ttccgtccga gcngtcagaa gctcctatga caatgcacta 60
cccgagacna tcaacggcct atgcaatacc nagctgatca aacccggcaa gccctggcgg 120
tccatcgagg atgtcgagtt ggccaccgcg cgctgggtcg actggttcaa ccatcgccgc 180
ctctaccggt actgcggcga catcccgccg gtctaactcg acgccgcctc actacgctca 240
acgccagaga ccanccgccg gctgacgtct cagatcagag agtctccgga ctcaccgggg 300
cggttcatcc ccactgtcga tagcgtctgt ggataacttt gtctgca 347

<210> SEQ ID NO 414
<211> LENGTH: 165
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 414
gcgcgtngaa ctgataggtg cggcccggct cgagcangcc ggccatttgt tcgatgcggt 60
taccgaagat ctcttcggtg acctgcccgc cgccggccag ctcggcccag tgcccggcgt 120
tggccgccgc ggcgacaatc ttggcgtcca cggtggtctg ggtca 165

<210> SEQ ID NO 415
<211> LENGTH: 317
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 415
ctcaagcttc aatacagagt tataaactgt gataatcaac cctcatcaat gatgacnaac 60
taacccccga tatcaggtca catgacgaag ggaaagagaa ggaaatcaac tgtgacaaac 120
tgccctcaaa tttggcttcc ttaaaaatta cagttcaaaa agtatgagaa aatccatgca 180
ggctgaagga aacagcaata actgtgacaa attaccctca gtaggtcaga acaaatgtga 240
cgaaccaccc tcaaatctgt gacagataac cctcagacta tcctgtcgtc atggaagtga 300
tatcgcggaa ggaaaat 317

<210> SEQ ID NO 416
<211> LENGTH: 379
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 416
ctcaagcttc gatcgacatt actcccgcct tgggtctggt ctccgagctg gtcggtcatg 60
gtcggacctg ctggtagtgg ggatctaacg caacatggtc gggattcatc atggtgtacc 120

-continued

```
cgtgataccc attcgcagct gccggtgaaa ccccgcgatg ccgggatttc cagccgcact    180

aggatgtcta gccggccagc cgctgccgcc ggacttcggg atgttcggta taccancgat    240

cggcaatctt gcgtatccgc cgatgctcga acgctancca cgccaaacca accactgtga    300

cnacaatcgc caccacacca aaggtcatgc cctcggcgtg atgtccggtg ccgaaagccg    360

caagagctcc gacgccgcc                                                 379
```

```
<210> SEQ ID NO 417
<211> LENGTH: 420
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 417

cattcccaat tgaatttccc natcccacaa tctcggttca gatacaggtc gccatacccc     60

ttacttcggc aacgctgggc ggattggccc tgccgctgca gcanaccatc gacgccatcg    120

aattgccggc aatctcgttc agccaatcca tacccatcga cattccgccg atcgacatcc    180

cggcctccac tatcaacgga atttcgatgt cggaggtcgt gccgatcgat gtgtccgtcg    240

acattccggc ggtcaccatc accggcacca ggatcgaccc gattccgctg aacttcgacg    300

ttctcagcag cgccggaccc atcaacatct cgatcatcga cattccggcg ctgccgggct    360

ttggcaactc gaccgagctg ccgtcgtcgg gcttcttcaa caccggcggc ggtggcggct    420
```

```
<210> SEQ ID NO 418
<211> LENGTH: 255
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 418

ctcaagcttt cggcggagac ggacannttg cgaacattga tgacaaaata gaaatcattg     60

atggtttgag tcaccaggcc gatcaagcct tcgccgagcc aaattccaat caagaggccc    120

aagcccgtac caatcagccc ggcaacgagg gattccgtca ttatcagcca aaataactgc    180

tctcgggtta cacccaaaca gcgcaatatg gcgaaaaacg gtcgccgttg cacgacatta    240

aatgtcacgg tattg                                                     255
```

```
<210> SEQ ID NO 419
<211> LENGTH: 359
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 419

agcttaactg ctccctaata cctggggctg tgcctgcggt gtatgcacgg catacggaca     60

tccntcccct gagacccncg gtctaatcag ccacgtgtcc accatcaggg gtcaaccccg    120

gccaagggcg acggcacccc aagttcgccg accgttaacc tattgctgtg agcttcattt    180
```

-continued gctgcgagca aaacagttgg tcggccgtta ggaactgaat tgacactcaa ccgatttggt 240
gccnccgtag gtgtcctggc tgcgggtgcg ctggtgttgt ccgcgtgtgg taacgaccac 300
aatgtgaccg ggggaggtgc aaccactggc cacgcgtccg cgaatgtcta ttgcggggg 359

<210> SEQ ID NO 420
<211> LENGTH: 314
<212> TYPE: DNA
<213> ORGANISM: Mycobacterium tuberculosis

<400> SEQUENCE: 420
ctcaagcttg gggtggcgct gtcggtcggt gtgcttggcg gcgtcggtat caacaccgcc 60
cacgaaatgg ggcacaagaa ggattcgctg gagcggtggc tgtccaaaat caccctcgcc 120
cagacctgct acgggcactt ctacatcgag cacaaccgtg gccatcacgt ccgggtgtcc 180
acaccggagg acccggcgtc ggcgcggttc ggcgaaacgt tgtgggagtt cctgccccgc 240
agtgttatcg gcggcttgcg ctcggccgtt catttggagg cccaacggct gcgtcggctc 300
ggcgtcagcc ccct 314

<210> SEQ ID NO 421
<211> LENGTH: 280
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 421
gcaccaaggc cccacacgtc accctgtgac ctcctgcgcc gaccccgccc gaggtcctgg 60
ccgttaccac ctgaacgggc gagccgggag tctggtacgc atcgaacaaa gagcaaggtg 120
catgggcgga gttgttccgc cacttcgtcg atgacggggt cnatccattc gaggtccgtc 180
gccgcgtcgg tcgagtggcg gtcacactcc aggtactcga cctcacagac gagaggactc 240
gatcccatct aggtgtggac gaaacagatc ttctgtccga 280

<210> SEQ ID NO 422
<211> LENGTH: 230
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 422
tcgcctccgc atatgggtcg acgccaagcg ggtccggatt tctgggcttc atcgctcgcg 60
ccgtcgcgac aaacagcgcg gtcgaaccga cactcgttgt gatgtcccag ctatcacctt 120
cggtacgcac ccaatcgacc ctacncggct atctcagccg cgatctccag gctccgccga 180
gccaggtgca tcccggtccg gatcccacta acccggcacc attggcgtcn 230

<210> SEQ ID NO 423
<211> LENGTH: 272
<212> TYPE: DNA
<213> ORGANISM: Mycobacterium tuberculosis
<220> FEATURE:
<221> NAME/KEY: unsure
<222> LOCATION: (various positions within the sequence)

-continued

<223> OTHER INFORMATION: applicants are uncertain of bases designated as "n"

<400> SEQUENCE: 423
gtcctcgagt gccgccgtcg ncacncccag cgcccgcgcg gccacttgga tgcgacccgt 60
ttcaagtccc ttcatcatct gcgaaaagcc ttgacccatg gctccgccca ggatcgccga 120
gaccggcacc cggaggttgt cgaacgacag ctcgcaggat tcgacgccct tgtaacccaa 180
cttcggcaag tcccgcgaca ccgtgagtcc cggcccgggt tcgacgagca cgatcgacat 240
gccttggtgc cgcggtgtgg cgttcgggtc gg 272

<210> SEQ ID NO 424
<211> LENGTH: 423
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 424
ggcataccaa tgtggacttc tgctcaccca cgatatccgt ggtctgatcc gctgctgcgg 60
cgggctgcna cctgcntctc ngcggcaccc gtnactacat ggcncgcgcc gcacgcatac 120
gtcgcggcgg gacccactcc nactggtcga cggtgctggc cgcgtgtccg cangtcccna 180
acccggccgc accgacgaaa ccggccgccg tccgttctgg accaacgctc atgtgccgtc 240
ggggtccatg ctcgacgcca tcgagaccgt aaccagcgtc ctcgagcggt tcgcctccgg 300
cttccgtgac atcttcgtgg ctgctcgcgc cgtgccgccg cgcggatggt cgaccacaac 360
gccaaccacc tcggcggtga catcaccgtc cgcgccactc gacctggcgc gcgatcgcgg 420
ccc 423

<210> SEQ ID NO 425
<211> LENGTH: 315
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 425
gtgagcagac ctacgccncc tggttgcgcc aactcggtac cgatcatggc gcgcngcctg 60
tcgtcaccga tacccagcga acaagacagc ccggtccgcg acaagatgac tttcccgatc 120
tcttcggcga cttccatggg gtcgtccgga gtcccgggcg ccaccgcgag gtaaccctcg 180
tctcagtccc atacgcgacc gggtatccac gtcgcgcaac aacgccacca cctccccaga 240
cgccncgttg tacgcggctg ggttccacng caataagtgg cctcanggca tcgtccggcg 300
gcggtccnca acgca 315

<210> SEQ ID NO 426
<211> LENGTH: 335
<212> TYPE: DNA
<213> ORGANISM: Mycobacterium tuberculosis

<400> SEQUENCE: 426
ctcaagcttg aggttaactt tgaacggatc gagctggacg ttcgagacgg tgatcgggcc 60

-continued

```
gaacctgaat tgtccggtaa tgcccaacgc aaaaagcagg gtggtggccg gggcggtgaa    120

accggcgtcg gcggcaccgt cgaaatctat gtggattgcc ggaatgggga tgtccggcac    180

ggcgaaaccg tagttcgctt gtcccgtgag gcccaggtgg atgggggaa agatcctggt    240

gtccgggata ataatggggc cgatgccgcc ggttgaagtc cactggatcg ggaattccgg    300

aatcttgatc cgacgttcag gccgaacagg ccctc                              335
```

<210> SEQ ID NO 427
<211> LENGTH: 346
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 427

```
cggcgacgtc gcgatacgcc gagcagttgg gaatcgctct gcagcaaacc aatattctgc     60

gcgacgttcg agaggacttt ttgaatggac ggatctacct gccgcgcgac gagctggacc    120

gattaggcgt acgcctccgc ctggacgaca ccggggcact cgatgacccc gacggacggc    180

tcgcggcnct gctgcggttc agtgccgacc gcgccgcaga ctggtnttcg ctgggactgc    240

ggctgattcc acacctcgac cgccgcagcg ctgcctgctg tgcggccatg tctggcatct    300

accgccgtca gctcgccttg atcagagcat cgccggcggt cgtcta                   346
```

<210> SEQ ID NO 428
<211> LENGTH: 332
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 428

```
ctataaaata ctcaagcttg atgccgccga aaccgagcgt gagcacgccg ccagccacca     60

cgcgcgggtc gggcgccggg cccgggccgc caggctgctc cgctcggtga tggcacgcca    120

ccgcgacacc acccggntgc gctacgtcna gccataccgg gcggagctac atcggctcgg    180

ccgcccagtg ttcgggccct ctttcgaggt cnaggtcnat accgatttgc gcatccgcag    240

ccgcaccctg aacnacanaa ccgtgcccta ctattgcttg tcnggcgggg ccaaaaaaca    300

gcttggcatc ctggcccnat tggccggcgc gg                                 332
```

<210> SEQ ID NO 429
<211> LENGTH: 276
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 429

```
cttcggtcgc agtgtgcgag tgatagatga cgaccgggac ctcgtcggca tcttccatag     60

cccgccacac cttcagttgc tcaccggaat ccaaccggta gaaggtcggc gagcgctcgg    120

cattggtcat cgggatatgc cgctcgggac ggtcagagcc ctcgggtccg gccagcactc    180
```

-continued

```
cgcaggcttc gtcggggtgg tcgcgacgcg catgggccac catcgcattc accaggtctg    240

cgcgaatcnc cancacgtan acngttcctt tcctaa                              276
```

<210> SEQ ID NO 430
<211> LENGTH: 420
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 430

```
ctggcaccaa ggccccacac gtcaccctgt gacctcctgc gccgaccccg cccgaggtcc     60

tggccgttac caccgaacgg gcgagccggg agtctggtnc gcatcgaaca aanagcaagg    120

tgcatgggcg gagttgttcc gccacttcgt cgatgacggg gtcnatccat tcgaggtccg    180

tcgccgcgtc ggtcnagtgg cggtcacact ccaggtactc gacctcacag acnaaaggac    240

tcnatcccat ctaggtgtgg acnaaacaga tcttctgtcc gacnactaca ccaccaccca    300

ggccatcgcc gccgcccgcg atgccaactt cgacgccgta ctggccccgg cgggggggcgc    360

tccccggttg tcaacacttg ccgtgttcnt tcacgcnctg ccccacatcc aaccccaacg    420
```

<210> SEQ ID NO 431
<211> LENGTH: 130
<212> TYPE: DNA
<213> ORGANISM: Mycobacterium tuberculosis

<400> SEQUENCE: 431

```
gttcttgggc ccatgcggag gtatcgccgt ttccaccacg cggtcggggt ggcgttgcat     60

tagctcaccg atggtgcgct tgtgcaggcc gccgggatac cccgagtgcc ggtaaaccat    120

cttgtgctgc                                                           130
```

<210> SEQ ID NO 432
<211> LENGTH: 215
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 432

```
caatactcaa gcttggcgtg ccgttccaac ccgaattggc tttcggcgcc atcggtgagg     60

acggcgtgcg ggtgctcaac nacnacgtcg tccgcgggac acacctcgat gctgccgcca    120

tggacgcggt cgaacgcaag cagctgatcg agctacaacg ccgcgcggaa cgcttccgcc    180

gcgggcgtga ccgcatcccg ttgaccgggc ggatc                               215
```

<210> SEQ ID NO 433
<211> LENGTH: 360
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 433

-continued

```
cntcatgatg atcatcaccc gaagtgtggt agccgcagtg gttatcgtgg gtaccgtcgt     60

gctttccatg ggcgcctctt tcgggctttc cgtattggtc tggcaggaca ttctgggtat    120

cgagttgtac tggatggtgt tggcgatgtc ggtgatcctg ctcctggcgg tgggatccga    180

ctacaatctg ctgctgattt cccggttgaa agaggaaatt ggggccggat tgaacaccgg    240

aattatccgt gccatggctg gtaccggggg agtggtgacg gctgccggca tggtgttcgc    300

cgttaccatg tcgttgtttg tgttcagcga tttgcgaatt attggtcaga tcggtaccac    360
```

```
<210> SEQ ID NO 434
<211> LENGTH: 265
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 434

atactcaagc ttttacggtg atcgcncatc acctggttca tgaactggaa gcagcgcagc     60

gcttcctttt cggccgcaac atgagccagc ctctcgtcgg cggtcgggtg caggtgctcg    120

ggcagctcgg ccgcnacagc cgcctgaccc tgaaaccagc ttccatatcc cgcgannaac    180

gacgccagtc cgctacgtna cccctccgcg actgtccatg gacaacagcg cgttctccac    240

cgaccgggcc cgggtgtggg gtntt                                          265
```

```
<210> SEQ ID NO 435
<211> LENGTH: 264
<212> TYPE: DNA
<213> ORGANISM: Mycobacterium tuberculosis

<400> SEQUENCE: 435

gctggtagag tcgctgaccg gtgcaggttt cgacaatgtg gtgccggttc ggcggctacg     60

tgccatcgag acactggcgc aggctatcgc acccgttatc ggctacgagc aaatcgcggt    120

atgcgttctt gagcatgagt cggcgaccgt cgtcatggtc gacacccacg acggaaagac    180

gcagatcgcc gtcaagcatg tgtgccgcgg attatcagga ctgacctcct ggctgaccgg    240

catgtttggt cgcgatgcct ggcg                                           264
```

```
<210> SEQ ID NO 436
<211> LENGTH: 335
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 436

gctttccgcc gatacccgcc atgtcncgca catccaggac ttctgggggg atccgctgac     60

agcggcggga tcccaaagtg cggatgatcg ggccgcctac gtcgtggtgt acctcgtcgg    120

taacaacgaa accgaagcgt atgactcggt ccacgcggtg cggcacatgg tggacaccac    180

accgccaccg cacggggtga aggcctatgt caccggtccg gcancactca atgccgacca    240

ggccgaggcc gganacaaaa ntatcgctaa ggtcaccgcg atcacnagca tggtgatcgc    300

agcaatgttg ctagtgatct atcgctccgt aatta                               335
```

-continued

<210> SEQ ID NO 437
<211> LENGTH: 304
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 437
cttccaaccc gaattggctt tcggcgccat cggtgaggac ggcgtgcggg tgctcaacga 60
cgacgtcgtc cgcgggacac acctcgatgc tgccgccatg gacgcggtcg aacgcaagca 120
gctgatcgag ctacaacgcc gcgcggaacg cttccgccgc gggcgtgacc gcatcccgtt 180
gaccgggcgg atcgcggtga tcgtcgatga cggcatcgcc accggagcga cggccaaggc 240
ggcgtgccan gtcgcccggg cgcacggtgc ggacaaggtg gtgctggcgg tcccgatcgg 300
ccca 304

<210> SEQ ID NO 438
<211> LENGTH: 223
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 438
tactcaagct tcgcgagatc cggatggcac tcacgctgga caagaccttc acaaaatctg 60
aaatcctgac ccgatacttg aacctggtct cgttcggcaa taactcgttc ggcgtgcagg 120
acgcggcgca aacgtncttc ggcatcaacg cgtccganct gaattggcag caagcggcgc 180
tgctggccgg catggtgcaa tcnaccagca cgctcaaccc gta 223

<210> SEQ ID NO 439
<211> LENGTH: 263
<212> TYPE: DNA
<213> ORGANISM: Mycobacterium tuberculosis

<400> SEQUENCE: 439
cccacgactt tctcctcgat cagttggatt tgtacgaaga ggcaacgaaa gcagtgatcc 60
tcgggatggt cgacgcctac atcgacccgc cgttcacgcc gcacagcctg ctagatgcgc 120
tgggcgagca ggtcccacag ttcgccgcta aggcacggcg tctgttcccg tccggatcgc 180
cattcggcct cggcgtcctg ctcccattcg atcaataggg ctggcagctc cgtcggcagg 240
ggcctacgcc tcaccccgtc acg 263

<210> SEQ ID NO 440
<211> LENGTH: 301
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 440
ctcaagctta tgcgcgccgg ccgaggtctg ctcacggcaa cccctgaagt ttaggggacn 60
acctactcag cgcaaaattt cgctaatgtg agtccgcccc accaggggna natcaaccca 120
tgtcgatcat gatctacccg gataccggat tggcggtagc gcccacgatc gtcnaaatnt 180
ccgcctgaat catcggatag ctgatccggc gtcaacgcgt tttganttca ccgcgcaaca 240
gccgccaggc cggcccgcan cganccgatc tcntcgggcc gcatgggccc caatcttntc 300
g 301

<210> SEQ ID NO 441
<211> LENGTH: 90
<212> TYPE: DNA
<213> ORGANISM: Mycobacterium tuberculosis

<400> SEQUENCE: 441
gtgtgtggtg gaacccatct gagcagtgtg ccaaaccggg gcagacagct cccaattgac 60
gtgagcccgc tcacttgctg ggtaagcgtc 90

<210> SEQ ID NO 442
<211> LENGTH: 183
<212> TYPE: DNA
<213> ORGANISM: Mycobacterium tuberculosis

<400> SEQUENCE: 442
ctttacactt cctgcatccg gctcgtatgt tgtgtggaat tgtgagcgga taacaatttc 60
acacaggaaa cagctatgac catgattacg ccaagctatt taggtgacac tatagaatac 120
tcaagcttgg gcgtgacggc caccggggcc actccgcacc atctgtaccc gaccaagatc 180
tac 183

<210> SEQ ID NO 443
<211> LENGTH: 348
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 443
caggcatgca agctttagct gcccgaatgc gtcaccccga tgcgcccaga tcggggcttc 60
gcagataaag cacgaacagg cgggcaaaac gtcnatctcg gagccggaag ggcaatcagc 120
cgaccgtcga cgaacgacac cggcgagacc acttaggcag tgacggccgg cccgaacatt 180
acgcgctcgt tgattaggcg ttcggtctcg tccgcggtca tgccgagcag cttgcggcag 240
atctgaacgc tgtcctgtcc gggcagcggc gccgggcgtt ggggtgcctg cccgaatgtg 300
acgaaacgga gccggacccg tctcggcggg ccgcggacgg cgatccgc 348

<210> SEQ ID NO 444
<211> LENGTH: 335
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 444
cncaagcttg cggatgttac ccctgacagc ctgaactatg tcnaaacaca cggcaccgga 60
acggtgttgg gggaccccat cganttcgag tcgctggcgg ccacttatgg cctgggtaaa 120

-continued ggccagggcn anagcccgtg cgcattgggg tcggtcaaaa ccaacatcgg ccacctggag 180
gcggccgccg gtgtggctgg atncatcaag gcggtgctgg cggtgcaacg tgggcacatt 240
ccccgcaact tgcacttcac ccggtggaac ccggccatcn acgcgtcggc nacgcggctg 300
ttcgtgccna ccnaaaaccc cccgtggccg gcggc 335

<210> SEQ ID NO 445
<211> LENGTH: 289
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 445
ggaaccggta accagatcag ctcgtcgacc tcactgccgg gggtgaattc cccaccggtg 60
ctgcgcgctg cccagtagtg caccttcttg acgcctcgaa aaggggagtc ggtcgggtag 120
gtcaccgtca ggagccgcct acccaggttg gcgcnatagc cggtctcctc gagtatctcc 180
cgcaccgccc ccaccggtgc ggtctcaccc anatccactt tgcccttggg cagcgaccag 240
tcgtcgtanc nggggcggtg aatgacaacg atctcgaccg gcccttccn 289

<210> SEQ ID NO 446
<211> LENGTH: 263
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 446
tactcaagct tcagaacagg cctgttgtgg gcncacccgg ctcgccgagt tctgcacgca 60
ccgcctcaag tgcggcccgc accgccggca tctcccggtc acgcagggcc gcggcccgcg 120
ccgcagcgac ggcgtgttcg cgcagttcgc cgtcaatgat gctgacctga tcggccaccc 180
gggcgttctc ggcgtcgtcg cgttcactaa tcgcggtgct cagcagcgtc tcgacagcca 240
ccacccgagt ggcgaccagc tgc 263

<210> SEQ ID NO 447
<211> LENGTH: 279
<212> TYPE: DNA
<213> ORGANISM: Mycobacterium tuberculosis

<400> SEQUENCE: 447
taatgtcttg ccaacgtcac cacaatcgcg atgaattcaa tcatgccgcc cagggcggcc 60
aacccaatgg tggccgcgag cggcagctcg atcgcagcgc ggaggttgcc ggccgccagt 120
tgattcacga acagggtgag gtcataggcg ggcaggatag tgacgaaggc aagacctata 180
tctgccgtcg gaagaagaat cgagtagccg gtcgacacaa cggaagcgaa agtgtccgcg 240
atgttgatga gcgtcgccgg ttgtggcggc ggtggcggc 279

<210> SEQ ID NO 448
<211> LENGTH: 295
<212> TYPE: DNA
<213> ORGANISM: Mycobacterium tuberculosis
<220> FEATURE:
<221> NAME/KEY: unsure -continued
<222> LOCATION: (various positions within the sequence)
<223> OTHER INFORMATION: applicants are uncertain of bases designated as "n"

<400> SEQUENCE: 448
tactcaagct ttcgtcagtt catcgcgcca gcagaccaac aagagcatcg ggacatacgg 60
agtcaactac ccggccaacg gtgatttctt ggccgccgct gacggcgcga acgacgccag 120
cgaccacatt cagcanatgg ccagcgcgtg ccgggccacg aggttggtgc tcggcggcta 180
ctcccagggt gcggccgtga tcgacatcgt caccgccgca ccactgcccg gcctcgggtt 240
cacgcagccg ttgccgcccg cagcgganna tcacatcgcc gcgatcgccc tgttc 295

<210> SEQ ID NO 449
<211> LENGTH: 280
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 449
ccacccgtgt aatttgggat gggcnaaaag gcnaagcacc gcgtggccac gaacgccggg 60
agggacaatc tcgggcggct agggcttctc gcgggaaggc ccgaacgtac ggcgtttcaa 120
cacgtcgcgt cgccctccga ccgcgaacat tcggggatgg cagcaacctg gtagcaccct 180
ggccgggcga tgatctgcag cgtcgccgcg ggtagtcgcc gcccgggcgg ctacagtctg 240
aaacgcgatg accatcgatg tgtggatgca gcatccgacg 280

<210> SEQ ID NO 450
<211> LENGTH: 320
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 450
tcaagcttta gctgcccgaa tccgtcancc cgatgcnccc agatcggggc ttcgcanata 60
aagcacnaac aggcgggcaa aacgtcnatc tcggagccgg aagggcaatc anccgaccgt 120
cnacaaacga caccggcgan accacttagg cagtgacggc cggcccgaac attacncgct 180
cgttgattag gcgttcggtc tcgtccgcgg tcatgccgag cagcttgcgg canatctgaa 240
cgctgtcctg tccgggcagc ggcgccgggc gttggggtgc ctgcggaatg tgacnaaacg 300
gagccggacc cntctcggcg 320

<210> SEQ ID NO 451
<211> LENGTH: 203
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 451
ccggggccac tccgcacaat cngtaccnna ccaanatcta caccatcgaa tacgacggcg 60

-continued

```
tcgccgantt tccgcggtac ccgctcaact ttgtgtcgac cctcaacgcc attgccggca    120

cctactacgt gcactccaac tacttcatcc tgacgccgga acaaatngac gcntcggttc    180

cgctgaccaa tacggtcggt ccc                                            203


<210> SEQ ID NO 452
<211> LENGTH: 287
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 452

nctggccttt ggtccacact aanacaatac tcaagcttcc ggccgcagag ccgccaactc     60

acgatatcgt taaccgatat cccgagccga tagctggcgg gctcgggtgg tggccagcgg    120

cgctgcgacn aaaggtgtga ccgtcatgaa acagacacca ccggcggccg tcggccgtcg    180

tcacctgctc ganatctcag catccgcagc cggtgtgatc gcgctttcgg cgtgtngtgg    240

gtcnccgccc gagcccggca aaggccggcc cgacacaacc ccggaac                  287


<210> SEQ ID NO 453
<211> LENGTH: 272
<212> TYPE: DNA
<213> ORGANISM: Mycobacterium tuberculosis

<400> SEQUENCE: 453

catctgccca ccacacggac cgcggtgcgg acgcggctga cgcgcctggt ggtcagcatc     60

gtggccggtc tgctgttgta tgccagcttc ccgccgcgca actgctggtg ggcggcggtg    120

gttgcgctcg cattgctggc ctgggtgctg acccaccgcg cgacgacacc ggtgggtggg    180

ctgggctacg gcctgctatt cggcctggtg ttctacgtct cgttgttgcc gtggatcggc    240

gagctggtgg gccccgggcc ctggttggca ct                                  272


<210> SEQ ID NO 454
<211> LENGTH: 364
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 454

gacaatactc aagcttgact ggccacccac cggcatgacc accgacaggc ccgactggtc     60

gtaccactcg aacgccgggg tgttgatgtc ccagccgctg aantcgtcct gcgcgcgcag    120

gccgtcnaac aggtacaggg cgggcgaatt ggcaccacca ctttggaatt ggaccttgat    180

gtcacggccc atcgacggcg acggcacctg caggtactcc accggcaagc ccggccggga    240

aaatgccccc gcggtcnccg tgccaccgac ggcgccganc aaacccgaca ctagggccgc    300

gccnacggcc ccgaccacna ntcnacgcga catacccgtg acggcgccac naaccctgtc    360

aaca                                                                 364


<210> SEQ ID NO 455
<211> LENGTH: 360
<212> TYPE: DNA
<213> ORGANISM: Mycobacterium tuberculosis
```

-continued

<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 455
cctccaactc ggcggggaag cgacnccagc ctaccgagct tggagtccan gacgccagcg 60
gcggcgtcgg tctgcgtcgt ggtgccgccg gggtggcgtt ggctggcaac gatctccacc 120
cagccggtcg ggttacccac gatctcggca tanacgcggg ccgaggccgg tgcgataccg 180
tattgcgtca attgggacgc ggttgtgcat tcggctagct cggttgccac acccgtcagg 240
ggttcgacgt tggcgggttc ggcgggcccc ancaccgctg tcaccatgcc cgccaagccg 300
acctgcggcg ccaccaactg cagcaccanc atgtcgccgt cgcgcgccgc gatcacatgg 360

<210> SEQ ID NO 456
<211> LENGTH: 311
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 456
ctcaagcttt ttgagcgtcg cgcggggcan cttcgccggc aattctacta ncgagaantc 60
tggcccgata cggatctgac cgaantcgct gcggtgcanc ccaccctcat tggcgatggc 120
gccgacnatg gcgcctggac cgatcttgtg ccgcttgccg acggcgacgc ggtaggtggt 180
caagtccggt ctacgcttgg gcctttgcgg acggtcccga cgctggtcgc ggttgcgccg 240
cnaaagcggc gggtcgggtg ccatcaggaa tgcctcnccg ccgcggcact gcacggccag 300
tgccgcggcg a 311

<210> SEQ ID NO 457
<211> LENGTH: 288
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 457
cnccagcttg attggtctgg ttgcattggc cagctgcgcg agcctggctc acttcaacta 60
cgacgaccgc aaacaattgc cgccttcgga tccgagttcg gttgggtacg cggcaatgga 120
gcaccatttc tcggtgaatc agactattcc tgagtacttg atcatccact ctgcacacga 180
cctgcgaacc ccgcgcggcc ttgccgacct ggagcagctg gcgcaacgtg tgagccagat 240
cccaggcgtt gccatggttc gcggtgtgac ccggccaaac ggggaaac 288

<210> SEQ ID NO 458
<211> LENGTH: 256
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

-continued

<400> SEQUENCE: 458
caatactcaa gcttgactgg gcccgcacct tcggcgccac ccacaccgtc aacgcccgcg 60
aagtcnacgt cgtccaggcc atcggcggcc tcacggatgg attcggcgcg gacgtggtga 120
tcgacgccgt cggccgaccg gaaacctacc agcaggcctt ctacgcccgc gatctcgccg 180
gaaccgttgt gctggtgggt gttccnacgc ccgacatgcg cctggacatg ccgctggtcn 240
acttcttctc tcacgg 256

<210> SEQ ID NO 459
<211> LENGTH: 327
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 459
tcgacggttt ggcggcctta aatgcactga ggtcgtcaat tgaccccaca gcggaaatgc 60
cgactattcg caggcctcct tcgccttggc tgccggagag gggctccgcg ggaaccgcat 120
gcaggtatat gacctcggtt tctcgggtgc taccgcgtgc cttgtntang atnanctcgg 180
cgttggaatt gtccagccgg cccaattcat cgagcgcana ttcgtacacn tggccggcgg 240
cgacatacgc ttcaccgtgg atctgctcca cacggaccgc cctgtcggga tcctgctcac 300
gggtaangga acttacgtgg cactcgg 327

<210> SEQ ID NO 460
<211> LENGTH: 100
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 460
gaccacgcca ggctaatcac gtgacgctac cgaataccct ncctagtggt gcaggctccc 60
gctggaaatg gccctgtacc aactcgcgca ccggtgccag 100

<210> SEQ ID NO 461
<211> LENGTH: 114
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 461
cggcacccga cccctttgag ccgtccgccg tggccgcggt ggaactggcc gacgagggac 60
tgatcgtgct gggcaaattg gtcgatggca cgctggccgc cgatctgaag gtcn 114

<210> SEQ ID NO 462
<211> LENGTH: 287
<212> TYPE: DNA
<213> ORGANISM: Mycobacterium tuberculosis
<220> FEATURE:
<221> NAME/KEY: unsure
<222> LOCATION: (various positions within the sequence)

-continued

<223> OTHER INFORMATION: applicants are uncertain of bases designated as “n”

<400> SEQUENCE: 462
ctcaagcttg ccgttacccc gacttccgga gggacaccat gagcaccgcc agccgagcac 60
gaggccaaac tccgccgacg caggccggtt ggacttgtcg tgctggacaa ggggtttagc 120
cgccgaagca gtgacgtaca tcggcgaaaa gcagttcgcc tgtcgaccga cggngcnnac 180
cgtgaggcta gggaagcgag gagcacatgg ccgccgaccc gcaatgtaca cgctgcaagc 240
aaaccatcga acccggatgg ctatncntca ccgcccatcg ccgcggt 287

<210> SEQ ID NO 463
<211> LENGTH: 288
<212> TYPE: DNA
<213> ORGANISM: Mycobacterium tuberculosis

<400> SEQUENCE: 463
catgtcgcgc acatccagga cttctggggg gatccgctga cagcggcggg atcccaaagt 60
gcggatgatc gggccgccta cgtcgtggtg tacctcgtcg gtaacaacga aaccgaagcg 120
tatgactcgg tccacgcggt gcggcacatg gtggacacca caccgccacc gcacggggtg 180
aaggcctatg tcaccggtcc ggcagcactc aatgccgacc aggccgaggc cggagacaaa 240
agtatcgcta aggtcaccgc gatcacgagc atggtgatcg cagcaatg 288

<210> SEQ ID NO 464
<211> LENGTH: 255
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 464
atactcaagc ttcggtacgg tggcgggccg tgctgctggc cgcggtcgcg gcgtgcgcgg 60
cctgcggtct cgtttacnag ctcgcgctgc tgacactggc ggcnagcctg aacggcggcg 120
ggatcgtggc cacctccctg atcgtcgcgg gctacatagc cgcgctggga gcaggcgcct 180
tgctgatcaa gccgctactt gcacacgcgg ccatcgcgtt catcgccgtg gaggcggtgc 240
tgggcatcat cggcg 255

<210> SEQ ID NO 465
<211> LENGTH: 288
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 465
tgtcaagtcc tttcagatct cntttttatg acatgactgg agatctgtct agattgcagc 60
tcctgtgagc gtgggtaccg gattcaagcc ggtcggtcac gccgcggtgg taccggcttt 120
gcggcagtgc tcggcctcga gttcggcgat cgcgcgcgaa gtgcgttcgc gcagcaagat 180
cgcggccgta atgccggcga tgaccgcgat gaccagcgcg atccaggaga accgttccaa 240
ccagtgctgg gcggccatcc cggcgaagta gaccagtgca gtggtgcc 288

-continued

<210> SEQ ID NO 466
<211> LENGTH: 224
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 466
caatactcaa gcttcaaaac aggcctgttg tgggcgcacc cggctcgccg agttctgcac 60
gcaccgcctc aantgcggcc cgcaccgccg gcatctcccg gtcacgcagg gccgcggccc 120
gcgccgcanc gacggngtgt tcgcgcagtt cgccgtcaat gatgctgacc tgatcggcca 180
cccgggcgtt ctcggcgtcg tcncgttcac taatcgcggt gctc 224

<210> SEQ ID NO 467
<211> LENGTH: 320
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 467
tacgctggcg ctggagggag ccanntacaa catccacgcc aatgctcttg ccccgatcgc 60
ggcgaccagg atgacccagg acatcctgcc gcccgaagta ctggaaaagc tcacacccga 120
gttcgtcgca ccggtggtgg cctacctgtg caccgaggag tgtgccgaca acgcatcggt 180
gtacgtcgtc ggtggtggca aggtgcagcg agttgcgctg tttggcaacg acggcgccaa 240
cttcgacaaa ccgccgtcgg tacaagatgt tgcggcgcgg tgggccgaga tcaccgatct 300
gtccggtgcg aaaattgctg 320

<210> SEQ ID NO 468
<211> LENGTH: 303
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 468
gcttttcccg tccgtcnncg ctcaaccgcg tgaggccgaa gcggntggtt acgactccct 60
gtttgtgatg gaccacttct accaactgcc catgttgggg acncccgacc agccgatgct 120
ggaggcctac acggcccttg gtgcgctggc cacggcgacc gancggctgc nnntgggcgc 180
gttggtgacc ggcaatacct accgcagccc gaccctgctg gcaaanatca tcaccacgct 240
cgacgtggtt agcgccggtc gagcgatcct cggcattgga gccggttggt ttganctgga 300
aca 303

<210> SEQ ID NO 469
<211> LENGTH: 391
<212> TYPE: DNA
<213> ORGANISM: Mycobacterium tuberculosis
<220> FEATURE:
<221> NAME/KEY: unsure
<222> LOCATION: (various positions within the sequence)

-continued

<223> OTHER INFORMATION: applicants are uncertain of bases designated
as "n"

<400> SEQUENCE: 469
cngcttttta atggccttga cntgggcgng ccggccaccg gggccactcc gcacaatctg 60
tacccgacca agatctacac catcgaatac gacggcgtcg ccgactttcc gcggtacccg 120
ctcaactttg tgtcgaccct caacgccatt gccggcacct actacgtgca ctccaactac 180
ttcatcctga cgccggaaca aattgacgca gcggttccgc tgaccaatac ggtcggtccc 240
acgatgaccc agtactacat cattcgcacg gagaacctgc cgctgctaga gccactgcga 300
tcggtgccga tcgtggggaa cccactggcg aacctggttc aaccaaactt gaaggtgatt 360
gttaacctgg gctacggcga cccggcctat g 391

<210> SEQ ID NO 470
<211> LENGTH: 343
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 470
ctcaagcttg ccgggagggt gcatggccga ctcggattta cccaccangg ggcgccaacg 60
cggtgtccgc gccgtcnagc tgaacgttgc tgcccgcctg gagaacctgg cgctgctgcg 120
caccctggtc ggcgccatcg gcaccttcga ggacctggat ttcgacgccg tggccgacct 180
gaggttggcg gtggacgagg tgtgcacccg gttgattcgc tcggccttgc cggatgccac 240
cctgcgcctg gtggtcgatc cgcgaaaana cgaanttgtg gtggaggctt ctgctgcctg 300
cgacacccac nacgtggtgg caccgggcag ctttagctgg cat 343

<210> SEQ ID NO 471
<211> LENGTH: 303
<212> TYPE: DNA
<213> ORGANISM: Mycobacterium tuberculosis

<400> SEQUENCE: 471
ccgacgccgt cgtggccacc aacaccgcga ccagcaccgt gacccggacc ggggtgccgc 60
gcgaaccggt cttggccaat tgccgcggca ccaagccgtc gcgcgccatg gcgaacagca 120
cgcggcattg cccgagcatc aacaccatca ccaccgtggt aagcccggcc agcgcgccga 180
cggagatgat gccgctggcc cagtacaccc cgttggcctg gaacgcggtg gccagatttg 240
ccggcccgcg gcccggtacg gtccgcagtt gggtgtatgg aaccatgccc gacagcacca 300
ccg 303

<210> SEQ ID NO 472
<211> LENGTH: 264
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 472
ttnactggcc tttggtccac actagacaat actcaagctt ccaggacatc gtcatcgcga 60

-continued

```
ccaaaaccgc gagctaggtc ggcatccggg aagcatcgcg acaccgtggc gccgagcgcc    120

gctgccggca ggccgattag gcgggcaaat tagcccgccg cggctcccgg ctccgantac    180

ggcgccccga atggcgtcac cggctggtaa ccacgcttgc gcgcctgggc ggcggcctgc    240

cggatcaggt ggtaaatgcc gaca                                           264
```

<210> SEQ ID NO 473
<211> LENGTH: 280
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 473

```
ngacgtcttc catccgcgcg tcgttttggc gggttggcca cagcagcccg ccggtgacgg     60

cgacgatgct gggctggttg cggccctgcg ccaccgcggc ttgcatgctg gttggctgtc    120

ttgggacgat cccgaaatag tccacgcgga tctggtgatt ttgcgggcta cccgcgatta    180

ccccgcgcgg ctcgacgagt ttttggcctg gactacccgc gtggccaatc tgctgaactc    240

gcggccggtg gtggcctgga atgtcgagcg ccgttaccta                          280
```

<210> SEQ ID NO 474
<211> LENGTH: 153
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 474

```
cttcctcctg agtaccnccc gtntactttg ggatgggtaa aaaggcgaat cnccgtttgg     60

tcacgaacgc cgggagggac aatctcgggc ggctggggcc tctcgcggga angcccgaat    120

gtacggtgtc tcgacacttc ccntccccct ccg                                 153
```

<210> SEQ ID NO 475
<211> LENGTH: 247
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 475

```
gagcatcggg acntacggag tcaactaccc ggccaacggt gatttcttgg ccgccgctga     60

cggcgcgaac gacgccngcg accacattca gcagatggcc agcgcgtgcc gggccacgag    120

gttggtgctc ggcggctact cccagggtgc ggccntgatc nacatcgtca ccgccgcacc    180

actgcccggc ctcgggttca cgcagccgtt gccgcccnca gcggacgatc acntcgccgc    240

gatcgcc                                                              247
```

<210> SEQ ID NO 476
<211> LENGTH: 264
<212> TYPE: DNA
<213> ORGANISM: Mycobacterium tuberculosis
<220> FEATURE:

-continued

<221> NAME/KEY: unsure
<222> LOCATION: (various positions within the sequence)
<223> OTHER INFORMATION: applicants are uncertain of bases designated
as "n"

<400> SEQUENCE: 476
tactcatgan catcctttaa tcanngcttt gcgttttttt attaaatctt gcaatttact 60
gcaaagcaac aacaaaatcg caaagtcatc aaaaaaccgc aaagttgttt aaaataagag 120
cancactaca aaaggagata agaagagcac atacctcagt cacttattat cactagcgct 180
cgccgcagcc gtgtaaccga gcatagcgag cgaactggcg aggaagcaaa gaagaactgt 240
tctgtcagat agctcttacg cnca 264

<210> SEQ ID NO 477
<211> LENGTH: 264
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 477
ctcaagcttc aggtcaatgt gcnccaagcc ctgacgctgg ccgaccaggc caccgccgcc 60
gganacnctg ccaaggccac cgaatacaac aacgccgccg aggcgttcgc ancccagctg 120
gtgaccgccg agcanancgt caaaaacctc aagacgctgc atgaccaggc gcttancncc 180
gcanctcagg ccaagaaggc cgtcnaacga aatgcgatgg tgctgcacca naagatcgcc 240
gagcgaacca agctgctcag ccng 264

<210> SEQ ID NO 478
<211> LENGTH: 352
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 478
catggtggca ctgtagcgac gtgctgcaat caaggtcatg cccgactctg gtcagctcgg 60
anccgctgac accccgctaa ggctgctcag ctcggtgcat tacctcaccg acggcgaact 120
cccccagctt tacgactatc cggatgacgg cacctggttg cgggcgaact tcatcatcag 180
cttggacggc ggcgctaccg tcgatggcac cagcggggcg atggccgggc ccggcgaccg 240
attcgtcttc aacctgttgc gtgaacttgc cgacgtcatc gtggtcggcg tgggcaccgt 300
gcgcattgag ggctactccg gcgtccggat gggtgtcgtc cagcgccagc ac 352

<210> SEQ ID NO 479
<211> LENGTH: 207
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 479
tactcaagct tgcgggtgat cgccttggtc aacggcaccg tgatcggatc ggggtcnacc 60

-continued gcacaaatgg actggagctt cggcgaantc atcgcctatg cctcgcgggg ggtgacgctg 120
accccgggtg acntgttcgg ctcgggcacg gtgcccacct gcacgctcgt ctatcacctc 180
nggccaccgg aatcattccc gggctgg 207

<210> SEQ ID NO 480
<211> LENGTH: 256
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 480
gttggngcct cgtcggcgaa cagttctcgc acgatttccg gattagcggg actggtcacc 60
agttgggtat gcgggaaggc gctgacgttc gccgcgatta gctgtttgat ggacgcggtg 120
gtgatgttct gatcacggaa ctggctgtaa tagcccaggg tcgccacgct ttcatccggg 180
cccggacccg gcgcaccgag cgtgtcgcgc aggtatgcga cgtgattttc gctgaagtcc 240
ccgtacccgg agaact 256

<210> SEQ ID NO 481
<211> LENGTH: 397
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 481
tgcttccggc tcgtatgttg tgtggaattg tgancggata acaatttcac acaggaaaca 60
gctatgacca tgattacgcc aagctattta ggtgacacta tagaatactc aagctccagg 120
tcaatgtgcg ccaagccctg acgctggccg accaggccac cgccgccgga gacgctgcct 180
ttgtcaccga atacaacaac gccgccgagg cgttcgcagc ccagctggtg accgccgagc 240
agagcgtcga agacctcaag acgctgcatg accaggcgct tagcgccgca gctcaggcca 300
agaatgccgt cgaacgaaat gcgatggtgc tgcggcataa gatcgccgag cgaaccaagc 360
tgctcagcca gctcgagcag gcgaagatgc acgagca 397

<210> SEQ ID NO 482
<211> LENGTH: 379
<212> TYPE: DNA
<213> ORGANISM: Mycobacterium tuberculosis

<400> SEQUENCE: 482
caggcatgca agcttcggag gcagacccgt gcatggtggc actgtagcga cgtgctgcaa 60
tcaaggtcat gcccgactct ggtcagctcg gagccgctga caccccgcta aggctgctca 120
gctcggtgca ttacctcacc gacggcgaac tcccccagct ttacgactat ccggatgacg 180
gcacctggtt gcgggcgaac ttcatcagca gcttggacgg cggcgctacc gtcgatggca 240
ccagcggggc gatggccggg cccggcgacc gattcgtctt caacctgttg cgtgaacttg 300
ccgacgtcat cgtggtcggc gtgggcaccg tgcgcattga aggctactcc ggcgtccgga 360
tgggtgtcgt ccatcgcca 379

-continued

<210> SEQ ID NO 483
<211> LENGTH: 264
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 483
tactcaagct tggggtggcg ctgtcggtcg gtgtgcttgg cggcgtcggt atcaacaccg 60
cccacgaaat ggggcacaag aaggattcgc tggagcggtg gctgtccaaa atcaccctcg 120
cccanacctg ctacgggcac ttctacatcg agcacaaccg tggccatcac gtccgggtgt 180
ccacaccgga ggacccggcg tcggcgcggt tcggcnaaac gttgtgggan ttcctgcccc 240
gcantgttat cggcggcttg cgct 264

<210> SEQ ID NO 484
<211> LENGTH: 351
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 484
ggccatcgcc accgcnccgc ggcgaacgct caaaggcacc tactggcacc aaggccccac 60
acgtcaccct gtgacctcct gcgccgaccc cgcccgaggt cctggccgtt accaccgaac 120
gggcgagccg ggagtctggt acgcatcgaa caaagagcaa ggtgcatggg cggagttgtt 180
ccgccacttc gtcgatgacg gggtcgatcc attcgaggtc cgtcgccgcg tcggtcgagt 240
ggcggtcaca ctccangtac tcgacctcac agacgagagg actcgatccc atctaggtgt 300
ggacgaaaca gatcttctgt ccgacgacta caccaccacc caggccatcg c 351

<210> SEQ ID NO 485
<211> LENGTH: 328
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 485
gcttgcgggt gatcgccttg gtcaacggca ccgtgatcgg atcggggtcn accgcncaga 60
tggactggan cttcggcgaa ntcntcgcct atgcctcgcg gggggtgacc ctgaccccgg 120
gtgacntgtt cggctcgggc acggtgccca cctgcacgct cgtcaagcac ctcnggccac 180
cggaatcatt cccgggctgg ctgcacnacg gcgacntggt cnccctccag gtcgaagggc 240
tgggcnaaac aangcagacc gtccggacaa ncggcactcc ttttccgttg gctcttcggc 300
cgaatccgga cgccnaaccc gaccggcg 328

<210> SEQ ID NO 486
<211> LENGTH: 344
<212> TYPE: DNA
<213> ORGANISM: Mycobacterium tuberculosis
<220> FEATURE:

-continued

<221> NAME/KEY: unsure
<222> LOCATION: (various positions within the sequence)
<223> OTHER INFORMATION: applicants are uncertain of bases designated as “n”

<400> SEQUENCE: 486
gttctcgcac gatttccgga ttagcgggac tggtcaccag ttgggtatgc gggaaggcgc 60
tgacgttcgc cgcgattagc tgtttgatgg acgcggtggt gatgtnctga tcacggaact 120
ggctgtaata ncccagggtc gccncgcttt catccgggcc cggacccggc gcaccgagcg 180
tgtcgcgcag gtatgcgacg tgattttcgc tgaagtcccc gtacccggag aactcgaaca 240
cgctgaggcg ctcgtcaccg tcgtnncggc gaccaagcgc ggcgagcaac tgcgcaaaat 300
cgttaagana ggtcgaatcg ttgaaattcg gcaccacctg cacc 344

<210> SEQ ID NO 487
<211> LENGTH: 285
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 487
cacaagacaa tactcaagct tcaggtcaat gtgcnccaag ccctgacgct ggccgaccag 60
gccaccgccg ccgganacgc tgccaaggcc accgaataca acaacgccgc cgaggcgttc 120
gcagcccagc tggtgaccgc cgagcananc gtcnaaaacc tcaagacgct gcatgaccag 180
gcgcttancg ccncagctca ggccaagaag gccgtcgaac gaaatgcgat ggtgctgcag 240
canaanatcg ccgancgaac caagctgctc agccagctcg agcag 285

<210> SEQ ID NO 488
<211> LENGTH: 280
<212> TYPE: DNA
<213> ORGANISM: Mycobacterium tuberculosis

<400> SEQUENCE: 488
ccacccgtgc atggtggcac tgtagcgacg tgctgcaatc aaggtcatgc ccgactctgg 60
tcagctcgga gccgctgaca ccccgctaag gctgctcagc tcggtgcatt acctcaccga 120
cggcgaactc ccccagcttt acgactatcc ggatgacggc acctggttgc gggcgaactt 180
catcagcagc ttggacggcg gcgctaccgt cgatggcacc agcggggcga tggccgggcc 240
cggcgaccga ttcgtcttca acctgttgcg tgaacttgcc 280

<210> SEQ ID NO 489
<211> LENGTH: 160
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 489
gctttccgcc gatacccncc atgtcccgca catccaggac ttctgggggg atccgctgac 60
agcggcggga tcccaaagtg cggatgatcg ggccgcctac gtcgtggtgt acctcgncgg 120
taacaacgaa accgaancgt atgactcngt ccacgcggtg 160

-continued

<210> SEQ ID NO 490
<211> LENGTH: 176
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 490
caacccgant tggctttcgg cgccntcggt gaggacggcg tgcgggtgct caacgacgac 60
gtcgtccgcg ggacacacct cgatgctgcc gccatggacg cggtcgaacg caagcagctg 120
atcgatctac nacgccgngn ggaacgcttc ngccgcgggc gtgaccgcnt cccgtt 176

<210> SEQ ID NO 491
<211> LENGTH: 216
<212> TYPE: DNA
<213> ORGANISM: Mycobacterium tuberculosis

<400> SEQUENCE: 491
gggatgggca aaaaggcgaa gcaccgcgtg gccacgaacg ccgggaggga caatctcggg 60
cggctagggc ttctcgcggg aaggcccgaa cgtacggcgt ttcaacacgt cgcgtcgccc 120
tccgaccgcg aacattcggg gatggcagca acctggtagc accctggccg ggcgatgatc 180
tgccagcgtc cccgcgggta gtcgccgccc gggcgg 216

<210> SEQ ID NO 492
<211> LENGTH: 163
<212> TYPE: DNA
<213> ORGANISM: Mycobacterium tuberculosis

<400> SEQUENCE: 492
cagcagacca acaagagcat cgggacatac ggagtcaact acccggccaa cggtgatttc 60
ttggccgccg ctgacggcgc gaacgacgcc agcgaccaca ttcagcagat ggccagcgcg 120
tgccgggcca cgaggttggt gctcggcggc tactcccacg gtt 163

<210> SEQ ID NO 493
<211> LENGTH: 80
<212> TYPE: DNA
<213> ORGANISM: Mycobacterium tuberculosis

<400> SEQUENCE: 493
ctcaagcttg actggccacc caccggcatg accaccgaca ggcccgactg gtcgtaccac 60
tcgaacgccg gggtgtttga 80

<210> SEQ ID NO 494
<211> LENGTH: 248
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 494
ttggtgcccg gaatggcgag tcccatttan tcgctgattt gtttgaacag cgacgaaacc 60
ggtgttgaaa atgtcgcctg ggtcggggat tccctctcca agcaagagta actggcccca 120
aataaagtta ctcgtcgtct tgcaaagacc gctacccgat gccatttatg tgtttcctta 180

-continued cgctcnnnnt tccggtgcgc catcattatc tgcacctttg cactgcacat tgagcttagc 240
agcgctcg 248

<210> SEQ ID NO 495
<211> LENGTH: 341
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 495
gaattngctt tcggcgccat cggcccagga ccgcgtgcgg gtgctcaacg acgacgtcgt 60
ccgcgggaca cacctcgatg ctgccgccat ggacgcggtc gaacgcaagc agctgatcga 120
gctacaacgc cgcgcggaac gcttccgccg cgggcgtgac cgcatcccgt tgaccgggcg 180
gatcgcngtg atcgtcgatg acggcatcgc caccggagcg acggccaagg cggcgtgcca 240
ggtcgcccgg gcgcacggtg cggacaaggt ggtgctggcg gtcccgatcg gcccagacga 300
catcgtggcg agattcgccg ggtacgccga tgaagtggtg t 341

<210> SEQ ID NO 496
<211> LENGTH: 420
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 496
taaagctttc gtcagttcat ngngcccccg gaccaacaaa agcatcggga catacggagt 60
caactacccg gccaacggtg atttcttggc cgccgctgac ggcgcnaacg acgccagcga 120
ccacattcag cagatggcca gcgcgtgccg ggccacgagg ttggtgctcg gcggctactc 180
ccagggtgcg gccgtgatcn acatcgtcac cgccgcacca ctgcccggcc tcgggttcac 240
gcagccgttg ccgcccgcag cggacgatca cntcgccgcg atcgccctgt tcgggaatcc 300
ctcgggccgc gctggcgggc tgatgagcgc cctgacccct caattcgggt ccaanaccat 360
cnacctctgc aacaacggcg acccgatttg ttcggacggc aaccggtggc gancgcacct 420

<210> SEQ ID NO 497
<211> LENGTH: 135
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 497
ccgggaggga ccatcncggg cggctncggc ttctctccgg aaggttctan ngtnnngcgt 60
ttcnacnctt cccgtcgccc tgcgaccgcc gaacattcgg ggtatggnng cancctgtna 120
gcatccnggc cgggc 135

<210> SEQ ID NO 498
<211> LENGTH: 277

-continued

<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 498
ctcaagcttc cgcatcagat cgctatagaa ccggtgcgcg tccccaccga gtggctggtc 60
gccttccagc acgatcgtta ccgcgttatc ggaatcaaac tcnccgaaca cctgaccaac 120
gcgcttgatc gcctgaatcg atgcggcgtc gctggggctc atcgataccg agtgtgcttt 180
tccgaccact tccagttgcg gtacggcgag attgacaaag gcggtgaagc ccagccagag 240
caggacgatc accnccgcaa accggcggat ttgcccg 277

<210> SEQ ID NO 499
<211> LENGTH: 323
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 499
gcttggcagc ctgcggctgg gcgccctnga gctcttcgat ctggatctcc ggactcgaga 60
tgctcacttg cccggccgtg gacgtaccca ttgcggccgg gaccccagcg ccccaggtga 120
ccagcgagtt gggctgcacg ctgaccggcc cgtcggggtc gacgccggta acggtcagca 180
gctccgangt ccnnctgatc ccgaccgcag ctgccaatgc gcggctggca gccgacgtgg 240
atgtgccggg gcctagatcg cggggcagca gcgagaccgc gtcaccgacg gtcatcacct 300
tgccgagttt nggcctgccg can 323

<210> SEQ ID NO 500
<211> LENGTH: 148
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 500
gcttccggct cgtatgttgt gtggaattgt gagcggataa caattncaca caggaaacag 60
ctatgaccat gattacgcca agctatctag gtgacactat agaatactca agcttgagcc 120
atcgggctat cagctggttg atgtcccg 148

<210> SEQ ID NO 501
<211> LENGTH: 242
<212> TYPE: DNA
<213> ORGANISM: Mycobacterium tuberculosis

<400> SEQUENCE: 501
caggcatgca agcttgtcgt ctatcacatc cgaccaccaa ccgcccgacg gctcggcaga 60
acgcctccgc atatgggtcg acgaccagcg ggtcggactt ctgggctgcc agcgctcgcg 120
ccgtcgcgac aaacagcgcg gtcgaaccga cactccttgt gatgtcccac ctatcacctt 180
cggtacgcac ccaatcgacc ctacgcggct agctcagccc cgatcttcca gagctccgcc 240

-continued cg 242

<210> SEQ ID NO 502
<211> LENGTH: 230
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 502
gctttttgag cgtcgcgcgg ggcggcttcc ccggcaattc tactagcgag aagtctggcc 60
cgatacggat ctgaccgaag tcgctgcggt gcagcccacc ctcattggcg atggcgccga 120
cnatggcgcc tggaccgatc ttgtgccgct tgccgacggc gacgcggtag gtggtcaatt 180
ccggtctacg cttgggcctt tgcggacggt cccgacgctg gtcgcggttg 230

<210> SEQ ID NO 503
<211> LENGTH: 235
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 503
cgancctgtt cgacggctac ctgaatcacc ccgatnccac cgccgcggcg ttcgacgccg 60
acagctggta ccgcaccggc gacgtcgcgg tggtcgacgg cagtgggatg caccgcatcg 120
tgggacgcga gtcggtcgac ttgatcaagt cgggtggata ccgggtcggc gccggtgaaa 180
ttgaaacggt gctgctcggg catccggacg tggcggaggc ggcagtcgtc ggggt 235

<210> SEQ ID NO 504
<211> LENGTH: 152
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 504
naagctttgt cacaccaagt gtttcnacca gncgctccat ccggcgaagt ggatactccc 60
agcaggtagc aggtcgccac cacgctggtc agtgcgcgtt cagctcgctt gcggcgctgc 120
agcagccagt ccgggaaata gctgccctgg cg 152

<210> SEQ ID NO 505
<211> LENGTH: 192
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 505
cgctggncgc cggcgctggg ctgcggtaac caattaccac aacacttttc ggtagccgaa 60

-continued

```
cagcggcgcg taccagcgaa atggcacagc caccgcagtc gccgacatcc cgcgaagatg    120

tggcagattt tcgtgcggtc gagccggcga aggcctagcg tcattgttgc ctggcaaggt    180

tgctgggccc gg                                                        192


<210> SEQ ID NO 506
<211> LENGTH: 312
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 506

ctcaagcttc ttctgcccct tgccgttncg gatnacatcc cgcagcgact cggcttcggc     60

gtcgatgtcg aagttctcga tcagcttctg gatcgactcc gcgcccatgg caccggtgaa    120

gtactcgccg tagcggtcga cnagttcgcg gtagaggttt tcgtcnacna tcagctgctt    180

gggcgccanc ttggtgaaag tgctccaaat gtcctccaac cggtccagct cacgctgcgc    240

gcggtcacgg atctggcgca tctcgcgctc gccgccgtcg cgaacttgcg ccgcgcatcg    300

gccttggggc cc                                                        312


<210> SEQ ID NO 507
<211> LENGTH: 296
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 507

gttcacacct acctactatg ccncaattcn ccgacacggg tggcatcaac acgggcgata     60

aggtggaaat cgctggggtg aacgtcgggc tggtgcgctc gctggcaatc cgcggcaacc    120

gcgtgttgat cggattctcg ttgcccggca agacaatcgg gatgcaaagc cgggcagcaa    180

ttcncnccna caccattctt ggccgtaaga acctggagat cgaaccccgc ggttcggagc    240

cgttgaaacc caacggtttc ctgccgttgg cgcanaccac tacgccatac caaatc        296


<210> SEQ ID NO 508
<211> LENGTH: 208
<212> TYPE: DNA
<213> ORGANISM: Mycobacterium tuberculosis

<400> SEQUENCE: 508

ctcaagcttt acgccgacgc cggcctacac aacaccaagg aaacgattgc ctactgccga     60

atcggggaac ggtcctcgca cacctggttc gtgttgcggg aattactcgg acaccaaaac    120

gtcaagaact acgacggcag ttggacagaa tacggctccc tggtgggcgc cccgatcgag    180

ttgggaagct gatatgtgct ctggaccc                                       208


<210> SEQ ID NO 509
<211> LENGTH: 278
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
```

as "n"

<400> SEQUENCE: 509
tcccncatgg gataacgggt ttagatttcn acaacggcac cgtgtttctc aacaagccgg 60
tcatcagctg ggccggcgac aacggtatct acttcacccg ctttcgcccg tacaagaaaa 120
accactaggc caccatcgag tccaagaaca accacctggt ccgcaagtac gcgttctact 180
accgctatga caccgccgag gaacgcgccg tgctcaaccg gatgtggaag ctggtcaacg 240
accgcctcaa ctacctcacc ccgaccatca aaccgatc 278

<210> SEQ ID NO 510
<211> LENGTH: 177
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 510
ctcaagcttg ggtgttgccg atcaccggaa gccncatgat cagccacgtt tcgcgccgcc 60
cggcatacgg cggcgtaccg atctccgcgt catacacccg cgggtaatcg ccgacggtgc 120
cggttcgcga gccgaaggtg acaacgctga ttgaatcnag ttccangtcc agcgggt 177

<210> SEQ ID NO 511
<211> LENGTH: 296
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 511
tnaacagctc gcggcagccc acgacctgct gcgtcggatt gccggcggcg agatcaattc 60
caggcagctc ccggacaatg cggctctgct ggcccgcaac gaangactcg aggtcacccc 120
ggtgcccggg gtcgtggtgc acctgccgat cgcacaggtt ggcccacaac cggccgcttg 180
atgnnnngtc ggcaagcccg gcagtngcca aacccagcgt gatcangctc ggctcgcgag 240
ttcggcgaan aagtggctcg cctgatcacc taccatcggc cangatctgc gtgtca 296

<210> SEQ ID NO 512
<211> LENGTH: 223
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 512
gccanccggc ttggcgtcga ctcccgttcn gcacatcata cggtccccgg tactgtccaa 60
ctgcgccggt gcgctagcca aacgtcacga ctctcagtga tcccagttcg tgatccggcc 120
ggtggcgccg ctgcggcggg ggctnatnta cttcggactn attatctcat ccaaaggaca 180
ccgggccggt ggctggaatc ccatggtgcg atcggccaca can 223

<210> SEQ ID NO 513

-continued

<211> LENGTH: 147
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 513
ccgacctggt atcttccgat agcgcgcgtt gatatccggt ctgatctcct gcccttaacg 60
ccggatctca gcaggtcccc atgcaaagat ccgaggtgtc ccngatctag gggtcctcgt 120
cctccagatg atggagcaag tcggccc 147

<210> SEQ ID NO 514
<211> LENGTH: 149
<212> TYPE: DNA
<213> ORGANISM: Mycobacterium tuberculosis

<400> SEQUENCE: 514
ctcaagcttc ggctcaggcg gcgctgccgg taacgtcgct gaccggtgca ggtttcgaca 60
atgtggtgcc ggttcggcgg ctacgtgcca tcaagacact ggcgcaggct atcgcacccg 120
ttatcggcta caaacaaatc gcggtatgc 149

<210> SEQ ID NO 515
<211> LENGTH: 238
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 515
catcacctgn ttcatgaact ggaagcaccg cagcgcttcc ttttcggccg caacatgagc 60
cagcctctcg tcggcggtcg ggtgcaggtg ctcgggcagc tcggccgcga cagccgcctg 120
accctgaaac cagcttccat atcccgcgac gaacgacgcc agtccgctac gtaacccctc 180
cgcgactgtc catggacaac agcgcgttct ccaccgaccg ggcccgggtg tggggtgt 238

<210> SEQ ID NO 516
<211> LENGTH: 175
<212> TYPE: DNA
<213> ORGANISM: Mycobacterium tuberculosis

<400> SEQUENCE: 516
agcttagctt cccgccccgg caatagggct ccagctcatc cggtgtgacc agataggggc 60
ccagggtgat accgctgtct ttgcccttgg cctgtccgat gcgcagctgg ccctccagca 120
tctgcaggtc ccgtgcggac cagtcgttga aaatggtata gccgatgatc gaccg 175

<210> SEQ ID NO 517
<211> LENGTH: 144
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 517

-continued ccngaacaga agcggnggtt cctaccgcgg tgtgcggccg gcgcgatatc ggccttttta 60
ctaaccgaac ccgatgtggg ctccgatccg gcgcgcatgg catcgacggc gacgccgatc 120
gatgaccgcc aggcttacca cctt 144

<210> SEQ ID NO 518
<211> LENGTH: 174
<212> TYPE: DNA
<213> ORGANISM: Mycobacterium tuberculosis

<400> SEQUENCE: 518
ctcaagcttg cgcgactcga caagcattct tgacagttgt tttggctcgg catggttagc 60
caaggttctg cggtcccacc agatcatctt ggtccggtag cgctcgtccg ggtatgctgc 120
cgccgggatt ctcgctgcta ttactccccc cgaagaacgc caccggtcca gcgc 174

<210> SEQ ID NO 519
<211> LENGTH: 187
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 519
gcnaggcggt atagcttccc gtcgtaccgg cgaccgccag ccgagaagct cgttttccca 60
gtgttgctgg ggattctcac gctgctgctg agtgcgtgcc agaccgcttc cgcttcgggt 120
tacaacgagc cgcggggcta cgatcgtgcg acgctgaagt tggtgttctc catggacttg 180
gggatgt 187

<210> SEQ ID NO 520
<211> LENGTH: 215
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 520
gtgtggaacc gtgagcggat aacaatttca cacaggaaac agctntgacc ttgattacgc 60
caagctattt aggtgaggct atattaatac tcaagattgc ggtcgagcac atcggcccaa 120
gaaccgccga aggcacggcg gaacgcctgc ggcacatggg gcgacgacca gcgggtcgga 180
cttctgggct gtccagccgg atcgcgccgt cgcga 215

<210> SEQ ID NO 521
<211> LENGTH: 406
<212> TYPE: DNA
<213> ORGANISM: Mycobacterium tuberculosis

<400> SEQUENCE: 521
cactgtcagt acatatgcgc cgctcctcct catcgctgcg ctcggcatcg tcgccggcgg 60
tcatggcgtc accctaccca agccgaacgc gaaacgagaa cgtgttccat tattagggtg 120
tgagcaccaa taccagattg ctcaccagga actcacgcag caccgggacg gatgtcagcc 180
accacgccca tctggggtgg tagcggggaa atacggctaa cgcggctccg gtgccggcag 240
cccagcgcag accctcggcg gcggacacgg caaacaacga cgacccatag ttgttctttg 300

-continued ccggatggcc gtgtttgcgg acatatcggg cggcggcgcg ggcgccgccg aggtagtggc 360
tgaggcccat ctcgtgcccg ccgaatggcc ccagccaaac cgtgta 406

<210> SEQ ID NO 522
<211> LENGTH: 180
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 522
ctcaagcttt tacggtgatc gcgcatcacc tggttcatga actggaagca gcgcagcgct 60
tccttttcgg ccgcaacatg agccancctc tcgtcggcgg tcgggtgcag gtgctcgggc 120
agctcggccg cgacagccgc ctgaccctga aaccagcttc catatcccgc gacnaacgac 180

<210> SEQ ID NO 523
<211> LENGTH: 69
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 523
ctcagaagcc gctagctggt agagtcgctg accggtgcac gtggcgncaa tgtgcgctgc 60
cggttcgcg 69

<210> SEQ ID NO 524
<211> LENGTH: 168
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 524
ctcaagcttg cgctcatcaa gcgcgaacag cagggcggtc ggctggtcgc catgacgggt 60
gacgggacca atgacgcacc cgcgctcgcg caagccgatg tcggggtggc natnaatacc 120
ggcacccagg cggcccggga agccggcaac atggtcnatc tccactcc 168

<210> SEQ ID NO 525
<211> LENGTH: 83
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 525
acttctattt cgactggtgt gctgtggcgc gatccgactg ccggcgtggt caaggccggc 60
cagttgtggg atnccacagg cac 83

<210> SEQ ID NO 526

-continued

<211> LENGTH: 173
<212> TYPE: DNA
<213> ORGANISM: Mycobacterium tuberculosis

<400> SEQUENCE: 526
gcttgtcgta ttccgtggca ctgtcagaca tatgcgccgc tcctcctcat cgctgcgctc 60
ggcatcgtcg ccggcggtca tggcgtcacc ctacccaagc cgaacgcgaa acgagaacgt 120
gttccattat tagggtgtga gcaccaatac cagattgctc accaggaact cac 173

<210> SEQ ID NO 527
<211> LENGTH: 38
<212> TYPE: DNA
<213> ORGANISM: Mycobacterium tuberculosis

<400> SEQUENCE: 527
cgatattcgt cggccgcgtt gtctcgactg ggtcgcgt 38

<210> SEQ ID NO 528
<211> LENGTH: 136
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 528
gacctcggcc accaagccgg acgcgaccgt cgaggtggcg atccggcttg gcgtcgaccc 60
gcgtaaggca gaccacatgg tccgcggcac ggccancctg ccacacggca ctggtaagac 120
tgcccgcgtc gcggcn 136

<210> SEQ ID NO 529
<211> LENGTH: 114
<212> TYPE: DNA
<213> ORGANISM: Mycobacterium tuberculosis

<400> SEQUENCE: 529
ccggaagtct aggggacgac ctactcagcg caaaatgtcg ctaatgtgag tccgccccac 60
cagggcagat caacccatgt cgatgatgac ctacccggat accggattgg cggt 114

<210> SEQ ID NO 530
<211> LENGTH: 119
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 530
agcttcagtt cctccacgac gcgttcccaa atgaatttcc cgatcccaca atctcggttc 60
agatacaggt cgccataccc cttacttcgg naacgctggg cggattggcc ctgccgctg 119

<210> SEQ ID NO 531
<211> LENGTH: 99
<212> TYPE: DNA
<213> ORGANISM: Mycobacterium tuberculosis

<400> SEQUENCE: 531
ccgcctacgg gtcgaacatg catcccgaga ccgatgctcg agcgcgcacc ccactcgccg 60

-continued

```
atggccggaa ccggctggtt acccgggtgg cggctgacc                          99


<210> SEQ ID NO 532
<211> LENGTH: 308
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 532

gcggctggtt acgactccct gtttgtgatg gaccacttct accaactgcc catgttgggg     60

acgcccgacc agccgatgct ggaggcctac acggcccttg gtgcgctggc cacggcgacc    120

gagcggctgc aactgggcgc nttggtnacc ggcaatacct accgcagccc gaccctgctg    180

gcaaagatca tcaccacgct cgacgtggtt agcgccggtc gagcgatcct cggcattgga    240

gccggttggt ttgagctgga acaccgccag ctcggcttcg agttcggcac tttcagtgac    300

cggttcan                                                             308


<210> SEQ ID NO 533
<211> LENGTH: 328
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 533

gcctttccgc acaatctgta ccccaggacc ntctaaaaaa tcgaatacga cggcgtcgcc     60

gactttccgc ggtacccgct caactttgtg tcgaccctca acgccattgc cggcacctac    120

tacgtgcact ccaactactt catcctgacg ccggaacaaa ttgacgcagc ggttccgctg    180

accantnntg tcggtcccac gatgacccag tactacatca ttcgcacgga gaacctgccg    240

ctgctagagc cactgcgatc ggtgccgatc gtggggaacc cactggcgaa cctggttcaa    300

ccaaacttga aggtgattgt taacctgg                                       328


<210> SEQ ID NO 534
<211> LENGTH: 75
<212> TYPE: DNA
<213> ORGANISM: Mycobacterium tuberculosis

<400> SEQUENCE: 534

gcagaccaac aagatgcatc gggatcatac gccgtcaact acccggccaa cggtgatttc     60

ttggccgccg cccac                                                      75


<210> SEQ ID NO 535
<211> LENGTH: 319
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 535

ctcaagcttg ccaaagagac ctcgtccacc aagcnggacg cgaccgtcna ggtggcgatc     60
```

-continued

```
cggcttggcg tccacccgcg taaggcanac canatggttc gcggcacggt caacctgcca    120

cacggcactg gtaanactgc ccgcgtcgcg gtattcgcgg ttggtgaaaa ggccgatgct    180

gccgttgccg cgggggcgga tgttgtcggg agtgacaatc tgatcganag gattcagggc    240

ggctggctgg aattcgatgc cgcgatcgcg acaccggatc agatggccaa agtcggtcnc    300

atcgctcggg tgctgggtc                                                 319
```

```
<210> SEQ ID NO 536
<211> LENGTH: 312
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 536

ccacggcgtg gatcaaggta ccggccggga tgttgcgcaa tggcaggttg ttgcccggct     60

tgatgtcggc gttagcgccg gattccacca catccccttg cgaaagtccg ttgggtgcaa    120

tgatgtagcg cttctcccca tcgagatagt ggagcaacgc aatccgtgcg gtacggttcg    180

ggtcntactc gatgtgcgcg accttggcgt tgacaccatc tttgtcattg cggcgaaagt    240

cgatcatccg gtaagcgcgc ttatgaccgc cgcctttgtg ccgggtggta atccggccat    300

gcgcgttgcg tc                                                        312
```

```
<210> SEQ ID NO 537
<211> LENGTH: 105
<212> TYPE: DNA
<213> ORGANISM: Mycobacterium tuberculosis

<400> SEQUENCE: 537

ggcggctgcg tcggcgagat gatcgcccgg tgccaccccg atccgtgcct cggtcagcgc     60

caacgtgctt tccggtccgg cgaccaccat gtcgcatgcg ccgac                    105
```

```
<210> SEQ ID NO 538
<211> LENGTH: 144
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 538

gcaatcgcct tggcggtcgc cgggttgtca ccggtgatca tcncggngcg gatgctcatn     60

cggcgcattt cgtcnaatcg ttcccgtatg cccaccttga cgatgtcctt catatggacc    120

acgccgatgg cccncgcgct nctg                                           144
```

```
<210> SEQ ID NO 539
<211> LENGTH: 431
<212> TYPE: DNA
<213> ORGANISM: Mycobacterium tuberculosis

<400> SEQUENCE: 539

ccggctcgta tgttgtgtgg aattgtgagc ggataacaat ttcacacagg aaacagctat     60

gaccatgatt acgccaagct atttaggtga cactatagaa tactcaagct tccacatcgg    120
```

-continued

```
tatgccaaag cattgcgccg ctatcgattt cgcgctggca tcgccaaggt ggacttcttg    180

ctcagcgacg agatcccgtg gtcggatccg cggctgcggc gggctgcgac cctgcatctc    240

ggcggcaccc gtgaccagat ggcgcgcgcc gaggcagacg tcgcggcggg acgccacgcc    300

gactggccga tggtgctggc cgcgtgtccg cacgtcgccg accccggccg catcgacgaa    360

accggccgcc gtccgttctg gacctatgcc cacgtgccgt cggggtccac gctcgacgcg    420

accgagaccg t                                                         431
```

<210> SEQ ID NO 540
<211> LENGTH: 462
<212> TYPE: DNA
<213> ORGANISM: Mycobacterium tuberculosis

<400> SEQUENCE: 540

```
cgcgtccacc gcagcgtgag attggtggcg ccattcgtcg tggtgtagct gctgttggcg     60

gcgtcgccgt attgtgcggg ccagccttgt gcgggggccg cttctaccca cgagtcggca    120

cttccgcaac cgcccagctc gaccgcgatt acggcggccg caacggccgc cggaaggcgt    180

ctcgcaagcg ccttatcctt tcgcaggttc ccagatcctt ccgctacgtg ggtcgctcat    240

cggcgggccc ggccgaatga gtacaggtga gggtaaccgc tacaaatgaa gttggtcagt    300

gctggccaac tgtgtaatgg ttgcccggct cgggtcacca cgtacattct ggcaaggcgg    360

gcgagattcg gttcctcgcg tccttggccg gtggcggttc ccggttgtcc gtgggcgtgt    420

cgtgtacgtg gtgtaagtgt cgtgaactcc tcagtttggg ct                       462
```

<210> SEQ ID NO 541
<211> LENGTH: 307
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 541

```
ctcaagcttg cgctggatct ggcggctgag cctgttcttg ggcaacatgc cgagggatcg     60

ccttttccac cacgcggtcg gggtggcgtt gcattagctc accgatggtg cgcttgtgca    120

ggccgccggg ataccccgag tgccggtaaa ccatcttgtg ctgcagtttg tcgccgctga    180

tggcgacctt gtcggcgttg atcacnatga cnaagtcacc gccatcgaca ttgggggcga    240

acgtcggctt gtgcttgccg cgcagcaggt tggccgccgc gacggcaagg cggccaanca    300

ccacgtc                                                              307
```

<210> SEQ ID NO 542
<211> LENGTH: 333
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 542

```
tttgggatgg gcaaaaaggc gaagcnccgc gtggccacga acgccgggag ggacaatctc     60

gggcggctag ggcttctcgc gggaaggccc gaacgtacgg cgtttcaaca cgtcgcgtcg    120

ccctccgacc gcgaacattc ggggatggca gcaacctggt agcaccctgg ccgggcgatg    180
```

atctgcagcg tcgccgcggg tagtcgccgc ccgggcggct acagtctgaa acgcgatgac 240
catcgatgtg tggatgcagc atccgacgca acggttccta cacggcgata tgttcgcctc 300
gctgcgccgg tggaccggtg ggtctatccc gga 333

<210> SEQ ID NO 543
<211> LENGTH: 234
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 543
ctcaagcttc gtcataagac catggtgcgc tttctttcac ccgtccanag tcgggggcat 60
ccgcaccggc tcgcatcgca tcatcctccc acgacgggcc gctcatcagc ttgggccatt 120
tcaatgtact tgataccccg cgctgcgggt aggccactgc nacaattcaa acacggtgtc 180
acacggtgaa tantgtcnan atgggctctg atcaaccgtc ncaaacccgg tttc 234

<210> SEQ ID NO 544
<211> LENGTH: 440
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 544
gaattctgcg tgcaccgcta tgggttgcag cagcggctgg cgccgcacac cccactggcc 60
cgggtgtttt cgcccccgaac ccggatcatg gtgagcgaaa aggagattcg cctgttcgat 120
gctgggattc gccaccgcga ggccatcgac cgattactcg ccaccggggt gcgagaggtg 180
ccgcagtccc gctccgtcga cgtctccgac gatccatccg gcttccgccg tcgggtggcg 240
gtagccgtcg atgaaatcgc tgccggccgc taccacaagg tgattctgtc ccgttgtgtc 300
gaagtgcctt tcgcgatcga ctttccgttg acctaccggc tggggcgtct gcacaacacc 360
ccggtgaggt cgtttttgtt gcagttgggc ggaatccgtg ctctgggtta cagccccgaa 420
ctcgtcncgg cggtgcgcgc 440

<210> SEQ ID NO 545
<211> LENGTH: 425
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 545
gcagttggga atcgctctgc agcaaaccan tattctgcgc gacgttcgag aggactnttt 60
gaatggacgg atctacctgc cgcgcgacga gctggaccga ttaggcgtac ncctccgcct 120
ggacgactcc ggggcactcg atgaccccga cggacggctc gcggcactgc tgcggttcan 180
tgccnaccgc gccgcanact ggtattcgct gggactgcgg ctgattccac acctcgaccg 240
ccgcagcgct gcctgctgtg cggccatgtc tggcatctac cgccgtcngc tcgccttgat 300

-continued cagaccatcg ccggcggtcg tctaccatcg gcgaatctct ctgttcggga ctgaanaang 360
cccaagtggc ggcggcagca ctggnctctt cggtaacctg cngaccgccc attggaccgc 420
taccg 425

<210> SEQ ID NO 546
<211> LENGTH: 401
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 546
ttgatctgga cgtctgagac ggtgatcggn ccgaacctga attgtccggt aatgcccagc 60
gcagaaagca nggtggtggc cggggcggtg aanccggcgt cggcggcacc gtcgaagtcg 120
atgtggattg ccggaatggg gatgtccggc acggcgaagc cgtagttcgc ttgtcccgtg 180
aggcccangt ggatgggggg aaggatcgtg gtgtccggga tgataatggg gccgatgccg 240
ccggttgaag tccagtggat cgggaattcg ggaatcgtga tgccgacgtt caggccgaac 300
aggccctcca agttgcctcg ccacnagatg ccgttgctga agttgcccga catgagggcg 360
ccggtgtcca cattgcccga attggcgacg ccggtgttgg c 401

<210> SEQ ID NO 547
<211> LENGTH: 391
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 547
cacgtaggcg ccgtccataa atnactccgc cgcgcttcgc acatcctcgt ancgatcctt 60
ggcgagcagg tcaaccgggc gctgcccgtc naggagccgg tttttggcgt gcagccactg 120
gccgacacct cggggggtaa gcgaatccga gagcaggagg acnaggtcac gaanctgcgc 180
cagccggtcg taccgctcag ggcggatgtc gccggtccgc cacccgcgta ccgccccgatc 240 ggacacctgt atgaccgcgg cgacntcgac ctgggtgacg ccgaagggtt tcagggcatc 300
nacnatctcg ctggcctcga ccgcccggtc cagggtgacc gccatcgtgg ttcctccgca 360
acttccggtt ctactaccgt aaacgctacc g 391

<210> SEQ ID NO 548
<211> LENGTH: 369
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 548
cggggaacgg tcctcgcaca cctggttcgt gttgcgggaa ttactcggac ancaaaacgt 60
caagaactac gacggcagtn ggacagaana cggctccctg gtgggcgccc cgatcgagtt 120
gggaagctga tatgtgctct ggacccaagc aaggactgac attgccggcc agcgtcgacc 180

-continued

```
tggaaaaaga aacggtgatc accggccgcg tagtggacgg tgacggccag gccgtgggcg    240

gcgcgtttcg tgcggctgct gggacncctc cgacgagttc accgccggga ggtcgtcgcg    300

tcggccaccg ggcgaatttc cggttcttcg ccgcgccccg ggatcctggg accgcnggcg    360

cgcgctgtt                                                            369


<210> SEQ ID NO 549
<211> LENGTH: 85
<212> TYPE: DNA
<213> ORGANISM: Mycobacterium tuberculosis

<400> SEQUENCE: 549

ctcaagcttt gtccgacaag cgttcccggg cggtcagcaa gcgaacgtcg gttggcccac     60

tgcgggtcga tattgccgcc aggga                                           85


<210> SEQ ID NO 550
<211> LENGTH: 101
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as “n”

<400> SEQUENCE: 550

cgtcagcacg gcgacgtcgc gntacgccga gcagttacac aatcgctctg cagcaaacca     60

atattctgcg cgacgttcga gaggacttct tgattggact g                        101


<210> SEQ ID NO 551
<211> LENGTH: 458
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as “n”

<400> SEQUENCE: 551

ctgcatccgg ctcgtatgtt gtgtggaatt gtgagcggat aacaatttca cacaggaaac     60

agctatgacc atgattacgc caagctattt aggtgacact atagaatact caagcttcgc    120

gcagcggcgg gttgacccgg ttcacgccgt catagctggc caatctggca tcgtcgatca    180

ncatgtggtg gggggtgacc tcggcggtga tcgaaatacc ctggtcctta tcccatttca    240

ggatttcgac ggtgcccgcg gccgacgcgt gacagatgtg cacccgggcg ccggcgtcac    300

gggccagcaa ggcgtcgcgg gcgacgatcg attcctcggc ggcccgcggc catcccgcca    360

ggcccagccg cgccgccatg ggtccctcgt gcgcgacggc gccgaccgtc agccggggct    420

cctcggcgtg ctgggcgatc agcacgccca aaccggtg                            458


<210> SEQ ID NO 552
<211> LENGTH: 463
<212> TYPE: DNA
<213> ORGANISM: Mycobacterium tuberculosis

<400> SEQUENCE: 552

ccgacgcgca ctacgtgctg gtgtccaccc gcgacccgca ccggcacgag ctacgcagct     60

accgcatcgt cgatggcgct gtcaccgagg aacctgtcaa tgtcgtcgag cagtactgaa    120
```

-continued

```
ccgttccgag aaaggccagc atgaacgtca ccgtatccat tccgaccatc ctgcggcccc    180

acaccggcgg ccagaagagt gtctcggcca gcggcgatac cttgggtgcc gtcatcagcg    240

acctggaggc cagctattcg ggcatttccg agcgcctgat ggacccgtct tccccaggta    300

agttgcaccg cttcgtgaac atctacgtca acgacgaaga cgtgcggttc tccggcggct    360

tggccaccgc gatcgctgac ggtgactcgg tcaccatcct ccccgccgtg gccggtgggt    420

gagcggacac atgacacgat acgactcact gttgcatgcc ttg                       463
```

<210> SEQ ID NO 553
<211> LENGTH: 453
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 553

```
tgcttccggc tcgtatgttg tgtggaattg tgagcggata acaatttcac acaggaaaca     60

gctatgacca tgattacgcc aagctattta ggtgacacta tagaatactc aagcttgccg    120

ggagggtgca tggccgactc ggatttaccc accaaggggc gccaacgcgg tgtccgcgcc    180

gtcgagctga acgttgctgc ccgcctggag aacctggcgc tgctgcgcac cctggtcggc    240

gccatcggca ccttcgagga cctggatttc gacgccgtgg ccgacctgag gttggcggtg    300

gacgangtgt gcacccggtt gattcgctcg gccttgccgg atgccaccct gcgcctggtg    360

gtcgatccgc gaaaagacga agttgtggtg gaggcttctg ctgcctgcga cacccacgac    420

gtggtggcac gggcagcttt agctggcatt cct                                 453
```

<210> SEQ ID NO 554
<211> LENGTH: 466
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 554

```
ggaaacaccg ncgccgtcgt ggccaccaac accgcgacca gcaccgtgac ccggaccggg     60

gtgccgcgcg aaccggtctt ggccaattgc cgcggcacca agccgtcgcg cgccatggcg    120

aacagcacgc ggcattgccc gagcatcaac accatcacca ccgtggtaag cccggccagc    180

gcgccgacgg agatgatgcc gctggcccag tacaccccgt tggcctggaa cgcggtggcc    240

agatttgccg gcccgcggcc cggtacggtc cgcagttggg tgtatggaac catgcccgac    300

agcaccaccg ataccgcgac gtagagaagg gtcacgaccc ccagcgacgc gagaatccct    360

cgagggacgt ctcgttgagg acgcttggtc tcctcggcca tggtggccac gatgtcaaac    420

ccgataaacg cgaagaacac gatcgatgcc cggccagcac gccgta                    466
```

<210> SEQ ID NO 555
<211> LENGTH: 466
<212> TYPE: DNA
<213> ORGANISM: Mycobacterium tuberculosis

<400> SEQUENCE: 555

```
cctgcttccg gctcgtatgt tgtgtggaat tgtgagcgga taacaatttc acacaggaaa     60
```

-continued

```
cagctatgac catgattacg ccaagctatt taggtgacac tatagaatac tcaagcttgt    120

cctcgggcgt ggcctcggcc aagaaatcgt cgacgccggc ctcctgtgca atcgccttgg    180

cggtcgccgg gttgtcaccg gtgatcatca cggtgcggat gctcattcgg cgcatttcgt    240

cgaagcgttc ccgtatgccc accttgacga tgtccttcag atggacgacg ccgatggccc    300

gcgcgctgct gttatcggtc cattccgcaa cgactagggg tgtccccccg ccggagctga    360

tgccgtcgac aatggcaccc acctcctcag tggggtggcc accgtgatcg caaaaccact    420

tcatcaccgc agccgcggca ccttgcggat ccgaacggat gcgctc                   466
```

<210> SEQ ID NO 556
<211> LENGTH: 467
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 556

```
ttcgttcgat ggcgccgccc cggctacggt ttgacctgtg ggtgtcgaat tggggtcaaa     60

ttccgaggtc ggcgcgctaa gagtggtcat cctgcaccgc ccgggggccg aactgcgccg    120

gctcacaccg cgcaacaccg accagctgct gttcgacggc ctgccctggg tatcccgcgc    180

gcatgacgag cacgacgaat tcgccgagct gctggcttcc cgcggtgcgg aagtgctgtt    240

gctgtcggac ctgttgactg aggcactaca tcacagcggg gccgcccgca tgcaggggat    300

cgccgctgcc gtcgacgcac cgcggctggg actgccgctg gcgcaagaac tttcggccta    360

cctgcgtatc tcgacccaag cangttggcg catgtgctga cgccggcatg acttcaacga    420

actcccntcc gacacgccga acgaagtgtc gttggtgttg cgtatgc                  467
```

<210> SEQ ID NO 557
<211> LENGTH: 142
<212> TYPE: DNA
<213> ORGANISM: Mycobacterium tuberculosis

<400> SEQUENCE: 557

```
gcggcgagtg tggtgggtgc cgaacacgaa tccaacgacg cactggcgga gagataccac     60

ttgctgtact ggaagcacgt gctgatgatc tcccgtggaa tgtgcctcgc cgccgtctat    120

cgaaaacagt gagcatgctg cg                                             142
```

<210> SEQ ID NO 558
<211> LENGTH: 217
<212> TYPE: DNA
<213> ORGANISM: Mycobacterium tuberculosis

<400> SEQUENCE: 558

```
caaccgcgct cggcgcgtct gggccttccg ccggctccgc cgacaattct atctctggat     60

cagcggggct ctccgggccg gcctccgcga actcaacagg ccgcgccttc cggccgaaac    120

attccctagc catatatgat cgcacctcga tacacgatct ggcggcaaca ccgcaaagcg    180

tccgacgggc ccaacctccg caattcaggt atccggg                             217
```

<210> SEQ ID NO 559
<211> LENGTH: 147
<212> TYPE: DNA
<213> ORGANISM: Mycobacterium tuberculosis -continued
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 559
gaaggtcggc gaaggtgtgg ctggntgccg atcacgaatc caatgatgca gtggtcggaa 60
gatattagcc acttgctgtt ctggagacag gtgctgatga tctcccgtgg aatgtccctc 120
gactccgtct atcgaaatct gtgaaca 147

<210> SEQ ID NO 560
<211> LENGTH: 177
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 560
tcctgcgctc tgggccattc tcgggtctgc cgacaattct atctctggat ctgtggggct 60
ctcttggccg gcctcngcga tctcttcang gcgcgccttc cggccgaaac attccctatc 120
catatatgat cgcacctcta tacaccgttt ggcggcaaca ccgcaaagtg tctgtcg 177

<210> SEQ ID NO 561
<211> LENGTH: 128
<212> TYPE: DNA
<213> ORGANISM: Mycobacterium tuberculosis

<400> SEQUENCE: 561
agctttacgc tggcgtatca gcgttggggc cgctgccatt tcggtcgccc aacgcgttgc 60
cagctccctg cgctgtcagg gcttgcgcgc caaactggcc accgcaacaa acttggctga 120
gcttgatc 128

<210> SEQ ID NO 562
<211> LENGTH: 142
<212> TYPE: DNA
<213> ORGANISM: Mycobacterium tuberculosis

<400> SEQUENCE: 562
ctctatctgg cgtcacattc gcaatcttta gattgcagat atcgataaaa tcacccgcgc 60
gacaagaccg ccatgtcatc ctttcgatgt tatttcgccg gcctggggaa agcgcaacga 120
cgttgcctac acgttccgcc gt 142

<210> SEQ ID NO 563
<211> LENGTH: 406
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 563
agctttncct tgcatctgca ccccgatcca cgtcagccac gtcggcgttc tccaccaaga 60
agttgcgggc attctccttg ccctggccga gctgctcgcc ctcgtaggtg aaccaggcac 120
ccgacttgcg gatgaggccc tgatccacac ccatgtcgat cagcgagccc tccctgctga 180

-continued

```
ttcccttgcc gtagaggatg tcgaactcgg cctgcttgaa gggggcgaa cagttgtgca    240

cgacaacccc ttcggcgacg agggtgtgca gttcctcgac ctcgaggtcg aacgttcgtg    300

cccgccgcgt tggcagcact tctcggatca cggaatagcg ganttcttcc gccagcatgt    360

cgtgcaggaa tttgtcatcc agggcatccg cgagcgcctg cacgcg                  406
```

<210> SEQ ID NO 564
<211> LENGTH: 311
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 564

```
actgtcnagg gaatgcttcg cagcatctac ctgcagtcgc ttgtgcataa gcggacggcc     60

cnacctgttc gtgttccggg acaccagacg cgggagcacc ggcagtacgg cgaaaggttt    120

gagcggaagg agttgcgcaa atcggggcgc cccaacaccc gtccgcaaga cgcggtcaac    180

gacctgtttc aggcgatcag ggtcaccgac tcacctgcac tgagaacaag cgatctgctg    240

atctgccaga agatggacat gaatgtccac ggcaagcctg atggcctgcc gctcttccgg    300

gaatgtttgg c                                                          311
```

<210> SEQ ID NO 565
<211> LENGTH: 310
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 565

```
tgaattatga tcccgacaca actgcatcan tttagccgcg tcgngatgct atccgccgac     60

ggtttgganc nggtccgtgt cgttcgtgtt gatctcaccc gaagttgtgt ccgccgccgc    120

cggggatcta gcgaacgtgg gatcgacaat cagcgccgcc aacaaggcgg cagcggctgc    180

gaccacgcag gtgctggccg cgggcgccga tnaggtgtca gcgcgcatcg cggcgctgtt    240

tggtatgtac ggcctgnaat atccggcgat cagtgcgcaa gttgccgcgt atcaccanca    300

gtccgtgcag                                                            310
```

<210> SEQ ID NO 566
<211> LENGTH: 326
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 566

```
aacggggacc ncaagaaacc attcaanaac gaggggtcgt caccaacgtc gaaaccgacg     60

gttgccagcc ggcccacgat attgcgtgct cgagggtccg ctgtaccctc accgaacgtg    120

agtcccacac cgcggaggcg ggcgactctg gcgtcgttag cagccgagct caaggtgtcc    180

cgcaccactg tctcgaatgc ttttaaccga ccggatcagc tctccgccga tctacgtgaa    240
```

-continued

```
cgagtgcttg ccacggccaa gcgactgggc tatgccggac cggatccggt ggcgcgatcg    300

ttgcggaccc gcaaagccgg tgcggt                                         326


<210> SEQ ID NO 567
<211> LENGTH: 374
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 567

agctttggag ccncnccgan ccnccggtac gccccgccac cgccgtaccc ggcacccgac     60

ccctttgagc cgttcgccgt ggccgcggtg ganctggccg acgagggact gatcgtgctg    120

ggcaaagtgg tcgatggcac gctggccgcc gatctgaagg tcggcatgga gatggagctg    180

acgaccatgc cgctgttcgc cgacnacgac ggtgtgcagc gcatcgtcta cgcgtggcgg    240

atcccatcgc gcgccggcga cnatgcanag cgcancgatg ctgaggagcg gcgccgatga    300

ggatgagcgc gccggaaccc gtttacntcc tgggtgccgg tatgcacccg tgggggaaat    360

ggggtaatga cttc                                                      374


<210> SEQ ID NO 568
<211> LENGTH: 422
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 568

ttctcncatc gttcgtactn ngatgggacg ctgctgcccg aggcgatcct ggccaaccgg     60

ctctcgccgg cgctgacctt cggcggggcg aacctgaact tctttccgat gggcgcttgg    120

gccaaacgta ccggggctat cttcattcgg cgtcagacga aagatattcc cgtctaccgc    180

ttcgtattac gtgcttacgc cgcgcagctg gtgcaaaacc atgtcaacct cacctggtcg    240

atcgaagggg gtcggaccag aacgggcaag ctacggccac cggtgttcgg gatcctgcgt    300

tacatcaccg atgcggtcga cgaaatcgac ggtcccgaag tgtatttggt gccgacctcg    360

atcgtgtacg aacagctgca cgaagtggaa gccatgacca ccgaagccta tggcgccgtg    420

aa                                                                   422


<210> SEQ ID NO 569
<211> LENGTH: 300
<212> TYPE: DNA
<213> ORGANISM: Mycobacterium tuberculosis

<400> SEQUENCE: 569

ttcttccggg taccgctgat cggcggcacc atcacgcacc cggtgcaggg cgaggcggcc     60

gccggtgtgg tgttgctacg gccggccagc ccgggtaccg gtgtgatcgc cggtggtgcg    120

gcccgcgcgg tgctggaatg tgcgggggtg cacgacatct tggccaagtc gctgggcagt    180

gacaacgcga tcaatgtggt gcacgccacc gtggccgcgc tcaagctgct gcaccgtccg    240

gaggaggtgg cggcgcgccg cggtttgcca atagaagacg tccccccggc cgggatgctg    300
```

-continued

<210> SEQ ID NO 570
<211> LENGTH: 343
<212> TYPE: DNA
<213> ORGANISM: Mycobacterium tuberculosis

<400> SEQUENCE: 570
gtcgaaagtg accatctcta ccttgagtgc cataccgccc gaccctatgc ctcggatagc 60
tcggcggaaa gaaacgcttg cagtgccgcc gaataggcgg ctacgtcgtg agcgcccatc 120
aactctcgcg cggagtgcat cgccagctgg gcggcgccga cgtcgaccgt ggggattccg 180
gtgcgcgccg cggccaacgg cccgatcgtc gacccgcacg gcagatcggc gcgatgttcg 240
taacgctgca taggcactcc cgcgcgctgg caggccagtt gcgaaacgcc cccgccgggt 300
gccttccgtc ggttggcttt accgcaaatt tggggttgcc cct 343

<210> SEQ ID NO 571
<211> LENGTH: 220
<212> TYPE: DNA
<213> ORGANISM: Mycobacterium tuberculosis

<400> SEQUENCE: 571
aaagccacgg aaacgattgc ctactgccga atcggggaac ggtcctcgca cacctggttc 60
gtgttgcggg aattactcgg acaccaaaac gtcaagaact acgacggcag ttggacagaa 120
tacggctccc tggtgggcgc cccgatcgag ttgggaaact gatatgtgct ctggacccaa 180
gcaaggactg acattgccgg ccagcgtcta cctggaaaaa 220

<210> SEQ ID NO 572
<211> LENGTH: 254
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 572
tttcgccacc gcnaggtcgt gcgcgttcca gaaaagcgtg gtttcgccgg gcgcgaggat 60
tcgacggtcc aactgaccag ccggtcccgc cacccgttag gcaggatcgc ggtgtctata 120
tgttcgccct cggcataaac gccattgctg cggtgaaaat cggacatctc gccgattgcc 180
acgtctacat gatccgcttt gtcccgcgcc gggtcgttga caaacgcgat gtcngcctcc 240
tgggaagcgg tggc 254

<210> SEQ ID NO 573
<211> LENGTH: 329
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 573
tcgccaagtg gattcgtgct caccnacgag atccgtggtc ggatccgcng ctgcggcggg 60
ctgcgaccct gcatctcggc ggcacccgtg accaaatggc gcgcgccgaa gcagacgtct 120
cggcgggacg ccacgccgac tggccgatgg tgctggccgc gtgtccgcnc gtcnccgacc 180
ccggccgcat cnaccaaacc ggccgccgtc cgttctggac ctatcccacg tgccntcggg 240

-continued

```
gtccacgctc gacgcgaccg anaacgtaac cagcgtcctc gancggttcg cccccggctt    300

ccgtgacatc gtggtggcgg ccgcgccgt                                      329
```

<210> SEQ ID NO 574
<211> LENGTH: 297
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 574

```
gtaccgtcac catgatcgcc cccatcggca tcggtgagct gatagatccc agccggtttc     60

gccaaccccg gagcgatctt ggcgcgctgc tngtngtcnc tganacntag ccaccaacag    120

agcccggtgt gcgacaagan gactgatcgg atctctccgg acacntcgag ggggtcntca    180

ggagnccggg cgccaccccg aggtaagcct ccgcccagcc tcacaccgcg accgggtatc    240

ncaagtcgcg caataanccc accacctcct cggaccccac gttgtatgcg gctgggt       297
```

<210> SEQ ID NO 575
<211> LENGTH: 401
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 575

```
atactcaagc ttagacctca ctgatgtggc gggacgcggg agataaccgc ggttcgagcc     60

gttcaacagt ggtggttccc acaccagttg tttgcctttg cgaagtaaag cgattcgatt    120

tgctcgaaaa gagggctggc tgctcgtgag ggacatccat ggccgatacc tcagcgatct    180

caacggtcaa gcgactgcat gtttggcgca aggtatcgct aagcataggt tcgtgacgga    240

tttgacagca agagctttcc aaagattgct gtccacatan tgattcgcat ctctacacct    300

cttcgccggt gctgtcaaga gccattcgaa tcagttatct cgctcgtgct tggaanaaat    360

tttcccagcc tgcgttggac aaaccgcgtc gccaaagcgg t                        401
```

<210> SEQ ID NO 576
<211> LENGTH: 453
<212> TYPE: DNA
<213> ORGANISM: Mycobacterium tuberculosis

<400> SEQUENCE: 576

```
agcttcccga gaaacagtgc attccctaag cagcccgttg tcacgccgat gagtgaagag     60

tgcacgcaat cgccggaatc cggcaaagcc ctgcacaagc gaaatcaacc cggaggctga    120

caaggcaacg tcggtgatcc gtaccgcctg gttggacaaa cggcagaagg cggcctcgtc    180

cggtccatct acgccgagca cactggtgat agcgcgcatc ggcatcggtg cggccacggt    240

ggagacgacg tccgcgggcg tctgggtcag taacccgccg accagttctc gggcaagctg    300

gtcgaccatc gggcgccacg tctccaacgc gccacgcgcc atacctggtg ccagttgctt    360

gcgcatccgg gtgtgcgccg gcggatcgga cgtcgcagaa acgcagccac cccgtgagaa    420

gtgacccacg gcgctggaca cgtgtctggt tac                                 453
```

-continued

<210> SEQ ID NO 577
<211> LENGTH: 474
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 577
cggccgggat gtgcgcaatg gcaggttgtc gcccggcttg atgtcggcgt tagcgccgga 60
ttccaccaca tcccccttgcg aaagtccgtt gggtgcaatg atgtancgct tctccccatc 120
gagatagtgg agcaacgcaa tccgtgcggt acggttcggg tcgtactcga tgtgcgcgac 180
cttggcgttg acaccatctt tgtcatggcg gcgaaagtcg atcatccggt aagcgcgctt 240
atgaccgccg cctttgtgcc nggtggtaat ccggccatgc gcgttgcgtc caccgcgacc 300
gtgcagcggg cgcaccagcg acntctccgg ggttgaccgg gtgatctcgg cgaaatcaga 360
tacgctggcg ccgcgacgac caggcgtcgt gggcttgtac ttgcgaattg ccatggtcta 420
atcaggtctt tctctcacct ctcgtcgccg ggctagggcg cattgcctgc tcct 474

<210> SEQ ID NO 578
<211> LENGTH: 357
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 578
tagcggtgta accaactccc gggtcaccac ccgcaaacct cttgcggcaa cagcaccgtc 60
gacgcgtcaa ccgggctgcc cggaatcctg tggatgggca tcgagtgcat ggtcacgacg 120
tccccgacgc ggccggtggc aacgacaagt ggcccggatg caccacaaat gacggccgca 180
caccggtggg gacggccagc acgagagccg tgtcgccgaa gtcgacgcta atgccgtagg 240
cattggccgt cacaacaggc gacgccccgc gtaccaccga gtccacggng gttgggcggt 300
ctcctcggcc aaccaggcgt gaacccggcg gatccgaatg cagcaagacc cgtgggc 357

<210> SEQ ID NO 579
<211> LENGTH: 269
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 579
ccattggtcg gtgtgcgcat accantacna cgcgccgggc acctgacgcg gcggccgcaa 60
ccattcggtg gccatcgcca tcgtctgcca cccggtcaac ggacgcacct tctcctggcc 120
gacctagtgc gcccacccgc cgccgttgcg tcccatcgat ccggtcaaca tgagcagcgc 180
caacaccgag cggtacatga catctgctgt ggaaccagtg acanattccg ccgcccatga 240
tgatcntcga ccgtcctccg gattcggtc 269

<210> SEQ ID NO 580

-continued

<211> LENGTH: 272
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 580
gccggcctgg tcaaaggggc gtccgaagga nccgggctgg gtaacaagtt cctggctcat 60
atccgcgaat gcgacgccat ttgtcaggtg gtgcgggtgt tcgtcgacga cnacgtgact 120
catgtcaccg gacgggtcga tccccagtcc gacattgagg tcgtcgagac cgagctgatc 180
ctggcagatc tgcaaaccct ggagcgggcc acgggccggc tggagaanga agcncgcacc 240
aacaaggcgc gcaagccggt ctacgacccg gc 272

<210> SEQ ID NO 581
<211> LENGTH: 373
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 581
gatccactga ccacgatgac atatcgaaat gctcgacgat tccgatggcg atcaaggcca 60
cgatgccctg gccgttgggc ggtatctggt ggatggtgta cccgcggtag gttcccgtga 120
tcgtgtcgac ccagtccacg cgatgggcgg cgaggtcgtc ggcacgcatc accccgccgt 180
ntgccgccga gtgcgcctcg agtttggcgg ccagctctcc ccggtagaac tctcaccgtt 240
ggtcgccgcg atcttctcta ncgtcgccgc gtggtcagga aaggtaaaca gctcaccggg 300
tttcggcgct cgtccgccgg gcatgaacgc atctgcgaat ccgggctggg atgcgaacaa 360
cggacctgtg ccg 373

<210> SEQ ID NO 582
<211> LENGTH: 314
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 582
tctactgccg aatcggggaa cggtcctcgc ccaccnggtt cgtgttgccg gaattactca 60
ggacaccgaa acgtcgagaa ctacgagcgg agttggacan aataccgctc ccnggtgggc 120
gcccccatcg anttgggaag cngaaatgtg ctctggaccc cacccaagaa tgacattgcc 180
ggccgccctc caactggaaa tagaaacngt gatcacccgc cgcgttcttg gaaggaatgg 240
catgccctgg gccgggcgtt ccttccgctg ccggactcct cccaccaatt caccgccgaa 300
ggcgtcccgt ctgc 314

<210> SEQ ID NO 583
<211> LENGTH: 135
<212> TYPE: DNA
<213> ORGANISM: Mycobacterium tuberculosis -continued

<400> SEQUENCE: 583
atactcaagc ttctgtcacc gaaatcccgc atgggataac gggtttagat ttcgacaacg 60
ggaccgtgtt tctcaacaag ccggtcatca gctgggccgg cgacaacggt atctacttca 120
cccgctttcg cccgt 135

<210> SEQ ID NO 584
<211> LENGTH: 221
<212> TYPE: DNA
<213> ORGANISM: Mycobacterium tuberculosis

<400> SEQUENCE: 584
ctggctcaag cgctcggcgc gcaggtgaac tcggaccggc tcgacgtcgc cgaacgcgag 60
gcggtgctgg cccacgccga cgccgtcgtc gcacatatcg gcaccgtgca caagtctaca 120
acaacgccgg catcgcgtac aacggcaacg tcgacaagtc ggagttcaag gacatcgagc 180
gcatcatcga cgtcgacttc tggggcgtcc tccacgggcc c 221

<210> SEQ ID NO 585
<211> LENGTH: 70
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 585
ccgccctccg cattatgggt caagaaccat cgggtcggac ttctgggctt ccaacgctcg 60 cgccgtcccn 70

<210> SEQ ID NO 586
<211> LENGTH: 241
<212> TYPE: DNA
<213> ORGANISM: Mycobacterium tuberculosis

<400> SEQUENCE: 586
ccgtggcact gtcagacata tgcgccgctc ctcctcatcg ctgcgctcgg catcgtcgcc 60
ggcggtcatg gcgtcaccct acccaagccg aacgcgaaac gagaacgtgt tccattatta 120
gggtgtgagc accaatacca gattgctcac caggaactca cgcagcaccg ggacggatgt 180
cggccaccac gcccatctgg ggtggtagcg gggaaatacc gctaacgcgg ctccggtgcc 240
g 241

<210> SEQ ID NO 587
<211> LENGTH: 492
<212> TYPE: DNA
<213> ORGANISM: Mycobacterium tuberculosis

<400> SEQUENCE: 587
tactcaagct tgtccaaata tcgaagcgtc gggtcgcgag gctcggtcgg cagctccagc 60
aaaacccgct ccacccctag atgccggtat ccctcaaggt ctttatccgc cgcttcaccc 120
cactggcaca cggtcaccgg cacgtcgccc ccggccatgg cgcgcaaccg ctgaagcgga 180
cccgacagcc gctgcggtga tggactgatc gcgatccacc cggcattgag ccgggctatc 240
cgcgggaagt tcgccggtcc cccgcccaca tacagcggag gatagggctt tgtcaccggc 300
ttcggccagc agtagatcgg atcgaagtcc acatatgtcc catggaattc cgcctgctcc 360

-continued

```
tgcgttcaga tctcgattat cgcgcgcaac cgctcatcga tcacacgtcc gcgcaccgca    420

gggtccacac catggttggc gacttcttcg cgcaaccagc cacacccacg ccgaaacgaa    480

accgtccctg cg                                                        492
```

<210> SEQ ID NO 588
<211> LENGTH: 313
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 588

```
caggcatgca agcttggcca actcctcatc ggacttgaag gtgccgtcct cgttggcggc     60

cctgctccac ggcacgttga tggcaccagg aatgtgtccg ggccgctggc tttgttcctg    120

cggcaggtgc gcgggggcca ggatcttgcc ggagaactcg tcgggagagc gcacgtcgat    180

gaggttcttg acgttgatgg ccgccaggac ctcgtcgcgg aatgcccgaa tcgtgttatc    240

cggcggggan gcggtgtagg aagtcaccgg ccggctgacc gggtcgctgg acagcgggcg    300

tccgtcgagc tcc                                                       313
```

<210> SEQ ID NO 589
<211> LENGTH: 305
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 589

```
atactcaagc ttcaaaacag gcctgttgtg ggcgcacccg gctcgccgag ttctgcacgc     60

accgcctcaa gtgcggcccg caccgccggc atctcccggt cacgcagggc cgcggcccgc    120

gccgcagcga cggcgtgttc gcgcagttcg ccgtcaatga tgctgacctg atcggccacc    180

cgggcggtct cggcgtcgtc ccgttcacta atcgcggtgc tcagcagcgt ctcgacagcc    240

accacccgag tggagaccag atgcnccacc acggaccgca gcgatgccag tcacctcacc    300

cgtcc                                                                305
```

<210> SEQ ID NO 590
<211> LENGTH: 394
<212> TYPE: DNA
<213> ORGANISM: Mycobacterium tuberculosis

<400> SEQUENCE: 590

```
caggcatgca agctttgcag ttgctgagta atgtcggcca acgtcaccac aatcgcgatg     60

aattcaatca tgccgcccag ggcggccaac ccaatggtgg ccgcgagcgg cagctcgatc    120

gcagcgcgga ggttgccggc cgccagttga ttcacgaaca gggtgaggtc ataggcgggc    180

aggatagtga cgaaggcaag acctagatct gccgtcggaa gaagaatcga gtatccggtc    240

gacacaacgg aagcgaaagt gtccgcgatg ttgatgagcg tcgccggttg tggcggcggt    300

ggcggcggta gcaccgtccg cacataccgc gggaacgcgg gcatccgaat ttggggcagg    360

gtgttcaagg cggctggcaa ctcaccatga atct                                394
```

-continued

<210> SEQ ID NO 591
<211> LENGTH: 457
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 591
ccggctcgta tgttgtgtgg aattgtgacc ggataacaat ttcacacagg aaacagctat 60
gaccatgatt acgccaagct atttaggtga cactatagaa tactcaagct tggccgcagg 120
gccgagtcga ttggtcgcgg tcgcctcgac agttagctta tgcaatgcta acttcggggc 180
aaagttcagg cggatcggcc gatggcgggc gtaggtgaag gagacagcgg aggcgtggag 240
cgtgatgaca ttggcatggt ggccgcttcc cccgtcgcgt ctcgggtaaa tggcaaggta 300
gacgctgacg tcgtcggtcg atttgccacc tgctgccgtg ccctgggcat cgcggtttac 360
cagcgtaaac gtccgccgga cctggctgcc gcccggtctg gtttcgccgc gctgacccgc 420
gtcgcccatg acagtgcgac cctgnaccgg gctggcc 457

<210> SEQ ID NO 592
<211> LENGTH: 438
<212> TYPE: DNA
<213> ORGANISM: Mycobacterium tuberculosis

<400> SEQUENCE: 592
gtgtgctgtc aattcagagc tgagcctgat gcactcaact tactgagcat gctaacgctg 60
gtcgtgcggg tcttgttccc gcgtgtcggc agggcacacg ctcggggcgt agctgggaga 120
ggccccggtc aagcccggag agcagtgctc agtccgccag cttgaccgac tttcgatgag 180
aacgcgcttc tcgccgtatt gaactggcgt gctgacggtc gctgagcagc gctcgccgag 240
tgcggccgct gattctttca tcgagccagg aggcgcattc gtgttcggcc gcctgcgggt 300
cggccccatc gtcgacgcga tccgtcaccc actcctcgat caggtctgcc tcatcgaacg 360
ggccaacggt gctgtcggag taagtgtgcg tgggcacgcg agccgggtgc tgtggtacac 420
ccaccgttgc atgaacaa 438

<210> SEQ ID NO 593
<211> LENGTH: 220
<212> TYPE: DNA
<213> ORGANISM: Mycobacterium tuberculosis

<400> SEQUENCE: 593
atactcaagc ttcaccaggc gccggcgggc cgcggcgcca agccaggcag ccgcgctcgg 60
cgcgtcgggg ccttccgccg gctcggccga cagttcgatc tctggatcgg cggggctctc 120
cgggccggcc tcggcgacct cagcgggccg cgccttccgg ccgaaccatt ccctagccat 180
agataaccgc acctcaatgc acggtttggc ggcaacccgg 220

<210> SEQ ID NO 594
<211> LENGTH: 266
<212> TYPE: DNA
<213> ORGANISM: Mycobacterium tuberculosis

<400> SEQUENCE: 594
agcttccgtc acgacccgcc ctcgccggtg ccggcgccat cggtcatcgg atctcatgac 60
gacgtcacgt aggcccgcta gccgcgagcg ggcgcggtca actggcgagg cggcggcgac 120

-continued

```
gtgactgagc tggccgagct ggaccggttc accgcggaac taccgttctc gctcgacgac    180

tttcagcagc gggcttgcag cgcgctggaa cgcggccacg gtgttgctgg tgtgcgcgcc    240

gaccggcgct ggcaagacgg tggtcg                                         266


<210> SEQ ID NO 595
<211> LENGTH: 105
<212> TYPE: DNA
<213> ORGANISM: Mycobacterium tuberculosis

<400> SEQUENCE: 595

atactcaagc ttgccgggac cgcggaacag aaccggcggt tcctaccgcg gtgtgcggcc     60

ggcgcgatat cggcctcccg actaaccgaa cccgatgtgg gctcc                    105


<210> SEQ ID NO 596
<211> LENGTH: 141
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as “n”

<400> SEQUENCE: 596

acgttggctc tgccggaacg tatttccagc ggcacgcatt cggcgtgggt gccgggcgcc     60

gagttgcgtc gctgggatca cgcagcagtc gccggcggct gccgtcgggc tatgaattgc    120

accgagccgg aaaatccnca c                                              141


<210> SEQ ID NO 597
<211> LENGTH: 234
<212> TYPE: DNA
<213> ORGANISM: Mycobacterium tuberculosis

<400> SEQUENCE: 597

atactcaagc ttgtcgtatt ccgtggcact gtcagacata tgcgccgctc ctcctcatcg     60

ctgcgctcgg catcgtcgcc ggcggtcatg gcgtcaccct acccaagccg aacgcgaaac    120

gagaacgtgt tccattatta gggtgtgagc accaatacca gattgctcac caggaactca    180

cgcagcaccg ggacggatgt cagccaccac ccccatctgg ggtggtagcg ggga          234


<210> SEQ ID NO 598
<211> LENGTH: 184
<212> TYPE: DNA
<213> ORGANISM: Mycobacterium tuberculosis

<400> SEQUENCE: 598

cgttggtagc ccgatatgca tagtgtatct tactgaacat gatttccatt atggagcccg     60

gggtgccggc agcgcgaacg gtgcgccgtc agacgcgggc ggcactgacc agggtgttgc    120

gggcgaacat cggcccggct tcggattccg gtccgggtac cgggcgaccc accgcttcga    180

ggta                                                                 184


<210> SEQ ID NO 599
<211> LENGTH: 351
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
```

-continued as "n"

<400> SEQUENCE: 599
atactcaagc ttggccaact cctcatcgga cttgaaggtg ccgtcctcgt tggcggccct 60
gctccacggc acgttgatgg caccaggaat gtgtccgggc cgctggcttt gttcctgcgg 120
caggtgcgcg ggggccatga tcttgccgga aaactcgtcg ggagagcgca cgtcgatgag 180
gttcttgacg ttgatggccg ccaggacctc gtcgcggaat gcccgaatcg tgttatccgg 240
cggggaggcg gtgtatgagg tcaccggccg gctgaccggg tcgctggaca gcgggcgtcc 300
gtccagctcc cacttcttgc gggcgccgtc caacnacttg acttctcctg g 351

<210> SEQ ID NO 600
<211> LENGTH: 438
<212> TYPE: DNA
<213> ORGANISM: Mycobacterium tuberculosis

<400> SEQUENCE: 600
atatcttaag cgtcgggtcc cgaggctcgg tcggcagctc cagcaaaacc cgctccaccc 60
ctagatgccg gtatccctca aggtctttag ccgccgcttc accccactgg cacacggtca 120
ccggcacgtc gcccccggcc atggcgcgca accgctgaag cggacccgac agccgctgcg 180
gtgatggact gatcgcgatc cacccggcat tgagccgggc tatccgcggg aagttcgccg 240
gtcccccgcc cacatacagc ggaggatagg gctttgtcac cggcttcggc cagcagtaga 300
tcggatcgaa gtccacatat gtcccatgga attccgcctg ctcctgcgtc cagatctcga 360
ttatcgcgcg caaccgctca tcgatcacac gtccgcgcac cgcagggtcc acaccatggt 420
tggcgacttc ttcgcgca 438

<210> SEQ ID NO 601
<211> LENGTH: 410
<212> TYPE: DNA
<213> ORGANISM: Mycobacterium tuberculosis

<400> SEQUENCE: 601
atactcaagc ttgtcgcggt aaacccgcag cagggcggtg ggtgcggtgt caaaaaacaac 60
cacacttctt tgcggttcgg tgatctcgac accggccgcg agccgaccac catgcgcgcg 120
taaatcggcg atcagcgcgt cggctatcgc ctgggtgccg cccaccggaa tcggccagcc 180
gaccgaatgg gccagcgttg ccagcatcag tccggcgccg gccgacacca gtgacggcaa 240
cggtgaaatc gcgtgggcgg caacgccggt gaacaacgcg cgggcatcct cgcccgccag 300
cgaccgccag gcaggggtgc cctgggccag catccgcagc ccgagacgca ggaccgagcc 360
cagtgcagta ggcaaagacc gcttgtcgga gacatgaact ccacgaccgt 410

<210> SEQ ID NO 602
<211> LENGTH: 456
<212> TYPE: DNA
<213> ORGANISM: Mycobacterium tuberculosis

<400> SEQUENCE: 602
agcttattga accgcgggtc gcaggcaaag tggacctcat aacgactcgg gtccagcgac 60
cgcgccaaca cgaacggccg gacgacgtgg gccagggtcg cggcctcccc tacaaacagg 120
atccgttgcc tgcgagcgac aggctccggt gcggcgttgg gcgccgtgct cgtcccagcg 180
tccggtcccg ggtcgccggc gacgcttgtt tcctccatac tcgcccccta atctcgaggc 240
agcccgtacc cgcaggcaac ctcccaaaaa tgcaatcccc caaaatgcaa tgcgtcgagc 300

-continued tatttctcac accgaccgct agttgcggat cagaaatccg ttgggcgcgg aagtccagcc 360
gaatttgttc tcccgctccg catcatgctt gtaatcgttt ggaaattcat cctcatatgc 420
ctcgatcgct tcatagggtc caggccaaac cgggca 456

<210> SEQ ID NO 603
<211> LENGTH: 217
<212> TYPE: DNA
<213> ORGANISM: Mycobacterium tuberculosis

<400> SEQUENCE: 603
cttccggctc gtatgttgtg tggaattgtg agcggataac aatttcacac aggaaacagc 60
tatgaccatg attacgccaa gctatttagg tgacactata gaatactcaa gcttggccac 120
ctcgcggtgt gtggtggaac ccatctgagc agtgtgccaa accggggcag acagctccca 180
attgacgtga gcccgctcac ttgctgggta agcgtcg 217

<210> SEQ ID NO 604
<211> LENGTH: 478
<212> TYPE: DNA
<213> ORGANISM: Mycobacterium tuberculosis

<400> SEQUENCE: 604
tagcgccccc tcccgggcgg agctccacgg cgtggatcaa ggtaccggcc gggatgttgc 60
gcaatggcag gttgttgccc ggcttgatgt cggcgttagc gccggattcc accacatccc 120
cttgcgaaag tccgttgggt gcaatgatgt agcgcttctc cccatcgaga tagtggagca 180
acgcaatccg tgcggtacgg ttcgggtcgt actcgatgtg cgcgaccttg gcgttgacac 240
catctttgtc attgcggcga aagtcgatca tccggtaagc gcgcttatga ccgccgcctt 300
tgtgccgggt ggtaatccgg ccatgcgcgt tgcgtccacc gcgaccgtgc agcgggcgca 360
ccagcgactt ctccggggtt gaccgggtga tctcggcgaa atcagatacg ctggcgccgc 420
gacgaccaag cgtcgtgggc ttgttcttgc gaattgcatg tctaatcagg tctttctc 478

<210> SEQ ID NO 605
<211> LENGTH: 459
<212> TYPE: DNA
<213> ORGANISM: Mycobacterium tuberculosis

<400> SEQUENCE: 605
tgaaactata taatactcaa gcttgccaaa gaagacctcg tcgaccaagc aggacgcgac 60
cgtcgaggtg gcgatccggc ttggcgtcga cccgcgtaag gcaaaccaga tggttcgcgg 120
cacggtcaac ctgccacacg gcactggtaa gactgcccgc gtcgcggtat tcgcggttgg 180
tgaaaaggcc gatgctgccg ttgccgcggg ggcggatgtt gtcgggagtg acgatctgat 240
cgaaaggatt cagggcggct ggctggaatt cgatgccgcg atcgcgacac cggatcagat 300
ggccaaagtc ggtcgcatcg ctcgggtgct gggtccgcgc ggcctgatgc ccaacccgaa 360
aaccggcacc gtcaccgccg acgtcgccaa ggccgtcgcg gacatcaagg gcggcaagat 420
caacttccgg gttgacaagc aggccaacct gcacttctc 459

<210> SEQ ID NO 606
<211> LENGTH: 464
<212> TYPE: DNA
<213> ORGANISM: Mycobacterium tuberculosis

<400> SEQUENCE: 606

-continued

```
gctgagctcc acggcgtgga tcaaggtacc ggccgggatg ttgcgcaatg gcaggttgtt     60

gcccggcttg atgtcggcgt tagcgccgga ttccaccaca tccccttgcg aaagtccgtt    120

gggtgcaatg atgtagcgct tctccccatc gagatagtgg agcaacgcaa tccgtgcggt    180

acggttcggg tcgtactcga tgtgcgcgac cttggcgttg acaccatctt tgtcattgcg    240

gcgaaagtcg atcatccggt aagcgcgctt atgaccgccg cctttgtgcc gggtggtaat    300

ccggccatgc gcgttgcgtc caccgcgacc gtgcagcggg cgcaccagcg acttctccgg    360

ggttgaccgg gtgatctcgg cgaaatcaga tacgctggcg ccgcgacgac caggcgtcgt    420

gggcttgtac ttgcgaattg ccatgtctaa tcaggtcttt ctct                      464
```

<210> SEQ ID NO 607
<211> LENGTH: 205
<212> TYPE: DNA
<213> ORGANISM: Mycobacterium tuberculosis

<400> SEQUENCE: 607

```
atactcaagc ttgttggtga cctcgccggc gaacagttct cgcacgattt ccggattagc     60

gggactggtc accagttggg tatgcgggaa ggcgctgacg ttcgccgcga ttagctgttt    120

gatggacgcg gcggtgatgt cctgatcacg gaactggctg taatagccca gggtcgccac    180

gcttccatcc gggcccggac ccggc                                           205
```

<210> SEQ ID NO 608
<211> LENGTH: 244
<212> TYPE: DNA
<213> ORGANISM: Mycobacterium tuberculosis

<400> SEQUENCE: 608

```
gatgatcgcc ggtgccaccc cgatccgtgc ctcggtcagc gcgaacgtgc tttccggtcc     60

ggcgaccacc atgtcgcacg caccgaccag gccgaacccg ccggcccgca catgcccgtt    120

gatggcgccg accaccggca gcggcgactc gacgatggcg cgcaacagcg ccgtcatttc    180

ccgcgcccgc gccaccgcca tccggtacgg atcaccacca cctccgccgg cctcgctgag    240

gtcc                                                                  244
```

<210> SEQ ID NO 609
<211> LENGTH: 289
<212> TYPE: DNA
<213> ORGANISM: Mycobacterium tuberculosis

<400> SEQUENCE: 609

```
atactcaagc ttgccgcaat cgaaaccaac ctgtttgtgc cgcaagaaat tacgccgtgg     60

cccggcgccg atcaagaaac gccccggcgc gcggcggtgt cgtcgtatgg catgacgggc    120

accaatgtgc acgccattgt cgagcaggca ccggtgccag cccccgaatc cggtgcacca    180

ggcgacaccc cggccacacc cggtatcgac ggcgcgctgc tgttcgcgct gtcggccagc    240

tcgcaggacg cgctgcggca aaccgccgcg cggctggccg attgggtct                 289
```

<210> SEQ ID NO 610
<211> LENGTH: 282
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

-continued

<400> SEQUENCE: 610
ttggcgggtt ggccacanca ncccgccggt gacggcgacg atgctgggct ggttgcggcc 60
ctgcgccacc gcggcttgca tgctggttgg ctgtcttggg acgatcccga aatagtccac 120
gcggatctgg tgattttgcg ggctacccgc gattaccccg cgcggctcga cgagtttttg 180
gcctggacta cccgcgtggc caatctgctg aactcgcggc cggtggtggc ctggaatgtc 240
cancgccgtt cacctacgtg accttgatgg gatccggggg nt 282

<210> SEQ ID NO 611
<211> LENGTH: 312
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 611
ncgtggacac cggtgtcgan cgccaccagc cgcatgtctg cangtcnatt ccgtcctcgg 60
caacatcttg aatgccgagc agcgcctggg cgtgatcggc aaccggggat gaccgctcgc 120
cgatccgctc gacaatcccg gcggcacgtg acatgccggc ggacggctcg acgagctgga 180
acttcagcga cgacgatccg gaattgatca ccagcacggt gctactcatg gacccctgcg 240
cctgaatccc gtgatggcca cggtgttgac tattcgtcga cagtgcaccc gagatagtct 300
tcacggctgc gt 312

<210> SEQ ID NO 612
<211> LENGTH: 349
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 612
catgtattgc cgtgctcacg gcgccacgct cgatggtttc tcgaagtctc cgggctggtg 60
tacagcttct cgttgatctc gttcgccacg ccgtcctctt cccgccgacg acccgatctc 120
gatctccana atgatcttgg cggccgccgc cgccttgagc agctcctggg cgatggccag 180
gttctcatcg atgggcactg ccgaccgtcc cacatgtgcg acggaacaaa gatgtcacct 240
tgctcacgcg tgcgcnagat cncanaaggg ccggacatac tgtcnacttg tccttgggca 300
gtggtccgtg tcagcccacg tgacgggtac ttggcgcgat aacgtggtg 349

<210> SEQ ID NO 613
<211> LENGTH: 350
<212> TYPE: DNA
<213> ORGANISM: Mycobacterium tuberculosis

<400> SEQUENCE: 613
gccaccacga cccggccgta actctgctca cggaaatgcg gccaggccgc gcgtagcacg 60
tggtatccgc cataaaggtg caccttaagc acggcgtccc aattctcgaa cgacatcttg 120
tggaaggtgc cgtcgcgcaa gatcccggcg ttgctcacca caccgtgcac ggcgccgaat 180
tcgtcaagcg cggtcttgat gatgttcgct gcgccgtcct cggtggcgac gctgtcctta 240
gttggcgacc gcccggcccc ccttgtcgcg aatctcggcg acgacctcat cggccatcgc 300
cgaacggcgc ccgtgcccgt cgcgggcgcc accgaggtcg ttgaccacga 350

<210> SEQ ID NO 614
<211> LENGTH: 126
<212> TYPE: DNA
<213> ORGANISM: Mycobacterium tuberculosis

<400> SEQUENCE: 614
caggcatgca acctttgtcc acacggcgtc tactccgtgc aaggtccgac cgcttccacg 60
tcccgccgtg acggtgctcc atctccctca gcaacgcgtg aagtggtccg atcccgcggc 120
ttcagg 126

<210> SEQ ID NO 615
<211> LENGTH: 395
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 615
gttgagacgc aaccagcgca caacgacgat ttggcgtagc ggcggacgtc tgctcgattc 60
gatcacgtcg cgctcgcatc gagcatggcc cgcgacgcta cacgatcgcc gtcgtcgatg 120
acacgaccga gccgtacgcc ggccgtaagc cgcgccagga ttcggcgaaa aacgtctacg 180
tggcgggtgt actgggtgtc gaatgattcg tggggtgcgt atgcgtcctg caatcgtcga 240
catagatccg tcgccgcatc gcgtcgacaa ctccgggtga gtggaataca cttgccgatc 300
acgcgacgtg cgcggatcga tgccgaccga aatacgacca catggctctt gttgcncagt 360
gttggcggca tcaaataccc tcagtgccgt ccgac 395

<210> SEQ ID NO 616
<211> LENGTH: 371
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 616
ttnccgcctt nacgcctact ccnagacgat gctcgacgcg tgtgagcaca cggcgctgct 60
gtagacggca cggcgcagct ggatcgcgct tggtgcaccc aagcctctac gcgcgtcgct 120
gcgtcgtcat cgggtaccga acatattccg gtcgttgcgc agagtgtgca tgtgcggctc 180
ttgtgaacga acatagcaaa gcgtatatgt ctgtggcggc tctgcagata tcgcgataat 240
acgtatatac ataaggtggc gcgcgatcta tcggtatatc cgttatggcg gacgtgcgtg 300
agcgtgagtc gcggcgcatc gcgcacttcg cgatcgcgtg actggtcctc gcgactgcgc 360
gcatgcgtag c 371

<210> SEQ ID NO 617
<211> LENGTH: 423
<212> TYPE: DNA
<213> ORGANISM: Mycobacterium tuberculosis
<220> FEATURE:
<221> NAME/KEY: unsure
<222> LOCATION: (various positions within the sequence)

-continued

<223> OTHER INFORMATION: applicants are uncertain of bases designated as "n"

<400> SEQUENCE: 617
ggtgatgacg cacttgcttc gaatgagtca ttgactactc ccgtggttgt cctgcgatgg 60
tggagtgccg cgcagccttg cccgangtcg cgatcgcgtc gcgggcttcg gggagcagac 120
tgacctgcag atggaagtcg tgccacatgc ccgcgaacgg cgagctcgat gcttgttttc 180
gaagngcgca ngcggtttcg atcttgtccg cgtcaacgca gatcggatct cgccgcggtc 240
tgcatgacga tgggcgcagg cccgctcatg tcccgtagac ggggagatac gggcagccgc 300
ggatcgagac ctacgtagcg cggcgcccat cgtgccatcg acgaagaatg acggatcgcg 360
cagcgccgtc gcgtcgcttc gatgtcacgc gagatcgcca cggcagatca gcgatgcgcg 420
ggc 423

<210> SEQ ID NO 618
<211> LENGTH: 354
<212> TYPE: DNA
<213> ORGANISM: Mycobacterium tuberculosis

<400> SEQUENCE: 618
cggtacgccg gcaacaaacg ccttgtgacg agcgcgtccg agcggtcatc ggcctccacc 60
gtcatgcaca gctccttctc caggtctacg ccgacgtcgc ggtccacatt ggtgagcttg 120
gcgaatgcct cggcaacctc gtcgaaatgc gcctccgcgt ccgcatcgaa ggtcgccatg 180
tcaaagatca actcgacgta gtagctagtt accgcatcag gtcagtgttt gctggcctcg 240
gagtccggcc gaacaatggc catttcccgc gactctagaa tccagtcatc gtctcggtga 300
cgacgccttg ccgatcacat agctcgaccg gatcggagag aatctggttc tcgt 354

<210> SEQ ID NO 619
<211> LENGTH: 128
<212> TYPE: DNA
<213> ORGANISM: Mycobacterium tuberculosis

<400> SEQUENCE: 619
atactcaagc ttaagcgcag cagtaccggc ggtgcctggg catcccagca aaacggggag 60
ctcaacgaac gattcctgaa cgaagggtcg tccaccaacc tccaaaccga acggttgcca 120
gccccggc 128

<210> SEQ ID NO 620
<211> LENGTH: 295
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 620
gcaagtccgc tcaatgtggt tgtgatcaca ngactacgtc gcctcaatca gctcaaacgt 60
caccccgtgg cgtgctgcgc agcatgaagg tcggcgcccg cacgatgtgg gcgaagcaac 120
aggtaataac tggtcggcat gggtcaaccc tcattgggcc gttgcggatc gggtgcacgc 180
ccggagtgcc ggtcgaactc aacaccgcct tcaccgatct tttcgtcgaa aatggcggtc 240
gtgtcggggt atacgtccgc gatcccacga ggcggaatcc gctgagccgc actga 295

-continued

<210> SEQ ID NO 621
<211> LENGTH: 361
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 621
atactcaagc ttcgcgccct caagcggctg aaggtggttc cggcgtncca acngtcgggc 60
aactcgccga tgggcatggt gctcgacncc gtcccggtga tcccgccgga gctgcgcccg 120
atggtgcagc tcgacggcgg ccggttcgcc ncgtccgact tgaacgacct gtaccgcagg 180
gtgatcaacc gcnacnncnn gntgaaaagg ctgatcgatc tgggtgcgcc ggaaatcatc 240
gtcaacaacn agaancggat gctgcnggaa tccgtggacg cgctgttcga caatggccgc 300
cgcggccggc ccgtcaccgg gccgggcaac cgtccgctca agtcgctttc cgatctgctc 360
a 361

<210> SEQ ID NO 622
<211> LENGTH: 361
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 622
tgcgcatggc agttgttgcc ggcttgagtc gcgttagcgc ggattccacc acatcccttg 60
cgaagtcgtg ggtgcaatga tgtagcgctt ctcccatcga gatagtggag caacgcaatc 120
cgtgcgtacg ttgggtcgta ctcgagtgcg cancttggcg ttgacaccat ctttgtcatt 180
gcggcgaagt cgatcatccg gtaagcgcgc ttatcgacgc cgcctctgtg ccgggtggta 240
atccggccat gcgcttgcgt ccaccgcgac gtgcagcggg cgcacaccga cttctccggg 300
tgacgggtga tctcggcgaa tcagaacctg gcgcgcgaca cagcgtcgtg gctgtacttg 360
c 361

<210> SEQ ID NO 623
<211> LENGTH: 312
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 623
tgggtgatca gatactggct agttggtcgg gtggggtgat cgaagatcgc ggtggccggc 60
agcgttactg cggtgacgct gttaagcggt tacgtactcc acggcactca angaattana 120
tcccgaatcg gcaaaccctg gccagcgtcg agtccgcagc gccgtcgcgc cccccaccgc 180
tgcggcatgc tcacatacca cctcgatcgc tgcgggagtt gctcgtcggc cgaccgaccg 240
gccagccggg cggcaaaccg gaggacccaa gattcagcac caccatcgct agcccgatct 300
ggccgcgcgt gg 312

-continued

<210> SEQ ID NO 624
<211> LENGTH: 454
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 624

```
tcgtagcggt tgcgaccant ccgcggacag ctccgccacg cgacgggtcg ggatcaccgc     60

ggtcaaacca ccgagcggcg aggatctctg gccgtcgacg tgaccgcgca cggccgcggt    120

gatggccagt cccgaccgcc gttccacttg gcgtacgcgc tggatgtgtt gtgccgcaac    180

ggaatcccac ctcaattatg acctcgttgt gggcgagcgc ggtatcgtac gcccgaccag    240

gaatcgtcga tgctatctca cgtcaccgaa ggcctctccc agcacaccgc atccagaacg    300

tgcacacngt cgacatgtct cggcggatcc gcctgcagaa cgaacgccan gtgcgctgtg    360

cgacacgggt cgcgatcacc gctcgcacgc ggagatcggc acacgcgcag cgcatcgatc    420

ataatctctc gatgcggtct ccaccaccga acag                                454
```

<210> SEQ ID NO 625
<211> LENGTH: 366
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 625

```
atactcaagc ttcgctgagg tggtggggca cgatcacgtc accgcaccgc tgtcggtggc     60

gctggatgcc ggccggatca accacgcgta cctgttctct gggccgcgtg gctgcggaaa    120

gacgtcgtca gcgcgtatcc tggcncggtc gttgaactgt gcgcagggcc ctaccgccaa    180

cccgtgcggg gtctgcgaat cctgcgtttc gttggcgccc aacgcccccg gcagcatcga    240

cgtggtagag ctggatgccg ccagccacgg cggcgtggac gacacccgcg agctgcggga    300

ccgcgcgttc tatgcgccgg tccactcacg gtaccgggta tttatcgtcg acgaggcgca    360

catggt                                                               366
```

<210> SEQ ID NO 626
<211> LENGTH: 363
<212> TYPE: DNA
<213> ORGANISM: Mycobacterium tuberculosis

<400> SEQUENCE: 626

```
gcactcacgc tggtacaaga ccttcacaaa atctgaaatc ctgacccgat acttgaacct     60

ggtctcgttc ggcaataact cgttcggcgt gcaggacgcg gcgcaaacgt acttcggcat    120

caacgcgtcc gacctgaatt ggcagcaagc ggcgctgctg gccggcatgg tgcaatcgac    180

cagcacgctc aacccgtaca ccaaccccga cggcgcgctg gcccggcgga acgtggtcct    240

cgacaccatg atcgagaacc ttcccgggga ggcggaggcg ttgcgtgccg ccaaggccga    300

tccgctgggg gtactgccgc agcccaatga gttgccgcgc ggctgcatcg cggccggcga    360

ccg                                                                  363
```

<210> SEQ ID NO 627

-continued

<211> LENGTH: 367
<212> TYPE: DNA
<213> ORGANISM: Mycobacterium tuberculosis

<400> SEQUENCE: 627
atactcaagc ttgtataaaa agatcggtga gcgcatcgat tcgctccgcc gggtttgccg 60
ctgcggcggc ggagctgccg tgaccgtcta tttgggtgat cagatactgg gctagttcgg 120
tcggggtggg gtgatcgaag atcgcggtgg ccggcagcgt tactgcggtg acggctgtta 180
agcggttacg tacctccacg gcactcaagg aattaaatcc cgaatcggca aacgcctggc 240
cagcgtcgaa tccggcagcg ccgtcgcgcc ccagcaccgc tgcggcatgc tcacatacca 300
cctccatcgc tgcggcgaat tgctcgtcgg ccgaccgacc ggccagccgg gcggcaaacc 360
cggaaga 367

<210> SEQ ID NO 628
<211> LENGTH: 518
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 628
cctcatcata tgccgataga gctctacata ttcaggagat caccatggct cgtgcggtcg 60
ggatcgactc gggaccacca actccgtcgt ctcggttctg gaangtggcg accnggtcgt 120
cgtcgccaac tccggagggc tccaggacca cccgtcaatt gtcgcgttcg cccgcaacgg 180
tgaggtgctg gtcngccagc ccgccaagaa caggcagtga ccaacgtcga tcgcaccgtg 240
cgctcggtca agcgaccatg ggcagcgact ggtccataga gattgacgca agaaatacac 300
gcccggagat ctcgccgcat tctgatgaac tgaacgcgac ccgaggctac tcggtganga 360
catnacgacg cgttatcaca ccccgcctnc ttcaatgacc ccacgtcngg caccaaggac 420
ccggcaatcg cggctcactt gngcgatngt cnacaaccaa cgcgncgcct ggctacgggc 480
tcaacaaggc anaagacaca atccgctctc gattggtg 518

<210> SEQ ID NO 629
<211> LENGTH: 435
<212> TYPE: DNA
<213> ORGANISM: Mycobacterium tuberculosis

<400> SEQUENCE: 629
atactcaagc ttatcgaggc ggcgcatacc gaagcgtggg aaatccagac cgaataccgc 60
gacgtgctgg acactttggc cggcgagctg ctggaaaagg agaccctgca ccgacccgag 120
ctggaaagca tcttcgctga cgtcgaaaag cggccgcggc tcaccatgtt cgacaacttc 180
ggtggccgga tcccgtcgga caaaccgccc atcaagacac ccggcgagct cgcgatcgaa 240
cgcggcgaac cttggcccca gccggtcccc gagccggcgt tcaaggcggc gattgcgcat 300
gctacccaag ccgctgaggc cgcccggtcc gacccggcca aaccgggcac ggcgccaacg 360
gttcgcccgc cggcaccacc ggtccggtga ccgcagtacg gtccccccag cctgactacc 420
gtgccccggc gggct 435

<210> SEQ ID NO 630
<211> LENGTH: 398
<212> TYPE: DNA

-continued

<213> ORGANISM: Mycobacterium tuberculosis

<400> SEQUENCE: 630
tggccgggct ggtagcccgc gtatggcaag gttccgctca atgtggttgt gatgcagcag 60
gactacgttc gcctcaatca gctcaaacgt cacccccgtg gcgtgctgcg cagcatgaag 120
gtcggcgccc gcacgatgtg ggcgaaggca acaggtaaga acctggtcgg catgggtcga 180
gccctcattg ggccgttgcg gatcgggttg cagcgcgccg gagtgccggt cgaactcaac 240
accgccttca ccgatctttt cgtcgaaaat ggcgtcgtgt ccggggtata cgtccgcgat 300
tcccacgagg cggaatccgc tgagccgcag ctgatccggg ctcgccgcgg cgtgatcctg 360
gcctgtggtg gtttcgagca taacgagcag atgcgaat 398

<210> SEQ ID NO 631
<211> LENGTH: 464
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 631
gtccagtcaa gcatcggtcc tctccgacta cgccaagant ggcgacgtgt cagtgcanac 60
agcgganatg gtggcgccta tgcgtcgacg ctcacaaacn gcggtgancg cgttctggtc 120
gtgcaccatc gagccgtgcc agcccggccg cgtgccgtca gccgcatcca ctggatgcct 180
tctcggngtt tcaatcangt acangcgacg ttcgccacca tcgtgccggg gcacggttag 240
cgagaaaccg ccgacttcac cgattgcctc ggtgatgccg tcgaacagat cgggcctatt 300
gtcgacagcc agtgtgatnc gtatttgccg ccgtgctcct cgtcgcaacg atgcgaacac 360
agatccgtgg nggacgatag cggctgacaa ngtgggggca acacaatcac atgccacatt 420
tcttcatttc acgcccacaa cccagacttc gtctcgatgn gccg 464

<210> SEQ ID NO 632
<211> LENGTH: 499
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 632
cacgcggtct ggcccgatcc gaagatccct ttgccggcgt ggcggctctg ctcggcggtg 60
ttgtacactt ctcgaacacc tcggcaccga caccaccacc gtngcttgaa caccgccaac 120
atcggcagca gatcttgatg gtcctggtga atcccacggt gactttggag tggaaggcgc 180
catactgatc gccgcgccag cacatgagct agcggcagga aaaccagcag ccgctcacct 240
tgcgcagcag cgtcnggtga tatgcctggc gcccttaatc tcgtgaacca gttggattgg 300
gtcaactggc agccttgggt ctccggtggt gccgangtgt anataagctc ccgggtccgt 360
caacgtantg cgcaggcggc ggttactcgg cgggtcaacg agccccgctc gtgagcnatc 420
agcctttgga ccgaacggga ttcatactcc gcaggcggcc ctccgaaatc ggcacatgtc 480
ctttgatcgt tcgcaacan 499

-continued

<210> SEQ ID NO 633
<211> LENGTH: 343
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 633
ggccatgtca catcggtggt acaggtaaac cgcgccgtgt gcgcggtctc ggagatcaga 60
acgtggtcgc agttgaaccg cgggctttca gccagtcgcg ataatcggcg gaagtcggcg 120
cctgccgccc caactagcgc gactcgccac ctagcacacc gatggcgaag gccatgtntc 180
cggccacgcc gccgcggtgc atcaccaagt catcgactag gaagctaagc gacancttgt 240
gcaggtgttc gggcagtagc tgctcggaaa atcggctgga aaccgcatca aatggtcggt 300
ccaatcgaac cggttacccg atcgtcacaa aaatctccgt cct 343

<210> SEQ ID NO 634
<211> LENGTH: 192
<212> TYPE: DNA
<213> ORGANISM: Mycobacterium tuberculosis

<400> SEQUENCE: 634
gggtctacaa ccaccgggtc tgacttctgg gcttccaccg ctcgcgccgt cgcgacaaac 60
agcgcggtcg aaccgacact cgttgtgatg tcccagctat cacctccggt aggcacccaa 120
tcgaccctac ccggctatct cacccccgat ctccaggctc cgccgatcca tgcgcatccc 180
ggtccggatc cc 192

<210> SEQ ID NO 635
<211> LENGTH: 376
<212> TYPE: DNA
<213> ORGANISM: Mycobacterium tuberculosis

<400> SEQUENCE: 635
caggcatgca agcttgtcgt attccgtggc actgtcagac atatgcgccg ctcctcctca 60
tcgctgcgct cggcatcgtc gccggcggtc atggcgtcac cctacccaag ccgaacgcga 120
aacgagaacg tgttccatta ttagggtgtg agcaccaata ccagattgct caccaggaac 180
tcacgcagca ccgggacgga tgtcagccac cacgcccatc tggggtggta gcggggaaat 240
acggctaacg cggctccggt gccggcagcc cagcgcagac cctcggcggc ggacacggct 300
aacaacgacg acccatagtt gttctttgcc ggatggccgt gtttgctgac atatcgggcg 360
cggcgccggc gccgcc 376

<210> SEQ ID NO 636
<211> LENGTH: 83
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 636
nctacgctgc tgaatgttgt gcgccggagg anctcaagac ccacgcggtt gtacgcggac 60
ntgcgacatg ttcaaccgcc gga 83

-continued

<210> SEQ ID NO 637
<211> LENGTH: 319
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 637
ctaaccaaca agccatggtg gttggcgccg tcgagaggtc ggcggtcgcc acaacgggaa 60
gatcgccttg agcgtcgctc gaccgccgcc tcgagttggg tcataacgaa gtactgatgc 120
cgatcatgtc gacgtgtccg tcgcatcagc gtgcagcggc gacccctcga cgagcctcgg 180
tgccgccgcg gccagggcac cagctgtttt agcgcattgt gctccgccgg taataaagga 240
ngtcggtcgc ctccgctgct gtggttgcgg aataacatct tcccttcctg caacaggatg 300
agaatggttt taattgctc 319

<210> SEQ ID NO 638
<211> LENGTH: 94
<212> TYPE: DNA
<213> ORGANISM: Mycobacterium tuberculosis

<400> SEQUENCE: 638
ctaagctttc gggtccgccg ccactagtac cgcgttgccg gccccgccga cctagaatgt 60
tccgcccatt gccgtttcct cccgccgccg ggtt 94

<210> SEQ ID NO 639
<211> LENGTH: 122
<212> TYPE: DNA
<213> ORGANISM: Mycobacterium tuberculosis

<400> SEQUENCE: 639
tctggtgccg ggtgtgccga cgggtccgtc cgcctctgct tcagtgattc tgtgatgcga 60
ccggcaacgt cctcgttgtt cggtgtctat gtggtccgtc tctccttgtt ccgcatacga 120
tt 122

<210> SEQ ID NO 640
<211> LENGTH: 210
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 640
gcgatcgntn accacaaggg cgcaaccgtt cgcgcgtcga ctgaacgtgc tgccgcctgg 60
agaactggcg ctgctgccac ctggtcggcg catcggcact tcgaggactg gatttcgacg 120
cgtggcccga cctgangtng gcggtggacn ngtgtgcacc cggttgattc ctcggccttg 180
ccgggatgcc acctgcgcct ggtggtcgat 210

<210> SEQ ID NO 641
<211> LENGTH: 328
<212> TYPE: DNA
<213> ORGANISM: Mycobacterium tuberculosis
<220> FEATURE:
<221> NAME/KEY: unsure -continued
<222> LOCATION: (various positions within the sequence)
<223> OTHER INFORMATION: applicants are uncertain of bases designated as "n"

<400> SEQUENCE: 641
cgtgaccgga cggggtgccg cgcgaaccgg tcttggccaa ttgccgggga ctggggctgg 60
agtataaagc gggcctgttg ccggaagata aagtcaaagc ggtgaccgag ctgaatcaac 120
atgcgccgct ggcgatggtc ggtgacggta ttaacgaccg ccagcgatga aagctgccgc 180
catcgggatt gcaatgggta gcggcacaga ctggcgctgg aaaccgccga cgcacattaa 240
ccataaccac ctgcgcggct ggtgcaaatg attgaactgg cacgnccact cacgccaata 300
tccgccagaa catcactatt gcgctggg 328

<210> SEQ ID NO 642
<211> LENGTH: 553
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 642
atactcaagc ttcttaccca nagcatgaac cccgccgtcc aatgccgcca ccgtggtgct 60
gtcggccggc cgggtgcggg cacaatcgcc gagttcggcg aacagatcct cgaaggtctt 120
cacggccagc gattgttgca cgtgtcagcc agccaagtca cggtggtttg acgccacacg 180
ttcgccaccg ccgcgccgcg cattagggca tcctaatata ggttaggcta ccctanttat 240
tcctgtggtc naaggaggca gccgaacgtg accttcccga tgtggttcgc agttccgccg 300
gaagtgccgt cagcatggct gtccaccggc atgggccccg gtccgctgct ggccgcggcc 360
agggcgtggc acgcgctggc cgcgcaatac accgaaattg caacggaact cgcaagcgtg 420
ctcgctgcgg tgcaggcaac tcgtggcagg ggcccagcgc cgacggttcg tcntccccat 480
caaccgttcc gtattggcta accacctgca cggtggcacc gcacaacgcc gccacaaacg 540
cgccccggta tac 553

<210> SEQ ID NO 643
<211> LENGTH: 486
<212> TYPE: DNA
<213> ORGANISM: Mycobacterium tuberculosis

<400> SEQUENCE: 643
ggccgaactt aatcggttgt tggcggctgc cgagttgggt cactcggggg gtgtgcactg 60
gcacatggtg ggccggattc aacgcaacaa agccgggtcg ctggctcgct gggcgcacac 120
cgctcactcg gtggacagct cgcggttggt gaccgcgctg gatcgggcgg ttgttgcggc 180
gctggccgaa caccgtcgtg gcgagcggct gcgggtttac gtccaggtca gcctcgacgg 240
tgacggatcc cggggcggcg tcgacagcac gacgcccggc gccgtagacc ggatttgcgc 300
gcaggtgcag gagtcagagg gcctcgaact ggtcgggttg atgggcattc cgccgctgga 360
ttgggacccg acgaagcctt tgaccggctg caatcggagc acaaccgggt gcgtgcgatg 420
ttcccgcacg cgatcggtct gtcgcgggca tgtccaacaa cttgaaatcc cgtcaacatg 480
gtcgac 486

<210> SEQ ID NO 644

-continued

<211> LENGTH: 146
<212> TYPE: DNA
<213> ORGANISM: Mycobacterium tuberculosis

<400> SEQUENCE: 644
gcttcccctg atactcgacc agccccactc gggccaatac gtgaatgtcc tagcattttt 60
cacccgttca cgggctagtc gagtagtaga cgattgatta gcctgaacgt acctccgacg 120
gccagctgac gaacgggttt gacgga 146

<210> SEQ ID NO 645
<211> LENGTH: 204
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 645
tcagctgtct gtagaagggc tggcgatact gtgcactgtc tgatatcgcn ncgtngtggg 60
actatncagn ccatnangat gcggttcngn nnntgcagag natcctggna cacatncggt 120
tcacgttaat cancatcgcg anttnctncg tnttcgatta nttctgctaa cgnntctnnn 180
agtgcctgcg ggtcgactct agag 204

<210> SEQ ID NO 646
<211> LENGTH: 209
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 646
nctctgccgg gcnagagcgc agagtcggac ggcttcgtcg atcgtgaagc gaccntgcga 60
tgancagata tcgntnacac tgctcanaaa cttcggatca tcgntgatac acaggccaac 120
gggtagcggt tgtccaaccg cttcgtcaac ganatgggat cgtgacganc ctacgctcgc 180
aggatatgtc gcngaccngn tctaganan 209

<210> SEQ ID NO 647
<211> LENGTH: 183
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 647
cacttcatgc tcgtgcgttg gcntcgattt gcncgagngg ttagctcctc gagtgngtga 60
cgtatcactc cggcngacta nccgtatcng cgtcccgcac cggtcaactg gtctagccac 120
accggggaga atncncgacc ggngctatcg accnatcacg gcttgtcgnn aagatagnca 180
gcc 183

<210> SEQ ID NO 648
<211> LENGTH: 154
<212> TYPE: DNA

-continued

<213> ORGANISM: Mycobacterium tuberculosis

<400> SEQUENCE: 648
atactcaagc ttgccaaccg ccaccctgca tccgggggc gagcactgct ccgccgacca 60
gtacgaacca acctgcggtg cccaggccat tgacaatgtg ctggtcggcg cccgcgagtt 120
ctagcacagc aacgccgcgg ccaccacagg ggcg 154

<210> SEQ ID NO 649
<211> LENGTH: 219
<212> TYPE: DNA
<213> ORGANISM: Mycobacterium tuberculosis

<400> SEQUENCE: 649
cggtcggtgt gcttggcggc gtcggtatca acaccgccca cgaaatgggg cacaagaagg 60
attcgctgga gcggtggctg tccaagatca ccctcgccca gacctgctac gggcacttct 120
acatcgagca caaccgtggc catcacgtcc gggtgtccac accggaagac ccggcgtcgg 180
cgcggttcgg caaaactttg tgggatttcc cgccccccc 219

<210> SEQ ID NO 650
<211> LENGTH: 307
<212> TYPE: DNA
<213> ORGANISM: Mycobacterium tuberculosis

<400> SEQUENCE: 650
aatactcaag cttcgcggag gtggtggggc aggagcacgt caccgcgccg ctgtcggtgg 60
cgctggatgc cggccggatc aaccacgcgt acctgttctc tgggccgcgt ggctgcggaa 120
agacgtcgtc agcgcgtatc ctggcgcggt cgttgaactg tgcgcagggc cctaccgcca 180
acccgtgcgg ggtctgcgaa tcctgcgttt cgttggcgcc caacgccccc ggcagcatcg 240
acgtggtaga gctggatgcc gccagccacg gcggcgtgga gcaaccccgc gagctgcggg 300
accgccc 307

<210> SEQ ID NO 651
<211> LENGTH: 252
<212> TYPE: DNA
<213> ORGANISM: Mycobacterium tuberculosis

<400> SEQUENCE: 651
gatggcactc acgctggaca agaccttcac aaaatctgaa atcctgaccc gatacttgaa 60
cctggtctcg ttcggcaata actcgttcgg cgtgcaggac gcggcgcaaa cgtacttcgg 120
catcaacgcg tccgacctga aattggcagc aaaccggcgc tgctgggccg ggcatggtgc 180
aatccgaaca agcacgctca acccgtacac caaccccgaa gggccgctgg cccggcggaa 240
ccttgtcctc ca 252

<210> SEQ ID NO 652
<211> LENGTH: 402
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 652
aacagctatg accatgatta cgccaagcta tttaggtgac actatagaat actcaagctt 60

-continued

```
ctgggcgtcg tggtgcccgg cctgccggtg caggaactgg attttactgc catctctcgc    120

gaccctgagg tggtccaggc ttacaacacc gacccactcg tgcaccacgg acgggttccg    180

gccgggattg gccgcgcgct gctgcangtg ggcgagacca tgccgcggcg ancaccggca    240

ttgaccgcgc cgctgctagt gctgcacggc accgatgacc ggctgatccc catcgaaggc    300

agccgtcgcc tggtcnaatg tntnggatcn gccgacgtgc anctgaanga ntatccccgg    360

ctgtnccacn aggtgttcaa cgaaccggan cgcaaccaag tg                       402
```

<210> SEQ ID NO 653
<211> LENGTH: 429
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 653

```
caaggcatac gccaagaccc aagggatcgc agtcacctcc gtcaacggcc tggtcgccgg     60

ccacgggtcc gtgcaggaga cgtggctggc catgcaaagc gccgccgcct tatcaggaac    120

gccccggctt gtcggctttt cctgcatcga cacatttccg gaggtgttgt ggttggcgca    180

ncgcgcgaga caggcctggg atggcgtgcg catcgtcatc gggaatgcga tggcaacact    240

gaactacgag cgcatcctgc gccagcatga ctgtttcgac tacgtcgtcg ttggcgacgg    300

ggangtagcg ttcaccaagc tggccttggc cctggcgaat gacctgcggt tgacgactcc    360

cgggactaac ccgccgtant gagcaaggac agattctgcg cacaccctcc tcgctggtcg    420

accttgaca                                                            429
```

<210> SEQ ID NO 654
<211> LENGTH: 353
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 654

```
aacagctatg accatgatta cgccaagcta tttaggtgac actatagaat actcaagctt     60

gccggtgatc tgggtggcca actcggcggg caccatctcc atcacgacng caaacgctcc    120

ggcttcggcg acagcgatcg cgtctgcgat ngtttgttcg gcggcgtctc cgcggccctg    180

cacccggaag ccgcccaagg tgttgacnct ttgcggggtg aagccgatgt gtgccatcac    240

cgggatnccc gccgcggtca gacangcgat ttgctcggcc acccgctcac cgccctcgan    300

cttgacngca tgtgcgccgc cgtccttgaa gaaaccggtg gcggnggcaa ccc           353
```

<210> SEQ ID NO 655
<211> LENGTH: 464
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 655

-continued

```
cgttgagatc cagctgcgca ctgtgcagcg cctcggtggt ctgctcggcc tgccgggata     60

actcgttgag cttggccagc gcgtcgtcgg ccggatcagc cagcacattc gcggccagga    120

cgccggagga gacggtgaag ctcgcaaaga aacctatggc ggaccgcatg attacacgcg    180

cgatcaacca cctctggtcg agcctcaaaa tttgcttcct taaacgggcc atcgacggat    240

gacgtcgagc tggtttaggt ctcaaacagg ttacgaaacg atctcggaat tgtccaaaag    300

gggaagttaa gaaaatggat agatttctac catttcgctg tggacgatcg tacttctgct    360

atagggctcc aggggcatcg acacgcaacg accttacgcg acaccggatc cgcgctggcg    420

gcggaacggc accangcgca accgaagggc caatccgaca tcgg                     464
```

<210> SEQ ID NO 656
<211> LENGTH: 515
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 656

```
atactcaagc ttatctaggc gccagcttga ttggtctggt tgcattggcc agctgcgcga     60

gcctggctca cttcaactac aacaaccgca aacaattgcc gccttcggat ccgagttcgg    120

ttgggtacgc ggcaatggan caccatttct cggtgaatca gactattcct gagtacttga    180

tcatccactc tgcacacgac ctgcgaaccc cgcgcggcct tgccgacctg gagcagctgg    240

cgcaacgtgt gagccanatc ccaggcgttg ccatggttcg cggtgtgacc cggccaaacg    300

gggaaaccct tgaacaggcc cgggcgacat accaagccgg ccaagttggc aaccggctgg    360

gcggcgcgtc gcgaatgatc gatgagcgca ccggcgacct gaatcggctg gcatcgggtg    420

ccaacctgtt ggccgacaat ctcggtgact tcgcggtcaa gtcagccggg ccgttgcggg    480

tgtccgcagc cttgtccagc ccctcgctta ctcca                               515
```

<210> SEQ ID NO 657
<211> LENGTH: 403
<212> TYPE: DNA
<213> ORGANISM: Mycobacterium tuberculosis

<400> SEQUENCE: 657

```
caggcatgca agctttttga gcgtcgcgcg gggcagcttc gccggcaatt ctactagcga     60

gaagtctggc ccgatacgga tctgaccgaa gtcgctgcgg tgcagcccac cctcattggc    120

gatggcgccg acgatggcgc ctggaccgat cttgtgccgc ttgccgacgg cgacgcggta    180

ggtggtcaag tccggtctac gcttgggcct ttgcggacgg tcccgacgct ggtcgcggtt    240

gcgccgcgaa agcggcgggt cgggtgccat caggaatgcc tcaccgccgc ggcactgcac    300

ggccagtgcc cgcggcgatt cagccatcgg gacatcatgc tcgcttcata ctcctcgacc    360

agtcggcgga acagctcgat tcccggaacg cccacgcatg gtg                      403
```

<210> SEQ ID NO 658
<211> LENGTH: 444
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

-continued

<400> SEQUENCE: 658
aacagctatg accatgatta cgccaagcta tttaggtgac actatagaat actcaagctt 60
gtagaaaaag atcggtgagc gcatcgattc gctccgccgg gtttgccgct gcggcggcgg 120
agctgccgtg accgtctatt tgggtgatca gatactgggc tagttcggtc ggggtggggt 180
gatcgaagat cgcggtggcc ggcagcgtta ctgcggtgac agctgttaag cggttacgta 240
tctccacggc actcaaggaa ttaaatcccg aatcggcaaa cgcctggcca gcgtcnagtc 300
cggcagcgcc gtcncgcccc agcaccgctg cggcatgctc acataccacc tcgatcgctg 360
cggcganttg ctcgtcngcc gaccgaccgg ccanccgggc ggcaaacccn gaagacccaa 420
gaattcatca ccaccatcgc tagc 444

<210> SEQ ID NO 659
<211> LENGTH: 437
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 659
ccttcttgac acccacctcg ccatcgacct tgagcactcc gtcgtagttg gtgaacatgt 60
gaccggcgat cgggcgggtg aacgcgtact gggtgtcggt gtcgacgttc atcttcacca 120
cgccgtagcg cagcgcctcc tcgatctccg acttaagcga acccgagccg ccgtggaaca 180
cgaaatcnaa cggcttggcg tcngccggca gtccgagctt ggccgccgcc acctgttgcc 240
cttgcgcaag gatgtcnggg cgaancttga cgttgccggg cttgtanacg ccatgcacgt 300
tgccgaacgt cncggccagc angtatttgc cgtgctcacc ggcgcccanc gcctcgatgg 360
ttttctcgaa gtcctccggg ctggtgtaca gcttctcgtt gatctcgttc gccacgccgt 420
cctcttcgcc gccgacg 437

<210> SEQ ID NO 660
<211> LENGTH: 422
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 660
aacagctatg accatgatta cgccaagcta tttaggtgac actatagaat actcaagctt 60
ggaaaggaga tccccgggaa cctggtggca accccgccat tggggttgtt gggattgccg 120
atcagcgtga angaaagctc gtctggagac agcgggtcgg ccgaagccgc aagattggcc 180
atcactagtg acganatcgt ggcgctctgc gagtanccna agacagtgac gttgttnccg 240
gcggcaattt gctgccgaat cgcactttcg agaatgacng caccctgcgc caccgangaa 300
tcnaaagtga ggttcttgat cacgaccacc gggtngagcc cttggggcgt gaagancgcc 360
tgcgcnataa cacccgggac gctgccactc atgtncagcg cgttcgcgan ctcnacatat 420
ct 422

<210> SEQ ID NO 661

-continued

<211> LENGTH: 412
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 661
tcctggtgat cganggccgc ggttccggcc gaaaatccgg ttcgggttcg ggtcgcggtt 60
ccaacttgan cgcggtccgc agctgattca ccgtggcaac gccggccaac tgcgcataat 120
gcgcatccga accctcaccc gcccgccccg cgatcacccc aacctgatcc aacgacaacc 180
gcccctcccg catacccggg gcgcagcgcg gaaactccgg caaccgccgc gccaccgtgg 240
cgatcgtgtg ggcgttgcct gacgaacanc ccatcttcca ggccaccaac cccgccaccg 300
accgcgcccc cgtcacaccc cacaacccgt cgcgatccag ctcagccacg atctccacaa 360
tgcgcccatc aatcgcattg cgctgaacgg gcaactccgc caactcctcc aa 412

<210> SEQ ID NO 662
<211> LENGTH: 467
<212> TYPE: DNA
<213> ORGANISM: Mycobacterium tuberculosis

<400> SEQUENCE: 662
aacagctatg accatgatta cgccaagcta tttaggtgac actatagaat actcaagatc 60
tggtacccat ccgtgataca ttgaggctgt tccctggggg tcgttacctt ccacgagcaa 120
aacacgtagc cccttcagag ccagatcctg agcaagatga acagaaactg aggttttgta 180
aacgccacct ttatgggcag caaccccgat caccggtgga aatacgtctt cagcacgtcg 240
caatcgcgta ccaaacacat cacgcatatg attaatttgt tcaattgtat aaccaacacg 300
ttgctcaacc cgtcctcgaa tttccatatc cgggtgcggt agtcgccctg ctttctcggc 360
atctctgata gcctgagaag aaaccccaac taaatccgct gcttcaccta ttctccagcg 420
ccgggttatt ttcctcgctt ccgggctgtc atcattaaac tgtgcaa 467

<210> SEQ ID NO 663
<211> LENGTH: 452
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 663
aacagctatg accatgatta cgccaagcta tttaggtgac actatagaat actcaagctt 60
ancgccacct cccgggcgga actccacggc gtggatnaag gtaccggccg ggatgttgcg 120
caatggcagg ttgttgcccg gcttgangtc cgcgttagcg ccggattcca ccacatcccc 180
ttgcgaaant ccgttgggtn cnatgatgtn ncgcttctcc ccntcnanat aatggancaa 240
cgcnatccgt gcggtacggt tcgggtcnta ctccatgtnc gcgaccttgg cgttganacc 300
atctttgtca ttgcggcgaa agtcnatcat ccggtnagcn cgcntatgan cgccgccttt 360
gtgccgggtg gtaatccggc catgcgcntt gcgtccaccg cgaacgtgca acgggggcnc 420
caacganttc tccngggttg aaccggtnat ct 452

-continued

<210> SEQ ID NO 664
<211> LENGTH: 93
<212> TYPE: DNA
<213> ORGANISM: Mycobacterium tuberculosis

<400> SEQUENCE: 664
tgtgtgtggt ggtaacccat ctgagcagtg tgccaaaccg gggcagccag ctcccaattg 60
acgtgagccc gctcacttgc tgggtaagcg tcg 93

<210> SEQ ID NO 665
<211> LENGTH: 352
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 665
aacagctatg accatgatta cgccaagcta tttaggtgac actatanaat actcaagctt 60
gcgggtnatn gccttggtca acggcaccgt gatcggatcn gggtctaccg cacacatnga 120
ctggagcttc ggcgaantca tcgcctatgc ctcgcggggg gtgacgctga ncccnggtga 180
cntgttcngc tcnggcacgg tgcccacctg cacgctcntc naacacctca ngccaccgga 240
atcattcccn ggctggctgc acganagcga nnttgtcncc ctccaagtct aaaggctggg 300
cgananaagc anaacgtccc gacnaacggc actccttttc cntttgctct tc 352

<210> SEQ ID NO 666
<211> LENGTH: 448
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 666
gaaatcattg atggtttgag tcaccaggcc gatcaagcct tcgccgagcc aaattccaat 60
caagaggccc aagcccgtac caatcagccc ggcaacgagg gattccgtca ttatcagcca 120
aaataactgc tctcgggtta cacccaaaca gcgcaatatg gcgaaaaacg gtcgccgttg 180
cacgacatta aatgtcacgg tattgtagat taaaaagata cccaccaaca angcaatcaa 240
actgagagcg gttaaattga ccgtaaaagc gtccgtcatc tgtttgacng tgtcccgttg 300
ggtatccgac gtttccatac gcacaccggc cggcagtctt tgttggatgc gtnttgcaat 360
ggcctcatct ttgatgatca aatcgatgtn gctcagtctt ccgggcatat ggaacaactc 420
ttgggccgtg gaaatatcag caatgata 448

<210> SEQ ID NO 667
<211> LENGTH: 386
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 667
ctttcgccca ggccggcgcg gatgtcctca tcgcttcacg aacatcatcc gagcttgacg 60

-continued ctgtcgccga acagatccgc gctgccggcc gccgcgccca caccgttgcc gccgatctgg 120
cccatcccga ggtgaccgcg cagctggctg gtcaggccgt cggagctttc gggaagctcg 180
acatcgtcgt caacaacgtt ggcggcacca tgcccaacac gctgctaagc acctcgacca 240
angacctcgc ggacgccttc gccttcaacg tgggcaccgc ccacgcgctg accgtcgcgg 300
cggtgccgtt gatgctggaa cactccggcg gcggcagcgt gatcaacatc agctccacca 360
tgggccggct ggcggcgcgg ggtttc 386

<210> SEQ ID NO 668
<211> LENGTH: 378
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 668
tgtgggctcc gatccggcgc gcatggcatc gacggcgacg ccgatcgatg acggccaggc 60
ttacgagctt gagggtgtga agttgtggac caccaacggt gtggtagcgg acctgctagt 120
ggttatggcg cgggtaccgc gcagtgaagg gcnccgaggg ggaatcancg cctttgtcgt 180
cgaggctgat tcgcccggga tcaccgtgga gcggcgcaac aagttcatgg gactgcgtgg 240
catcgaaaac ggcgtgaccc ggcttcntcg cgtcagggtg cccaaagaca acttgatcgc 300
anggaagcga cggtctgaag atcgcgctga ccacactcaa cgccggacgg ctgtccctac 360
cggcgatcca accggagt 378

<210> SEQ ID NO 669
<211> LENGTH: 344
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 669
gagctggccg agctggaccg gttcaccgcg gaactaccgt tctcgctcga cgactttcag 60
cagcgggctt gcagcgcgct ggaacgcggc cacggtgtgc tggtgtgcgc gccgaccggc 120
gctggcaaga cagtggtcgg cgagttcgcc gtgcacctgg cgctggcggc cggcagtaaa 180
tgtttctaca ccacgccgct gaaagccctg agcaaccaaa agcacaccga tctcacagca 240
cgctacggcc gtgaccagat ctggctgctg accggtgacc tgtcngtcaa cggcaaccgc 300
cggtggtggt gatgaccacc gaaatgctgc gcaacatgct ctac 344

<210> SEQ ID NO 670
<211> LENGTH: 411
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 670
gatctctgga tcggcggggc tctccgggcc ggcctcggcg acctcagcgg gccgcgcctt 60

-continued

```
ccggccgaac cattccctag ccatagatga ccgcacctcg atgcacggtt tggcggcaac    120

gcggcaaggc gtcngtcggg cccagccgcg gcaatgcggg tacccgggag cgcgggtcng    180

tanaccancg ctggactgcg tcgcgcggtg cgtcnacntc aaagtccccg gcgtcccata    240

tcgcgtatga cgcgggcgcg cccggcacca ngggtgccga tccggccgtc tcgaacacca    300

ccggcccgcc agccgccgcg ggtccggcag cnaacccgcc cgcgccgata cccgctgccc    360

gcgtgcgtga ttgaccgccg cgcgcacgct ggccanggat caaagcccgt g             411
```

<210> SEQ ID NO 671
<211> LENGTH: 473
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 671

```
ggacgcgtag cccgccaggc cggtcagggt gcccttccag tccacgccgc tgtggtcggc     60

gaaccgctta tcttcaatcg agacgatcgc cagcttcatc gtgttggcga tcttgtccga    120

gggcacctcg aaccggcgct gcgagtncag ccacgcgatc gtgttgccct tcgcgtcgac    180

catcgtcgat accgcaggca cttgcccctc gagcagctgg gccgagccgt tggcaacgac    240

ctcagangca cgattggaca tcagccctag cccgcctgcg aacgggaacg tcagcgcagt    300

ggcgacgaca ctggccaaca gacagcaccc agccagcttc agaacggtga tcgcggccgg    360

gaagcgctcg ggcatgcgtn ctacagtagc gacctcctgt cactccacgt gccgctcggt    420

ccaatagaat ctttccgcgg gcgggtgaat ctctgcngga tcggggcngg cgc           473
```

<210> SEQ ID NO 672
<211> LENGTH: 357
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 672

```
gctcgttgcc ggcggcgatc tcgtcgagct cgtcttccat cgccgcggtg aagtcgtagt     60

cgacgagccg accgaaatgc tgctcgagca gaccggttac cgcgaacgcc acccatgacg    120

gcaccagtgc actgcccttc ttgtgcacgt ngccgcgatc ctggatggtc ttgatgatcg    180

acgantaggt cgacgggcgg ccgatgccca gctcctcgag cgctttgacc agcgacgcct    240

cngtgtnncg ggccggcggg ttggtggcat ggccgtctgg ggtcaactcg acnatgtcca    300

accgttgacc cggggtcaga tggggcagtc gccgctcggc atcgtcagcc tcgccgc       357
```

<210> SEQ ID NO 673
<211> LENGTH: 402
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 673

-continued gtctttcgat ggctgcttct tcggcgctga cgctggcgat ctatcacccc cagcagttcg 60
tctacgcggg agcgatgtcg ggcctgttgg acccctccca ggcgatgggt cccaccctga 120
tcggcctggc gatgggtgac gctggcggct acaaggcctc cgacatgtgg ggcccgaagg 180
aggacccggc gtggcagcgc aacgacccgc tgttgaacgt cnggaanctg atcgccaacn 240
acacccncgt ctgggtgtac tgcggcaacn gcaagccgtc ggatctgggt ggcaacaacc 300
tgccggccaa gttcctcgag ggcttcgtgc ggaccatcaa catcaagttc caagacgcct 360
acaacgccng tggcggccac aaccgcgtgt tcgacttccc gg 402

<210> SEQ ID NO 674
<211> LENGTH: 336
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 674
gccaggtcga ggtcccatgc gcgtgggcca ttgatgctga tcgccaggac gtcaaanatt 60
tggtccggcg tcagctgggc gaaaaacgtg ggccccagga cttgcccgga gctgcccggg 120
ttcccgtcgc gcagctcggc ggccccggtc agaaanaaat tgcgccaggt cgcacactcc 180
gcgccgtang ccagctgctc cagggtgtcg gcatagagcc cgcgggccgc agcgtgctcg 240
ctgtcggcga acaccgcatg gtcgagaagc gttgccgccc aacggaaatc acctgcgtcn 300
aangcttcgc gggccaactc cagcactcgg tcgatg 336

<210> SEQ ID NO 675
<211> LENGTH: 405
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 675
naaacgttcc ggcttnggtg ccgggcgctt atttgcgtct ctgggatcac nctcagtcgc 60
cggcggctgc cgttgggcta tnanttgcac cganccggaa aatccgcacn anaactgcna 120
gtagcggcct gcagaantgc atcctcggcg aancngacta ccggtggaca ncnacaagcg 180
ccgccgaaca acgcactggc ccgagggatn ggcgtctatc ggccccgccc gtcgaactng 240
gaacagacng tgcggttcta ccgtgatctg gtgggaatgc tcnaccanac cttcccnann 300
gctacggaac nacggcgcga tattcngccn tcccanctcg agcctgacnc tngatatcgt 360
cgannctcac catcncgatc ngctgtgccg gtnttgctcg gactn 405

<210> SEQ ID NO 676
<211> LENGTH: 389
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 676

-continued

```
cgaacgacga acnccncaag ccatggtggt tggcgccgtc aaaaggtccg cggtcgccac     60

tactggaaaa tcgccttgag cgtcnctcga ccnccgcctc gagttgggtc ntaacgaaat    120

acctgatgcc gatcangtcn acgtctccgt cgcnncaacg tgcagcggcg acccactcta    180

cnangtctcg gtnccgccnc ggccagngca ccaccagtga cnaatccntg cgccntcggg    240

ccnagcantc ccggtgcnac cgnggtgggt ccggcgatgg tngggtgtnc tcnntacngg    300

aacgccagcg cnatcancat cggcanactc ncgtcgatgt gccgcggcgc aaccatcccc    360

cacaatgatc nggtgcgtct gatcaggcn                                      389


<210> SEQ ID NO 677
<211> LENGTH: 135
<212> TYPE: DNA
<213> ORGANISM: Mycobacterium tuberculosis

<400> SEQUENCE: 677

ttaggcgtga cggccaccgg ggccactccg cacaatctgt acccgaccaa gatctacacc     60

atcgaatacg acggcgtcgc cgactttccg cggtacccgc tcaactttgt gtcgaccctc    120

aacgccattg ccggc                                                     135


<210> SEQ ID NO 678
<211> LENGTH: 140
<212> TYPE: DNA
<213> ORGANISM: Mycobacterium tuberculosis

<400> SEQUENCE: 678

cgtcaccccg atgcgcccag atcggggctt cgcagataaa gcacgaactg gcgggcaaaa     60

cgtcgatctc ggagccggaa gggcaatcag ccgaccgtcg acgaacgaca ccggcgagac    120

cacttaggca gtgacggcct                                                140


<210> SEQ ID NO 679
<211> LENGTH: 272
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 679

cttttcncga tgtctcatga tnccnangga gaacnntgcn ancncngccg ctgacntngc     60

ncaccgctnt ggcngnggtg acattggtgg tggttgcggg ctgcnacgcc cgactcgang    120

ccganccatn tnttgcggcc gaccgcntnt cgtctcnacc gcanncccna tctcngccgc    180

ncccggtgga nctacngctn cttcgccatc tctcgccnat ggctccngcg nntcgcncaa    240

cgtntggttt ggtnanctgc ctacctggtc nt                                  272


<210> SEQ ID NO 680
<211> LENGTH: 507
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 680
```

-continued

```
gctgcgccag tcgttcggtg cggtcatgcc gttggaccna ccatcggagt tagttgccga     60

accgcggacc accgcaagca cccggtcctg gtcgcgcacc gcgtcggcca accgcttgag    120

caccaccacg ccgcagccct cgccgcgcac gaatccatcc gcgttggcgt cnaanctgtn    180

gcatcggtcg gtcggtgaca gcgccgacca cttggacagc gcgatggcgg tgaacggtna    240

ntaggtgacc tgccnccncg cccgccaatg cccacctccg cttcacncat gcgaatggtc    300

tgacacgccn agtgaattgc caccagcgac aacaaaaatc ggtatctncn gcgacggcgg    360

acacgcnatc ccnactgata ctcgatccgc cccaccgctt gnanctccgg gttccngtgc    420

tcatgtaccn tcatgtcggt ctgcgcncga tattgacgat cgtgtttccc acgannanag    480

ancctcatca cgccggttcg agtgccg                                         507
```

<210> SEQ ID NO 681
<211> LENGTH: 470
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 681

```
ctgtgtgcgg ncggcgcgat atcggccttt ttactaaccg aacccgatgt gggctccgat     60

ccggcgcgca tggcatctac ngcgacgccg atcgatgacg gccaggctta cgagcttgag    120

ggtgtgaant tgtggaccnc caacggtgtg gtagcggacc tgctantggt tatggcgcgg    180

gtaccgcgca gtgaanggca ccgaggggga atcancgcct ttgtcgtcta ngctgattct    240

cccgggatca ccntggagcg cnccncnant tcatgggact gcgtggcatc caanacggcg    300

tgaccggctt catccntcng ggtgcccaaa gacaacttga tcngcnngga agcgacgtct    360

gaanatcgcg ctgatcncac tcaacgccgg acgctgtcct accggcgatc gcaccggant    420

tgccaanccg cgctnannat ncgcgngaat gnccgtccac nantgcatgg                470
```

<210> SEQ ID NO 682
<211> LENGTH: 346
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 682

```
tggggtgccg ggcgccgagt tgcgtccctg ggatcacgca gagtcgccgg cggctgccgt     60

tgggctatga attgcaccga gccggaaaat ccgcancaaa actgcgagta gcggcctgca    120

gaagtgcanc ctcggcgaaa cggagtacgg tggacaacga aaagcgccgc cgaacnacgc    180

actggcccga gggattggcg tcaatcggcc ccgcccgtcg aacttggaag anacantgcg    240

gttctaccgt gatctggtgg gaatgctcca acnnaccttc nccgaaagct acggaagcna    300

cggcgcgatn ttcggccttc ccagctcgac ctgacgctgg aaatcg                    346
```

<210> SEQ ID NO 683
<211> LENGTH: 453
<212> TYPE: DNA
<213> ORGANISM: Mycobacterium tuberculosis
<220> FEATURE:
<221> NAME/KEY: unsure -continued
<222> LOCATION: (various positions within the sequence)
<223> OTHER INFORMATION: applicants are uncertain of bases designated as "n"

<400> SEQUENCE: 683
nggcngggaa gttaatgccc tactggttcn atgctcncac ntcnccngtg acnncctgcn 60
ccgacccgcc gaggtcctgn ccgtnaccac cgancnggcg atccgggact ctngtacgca 120
tccaacanng ancaacgtgc acgggcggag tngtnccgcc acttcgncna tgacggggtc 180
gatccnttcg acgtccgtcg ccgcgtcggt cgagtggcgg tcacnctccn ngtactcgac 240
cncacngacg agaggactcg ancccatcta cgtgtggacg aaacanatct tctgtccnac 300
gactacacca ccacccaggc catcgccgnc gcccgcgang ccccttcgac gccntactgg 360
tccngnggng gcgctctccg gttgtctnnc ncntgncgtg ttccttcacn cactgcccna 420
catcganccc gagcnatncn angtccgtca atc 453

<210> SEQ ID NO 684
<211> LENGTH: 382
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 684
ggacactgtt cgcgtgcccc tcgtcaaagc cggagtggtc gtgctgcgcc ggacccgacc 60
cgaccttcag cgggggttca cagctccgtg ggtgccgtta cttccgatcg ccgcagtgtg 120
cgcgtgcctg tggctgatgc tgaacctcac cgcgttgact tggatccggt tcgggatctg 180
gctggtggcc ggaaccgcga tttatgtcng ctacgggcgc cggcactcgg cgcatggcct 240
tcggcaagcn cnananaacg cgacccggag gtgttgaact agcttcgccg cgtatttaca 300
aattgcntta tatgtctaca cataagacgc aaactgctct attgtcaant cccancgtgg 360
tgtggcncat gaagatgttt gg 382

<210> SEQ ID NO 685
<211> LENGTH: 408
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 685
tccttctcgg tatcggtttg ggctgtcacc ancagttggt agttcttcac gtnctgttgt 60
tcgagcgtcn agccgtcgcg cgtgtcnang tcnccggacg cgtatcccgc caggccggtc 120
anggtgccct tccantccac gccgctgtgg tcggcgaacg ctnatcttca atcgagacca 180
tcgccagctt catcntgttg gcgatcttgt cnnacggcac ctcnaaccgg cgctnctagt 240
acnccacncn atcntgttnc cttcncgtcn acatcctcga tnccncntgc actttccctc 300
gancncctgg gccgagccgt tggcantnac ctcngagccc cattggacat cancccancc 360
cgcctgcgaa cgggaacgtc agcncnctgg cgacaacctg gccaacan 408

<210> SEQ ID NO 686
<211> LENGTH: 372

-continued

<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 686
cacnccgtga tcgcnagccc cngtagaaat ngttgagcca gttggtgcgg cgctcgttgc 60
cggcggtnat ctcgtcgagc tcntcttcca tcgccgcggt gaagtcgtac tcgacnagcc 120
gaccnaaatg ctgctcnagc agaccggtta ccnnnaacnc cncctcntga cngcaccagt 180
gcnctgccct tcttgtgcac gtacccgcna tcctggatgg tcttgatgat cnactantnt 240
gtcgacgggc ggccgatgcc catctcctcn agcgctttga ccagcgacnc ctcggtgtat 300
cgggccggcg ggttngtggc atggccgtct ggggtcanct cnacnatntt canccgttga 360
cccggggtca ca 372

<210> SEQ ID NO 687
<211> LENGTH: 403
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 687
tggccttctt gncangggcn nacatnngct atngcgagcg tgtaaccgat catcntccng 60
gcgactgtgg cctgancggc aagggtngcc tnattcntcc tcctgnggca tggttnccac 120
acggaatgnc ggtaagtctg gtcggcaacc tggcccgctg cgggttgggt tcggattcgc 180
tcggctanta aggtgctcgc ctggtgtnac nactaatcnc natatacnct tancgggagt 240
ngncgtcccg atcctngccc tgccgcnggc gatcncgttc gcancaccgc caccggaact 300
cncaangtgc gctcatcggg ctctacgcgc catcttcccc ggattcttcg cggcngngtn 360
ccgngggacc ccggactgtg acnggcccaa cggctcatca tcg 403

<210> SEQ ID NO 688
<211> LENGTH: 356
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 688
ccggatagcg gtgtctgaac ttcgcccgtt ccctccancg cattgagctt cagcccgacc 60
ggcaggtnng gagtcggcat gcggtccttc gccccgaccc cgctggctaa atanccaccc 120
ccgagcgcgg tcacggtctt tgcaccggga cgacgcatac cggcagcgcg aacatcnccg 180
cgggctgcag cntgaacgtc caataccant cnaacagtgt ccgcgcgtna aaacccganc 240
cggcggtcgc ttcngtaatc aacggctcct gcgcaaccag ctgcaagtcg ccggtgccac 300
cggcgttgac gatcttgatg tctgcganct cgcgcaccag ctcgacggcc cgggca 356

<210> SEQ ID NO 689
<211> LENGTH: 439

-continued

<212> TYPE: DNA
<213> ORGANISM: Mycobacterium tuberculosis

<400> SEQUENCE: 689
cctcccgacc acatacaggc aaagtaatgg cattaccgcg agccattact cctacgcgcg 60
caattaacga atccaccatc ggggcagctg gtgtcgataa cgaagtatct tcaaccggtt 120
gagtattgag cgtatgtttt ggaataacag gcgcacgctt cattatctaa tctcccagcg 180
tggtttaatc agacgatcga aaatttcatt gcagacaggt tcccaaatag aaagagcatt 240
tctccaggca ccagttgaag agcgttgatc aatggcctgt tcaaaaacag ttctcatccg 300
gatctgacct ttaccaactt catccgtttc acgtacaaca ttttttagaa ccatgcttcc 360
ccaggcatcc cgaatttgct cctccatcca cggggactga gagccattac tattgctgta 420
tttggtaagc aaaatacgt 439

<210> SEQ ID NO 690
<211> LENGTH: 442
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 690
cttcacntcc gtacggctcg ggtacgcttc ggtcncattg tgcgagtgat agatgacgac 60
cgggacctcg tcggcatctt ccatagcccg ccacaccttc agttgctcac cggaatccaa 120
ccggtanaag gtcggcganc gctcngcatt ggtcatcggg atatgccgct cgggacggtc 180
anagccctcg ggtccggcca gcactccgca ggcttcgtcg gggtggtcgc gacgcgcatg 240
ggccaccatc gcattcacca ggtctgcgcg aatcaccagc acgtanacgg ttcctttcct 300
aagcaacacc gaantttcag gacccgaatg ctccgggaaa catgtcacgg taggtcggta 360
ttccggctac cggctganca ttgagcacgc cggccagcac cgcacgaacc aggcaatcag 420
ccgccgccgc acccgaccgc gg 442

<210> SEQ ID NO 691
<211> LENGTH: 365
<212> TYPE: DNA
<213> ORGANISM: Mycobacterium tuberculosis

<400> SEQUENCE: 691
caggcatgca agcttgatgc cgccgaaacc gagcgtgagc acgccgccag ccaccacgcg 60
cgggtcgggc gccgggcccg ggccgccagg ctgctccgct cggtgatggc acgccaccgc 120
gacaccaccc ggctgcgcta cgtcgagcca taccgggcgg agctacatcg gctcggccgc 180
ccagtgttcg ggccctcttt cgaggtcgag gtcgataccg atttgcgcat ccgcagccgc 240
accctggacg acagaaccgt gccctacgaa ttgcttgtcg ggcggggcca aagaacagct 300
tggcatcctg gcgcgattgg ccggcgcggc gctggtcgcc aaggaagacc cgttccggtg 360
ctgat 365

<210> SEQ ID NO 692
<211> LENGTH: 307
<212> TYPE: DNA
<213> ORGANISM: Mycobacterium bovis
<220> FEATURE:
<221> NAME/KEY: unsure -continued
<222> LOCATION: (various positions within the sequence)
<223> OTHER INFORMATION: applicants are uncertain of bases designated as "n"

<400> SEQUENCE: 692
aagntcgggt ttccacacgc gcggtttgac cctagtcata tgtaatcatg tgtaccatgt 60
gcgggcgctt ttcgacggcc gcgaaccacc gganatttcc tgtgatttca ctgcatgcgt 120
accatctggc acaattgagc anttgtctnt cgcggtggtc ggncgggttg cgtgccgcct 180
gctgcganat gcaccantaa gcccgaaccc accggcttgg tgaccaccgc acgctgcgtg 240
tggggggtaa ccactccgcg accccaagga tggtcatttc caatgaaccg gctggacttc 300 gtccana 307

<210> SEQ ID NO 693
<211> LENGTH: 414
<212> TYPE: DNA
<213> ORGANISM: Mycobacterium bovis

<400> SEQUENCE: 693
gtcgcggttc gatcgacccg atcttcacct cgtaacctcg atgcttagca ggatccagct 60
tgaccgcgtt tggctctacc cactctttga gtggcgccgt cgcctgtgcc ccatcggtgt 120
tcatgacgaa cgcttcgaaa gacttcctct tgtgagccgg aatgtctgcg taaagaagtt 180
ccatgtccgg gaagtagacc cggtcgccct ccacgtggta ctccttcgag gtccgcttct 240
cgccggatcc gataaacacc ggccccaggc accgcagcgt gagttcgaac ggcttcaggt 300
aggtgttcat gcggcggact ccgggagtgc gagaaatagc ggtcgcgcgt agctgtagac 360
cggatggttt ccgcccaggc tgacgtcgaa gatgcctcct tggaaggggc gcga 414

<210> SEQ ID NO 694
<211> LENGTH: 256
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 694
aactcaagtt tttacggtga tcgcgcatca cctggttcat gaactggaag cagcgcagcg 60
cttccttttc ggccgcaaca tgagccagcc tctcgtcggc ggtcgggtgc aggtgctcgg 120
gcagctcggc cgcgacagcc gcctgaccct gaaaccagct tccatatccc gcgacnaacg 180
acgccagtcc gctacgtaac ccctccgcga ctgtccatgg acaacagcgc gttctccacc 240
gaccgggccc gggtgt 256

<210> SEQ ID NO 695
<211> LENGTH: 328
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 695
gtgcaggttt cgacaatgtg gtgccggttc ggcggctacg tgccatcgag acactggcgc 60
angctatcgc acccgttatc ggctgcgagc aaatcgcggt atgcgttctt gagcatgagt 120

-continued

```
cggcgaccgt cgtcatggtc gacacccacg acggaaagac gcagatcgcc gtcaagcatg    180

tgtgccgcgg attatcagga ctgacctcct ggctgaccgg catgtttggt cgcgatgcct    240

ggcgcccggc cggcgtggtc gtggtcggct cggatagcga ggtcagcgaa ttctcgtggc    300

agctcgaaag ggtcctgccg gtgccggt                                       328
```

<210> SEQ ID NO 696
<211> LENGTH: 278
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 696

```
ttcgagtcat gcgcccgcct cgaccacgaa natgcacgtc gnggttcgat cgacccgatc     60

ttcacctcgt aacctcgatg cttagcagga tccagcttga ccgcgtttgg ctctacccac    120

tctttgagtg gcgccgtcgc ctgtgcccca tcggtgttca tgacgaacgc ttcgaaagac    180

ttcctcttgt gagccggaat gtctgcgtaa agaagttcca tgtccgggaa gtagacccgg    240

tcgccctcca cgtggtactc cttcgaggtc cgcttctc                           278
```

<210> SEQ ID NO 697
<211> LENGTH: 264
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 697

```
gtcatgtgta ccatttgcgg gcgcttttcg acggccgcga aacaccggag atttcctgtg     60

atttcactgc atgcgtaccg tctggcacaa ttgagcagtt gtctgtcgcg gtggtcggcc    120

gggttgcgtg ccgcctgctg cgagatgcac caataagccc gaacccaccg gcttggtgac    180

caccgcacgc tgcgtgtggg gggtaaccac gccgcgaccc caaggatggt catttccaat    240

gaaccggctg gacttcntca acaa                                           264
```

<210> SEQ ID NO 698
<211> LENGTH: 169
<212> TYPE: DNA
<213> ORGANISM: Mycobacterium bovis

<400> SEQUENCE: 698

```
aacagcgcgg ttgaactgat aggtgcggcc cggctcgagc aggccgggcc atttgttcga     60

tgcggttacc gaaagatctc ttcggtgacc tgcccgccgc cggccagctc ggcccagtgc    120

ccggcgttgg ccgccgcggc gacgatcttg gcgtccacgg tggtcgggg                169
```

<210> SEQ ID NO 699
<211> LENGTH: 256
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

-continued

<400> SEQUENCE: 699
gcatctgggc tggcggtggt tcgccgctcc gaagccgtcg aacaccatcg ccagcgcggc 60
ttccacatca acgaccattt cggccagctt gcggcgcatc agcggcttgt cgatgagcgc 120
cccaccgaat gcccgccgct gcccggcgta ncacagcgat tcgaccagcg cgcggcgcgc 180
gttgccgagg gcgaacgaag cggtgcccaa ccgcaatctg ttggtcagct ccatcatgcg 240
ggtgagtccc ttgccg 256

<210> SEQ ID NO 700
<211> LENGTH: 291
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 700
atcggtttcc agcaacagcc gatcgacggc ttcgcccagg ccgctcccgg gcgacccgac 60
cattgctgtc gccgcgtaac gccatcacgg atgacgcgca gttcgtcgct gtctagctcc 120
accatcgcct gcacaccggc ggccagnacc cattggccgt cgcactcgta nagcaggtaa 180
tcctcgtcga cggactcggt aaccaccgcc gccagctccg ctgccaggtc ggcggggttg 240
acaccggcgg gcatcgggat ggacgacgac gcggtgctga cggcgcctgt c 291

<210> SEQ ID NO 701
<211> LENGTH: 315
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 701
agcggtttcc cangcgggat gtgctgtgag cgccgcacca ccagcgccga cgctaaggat 60
ggaacgcacg gcatcttctg acgcgtaacc gcgttgtgat cgcgagctga ggagacggta 120
tgggggaggg ttctcggagg ccatctggga tgttgatgtc tgtcgatctt gagccggtgc 180
aactcgtcgg cccggacggt acgccgacgg ccgaacgccg ctaccaccgt gaccttcctg 240
aggaaacgct gcgttggctc tacgagatga tggtggtcac ccgcgagctg gataccgaat 300
tcgtcaatct gcacg 315

<210> SEQ ID NO 702
<211> LENGTH: 328
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 702
caagcttcca caggtaggga tcgaggaaca gcgcgttgaa ctgataggtg cggcccggct 60
cgagcaggcc ggccatttgt tcgatgcggt taccgaaaat ctcttcggtg acctgcccgc 120
cgccggccag ctcggcccag tgcccggcgt tggccgccgc ggcaacgatc ttggcgtcca 180

-continued cggtggtcgg ggtcatgccc gcgagcagga tcggcgagcg gccggtcagc cgggtgaact 240
tcgtcgaaag cttgaccctg ccgtcgggga ggcgaaccac ggtcggtgcg tanctccacc 300
aagcccgggc aacctcgggg gtggcgcc 328

<210> SEQ ID NO 703
<211> LENGTH: 352
<212> TYPE: DNA
<213> ORGANISM: Mycobacterium bovis

<400> SEQUENCE: 703
tggacctcat gacaacgcgg cggcgattac ccccgctacc gccagcagca tgacggcggt 60
agcgaacacc gccggatgca gcgcaggtgc gtcgatgtgc tcacggaatc gccccggcac 120
cgcgatctcg aggatcacca gtgccacccc ctgcagcgcg acaccgacga ttccgtacac 180
cgccacgccg atcaggccct gggccagctg gcgtatatgg cggcgatggt gacgatggcc 240
agcgccacat acattgtggc ggccagaacc acggcgttgg ggcggcggtc gatgaacact 300
aggcgacgca gatcgcccgg ggtcaacagg ttgaccatca gaaagcctgc ga 352

<210> SEQ ID NO 704
<211> LENGTH: 315
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 704
tttggtgcgg ccggcaatca acttcngctc ncagcggttt cccaggcggg atgtgctgtg 60
agcgccgcac caccagcgcc gacgctaagg atggaacgca cggcatcttc tgacgcgtaa 120
ccgcgttgtg atcgcgagct gaggagacgg tatgggggag ggttctcgga ggccatctgg 180
gatgttgatg tctgtcgatc ttgagccggt gcaactcgtc ggcccggacg gtacgccgac 240
ggccgaacgc cgctaccacc gtgaccttcc tgaggaaacg ctgcgttggc tctacgatat 300
gatggtggtc acccg 315

<210> SEQ ID NO 705
<211> LENGTH: 390
<212> TYPE: DNA
<213> ORGANISM: Mycobacterium bovis

<400> SEQUENCE: 705
cgcccagggc cgctcccggg cgacccgacc attgctgtcg ccgcgtaacg ccatcacgga 60
tgacgcgcag ttcgtcgctg tctagctcca ccatcgcctg cacaccggcg gccaggaccc 120
attggccgtc gcactcgtag agcaggtaat cctcgtcgac ggactcggta accaccgccg 180
ccagctccgc tgccaggtcg gcggggttga caccggcggg catcgggatg gacgacgacg 240
cggtgctgac ggcgcctgtc gcgacgctga gctcggacac agctagtaaa tgtagcctaa 300
cctacttaat gggtcgcagc cccccggggt cgtcgcatgt ccaacgttgc tcgactggaa 360
gaaaatgctc gtcggggagc aaatggcacc 390

<210> SEQ ID NO 706
<211> LENGTH: 322
<212> TYPE: DNA
<213> ORGANISM: Mycobacterium bovis -continued

<400> SEQUENCE: 706
aatactcaat cttgatcggt ttccagcaac agccgatcga cggcttcgcc cagggccgct 60
cccgggcgac ccgaccattg ctgtcgccgc gtaacgccat cacggatgac gcgcagttcg 120
tcgctgtcta gctccaccat cgcctgcaca ccggcggcca ggacccattg gccgtcgcac 180
tcgtagagca ggtaatcctc gtcgacggac tcggtaacca ccgccgccag ctccgctgcc 240
aggtcggcgg ggttgacacc ggcgggcatc gggatggacg acgacgcggt gctgacggcg 300
cctgtcgcga ctctgagctc gg 322

<210> SEQ ID NO 707
<211> LENGTH: 398
<212> TYPE: DNA
<213> ORGANISM: Mycobacterium bovis

<400> SEQUENCE: 707
ggatgtgctg tgagcgccgc accaccagcg ccgacgctaa ggatggaacg cacggcatct 60
tctgacgcgt aaccgcgttg tgatcgcgag ctgaggagac ggtatggggg agggttctcg 120
gaggccatct gggatgttga tgtctgtcga tcttgagccg gtgcaactcg tcggcccgga 180
cggtacgccg acggccgaac gccgctacca ccgtgacctt cctgaggaaa cgctgcgttg 240
gctctacgag atgatggtgg tcacccgcga gctggatacc gaattcgtca atctgcagcg 300
ccagggggaa gctggcgttg tacacgccct gtcgcgggca ggaagccgcg caggtgggtg 360
cggcggcttg cctacgcaaa accgactggt tgttcccc 398

<210> SEQ ID NO 708
<211> LENGTH: 175
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 708
atcacgacaa cagcgacggt gtgtcggatc agcggccccc gttgccgggc aatgttgagg 60
cgtttctgcg tctggttgag gccggctggg acnccgaggt ggctcgtcgg ccacatgggc 120
agcacaccac cgtggtgatg catctagacg tgcaggaccg tgccgctggc ctgca 175

<210> SEQ ID NO 709
<211> LENGTH: 210
<212> TYPE: DNA
<213> ORGANISM: Mycobacterium bovis

<400> SEQUENCE: 709
gcggctacgt gccatcgaga cactggcgca ggctatcgca cccgttatcg gctgcgagca 60
aatcgcggta tgcgttcttg agcatgagtc ggcgaccgtc gtcatggtcg acacccacga 120
cggaaagacg cagatcgccg tcaagcatgt gtgccgcgga ttatcaggac tgacctcctg 180
gctgaccggc atgtttggtc gcgatgcctg 210

<210> SEQ ID NO 710
<211> LENGTH: 312
<212> TYPE: DNA
<213> ORGANISM: Mycobacterium bovis

<400> SEQUENCE: 710

```
tacaagcggc acctcgccgg tgaactgacc gttcgcacgc tgcgcaccgc cgccgggcgc    60

gtgctcggcg cgccggcggc ccccgaggcc tgagagggga accaaccatg caggtgaaca   120

tgacggtaaa cggcgagccc gtcaccgccg aggtcgaacc ccggatgctg ctggtccatt   180

ttctccgtga tcagctgcgg ctcaccggaa ctcactgggg ctgtgatacc agcaactgcg   240

ggacatgcgt ggtggaggtc gacggcgtgc cggtgaaatc ctgcacgatg ctcgccgtga   300

tggcctccgg gc                                                      312
```

<210> SEQ ID NO 711
<211> LENGTH: 255
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 711

```
agcggctggt tacgactccc tgtttgtgat ggaccacttc taccaactgc ccatgttggg    60

gacgcccgnc cntccgatgc tggaagccta cactgccctt ggtgcgctgg ccncngcgac   120

cgagcggctg caactgggcg cnttggtgac cngcaatacc taccgcaccc cnaccctgct   180

ggncaaanat catcaccacg ctcgacttgg ttagcgccgg tcgancgatc ctcggcattg   240

gaaccggttg gtttn                                                   255
```

<210> SEQ ID NO 712
<211> LENGTH: 304
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 712

```
acgcgcgccg atcatatctg ctatggatgt acaattcagc tcttgctgtt ataccagtat    60

atggtgtact atttgatcta tgctgacgtg tgagatgcgg gaatcggccc tggctcgact   120

cggccgggct ctggctgatc cgacgcggtg ccggattctg gtggcgttgc tggatggcgt   180

ttgctatccc ggccagctag ctgcgcacct cgggttgacc cgatcgaatg tgtccaacca   240

tctgtcgtgt ttgcggggct gcgggctggt antcccaacc tatgagggcc ggcaggttcg   300

gtat                                                               304
```

<210> SEQ ID NO 713
<211> LENGTH: 352
<212> TYPE: DNA
<213> ORGANISM: Mycobacterium bovis

<400> SEQUENCE: 713

```
ccgcgctgct gctgacgtcg gtcgaacgtg cgacacgtct gcgaataccg gccgaacgct    60

gggtttatcc acaggctggc accgacgccc acgacacacc ggccgtcgcc gaccgccacc   120

gactgcatcg gtcgacggcc attcggatcg ccggtgcccg ggcgctggaa ctggctgggc   180

tggggctcga tgacatcgaa tacgtcgacc tgtattcgtg ctttccctcc gctgtccaag   240

tcgccgcaat cgaactcggc ctggacaccg acgatcctgc ccgcccgctg accgtcaccg   300
```

-continued ggggcctgac cttcgccggc gggccgtgga gcaattacgt cacgcactcc at 352

<210> SEQ ID NO 714
<211> LENGTH: 233
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 714
caggcgtgca atgacctgca ctgcgccgga nantccctaa cccactaaac cggggccgct 60
cacaagccgt gcagctcggt cagcgtcagg tgcgcgacca ggaantaaat gagcagaccc 120
gtgccgtcaa cgatggtggc gatcatcggc cccgaaacga tggccgggtc natgcgcaac 180
ttcttcagca gcggcggaag gacggcancc accagcgacn accacaccac gat 233

<210> SEQ ID NO 715
<211> LENGTH: 335
<212> TYPE: DNA
<213> ORGANISM: Mycobacterium bovis

<400> SEQUENCE: 715
gcgaacactt cgtcaacttc cagggctgcc cgcaccaagt atttcgacga gtatttccgt 60
cgggccgccg ccgccggcgc gcggcaggtg gtcatcctgg cggcggggct ggactcgcgc 120
gcgtaccggc tgccttggcc cgacgggacc acggtttttg agctggaccg cccgcaggtc 180
cttgatttca agcgcgaggt gctcgccagc cacggtgccc aaccgcgcgc cctgcgccgc 240
gagatcgccg tcgacctgcg tgacgattgg ccacaagcct tgcgggacag tggtttcgat 300
gcggctgcac cgtcggcatg gattgccgaa gggct 335

<210> SEQ ID NO 716
<211> LENGTH: 274
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 716
ttgggcnttg cccncaatan ggccccaatc aaaagccgag caggtggaac ctanncgcat 60
tcgcctcntc gtntgtgcac ccgagccatc gcacgcgcgg gaattcccgg atntcnccgt 120
attctccggc ggccgggcta acccatccca ngccgaacgg ttggctcntg ccgtgggtcc 180
cgtgttggcc gatcggggcg tcaccggggg tgctcgggtg cggntgacca tggcnaactg 240
ccccnatggg ccgaccctgg tgcagataaa cctg 274

<210> SEQ ID NO 717
<211> LENGTH: 327
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 717

-continued

```
tggtggaggt ccccaccaan acccggccgt aactctgctc acggaaatgc ggncaggccg     60

cgcgtagcac gtggtatccg ccataaaggt gcaccttaag cacggcgtcc caattctcga    120

acgacatctt gtggaaggtg ccgtcgcgca agatcccggc gttgctcacc acaccgtgca    180

cggcgccgaa ttcgtcaagc gcggtcttga tgatgttcgc tgcgccgtcc tcggtggcga    240

cgctgtcggt anttggcgac cgcccggccc cccttgtcgc gaaatctcgg cgacgacctc    300

atcggccatc gccgaaccgg gcgcccg                                        327
```

<210> SEQ ID NO 718
<211> LENGTH: 344
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 718

```
gccggccaaa ctggccggcg gggttgctgt cntcaaggtg ggttccgcca ccaanaccnc     60

actcaaggat cgcaaggaaa gcntcaagga tgcggtcgcg gccgccaagg ccgcggtcaa    120

ggagggcatc gtccctggtg ggggancctc cctcatccac caggcccgca aggcgctgac    180

cgaactgcnt gcgtcncnga ccggtgacaa ngtcctcggt gtccacgtgt nctccgaagc    240

ccttgccgct ccgttgttct ggatcnccnc caacnctggc ttggacggct cngtggtggt    300

caacaaggtc agcgagctac ccgccgggca tgggctgaac gtga                     344
```

<210> SEQ ID NO 719
<211> LENGTH: 271
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 719

```
cgaacctnaa ttgtcctgta atgcccagct caccaangca tggctggtgg ccggggcggt     60

gaagccggcg tctgcggcac cgtccaactc natgtggatn gccggaatgg ggatgtccgg    120

nacggcgaat ccgtanttcg cttgtcccgt gaggcccagg tggatggggg gaaggatcnt    180

ggtgtccggg atgatnatgg ggccgatgcc gccggttgaa gtccactgga tcgggaattc    240

gggaatcgtg atnccgacgt tcaggccgaa c                                   271
```

<210> SEQ ID NO 720
<211> LENGTH: 302
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 720

```
ctaacggaat gaaagccctg gtggccgtnt cggcggtggc cgtcgtcgca ctgctcggtg     60

tatcttccgc ccaagctgat cccgaggcgg atcccggcgc aggtgaggcc aactatggtg    120

gccccccaag ttccccacgt cttgtcgatc acaccgaatg ggcgcantgg ggaattctgc    180
```

-continued

```
ccagcctccg ggtctacccg tcccaagttg ggcgtacanc ctcccgccgc ctcgggatgg    240

ccgctgccga cccggcctgg gccnaggttc tcgcgctgtc accggaagcc gacactgccg    300

gc                                                                   302
```

```
<210> SEQ ID NO 721
<211> LENGTH: 303
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 721

ccgcgggaca cncctcnatg ctgccgccat ggacgcggtc gaacgcaagc agctgatcga     60

gctacaacgc cgcgcggaac gcttccgccg cgggcgtgac cgcatcccgt tgaccgggcg    120

gatcgcggtg atcgtcgatg acggcatcgc caccggagcg acggccaagg cggcgtgcca    180

ggtcgcccgg gcgcacggtg cggacaaggt ggtgctggcg gtcccgatcg gcccanacga    240

catcgtggcg aagattcgcc gggtacgccg atgatgtggt gtgtttggcg acgccggcgt    300

tgt                                                                  303
```

```
<210> SEQ ID NO 722
<211> LENGTH: 280
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 722

ctctgggacc ggccacggtg ccnccggcgt tcccggacgt gctgcgccag gtgtccggcg     60

gccgcgtgca tggtgttccc ggatcggccg ctggccagag cccaccggtg aatctggcgc    120

ctggccgacc accgtgcgcc gtaggcttgc gatcgtgcag cgctggcgtg gccaggacga    180

gatcccgacg gattggggca gatgcgtgct caccatcggg gtatttgacg gcgtgcaccg    240

cgggcacgcc gaactgatcg cgcacgcggt caaaggcggc                          280
```

```
<210> SEQ ID NO 723
<211> LENGTH: 333
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 723

aatactcaag ctttcgtcag ttcattgcgc cagcagacca acaanagcat cgggacatac     60

ggantcaact acccggccaa cggtgatttc ttggccgccg ctgacggcgc gaacgacgcc    120

agcgaccacn ttcagcaaat ggccancgcg tgccgggcca cgaggttggt gctcggcggc    180

tactcccagg gtgcggccgt gatcnacatc ntcaccgccg caccactgcc cggcctcggg    240

ttcacgcagc cgttgccgcc cgcagcggac natcacatcg ccgcgatcgc cctgttcggg    300

aatccctcng gccgcgctgg cgggctgatt aac                                 333
```

-continued

<210> SEQ ID NO 724
<211> LENGTH: 320
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 724
tgccgcggat ttggctggct gcccaatatt cagaatcggg cctttctttt tgcgcgacaa 60
taaggtcaca gtaaaccctc gttttgtgag atgcggggcg ggccgggcga antcgacctc 120
gagtgaatgg atctcgagtg aatggacagg gcatcgccta cgagtcgcat ccccatccaa 180
cagaccggtg ctcttgcatc ggaccctgaa ggtcccgcac ggagggtgtg gttgccggcg 240
cggggtcacg gtgcggtagc gacgtagtgt ttgaacgaat ttcttgatgc tccaacctgt 300
ttggtgttca atccagttct 320

<210> SEQ ID NO 725
<211> LENGTH: 296
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 725
aancttgcgc gctcggccgg gtcnagcatc cagctgctcg gcaaggaggc cagctacncn 60
tcgctgcgta tgcccagcgg tgagatccgc cgggtcnacg tccgctgccg cgcgaccgtc 120
ggcgaagtgg gcaatgccga gcaggcaaac atcaactggg gcaaggccgg tcggatgcgg 180
tggaagggca agcgcccgtc ggtccggggc gtggtgatna acccggtcna ccacccgcac 240
ggcggtggtg agggtaaaac ctccggcggc cgtcacccgg ttagcccgtg gggcaa 296

<210> SEQ ID NO 726
<211> LENGTH: 304
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 726
antcgaaagt gaccatctct accttgagtg ccataccgcc cgaccctatg cctcggatag 60
ctcggcggaa agaaacgctt gcagtgccgc cgaataggcg gctacgtcgt gagcgcccat 120
caactctcgc gcggagtgca tcgccagctg ggcggcgccg acgtcgaccg tggggattcc 180
ggtgcgcgcc gcggccaacg gcccgatcgt cgacccgcac ggcagatcgg cgcgatgttc 240
gtaacgctgc ataggcactc ccgcgcgctg gcaggccagt gcgaacgccg ccgcggtgcg 300
tccg 304

<210> SEQ ID NO 727
<211> LENGTH: 318
<212> TYPE: PRT
<213> ORGANISM: Mycobacterium sp.

-continued

<400> SEQUENCE: 727

Pro Thr Gln Thr Leu Thr Gly Arg Pro Leu Ile Gly Asn Gly Thr Pro
1 5 10 15

Gly Ala Val Gly Ser Gly Ala Thr Gly Ala Pro Gly Gly Trp Leu Leu
20 25 30

Gly Asp Gly Gly Ala Gly Gly Ser Gly Ala Ala Gly Ser Gly Ala Pro
35 40 45

Gly Gly Ala Gly Gly Ala Ala Gly Leu Trp Gly Thr Gly Gly Ala Gly
50 55 60

Gly Ala Gly Gly Ser Ser Ala Gly Gly Gly Gly Ala Gly Gly Ala Gly
65 70 75 80

Gly Ala Gly Gly Trp Leu Leu Gly Asp Gly Gly Ala Gly Gly Ile Gly
85 90 95

Gly Ala Ser Thr Val Leu Gly Gly Thr Gly Gly Gly Gly Gly Val Gly
100 105 110

Gly Leu Trp Gly Ala Gly Gly Ala Gly Gly Ala Gly Gly Thr Gly Leu
115 120 125

Val Gly Gly Asp Gly Gly Ala Gly Gly Ala Gly Gly Thr Gly Gly Leu
130 135 140

Leu Ala Gly Leu Ile Gly Ala Gly Gly Gly His Gly Gly Thr Gly Gly
145 150 155 160

Leu Ser Thr Asn Gly Asp Gly Gly Val Gly Gly Ala Gly Gly Asn Ala
165 170 175

Gly Met Leu Ala Gly Pro Gly Gly Ala Gly Gly Ala Gly Gly Asp Gly
180 185 190

Glu Asn Leu Asp Thr Gly Gly Asp Gly Gly Ala Gly Gly Ser Ala Gly
195 200 205

Leu Leu Phe Gly Ser Gly Gly Ala Gly Gly Ala Gly Gly Phe Gly Phe
210 215 220

Leu Gly Gly Asp Gly Gly Ala Gly Gly Asn Ala Gly Leu Leu Leu Ser
225 230 235 240

Ser Gly Gly Ala Gly Gly Phe Gly Gly Phe Gly Thr Ala Gly Gly Val
245 250 255

Gly Gly Ala Gly Gly Asn Ala Gly Trp Leu Gly Phe Gly Gly Ala Gly
260 265 270

Gly Val Gly Gly Ser Ala Gly Leu Ile Gly Thr Gly Gly Asn Gly Gly
275 280 285

Asn Gly Gly Thr Gly Ala Asn Ala Gly Ser Pro Gly Thr Gly Gly Ala
290 295 300

Gly Gly Leu Leu Leu Gly Gln Asn Gly Leu Asn Gly Leu Pro
305 310 315

<210> SEQ ID NO 728
<211> LENGTH: 334
<212> TYPE: PRT
<213> ORGANISM: Mycobacterium sp.

<400> SEQUENCE: 728

Pro Thr Gln Thr Leu Thr Gly Arg Pro Leu Ile Gly Asn Gly Thr Pro
1 5 10 15

Gly Ala Val Gly Ser Gly Ala Thr Gly Ala Pro Gly Gly Trp Leu Leu
20 25 30

Gly Asp Gly Gly Ala Gly Gly Ser Gly Ala Ala Gly Ser Gly Ala Pro
35 40 45

-continued

```
Gly Gly Ala Gly Gly Ala Ala Gly Leu Trp Gly Thr Gly Gly Ala Gly
     50                  55                  60

Gly Ile Gly Gly Ala Ser Thr Val Leu Gly Gly Thr Gly Gly Gly Gly
 65                  70                  75                  80

Gly Val Gly Gly Leu Trp Gly Ala Gly Gly Ala Gly Gly Ala Gly Gly
                 85                  90                  95

Thr Gly Leu Val Gly Gly Asp Gly Gly Ala Gly Gly Ala Gly Gly Thr
            100                 105                 110

Gly Gly Leu Leu Ala Gly Leu Ile Gly Ala Gly Gly Gly His Gly Gly
        115                 120                 125

Thr Gly Gly Leu Ser Thr Asn Gly Asp Gly Gly Val Gly Gly Ala Gly
    130                 135                 140

Gly Asn Ala Gly Met Leu Ala Gly Pro Gly Gly Ala Gly Gly Ala Gly
145                 150                 155                 160

Gly Asp Gly Glu Asn Leu Asp Thr Gly Gly Asp Gly Gly Ala Gly Gly
                165                 170                 175

Ser Ala Gly Leu Leu Phe Gly Ser Gly Gly Ala Gly Gly Ala Gly Gly
            180                 185                 190

Phe Gly Phe Leu Gly Gly Asp Gly Gly Ala Gly Gly Asn Ala Gly Leu
        195                 200                 205

Leu Leu Ser Ser Gly Gly Ala Gly Gly Phe Gly Gly Phe Gly Thr Ala
    210                 215                 220

Gly Gly Val Gly Gly Ala Gly Gly Asn Ala Gly Trp Leu Gly Phe Gly
225                 230                 235                 240

Ala Gly Gly Ile Gly Gly Ile Gly Gly Asn Ala Asn Gly Gly Ala Gly
                245                 250                 255

Gly Asn Gly Gly Thr Gly Gly Gln Leu Trp Gly Ser Gly Gly Ala Gly
            260                 265                 270

Val Glu Gly Gly Ala Ala Leu Ser Val Gly Asp Thr Gly Gly Ala Gly
        275                 280                 285

Gly Val Gly Gly Ser Ala Gly Leu Ile Gly Thr Gly Gly Asn Gly Gly
    290                 295                 300

Asn Gly Gly Thr Gly Ala Asn Ala Gly Ser Pro Gly Thr Gly Gly Ala
305                 310                 315                 320

Gly Gly Leu Leu Leu Gly Gln Asn Gly Leu Asn Gly Leu Pro
                325                 330
```

<210> SEQ ID NO 729
<211> LENGTH: 650
<212> TYPE: DNA
<213> ORGANISM: Mycobacterium sp.

<400> SEQUENCE: 729

```
gcggccgcaa ggggttcgcg tcagcgggtg ttggcgggtg tcggggctgg cttaactatg     60

cggcatcaga gcagattgta ctgagagtgc accatatgcg gtgtgaaata ccgcacagat    120

gcgtaaggag aaaataccgc atcaggcgcc attcgccatt caggctgcgc aactgttggg    180

aagggcgatc ggtgcgggcc tcttcgctat tacgccagct ggcgaaaggg ggatgtgctg    240

caaggcgatt aagttgggta acgccagggt tttcccagtc acgacgttgt aaaacgacgg    300

ccagtgaatt gtaatacgac tcactatagg gcgaattcga gctcggtacc cggggatcct    360

ctagagtcga cctgcaggca tgcaagcttg agtattctat agtgtcacct aaatagcttg    420

gcgtaatcat ggtcatagct gtttcctgtg tgaaattgtt atccgctcac aattccacac    480

aacatacgag ccggaagcat aaagtgtaaa gcctggggtg cctaatgagt gagctaactc    540
```

-continued

```
acattaattg cgttgcgctc actgcccgct ttccagtcgg gaaacctgtc gtgccagctg    600

cattaatgaa tcggccaacg cgaacccctt gcggccgccc gggccgtcga              650


<210> SEQ ID NO 730
<211> LENGTH: 8
<212> TYPE: PRT
<213> ORGANISM: Mycobacterium sp.
<220> FEATURE:
<221> NAME/KEY: Unsure
<222> LOCATION: (1-8)
<223> OTHER INFORMATION: applicants are uncertain of residues designated
      as "xaa"

<400> SEQUENCE: 730

Asn Xaa Gly Xaa Gly Asn Xaa Gly
  1               5


<210> SEQ ID NO 731
<211> LENGTH: 9
<212> TYPE: PRT
<213> ORGANISM: Mycobacterium sp.
<220> FEATURE:
<221> NAME/KEY: Unsure
<222> LOCATION: (1-9)
<223> OTHER INFORMATION: applicants are unsure of residues designated
      as "xaa"

<400> SEQUENCE: 731

Gly Xaa Xaa Ser Val Pro Xaa Xaa Trp
  1               5


<210> SEQ ID NO 732
<211> LENGTH: 29
<212> TYPE: PRT
<213> ORGANISM: Mycobacterium sp.

<400> SEQUENCE: 732

Gly Gly Ala Gly Gly Ala Gly Gly Ser Ser Ala Gly Gly Gly Gly Ala
  1               5                  10                  15

Gly Gly Ala Gly Gly Ala Gly Gly Trp Leu Leu Gly Asp
             20                  25


<210> SEQ ID NO 733
<211> LENGTH: 45
<212> TYPE: PRT
<213> ORGANISM: Mycobacterium sp.

<400> SEQUENCE: 733

Gly Ala Gly Gly Ile Gly Gly Ile Gly Gly Asn Ala Asn Gly Gly Ala
  1               5                  10                  15

Gly Gly Asn Gly Gly Thr Gly Gly Gln Leu Trp Gly Ser Gly Gly Ala
             20                  25                  30

Gly Val Glu Gly Gly Ala Ala Leu Ser Val Gly Asp Thr
         35                  40                  45


<210> SEQ ID NO 734
<211> LENGTH: 21
<212> TYPE: DNA
<213> ORGANISM: Mycobacterium sp.

<400> SEQUENCE: 734

agttagctca ctcattaggc a                                               21
```

-continued

<210> SEQ ID NO 735
<211> LENGTH: 21
<212> TYPE: DNA
<213> ORGANISM: Mycobacterium sp.

<400> SEQUENCE: 735
ggatgtgctg caaggcgatt a 21

<210> SEQ ID NO 736
<211> LENGTH: 27
<212> TYPE: DNA
<213> ORGANISM: Mycobacterium sp.

<400> SEQUENCE: 736
aaacagctat gaccatgatt acgccaa 27

<210> SEQ ID NO 737
<211> LENGTH: 24
<212> TYPE: DNA
<213> ORGANISM: Mycobacterium sp.

<400> SEQUENCE: 737
tcctctagag tcgacctgca ggca 24

<210> SEQ ID NO 738
<211> LENGTH: 18
<212> TYPE: DNA
<213> ORGANISM: Mycobacterium sp.
<220> FEATURE:
<221> NAME/KEY: variation
<222> LOCATION: (1-18)
<223> OTHER INFORMATION: bases designated as "n" may be A,T,C or G

<400> SEQUENCE: 738
tctagannnn nntccggc 18

<210> SEQ ID NO 739
<211> LENGTH: 18
<212> TYPE: DNA
<213> ORGANISM: Mycobacterium sp.
<220> FEATURE:
<221> NAME/KEY: variation
<222> LOCATION: (1-18)
<223> OTHER INFORMATION: bases designated as "n" may be A, T, C or G

<400> SEQUENCE: 739
tctagannnn nngggccc 18

<210> SEQ ID NO 740
<211> LENGTH: 20
<212> TYPE: DNA
<213> ORGANISM: Mycobacterium sp.
<220> FEATURE:
<221> NAME/KEY: variation
<222> LOCATION: (1-20)
<223> OTHER INFORMATION: bases designated as "n" may be A, T, C, or G

<400> SEQUENCE: 740
cgtttaaann nnnwaggccg 20

<210> SEQ ID NO 741
<211> LENGTH: 21
<212> TYPE: DNA
<213> ORGANISM: Mycobacterium sp.
<220> FEATURE:
<221> NAME/KEY: variation
<222> LOCATION: (1-21)

-continued

```
<223> OTHER INFORMATION: bases designated as "n" may be A, T, C, or G

<400> SEQUENCE: 741

ggtactagtn nnnnwtccgg c                                            21


<210> SEQ ID NO 742
<211> LENGTH: 22
<212> TYPE: DNA
<213> ORGANISM: Mycobacterium sp.

<400> SEQUENCE: 742

acgacctcat attccgaatc cc                                           22


<210> SEQ ID NO 743
<211> LENGTH: 23
<212> TYPE: DNA
<213> ORGANISM: Mycobacterium sp.

<400> SEQUENCE: 743

gcatctgttg agtacgcact tcc                                          23
```

METHOD FOR ISOLATING A POLYNUCLEOTIDE OF INTEREST FROM THE GENOME OF A *MYCOBACTERIUM* USING A BAC-BASED DNA LIBRARY: APPLICATION TO THE DETECTION OF MYCOBACTERIA

This application is a continuation of application Ser. No. 09/670,314, filed Sep. 26, 2000, now U.S. Pat. No. 6,492,506, which is a division of application Ser. No. 09/060,756, filed Apr. 16, 1998 now U.S. Pat. No. 6,183,957 which is incorporated herein by reference.

BACKGROUND OF THE INVENTION

The present invention pertains to a method for isolating a polynucleotide of interest that is present in the genome of a mycobacterium strain and/or is expressed by said mycobacterium strain and that is absent or altered in the genome of a different mycobacterium strain and/or is not expressed in said different mycobacterium strain, said method comprising the use of at least one clone belonging to a genomic DNA library of a given mycobaterium strain, said DNA library being cloned in a bacterial artificial chromosome (BAC). The invention concerns also polynucleotides identified by the above method, as well as detection methods for mycobacteria, particularly *Mycobacterium tuberculosis*, and kits using said polynucleotides as primers or probes. Finally, the invention deals with BAC-based mycobacterium DNA libraries used in the method according to the invention and particularly BAC-based *Mycobacterium tuberculosis* and *Mycobacterium bovis* BCG DNA libraries.

Radical measures are required to prevent the grim predictions of the World Health Organisation for the evolution of the global tuberculosis epidemic in the next century becoming a tragic reality. The powerful combination of genomics and bioinformatics is providing a wealth of information about the etiologic agent, *Mycobacterium tuberculosis*, that will facilitate the conception and development of new therapies. The start point for genome sequencing was the integrated map of the 4.4 Mb circular chromosome of the widely-used, virulent reference strain, *M. tuberculosis* H37Rv and appropriate cosmids were subjected to systematic shotgun sequence analysis at the Sanger Centre.

Cosmid clones (Balasubramanian et al., 1996; Pavelka et al., 1996) have played a crucial role in the *M. tuberculosis* H37Rv genome sequencing project. However, problems such as under-representation of certain regions of the chromosome, unstable inserts and the relatively small insert size complicated the production of a comprehensive set of canonical cosmids representing the entire genome.

SUMMARY OF THE INVENTION

In order to avoid the numerous technical constraints encountered in the state of the art, as described hereabove, when using genomic mycobacterial DNA libraries constructed in cosmid clones, the inventors have attempted to realize genomic mycobacterial DNA libraries in an alternative type of vectors, namely Bacterial Artificial Chromosome (BAC) vectors.

The success of this approach depended on whether the resulting BAC clones could maintain large mycobacterial DNA inserts. There are various reports describing the successful construction of a BAC library for eucaryotic organisms (Cai et al., 1995; Kim et al., 1996; Misumi et al., 1997; Woo et al., 1994; Zimmer et al., 1997) where inserts up to 725 kb (Zimmer et al., 1997) were cloned and stably maintained in the *E. coli* host strain.

Here, it is shown that, surprisingly, the BAC system can also be used for mycobacterial DNA, as 70% of the clones contained inserts in the size of 25 to 104 kb.

This is the first time that bacterial, and specifically mycobacterial, DNA is cloned in such BAC vectors.

In an attempt to obtain complete coverage of the genome with a minimal overlapping set of clones, a Bacterial Artificial Chromosome (BAC) library of *M. tuberculosis* was constructed, using the vector pBeloBAC11 (Kim et al., 1996) which combines a simple phenotypic screen for recombinant clones with the stable propagation of large inserts (Shizuya et al., 1992). The BAC cloning system is based on the *E. coli* F-factor, whose replication is strictly controlled and thus ensures stable maintenance of large constructs (Willets et al., 1987). BACs have been widely used for cloning of DNA from various eucaryotic species (Cai et al., 1995; Kim et al., 1996; Misumi et al., 1997; Woo et al., 1994; Zimmer et al., 1997). In contrast, to our knowledge this report describes the first attempt to use the BAC system for cloning bacterial DNA.

A central advantage of the BAC cloning system over cosmid vectors used in prior art is that the F-plasmid is present in only one or a maximum of two copies per cell, reducing the potential for recombination between DNA fragments and, more importantly, avoiding the lethal overexpression of cloned bacterial genes. However, the presence of the BAC as just a single copy means that plasmid DNA has to be extracted from a large volume of culture to obtain sufficient DNA for sequencing and it is described here in the examples a simplified protocol to achieve this.

Further, the stability and fidelity of maintenance of the clones in the BAC library represent ideal characteristics for the identification of genomic differences possibly responsible for phenotypic variations in different mycobacterial species.

As it will be shown herein, BACs can be allied with conventional hybridization techniques for refined analyses of genomes and transcriptional activity from different mycobacterial species.

Having established a reliable procedure to screen for genomic polymorphisms, it is now possible to conduct these comparisons on a more systematic basis than in prior art using representative BACs throughout the chromosome and genomic DNA from a variety of mycobacterial species.

As another approach to display genomic polymorphisms, the inventors have also started to use selected H37Rv BACs for "molecular combing" experiments in combination with fluorescent in situ hybridization (Bensimon et al., 1994; Michalet et al., 1997). With such techniques the one skilled in the art is enabled to explore the genome of mycobacteria in general and of *M. tuberculosis* in particular for further polymorphic regions.

The availability of BAC-based genomic mycobacterial DNA libraries constructed by the inventors have allowed them to design methods and means both useful to identify genomic regions of interest of pathogenic mycobacteria, such as *Mycobacterium tuberculosis*, that have no counterpart in the corresponding non-pathogenic strains, such as *Mycobacterium bovis* BCG, and useful to detect the presence of polynucleotides belonging to a specific mycobacterium strain in a biological sample.

By a biological sample according to the present invention, it is notably intended a biological fluid, such as plasma, blood, urine or saliva, or a tissue, such as a biopsy.

Thus, a first object of the invention consists of a method for isolating a polynucleotide of interest that is present in the genome of a mycobacterium strain and/or is expressed by said mycobacterium strain and that is absent or altered in the genome of a different mycobacterium strain and/or is not expressed in said different mycobacterium strain, said method comprising the use of at least one clone belonging to a genomic DNA library of a given mycobaterium strain, said DNA library being cloned in a bacterial artificial chromosome (BAC).

The invention is also directed to a polynucleotide of interest that has been isolated according to the above method and in partoular a polynucleotide containing one or several Open Reading Frames (ORFs), for example ORFs encoding either a polypeptide involved in the pathogenicity of a mycobacterium strain or ORFs encoding Polymorphic Glycine Rich Sequences (PGRS).

Such polynucleotides of interest may serve as probes or primers in order to detect the presence of a specific myobacterium strain in a biological sample or to detect the expression of specific genes in a particular mycobacterial strain of interest.

The BAC-based genomic mycobacterial DNA libraries generated by the present inventors are also part of the invention, as well as each of the recombinant BAC clones and the DNA insert contained in each of said recombinant BAC clones.

The invention also pertains to methods and kits for detecting a specific mycobacterium in a biological sample using either at least one recombinant BAC clone or at least one polynucleotide according to the invention, as well as to methods and kits to detect the expression of one or several specific genes of a given mycobacterial strain present in a biological sample.

BRIEF DESCRIPTION OF THE FIGURES

In order to better understand the present invention, reference will be made to the appended figures which depicted specific embodiments to which the present invention is in no case limited in scope with.

FIG. 6: Variation in the C-terminal part of a PE-PGRS open reading frame in *M. tuberculosis* strain H37Rv relative to *M. bovis* BCG strain Pasteur. The numbers on the right side of the Figure denote the position of the end nucleotides, taking as the reference the *M. tuberculosis* genome.

FIG. 7: Polynucleotide sequence next to the HindIII cloning site in the BAC vector pBeloBAC11 (Kim et al., 1996) used to clone the inserts of the BAC-based myobacterial genomic DNA library according to the invention. Notl: location of the Notl restriction sites. Primer T7-BAC1: nucleotide region recognized by the T7-BAC1 primer shown in Table 1. T7 promoter: location of the T7 promoter region on the pBeloBac11 vector. Primer T7-Belo2: nucleotide region recognized by the T7; -Belo2 pimer shown in Table 1. Hind III: the HindIII cloning site used to clone the genomic inserts in the pBeloBAC11 vector. SP6-Mid primer: nucleotide region recognized by the SP6 Mid primer shown in Table 1. SP6-BAC1 primer: nucleotide region recognized by the SP6 BAC1 primer shown in Table 1. SP6 promoter: location of the SP6 promoter region on the pBeloBac11 vector.

DETAILED DESCRIPTION OF THE PREFERRED EMBODIMENTS

Figure 1A:
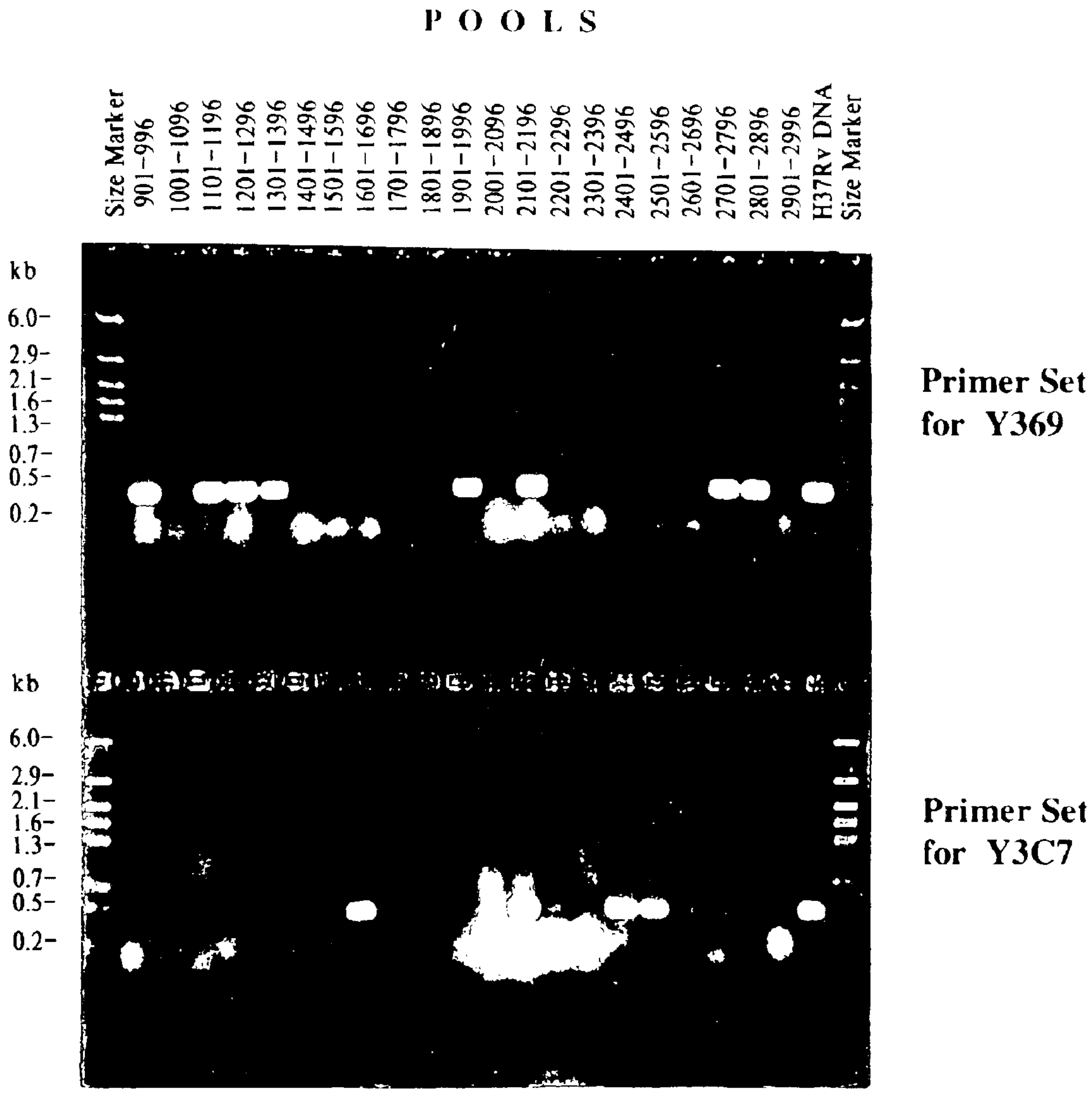
FIGS. 1A and 1B: PCR-screening for unique BAC clones with specific primers for 2 selected genomic regions of the H37Rv chromosome, using 21 pools representating 2016 BACs (Panel A) and sets of 20 subpools from selected positive pools (Panel B).

As already mentioned hereinbefore, the present invention is directed to a method for isolating a polynucleotide of interest that is present in the genome of a mycobacterium strain and/or is expressed by said mycobacterium strain and that is absent or altered in the genome of a different mycobacterium strain and/or is not expressed in said different mycobacterium strain, said method comprising the use of at least one clone belonging to a genomic DNA library of a given mycobaterium strain, said DNA library being cloned in a bacterial artificial chromosome (BAC).

For this purpose, the inventors have constructed several BAC-based mycobacterial genomic DNA libraries that may be used in order to perform the above described method.

Because it is the first time that mycobacterial genomic DNA has been successfully cloned in BAC type vectors, and because these DNA libraries are then novel and nonobvious, an object of the present invention consists in a myobacterial genomic DNA library cloned in such a BAC type vector.

As an illustrative example, a BAC-based DNA library of *Mycobacterium tuberculosis* has been realized. Forty-seven cosmids chosen from the integrated map of the 4.4 Mb circular chromosome (Philipp et al., 1996a) were shotgun-sequenced during the initial phase of the H37Rv genome sequence project. The sequences of these clones were used as landmarks in the construction of a minimally overlapping BAC map. Comparison of the sequence data from the termini of 420 BAC clones allowed us to establish a minimal overlapping BAC map and to fill in the existing gaps between the sequence of cosmids. As well as using the BAC library for genomic mapping and sequencing, we also tested the system in comparative genomic experiments in order to uncover differences between two closely related mycobacterial species. As shown in a previous study (Philipp et al., 1996b), *M. tuberculosis, M. bovis and M. bovis* BCG, specifically BCG Pasteur strain, exhibit a high level of global genomic conservation, but certain polymorphic regions were also detected. Therefore, it was of great interest to find a reliable, easy and rapid way to exactly localize polymorphic regions in mycobacterial genomes using selected BAC clones. This approach was validated by determining the exact size and location of the polymorphisms in the genomic region of DraI fragment Z4 (Philipp et al., 1996b), taking advantage of the availability of an appropriate BAC clone covering the polymorphic region and the H37Rv genome sequence data. This region is located approximately 1.7 Mb from the origin of replication.

The Bacterial Artificial Chromosome (BAC) cloning system is capable of stably propagating large, complex DNA inserts in *Escherichia coli.* As part of the *Mycobacterium tuberculosis* H37Rv genome sequencing project, a BAC library was constructed in the pBeloBAC11 vector and used for genome mapping, confirmation of sequence assembly, and sequencing. The library contains about 5000 BAC clones, with inserts ranging in size from 25 to 104 kb, representing theoretically a 70 fold coverage of the *M. tuberculosis* genome (4.4 Mb). A total of 840 sequences from the T7 and SP6 termini of 420 BACs were determined and compared to those of a partial genomic database. These sequences showed excellent correlation between the estimated sizes and positions of the BAC clones and the sizes and positions of previously sequenced cosmids and the resulting contigs. Many BAC clones represent linking clones between sequenced cosmids, allowing full coverage of the H37Rv chromosome, and they are now being shotgun-sequenced in the framework of the H37Rv sequencing project. Also, no chimeric, deleted or rearranged BAC clones were detected, which was of major importance for the correct mapping and assembly of the H37Rv sequence. The minimal overlapping set contains 68 unique BAC clones and spans the whole H37Rv chromosome with the exception of a single gap of ~150 kb. As a post-genomic application, the canonical BAC set was used in a comparative study to reveal chromosomal polymorphisms between *M. tuberculosis, M. bovis and M. bovis* BCG Pasteur, and a novel 12.7 kb segment present in *M. tuberculosis* but absent from *M. bovis* and *M. bovis* BCG was characterized. This region contains a set of genes whose products show low similarity to proteins involved in polysaccharide biosynthesis. The H37Rv BAC library therefore provides the one skilled in the art with a powerful tool both for the generation and confirmation of sequence data as well as for comparative genomics and a plurality of post-genomic applications.

The above described BAC-based *Mycobacterium tuberculosis* genomic DNA library is part of the present invention and has been deposited in the Collection Nationale de Cultures de Microorganismes (CNCM) on Nov. 19, 1997 under the accession number I-1945.

Another BAC-based DNA library has been constructed with the genomic DNA of *Mycobacterium bovis* BCG, Pasteur strain, and said DNA library has been deposited in the Collection Nationale de Cultures de Microorganismes (CNCM) on Jun. 30, 1998 under the accession number I-2049.

Thus, as a specific embodiment of the above described method for isolating a polynucleotide of interest said method makes use of at least one BAC-based DNA library that has beeen constructed from the genomic DNA of *Mycobacterium tuberculosis*, more specifically of the H37Rv strain and particularly of the DNA library deposited in the accession number I-1945.

In another specific embodiment of the above described method for isolating a polynucleotide of interest said method makes use of at least one BAC-based DNA library has beeen constructed from the genomic DNA of *Mycobacterium bovis* BCG, more specifically of the Pasteur strain and particularly of the DNA library deposited in the accession number I-2049.

In more details, the method according to the invention for isolating a polynucleotide of interest may comprise the following steps:

a) Isolating at least one polynucleotide contained in a clone of a BAC-based DNA library of mycobacterial origin;

b) Isolating:

at least one genomic or cDNA polynucleotide from a mycobacterium, said mycobacterium belonging to a strain different from the strain used to construct the BAC-based DNA library of step a); or alternatively at least one polynucleotide contained in a clone of a BAC-based DNA library prepared from the genome of a mycobacterium that is different from the mycobacterium used to construct the BAC-based DNA library of step a);

c) Hybridizing the at least one polynucleotide of step a) to the at least one polynucleotide of step b);

d) Selecting the at least one polynucleotide of step a) that has not formed a hybrid complex with the at least one polynucleotide of step b);

e) Characterizing the selected polynucleotide.

Following the above procedure, the at least one polynucleotide of step a) may be prepared as follows:

1) Digesting at least one recombinant BAC clone by an appropriate resctriction endonuclease in order to isolate the polynucleotide insert of interest from the vector genetic material;

2) Optionally amplifying the resulting polynucleotide insert;

3) Optionally digesting the polynucleotide insert of step 1) or step 2) with at least one restriction endonuclease.

The above method of the invention allows the one skilled in the art to perform comparative genomics between different strains or species of mycobacteria cells, for example between pathogenic strains or species and their non pathogenic strains or species counterparts, as it is the illustrative case for the genomic comparison between *Mycobacterium tuberculosis* and *Mycobacterium bovis* BCG that is described herein in the examples.

Restriction digests of a given clone of a BAC library according to the invention may be blotted to membranes, and then probed with radiolabeled DNA form another strain or another species of mycobacteria, allowing the one skilled in the art to identify, characterize and isolate a polynucleotide of interest that may be involved in important metabolical and/or physiological pathways of the mycobacterium under testing, such as a polynucleotide functionally involved in the pathogenicity of said given mycobacteria for its host organism.

More specifically, the inventors have shown in Example 6 that when restriction digests of a given clone of the BAC library identified by the CNCM accession number I-1945 are blotted to membranes and then probed with radiolabeled total genomic DNA from, for example, *Mycobacterium bovis* BCG Pasteur, it is observed that restriction fragments that fail to hybridize with the *M. bovis* BCG Pasteur DNA are absent from its genome, hence identifying polymorphic regions between *M. bovis* BCG Pasteur and *M. tuberculosis* H37Rv.

Thus, a further object of the present invention consists in a polynucleotide of interest that has been isolated according to the method described herein before.

In Example 6, a polynucleotide of approximately 12.7 kilobases has been isolated that is present in the genome of *M. tuberculosis* but is absent of the genome of *M. bovis* BCG. This polynucleotide of interest contains 11 ORFs that may be involved in polysaccharide biosynthesis. In particular, two of said ORFs are of particular interest, namely ORF6 (MTCY277.33; Rv1511) that encodes a protein that shares significant homology with bacterial GDP-D-mannose dehydratases, whereas the protein encoded by ORF7 (MTCY277.34; Rv1512) shares significant homology with a nucleotide sugar epimerase. As polysaccharide is a major constituent of the mycobacterial cell wall, these deleted genes may cause the cell wall of *M. bovis* BCG to differ from that of *M. tuberculosis*, a fact that may have important consequences for both the immune response to *M. bovis* BCG and virulence. Detection of such a polysaccharide is of diagnostic interest and possibly useful in the design of tuberculosis vaccines.

Consequently, the polynucleotide of interest obtained following the method according to the invention may contain at least one ORF, said ORF preferably encoding all or part of a polypeptide involved in an important metabolical and/or physiological pathway of the mycobacteria under testing, and more specifically all or part of a polypeptide that is involved in the pathogenicity of the mycobacteria under testing, such as for example *Mycobacterium tuberculosis*, and more generally mycobacteria belonging to the *Mycobacterium tuberculosis* complex.

The *Mycobacterium tuberculosis* complex has its usual meaning, i.e. the complex of mycobacteria causing tuberculosis which are *Mycobacterium tuberculosis, Mycobacterium bovis, Mycobacterium africanum, Mycobacterium microti* and the vaccine strain *Mycobacterium bovis* BCG.

An illustrative polynucleotide of interest according to the present invention comprises all or part of the polynucleotide of approximately 12.7 kilobases that is present in the genome of *M. tuberculosis* but is absent from the genome of *M. bovis* BCG disclosed hereinbefore. This polynucleotide is contained in clone Rv58 of the BAC DNA library I-1945.

Generally, the invention also pertains to a purified polynucleotide comprising the DNA insert contained in a recombinant BAC vector belonging to a BAC-based mycobacterial genomic DNA library, such as for example the I-1945 BAC DNA library.

Advantageously, such a polynucleotide has been identified according to the method of the invention.

Such a polynucleotide of interest may be used as a probe or a primer useful for specifically detecting a given mycobacterium of interest, such as *Mycobacterium tuberculosis* or *Mycobacterium bovis* BCG.

More specifically, the invention then deals with a purified polynucleotide useful as probe or a primer comprising all or part of the nucleotide sequence SEQ ID No1:

```
ACCTGCGCTT GCAGAGATCA AATAGGGCGC ATGGGTCAGC ATAGTACAGG TCGTCGCGCA   60
TCTTTGATGC ATCGGAATAA GATGTCAGGC AATTAAAAGA GAAGCCACGG CGACTCGCGG  120
CATTCAGCAT GTCGAGCGTC GCTTCGATGT GAGCGCACCA TTCCGTGTCC AACGATTTCA  180
GACGAACATT GAATATTCCA CTCGCGACGC TATAGTCCGC CTCCCGATCT ATGCGCGCCG  240
CGCAGATGAA GTCTGCGTTC GCCCGACCTT CGAAACGTAG TGCGGCCGCG CGCACCATTT  300
CGGGGGAGAC GTCGATGCCG GTGTAATCAG TTTTGAAGCC ACGCGCATCT AGGTAGTCCA  360
GTAGAGCCCC ATAGCCACAG CCTAGATCGT TGATCGAAAA TGGGTCCGCC GCATTGACAA  420
TGCGCACCAG CTGGTCAAAG CGCAACGCCT GCCCGGCTTC GCCGTTCCAA TCGACGCCGC  480
GCGGGTGCCG TGTGCTTCGA GTTTCGATGC GTAGTAACGG GCCACGTCAG CGAGCATGGT  540
CGTTGCGTCT TCCGCCATGA AGCTGCCTCA CGATTTGTGT GTGTGGGCGT CGGTGCGTGG  600
GTCCGAGACT ATACCTTCAA CAGTTGCATG CCGAGGCTGC GGCGGGCAAT GACCCAAAAA  660
CCCGCCGGCA CGGTTCGCCG AGCAAGGAAG CGTGGAGACG ATAGATAATT TCACTGGCGA  720
CAGTACCTCA AATAGTCCGG AGCCTCGGCT CCGACGTTAA AGAGCAGATC CAGAATCGAC  780
ACGGCGGGCT CGAACCCTCC CCACAATTGC TTATAATCGC GGTAGCCGTC ATAATCGAAC  840
CAAGTTACCC GGATGCTAAG TTCGTCGAAC ACGCGCTCAT CGACATACGA ACGGGCTGAG  900
GGGCCAGAGA CATATTCGGT CGCTGCGGCC TGTTGGCAGA GGTTGGCCAG TCTCTCGGTC  960
TTGCCGTCGG CTAATTCGTA GTCCCACGAA TTTGCCAGTC GCGTGCTGAT ACCGAGATAA 1020
CTGCAAATCG CATTCAATAG ACGCCTGTTG AGTAAGGAAA GATTCGTGTG CTGTTCTTCG 1080
AGGTAAATCG GCGCGAGCCA GTCAGCGATC TCCGCAAAAT GAGCGGCCGC GCTGTAGTTG 1140
AATTCTAGTG CCCGCCAGTG CGCTTTCGCC CAATCGGTGC CGTCGATCAG CGTCTCACGT 1200
ATCTTTTGAT GGAAACGTCC CTTCACCTGG ACGGGAACAG TTATCCACTG TAACCCCTGG 1260
CTCGTTTTGA TCCGATTTCT GTTTCGCCAA TCACGCTTGG TATATTGCAT GTCATCATAG 1320
ATGATGAATT CATCGACGAA TGCAATCAGG TCAAAATATC CTCGCCAAGG TATGTAATTT 1380
```

-continued

```
GATTGAACAA TCGCGACTTT CTTCAACGCG GTGTCTCCAA TTTAGAATAA CAAATACGTC  1440
GCGCCCGCGA CAGCTCCGCT GGAGCGAGTT CAAGCGATTC TGCGACATAT TCAATATGGT  1500
GCTCGGGAAG GCCAGGATGG GCCGCGACCC GGGGCGTCCG GTGCGCGATG AACGTCGCAT  1560
CGTCTCCTGT GAGATAATTG CATCCGATCA TATAGGGCTG GCTGCGGCTA GGTTGCTGGC  1620
AAAAAGATAT CGCGGCCGAT CCGTTTCTGG TTTTGTCTTG ATGATCAAAT CCGCTTCCGT  1680
TCACGAGATC GATTCCTGGT CTTCCCCCAG CGTCGCGATG TCGATAGGTG TCGCGCTTTG  1740
TTCGTACCCG CACTACGCGG CGGCGAGAAC CTCGCCACCG AATCGGGATT GGGGGGAGGA  1800
TACCACTCGG TCGAGGCCCG TCACCGGCCT TCTAGCGGGT TGACCATCAG TGTTTGCAGG  1860
GCCCTATCCC GGTATGGCGC ACCACGGGAT CGGCAGCGTT CCGGTTGCTG GCGTGGTACC  1920
TCGTTGTGGC GCCGTGGTCC ATGTCGATTG AGTGCGTGGA TCAGTGTAAA CCGTTGCGCG  1980
CCATGTTCTG TAGGCACTGG TTCGGGTTGT GGTTAGGCTG CACGGTTGGC AGGTTACCAA  2040
CCACTGAGCC CCTGGGCGGA TGTGAGCTCG GACTCCGCCT ATGGGGTGTA ATTTTGGCAG  2100
ATTGGGCCGG GTCCCCGTGG TGAGGACTCC TCAACCGGAT TGGGTAAGCA TGAGGTGGTG  2160
CTGGCAGCGG TGTCCTGGTC GCTCTCCCGA GTAGGCCCGT TGTGACTGTC ATGTGGGCGA  2220
GCGGGTTTGC GCGCGTAGGA GACGATGATT ACTACGCACG TGACCAACCA CAAGAACGGT  2280
GCCCATGTCA CCGTGGTGAA AACGAGTGGC GTGGTACCGA CTACCCCTTT GGCTCCCAGC  2340
TGTCCATAGA GCGGCACGTA GAACGGCTCG CCCGGGACCG CGACGTTGAC GATGCTCAGC  2400
GCCACCGCCA AACTCACGCA GACGCCGACC GCGCGGCGGC GGTCTCCATG GGCTGCGAGT  2460
TGGTCGAATA TCCCAGCACC AGGAGGCCCG TTGGGGTCTC GGGCTACCAG TGCAGCGATT  2520
GGCAAGACGA AAACGAGATA GTAGAAGGCG ACGTCCGCGG GGGAGAACGT GGCGGTGGCG  2580
AGCAACACAA TCCCCACCAT GACAGGCGGG ATACGGCGTC CGAGCGCCAG CACGGCGACC  2640
ACGACTATGA CTAGGACAGC AAACCCGATC TGCGTTCGCG GACCAGTGAG GAAACCCTCT  2700
GGGATCTTGC CCGATTGATA GTTCTTGATG CTATCGGGGA TCAGCAGGAG TGCCTTGCCA  2760
AAGGACACGT TCCGCGGGTC TCGAAGCCCT CCGAACGAAC TATTGAACTT GATGATGCCG  2820
TGGATCGACT GTGCGATCGT CCCCGGGAAG CCTCGTGGCC ACAACAGAAA GGCTGCGATA  2880
TTGGACACCA CCACGCCGGT GATCCCGATA CCAGCCCACC GCCATTGTCG AGCCGCCAAC  2940
AACACCACGC CGAGAACGAC GAACTGCGGC TTTACCAGGA CGGCCAAGAT CACCGTGATG  3000
GTGGCGAGGC CCCACCGCTG TCGGGACAAC GCCACGAAGT AAGCCAGCGC GATCGGTACC  3060
ACGAACCCTG TCGAGTTGCC TCGATCGATG ACCCCCCACG CCGGGATGGC CGCGGCGCCC  3120
AGTGTCACGA AGATGACCAC TCGCTCCAGA CCACGTGCCC CCCGGGCCGC CCAGATGGCG  3180
GGAGATATGA CCGCCATCGT TAGGGCGACC AGGTAACAGA TCAGCCCCAA GCGCGGCGCA  3240
CCCAGCCAAT GGCTGGGTAG TCCGAAAATC GCATACGGTA TGCGGGCGGG GGCCCATGCA  3300
GCAACCGCGG TCGGCTGGTA ATCGGCGGGT AGCGAGATCA GGTAGTCCGC GGGATTGGGT  3360
TGAATCCCGG CGGCGGCGAC CATGGCGTAG TCGCTGAAGC AGTGCCGACC GATATTCATG  3420
CCCCAATCAA GCCAACAGTC CCCAGGGACT ACCAAAAGAG TGGAAAAGAC GTCGACCGCG  3480
TACCACTGAC TGAGGGCGTA CGCCGTCGCC GCCGAAATCA CCGACGCCAG CAGGATGGTG  3540
CCGAGCATGA GGGTGCGCTC GGATTGGGAG CCGATCGCCC AGAGCCGCTC CCGGCTCGCG  3600
GTCACGGCAC CGCGCAACAC CTCCGGGGGT CGCTTCATCT GGATTCTCCT CGGTTCTGCG  3660
CGAAACGGTA GCAGAGCGCC ATGGTTGCCA ACGCGGTCGC CGGGCAGTCT AGACCGGATC  3720
TTCCTCGTGG CAACCGACAA CAGGACGTCG TTGCCGAAAG GGCGCTGGGC ACCGACATCT  3780
```

-continued

```
AGGATGAACC CACAGCCACG CCCCGACGTT ATGCCATGGC GAAGAGCGAC CGGCAGGAGC  3840
GGGAACCCAG TGAAGCGAGC GCTCATCACC GGAATCACAG GACCGGACGG CTCGTATCTC  3900
GCTAAGCTCC CGCTGAAGGG ATATGTGGCC GCTGGTAGCC CGGCCGAGGT CTATTTCTGC  3960
TGGGCGACAC GGAATTATCG CGAATTGTAT GGGTTGCTCG CGGTCAACAG CATCTGGTTC  4020
AATCACGAAT CACCGCGTCA CGGCGAGACA TTCATGACTC GTAATCCTGC ACCATATCGC  4080
GGTCGGCAAC GAGGCGCTGA TCGATGCGCA GACGCTGATG CGCCGGCCCA CCCGGATAGG  4140
TATCAGTATT GGGGCGTTCC GGCCAGCGTA CGAGGCGTGA TCGACGCCGC AATGGGTGTT  4200
TGCGTTGAGT AATAATCTGA ACCGTGTGAA CGCATGCATG GATGGATTCC TTGCCCGTAT  4260
CCGCTCACAT GTTGATGCGC ACGCGCCACA ATTGCGTTCA CTGTTCGATA CGATGGCGGC  4320
CGACGCCCGA TTTGCACGCG ACTGGCTGTC CGAGGACCTC GCGCGGTTGC CTGTCGGTGC  4380
AGCATTGCTG GAAGTGGGCC GGGGGGTACT TCTGCTCAGC TGTCAACTGG CGGCGGAGGG  4440
ATTTGACATC ACCGCCATCG AGCCGACGGG TGAAGGTTTT GGCAAGTTCA GACAGCTTGG  4500
CGACATCGTG CTGGAATTGG CTGCAGCACG ACCCACCATC GCGCCATGCA AGGCGGAAGA  4560
CTTTATTTCC GAGAAGCGGT TCGACTTCGC CTTCTCGCTG AATGTGATGG AGCACATCGA  4620
CCTTCCGGAT GAGGCAGTCA GGCGGGTATC GGAAGTGCTG AAACCGGGGG CCAGTTACCA  4680
CTTCCTGTGC CCGAATTACG TATTCCGCTA CGAACCGCAT TTCAATATCC CAACATTCTT  4740
CACCAAAGAG CTGACATGCC GGGTGATGCG ACATCGCATC GAGGGCAATA CGGGCATGGA  4800
TGACCCGAAG GGAGTCTGGC GTTCGCTCAA CTGGATTACG GTTCCCAAGG TGAAACGCTT  4860
TGCGGCGAAG GATGCGACGC TGACCTTGCG CTTCCACCGT GCAATGTTGG TATGGATGCT  4920
GGAACGCGCG CTGACGGATA AGGAATTCGC TGGTCGCCGG GCACAATGGA TGGTCGCTGC  4980
TATTCGCTCG GCGGTGAAAT TGCGTGTGCA TCATCTGGCA GGCTATGTTC CCGCTACGCT  5040
GCAGCCCATC ATGGATGTGC GGCTAACGAA GAGGTAATGA CATGGCGCAA GCGACATCGG  5100
GCATTCGCGC GGCACTTTCG CAACCTGCTG TGTATGAGGC GTATCAGCGG ATTGCGGGCG  5160
CTAAAAGCGG GCTTGCGTGG ATCACAACCG ACCCCATCCA GTCGTTGCCA GGCATGCGTA  5220
CTCTCGACCT CGGTTCCTGG CCAGCGGTGA TACACAGCTC CCCGCCAGTG GACGTGACAT  5280
GTACGAGAGA CGGCATGAGC GCGGAATGTG CGACCGTGCC GTCGAGATGA CCGACGTCGG  5340
CGCTACGGCA GCCCCCACCG GACCTATCGC GCGGGGCAGC GTCGCTCGGG TCGGCGCGGC  5400
GACCGCGTTG GCCGTTGCCT GCGTCTACAC GGTCATCTAT CTGGCGGCCC GCGACCTACC  5460
CCCGGCTTGT TTTTCGATAT TCGCGGTGTT TTCGGGGGCG CTCGGCATTG CCACCGGCGC  5520
CACCCACGGC CTCCTGCAAG AAACGACCCG CGAGGTCCGC TGGGTGCGCT CCACCCAAAT  5580
AGTTGCGGGC CATCGTACCC ATCCGCTGCG GGTGGCCGGG ATGATTGGCA CCGTCGCGGC  5640
CGTCGTAATT GCGGGTAGCT CACCGCTGTG GAGCCGACAG CTATTCGTCG AGGGGCGCTG  5700
GCTGTCCGTG GGGCTACTCA GCGTTGGGGT GGCCGGGTTC TGCGCGCAGC CGACCCTGCT  5760
GGGCGCGCTG GCCGGCGTCG ACCGGTGGAC ACAGTACGGG TCACTGATGG TGACCGACGC  5820
GGTCATCCGG TTGGCGGTCG CCGCGGCAGC GGTTGTGATC GGATGGGGTC TGGCCGGGTA  5880
CTTGTGGGCC GCCACCGCGG GAGCGGTGGC GTGGCTGCTC ATGCTGATGG CCTCGCCCAC  5940
CGCGCGCAGC GCGGCCAGCC TGCTGACGCC CGGGGCAATC GCCACGTTCG TGCGCGGTGC  6000
CGCTCATTCG ATAACCGCCG CGGGTGCCAG CGCGATTCTG GTAATGGGTT TCCCAGTGTT  6060
GCTCAAAGTG ACCTCCGACC AGTTAGGGGC AAAGGGCGGA GCGGTCATCC TGGCTGTGAC  6120
CTTGACGCGT GCGCCGCTTC TGGTCCCACT GAGCGCGATG CAAGGCAACC TGATCGCGCA  6180
```

-continued

TTTCGTCGAC CGGCGCACCC AACGGCTTCG GGCGCTGATC GCACCGGCGC TGGTCGTCGG 6240

CGGCATCGGT GCGGTCGGGA TGTTGGCCGC AGGGCTTACC GGTCCCTGGT TGCTGCGTGT 6300

TGGATTCGGC CCCGACTACC AAACTGGCGG GGCGTTGCTG GCCTGGTTGA CGGCAGCGGC 6360

GGTAGCTATC GCCATGCTGA CGCTGACCGG CGCCGCCGCG GTCGCGGCCG CACTGCACCG 6420

GGCGTATTTG CTGGGCTGGG TCAGCGCGAC GGTGGCGTCG ACGCTGTTGC TGCTGCTGCC 6480

GATGCCGCTG GAGACGCGCA CCGTGATCGC GCTGTTGTTC GGTCCAACGG TGGGAATCGC 6540

CATCCATGTG GCCGCGTTGG CGCGGCGACC CGACTGATTT GTGCCCCAGG TCGACAAATC 6600

ACGCCGTCTC GTCAGTGAGC ACTCCGTCCT CGGGTCCGAT CCTTCCAGGA GACGTTGCAA 6660

CCTGATTTGG CTCAAATTGG TGCGCACCGA GGGTCGGGCA CATCGTAGGG TCGCAACAGT 6720

CACATGTGTC ACTGCACCGG GCGACACCCG ATGTCCCGGC TCTCAGCGAC AGCTGTCTGA 6780

CCTGTGGTTT TGTTCCCAAG TTGGTCGTGG CTGTGCGGGA TTGGAGGTGG CGTGGGGGTC 6840

GCGTCGTATG GATTCTCCTC CTCGGTTCCG CGCGAAACGG CCGCAGGCGC AATGGTCACC 6900

AACTTGGCCG CGGTGGAGTC TAGCCTCACA TTTTCCTGGT CGCCCCCGAC AACCAGGAGG 6960

TCGCTGCAGA ACGGGCGTTC CCTACCCACA TCTACTATGA AGCGACAGCG GCGCCCCGCT 7020

GTGATGGCTG AGCATGACCG ACAGAGGCGG GAAGACAGTG AAGCGAGCGC TCATCACCGG 7080

AATCACCGGC CAGGACGGCT CGTATCTCGC CGAACTGCTG CTGGCCAAGG GGTATGAGGT 7140

TCACGGGCTC ATCCGGCGCG CTTCGACGTT CAACACCTCG CGGATCGATC ACCTCTACGT 7200

CGACCCGCAC CAACCGGGCG CGCGGCTGTT TCTGCACTAT GGTGACCTGA TCGACGGAAC 7260

CCGGTTGGTG ACCCTGCTGA GCACCATCGA ACCCGACGAG GTGTACAACC TGGCGGCGCA 7320

GTCACACGTG CGGGTGAGCT TCGACGAACC CGTGCACACC GGTGACACCA CCGGCATGGG 7380

ATCCATGCGA CTGCTGGAAG CCGTTCGGCT CTCTCGGGTG CACTGCCGCT TCTATCAGGC 7440

GTCCTCGTCG GAGATGTTCG GCGCCTCGCC GCCACCGCAG AACGAGCTGA CGCCGTTCTA 7500

CCCGCGGTCA CCGTATGGCG CCGCCAAGGT CTATTCGTAC TGGGCGACCC GCAATTATCG 7560

CGAAGCGTAC GGATTGTTCG CCGTTAACGG CATCTTGTTC AATCACGAAT CACCGCGGCG 7620

CGGTGAGACG TTCGTGACCC GAAAGATCAC CAGGGCCGTG GCACGCATCA AGGCCGGTAT 7680

CCAGTCCGAG GTCTATATGG GCAATCTGGA TGCGGTCCGC GACTGGGGGT ACGCGCCCGA 7740

ATACGTCGAA GGCATGTGGC GGATGCTGCA GACCGACGAG CCCGACGACT TCGTTTTGGC 7800

GACCGGGCGC GGTTTCACCG TGCGTGAGTT CGCGCGGGCC GCGTTCGAGC ATGCCGGTTT 7860

GGACTGGCAG CAGTACGTCA AATTCGACCA ACGCTATCTG CGGCCCACCG AGGTGGATTC 7920

GCTGATCGGC GACGCGACCA AGGCTGCCGA ATTGCTGGGC TGGAGGGCTT CGGTGCACAC 7980

TGACGAGTTG GCTCGGATCA TGGTCGACGC GGACATGGCG GCGCTGGAGT GCGAAGGCAA 8040

GCCGTGGATC GACAAGCCGA TGATCGCCGG CCGGACATGA ACGCGCACAC CTCGGTCGGC 8100

CCGCTTGACC GCGCGGCCCG GGTCTACATC GCCGGGCATC GCGGCCTGGT CGGGTCCGCG 8160

CTGCTACGCA CGTTTGCGGG CGCGGGGTTC ACCAACCTGC TGGTGCGGTC ACGCGCCGAG 8220

CTTGATCTGA CGGATCGGGC CGCGACGTTC GACTTCGTTC TGGAGTCGAG GCCGCAGGTC 8280

GTCATCGACG CGGCGGCCCG GGTCGGCGGC ATCCTGGCCA ACGACACCTA CCCGGCCGAT 8340

TTCCTGTCGG AAAACCTCCA GATCCAGGTC AACCTGCTGG ATGCCGCCGT GGCGGCGCGG 8400

GTGCCGCGGC TGCTGTTCCT GGGCTCGTCG TGCATCTACC CGAAACTCGC CCCGCAGCCG 8460

ATCCCGGAGA GCGCGCTGCT CACCGGTCCG TTGGAGCCGA CCAACGACGC GTACGCGATC 8520

GCCAAAATCG CCGGCATCCT TGCGGTCCAG GCGGTGCGCC GCCAACATGG CCTGCCGTGG 8580

-continued

ATCTCGGCGA TGCCCACCAA CCTGTACGGG CCAGGCGACA ACTTTTCGCC GTCCGGCTCG 8640

CATCTGCTGC CGGCACTCAT CCGCCGCTAT GACGAGGCCA AAGCCAGTGG CGCGCCCAAC 8700

GTGACCAACT GGGGCACCGG CACGCCCCGA CGGGAGTTGC TGCACGTCGA CGACCTGGCG 8760

AGCGCATGCC TGTATCTGCT GGAACATTTC GACGGGCCGA CCCATGTCAA CGTGGGAACC 8820

GGCATCGACC ACACCATCGG CGAGATCGCC GAGATGGTCG CCTCGGCCGT AGGCTATAGC 8880

GGCGAAACCC GCTGGGATCC AAGCAAACCG GACGGAACAC CACGCAAACT GCTGGATGTT 8940

TCGGTGCTAC GGGAGGCGGG ATGGCGGCCT TCGATCGCGC TGCGCGACGG CATCGAGGCG 9000

ACGGTGGCGT GGTATCGCGA GCACGCGGGA ACGGTTCGGC AATGAGGCTG GCCCGTCGCG 9060

CTCGGAACAT CTTGCGTCGC AACGGCATCG AGGTGTCGCG CTACTTTGCC GAACTGGACT 9120

GGGAACGCAA TTTCTTGCGC CAACTGCAAT CGCATCGGGT CAGTGCCGTG CTCGATGTCG 9180

GGGCCAATTC GGGGCAGTAC GCCAGGGCTC TGCGCGGCGC GGGCTTCGCG GGCCGCATCG 9240

TCTCGTTCGA GCCGCTGCCC GGGCCCTTTG CCGTCTTGCA GCGCAGCGCC TCCACGGACC 9300

CGTTGTGGGA ATGCCGGCGC TGTGCGCTGG GCGATGTCGA TGGAACCATC TCGATCAACG 9360

TCGCCGGCAA CGAGGGCGCC AGCAGTTCCG TCTTGCCGAT GTTGAAACGA CATCAGGACG 9420

CCTTTCCACC AGCCAACTAC GTGGGCGCCC AACGGGTGCC GATACATCGA CTCGATTCCG 9480

TGGCTGCAGA CGTTCTGCGG CCCAACGATA TTGCGTTCTT GAAGATCGAC GTTCAAGGAT 9540

TCGAGAAGCA GGTGATCGCG GGTGGCGATT CAACGGTGCA CGACCGATGC GTCGGCATGC 9600

AGCTCGAGCT GTCTTTCCAG CCGTTGTACG AGCGTGGCAT GCTCATCCGC GAGGCGCTCG 9660

ATCTCGTGGA TTCGTTGGGC TTTACGCTCT CGGGATTGCA ACCCGGTTTC ACCGACCCCC 9720

GCAACGGTCG AATGCTGCAG GCCGATGGCA TCTTCTTCCG GGGCAGCGAT TGACGCGCCG 9780

GCGCGTCAAT CTATTTCGAC ATTCGCGTGA AGACGTTTTC CCAGAATCGA CTGTTGTAGG 9840

CGTAGAACTC CCGGCCGCGT AGGTAGGCAT GTGATATTCG CCTTCCCCCG AACGGGTAGC 9900

GGCGATGAAG GTCGCCCATG CGGCGCAGAT CACCGAAGAC CGCGCTTGGT TCCCGGTGCG 9960

AGCCGACGCC CGTGGTGTCG AACTCGCACA GCACACACCG AATCGTGACC GGCTCGCATA 10020

CCAGCGCGGC CCGCAATATG AATTCCTGGT CGGCGGCGAT CCCGAAATCA AGGTCGTAGC 10080

CACCGATCTT GGCCACCAGC GATGATCCGA AGAACGATGC TTGATGCGGA ACAACCTGCT 10140

TGCCGGCCAG GAATTTGCGC AGGCTGAAAG GTATCGGGCC GCGCACCCGA TCGAGCCCGA 10200

CGAGACGATC CATCCCGAAG CCCCACAATT CGGACACCGG TCCCTTGCCG GATAGCGCCT 10260

CCACGGCCTG GGCTACCACG TCGGGCCCGG AAAAACGATC GGCGGAGTGC AAGAACCACA 10320

ACAGATCACC CGATGCGTGC GCGATGCCCT GGTTCATCGC GTCGTACCGC CCGCCGTCGG 10380

GCTCGGACTG CCAATACGCG AAGCCTGGTT CACACCCGGA CAGGTATGCC ACCACGTCGT 10440

CGCCGCTGCC ACCGTCGATT ACGATGTGCT CGATGCGTCC CCGGTAGCGT TGCGCCCGCA 10500

CACTTTTCAC CGTGCGCTGC AACCCGTCGA GGTCGTTGAA CGAGATCGTT ATCACCGAGA 10560

CGGTCGGAGC AGACGTCACC GAGTTCCCCT AGGTTGCTGG CGGCGATTGT GGATCACCGG 10620

GTCTTCATAC CGATGAAGGT GCCTCGAAGA TTCGCCGCAT AGGAACCTCC GAGCAACGAC 10680

TCGGCGATGC TTGGTTCCAA GTTGTCGTAC TCCTCCATCA CCAGGTCGAC GCCGACGTCT 10740

TTGATGGCCT GAAGTAGGTG CTCGCGTTGA ATCCAGAATG ACCCGCGATT GTCCCAGGAC 10800

GCCCATTTTG CGGTGTCGCG CTGGCCAAAC GAGCGGTCGT CGGAAAACTC GGTAAACCAC 10860

CTACCGGGAA GTCCCTCATG TTCGGTGGGC GCCGAGAGCA TGAACTTCAC CGGCGCCGGC 10920

CGCCGCAGCA ACCGATCGGT CAATTGTCGT GCCGTCGTGG GCAACCGGAG CCATTTATCG 10980

-continued

```
CTCCGGTTGA TGATCGAGAA GTGCGTCTGG AGAATCAGCA GCTTGTTCGT TACCGACGAG  11040

AGGGTTTCCA GGTATTGCTT CGGATTCTCC AGGTGGTAGA AGAGGCCGCA GCAGAAGACG  11100

GTATCGAAGA GCCCGTGGTT GGCGATGTTG AGGGCGTTGT CGTGGACGAA CCGGAGATTC  11160

GGCAGGTTGG TCTTCGATTT GATGTAGTTG CAGGCCGCCA TGTTCAGCTC GCGAACCTCG  11220

ATCCCGAGGA CCTGAAATCC CATGCGCGCG AACCCGACCG CGTACCCGCC TTCCAAGCAG  11280

CCGACATCGG CCACGCGTAG GTGGCTCTTG TCCCCGGGAA AGACGGTTTC CAGAATCCCG  11340

CGCGCCGAGA TGAACCAGGA CGATTCGTCT AACGTGCGCG AGGACTCCGG TATCGTCAAG  11400

GTTCCGTCGT CGAGGCGAAC GTTGTGGGCG GTGAATTGTA CCGCGCCGGC CGAATGTTCC  11460

TCTGCCATCA CTTGGTTAGC CCCTTCGGCT GGTCCTGGGT TTGTCGACAT GGTCAGGCTC  11520

GACAGCCGCG TCGGAGCCGG GAGGGCCACA CATCCACGAG CCCCCTGCCG CTCGGCGTCG  11580

CGGCGGCGAG CTTGCGCCAC TGGGTCTTGA GCCGCCGCGC GGGTGTCGCC CCGCGGTGCT  11640

GCAGCGCCAG CATGGCGATC CGGGGATGGC GCGCGATGGT TTCCTGCAGC GCGGCGCGCC  11700

CCTCCGGGCC TGGAACGTTG GCGATCTGGC GAAGGATCCA GTCGGCCATG ACGGCGATGA  11760

GCTCCTCGCG CGCGGGGTCT CCCGGGAACA GGTCGAGCAT CGCGTCAAAC GTCGCCGCAT  11820

GCCCCGGACC CTGCGTCAAC CAGAACTTTG GCGGGTCCAC CACCTGGTTG TGCCACATGC  11880

CTTGGGCGTG GCGGCGATAC ACCGCCATGG TGTCGCGCAA CATGGCGATG TCGCCATGCA  11940

CCGCGTGCCG GACGTGCAGA TACCAGTCCA GGGGCATGAC GTCGGCAGGA ATGTCGTCGT  12000

AGCGCTCGAG GCGACGGTAC ACGGCCGAGT TGGTCTGGAT GAAGTTCATC AAGATCAACG  12060

CATCCAGGCT CAAGTTGCCC CGCACCCGAA CCGGGGGGAA CTTCGAGTCC TTGGCATGGC  12120

CGTCCTCCCA TATCACTCGG ACGGGATGGA AGCACACCGT CGTCTTGGGG TGCCGGTCGA  12180

GGAATGCGAC CTGTTTGCTT AGCTTCAGCG GATCGATCCA GTAGTCGTCC GCCTCGCACA  12240

ACGCGACGTA CTCGCCGCCA GCGGCCGACA GGGCGCCGGT CAGGTTCCCA TTGAGGCCGA  12300

GGTTTTCGGT CCTGAAGATC GGCCGGAACA CGTGCGGGTA CCGCTCGGCG TACTCACGGA  12360

TGATCGCCGG GGTGGCATCG GTCGACGCGT CGTCGGCGAC GATGATCTCC ACCGGGAAGT  12420

CGGTTTGCTG GTCGAGAAAG CTGTCGAAGG CCTGACGGGC GTAGCCCGCC TGGTTGTGAG  12480

TGGTCGAGAC GATGCTCACC TTGGGGCAAA GCTGGGGACT CACCGTCGGC CCTTTTCCTG  12540

CGCGGCCGCA AGGGTATTGC GATGGCGAAC GTGAATCGCC TGTGCCCGCC GGCCGTCGGC  12600

CGTCGTGGCC TGGTGGTCGG CGGACGTACG GCACACGCTG GCGAAGTATA GCGAGGGTGC  12660

ACTGACGTTG GGCTCGAACC GCGTGGCGCG CGGTGTGGGC GCACCGTCTC GAGTCGGTGC  12720

TGGTTCGCTC GC                                                      12732
```

The location, on the *Mycobacterium tuberculosis* chromosome, of the above polynucleotide of sequence SEQ ID No1 has now been ascribed to begin, at its 5' end at nucleotide at position nt 1696015 and to end, at its 3' end, at nucleotide at position nt 1708746.

For diagnostic purposes, this 12.7 kb deletion should allow a rapid PCR screening of tubercle isolates to identify whether they are bovine or human strains. The primers listed in Table 1 are flanking the deleted region and give a 722 bp amplicon in *M. bovis* or *M. bovis* BCG strains, but a fragment of 13,453 bp in *M. tuberculosis* that is practically impossible to amplify under the same PCR conditions. More importantly, assuming that some of the gene products from this region represent proteins with antigenic properties, it could be possible to develop a test that can reliably distinguish between the immune response induced by vaccination with *M. bovis* BCG vaccine strains and infection with *M. tuberculosis* or that the products (e.g. polysaccharides) are specific immunogens.

The invention also provides for a purified polynucleotide useful as a probe or as a primer, said polynucleotide being chosen in the following group of polynucleotides:

a) a polynucleotide comprising at least 8 consecutive nucleotides of the sequence SEQ ID No1.

b) a polynucleotide whose sequence is fully complementary to the sequence of the polynucleotide defined in a);

c) a polynucleotide that hybridizes under stringent hybridization conditions with the polynucleotide defined in a) or with the polynucleotide defined in b).

For the purpose of defining a polynucleotide or oligonucleotide hybridizing under stringent hybridization conditions, such as above, it is intended a polynucleotide that hybridizes with a reference polynucleotide under the following hybridization conditions:

The hybridization step is realized at 65° C. in the presence of 6×SSC buffer, 5×Denhardt's solution, 0,5% SDS and 100 μg/ml of salmon sperm DNA.

For technical information, 1×SSC corresponds to 0.15 M NaCl and 0.05M sodium citrate; 1×Denhardt's solution corresponds to 0.02% Ficoll, 0.02% polyvinylpyrrolidone and 0.02% bovine serum albumin.

The hybridization step is followed by four washing steps:

two washings during 5 min, preferably at 65° C. in a 2×SSC and 0.1% SDS buffer;

one washing during 30 min, preferably at 65° C. in a 2×SSC and 0.1% SDS buffer, one washing during 10 min, preferably at 65° C. in a 0.1×SSC and 0.1% SDS buffer A first illustrative useful polynucleotide that is included in the polynucleotide of sequence SEQ ID No1 is the following polynucleotide of sequence SEQ ID No2 that corresponds to the Sp6 endsequence of SEQ ID No1:

```
ATACTCAAGC TTGCCGCAAT CGAAACCAAC CTGTTTGTGC CGCAAGAAAT TACGCCGTGG  60

CCCGGCGCCG ATCAAGAAAC GCCCCGGCGC CCGGCGGTGT CGTCGTATGG CATGACGGGC  120

ACCAATGTGC ACGCCATTGT CGAGCAGGCA CCGGTGCCAG CCCCCGAATC CGGTGCACCA  180

GGCGACACCC CGGCCACACC CGGTATCGAC GGCGCGCTGC TGTTCGCGCT GTCGGCCAGC  240

TCGCAGGACG CGCTGCGGCA AACCGCCGCG CGGCTGGCCG ATTGGGTCT             289
```

A second illustrative useful polynucleotide that is included in the polynucleotide of sequence SEQ ID No1 is the following polynucleotide of sequence SEQ ID No3 that corresponds to the T7 endsequence of SEQ ID No1, located on the opposite strand:

```
TTGGCGGGTT GGCCACACAC CCGCCGGTGA CGGCGACGAT GCTGGGCTGG TTGCGGCCCT  60

GCGCCACCGC GGCTTGCATG CTGGTTGGCT GTCTTGGGAC GATCCCGAAA TAGTCCACGC  120

GGATCTGGTG ATTTTGCGGG CTACCCGCGA TTACCCCGCG CGGCTCGACG AGTTTTTGGC  180

CTGGACTACC CGCGTGGCCA ATCTGCTGAA CTCGCGGCCG GTGGTGGCCT GGAATGTCCA  240

CGCCGTTCAC CTACGTGACC TTGATGGGAT CCGGGGGT                         278
```

The polynucleotide of sequence SEQ ID No1 contains 11 ORFs, the respective locations of which, taking into account the orientation of each ORF on the chromosome, on the sequence of the *Mycobacterium tuberculosis* chromosome, is given hereafter:

The location of ORF1 is comprised between nucleotide at position nt 1695944 and nucleotide at position nt1696441.

The location of ORF2 is comprised between nucleotide at position nt 1696728 and nucleotide at position nt1697420.

The location of ORF3 is comprised between nucleotide at position nt1698096 and nucleotide at position nt1699892. ORF3 probably encodes a protein having the characteristics of a membrane protein.

The location of ORF4 is comprised between nucleotide at position nt 1700210 and nucleotide at position nt1701088.

The location of ORF5 is comprised between nucleotide at position nt 1701293 and nucleotide at position nt1702588. ORF5 encodes a protein having the characteristics of a membrane protein.

The location of ORF6 is comprised between nucleotide at position nt 1703072 and nucleotide at position nt1704091. ORF6 encodes a protein having the characteristics of a GDP-D-mannose dehydratase.

The location of ORF7 is comprised between nucleotide at position nt 1704091 and nucleotide at position nt1705056. ORF7 encodes a protein having the characteristics of a nucleotide sugar epimerase involved in colanic acid biosynthesis.

The location of ORF8 is comprised between nucleotide at position nt 1705056 and nucleotide at position nt1705784.

The location of ORF9 is comprised between nucleotide at position nt 1705808 and nucleotide at position nt1706593. ORF9 encodes a protein having the characteristics of colanic acid biosynthesis glycosyl transferase.

The location of ORF10 is comprised between nucleotide at position nt 1706631 and nucleotide at position nt1707524.

The location of ORF11 is comprised between nucleotide at position nt 1707530 ; and nucleotide at position nt1708648. ORF11 % encodes a protein similar to a spore coat polysaccharide biosynthesis.

A polynucleotide of interest obtained by the above-disclosed method according to the invention may also contain at least one ORF that encodes all or part of acidic, glycine-rich proteins, belonging to the PE and PPE families, whose genes are often clustered and based on multiple copies of the polymorphic repetitive sequences. The names PE and PPE derive from the fact that the motifs ProGlu (PE, positions 8, 9) and ProProGlu (PPE, positions 7 to 9) are found near the N-terminus in almost all cases. The PE protein family all have a highly conserved N-terminal domain of ~110 amino acid residues, that is predicted to have a globular structure, followed by a C-terminal segment which varies in size, sequence and repeat copy number. Phylogenetic analysis separated the PE family into several groups, the larger of which is the highly repetitive PGRS class containing 55 members whereas the other groups share very limited sequence similarity in their C-terminal domains. The predicted molecular weights of the PE proteins vary considerably as a few members only contain the ~110 amino acid N-terminal domain while the majority have C-terminal extensions ranging in size from 100 up to >1400 residues. A striking feature of the PGRS proteins is their exceptional glycine content (up to 50%) due to the presence of multiple tandem repetitions of GlyGlyAla or GlyGlyAsn motifs or variations thereof.

Like the PE family, the PPE protein family also has a conserved N-terminal domain that comprises ~180 amino acid residues followed by C-terminal segments that vary considerably in sequence and length. These proteins fall into at least three groups, one of which constitutes the MPTR class characterised by the presence of multiple, tandem copies of the motif AsnXGlyXGlyAsnXGly (SEQ ID NO: 730). The second subgroup contains a characteristic, well-conserved motif around position 350 (GlyXXSerValProXXTrp)(SEQ ID NO: 731), whereas the other group contains proteins that are unrelated except for the presence of the common 180-residue PPE domain. C-terminal extensions may range in size from 00 up to 3500 residues.

One member of the PGRS sub-family, the WHO antigen 22T (Abou-Zeid et al., 1991), a 55 kD protein capable of binding fibronectin, is produced during disease and elicits a variable antibody response suggesting either that individuals mount different immune responses or that this PGRS-protein may not be produced in this form by all strains of *M. tuberculosis*. In other words, at least some PE_PGRS coding sequences encode for proteins that are involved in the recognition of *M. tuberculosis* by the immune system of the infected host. Therefore, differences in the PGRS sequences could represent the principal source of antigenic variation in the otherwise genetically and antigenically homogeneous bacterium.

By performing the method of the invention using the *M. tuberculosis* BAC based DNA library I-1945, the inventors have discovered the occurence of sequence differences between a given PGRS encoding ORF (ORF reference on the genomic sequence of *M. tuberculosis* Rv0746) of *M. tuberculosis* and its counterpart sequence in the genome of *M. bovis* BCG.

More precisely, the inventors have determined that one ORF contained in BAC vector N Rv418 of the *M. tuberculosis* BCG I-1945 DNA library carries both base additions and base deletions when compared with the corresponding ORF in the genome of *M. bovis* BCG that is contained in the BAC vector N X0175 of the *M. bovis* BCG I-2049 DNA library. The variations observed in the base sequences correspond to variations in the C-terminal part of the aminoacid sequence of the PGRS ORF translation product.

As shown in FIG. 6, an amino acid stretch of 29 residues in length is present in this *M. tuberculosis* PGRS (ORf reference Rv0746) and is absent from the ORF counterpart of *M. bovis* BCG, namely the following amino acid sequence: $NH_2$-GGAGGAGGSSAGGGGAGGAGGAG GWLLGD-COOH (SEQ ID NO: 732). Furthermore, FIG. 6 shows also that an amino acid stretch of 45 residues in length is absent from this *M. tuberculosis* PGRS and is present in the ORF counterpart of *M. bovis* BCG, namely following amino acid sequence: $NH_2$-GAGGIGGIGGNANGG AGGNGGTGGQLWGSGGAGVEGGAALSVGDT-COOH (SEQ ID NO: 733).

Similar observations were made with PPE ORF Rv0442, which showed a 5 codon deletion relative to a *M. bovis* amino acid sequence.

Given that the polymorphism associated with the PE-PGRS or PEE ORFS resulted in extensive antigenic variability or reduced antigen presentation, this would be of immense significance for vaccine design, for understanding protective immunity in tuberculosis and, possibly, explain the varied responses seen in different BCG vaccination programmes.

There are several striking parallels between the PGRS proteins and the Epstein-Barr virus-encoded nuclear antigens (EBNA). Both polypeptide families are glycine-rich, contain Gly-Ala repeats that represent more than one third of the molecule, and display variation in the length of the repeat region between different isolates. The Gly-Ala repeat region of EBNA1 has been shown to function as a cis-acting inhibitor of antigen processing and MHC class I-restricted antigen presentation (Levitskaya et al., 1995). The fact that MHC class I knock-out mice are extremely suscepible to *M. tuberculosis* underlines the importance of MHC class I antigen presentation in protection against tuberculosis. Therefore, it is possible that the PE/PPE protein family also play some role in inhibiting antigen presentation, allowing the bacillus to hide from the host's immune system.

As such the novel and nonobvious PGRS polynucleotide from *M. bovis* which is homolog to the *M. tuberculosis* ORF Rv0746, and which is contained in the BAC clone N X0175 (See Table 4 for SP6 and T7 endsequences of clone no X0175) of the I-2049 *M. bovis* BCG BAC DNA library is part of the present invention, as it represents a starting material in order to define specific probes or primers useful for detection of antigenic variability in mycobacterial strains, possible inhibition of antigen processing as well as to differentiate *M. tuberculosis* from *M. bovis* BCG.

Thus, a further object of the invention consists in a polynucleotide comprising the following sequence SEQ ID No4:

```
CCGACCCAGA CACTGACCGG GCGACCGCTG ATCGGCAACG GCACCCCCGG GGCGGTCGGC  60
AGCGGGGCCA CCGGGGCCCC CGGTGGGTGG CTGCTCGGCG ACGGCGGGGC CGGCGGGTCC  120
GGCGCGGCGG GCTCGGGCGC GCCCGGCGGG GCGGGCGGGG CTGCCGGGCT GTGGGGTACC  180
GGCGGGGCCG GCGGGATCGG CGGAGCCAGC ACCGTACTCG GCGGCAGCGG CGGGGGAGGC  240
GGGGTCGGTG GGCTGTGGGG CGCCGGTGGG GCCGGCGGGG CCGGTGGAAC CGGCCTTGTT  300
GGTGGCGACG GCGGGGCCGG TGGGGCCGGC GGGACCGGCG GACTGCTGGC CGGGCTGATC  360
GGTGCCGGCG GAGGTCACGG CGGGACCGGC GGGCTCAGCA CTAATGGCGA CGGCGGGGTT  420
GGCGGGGCCG GCGGGAATGC CGGAATGCTC GCCGGGCCGG GCGGCGCCGG CGGAGCCGGC  480
```

-continued

```
GGTGACGGCG AAAACCTGGA CACCGGTGGG GACGGCGGGG CCGGCGGTAG CGCAGGGCTG 540

CTGTTCGGCA GCGGCGGCGC CGGCGGCGCC GGCGGATTTG GTTTCCTCGG TGGGGACGGC 600

GGGGCCGGTG GCAACGCCGG GCTGCTGTTG TCCAGCGGCG GGCCCGGCGG GTTCGGCGGG 660

TTCGGCACCG CCGGTGGGGT CGGTGGGGCC GGCGGCAATG CCGGCTGGCT GGGCTTCGGC 720

GGGGCCGGGG GCATCGGCGG AATCGGCGGT AACGCTAACG GGGGCGCCGG TGGGAACGGC 780

GGCACCGGCG GTCAGTTATG GGGTAGCGGC GGCGCCGGCG TCGAAGGCGG CGCAGCCTTA 840

AGCGTCGGCG ACACCGGCGG GGCCGGTGGC GTCGGCGGCA CCGCCGGGCT GATCGGCACC 900

GGCGGCAACG GCGGCAACGG CGGCACCGGC GCCAACGCCG GCAGCCCCGG AACCGGCGGC 960

GCCGGCGGGT TGCTGCTGGG CCAAAACGGG CTCAACGGGT TGCCGTAGCC GGGCGGCACG 1020

GCATGGCTTC CGGGCGTCAA CCACTCGCCG GTGATGCAGA TCGGCTGCGG AGCGGGCCGC 1080

CAAAATGGGG GCCGCCGCGC CAGGTATCTC GGCGAAGATC CCCGGCGCTC GAGCGCTTTG 1140

TCAGAGGCCC GTCGCGGGTC GTCGTGACGA CGGCTATCCG GGCGGTGCGG GTTTCGCGGC 1200

GCGCCCTGTG CCCGGCACCG CCGCCCGTTT GTCGGCAACG CCGCCGCGAC CCGTGAGCCG 1260

TCCAGCAGCT GGCGCCTGCG                                            1280
```

Polynucleotides of interest have been defined by the inventors as useful detection tools in order to differentiate *M. tuberculosis* from *M. bovis* BCG. Such polynucleotides are contained in the 45 aminoacid length coding sequence that is present in *M. bovis* BCG but absent from *M. tuberculosis*. This polynucleotide has a sequence beginning (5' end) at the nucleotide at position nt 729 of the sequence SEQ ID No4 and ending (3' end) at the nucleotide in position nt 863 of the sequence SEQ ID No4.

Thus, part of the present invention is also a polynucleotide which is chosen among the following group of polynucleotides:

a) A polynucleotide comprising at least 8 consecutive nucleotides the following nucleotide sequence SEQ ID No5:

```
GGGCATCGGC GGAATCGGCG GTAACGCTAA CGGGGGCGCC GGTGGGAACG GCGGCACCGG 60

CGGTCAGTTA TGGGGTAGCG GCGGCGCCGG CGTCGAAGGC GGCGCAGCCT TAAGCGTCGG 120

CGACACC                                                          127
```

b) A polynucleotide which sequence is fully complementary to the sequence of the polynucleotide defined in a);

c) A polynucleotide that hybridizes under stringent hybridization conditions with the polynucleotide defined in a) or with the polynucleotide defined in b).

The stringent hybridization conditions for the purpose of defining the above disclosed polynucleotide are defined herein before in the specification.

The invention also provides for a BAC-based *Mycobacterium tuberculosis* strain H37Rv genomic DNA library that has been deposited in the Collection Nationale de Cultures de Microorganismes on Nov. 19, 1997 under the accession number I-1945.

A further object of the invention consists in a recombinant BAC vector which is choosen among the group consisting of the recombinant BAC vectors belonging to the BAC-based DNA library I-1945.

Generally, a recombinant BAC vector of interest may be choosen among the following set or group of BAC vectors contained in the BAC-based DNA library I-1945: Rv101; Rv102; Rv103; Rv104; Rv105; Rv106; Rv107; Rv108; Rv109; Rv10; Rv110; Rv111; Rv112; Rv113; Rv114; Rv115; Rv116; Rv117; Rv118; Rv119; Rv11; Rv120; Rv121; Rv122; Rv123; Rv124; Rv126; Rv127; Rv128; Rv129; Rv130; Rv132; Rv134; Rv135; Rv136; Rv137; Rv138; Rv139; Rv13; Rv140; Rv141; Rv142; Rv143; Rv144; Rv145; Rv146; Rv147; Rv148; Rv149; Rv14; Rv150; Rv151; Rv152; Rv153; Rv154; Rv155; Rv156; Rv157; Rv159; Rv15; Rv160; Rv161; Rv162; Rv163; Rv164; Rv165; Rv166; Rv167; Rv169; Rv16; Rv170; Rv171; Rv172; Rv173; Rv174; Rv175; Rv176; Rv177; Rv178; Rv179; Rv17; Rv180; Rv181; Rv182; Rv183; Rv184; Rv185; Rv186; Rv187; Rv188; Rv18; Rv190; Rv191; Rv192; Rv193; Rv194; Rv195; Rv196; Rv19; Rv1; Rv201; Rv204; Rv205; Rv207; Rv209; Rv20; Rv214; Rv215; Rv217; Rv218; Rv219; Rv21; Rv220; Rv221; Rv222; Rv223; Rv224; Rv225; Rv226; Rv227; Rv228; Rv229; Rv22; Rv230; Rv231; Rv232; Rv233; Rv234; Rv235; Rv237; Rv240; Rv241; Rv243; Rv244; Rv245; Rv246; Rv247; Rv249; Rv24; Rv251; Rv252; Rv253; Rv254; Rv255; Rv257; Rv258; Rv259; Rv25; Rv260; Rv261; Rv262; Rv263; Rv264; Rv265; Rv266; Rv267; Rv268; Rv269; Rv26; Rv270; Rv271; Rv272; Rv273; Rv274; Rv275; Rv276; Rv277; Rv278; Rv279; Rv27; Rv280; Rv281; Rv282; Rv283; Rv284; Rv285; Rv286; Rv287; Rv288; Rv289; Rv28; Rv290; Rv291; Rv292; Rv293; Rv294; Rv295; Rv296; Rv29; Rv2; Rv301; Rv302; Rv303; Rv304; Rv306; Rv307; Rv308; Rv309; Rv30; Rv310; Rv311; Rv312; Rv313; Rv314; Rv315; Rv316; Rv317; Rv318; Rv319; Rv31; Rv32; Rv322; Rv327; Rv328; Rv329; Rv32; Rv330; Rv331; Rv333; Rv334; Rv335; Rv336; Rv337; Rv338; Rv339; Rv33; Rv340; Rv341; Rv343; Rv344; Rv346; Rv347; Rv348; Rv349; Rv34; Rv350; Rv351; Rv352; Rv353; Rv354; Rv355; Rv356;

Rv357; Rv358; Rv359; Rv35; Rv360; Rv361; Rv363; Rv364; Rv365; Rv366; Rv367; Rv368; Rv369; Rv36; Rv370; Rv371; Rv373; Rv374; Rv375; Rv376; Rv377; Rv378; Rv379; Rv37; Rv381; Rv382; Rv383; Rv384; Rv385; Rv386; Rv387; Rv388; Rv389; Rv38; Rv390; Rv391; Rv392; Rv393; Rv396; Rv39; Rv3; Rv40; Rv412; Rv413; Rv414; Rv415; Rv416; Rv417; Rv418; Rv419; Rv41; Rv42; Rv43; Rv44; Rv45; Rv46; Rv47; Rv48; Rv49; Rv4; Rv50; Rv51; Rv52; Rv53; Rv54; Rv55; Rv56; Rv57; Rv58; Rv59; Rv5; Rv60; Rv61; Rv62; Rv63; Rv64; Rv65; Rv66; Rv67; Rv68; Rv69; Rv6; Rv70; Rv71; Rv72; Rv73; Rv74; Rv75; Rv76; Rv77; Rv78; Rv79; Rv7; Rv80; Rv81; Rv82; Rv83; Rv84; Rv85; Rv86; Rv87; Rv88; Rv89; Rv8; Rv90; Rv91; Rv92; Rv94; Rv95; Rv96; Rv9.

The end sequences of the polynucleotide inserts of each of the above clones corresponding respectively to the sequences adjacent to the T7 promoter and to the Sp6 promoter on the BAC vector are shown in Table 3.

It has been shown by the inventors that the minimal overlapping set of BAC vectors of the BAC-based DNA library I-1945 contains 68 unique BAC clones and practically spans almost the whole H37Rv chromosome with the exception of a single gap of approximately 150 kb.

More specifically, a recombinant BAC vector of interest is choosen among the following set or group of BAC vectors from the BAC-based DNA library I-1945, the location of which vector DNA inserts on the chromosome of *M. tuberculosis* is shown in FIG. 3: Rv234; Rv351; Rv166; Rv35; Rv415; Rv404; Rv209; Rv272; Rv30; Rv228; Rv233; Rb38; Rv280; Rv177; Rv48; Rv374; Rv151; Rv238; Rv156; Rv92; Rv3; Rv403; Rv322; Rv243; Rv330; Rv285; Rv233; Rv219; Rv416; Rv67; Rv222; Rv149; Rv279; Rv87; Rv273; Rv266; Rv25; Rv136; Rv414; Rv13; Rv289; Rv60; Rv104; Rv5; Rv165; Rv215; Rv329; Rv240; Rv19; Rv74; Rv411; Rv167; Rv56; Rv80; Rv164; Rv59; Rv313; Rv265; Rv308; Rv220; Rv258; Rv339; Rv121; Rv419; Rv418; Rv45; Rv217; Rv134; Rv17; Rv103; Rv21; Rv22; Rv2; Rv270; Rv267; Rv174; Rv257; Rv44; Rv71; Rv7; Rv27; Rv191; Rv230; Rv128; Rv407; Rv6; Rv39; Rv255; Rv74; Rv355; Rv268; Rv58; Rv173; Rv264; Rv417; Rv401; Rv144; Rv302; Rv81; Rv163; Rv281; Rv221; Rv420; Rv175; Rv86; Rv412; Rv73; Rv269; Rv214; Rv287; Rv42; Rv143.

The polynucleotides disclosed in Table 3 may be used as probes in order to select a given clone of the BAC DNA library I-1945 for further use.

The invention also provides for a BAC-based *Mycobacterium bovis* strain Pasteur genomic DNA library that has been deposited in the Collection Nationale de Cultures de Microorganismes on Jun. 30, 1998 under the accession number I-2049.

A further object of the invention consists in a recombinant BAC vector which is chosen among the group consisting of the recombinant BAC vectors belonging to the BAC-based DNA library I-2049. This DNA library contains approximately 1600 clones. The average insert size is estimated to be ~80 kb.

Generally, a recombinant BAC vector of interest may be chosen among the following set or group of BAC vectors contained in the BAC-based DNA library I-2049: X0001; X0002; X0003; X0004; X0006; X0007; X0008; X0009; X0010; X0012; X0013; X0014; X0015; X0016; X0017; X0018; X0019; X0020; X0021; X0175.

The end sequences of the polynucleotide inserts of each of the above clones corresponding respectively to the sequences adjacent to the T7 promoter and to the Sp6 promoter on the BAC vector are shown in Table 4.

The polynucleotides disclosed in Table 4 may be used as probes in order to select a given clone of the BAC DNA library I-2049 for further use.

Are also part of the invention the polynucleotide inserts that are contained in the above described BAC vectors, that are useful as primers or probes.

These polynucleotides and nucleic acid fragments may be used as primers for use in amplification reactions, or as nucleic probes.

PCR is described in the U.S. Pat. No. 4,683,202. The amplified fragments may be identified by an agarose or a polyacrylamide gel electrophoresis, or by a capillary electrophoresis or alternatively by a chromatography technique (gel filtration, hydrophobic chromatography or ion exchange chromatography). The specificity of the amplification may be ensured by a molecular hybridization using, for example, one of the initial primers as nucleic probes.

Amplified nucleotide fragments are used as probes in hybridization reactions in order to detect the presence of one polynucleotide according to the present invention or in order to detect mutations in the genome of the given mycobacterium of interest, specifically a mycobacterium belonging to the *Mycobacterium tuberculosis* complex and more specifically *Mycobacterium tuberculosis* and *Mycobacterium bovis* BCG.

Are also part of the present invention the amplified nucleic fragments (<<amplicons>>) defined herein above.

These probes and amplicons may be radioactively or non-radioactively labeled, using for example enzymes or fluorescent compounds.

Other techniques related to nucleic acid amplification may also be used and are generally preferred to the PCR technique.

The Strand Displacement Amplification (SDA) technique (Walker et al., 1992) is an isothermal amplification technique based on the ability of a restriction enzyme to cleave one of the strands at his recogntion site (which is under a hemiphosphorothioate form) and on the property of a DNA polymerase to initiate the synthesis of a new strand from the 3'OH end generated by the restriction enzyme and on the property of this DNA polymerase to displace the previously synthesized strand being localized downstream. The SDA method comprises two main steps:

a) The synthesis, in the presence of dCTP-alpha-S, of DNA molecules that are flanked by the restriction sites that may be cleaved by an appropriate enzyme.

b) The exponential amplification of these DNA molecules modified as such, by ezyme cleavage, strand displacement and copying of the displaced strands. The steps of cleavage, strand displacement and copy are repeated a sufficient number of times in order to obtain an accurate sensitivity of the assay.

The SDA technique was initially realized using the restriction endonuclease HincII but is now generally practised with an endonuclease from *Bacillus stearothermophilus* (BSOBI) and a fragment of a DNA polymerase which is devoid of any 5'→3' exonuclease activity isolated from *Bacillus cladotenax* (exo−Bca) [=exo-minus-Bca]. Both enzymes are able to operate at 60° C. and the system is now optimized in order to allow the use of dUTP and the decontamination by UDG. When unsing this technique, as described by Spargo et al. in 1996, the doubling time of the target DNA is of 26 seconds and the amplification rate is of $10^{10}$ after an incubation time of 15 min at 60° C.

The SDA amplification technique is more easy to perform than PCR (a single thermostated waterbath device is necessary) and is faster thant the other amplification methods.

Thus, another object of the present invention consists in using the nucleic acid fragments according to the invention (primers) in a method of DNA or RNA amplification according to the SDA technique. For performing SDA, two pairs of primers are used: a pair of external primers (B1, B2) consisting of a sequence specific for the target polynucleotide of interest and a pair of internal primers (S1, S2) consisting of a fusion oligonucleotide carrying a site that is recognized by a restriction endonuclease, for exemple the enzyme BSOBI.

The operating conditions to perform SDA with such primers are described in Spargo et al, 1996.

The polynucleotides of the invention and their above described fragments, especially the primers according to the invention, are useful as technical means for performing different target nucleic acid amplification methods such as:

TAS (Transcription-based Amplification System), described by Kwoh et al. in 1989;

SR (Self-Sustained Sequence Replication), described by Guatelli et al. in 1990.

NASBA (Nucleic acid Sequence Based Amplification), described by Kievitis et al. in 1991.

TMA (Transcription Mediated Amplification).

The polynucleotides according to the invention are also useful as technical means for performing methods for amplification or modification of a nucleic acid used as a probe, such as:

LCR (Ligase Chain Reaction), described by Landegren et al. in 1988 and improved by Barany et al. in 1991 who employ a thermostable ligase.

RCR (Repair Chain Reaction) described by Segev et al. in 1992.

CPR (Cycling Probe Reaction), described by Duck et al. in 1990.

Q-beta replicase reaction, described by Miele et al. in 1983 and improved by Chu et al. in 1986, Lizardi et al. in 1988 and by Burg et al. and Stone et al. in 1996.

When the target polynucleotide to be detected is a RNA, for example a mRNA, a reverse transcriptase enzyme will be used before the amplification reaction in order to obtain a cDNA from the RNA contained in the biological sample. The generated cDNA is subsequently used as the nucleic acid target for the primers or the probes used in an amplification process or a detection process according to the present invention.

The non-labeled polynucleotides or oligonucleotides of the invention may be directly used as probes. Nevertheless, the polynucleotides or oligonucleotides are generally labeled with a radioactive element ($^{32}P$, $^{35}S$, $^{3}H$, $^{125}T$) or by a non-isotopic molecule (for example, biotin, acetylaminofluorene, digoxigenin, 5-bromodesoxyuridin, fluorescein) in order to generate probes that are useful for numerous applications.

Examples of non-radioactive labeling of nucleic acid fragments are described in the french patent No FR-7810975 or by Urdea et al. or Sanchez-Pescador et al., 1988.

In the latter case, other labeling techniques may be also used such as those described in the french patents FR-2, 422,956 and 2,518,755. The hybridization step may be performed in diffrent ways (Matthews et al., 1988). The more general method consists of immobilizing the nucleic acid that has been extracted from the biological sample onto a substrate (nitrocellulose, nylon, polystyrene) and then to incubate, in defined conditions, the target nucleic acid with the probe. Subsequently to the hybridization step, the excess amount of the specific probe is discarded and the hybrid molecules formed are detected by an appropriate method (radioactivity, fluorescence or enzyme activity measurement).

Advantageously, the probes according to the present invention may have structural characteristics such that they allow the signal amplification, such structural characteristics being, for example, branched DNA probes as those described by Urdea et al. in 1991 or in the European patent No EP-0225,807 (Chiron).

In another advantageous embodiment of the probes according to the present invention, the latters may be used as <<capture probes>>, and are for this purpose immobilized on a substrate in order to capture the target nucleic acid contained in a biological sample. The captured target nucleic acid is subsequently detected with a second probe which recognizes a sequence of the target nucleic acid which is different from the sequence recognized by the capture probe.

The oligonucleotide probes according to the present invention may also be used in a detection device comprising a matrix library of probes immobilized on a substrate, the sequence of each probe of a given length being localized in a shift of one or several bases, one from the other, each probe of the matrix library thus being complementary to a distinct sequence of the target nucleic acid. Optionally, the substrate of the matrix may be a material able to act as an electron donor, the detection of the matrix poisitons in which an hybridization has occurred being subsequently determined by an electronic device. Such matrix libraries of probes and methods of specific detection of a targer nucleic acid is described in the European patent application No EP-0713, 016 (Affymax technologies) and also in the U.S. Pat. No. 5,202,231 (Drmanac).

Since almost the whole length of a mycobacterial chromososme is covered by a BAC-based genomic DNA libraries according to the present invention (i.e. 97% of the *M. tuberculosis* chromosome is covered by the BAC library I-1945), these DNA libraries will play an important role in a plurality of post-genomic applications, such as in mycobacterial gene expression studies where the canonical set of BACs could be used as a matrix for hybridization studies. Probing such matrices with CDNA probes prepared from total mRNA will uncover genetic loci induced or repressed under different physiological conditions (Chuang et al., 1993; Trieselmann et al., 1992). As such, the H37Rv BAC library represents a fundamental resource for present and future genomics investigations.

The BAC vectors or the polynucleotide inserts contained therein may be directly used as probes, for example when immobilized on a substrate such as described herein before.

The BAC vectors or their polynucleotide inserts may be directly asdorbed on a nitrocellulose membrane, at predetermined locations on which one or several polynucleotides to be tested are then put to hybridize therewith.

Preferably, a collection of BAC vectors that spans the whole genome of the mycobacterium under testing will be immobilized, such as, for example, the set of 68 BAC vectors of the I-1945 DNA library that is described elsewhere in the specification and shown in FIG. 3.

The immobilization and hybridization steps may be performed as described in the present Materials and Methods Section.

As another illustrative embodiment of the use of the BAC vectors of the invention as polynucleotide probes, these vectors may be useful to perform a transcriptional activity analysis of mycobacteria growing in different environmental conditions, for example under conditions in which a stress response is expected, as it is the case at an elevated temperature, for example 40° C.

In this specific embodiment of the invention, Genescreen membranes may be used to immobilize the restriction endonuclease digests (HindIII digests for the BAC DNA library I-1945) of the BAC vectors by tranfer from a gel (Trieselmann et al., 1992).

Alternatively, the BAC vectors may be immobilized for dot blot experiments as follows. First, the DNA concentration of each BAC clone is determined by hybridization of blots of clone DNAs and of a BAC vector concentration standard with a BAC vector specific DNA probe. Hybridization is quantified by the Betascope 603 blot analyzer (Betagen Corp.), which colects beta particles directly from the blot with high efficiency. Then, 0.5 μg of each clone DNA is incubated in 0.25 M NaOH and 10 mM EDTA at 65° C. for 60 min to denature the DNA and degrade residual RNA contaminants. By using a manifold filtration system (21 by 21 wells), each clone DNA is blotted onto a GeneScreen Plus nylon membrane in the alkaline solution. After neutralization, the blots are baked at 85° C. for 2 h under vacuum. Positive and negative controls are added when necessary. In order to perform this procedure, it may be referred to the article of Chuang et al. (1993).

For RNA extractions, cells grown in a suitable volume of culture medium may, for example, be immediately mixed with an equal volume of crushed ice at −70° C. and spun at 4° C. in a 50 ml centrifugation tube. The cell pellet is then suspended in 0.6 ml of ice-cold buffer (10 mM KCl, 5 mM MgCl, 10 mM Tris; pH 7.4) and then immediately added to 0.6 ml of hot lysis buffer (0.4 M NaCl, 40 mM EDTA, 1% beta-mercaptoethanol, 1% SDS, 20 mM Tris; pH 7.4) containing 100μl of water saturated phenol. This mixture is incubated in a boiling water bath for 40 s. The debris are removed by centrifugation. The supernatant is extracted with phenol-chloroform five times, ethanol precipitated, and dried. The dried RNA pellet is dissolved in water before use.

Then labeled total cDNA may be prepared by the following method. The reaction mixture contains 15 μg of the previously prepared total RNA, 5 μg of pd($N_6$) (random hexamers from Pharmacia Inc.), 0.5 mM dATP, 0.5 mM dGTP and 0.5 mM DTTP, 5 μM dCTP, 100 μCi of [α-$^{32}$P] dCTP (3,000 Ci/mmol), 50 mM Tris-HCl (pH 8.3), 6 mM $MgCl_2$, 40 mM Kcl, 0.5 U of avian myeloblastosis virus reverse transcriptase (Life Science Inc.) in a total volume of 50 μl. The reaction is allowed to continue overnight at room temperature. EDTA and NaOH are then added to final concentrations of 50 mM and 0.25 M, respectively, and the mixture is incubated at 65° C. for 30 min to degrade the RNA templates. The cDNA is then ready to use after neutralization by adding Hcl and Tris buffer.

The hybridization step may be performed as described by Chuang et al. (1993) and briefly disclosed hereinafter. The DNA dot blot is hybridized to $^{32}$P-labeled total cDNA in a solution containing 0.1% polyvinylpyrrolidone, 0.1% Ficoll, 0.1% sodium Pp, 0.1% bovine serum albumin, 0.5% SDS, 100 mM NaCl, and 0.1 mM sodium citrate, pH 7.2, at 65° C. for 2 days and then washed with a solution containing 0. 1% SDS, 100 mM NaCl, and 10 mM Na-citrate, pH 7.2. The same dot blot is used for hybridization with both control and experimental cDNAs, with an alkaline probe stripping procedure (soaked twice in 0.25 M NaOH-0.75 M NaCl at room temperature, 30 min each, neutralized, and completely dried at 65° C. for at least 30 min) between the two hybridizations. Quantification may be done with the Betascope 603 blot analyzer (Betagen Corp.).

As it flows from the above technical teachings, another object of the invention consists in a method for detecting the presence of mycobateria in a biological sample comprising the steps of:

a) bringing into contact the recombinant BAC vector or a purified polynucleotide according to the invention with a biological sample.

b) detecting the hybrid nucleic acid molecule formed between said purified polynucleotide and the nucleic acid molecules contained within the biological sample.

The invention further deals with a method for detecting the presence of mycobacteria in a biological sample comprising the steps of:

a) Bringing into contact the recombinant BAC vector or a purified polynucleotide according to the invention that has been immobilized onto a substrate with a biological sample.

b) Bringing into contact the hybrid nucleic acid molecule formed between said purified polynucleotide and the nucleic acid contained in the biological sample with a labeled recombinant BAC vector or a polynucleotide according to the invention, provided that said polynucleotide and polynucleotide of step a) have non-overlapping sequences.

Another object of the invention consists in a method for detecting the presence of mycobacteria in a biological sample comprising the steps of:

a) Bringing into contact the nucleic acid molecules contained in the biological sample with a pair of primers according to the invention.

b) Amplifying said nucleic acid molecules;

d) detecting the nucleic acid fragments that have been amplified, for example by gel electrophoresis or with a labeled polynucleotide according to the invention.

In one specific embodiment of the above detection and/or amplification methods, said methods comprise an additional step wherein before step a), the nucleic acid molecules of the biological sample have been made available to a hybridization reaction.

In another specific embodiment of the above detection methods, said methods comprise an additional step, wherein, before the detection step, the nucleic acid molecules that are not hybridized with the immobilized purified polynucleotide are removed.

Also part of the invention is a kit for detecting mycobacteria in a biological sample comprising:

a) A recombinant BAC vector or a purified polynucleotide according to the invention;

b) Reagents necessary to perform a nucleic acid hybridization reaction.

The invention also pertains to a kit for detecting a mycobacteria in a biological sample comprising:

a) A recombinant BAC vector or a purified polynucleotide according to the invention that is immobilized onto a substrate.

b) Reagents necessary to perform a nucleic acid hybridization reaction.

c) A purified polynucleotide according to the invention which is radioactively or non-radioactively labeled, provided that said polynucleotide and the polynucleotide of step a) have non-overlapping sequences.

Moreover, the invention provides for a kit for detecting mycobacteria in a biological sample comprising:

a) A pair of purified primers according to the invention;

b) Reagents necessary to perform a nucleic acid amplification reaction;

c) Optionally, a purified polynucleotide according to the invention useful as a probe.

The invention embraces also a method for detecting the presence of a genomic DNA, a cDNA or a mRNA of mycobacteria in a biological sample, comprising the steps of:

a) Bringing into contact the biological sample with a plurality of BAC vectors according to the invention or purified polynucleotides according to the invention, that are immobilized on a substrate;

b) Detecting the hybrid complexes formed.

The invention also provides a kit for detecting the presence of genomic DNA, cDNA or mRNA of a mycobacterium in a biological sample, comprising:

a) A substrate on which a plurality of BAC vectors according to the invention or purified polynucleotides according to the invention have been immobilized;

b) Optionally, the reagents necessary to perform the hybridization reaction.

Additionally, the recombinant BAC vectors according to the invention and the polynucleotide inserts contained therein may be used for performing detection methods based on <<molecular combing>>. Said methods consist in methods for aligning macromolecules, especially DNA and are applied to processes for detecting, for measuring intramolecular distance, for separating and/or for assaying a macromolecule, especially DNA in a sample.

These <<molecular combing>> methods are simple methods, where the triple line S/A/B (meniscus) resulting form the contact between a solvent A and the surface S and a medium B is caused to move on the said surface S, the said macromolecules (i.e. DNA) having a part, especially an end, anchored on the surface S, the other part, especially the other end, being in solution in the solvent A. These methods are particularly fully described in the PCT Application No. PCT/FR 95/00165 files on Feb. 11, 1994 (Bensimon et al.).

When performing the <<molecular combing>>method with the recombinant BAC vectors according to the inventions or their polynucleotide inserts, the latters may be immobilized (<<anchored>>) on a suitable substrate and aligned as described in the PCT Application no. PCT/FR 95/00165, the whole teachings of this PCT Application being herien incorporated by reference. Then, polynucleotides to be tested, preferably under the form of radioactively or non radioactively labeled polynucleotides, that may consist of fragments of genomic DNA, cDNA etc. are brought into contact with the previously aligned polynucleotides according to the present invention and then their hybridization position on the aligned DNA molecules is determined using any suitable means including a microscope or a suitable camera device.

Thus, the present invention is also directed to a method for the detection of the presence of a polynucleotide of mycobacterial origin in a biological sample and/or for physical mapping of a polynucleotide on a genomic DNA, said method comprising:

a) Aligning at least one polynucleotide contained in a recombinant BAC vector according to the invention on the surface of a substrate;

b) Bringing into contact at least one polynucleotide to be tested with the substrate on which the at least one polynucleotide of step a) has been aligned;

c) detecting the presence and/or the location of the tested polynucleotide on the at least one aligned polynucleotide of step a).

The invention finally provides for a kit for performing the above method, comprising:

a) a substrate whose surface has at least one polynucleotide contained in a recombinant BAC vector according to the invention;

b) optionally, reagents necessary for labeling DNA;

c) optionally, reagents necessary for performing a hybridization reaction.

In conclusion, it may be underlined that the alliance of such BAC-based approaches such as described in the present specification to the advances in comparative genomics by the availability of an increased number of complete genomes, and the rapid increase of well-characterized gene products in the public databases, will allow the one skilled in the art an exhaustive analysis of the mycobacterial genome.

MATERIALS AND METHODS

1. DNA-preparation. Preparation of *M. tuberculosis* H37Rv DNA in agarose plugs was conducted as previously described (Canard et al., 1989; Philipp et al., 1996b). Plugs were stored in 0.2 M EDTA at 4 C and washed 3 times in 0.1% Triton X-100 buffer prior to use.

2. BAC vector preparation. pBeloBACI 1 was kindly provided by Dr. Shizuya, Department of Biology, California Institute of Technology (Pasadena, Calif.). The preparation followed the description of Woo et al., 1994 (Woo et al., 1994).

3. Partial digestion with HindIII. Partial digestion was carried out on plugs, each containing approximately 10 μg of high molecular weight DNA, after three one hour equilibration steps in 50 ml of HindIII 1 X digestion buffer (Boehringer Mannheim, Mannheim, Germany) plus 0. 1% Triton X-100. The buffer was then removed and replaced by 1 ml/plug of ice-cold HindIII enzyme buffer containing 20 units of Hindlll (Boehringer). After two hours incubation on ice, the plugs were transferred to a 37° C. water bath for 30 minutes. Digestions were stopped by adding 500 μl of 50 mM EDTA (pH 8.0).

4. Size selection. The partially digested DNA was subjected to contour-clamped homogenous electric field (CHEF) electrophoresis on a 1% agarose gel using a BioRad DR III apparatus (BioRad, Hercules, Calif.) in 1X TAE buffer at 13° C., with a ramp from 3 to 15 seconds at 6 V/cm for 16 hours. Agarose slices from 25 to 75 kb, 75 to 120 kb and 120 to 180 kb were excised from the gel and stored in TE at 4° C.

5. Ligation and transformation. Agarose-slices containing fractions from 25 to 75 kb, 75 to 120 kb and 120 to 180 kb were melted at 65° C. for 10 minutes and digested with Gelase (Epicentre Technologies, Madison, Wis.), using 1 unit per 100 μl gel-slice. 25–100 ng of the size-selected DNA was then ligated to 10 ng of HindIII digested, dephosphorylated pBeloBAC11 in a 1:10 molar ratio using 10 units of T4 DNA ligase (New England Biolabs, Beverly, Mass.) at 16° C. for 20 hours. Ligation mixtures were heated at 65° C. for 15 minutes, then drop-dialysed against TE using Millipore VS 0.025 mM membranes (Millipore, Bedford, Mass.). Fresh electrocompetent *E. coli* DH10B cells (Sheng et al., 1995) were harvested from 200 ml of a mid-log ($OD_{550}$=0.5) culture grown in SOB medium. Cells were washed three times in ice-cold water, and finally resuspended in ice-cold water to a cell density of $10^{11}$ cells/ml ($OD_{550}$=150). 1 μl of the ligation-mix was used for electroporation of 30 μl of electrocompetent DH10B *E. coli* using a Eurogentec Easyject Plus electroporator (Eurogentec, Seraing, Belgium), with settings of 2.5 kV, 25 μF, and 99 ½, in 2 mm wide electroporation cuvettes. After electroporation, cells were resuspended in 600 μl of SOC medium, allowed to recover for 45 minutes at 37° C. with gentle shaking, and then plated on LB agar containing 12.5 μg/ml chloramphenicol (CM), 50 μg/ml X-gal, and 25 μg/ml IPTG. The plates were incubated overnight and recombinants (white colonies) were picked manually to 96 well plates. Each clone was inoculated 3 times (2×200 μl and 1×100 μl of 2YT/12.5 μg/ml CM per clone) and incubated overnight. One of the microtiter plates, containing 100 μl culture per well, was maintained as a master plate at −80° C. after 100 ml of 80% glycerol were added to each well, while minipreps (Sambrook et al., 1989) were prepared from the remaining two plates to check for the presence of inserts. Clones containing inserts were then designated "Rv" clones, repicked from the master plate to a second set of plates for storage of the library at −80° C.

6. Preparation of DNA for sizing, direct sequencing and comparative genomics. A modified Birnboim and Doly protocol (Birnboim et al., 1979) was used for extraction of plasmid DNA for sequencing purposes. Each Rv clone was inoculated into a 50 ml Falcon polypropylene tube containing 40 ml of 2YT medium with 12.5 μg/ml of CM and grown overnight at 37° C. with shaking. Cells were harvested by centrifugation and stored at −20° C. The frozen pellet was resuspended in 4 ml of Solution A (50 mM glucose, 10 mM EDTA, 25 mM Tris, pH 8.0) and 4 ml of freshly prepared solution B (0.2 M NaOH, 0.2% SDS) was then added. The solution was gently mixed and kept at room temperature for 5 minutes before adding 4 ml of ice-cold solution C (3 M Sodium Acetate, pH 4.7). Tubes were kept on ice for 15 min, and centrifuged at 10,000 rpm for 15 min. After isopropanol precipitation, the DNA pellet was dissolved in 600 μl RNase solution (15 mM Tris HCl pH 8.0, 10 μg/ml RNase A). After 30 minutes at 37° C. the DNA solution was extracted with chloroform:isoamylalcohol (24:1) and precipitated from the aqueous phase using isopropanol. The DNA pellet was then rinsed with 70% ethanol, air-dried and dissolved in 30 μl distilled water. In general, DNA prepared by this method was clean and concentrated enough to give good quality results by automatic sequencing (at least 300 bp of sequence). For a few DNA preparations, an additional polyethylene glycol (PEG) precipitation step was necessary, which was performed as follows. The 30 μl of DNA solution were diluted to 64μl, mixed gently and precipitated using 16 μl 4 M NaCl and 80 μl of 13% PEG 8000. After 30 min on ice the tubes were centrifuged at 4° C., the pellet carefully rinsed with 70% ethanol, air-dried and diluted in 20 μl of distilled water.

7. Sizing of inserts. Insert sizes were determined by pulsed-field gel electrophoresis (PFGE) after cleavage with DraI (Promega). 100–200 ng of DNA was DraI-cleaved in 20 μl total reaction volume, following the manufacturer's recommendations, then loaded onto a 1% agarose gel and migrated using a pulse of 4 s for 15 h at 6.25 V/cm at 10° C. on an LKB-Pharmacia CHEF apparatus. Mid-range and low-range PFGE markers (New England Biolabs) were used as size standards. Insert sizes were estimated after ethidium bromide staining of gels.

8. Direct sequencing. For each sequencing reaction 7 μl BAC DNA (300–500 ng), 2 μl primer (2 μM), 8 μl reaction mix of the Taq DyeDeoxy Terminator cycle sequencing kit (Applied Biosystems) and 3 μl distilled water were used. After 26 cycles (96° C. for 30 sec; 56° C. for 15 sec; 60° C. for 4 min) in a thermocycler (MJ-research Inc., Watertown, Mass.) DNA was precipitated using 70 μl of 70% ethanol/0.5 mM $MgCl_2$, centrifuged, rinsed with 70% ethanol, dried and dissolved in 2 μl of formamide/EDTA buffer. SP6 and T7 samples of 32 BAC clones were loaded onto 64 lane, 6% polyacrylamide gels and electrophoresis was performed on a Model 373A automatic DNA sequencer (Applied Biosystems) for 12 to 16 hours. The sequences of oligonucleotides used as primers are shown in Table 1.

9. DOP-PCR. As an alternate procedure we used partially degenerate oligonucleotides in combination with vector-specific (SP6 or T7) primers to amplify insert ends of BAC clones, following a previously published protocol for P1 clones (Liu et al., 1995). The degenerate primers Deg2, Deg3, Deg4, Deg6 (Table 1) gave the best results for selected amplification of insert termini.

TABLE 1

| Primers used for PCRs and sequencing |
|---|
| Vector specific Primers for DOP PCR- first amplification step: |
| SP6-BAC1: AGT TAG CTC ACT CAT TAG GCA (SEQ ID NO: 734) |
| T7-BAC1: GGA TGT GCT GCA AGG CGA TTA (SEQ ID NO: 735) |
| Vector specific Primers (direct sequencing, nested primer for second PCR step) |
| SP6 Mid: AAA CAG CTA TGA CCA TGA TTA CGC CAA (SEQ ID NO: 736) |
| T7-Belo2: TCC TCT AGA GTC GAC CTG CAG GCA (SEQ ID NO: 737) |
| Degenerate Primers: |
| Deg2: TCT AGA NNN NNN TCC GGC (SEQ ID NO: 738) |
| Deg3: TCT AGA NNN NNN GGG CCC (SEQ ID NO: 739) |
| Deg4: CGT TTA AAN NNN NWA GGC CG (SEQ ID NO: 740) |
| Deg6: GGT ACT AGT NNN NNW TCC GGC (SEQ ID NO: 741) |
| Primers used for the amplification of *M. bovis* DNA in polymorphic chromosomal region of Rv58: |
| Primer 1: ACG ACC TCA TAT TCC GAA TCC C (SEQ ID NO: 742) |
| Primer 2: GCA TCT GTT GAG TAC GCA CTT CC (SEQ ID NO: 743) |

Figure 1B:
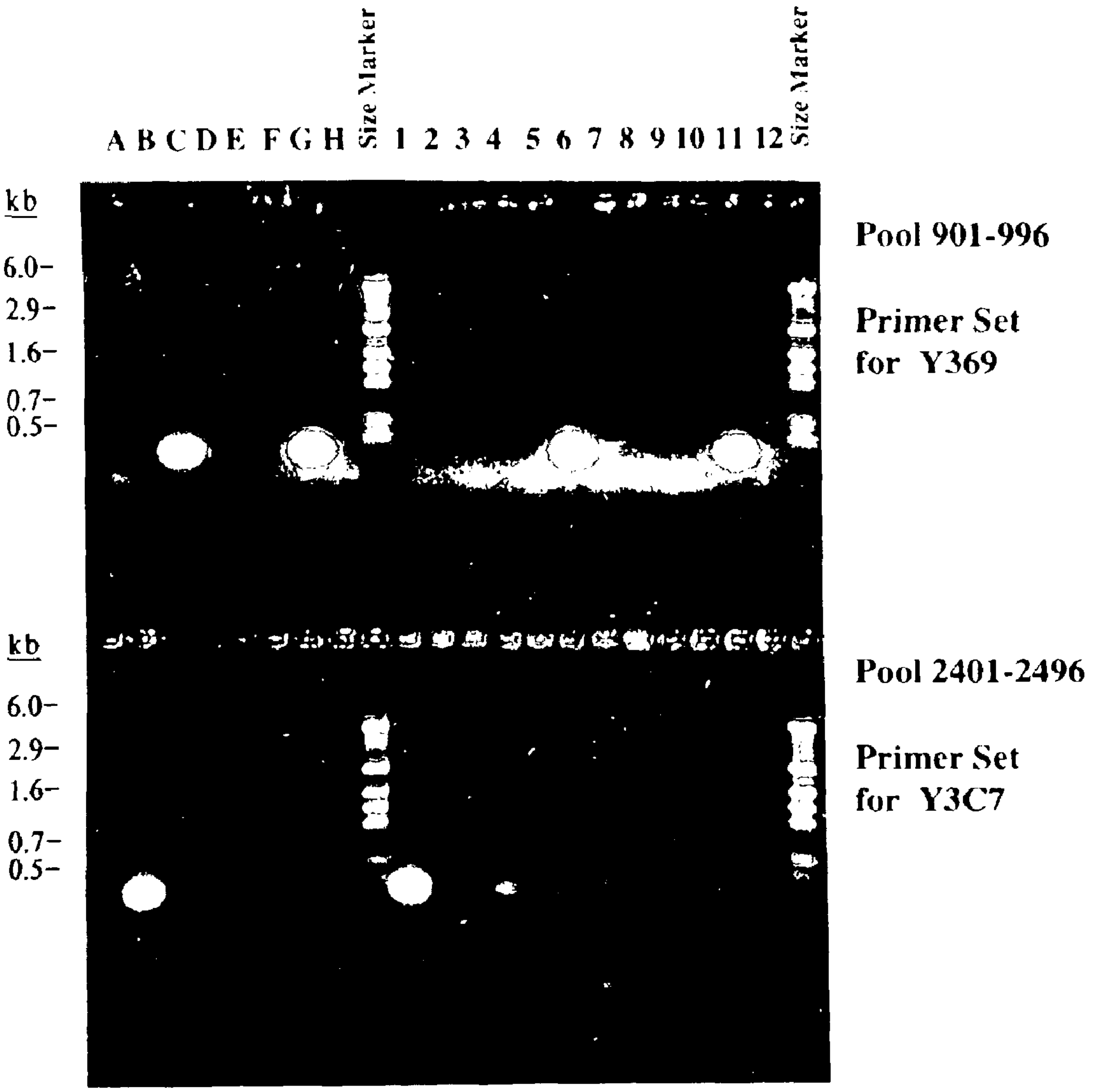

10. Screening by pooled PCR. To identify particular clones in the library which could not be detected by random end-sequencing of the 400 BAC clones, PCR- screening of DNA pools was performed. Primers were designed for regions of the chromosome where no BAC coverage was appearent using cosmid-or H37Rv whole genome shotgun sequences. Primers were designed to amplify approximately 400–500 bp. Ninety-six-well plates containing 200 μl 2YT/12.5 μgl/ml CM per well were inoculated with 5 μl of −80° C. glycerol stock cultures each from the master plates and incubated overnight. The 96 clones of each plate were pooled by taking 20 μl of culture from each well and this procedure was repeated for 31 plates. Pooled cultures were centrifuged, the pellets were resuspended in sterile water, boiled for 5 minutes, centrifuged and the supernatants kept for PCRs. As an initial screening step, the 31 pools of a total of 2976 BACs, representing about two thirds of the library were tested for the presence of a specific clone using appropriate PCR primers. PCR was performed using 10 μl of supernatant, 5 μl of assay buffer (100 mM b-mercaptoethanol, 600 mM Tris HCl (pH 8.8), 20 mM $MgCl_2$, 170 mM $(NH_4)_2SO_4$), 5 μl of Dimethylsulfoxide (DMSO), 5 μl of dNTPs (20 mM), 5 μl of water, 10 μl primer (2 μM), 10 μl inverse primer (2 μM) and 0.2 units of Taq DNA polymerase (Boehringer). 32 cycles of PCR (95° C. for 30 s, 55° C. for 1 min 30 s, 72° C. for 2 min) were performed after an initial denaturation at 95° C. for 1 min. An extension step at 72° C. for 5 min finished the PCR. If a pool of 96 clones yielded an appropriate PCR product (FIG. 1A), subpools were made to identify the specific clone. Subpools representative for lane A of a 96 well plate were made by pooling clones 1 to 12 from lane A into a separate tube. Subpools for lanes B to H were made in the same way. In addition, subpools of each of the 12 rows (containing 8 clones each) were made, so that for one 96 well plate, 20 subpools were obtained. PCR with these 20 subpools identified the specific clone (FIG. 1B, lower gel portion). If more than one specific clone was present among the 96 clones of one plate (FIG. 1B, upper gel portion), additional PCR reactions had to be performed with the possible candidates (data not shown).

11. Genomic comparisons. DNA from the BAC clone Rv58 was digested with the restriction endonucleases EcoR1 and PvuII, and resolved by agarose gel electrophoresis at low voltage overnight (1.5 V/cm). DNA was transferred via the method of Southern to nitrocellulose membranes (Hybond C extra, Amersham) following standard protocols (Sambrook et al., 1989), then fixed to the membranes at 80° C. for 2 hours. The blot was hybridized with $^{32}P$ labelled total genomic DNA from *M. tuberculosis* H37Rv, *M bovis* type strain (ATCC 19210) or *M. bovis* BCG Pasteur. Hybridization was performed at 37° C. overnight in 50% formamide hybridization buffer as previously described (Philipp et al., 1996b). Results were interpreted from the autoradiograms.

12. Computer analysis. Sequence data from the automated sequencer AB1373A were transferred as binary data to a Digital Alpha 200 station or Sun SparcII station and analysed using TED, a sequence analysis program from the Staden software package (Dear et al., 1991). Proof-read sequences were compared using the BLAST programs (Altschul et al., 1990) to the *M. tuberculosis* H37Rv sequence databases of the Sanger Centre, containing the collected cosmid sequences (TB.dbs) and whole-genome shotgun reads (TB_shotgun_all.dbs) (http://www.sanger.ac.uk/). In addition, local databases containing 1520 cosmid endsequences and the accumulating BAC endsequences were used to determine the exact location of end-sequenced BACs on the physical and genetic map. MycDB (Bergh et al., 1994) and public databases (EMBL, Genbank) were also used to compare new sequences, but to a lesser extent. The organization of the open reading frames (ORFs) in the polymorphic region of clone Rv58 was determined using the DIANA software established at the Sanger Centre.

EXAMPLES

Example 1: Construction of a pBeloBAC11 library of *M. tuberculosis* H37Rv.

Partial HindIII fragments of H37Rv DNA in the size range of 25 to 180 kb were ligated into pBeloBAC11 and electroporated into strain *E. coli* DH10B. While cloning of fractions I (25 to 75 kb) and I (75 to 120 kb) gave approximately 4 $\times 10^4$ transformants (white colonies), cloning of fraction III (120 to 180 kb) repeatedly resulted in empty clones. Parallel cloning experiments using partial HindIII digests of human DNA resulted in stable inserts for all three fractions (data not shown), suggesting that the maximum size of large inserts in BAC clones is strongly dependent on the source of the DNA. Analysis of the clones for the presence of inserts revealed that 70% of the clones had an insert of the appropriate size while the remaining 30% of white colonies represented empty or lacZ'-mutated clones. Size determination of randomly selected, DraI-cleaved BACs via PFGE showed that the insert sizes ranged for the majority of the clones between 40 kb and 100 kb with an average size of 70 kb. Clones with inserts of appropriate size were designated with "Rv" numbers, recultured and stored at −80° C. for further use.

Example 2: Direct DNA sequence analysis of BACs.

To characterize the BAC clones, they were systematically subjected to insert termini sequencing. Two approaches, direct sequencing of BAC DNA and PCR with degenerate oligonucleotide primers (DOP), adapted to the high G+C content of mycobacterial DNA, were used. In a first screening phase, 50 BAC clones designated Rv1 to Rv50 were analysed using both methods in parallel. Except for two clones, where the sequences diverged significantly, the sequences obtained by the two methods only differed in length. Sequences obtained directly were on average about 350 bp long and for 95% of the clones both the SP6 and T7 endsequences were obtained at the first attempt. Sequences obtained by DOP-PCR were mostly shorter than 300 bp. For 40% of the BACs we obtained only very short amplicons of 50 to 100 base pairs from one end. In two cases the sequence obtained with the DOP-PCR differed from the sequences obtained by direct sequencing, and in these cases *E. coli* or vector sequences were amplified (data not shown). Taking the advantages and disadvantages of both methods into account, we decided to use direct termini sequencing for the systematic determination of the SP6 and T7 end-sequences.

Example 3: Representativity of the library.

After having determined the end-sequences of 400 BACs a certain redundancy was seen. The majority of clones were represented at least 3 to 4 times. Maximum redundancy was seen in the vicinity of the unique rrn operon, as 2.5% of the clones carried identical fragments that bridge the cosmids Y50 and Y130 (FIG. 3, approximate position at 1440 kb). The majority of clones with identical inserts appeared as two variants, corresponding to both possible orientations of the HindIII fragment in pBeloBAC11. This suggests that the redundancy was not the result of amplification during library construction, but due to the limited number of possible combinations of partial HindIII fragments in the given size-range of 25 to 120 kb. To detect rare BAC clones, a pooled PCR protocol was used. Primers were designed on the basis of the existing cosmid sequences and used to screen 31 pools of 96 BAC clones. When positive PCR products of the correct size were obtained, smaller subpools (of 8 or 12 clones each) of the corresponding pool were subsequently used to identify the corresponding clone (FIG. 1). With this approach 20 additional BACs (Rv401–Rv420) were found for the regions where no BACs were found with the initial systematic sequencing approach. The endsequences of these BACs (Rv401–420) were determined by direct sequencing, which confirmed the predicted location of the clones on the chromosome. A 97% coverage of the genome of H37Rv with BAC clones was obtained. Only one region of ~150 kb was apparently not represented in the BAC library as screening of all pools with several sets of specific primers did not reveal the corresponding clone. This was probably due to the fact that HindIII fragments of mycobacterial DNA larger than 110 kb are very difficult to establish in *E. coli* and that a HindIII fragment of ~120 kb is present in this region of the chromosome (data not shown).

Example 4: Establishing a BAC map.

Figure 2:
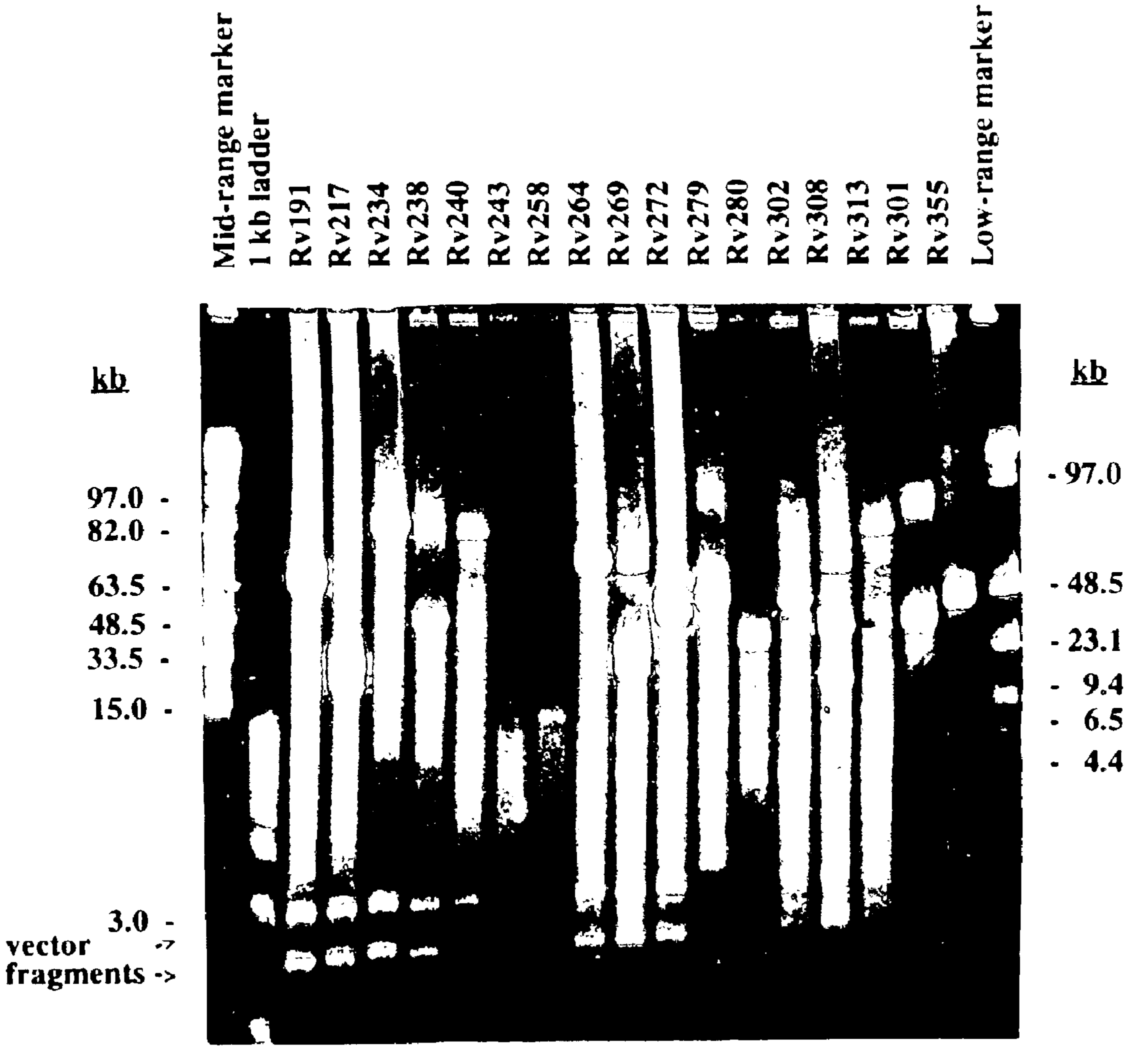
FIG. 2: Pulsed-field gel electrophoresis gel of DraI-cleaved BAC clones used for estimating the insert sizes of BACs.
Figure 3A:
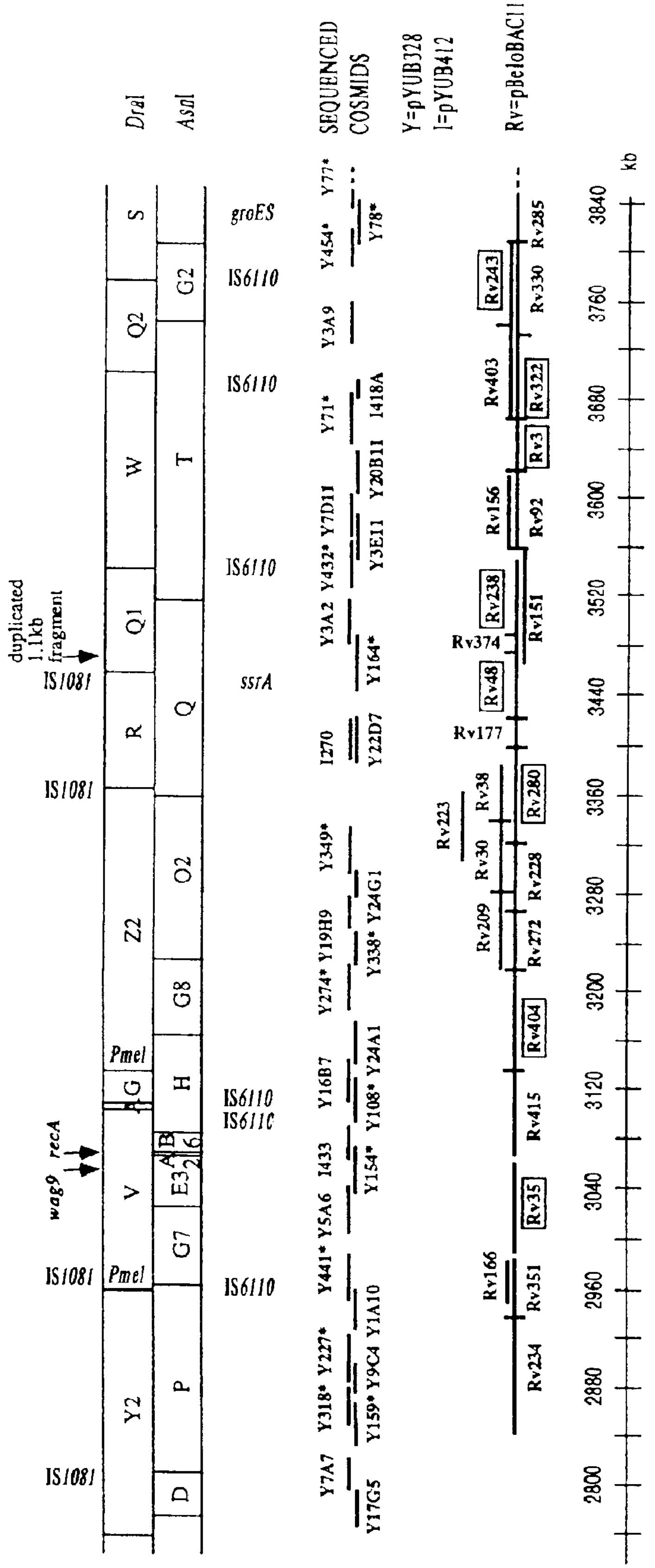
FIGS. 3A–3D: Minimal overlapping BAC map of *M. tuberculosis* H37Rv superimposed on the integrated physical and genetic map established by Philipp et al. (18). Y- and I- numbers show pYUB328 (2) and pYUB412(16) cosmids which were shotgun sequenced during the H37Rv genome sequencing project. Y-cosmids marked with ·X· were shown in the integrated physical and genetic map (18). Rv numbers show the position of representative BAC clones relative to sequenced Y- and I- clones. Squared Rv numbers show BACs which were shotgun sequenced at the Sanger Centre.
Figure 3B:
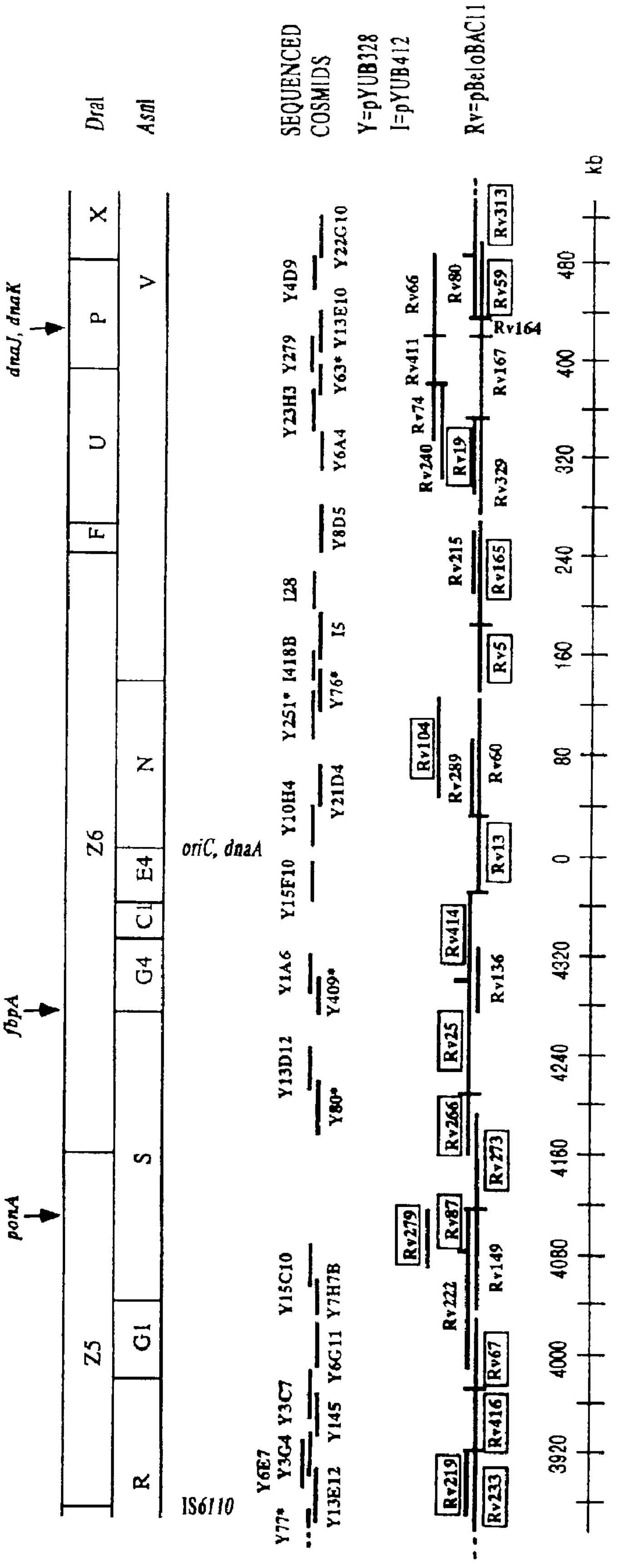
Figure 3C:
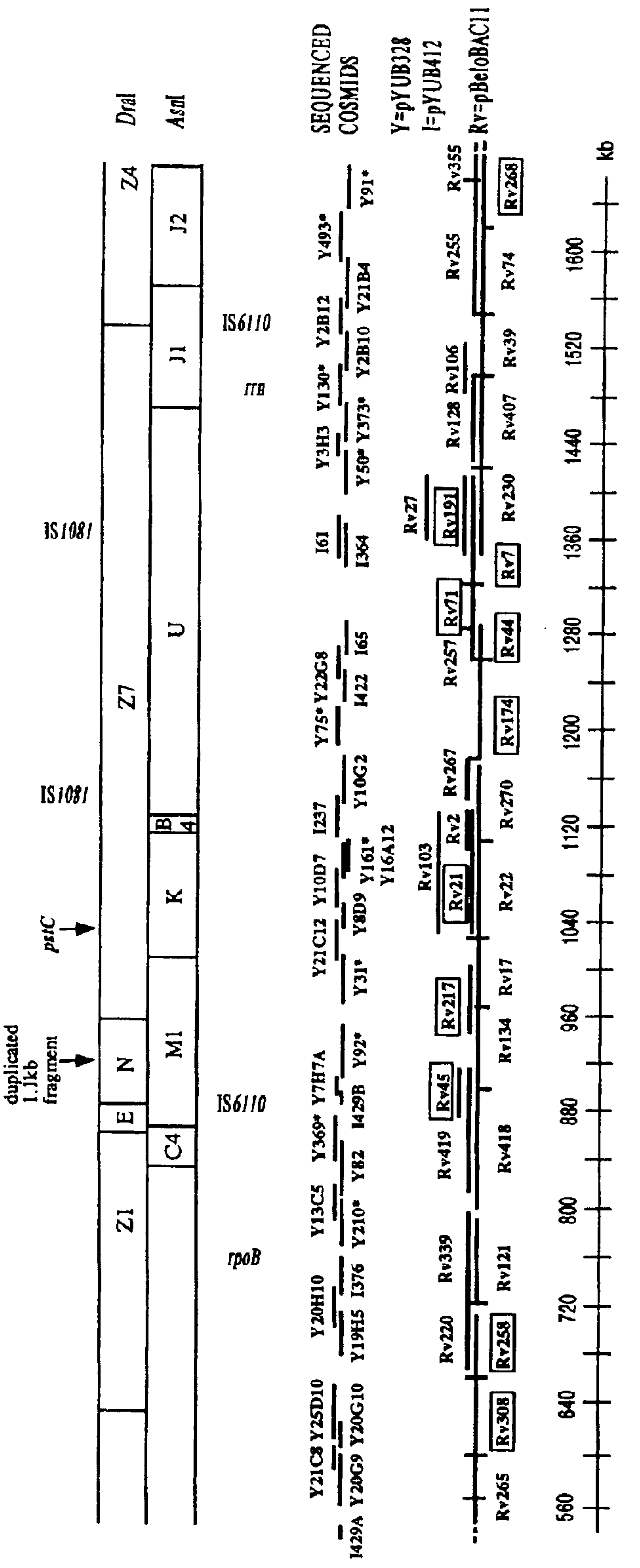
Figure 3D:
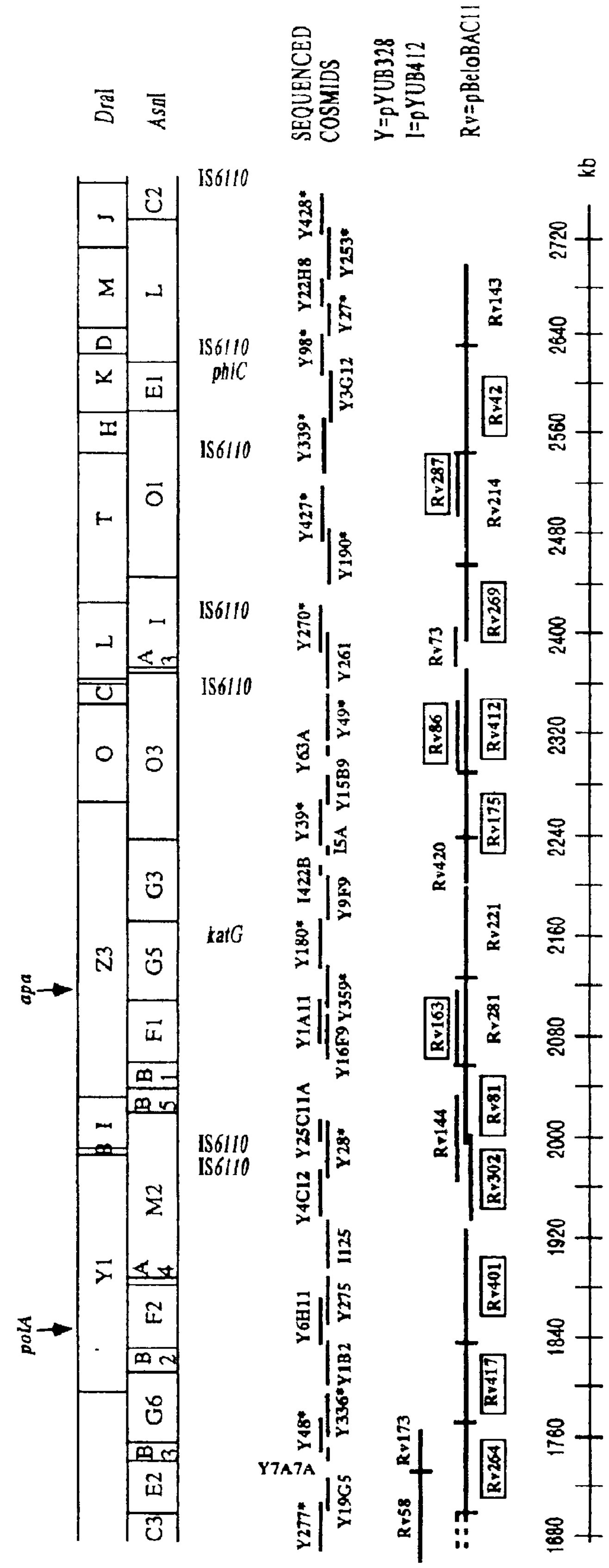

Using all endsequence and shotgun-sequence data from the H37Rv genome sequencing project, most of the BAC clones could then be localized by sequence comparison on the integrated map of the chromosome of *M. tuberculosis* strain H37Rv (Philipp et al., 1996b) and an ordered physical map of the BAC-clones was established. PCR with primers from the termini sequences of selected BACs were used for chromosomal walking and confumation of overlapping BACs (data not shown). The correct order of BACs on the map was also confirmed more recently, using 40,000 whole genome shotgun reads established at the Sanger Centre. In addition, pulsed-field gel electrophoresis of DraI digests of selected BACs was performed (FIG. 2) in order to see if the approximate fragment size and the presence or absence of DraI cleavage sites in the insert were consistent with the location of the BACs on the physical map (FIG. 3). Comparison of the sequence-based BAC-map with the physical and genetic map, established by PFGE and hybridization experiments (Philipp et al., 1996b), showed that the two maps were in good agreement. The positions of 8 genetic markers previously shown on the physical and genetic map were directly confirmed by BAC-endsequence data (Table 2, FIG. 3). The position of 43 from 47 Y-clones (91%) shown on the physical and genetic map, which were later shotgun sequenced, was confirmed by the BAC endsequences and shotgun sequence data. Four clones (Y63, Y180, Y251, and Y253) were located to different positions than previously thought and this was found to be due to book keeping errors or to chimeric inserts. Their present approximate location relative to the oriC is shown in FIG. 3: Y63 at 380 kb, Y63A at 2300 kb, Y180 at 2160 kb, Y251 at 100 kb, and Y253 at 2700 kb. A total of 48 BACs, covering regions of the chromosome, not represented by cosmids were then shotgun sequenced (Cole et al., 1997), and these are squared in FIG. 3. No chimeric BACs were found, which is consistent with the observations of other research groups for other BAC libraries (Cai et al., 1995; Zimmer et al;, 1997). The absence of chimeric BACs was of particular importance for the correct assembly of the *M. tuberculosis* H37Rv sequence. The exact position of the BAC termini sequences on the chromosome will be available via the world wide web (http://www.pasteur.fr/MycDB).

TABLE 2

Identities of genetic markers previously shown on the integrated and genetic map of H37Rv (Phlipp et al., 1996b) wich showed perfect sequence homology with BAC end sequences.

| Locus | BAC end sequence | Description of genetic marker | Organism | GenBank Accession n° |
|---|---|---|---|---|
| apa | Rv163SP6 | Secreted alanine-proline-rich antigen | *M. tuberculosis* | X80268 |
| dnaJ, dnaK | Rv164T7 | DnaJ hsp | *M. leprae* | M95576 |
| fop-A | Rv136T7 | Fibronectin binding protein | *M. tuberculosis* | M27016 |
| polA | Rv401T7 | DNA polymerase I | *M. tuberculosis* | L11920 |
| ponA | Rv273T7 | Penicillin binding protein | *M. leprae* | S82044 |
| pstC | Rv103T7 | Putative phosphate transport receptor | *M. tuberculosis* | Z48057 |
| recA | Rv415SP6 | Homologous recombination | *M. tuberculosis* | X58485 |
| wag9 | Rv35SP6 | 35-kDa antigen | *M. tuberculosis* | M69187 |

Example 5 Repetitive endsequences.

Repetitive sequences can seriously confound mapping and sequence assembly. In the case of the BAC endsequences, no particular problems with repetitive sequences were observed. Although nine clones with one end in an IS1081 (Collins et al., 1991) sequence were identified, it was possible to correctly locate their position on the map using the sequence of the second terminus. Moreover, these BACs were used to determine the exact locations of IS1081 sequences on the map. Five copies of this insertion sequence, which harbors a HindIII cleavage site, were mapped on the previous physical and genetic map. In contrast, BAC endsequence data revealed an additional copy of IS1081 on the *M. tuberculosis* H37Rv chromosome. The additional copy was identified by six clones (Rv27, Rv118, Rv142, Rv160, Rv190, Rv371) which harbored an identical fragment linking Y50 to 1364 (FIG. 3, at ~1380 kb). This copy of IS1081 was not found by previous hybridization experiments probably because it is located near another copy of IS1081, localized on the same DraI fragment Z7 and AsnI fragment U (FIG. 3, at ~1140 kb). Furthermore, the position of a copy of IS1081 previously shown in DraI fragment Y1 (FIG. 3, at ~1840 kb) had to be changed to the region of Y349 (FIG. 3, at ~3340 kb) according to the endsequences of BAC Rv223. The positions of the four other IS1081 copies were confirmed by the sequence data and therefore remained unchanged. In total 6 copies of IS1081 were identified in the H37Rv genome in agreement with the findings of others (Collins et al., 1991).

In addition, a sequence of 1165 bp in length containing a HindIII site was found in two copies in the genome of H37Rv in different regions. The endsequences of BAC clones Rv48 and Rv374, covering cosmid Y164, as well as Rv419 and Rv45, that cover cosmid Y92, had perfect identity with the corresponding parts of this 1165 bp sequence (FIG. 3, at ~3480 kb and 900 kb). Analysis of the sequence did not reveal any homology with insertion sequences or other repetitive elements. However, as each of the two locations showed appropriate BAC coverage, chimerism of the sequenced cosmids Y164 and Y92 can be ruled out as the probable cause.

Example 6: Using BAC clones in comparative genomics.

Figure 4A:
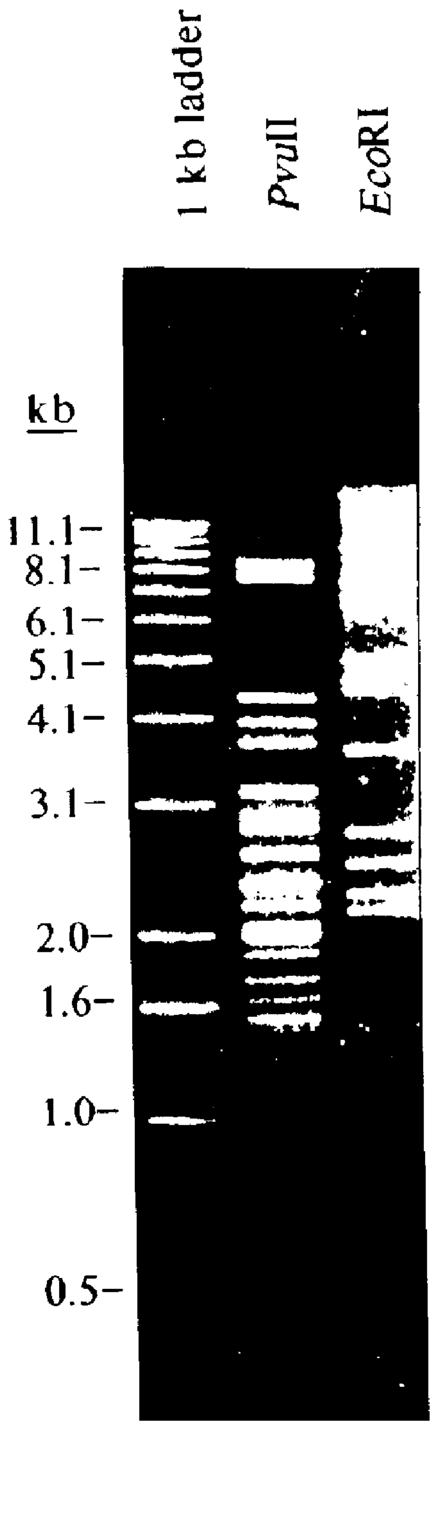
FIGS. 4A and 4B: Ethidium bromide stained gel (Panel A) and corresponding Southern blot (Panel B) of EcoR1 and PvuII digested Rv58 DNA hybridized with $^{32}P$ labeled genomic DNA preparations from *M. tuberculosis* H37Rv, *M. bovis* ATCC 19210 and *M. bovis* BCG Pasteur.
Figure 4B:
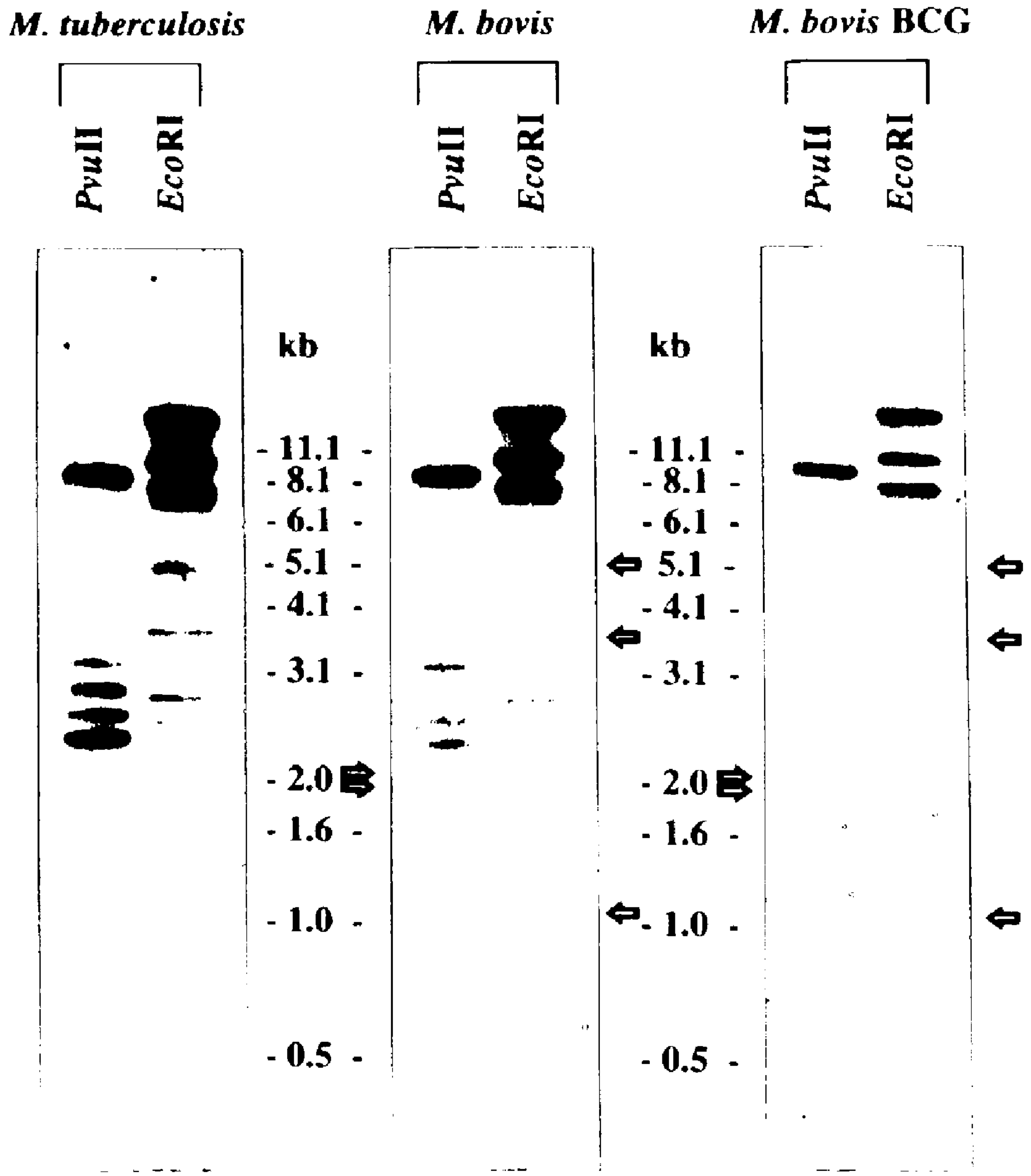
Figure 5:
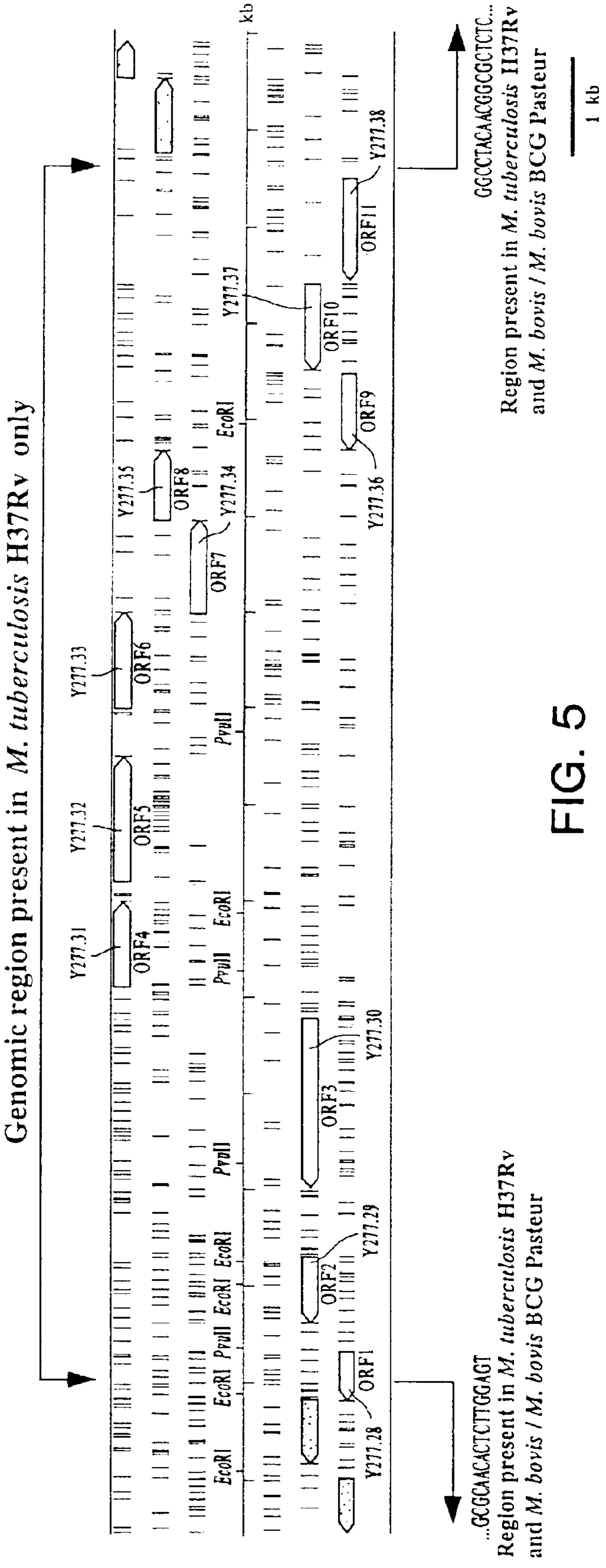
FIG. 5: Organisation of the ORFs in the 12.7 kb genomic region present in *M. tuberculosis* H37Rv but not present in *M. bovis* ATCC 19210 and *M. bovis* BCG Pasteur. Arrows show the direction of transcription of the putative genes. Positions of EcoR1 and PvuII restriction sites are shown. Vertical dashes represent stop codons. The 11 ORFs correspond to the ORFs MTCY277.28 to MTCY277.38/accession number Z79701-EMBL Nucleotide Sequence Data Library. The junction sequences flanking the polymorphic region are shown.

The minimal overlapping set of BAC clones represents a powerful tool for comparative genomics. For example, with each BAC clone containing on average an insert of 70 kb, it should be possible to cover a 1 Mb section of the chromosome with 15 BAC clones. Restriction digests of overlapping clones can then be blotted to membranes, and probed with radiolabelled total genomic DNA from, for example, *M. bovis* BCG Pasteur. Restriction fragments that fail to hybridize with the *M. bovis* BCG Pasteur DNA must be absent from its genome, hence identifying polymorphic regions between *M. bovis* BCG Pasteur and *M. tuberculosis* H37Rv. The results of such an analysis with clone Rv58 (FIG. 3, at ~1680 kb) are shown here. This clone covers a previously described polymorphic genomic region between *M. tuberculosis* and *M. bovis* BCG strains (Philipp et al., 1996a). EcoR1 and PvuII digests from clone Rv58, fixed on nitrocellulose membranes, were hybridized with $^{32}P$-labelled total genomic DNA from *M. tuberculosis* H37Rv, *M. bovis* (ATCC 19120), and *M. bovis* BCG Pasteur. FIG. 4 presents the results of this analysis, where it is clear that several restriction fragments from clone Rv58 failed to hybridize with genomic DNA from either *M. bovis* or *M. bovis* BCG Pasteur. On the basis of the various missing restriction fragments, a restriction map of the polymorphic region was established and compared to the H37Rv sequence data. The localization of the polymorphism could therefore be estimated, and appropriate oligonucleotide primers (Table 1) were selected for the amplification and sequencing of the corresponding region in *M. bovis*. The alignment of *M. bovis* and *M. tuberculosis* H37Rv sequences showed that 12,732 bp were absent from the chromosomal region of the *M. bovis* type strain and *M. bovis* BCG Pasteur strain. The G+C content of the polymorphic region is 62.3 mol %, which is the same as the average genome G+C content of the *M. tuberculosis* genome, hence indicating that this region is not a prophage or other such insertion. Subsequent PCR studies revealed that this segment was also absent from the Danish, Russian, and Glaxo substrains of *M. bovis* BCG, suggesting that this polymorphism can be used to distinguish *M. bovis* from *M. tuberculosis*. Analysis of this sequence showed that 11 putative open reading frames (ORFs) are present in *M. tuberculosis*, corresponding to ORFs MTCY277.28 to MTCY277.38/accession number Z79701-EMBL Nucleotide Sequence Data Library (FIG. 5). FASTA searches against the protein and nucleic acid databases revealed that the genes of this region may be involved in polysaccharide biosynthesis. Among these putative genes, the highest score was seen with ORF 6 (MTCY277.33), whose putative product shows a 51.9% identity with GDP-D-Mannose dehydratase from *Pseudomonas aeruginosa* (accession number U18320-EMBL Nucleotide Sequence Data Library) in a 320 amino acid overlap. The novel *M. bovis* sequence of the polymorphic region was deposited under accession number AJ003103 in the EMBL Nucleotide Sequence Data Library.

As it appears from the teachings of the specification, the invention is not limited in scope to one or several of the above detailed embodiments; the present invention also embraces all the alternatives that can be performed by one skilled in the same technical field, without deviating from the subject or from the scope of the instant invention.

TABLE 3

| End sequences of the polynucleotide inserts cloned in the named recombinant |
|---|
| Clone Rv101 |
| ::::::::::::::Rv101SP6.seq:::::::::::::: |
| AATACTCAAGCTTGCCCAGCCGTCGATGACAAGAAATATGTCCGCAAAAGACTCAGCGGCCGACTTTGCTCGCAGCTGGCGGTACCGCGCCACCGATTCTATG |
| CCGTGGTCGCGGAAAAATGCCTCCCGAAATCGCACGGCCGACTCCAGTTCGGCGAGCATCCGCGATGCCAGCTGCGGCTGCGCCCTGCCGGCCACGGCACCCA |
| CATGCGGCAGTTCGTCCACCTGGGCCAGCGCCCCGCCGCCGAATTCCAAACAATAGAACTGCACCCGGCCCGCATCGTGGGTAACAGCCAACGCCATGATCAG |
| CGTCCGCAGCGCGGTTGACTTGCCCGTTTGCGGTGCACCTACGAACGCGACATTGCCTGCGGCCCCGGACAAGTCGATCGTGCGCGGCACCCGTGACTGCTCT |
| AACGGGCGATTGAAATTCCGAT (SEQ ID NO. 6) |
| ::::::::::::::Rv101T7.seq:::::::::::::: |
| CCACCCGTGTAATTTGGGATGGGCAAAAAGGCGAAGCACCGCGTGGCCACGAACGCCGGGAGGGACAATCTCGGGCGGTTAGGGCTTCTCGCGGGAAGGCCCG |
| AACGTACGGCGTTTCAACACCTCGCGTCGCCCTCCGACCGCGAACATTCGGGGATGGCAGCAACCTGCTGGCACCCTGGCCGGGCGATGATCTGCAGCGTCGC |
| CGCGGGTAGTCGCCGCCCGGGCGGCTACACTCTGAAACGCGATGACCATCGATGTGTGGATGCAGCATCCCGACGCAACGGTTCCTACACCGCGATATGTTCG |
| CCTCGCTGCCCCGGTGGACCGGT (SEQ ID NO. 7) |
| Clone Rv102 |
| ::::::::::::::Rv102SP6.seq:::::::::::::: |
| AATACTCAAGCTTTCCGCCGATACCCGCCATGTCGCGCACATCCAGGACTTCTGGGGGGATCCGCTGACAGCGGCGGGATCCCAAAGTGCGGATGATCGGGCC |
| GCCTACGTCGTGGTGTACCTCGTCGGTAACAACGAAACCGAAGCGTATGACTCGGTCCACGCGGTGCGGCACATGGTGGACACCACACCGCCACCGCACGGGG |
| TGAAGGCCTATGTCACCGGTCCGGCAGCACTCAATGCCGACCAGGCCGAGGGCGGAGACAAAAGTATCGCTAAGGTCACCGCGATCACCAACATGGTGATCGC |
| AGCAATGTTGCTAGTGATCTATCGCTCCGTAATTACCGCGGTTCT (SEQ ID NO. 8) |
| ::::::::::::::Rv102T7.seq:::::::::::::: |
| GTGCCGTTCCAACCCGAATTGGCTTTCGGCGCCATCGGTGAGGACGGCGTGCGGGTGCTCAACGACGACGTCGTCCGCGGGACACACCTCGATGCTGCCGCCA |
| TGGACGCGGTCGAACGCAAGCAGCTGATCGAGCTACAACGCCGCGCGGAACGCTTCCGCCGCGGGCGTGACCGCATCCCGTTGACCGGGCGGATCGCGGTGAT |
| CGTCGATGACGGCATCGCCACCGGAGCGACGGCCAAGGCGGCGTGCCAGGTCGCCCGGGCGCACGGTGCGGACAAGGTGGTGCTGGCGGTCCCGATCGGCCCA |
| GACGACATCGTGGCGAGATTCGCCGGGTACGCCGATGAGGTGGT (SEQ ID NO. 9) |
| Clone Rv103 |
| ::::::::::::::Rv103SP6.seq:::::::::::::: |
| AATACTCAAGCTTTCGGCGGAAACGGACACATTGCGAATATTGATGACAAAATAAAAATCATTGATGGTTTGAGTCACCAGGCCGATCAAGCCTTCGCCGAGC |
| CAAATTCCAATCAAGAGGCCCAAGCCCGTACCAATCAGCCCGGCAACGAGGGATTCCGTCATTATCAGCCAAAATAACTGCTCTCGGGTTACACCCAAACAGC |
| GCAATATGGCGAAAAACGGTCGCCGTTGCACGACATTAAATGTCACGGTATTGTAGATTAAAAAGATACCCAC (SEQ ID NO. 10) |
| ::::::::::::::Rv103T7.seq:::::::::::::: |
| TGCTCCCGAAACCTGGGGGTGTGCCTGCTCTGTATGCACGGCATACGGACATCCTTCCCCTGAGACCCGCGGTCGAACCAGCCACGTGTCCATCATAGNGGGT |
| CAACCCCGGCCAAGGGCGACGGCACGCCAAGTTCGCCGACCGTTAACCTAGTGCTGTTAGCTTCATTTGCTGCGATCAAAACAGCTGGTCGGCCGTTAGGAAC |
| TGAATTGAAACTCAACCGATTTGGTGCCGCCGTAGGTGTCCTGGCTGCGGGTGCGCTGGTGTTGTCCGCGTGTGGTAACGACGACAATGTGACCGGGGGAGGT |
| GCAACCACTGGCCAGGCGTCGGCAAAGGTCGATTGCGGGGGGAAGAAGACACTCAAAGCCAGTGGGT (SEQ ID NO. 11) |

TABLE 3-continued

End sequences of the polynucleotide inserts cloned in the named recombinant

Clone Rv104
:::::::::::::Rv104SP6.seq::::::::::::
ATACTCAAGCTTTGCCGACGAGCGGGCGATGTTGATGACGGGAAACCCCAGCGCACAACCGACGATTTTGGCGTAGCCGGCGGACGTCTGCTCGATTCCGATC ACGTCGGCGCTCGCATCGAGCATGGCGCCGGCGACGGCTAGCAGCGATCCGCCGTCGTCGAGGAGCACGACACGAGCCGTACGCCCGGCCGTAAGCCGCGCCC AGGATTCGGCGAAAAACCGTTCTACGTGGCGGGTGTACTGGGTGTCGAATGATTCGTGGGGTGCGTAGGCGTCGCTGCAATCGTCGACATAGATGCCGTCGGG CCGCATCGCGTCGACAACTCCGGGTGAGTGGAATAGCACTTGCCGATCACCGCGACGTTGCGCGGATGAGGCCGAACCCGAATA (SEQ ID NO. 12)

:::::::::::::Rv104T7.seq::::::::::::
TCCTATGTCCCTGCCGAGCANGTGATCGAACGCGGTGACAGATTTGTCTATCCTGGACCTGACGGTGAGGTCGAAGTTTTCCAGGAATTCGGCAAAATCGGTA AGAGCCTGAAGAATTCGGTATCGCCGGACGAAATCTGCGACGCATACGGGGGCATATACGCTTCGGGTTTACGAGATGTCGATGGGGCCGCTGGAGGCTTCAC GTCCATGGGCCACAAAGGATGTTGTCGGCGCGTACCGTTTTCTGCAGCGGGTGTGGCGCTTGGTCG (SEQ ID NO. 13)

Clone Rv105
:::::::::::::Rv105SP6.seq::::::::::::
ATACTCAAGCTTGATTCCGCCGAAACCGACCGTGAGCACCCCGCCAGCCACCACGCTCGGGTCGGGCGCCGGGCCCGGGCCGCCAGGCTGCTCCGCTCGGTGA TGGCACGCCACCGCGACACCACCCGGCTGCGCTACGTCTAACCATTCCAGGCGGAGCTACATCAGCTCGGCCGCCCAGTGTTCGGGCCCTCTTTCCAGGTCGA AGTCTATACCGATATGCGCATCCGCAGCCGCCACCCTGGAGAACAGAACGATGCCCTACTAATGCTTGTCTGGCGGGGCC (SEQ ID NO. 14)

:::::::::::::Rv105T7.seq::::::::::::
GGTACGCTTCGGTCGCAGTCTGCGAGTGATGCATGACGACCGGGACCTCGTCGGCATCTTCCATAGCCCGCCACACCTTCAGTTGCTCACCGGAATCCAACCG GTAGAAGGTCGGCGAGCGCTCGGCATTGGTCATCGGGATATGCCGCTCGGGACGGTCAGAGCCCTCGGGTCCGGCCAGCACTCCGCAGGCTTCGTCGGGGTGG TCGCGACGCGCATGGGCCACCATCGCATTCACCAGGTCTGCGCGAATCACCAGCACGTAGACGGTTCCTTTCCTAAGCAACACCGAAGTTTCAGGACCCGAAT

GCTCCGGGAAACATGTCACGGTAGGTCGGTATTCCGGCTACCGGCTGA (SEQ ID NO. 15)

Clone Rv106
:::::::::::::Rv106SP6.seq::::::::::::
GGCGTCAACGGTGTCGGAACCCGCGTCAAGCAATTGGTAGGCCTGCAGTCTGTGAATCAGGCCGACGCTGTGGCCGCCGCGGC (SEQ ID NO. 16)

:::::::::::::Rv106T7.seq::::::::::::
GGCTNGCGTACCCGGTACCGGCCGCGGGCCTACCACGTGCCGGAACTGGAAGCGCAGTAAGCCCTCAACGCGCCACCGCTTTGGCCCGCGCGCCCGGCGTAGG CGCATCGGCGGTGGCCGTGGGGCGGCGCACTGCGACCTCACCAGCGGCTTTCGAGCTTTGTTCGATCAACCGGCCAGCATGGTCGANGATGCATTCGAGACCA TATTCGAAATTGGTTTCATCGGGGGCCCCGATCCGATGCCCCCTCCCAGTTGCGTGAGCAANCAGCGGAGTCNTCGCGGGATCGATGGCCACGGGGTGTTCAA TGGCGGATGGTCCGCTGCCCGCCGACTGGCTCTTGCGGGAGAACCGATCTAGCACCACCGATCCGCGCACGTNG (SEQ ID NO. 17)

Clone Rv107
:::::::::::::Rv107T7D4.seq::::::::::::
CGTAATNTCGCGCACANCCANGACTTCTGGGGGGATCNGCTGACAGTGGTNGGATCCCAAATTGCGGATGATCGGGCCGCCNACGTCGTTGTGTACCTCNTCN GTCACAACNAANCCGAANCGTATGACTCGGTCCACGCGGTGCGGCACATGGTGGACACCACACCGCCACCGCNCGGGGTGAAGGCCTATGTCACCGGTCCGGC AACACTCAATGCCGACCAGGCCGANGCCGGACACNANAGTATCNCTAACGTCACCGCGATCACGAGCATGGTGATCGNNCAATGTTNCTANTGATCTATCGCT CCGTAATTACCGCGGTTCTCGTCTTGATCATGGTCGCANCGAACTCCGGCGCAATCCGCGGATTCATCGNCTTGCTCGCCGATCACATATTTTCAGCCTTTCA CATTGCAACNAACCTGCTCGTCTCATGGNGATGCGGCGACACGGACTACCGATATCATGCTCGCCGTTACACAATCNCGCCACGCCGCGAAGACNGGAAACGC TTCTACACAATNTTCNCGGGACGCCACTNAACTTGGTTCNGGTTTGACATTGCCGCGCATGTNTGCCCAGCTTTGCCGGCTCCCCTTA (SEQ ID NO. 18)

Clone Rv108
:::::::::::::Rv108T7D4.seq::::::::::::
TGAATTTCCCGATCCCACAATCTCGGTTCAGATACAGGTCGCCATACCCCTTACTTCGGCAACGCTGGGCGGATTGGCCCTGCNGCTGCAGCANACCATCGAC GCCATCGAATTGCCGGCAATCTCGTTCAGCCAATCCATACCCATCGACATTCCGCCGATCGACATCCCGGCCTTCNCCCTTTAACGG (SEQ ID NO. 19)

Clone Rv109
:::::::::::::Rv109SP6.seq::::::::::::
AACAGCTATGACCATGNTTACGCCAAGCTATTTAGGTAACACTATANAATACTCAAGCTTTTACGGTGATCGCGCATCACCTGGTTCATGAACTGGAAGCAGC GCANCGCTTCCTTTTCGGCCGCAACATGAGCCAGCCTCTCGTCCGCGGTCNGGTGCAGGTGCTCGGGCAGCTCGGCCGCGACAGCCGCCTGACCCTGAAACCA GCTTCCATATCCCGCGACNAACNACNCCAGTCCGCTACGTAACCCCTCCGCGACTGTCCATGGACAACAGCGCGTTCTCCACCGACCGGGCCCGGGTGTGGGG TABLE 3-continued

| End sequences of the polynucleotide inserts cloned in the named recombinant |
|---|
| TGTTTCGGCGACCGGCAGCCAGGTGGTCCACACTGCCGACGGGCGCCGCGAGCCGTTCACCGACCAAGCCGCCGAACAAGTCCGCCCGATCGCATACTCCAAC |
| CGGTTGCGGTACTGCAGGTCAGCTGGCGTACCTCCTCNTCNCGCTCGGCGAAGTCTTGCTCCANCACGTCGCAGAACGGCAAGGAACACGTTCA |
| (SEQ ID NO. 20) |
| ::::::::::::Rv109T7.seq:::::::::::: |
| GACCGNNCCATGTTTCCACAATGTGGTGCCAGTNCGGNGGCTACGTGCCATCNANACACTGGCGCAGGCTATCGCACCCGTTATCNGCTACGAACAAATCNCG |
| GTATGCGTTCTTTANCATGAGTCGGCGACCGNCGATCATGGTCGACACCCACGACNGAAATACGCAGATCGCCNTCNAGCNTGTGTGCCGCGGATTATCANGA |
| CTGACCTCCTGGCTGACCGGNNTGTNTGGTCGCGATGCCTGGCGCCCGGCCGGCGTGNTCGTGGTCGGCTCGGATAGCGAAGTCAGCTAATTCTCGTGGCAGC |
| TCGAAAGGGTCCTGCCGGTGCCGGTCTTTGCGCAAACCATGCNCATGTTACGGTCCCTCGGGTGCGGCCTGGCGGCGGC (SEQ ID NO. 21) |
| Clone Rv10 |
| ::::::::::::Rv10SP6D2.seq:::::::::::: |
| GGATGGGCGGGCCCGCTAAACTCTTCGTGTTCCACTAACTCCGGGAGGGNCAATCTCGGGCCGTTATGGCTCACGTCGCGTCGCCCTCCGACCGCGAACATT |
| CGGAGTTGGCAGCAACCTGGTAGCACCCTGGCCGG (SEQ ID NO. 22) |
| ::::::::::::Rv10T7D4.seq:::::::::::: |
| NCCGTCGTTGACAAGTAAATATGTCCGCAAAAGTCTCAGCGGCCGACTTTGCTCGCAGGTGGCGGTACCGCGCCACCGAGTCGATGCCGTGGTCGCGGAAGAA |
| TGCCTCCCGAAATCGCACGGCCTTCCCNNTTTAAACGGA (SEQ ID NO. 23) |
| Clone Rv110 |
| ::::::::::::Rv10SP602.seq:::::::::::: |
| TTTAGGTGACACTATAGAATACTCAAGCTTTTGGTCTAGCCGGCCGAGCACGATACGGGTGTCATTGGCCACCGGCGGCGGCTGTCCGGGAAATGGCGGGTCC |
| CCGGTGGTTTTGCTGATGAGTGCTGAACCGTANTCGAAGTGGGCGGCGTCAGACTCCACCCANCCAGCAGGCAGCGCGAAGCTGAATCCTCCAACCGGGTTGT |
| CNATCCGGACAAGTTGGGGTGCGTTTGGGGCAATGACAGGTGGCNGCGGTGCGTTCGGGTCCGCCGGCGGAAGTGCTGCGTTGGGATCNCCCGCTGGGCATTC |
| GGCNTTTTTGCGGCGGCCGGTGGTNGGGGGGCAACAGGTNTCCCNGTGCGGGTGGCGCTCAACGGTCNACGGCGCAAGCCGCCGTTGTTGGTACCNGGGGCGC |
| TGGCTCCGGATCGCGTTGGCGGTCNCCGG (SEQ ID NO. 24) |
| ::::::::::::Rv110T7.seq:::::::::::: |
| CTACACCATCGAATACGACGGCGTCGCCNACTTTCCGCGGTACCCGCTCAACTTTGTGTCGACCCTCAACGCCATTGCCGGCACCTACTACGTGCACTCCAAC |
| TACTTCATCCTGACGCCGGAACAAATTGACGCAGCGGTTCCGCTGACCAATACGGTCGGTCCCACGATGACCCAGTACTACATCATTCGCACGGANAACCTGC |
| CGCTGCTAGAGCCACTGCGATCGGTGCCGATCGTGGGGAACCCACTGGCGAACCTGGTTCAACCAAACTTGAANGTGATTGTTAACCTGGGCTACNGCGACCC |
| GGCCTATGGTTATTCNACCTCNCCGCCCAATGTTGCGACTCCGTTCGGGTTGTTCCCANAAGTCNNCCCGGTCGTCATCGCCGAANCTCTCNTCCCGGGACCC |
| ACAGGGAATCNGCNATTTCNCCTACAAATCANCCACCTCCA (SEQ ID NO. 25) |
| Clone Rv111 |
| ::::::::::::Rv111T7.seq:::::::::::: |
| GCATGATCGGCCACCTTTCGGGCCGCCCGGCATACGGCGGCGTACCGATCTCCGCGTCATACACCCGCGGGTAATCGCCGACGGTGCCGGTTCGCGAGCCGAA |
| GGTGACGACTCTGATTGAATCGAGTTCCAGGTCCAGCGGGTGGCGCACCAACGGCGCGAGCTCAACGACGTCAATCNCGTTGTCGCTTTCTACGGTCACCGAC |
| CCTGGTGACCGTAGTTCNCCCG (SEQ ID NO. 26) |
| Clone Rv112 |
| ::::::::::::Rv112SP6.seq:::::::::::: |
| GACACTATAGAATACTCAAGCTTGCCAACCGCCAGCCTGCATCCGGCGGCGANCACTGCTCCGCCGACCAGTACGAACCAACCTGCGGTGCCCAGGCCATTGA |
| CGATGTGCTGGTCGGCGCCCGCGAGTCCGCGCACCATCAACGCCGCGGGCACCACCANGGCGGCCCCACCCTGCACGGCGACGATCATTCCGGCGCCGCTCAC |
| GGCGGGCGGGGCTCGAACANGCACAGCATCAACGTNGTCACCCGGCCGTGACCGGCCCGCATCGTCACACCACCCAAGCCCATTGCCGTCCTCCTCAACNGGG |
| CGACCCGGCCCGCATCGTCACACGGNCTAAGGCCATTGCCGTCCTCCT (SEQ ID NO. 27) |
| ::::::::::::Rv112T7.seq:::::::::::: |
| TCGGCGCCATCGGCACCTTCGAGGACCTGTATTTCGACGCCGTGGCCNACCTGAGGTTGGCGGTGGACNAAGTGTGCACCCGGTTGATTCGCTCGGCCTTGCC |
| GGATGCCACCCNGCGCCTGGTGGTCGATCCGCNAANAGACAANTTGTGGTGGANGCTTCTGCTGCCTGCGACACCCACNACGTGGTGGCACCGGGCAGCTTTA |
| GCTGGCATGTCCTGACCGCGCTGGCCGACNACTCCAGACNTTCCACNAANGGTCGCCNNCCCAATGTNCCGNANTGTCTCCGGNTCCCTTTACCNCCCAATGG |
| GCNGNTTCCACNGGTTACGGGCCCCNTNCCGGCGGGTCTNCCTCCCAANCTACCAAATACGCCCGACNTTCCGGA (SEQ ID NO. 28) |
| Clone Rv113 |

TABLE 3-continued

End sequences of the polynucleotide inserts cloned in the named recombinant

::::::::::::Rv113SP6.seq::::::::::::
ATACTCAAGCTTTTATGGTGATCGCGCATCACCTGGTTCATGAACTGGAAGCAGCGCAGCGCTTCCTTTTCGGCCGCAACATGAGCCAGCCTCTCGTCGGCGG TCGGGTGCAGGTGCTCGGGCAGCTCGGCCGCGAACAGCCCGGCTTGAACCCTGAAAACCNGCTTTCCATATCCCGCGACGAAAGAACGCCAGTTCCGCTACTT

AACCCCTCCGCGAACCGTCCATGGACAACAGCGCGTTCTCCACCAACCGGGCCCGGGTGT (SEQ ID NO. 29)

::::::::::::Rv113T7.seq::::::::::::
TCGGCTCAGGCCGCGCTGCTGGTAGAGTCGCTGACCGGTGCAGGTTTCGACAATGTGGTGCCGGTTCGGCGGCTACGTGCCATCGAGACACTGGCGCAGGCTA TCGCACCCGTTATCGGCTACGAAGCAAATCGCGGTATGCGTTCTTGAGCATGAGTCGGCGACCGTCGTCATGGTCGACACCCACGACGGAAAGACGCAGATCG CCGTCAAGCATGTGTGCCGCGGATTATCAGGACTGACCTCCTGGCTGACCGGCATGTTTGGTCGCGATGCCTGGCGCCCGGCCGGCGTGGTCGTGGTCGGCTC GGATAGCGAGGTCAGCGAATTCTCGTGGCAGCTCGAAAGGGTCCTGCCGGTGCCGGTCTTTGCGCAAACAATAGCGCAGGTTACGGTCGCGCGGGGTGCGGCC

TGGCGGCGGCC (SEQ ID NO. 30)

Clone Rv114
::::::::::::Rv114SP6.seq::::::::::::
CAAGCTATTTAGGTGACACTATAGAATACTCAAGCTTCGCGTCTACGCCGGCCCGGAGCATCCGCACAGCGCTCAGCAGCCGGTTCCGTACGANCTCAAGCAG GTGGCGCAATGACCGAAACCACCCCAGCCCCGCAAACCCCGGCGGCCCCGGCCGGGCCCGCACAATCGTTCGTGTTGGAGCGGCCCATCCANACCGTTGGGCG CCGTAAGGANGCCGTGGTACGAATGCGGCTGGTGCCCGGCACCGGCAAGTTCGACCTCAACGGCCGCAGCTTGGANGACTACTTCCCAAACAAGGTGCACCAG CAGTTGATCAAGGCACCCCTGGTCACCGTGGATCGGGTGGAAAGTTTCGACATCTTTGCCCACCTGGGCGGCGGCGGCCGTCCGGTCAGGCCGGGCCTGCCCT

GGGTATCGCCCGGGCATTGATTCTGGTATCCCCNGAAGAACCG (SEQ ID NO. 31)

::::::::::::Rv114T7.seq:::::::::::
CGGTTGGCCACCGCTTCTGCGGTGCCGCCGCCGTCGACAATGACCGTGTCGTCCTTGCTGACCACCACGCGTCGGGCCGAGCCCAGCACCTCCAAGCCCACCT CGCGCAGCACCATGCCGGCGTCGGGGTTGACCACCTGGCCACCCGTCACCACCGCCAGGTCCTCAAGGAAACGCCTTACGGCGGTCACCGAAGTACGGCCCCT TGACCGCGACCGCTTTCAACGTCTTGCGAATCGCGTTGACGACCAGCGTCGCCAACGCTTCGCCCTCCACGTCTTCAGCCACGATCAGTAGTGGCTTACCCGT

TCCTGCAACCTTTTCCAGCAATGGCAACAGATCGGGAAGCGANCTGATCTTGTCTTGGTGCN (SEQ ID NO. 32)

Clone Rv115
::::::::::::Rv115SP6.seq:::::::::::
CCAAGCTATTTAGGTGACACTATAGAATACTCAAGCTTTTGGCTGGGTCGCCTTCGAATTCNGCGTGCACCGCTATGGGTTGCANCAGCGGCTGGCGCCGCAC ACCCCACTGGCCCGGGTGTTTTCGCCCCGAACCCGGATCATGGTGAGCGAAAAGGANATTCNCCTGTTCGATGCTGGGATTCGCCACGCCAAGGCATCTANCG ATTACTCTCCNCGGGGTGGGAAAAGTGCCCAATCCCCCTCCCTCCAACTTTCCNAACAATCATTCCGGTTCCNCCNTCCGGTTGGNGGTAACCNNCCAATAAA

ACCCCTGCCCG (SEQ ID NO. 33)

::::::::::::Rv115T7.seq:::::::::::
GCCCGCNCATGGCCAATCCCCGAAGACATCATTGGCCAGTGGCCGGGCGCTAACAGGTTCCAGCCCCCCACCANTGCCGCTCGAACATGCGGTGCAACCCATT CGCAGGCCGGCAGGGAAAGCACCGCGGAAGCCGCAAAGGGCTGCAGTTCCGCGCCCAATAATGTCGTCCGCAACCAGATGCGCTCNAAAACCNCNCCGGCAGT CAGCGCACCCGACGCGANGTCGAAAGACGTCNTCAGCGCGCCCACATGGGGTGCCAATCGGCACGGCAGGTATGCCGCGCGCAACCCGAGCGCGTGGTGCATG CCCACGGTCCGCANGANGCGANCACCCGCCAATGCCAANCCCACGAAACATCGGGCGCATCCACCTTCAACC (SEQ ID NO. 34)

Clone Rv116
::::::::::::Rv116SP6.seq:::::::::::
ATACTCAAGCTTGCCCAGCCGTCGATGACAAGAAATATGTCCGCAAAAGACTCAGCGGCCGACTTTGCTCGCAGCTGGCGGTACCGCGCCACCGAGTCGATGC CGTGGTCGCGGAAGAATGCCTCCCGAATTCGCACGGCCAATTCCATTCCGGGAAGCATCCGCAATGCCAGCTGCGGTTGCCCCCTGCCGGCCACGGCACCCAC TTGCGGCATTGCGTCCACCTGGGCCAGCGCCCCGCCGCCAAATTCCAAACAATAAAAATTGCACCCGGC (SEQ ID NO. 35)

::::::::::::Rv116T7.seq:::::::::::
CCACCCGTGTATTTTGGGATGGGCAAAAAGGCGAAGCACCGCGTGGCCACGAACGCCGGGAGGGACAATCTCGGGCGGCTAGGGCTTCTCGCGGGAAGGCCCG AACGTACGGCGTTTCAACACGTCGCGTCGCCCTCCGACCGCGAACATTCGGGGATGGCAGCAACCTGGTAGCACCCTGGCCGGGCGATGATCTGCAGCGTCGC CGCGGGTAGTCGCCGCCCGGGCGGCTACAGTCTGAAACGCGATGACCATCGATGTGTGGATGCAGCATCCGACGCAACGGTTCCTACACGGCGATATGTTCGC

CTCCCTGCCCCGT (SEQ ID NO. 36)

Clone Rv117
::::::::::::Rv117SP6D2.seq::::::::::::

TABLE 3-continued

| End sequences of the polynucleotide inserts cloned in the named recombinant |
|---|

CTGCCCATGTTTGGGGACGCCCGACCAGCCGATGCTGGAGGCCTACACGGCCCTTGGTGCGCTGGCCACGGCGACCGAGCGGCTGCAACTGGGCGCGTTGGTG

ACCGGCAATACCTACCGCAGCCNGACCCCTNTCNCAANAGGATNTTGTTCGCCGGACCCCNCTC (SEQ ID NO. 37)

::::::::::::Rv117T7D4.seq:::::::::::
CCGACTTTCCGCGGTACCCGCTCAACTTTGTGTCGACCCTCAACGCCATTGCCGGCACCTACTACGTGCACTCCAACTACTTCATCCTGACGCCGGAACAAAT TGACGCAGCGGTTCCGCTGACCAATACGGTCGGTCCCACGATGACCCAGTACTACATCATTCGCACGGAGAACCTGCCGCTGCTAGAGCCACTGCGATCGGTG CCGATCGTGGGGAACCCACTGGCGAACCTGGTTCAACCAAACTTGAAGGTGATTGTTAACCTGGGCTACGCGACCGCCTTT (SEQ ID NO. 38)

Clone Rv118
::::::::::::Rv118SP6.seq:::::::::::
ATACTCAAGCTTTGTCACACCAAGTGTTTCGACCAGGCGCTCCATCCGGCGAGTGGATACTCCCAGCAGGTAGCAGGTCGCCACCACGCTGGTCAGTGCGCGT TCAGCTCGCTTGCGGCGCTGCAGCAGCCATTCGGGGAAATACCTGCCCTGGCGCAGCTGGGGGATCCCAACTTCAATGGTTGCGGCACGGGTGTCAAATTCAC GGTGGCGGTAGCCGTTGCCCTAATTGGACCGCTCATCGCTGCTTTCGCGGTACCCCGCCCCGCACAGGGCTTCGGCTTCAGCCCCCATCAGGGCGGCAATAAA

CTTCAAGAGCACC (SEQ ID NO. 39)

::::::::::::Rv1118T7.seq:::::::::::
GAGGCAGCTTCGCCGGCAATTCTACTAGCGAGAAGTCTGGCCCGATACGGATCTGACCGAAGTCGCTGCGGTGCAGCCCACCCTCATTGGCGATGGCGCCGAC GATGGCGCCTGGACCGATCTTGTGCCGCTTGCCGACGGCGACGCGGTAGGTGGTCAAGTCCGGTCTACGCTTGGGCCTTTGCGGACGGTCCCGACGCTGGTCG CGGTTGCGCCGCGAAAGCGGCGGGTCGGGTGCCATCAGGAATGCCTCACCGCCGCGGCACTGCACGGCCAGTGCCGCGGCGATGTCAGCCATCGGGACATCAT GCTCGCGTTCATACTCCTCGACCAGTCGGCGGAACAGCTCGATTCCCGGACCGCCCAGCGCATTGGTGATGGAATCGGCGAACTTGGCCACCCGCTGGGTGTT

GACATCCTCGACGGTGGGCAATTGCGCCTCGGTAAGCTTTGCCGCGTAGCCTTTTCATC (SEQ ID NO. 40)

Clone Rv119
::::::::::::Rv119SP6.seq:::::::::::
ATACTCAAGCTTCACTGACAAGGGACGAATTCGTCGGCCGCCTGTTCGACTGGGTGGTGGCCGAGCTGGTCGCCACCACTCAGGCCGCGGTCACGGCGGTACC GGCGCGGGAGCAAACTCGCGCGGGCATGGCCAACTTCTTGCGGACCATCACCGCAGACGCCCGCTTCGGACCCCTGCTGTCCACCACACAGTTGGCCAACGCA

TTAATCACCCGCAAGCTTGCGGAATCCACCGCCCTGTTCGC (SEQ ID NO. 41)

::::::::::::Rv119T7.seq:::::::::::
TCCATCACCCGATGTGGCNGGAGCACTGCCATGTCGATCTCAACTACCACCTCCGGCCGTGGCGGTTGCGCGCCCCGGGGGGTCCGCGCGAACTCGACGAGGC GGTCGGAGAAATCGCCANCACCCCGCTGAACCGCGACCACCCGCTGTGGGAGATGTACTTCGTTGAGGGGCTTGCCAACCACCGGATCGCGGTGGTTGCCAAA ATTCACCATGCGTTGGCTGACGGTGTTGCCTCGGCAAACATGATGGCACGGGGGATGGATCTGCCGCCGGGACCGGAGGTCGGCCGCTATGTGCCTGACCCCG

CTCCTACCAAGCGGCA (SEQ ID NO. 42)

Clone Rv11
::::::::::::Rv11SP6.seq:::::::::::
AGCTTTGCAGTTGCTGAGTAATGTCGGCCAACGTCACCACAACCGCGATGAATTCAATCATGCCGCCCAGGGCGGCCAACCCAATGGTGGCCGCGAGCGGCAG CTCGATCGCAGCGCGGAGGTTGCCGGCCGCCAGTTGATTCACGAACAGGGTGAGGTCATAGGCGGGCAGGATAGTGACGAAGGCAAGACCTCCATCTGCCGTC

GGAAGAAGTATCGAG (SEQ ID NO. 43)

::::::::::::Rv11T7.seq:::::::::::
AGCTTCAGAACAGGCCTGTTGTGGGCGCACCCGGCTCGCCGAGTTCTGCACGCACCGCCTCAAGTGCGGCCCGCACCGCCGGCATCTCCCGGTCACGCAGGGC CGCGGCCCGCGCCGCAGCGACGGCGTGTTCGCGCAGTTCGCCGTCAATGATGCTGACCTGATCGGCCACCCGGGCGTTCTCGGCGTCGTCGCGTTCACTAATC GCGGTGCTCAGCAGCGTCTCGACAGCCACCACCCGAGTGGCGACCAGCTGCTCCACCACGGACCGCAGCGATGCCCGTC (SEQ ID NO. 44)

Clone Rv120
::::::::::::Rv120SP6.seq:::::::::::
ATACTCAAGCTTCAGTTCCTCCACGACGCGTTCCCAAATGAATTTCCCGATCCCACAATCTCGGTTCAGATACAGGTCGCCATACCCCTTACTTCGGCAACGC TGGGCGGATTGGCCCTGCCGCTGCACCAAACCATCAACGCCTTCAAATTGCCGGCAATCTCGTTCAGCCAATCCAT (SEQ ID NO. 45)

::::::::::::Rv120T7.seq::::::::::::
GCTCTACGCCGCCTACGGGTCGAACATGCATCCCGAGCAGATGCTCGAGCGCGCACCCCACTCGCCGATGGCCGGAACCGGCTGGTTACCCGGGTGGCGGCTG ACGTTCGGCGGCGAGGACATCNGCTGGGAAGGGGCGCTTGCCACCGTCGTCNAAGACCCAAATTCGAAGGTGTTCGTCGTGCTCTACGACATGACCCCGGCGG ACGAGAAGAACCTTGACCGGTGGGAAGGCTCCGAGTTCGGTATCCACCAGAAGATCCGATGCCGCGTGGAGCGCATTTCCTCGGACACCACAACGGGATCCCG TABLE 3-continued End sequences of the polynucleotide inserts cloned in the named recombinant

TCCTCG (SEQ ID NO. 46)

Clone Rv121
::::::::::::Rv121SP6.seq::::::::::::
ATACTCAAGCTTGCCAAAGAGACCTCGTCCACCAAGCAGGACGCGACCGTCGAGGTGGCGATCCGGCTTGGCGTCGACCCGCGTAAGGCAAACCAGATGGTTC GCGGCACGGTCAACCTGCCCACACCGGCACTGGTTAAGAACTGCCCGCGTCGCGGTTTTCGCGGTTGGTGAAAAGGCCAATGCCTGCGTTTGCCGTGGGGGCG GATGTTGTCGGAGTGACAATCTGATCAAAAGGATTCAGGGCGGTTGGCTGGAATTCAATGCCGCAATCGCGACACCGG (SEQ ID NO. 47)

::::::::::::Rv121T7.seq::::::::::::
CCACGGCGTGGATCAAGGTACCGGCCGGGATGTTGCGCAATGGCAGGTTGTTGCCCGGCTTGATGTCGGCGTTAGCGCCGGATTCCACCACATCCCCTTGCGA AAGTCCGTTGGGTGCAATGATGTAGCGCTTCTCCCCATCGAGATAGTGGAGCAACGCAATCCGTGCGGTACGGTTCGGGTCGTACTCGATGTGCGCGACCTTG GCGTTGACACCATCTTTGTCATTGCGGCGAAAGTCGATCATCCGGTAAGCGCGCTTATGACCGCCGCCTTTGTGCCGGGTGGTAATCCGGCCATGCGCGTTGC

GTCCACCGCGACGTGCAGCGGGCGCACCAGCGACTTCTCCGGGGTTGACCGGGTNATCTC (SEQ ID NO. 48)

Clone Rv122
::::::::::::Rv122SP6D2.seq:::::::::::
GCAGCATGACGGCGGTAGCGAACACCGCCGGATGCAGCGCAAGTAGCGTCGATGTGCTCACGGAATCGCCCCGGCACCGCGATCTCGANGATCACCAGTGCCA CCCCCTGCAGCGCNACACCGACGATTCCGTACACCGCCACGCCGATCAGGCCCTGGGCCATCTGATTGGAGCTGGCGTANATGGCGGCGATGGTGACGATGGC CAGCGCCACATACATTGTGGCGGCCAGAACCACGGCGTTGGGGCGGCGGTCGATGAACACTAGGCGACGCAGATCGCCCGGGGTCAACAGGTTGACCATCAGA AAGCCTGCGACTAGCACGGCGGCGCCACTAGGAAGTACAAGAANGTGGCCACCACCCCATGCAGGATCGGGGTAAGGCTGATGGTCCCGAAATCGACTCCGGC

CTAATACATGACTCTCTCCTTTGCGTCATCGCCTTACTTGTGCGCGGAA (SEQ ID NO. 49)

Clone Rv
::::::::::::Rv123SP6D2.seq:::::::::::
GGGACACACCTCGATGCTGCCGCNATGGACGCGGTCGAACGCAAGCAGCTGATCGAGCTACAACGCCGCGCGGAACGCTTCCGCCGCGGGCGTGACGCATCCC

GTTGACCGGCCGGANCNCTCTCTA (SEQ ID NO. 50)

::::::::::::Rv123T7D4.seq:::::::::::
TGGGCGCCTCTTTCGGCCTTCCCNNTTTAAACGNAGCANGACATTCTGGGTATCGAGTTGTACTGGATGGTGTTGGCGATGTCGGTGATCCTGCTCCTGGCGG TGGGATCCGACTACAATCTGCTGCTGATTTCCCGGTTGAAAGAGGAAATTGGGGCCGGATTGAACACCGGAATTATCCGTGCCATGGCTGGTACCGGGGGAGT GGTGACGGCTGCCGGCATGGTGTTCGCCGTTACCATGTCGTTGTTTGTGTTCAGCGATTTGCGAATTATTGGTCAGATCGGTACCACCATCGCCTTCCC (SEQ ID NO. 51)

Clone Rv124
::::::::::::Rv124SP6D2.seq:::::::::::
CCGATCGGCGCCGCANCTGGTTGGTGTTNCGGATGAATCCGCAGCGAAAATGTAGCTGCGGTGGCGTGTCGTGACTCGTNGGCGTCGACGCTCGTGGCAGCCA CCGANCGGTTGGTCCAGGATCTGGATGGGCAAAGTTGTGCGGCCCGGCCGGTGACGGCCGATGAGCTGACCGAGGTCGACAGCGCCGTGTTGGCTGACTTGGA ACCGACATGGAGTCGCCCCGGTTGGCGTCACCTCAAGCATTTCAATGGTTATGCGACCAGTTTTTGGGTTACGCCGTCAGACATCACGTCGGAGACTTGGATG AGCTGTGTCTGCCAGATAGCCCCGAATCGGGACGACCGTGGTCACGGTGCGTCTGACCACTCGGGTCGGGTCGCCCGCGCTATCGGCATGGGTGCGTNATCAC

AGCGACACGCGCCTGCCCAAGGANGTNCGGNCGGACC (SEQ ID NO. 52)

::::::::::::Rv124T7D4.seq:::::::::::
CGGGTTGCGGATCCACGCGTGCGGGTTGTCAGCAGCTACGGCACTGAACCGCGCCCACAGCTCGCCGATCCGCTTTCGGTGGTTCTCGATCGACTCGCCGTAG

GCGATGCGCAGCGCCTGCTCGAATATCGGGTACACGTAGGCCGGCCTTCCCNCTTTA (SEQ ID NO. 53)

Clone Rv126
::::::::::::Rv126SP6.seq:::::::::::
CTTGATTTTGATCATCATGACGATCATCACCCTAATTTTGCTACCCGCACTGGTTATCGTGGGTACCGTCGTGCTTTCCATGGGCGCCTCTTTCGGGCTTTCC GTATTGGTCTGGCAGGACATTCTGGGTATCGATTTGTACTGGATGGTGTTGGCGATGTCGGTGATCCTGCTCCTGGCGGTGGGATCCGACTACAATCTGCTGC TGATTTCCCGGTTGAAAAAGGAAATTGGGGCCGGATTGAACACCGGAATTATCCGTGCCATGGCTGGTACCGGGGGAGTGGTGACGGCTGCCGGCATGGTGT (SEQ ID NO. 54)

::::::::::::Rv126T7.seq:::::::::::
GGGGATCCCTAGATCGACCTGCAGGCATGCAAGCTTGGCGTGTCGTTCCAACCCGAATTGGCTTTCGGCGCCATCGGTGAGGCGGGACACACCTCGATGCTGC CGCCATGGACGCGGTCGAACGCAAGCAGCTGATCGAGCTACAACGCCGCGCGGAACGCTTCCGCCGCGGGCGTGACCGCATCCCGTTGACCGGGCGGATCGCG TABLE 3-continued End sequences of the polynucleotide inserts cloned in the named recombinant GTGATCGTCGATGACGGCATCGCCACCGGAGCNACTGTCAAGGCGGCGTGCCAGGTCGCCCGGGCGCACGGTGCGGACAAGGTGGTGCTGGCGGTCCCGATCG GCCCAGACGACATCGTGGCGAGATTCGNCGGGTACGCCGATGAGGTGGTGTGTTTGGCGACGCCGGCGTNGTTCTTCGCCGNCGGGCANGGTTACCGCAACTT

CACCCAGACCTCCGACGACGAGGTGGTGGCGTCTCCTGGATCGTGCTC (SEQ ID NO. 55)

Clone Rv127
::::::::::::Rv127SP6.seq:::::::::::
AAGGCTGCAGGTCGAAGCGGNTGGTTACGACTCCCTGTGTGTGATGGACCAGTTCTACTATCTGCGTCTACACGGCCCTTGGTGCGCTGGCCACGGCGACCGA GCGGCTGCAACTGGGCGCGTTGGTGACCGGCAATACCTACCGCAGCCCCGACCCTGCTGGCAAAGATNATCACCACGCTCGACGTGGTTAGCGCCGGTCGAGC GATCCTCGGCATTGGAGCCGGCGGGTTTGAACTGGAACACCGCCAGCTCGGCTTCGAGTCCGGCACTTCCAGTGACCGGTTCAACCGGCTCGA (SEQ ID NO. 56)

::::::::::::Rv127T7.seq:::::::::::
CTTTCCGCGGTACCCGCTCAACTTTGTGTCGACCCTCAACGCCATTGCCGGCACCTACTACGTGCACTCCAACTACTTCATCCTGACGCCGGAACAAATTGAC GCNGCGGTTCCGCTGACCAATACGGTCGGTCCCACGATGACCCAGTACTACATCATTCGCACGGAGAACCTGCCGCTGCTACAGCCACTGCGATCGGTGCCGA TCGTGGGGAACCCACTGGCGAACCTGGTTCAACCAAACTTGAAGGTGATTGTTAACCTGGGCTACGGCGACCCGGCCTATGGTTATTCGACCTCGCCGNCCAA

TGTTGCGACTCCGTTCGGGTTGTTCCAGANGTCAGCCCGGTCGTCATCGCCGACGCTCTCGTCN (SEQ ID NO. 57)

Clone Rv128
::::::::::::Rv12SP6.seq:::::::::::
CGGTCATAGCCCTCGGGTCCGGCCAGCACTCCGCAGGCTTCGTCGGGGTGGTCGCGACGCGCATGGGCCACCATCGCATTCACCAGGTCTGCGCGAATCACCA GCACGTAGACGGTTCCTTTCCTAAGCAACACCGAAGTTTCACGACCCGAATGCTCCGGGAAACATGTCACGGTAGGTCGGTATTCCGGCTACCGGCTGAGCAT TGAGCACGCCGGCCAGCACCGCACGAGCCAGGCAATCAGCCGCCGCCGCACCGATCGCGGTGACCAGCTGAGTCTCCGGAGACAATGCGGCCGGCACGCCGGN

CTCCGGCGGCACCGCTACNGCGCCCGTGG (SEQ ID NO. 58)

::::::::::::Rv128T7.seq:::::::::::
GTGATGGCACGCCACCGCGACACCACCCGGCTGCGCTACNTCGAGCCATACCGGGCGGAGCTACATCGGCTCGGCCGCCCAGTGTTCGGGCCCTCTTTCGAGG TCGAGGTCGATACCGATTTGCGCATCCGCANCCGCNCCCTGGACGACAGAACCGTGCCCTACGAGTGCTTGTCGGGCGGGGCCAAAGAACAGCTTGGCATCCT GGCGCGATTGGCCGGCGCGGCGCTGGTCGCCAAGGACGACGCCGTTCCGGTGCTGATCGACGACGCGCTGGGGTTCACCGATCCGGAGCGACTATCAAGATGG GGGAGGTCTCTGACACCATCGGCCCCNACGGACATGTGATCGTGCCGACGTGCAGTCCCACCCCG (SEQ ID NO. 59)

Clone Rv129
::::::::::::Rv129SP6.seq:::::::::::
GCGAAAGTCCGTTGGGTGCAATGATGTAGCGCTTCTCCCCATCGAGATAGTGGAGCAACGCAATCCGTGCGGTACGGTTCGGGTCGTACTCGATGTGCGCGAC CTTGGCGTTGACACCATCTTTGTCATTGCGGCGAAAGTCGATCATCCGGTNNGCGCGCTTATGACCGCCGCCTTTGTGCCGGGTGGTAATCCGGCCATGCGCG TTGCGTCCACCGCGACCGTGCAGCGGGCGCACCAGCGACTTCTCCGGGGTTGACCGGGTGATCTCGGCGAAATCAGATACGCTGGCGCCGCGACGACCAGGCG TCGTGGGCTTGTNCTTGCGAATTGNCATGTCTAATCANGTCTTTCTCTCACGCTCTCGTCGCCGGGCTAGGCCGCATTGCCCTGCTCCTCCTCATCGCTTCGC

TCTGCATCGTCCCCGGGCTAAGCCCGTGCCCCGAAA (SEQ ID NO. 60)

::::::::::::Rv129T7.seq:::::::::::
GATGGTTCGCGGCACGGTCAACCTGCCACACGGCACTGGTAAGACTGCCCGCGTCGCGGTATTCGCGGTTGGTGAAAAGGCCGATGCTGCCGTTGCCGCGGGG GCGGATGTTGTCGGGAGTGACGATCTGATCGAGAGGATTCAGGGCGGCTGGCTGGAATTCGATGCCGCGATCGCGAACACCGGATCAGAATGGCCAAAGTCGG TCGCATCGCTCGGGTGCTGGGTCCGCGCGGCCTGATGCCCAACCCGAAAACCGGCACCGTCACCGCCGACTCCCCATGGCGTCCCGGATATCAAGGGCCGGCA

AATCAACTTCCCGGTTGATCAGCAAGGCAACCTGCCTCCNCCTCCGG (SEQ ID NO. 61)

Clone Rv130
::::::::::::Rv130P6.seq:::::::::::
ATACTCAAGCTTCGTCATAAGACCATGGTGCGCTTTCTTTCACCCGTCCAGAGTCGGGGGCATCCGCACCGGCTCGCATCGCATCATCCTCCCACGACGGGCC GCTCATCAGCTTGGGCCATTTCAATGTACTTGATACCCCGCGCTGCGGGTAGGCCACTGCGACAATTCAAACACGGTGTCACACGGTGAATAGTGTCGAGATG GGCTCTGATCAACCGTCGCAAACCCGGTTTCGCATCAATAGCGGAATCCCACCGGGTTGCATGGAGGCTGCTGACCTTGGAAAACAAAATTTTTTCATTACAA

CAAAACAACCGCCNCGGAAACTTTGCA (SEQ ID NO. 62)

::::::::::::Rv130T7.seq:::::::::::

TABLE 3-continued

End sequences of the polynucleotide inserts cloned in the named recombinant

CGAATTCGGCGTGCACCGCTATGGGTTGCAGCAGCGGCTGGCGCCGCACACCCCACTGGCCCGGGTGTTTTCGCCCCGAACCCGGATCATGGTGAGCGAAAAG

GAGATTCGCCTGTTCGATGCTGGGATTCGCCACCGCGAGGCCATCGACCGATTACTCGCCACCGGGGTGCGAGAGGTGCCGCAGTCCCGCTCCGTCGACGTCT

CCGACGATCCATCCGGCTTCCGCCGTCGGGTGGCGGTAGCCGTCGATGAAATCGCTGCCGGCCGCTACCTGCAAGGTGATTCTGTCCCGTTGTGTCGAAGTGC

CTTTCGCGATCGACTTTCCGTTGACCTACCGGCTGGGGCGTCGGCACAACACCCCGGTGAGGTCGTTTTTGTTGCAGTTGGGCGGAATCCGTGCTCTGGGTTA

CAGCCCCGAACTCGTCACGGCGGTGCGCGCCGACGGAGTTGTTATCACCGATCCGTTGGCCGTACCGCGCCTTGGGC (SEQ ID NO. 63)

Clone Rv132
::::::::::::Rv132SP6.seq:::::::::::
TCAGACTCCACCCAGCCAGCAGGCAGCGCGAAGCTGAATCCTCCAACCGGGTTGTCGATCCGGACAGGTTGGGGTGCGTTTGGGGCAATGACAGGTGGCGGCG GTGCGTTCGGGTCGGCCGGCGGAGGTGCTGCGTTGGGATCGCCCGGCTGGGCATTCNGCGTGTTGGCGGCGGCCGGTGGTGGGGGGGCAACAGGTGTCGCCGG TGCGGGTGGCGCTGCAGCGGTCGACGGCGGCGAAGCGGCCGTTGTGGGTACCGGGGGCGCTGGCTCCGGATCGGCGTTGGCGGTCGCGGGCACCGCAACGGTC ACCAAGCTGGCGCTGGCCATCGCCGCGATAGCCAGTGCCGCCAATCGTCCCTTGCGACGTGTCAAGTNGGGGTCCACCTGATGCATGGCCAAAGAACCTACCG

TGTTAACGGCNCAACNCAAGGACCGCGCCGGTCGCN (SEQ ID NO. 64)

::::::::::::Rv132T7.seq:::::::::::
TTTCCGCGGTACCCGCTCAACTTTGTGTCNACCCTCAACGCCATTGCCGGCACCTACTACGTNCACTCCAACTACTTCATCCTGACGCCGGAACAAATTGACG CAGCGGGTCCGCTGAACAATTCGGTCCGTCCCACGAAAGAACCAGTTTTNCNTCTTTCNCACGGAGAACCTGCCGCTGCTAGAGCCACTGCGATCGGTGCCGA TCGTGGGGAACCCACTGGCGAACCTGTGTTTCAACCAACACTTAGAGTGTAATTGTAAACCTGGGCTAGGGGAAACCGGCTCTAGTTTTTCCACCNTCTCCGC

CCCNTGTTTCGAATACTCCGTTCGGGTTGTCCCCAAA (SEQ ID NO. 65)

Clone Rv134
::::::::::::Rv134SP6.seq:::::::::::
GCTTCCGGCTCGTATGTTGTGTGGAATTGTGACCGGATACCAATTTCACACAGGAAACAGCTATGACCATGATTACGCCAAGCTAGTTAGGTGACACTATACA ATACTCAAGCTTGCCGGCTGGTGGGCCGACCACTTCGATGGCACGACCCGTGAACTGCTGCCCGGCCAATTCTTCTTGGTCGCCCGGACCGATGGACCGCGGC TGGGATTCCAGAAGGTGCCCGATCCCGCCCCTGGGAAAAACCGCGTGCACCTCTACTTCACGACCAACGAC (SEQ ID NO. 66)

::::::::::::Rv134T7.seq:::::::::::
CCGATCGACTGATGCGCCGACAACCACGCCCCAACAACTGGAATGAACCGTCGTGACCATCATCAGCACGCGGTTGTAGGCGACTTGCGACATGTTCAACCCG CCGTACTCGGACGGAATCTTCAAACCGAAACAGCCCAGCTCGGCCAGGCCTTTCACGTACTCGTCGGGGATCTGGGCACCACGCTCGAGGACGCTGCCGTCCA CGGTGTCTAGGAATTCCCGCAGTTTGACCAGAAACGCCTCGGTTCGGGCCTCCTCGGCGTCCGACGGCTTGGGAAATGGGTGTATGAGCCCTACGGGAAACCG GCCCACAAAGAGTTCTTTGGCGAAGGACGGTTTATCCCAACCACTTTCGCGAGATTCCTCGGCAAGGGCCCGCGCTTGCTCCTCGGTGACCTGAGTTTGCTGT

GCCATCGCCGCCTCCTCCCTGA (SEQ ID NO. 67)

Clone Rv135
::::::::::::Rv13SP6.seq:::::::::::
TGCATCCGGCTCGTATGTTGTGTGGAATTGTGAGCGGATAACAATTTCACACAGGAAACAGCTATGACCATGATTACGCCAAGCTATTTAGGTGACACTATAG AATACTCAAGCTTTTACGGTGATCGCGCATCACCTGGTTCATGAACTGGAAGCAGCGCAGCGCTTCCTTTTCGGCCGCAACATGAGCCAGCCTCTCGTCGGCG GTCGGGTGCAGGTGCTCGGGCAGCTCGGCCGCGACAGCCGCCTGACCCTGAAACCAGCTTCCATATCCCGCGACGAACGACGCCAGTCCGCTACGTAACCCCT CCGCGACTGTCCATGGACAACAGCGCGTTCTCCACCGACCGGGCCCGGGTGTGGGGTGTTTCGGCGACCGGCAGCCAGGTGGTCCACACTGCCGACGGGCGCC

GCGAGCCGTTCACCGACCAGGCCGCCGAGCAAGTCCGCCCGAT

ACTCC (SEQ ID NO. 68)

::::::::::::Rv135T7.seq:::::::::::
GGGGGCGCTGCTGGTATAGTCGCTGACCGGTGCAGGTTTCGACAATGTGGTGCCGGTTCGGCGGCTACGTGCCATCGAGACACTGGCGCAGGCTATCGCACCC GTTATCGGCTACGAGCAAATCGCGGTATGCGTTCTTGAGCATGAGTCGGCGACCGTCGTCATGGTCGACACCCACGACGGAAAGACGCAGATCGCCGTCAAGC ATGTGTGCCGCGGATTATCAGGACTGACCTCCTGGCTGACCGGCATGTTTGGTCGCGATGCCTGGCGCCCGGCCGGCGTGGTCGTGGTCGGCTCGGATAGCGA GGTCAGCGAATTCTCGTGGCAGCTCGAAAGGGTCCTGCCGGTGCCGGTCTTTGCGCAAACGATGGCGCAGGTTACGGTCGCGCGGGGTGCGGCCTGGCGGCGG

CCAGAGCACGAGTTCACCGATGCGCAGCTAGTGGCGACAGCGTCAGCCAAC (SEQ ID NO. 69)

Clone Rv136
::::::::::::Rv136SP6.seq:::::::::::

TABLE 3-continued

| End sequences of the polynucleotide inserts cloned in the named recombinant |
| --- |

TGCTTCCGGCTCGTATGTTGTGTGGAATTGTGAGCGGATAACAATTTCACACAGGAAACAGCTATGACCATGATTACGCCAAGCTATTTAGGTGACACTATAG

AATACTCAAGCTTCCGTACAGGTCGCCTCCAACACGGCGGGGAAGCGACACCAGCCTACCGAGCTTGGAGTCCAGGACGCCAGCGGCGGCGTCGGTCTGCGTC

GTGGTGCCGCCGGGGTGGCGTTGGCTGGCAACGATCTCCACCCAGCCGGTCGGGTTACCCACGATCTCGGCATAGACGCGGGCCGAGGCCGGTGCGATACCGT

ATTGCGTCAATTGGGACGCGGTTGTGCATTCGGCTAGCTCGGTTGCCACACCCGTCAGGGGTTCGACGTTGGCGGGTTCGGCGGCCCCAGCACCGCTGTCAC

CATGCCCGCCAAGCCGACCTGCGGCGCCACCAACT (SEQ ID NO. 70)

::::::::::::Rv136T7.seq:::::::::::
CGGCATGACCACCGACAGGCCCGACTGGTCGTACCACTCGAACGCCGGGGTGTTGATGTCCCAGCCGCTGAAGTCGTCCTGCGCGCGCAGGCCGTCGAGCAGG TACAGGGCGGGCGAGTTGGCACCACCACTTTGGAATTGGACCTTGATGTCACGGCCCATCGACGGCGACGGCACCTGCAGGTACTCCACCGGCAAGCCCGGCC GGGAAAATGCCCCCGCGGTCGCCGTGCCACCGACGGCGCCGACCAGACCCGACACTAGGGCCGCGCCGACGGCCCCGACCACGAGTCGACGCGACATACCCGT GACGGCGCCACGAACCCTGTCAACAAGCTGCATTCTTGCTTCCCTCATCCTCATCTCAACGCATCCATGCATGTTTGGGCGCATCCTGAATTANGTCAGACTG

CAGGCGCTGGGCCGGCAGTGCTCGTGTATCAACCACAACTTCGGGCGT (SEQ ID NO. 71)

Clone Rv137
::::::::::::Rv137SP6.seq:::::::::::
TTCCAACCCTAATTGGCTTTCGGCCCCATCCGTGAGGACGGGGTGCGGGTGCTCAACAACAACGTCGTCCGCGGGACACACCTCTATGCTGCCGCCATGGACG CGGTCCAACGCAAGCAGCTGATCGAGCTACAACCCCGCGCGGAACGCTTCCGCCGCGGGCGTGACCGCATCCCGTTGACCGGGCGGATCGCGGTGATCGTCGA TGACGGCATCGCCACCGGAGCGACGGCCAAGGCGGCGTGCCACGTCGCCCGGGCGCACGGTGCGGACAAGGTGGTGCTGGCGGTCCCGATCGGCCCAAACGAC ATCGTGGCGAGATTCGCCGGGTACGCCGATGAGGTGGTGTGTCTGGCGACGCCGGCGTTGTTCTTCGCCCTCGGGCAGGGTTACCGCAACTTCAC (SEQ ID NO. 72)

::::::::::::Rv137T7.seq::::::::::::
CAGGCATGCAAGCTTTCCGCCGATACCCGCCATGTCGCGCACATCCAGGACTTCTGGGGGGATCCGCTGACAGCGGCGGGATCCCAAAGTGCGGATGATCGGG CCGCCTACGTCGTGGTGTACCTCGTCGGTAACAACGAAACCGAAGCGTATGACTCGGTCCACGCGGTGCGGCACATGGTGGACACCACACCGCCACCGCACGG GGTGAAGGCCTATGTCACCGGTCCGGCAGCACTCAATGCCGACCAGGCCGAGGCCGGAGACAAAAGTATCGCTAAGGTCACCGCCGATCACNAGCATGGTGAT CGCAGCAATGTTGCTAGTGATCTATCGCTCCGTAATTACCGCGGTTCTCGTCTTGATCATGGTCGGCATCGACTCGGCCAATCCGCGGATTCATCGCCTTGCT

CGCCGAACACAACATTTTCACCTTTCACATTTGCACCAACCTGCTCTTCTCAT (SEQ ID NO. 73)

Clone Rv138
::::::::::::Rv138SP6.seq::::::::::::
CACTACTCAAGCTCTCTCNTCATTACCACCCCTGTAATTTGGGATGGGCAAAAAGGCGAAGCACCGCTTGGCCACNAACGCCGGGAGGGACAATCTCGGGCGG CTATGGCTTCTCCCGGGAAGGCCCCAACGTACGGCGTTTCAACACGTCGCGTCGCCCTCCGACCGCGAACATTCGGGGATTGGCACCAACCTGNTACCACCCT GGCCGGGCGATGATCTGCAGCGTCGCCGCGGGTAGTCCCCGCCCGGGCGGCTACAGTCTGAAACCCCGATGACCATCGATGTGTGGATGCAGCATCCGACGCA ACGGTTCCTACACGGCGGATATGTTCTCCTCGCTGCGCCGGTGGACCGGTGGGTCTATCCCCTGAACCGACATCCCN (SEQ ID NO. 74)

::::::::::::Rv138T7.seq::::::::::::
CAGGCATGCAAGCTTTCGTCAGTTCATTGCGCCAGCAGACCAACAAGAGCATCGGGACATACGGAGTCAACTACCCGGCCAACGGTGATTTCTTGGCCGCCGC TGACGGCGCGAACGACGCCAGCGACCACATTCAGCAGATGGCCAGCGCGTGCCGGGCCACGAGGTTGGTGCTCGGCGGCTACTCCCAGGGTGCGGCCGTGATC GACATCGTCACCGCCGCACCACTGCCCGGCCTCGGGTTCACGCAGCCGTTGCCGCCCGCAGCGGACGATCACATCGCCGCGATCGCCCTGTTCGGGAATCCCT CGGGCCGCGCTGGCGGGCTGATGAGCGCCCTGACCCCTCAATTCGGGTCCAAGAACATCAACCTCTGCAACAACGGCGACCCATTTGTTCGGACGGCAACCGG

TGGCAACGCACCTAAGCTACTTGCCCGGGATGA (SEQ ID NO. 75)

Clone Rv139
::::::::::::Rv139SP6.seq::::::::::::
GTTTATGCACTGGTTAGGTGTTTCCATGAGTTTCATTCTGAACATCCTTTAATCATTGCTTTGCGTTTTTTTATTAAATCTTGCAATTTACTGCAAAGCAACA ACAAAATCGCAAAGTCATCAAAAAACCGCAAAGTTGTTTAAAATAAGAGCAACACGTACACAAGGAGATAAGAAGAGCACATACCTCAGTCACTTATTATCAC TAGCGCCCGCCGCAGCCGTGTAACCGAGCATAGCGAGCGAACTGGCGAGGAAGCAAAGAAGAACTGTTCTGTCAGATAGCTCTTACGCTCAGCGCAAGAAGAA

ATATCCACCGTGGGGAAAAACTCCAGGTAGAGGTAC (SEQ ID NO. 76)

Clone Rv13
::::::::::::Rv13SP6.seq:::::::::::

TABLE 3-continued

End sequences of the polynucleotide inserts cloned in the named recombinant

ATACTCAAGCTTGGGTGTAGCCGATCACCGGAAGTCNCATGATCAGCCACGTTCCGCGCCGCCCGGCATACGGTGGTGTACCGATCTCCGCGTCATACACCCG

CGGGTAATCGCCGACGGTGCCGGTTCGCGAGCCGAA (SEQ ID NO. 77)

::::::::::::Rv13T7.seq:::::::::::
AGCTTTATCGAAAGCGCGAACAGCTCGCGGCGGCCCACGACGTGCTGCGTCGGATTGCCGGCGGCGAGATCAATTCCAGGCAGCTCCCGGACAATGCGGCTCT GCTGGCCCGCAACGAAGGACTCGAGGTCACCCCGGTGCCCGGGGTCGTGGTGCACCTGCCGATCGCACAGGTTGGCCCACAACCGGCCGCTTGATGCCCGGTC GGCAAGCCCGGCAGTTGCCAAACCCATCGTGATCAGGCTCGGCTCGCGAGTTCGGCGAAGAAATGGTTCGCCTGATCACCTACCATCGGCCA (SEQ ID NO. 78)

Clone Rv140
::::::::::::Rv140SP6.seq::::::::::::
TCAACACGCCGCCAGCCACCACGCGCGGGTCGGGCGCCGGGCCCGGGCCTCCAGGCTNCTCCGCTCGGTGATGGCACGCCACCGCGACACCACCCGGCTGCGC TACGTCGAGCCATACCGGGCGGAGCTACATCGGCCCGGCCGCCCAGTGTTCGGGCCCTCTCGCCCAGGTCGAGGTCGACACCGATTTGCGCATCCGCAGCCGC ACCCTGCGACGACAGAACCGCGGCCCTACCCACTGCTTGTCGGGCGGGGGCCAAAGAACCAGCTTGNCATCCTGCCACAATTGGCCGGCGCCCG (SEQ ID NO. 79)

::::::::::::Rv140T7.seq::::::::::::
CAGGCATGCAAGCTTCACGTCCGTACGGCTCGGGTACGCTTCGGTCGCAGTGTGCGAGTGATAGATGACGACCGGGACCTCGTCGGCATCTTCCATAGCCCGC CACACCTTCAGTTGCTCACCGGAATCCAACCGGTAGAAGGTCGGCCAGCGCTCGGCATTGGTCATCGGGATATGCCGCTCGGGACGGTCAGAGCCCTCGGGTC CGGCCAGCACTCCGCAGGCTTCGTCGGGGTGGTCGCGACGCGCATGGGCCACCATCGCATTCACCAGGTCTGCGCGAATCACCAGCACGTAGACGGTTCCTTT

CCTAAGCAACAC (SEQ ID NO. 80)

Clone Rv141
::::::::::::Rv14SP6.seq:::::::::::
AATATTCAAGCTTTCGGCGGAAACGGACNCCTTGCGAACATTGATAACAAAATAGAAATCATTGATGGTTTGAGTCACCAGGCCGATCAAGCCTTCGCCGAGC CAAATTCCAATCAAGAGGCCCAAGCCCGTACCAATCAGCCCGGCAACGAGGGATTCCGTCNTTATCAGCCNAAATAACTGCTCTCGGGTACCACCCAAACAGC GCAATATGGCGAAAAACGGTCGCCGTTGCACAACATTAAATGTCTCGGTATTGTTGATTAAAAAGATACCCACCACCAGGGCAATCCAACTGAGAGCGGTTAA

ATTGACCGTAAAAACCTCCCGTCATCTGTTT (SEQ ID NO. 81)

::::::::::::Rv141T7.seq::::::::::::
CAGGCATGCAAGCTTGCTGCATCTTCCTGTGACTGCTCCCGAAACCTGGGGGTGTGCCTGCTGTGTATGCACGGCATACGGACATCCTTCCCCTGATACCCGC GGTCGAACCAGCCACGTGTCCATCATCAGGGGTCAACCCCGGCCAAGGGCGACGGCACGCCAAGTTCGCCGACCGTTAACCTAGTGCTGTTAGCTTCATTTGC TGCGAGCAAAACAGCTGGTCGGCCGTTAGGAACTGAATTGAAACTCAACCGATTTGGTGCCGCCGTAAGTGTCCTGTCTGCGGGTGCGCTGGTGTTGTCCGCG TGTGGTAACGACGACAATGTGACCGGGGGAGGTGCAACCACTGGCCAGGCGTCCGCGAAAGTCCATTGCNGGGGGAAGAAGACAC (SEQ ID NO. 82)

Clone Rv142
::::::::::::Rv142IS1081.seq::::::::::::
GAAAGTGCCCCAAGGTGTTGGTGAAACTCGCTGGACGGTCCCCAGGATGTTGGCAGCACATTCACCGGACATGACCGGAGCAAGACCGGACATCCTCCCATAC CGTCGTCGCCGTGTACATCCGTAGCCCGTCCTGGCAGGTGCTGGGTTGAACAAAATCAGCCCAACACCTGCCACGACGAAGAAGCGGGTTGCGCTGGCATGTC TTGTCGGCTCGGCGATCGAATTCTACGAATTCCTTATCTACGGGACCGCTGCGGCGCTGGTGTTTCCCACCGTGTTCTTCCCACACCTGGATCCCACGGTGGC CGCCGTGGCCTCCAAGGGGACATTTGCTGTGGCGTTCCTATCCCGGCCGTTCGGCGCGGCCGTCTTTGGATACTTTGGAGACCGCCTCGGCCGCCAGAAGACC CTGGTCGCCACACTGTTGATCATGGGCCTGGCAACCGTGACTGTTGGGCTGGTTCCACGACAGTGGCCATCGCGC (SEQ ID NO. 83)

::::::::::::Rv142SP6.seq::::::::::::
ATATTCAAGCTTTGTCACACCAAGTGTTCCGACCAANCGCTCCATCCGGCGAGTGGATACTCCCAGCAGGTAGCAGGTCGCCACCACGCTGGTCAGTGCGCGT TCATCTCGCTTGCGGCGCTGCAGCAGCCAGTCCGGGAAATAGCTGCCCTGGCGCAGCTTGGGGATCGCGACGTCGATGGTTGCGGCACGGGTGTCGAAATCAC GGTGGCGGTAGCCGTTGCGCTGATTGGACCGCTCATCGCTGCGTTCGCGGTAGCCCNCCCCGCACAGGGCGTCGGCTTCAGCCCCCATCCAAGGCGGCGATGA ACGTCGAGAGCAGCCCGCGCAGCAAATCCGGGCTCGCCTGTGCGAGTTGGTAGCCAGAAGCTGCTCGGTGTCATAAGATGAGAAGAGGTCAGTGCGTCCTTT

CCTTCG (SEQ ID NO. 84)

::::::::::::Rv142T7.seq::::::::::::
CAGGCATGCAAGCTTTTTGAGCGTCTCGCGGGGCAGCTTCGCCGGCAATTCTACTAGCGAGAAGTCTGGCCCGATACGGATCTGACCGAAGTCGCTGCGGTGC TABLE 3-continued End sequences of the polynucleotide inserts cloned in the named recombinant AGCCCACCCTCATTGGCGATGGCGCCGACGATGGCGCCTGGACCGATCTTGTGCCGCTTGCCGACGGCGACGCGGTAGGTGGTCAAGTCCGGTCTACGCTTGG GCCTTTGCGGACGGTCCCGACGCTGGTCGCGGTTGCGCCGCCAAAGCGGCGGGTCGGGTGCCATCATGAATGCCTCACCGCCGCCGCACTGCACGGCCAGTGC CCCGGCGATGTCAGCCATCGGGACATCATGCTCGCGTTCATACTCCTCGACCAGTCCGCGGAACAGCTCCATTCCCGGACCGCCCAACGC (SEQ ID NO. 85)

Clone Rv143
::::::::::::Rv143SP6.seq::::::::::::
ATACTCAAGCTTTTGGCTGGGTCGCCTTCCAATTCAGCGTGCACCGCTATGGGTTGCAGCAGCGGCTGGCNCCGCACACCCACTGGCCCGGGTGTTTTCGCC CCGAACCCGGATCATGGTGAGCGAAAAGGAGATTCNCCTGTTCGATGCTGGGATTCGCCACCGCGAGGCCATCGACCGATTACTCGCCACCGGGGTGCGAGAG GTGCCGCAGTCCCGCTCCGTCGACGTCTCCGACGATCCATCCGGCTTCCGCCGTCGGGTGGCGGTAGCCGTCGATGAAATCGCTGCCGGCCGCTACCACAAGG TGATTCTGTCCCGTTGTGTCCAAGTGCCTTTCGCGATCGACTTTCCGTTGACCTACCGGCTGGGGCGTCGGCACAACACCCCGGTGAGGTCGTTTTTGTTGCA

GTTGGGCGGAATCCGTGCTCTGGGTTACAGCCCCGAACTCGTCACGGCGGTGCGCCGCCGAC (SEQ ID NO. 86)

::::::::::::Rv143T7.seq::::::::::::
CAGGCATGCAAGCTTCAACCTATTGACGCATTGTGCGAACTGACGGCGCCCGCGCATGGCCAATCCGGAAGACCATCATTGGCCAGTGGCCGGGCGCTAACAG GTTCCAGCCCCCCACCAGTGCCGCTCGAACATGCGGTGCAACCCATTCGCAGGCCGGCAGGGAAAGCACCGCGGAAGCCGCAAAGGGCTGCAGTTCCGCGCCC AATAGTGTCGTCCGCAACCAGATGCGCTCGAAAACCGCCGCCGGCAGTCAGCGCACCCGACGCGAGGTCGAGAGACGTCGTCAGCGCGCCCACATGGGGTGCC AATCGGCACGGCAGGTAGGCCGCGCGCAACCCCAACGCGTGGTGCATGCCACGGTCCGCAGGAGGCCACCACCC (SEQ ID NO. 87)

Clone Rv144
::::::::::::Rv144SP6.seq::::::::::::
ATACTCAAGCTTCCCGGCCGCAGGTGACGGCGCGGCCTAGCGCCACTTGATGCCGCACCCGATCGACGGNCGTTGGTCGGGGTTGACTGGCCGCCCGGCGAGC AGGGCGTCAACCGCGGCCCGGACGTCGGCGGCCGTCACCGGTCGGCCATTGCCCGGGCGGGAGTCGTCGAGCTGACCACGGTAGACAAGTCGGCGCTGGCCGT CGAAGACAAACGTGTCGGGTGTGCAGGCCGCGGAGAAGGCGCNGGCGACGTCTCGGGTTTCGTCGTAGAGATACGGGAACGTCCAGCCGTGGCGGCGGGCCTC GGCGACCATCTGATCGGGCCCGTCCTGCGGGTAGGTGACCACGTCCTTACTGGAGATACCGACCATCGGGACCCTTTGATCGGCGAGGTCCCGGCCGACCGTG

GCCAATCCGGCGGCGACGTGTCGCCCGTACCGGCCAGTGGTTC (SEQ ID NO. 88)

::::::::::::Rv144T7.seq::::::::::::
CAGGCATGCAAGCTTTANCANCATCAACCCCGCCCCGCACCAGCACCGACACGATGTCGATGCCATCGAGGTGAATGTCGAACTGGCNCAAACCATCTGGCGA CCGCGACCACCGGCAACATGGGTACCGGCGATTTCCGGTGCCAATGCCGACCCGACGGGCCGCTCTCACCGCAGGTGACTTCGATCACCGAGACCAGCCGGCC GTTATACTCACGCACCCCTACCGTGTCACGCCCAAAACGGCGCTGGTGGTCGATTGCCGGAGTGCACCCCGCACCCAGTGTCGTGCCCGGATCCGCCGACCAA TCCCGCACCGACGTCGCCAAACCCGAAATCACCGTGATGCCGTGGTAACTGACCACCGACAGTAACGTCACTACGGCCGCCACGCCGACGCCGAACCACCACG

CACATGATGATCGGCTG (SEQ ID NO. 89)

Clone Rv145
::::::::::::Rv145SP6.seq::::::::::::
ATATTCAACCTTGCACACATTGACGATACCTTGGTCACGAGACCCCAAAAGCTGGCCTCCACCGCGCGCCGGGGACCACGGTCATACCTTGANNCNGCTTTCG ATCGTTGATGCTGCGTCTTGGTCCGCGGAAACCGCAGGCTGGCATATGCACGTGGGCGCACTGGCGATCTGCGATCCCCACCGATTCGCCCGAATACAGCTTT CAGCGGCTCCCCAAGTTGATCATCGACCGGCTGCCGGATATCCCGCACTTGCGGTGGCGGGTCACCGGCGCCCCGCTCGGACTGGACCGGCCGTGGTTCGTCG

AGGACCACGAAC (SEQ ID NO. 90)

::::::::::::Rv145T7.seq::::::::::::
CAGGCATGCAAGCTTCATGCCCGCGGCATGATAGCCACATGCACGCAATCGAACTCAGCGAAACCGGCGGGCCAGGCGTCTTACGCCACCTCACCAGCGCGCA

ACCTCAACCCGGCCACGGAGACCTCCTGATC (SEQ ID NO. 91)

Clone Rv146
::::::::::::Rv146SP6.seq::::::::::::
ATACTCAAGCTTGATTTTGATCATCATGATGATCATCACCCGAATTGTGGTAGCCGCAGTGGTTATCGTGGGTACCGTCGTGCTTTCCATGGGCGCCTCTTTC GGGCTTTCCGTATTGGTCTGGCAGGACATTCTGGGTATCGAGTTGTACTGGATGGTGTTGGCGATGTCGGTGATCCTGCTCNTGGCGGTGGGATCCGACTACA ATCTGCTGCTGATTTCCCGGTTGAAAGAGGAAATTGGGGCCGGATTGAACACCGGAATTATCCGTGCCATGGCTGGTACCGGGGGAGTGGTGACGGCTGCCGG CATGGTGTTCGCCGTTACCATGTCGTTGTTTGTGTTCAGCGATTTGCGAATTATTGGTCAGATCGGTACCACCATCGGCCTGGGCTTGCTGTTCGACACCCTC TABLE 3-continued

| End sequences of the polynucleotide inserts cloned in the named recombinant |
|---|

GTCGTGCCTCGTTCATGAAACCGTCCATTGCTGCCCTGCTGGGACCTGGTTCTGGTGGCCGCTACGGGTGCGCCCGCGCCCGGCAGTCAAATCTTCCGCCG (SEQ ID NO. 92)

::::::::::::Rv146T7.seq::::::::::::
CAGGCATGCAAGCTTGGCGTGCCGTTCCAACCCGAATTGGCTTTCGGCGCCATCGGTGAGGACGGCGTGCGGGTGCTCAACGACGACGTCGTCCGCGGGACAC ACCTCGATGCTGCCGCCATGGACGCGGTCGAACGCAAGCAGCTGATCGAGCTACAACGCCGCGCGGAACGCTTCCGCCGCGGGCGTGACCGCATCCCGTTGAC CGGGCGGATCGCGGTGATCGTCGATGACGGCATCGCCACCGGAGCGACGGCCAAGGCGGCGTGCCAGGTCGCCCGGGCGCACGGTGCGGACAACGTGGTGCTG

GCGGTCCCCATCGGCCCAGACGACATCGTGGCGAGA (SEQ ID NO. 93)

Clone Rv147
::::::::::::Rv147SP6.seq::::::::::::
ATACTCAAGCTTTTACGGTGATCGCGCATCACCTGGTTCATGAACTGGAAGCAGCGCAGCGCTTCCTTTTCGGCCGCAACATGAGCCAGCCTCTCGTCGGCGG TCGGGTGCAGGTGCTCGGGCAGCTCGGCCGCGACAGCCGCCTGACCCTGAAACCAGCTTCCATATCCCGCGACGAACGACGCCAGTCCGCTACGTAACCCCTC CGCGACTGTCCATGGACAACAGCGCGTTCTCCACCGACCGGGCCCGGGTGTGGGGTGTTTCGGCGACCGGCAGCCANGTGGTCCACACTGCCGAAG (SEQ ID NO. 94)

::::::::::::Rv147T7.seq::::::::::::
TAGTCGCTGACCGGTGCAGGTTTCGACNATGTGGTGCCGGTTCGGCGGCTACGTGCCATCGAGACACTGGCGCAGGCTATCGCACCCGTTATCGGCTACGAGC AAATCGCGGTATGCGTTCTTGAGCATGAGTCGGCGACCGTCGTCATGGTCGACACCCACGACGGAAAGACGCAGATCGCCGTCTANCNTGTGTGCCGCGGATT ATCAGGACTGACCTCCTGGCTGACCGGCATGTTTGGTCGCGATGCCTGGCGCCCGGCCGGCGTGGTCGTGGTCGGCTCGG (SEQ ID NO. 95)

Clone Rv148
::::::::::::Rv148SP6.seq::::::::::::
ATACTCAAGCTTTCCGCCGATACCCGCCATGTCGCGCACATCCAGAACTTCTGGGGGGATCCGCTGACAGCGGCGGGATCCCAAAGTGCGGATGATCGGGCCG CCTACGTCGTGGTGTACCTCGTCGGTAACAACGAAACCGAAGCGTATGACTCGGTCCACGCGGTGCGGCACATGGTGGACACCACACCGCCACCGCACGGGGT GAAGGCCTATGTCACCGGTCCGGCAGCACTCAATGCCGACCAGGCCGAGGCCGGAGACAAAAGTATCGCTAAGGTCACCGCGATCACGAGCATGGTGATCGCA GCAATGTTGCTAGTGATCTATCGCCCCGTAATTACCGCGGTTCTCGTCTTGATCATGGTCGGCATCGACCTCGGCGCAATCCGCGGATTCNTCGCCTTGCTCG CCGACCACAACATTTTCAGCCTTTCAACATTTGCGACAACCTGCTCGTTCTCATGGCGATTGCNGCGAAC (SEQ ID NO. 96)

::::::::::::Rv148T7.seq::::::::::::
CAGGCATGCAAGCTTGGCGTGCCGTTCCAACCCGAATTGGCTTTCGGCGCCATCGGTGAGGACGGCGTGCGGGTGCTCAACGACGACGTCGTCCGCTGGACAC ACCTCGATGCTGCCGCCATGGACGCGGTCGAACGCAAGCAGCTGATCGAGCTACAACGCCGCGCGGAACGCTTCCGCCGCGGGCGTGACCGCATCCCGTTGAC CGGGCGGATCGCGGTGATCGTCGATGACGGCATCGCCACCGGAGCGACGGCCAAGGCGGCGTGCCAGGTCGCCCGGGCGCACGGTGCGGACAAGGTGGTGCTG GCGGTCCCGATCGGCCCAGACGACATCGTGGCGAGATTCGCCGGGTACGCCGATGAAGTGGTGTTGTTTGGCGACCCGGCGTTGTT (SEQ ID NO. 97)

Clone Rv149
::::::::::::Rv149SP6.seq::::::::::::
ATACTCAAGCTTTGGCATTGTGCACATTTTCCACCCGTGCTCTATTAATGCTGAGCCGCTAATTGTGACCCCAGTCGGGAAACACGCGGAGCACCAAATTCAC CGCAGCGGCCGGGGCGGTTCAACTCACCATGGATCGCTCTCGTCGTCTGGTGCTGGACAATCGTCGCTGTAGCGCGTCGCGAACACCTCAGCTTCTGCTGCCG CGGCTTCTTCCGGCGATGGTAACCCCCAGGTTTCGCCCACGGTCTTACGTAGCAGTGCGACGCGGTGTTCATCTGCATCGACCTGTTGACTCATCCTGTCAAG GATGAAGGCGTACTGGGCCGACTGCGCCTTCTGCCGCGCCAGGTCGGCAATCACCAGGATCTCAGAAACGAGCTGCGACTCACTCTTCCAGGCCACCCTGGCC

GAAAGCTCGACATGGTCAATCCGGCCG (SEQ ID NO. 98)

::::::::::::Rv149T7.seq::::::::::::
CAGGCATGCAAGCTTGCGGGCCGGAGTGGTTTCGACGGCCGCTCGCTTCTCGGCATCGGTTTGGGCTGTCACCAGCAGTTGGTAGTTCTTCACGTACTGTTGT TCGAGCGTCGAGCCGCCGCGCGTGTCGAGGTCGCCGGACGCGTATCCCGCCAGGCCGGTCAGGGTGCCCTTCCAGTCCACGCCGCTGTGGTCGGCGAACCGCT TATCTTCAATCGAGACGATCGCCAGCTTCATCGTGTTGGCGATCTTGTCCGAGGGCACCTCGAACCGGCGCTGCGAGTACAGCCACGCGATCGTGTTGCCCTT

CGCGTCGACCATCGTCGATACCGCAGGCACTTGCCCCTC (SEQ ID NO. 99)

Clone Rv14
::::::::::::Rv14SP6.seq::::::::::::
ATACTCAAGCTTCCCGGCGGCCAGTACCGAAAGCGCGAACAGCTCGCGGCAGCCCACGACGTGCTGCGTCGGATTGCCGGCGGCGAAATCAATTCCAGGCAGC TCCCGGACAATGCGGCTCTGCTGGCCCGCAACGAAGGACTCGAGGTCACCCCGGTGCCCGGGGTCGTGGTGCACCTGCCGATCGCACAGGTTGGCCCACAACC TABLE 3-continued End sequences of the polynucleotide inserts cloned in the named recombinant GGCCGCTTGATGCCCGGTCGGCAAGCCCGGCAGTTGCCAAACCCAGCGTGATCAGGCTCGGCTCGCGAGTTCGGCGAAGAAGTGGCTCGCCTGATCACCTACC ATCGGCCAGGATCTGCGTGTCATCACAACGCTCGCCAAGGAGGTTGTTGTGGTGCTATCGACGGCCTTTAGCCAGATGTTCGGAATCGACTATCCGATAGTGT

CCGCGCCAATGGACTTGATCGCCG (SEQ ID NO. 100)

::::::::::::Rv14T7.seq::::::::::::
AGCTTCGGTGTAGCCGATCACCGGAAGCCGCATGATCAGCCACGTTTCGCGCCGCCCGGCATACGGCGGCGTACCGATCTCCGCGTCATACACCCGCGGGTAA TCGCCGACGGTGCCGGTTCGCGAGCCGAAGGTGACGACGCTGATTGAATCGAGTTCCAGGTCCAGCGGGTGGCGCAGCAACGGCGCGAGCTCAACGACGTCAA TCACGTTGTCGCTTTCTACGGTCACCGACCCGGTGACCGTAGTCGCCCGGTGCGCTCGGCCGAGAAGTTGCACCGCCACCACCGCGACACCGTCTTGCACGCG GACGCCACCCCCGGATCGGTTGTTGGCCAAGGTAATTGGGTCATTCCATTTGACGGGACGCCGACCCCGCAGCCCCAGTACCGCCCACGACCACGCCGGCTGA

CCCACCACTGTACGAACACCAAGGCGACGCCGA (SEQ ID NO. 101)

Clone Rv15
::::::::::::Rv150SP6.seq::::::::::::
ATACTCAAGCTTCGGTGGCTTCGCCCGCCCTGCCGGGTGGACTTCATGACAACGCGGGGGCGATTACCCCCGCTACCGCCAGCAGCATGACGGCGGTACCTAA CACCGCCCGGATGCCTCGCACGTGCCTCGATGTGCTCACGGAATCGCCCCGGCACCGCGATCTCGAGGATCACCAGCGTTACCCCCGGCAGCGCGACACCGAC

AATTCCGTACACCGCCACGCCGATCCGGCCCTGGGCCAGCTGATTGGAGCTGGCG (SEQ ID NO. 102)

::::::::::::Rv150T7.seq::::::::::::
CAGGCATGCAAGCTTCCACATGTACGGATCCACGAACATCCCGTTGAACTGACAGGTGCGGCCCGGCTCGATCAGGCCGGCCACTTGTTCTACGCGGTTACCG AAGATCTCTTCGGTGACCTGCCCGCCGCCGGCCAGCTCGGCCCAGTGCCCGGCGTTGGCCGCCGCGGCGACGATCTTGGCGTCCACGGTGGTCCGGGTCTTGC

CCGCTAGCACGATCCGCGAGTCGGCCGGTCACCCGGGT (SEQ ID NO. 103)

Clone Rv151
::::::::::::Rv151SP6.seq::::::::::::
ATACTCAAGCTTTCCAAGTCCCAAGTGTCGATCATGGCCAAAGAGCTCGACAAAGCCGTAGAGGCGTTTCGGACCCGCCCGCTCGATGCCGGCCCGTATACCT TCCTCGCCGCCGACGCCCTGGTGCTCAAGGTGCGCGAGGCAGGCCGCGTCGTCGGGGTGCACACCTTGATCGCCACCGGCGTCAACGCCGAGGGCTACCGAAA GATCCTGGGCATCCAGGTCACCTCCGCCGAAGACGGGGCCGGCTGGCTGGCGTTCTTCCGCGACCTGGTCGCCCGCGGCCTGTCCGGGGTCGCGCTGGTCACC AGCGACGCCCACGCCGGCCTGGTGGCCGCGATCGGGGCACCCTGCCCGCAGCGGGCCTGGCAGCGCT (SEQ ID NO. 104)

::::::::::::Rv151T7.seq::::::::::::
CAGGCATGCAAGCTTCACACGTAGGCGCCGTCGATAAATGACTCCGCCGCGCTTCGCACATCCTCGTAGCGATCCTTGGCGAGCAGGTCAACCGGGCGCTGCC CGTCGAGGAGCCGGTTTTTGGCGTGCAGCCACTGGCCGACACCTCGGGGGGTAAGCGAATCCGAGAGCAGGAGGACGAGGTCACGAAGCTGCGCCAGCCGGTC GTACCGCTCAGGGCGGATGTCGCCGGTCCGCCACCCGCGTACCGCCCGATCGGACACCTGTATGACCGCGGCGACGTC (SEQ ID NO. 105)

Clone Rv152
::::::::::::Rv152SP6.seq::::::::::::
CGCGGCGGCGCATTACCCCCGCTACCGTCAGCAGCTTGACGGCGGTAGCGAACACCGCCGGATGCAGCGCAGGTGCGTCTATGTGCACACGGAATCGCCCCGG

CACCGCGATCTCGAGGATCACCAGTGCCCGCCCCCTG (SEQ ID NO. 106)

::::::::::::Rv152T7.seq::::::::::::
GGGATCGAGGAACAGCGCGTTGAACTGATAGGTGCGGCCCGGCTCGAGCAGGCCGGCCATTTGTTCGATGCGGTTACCGAAGATCTCTTCGGTGACCTGCCCG CCGCCGGCCAGCTCGGCCCAGTGCCCGGCGTTGGCCGCCGCGGCGACGATCTTGGCGTCCACGGTGGTCGGGGTCATGCCCGCGAGCAGGATCGGCGAGCGGC CGGTCAGCCGGGTGAACTTCGTCGAGAGCTTGACCCTGCCGTCGGGGAGGCGAACCACGGTCGGTGCGTATCTCGACCAGGCCCGGGCAACCTCGGGGGTGGC GCCGACGGTGAACAGGTTGCGCTGGCCACCGCGGGTAGCCGCCGGCACTATGCCGATGCCCAGGCCGCGGATCACCGGTGCGGTCAGTCGGGTCAGGATGTCG CCCGGCCCCAGGTCGAAGATCCAGCGGGCGCCGGCCGCGTGGACACNGGTGATCTCGTCCACCATCGACTTTCTGATCA (SEQ ID NO. 107)

Clone Rv153
::::::::::::Rv153SP6.seq::::::::::::
TAACTCAAGGCTTGCGTTGAGGCCCCAGGCCCATCGACGGTTTGGCGGCCTTAAATGCACTGAGGTCGTCAATTGACCCCACAGCGGAAATGCCGACTATTCG CAGGCCTCCTTCGCCTTGGCTGCCGGAGAGGGGCTCCGCGGGAACCGCATGCAGGTATATGACCTCGGTTTCTCGGGTGCTACCGCGTGCCTTGTCGAGGATG AACTCGGCGTTGGAATTGTCCAGCCGGCCCAATTCATCGAGCGCAGATTCGTACACATGGCCGGCGGCGACATACGCTTCACCGTGGATCTGCTCCACACGGA

CCGCCCTGTCGGGATCCTGCTCACGGGTAAAGGAACTTACNTGGCNCTCGGTGCC (SEQ ID NO. 108)

TABLE 3-continued

End sequences of the polynucleotide inserts cloned in the named recombinant

::::::::::::Rv153T7.seq::::::::::::
CCTTCTGCGCCACCCACACCGTCAACGCCCGCGAAGTCGACGTCGTCCAGGCCATCGGCGGCCTCACGGATGGATTCGGCGCGGACGTGGTGATCGACGCCGT CGGCCGACCGGAAACCTACCAGCAGGCCTTCTACGCCCGCGATCTCGCCGGAACCGTTGTGCTGGTGGGTGTGCCGACGCCCGACATGCGCCTGGACATGCCG CTGGTCGACTTCTTCTCTCACGGCGGTGCGCTGAAGTCGTCGTGGTACGGCGATTGCCTGCCCGAAAGCGACTTCCCCACGCTGATCGACCTTGACCTGCATG GCCGGCTGCCGCTGCAGCGGTTCGTTTCCGAACGCATCGGGCTCGAAGACGTCGAGGAGGCGTTCCACAAGATGCATGGCGGCAAGGTATTGCGTTCGGTGGT

GATGTTGTGATGGCCGCCATCGAGCGCGTCATCACCCACGG (SEQ ID NO. 109)

Clone Rv154
::::::::::::Rv154SP6.seq::::::::::::
ATACTCAAGCTTGATTTTGATCATCATGATGATCATCACCCGAAGTGTGGTAGCCGCAGTGGTTATCGTGGGTACCGTCGTGCTTTCCATGGGCGCCTCTTTC GGGCTTTCCGTATTGGTCTGGCAGGACATTCTGGGTATCGAGTTGTACTGGATGGTGTTGGCGATGTCGGTGATCCTGCTCCTGGCGGTGGGATCCGACTACA ATCTGCTGCTGATTTCCCGGTTGAAAAAAGAAATTGGGGCCGGATTGAACACCGGAATTATCCGTGCCATGGCTGGTACCGGGGGAGTGGTTACCGCTGCCGG

CATGGTGTTCGCCGTTACCA (SEQ ID NO. 110)

::::::::::::Rv154T7.seq::::::::::::
ATTGNCTTTCGGCGCCATCGGTGAGGACGGCGTGCGGGTGCTCAACGACGACGTCGTCCGCGGGACACACCTCGATGCTGCCGCCATGGACGCGGTCGAACGC AAGCAGCTGATCGAGCTACAACGCCGCGCGGAACGCTTCCGCCGCGGGCGTGACCGCATCCCGTTGACCGGGCGGATCGCGGTGATCGTCGATGACGGCATCG CCACCGGAGCGACGGCCAAGGCGGCGTGCCAGGTCGCCCGGGCGCACGGTGCGGACAAGGTGGTGCTGGCGGTCCCGATCGGCCCAGACGACATCGTGGCGAG ATTCGCCGGGTACGCCGATGAGGTGGTGTGTTTGGCGACGCCGGCGTTGTTCTTCGCCGTCGGGCAGGGTTACCGCAACTTCACCCAGACCTCCGACGAAGAA

GTGGTGGCGTTTTCTGGATCGTGCTC (SEQ ID NO. 111)

Clone Rv155
::::::::::::Rv155SP6.seq::::::::::::
ATACTCAAGCTTTTCCCGTCCGTCATCGCCCAAGCGCGTGAGGCCGAAGCGGCTGGTTACGACTCCCTGTTTGTGATGGACCACTTCTACCAACTGCCCATGT TGGGGACGCCCGACCAGCCGATGCTGGAGGCCTACACGGCCCTTGGTGCGCTGGCCACGGCGACCGAGCGGCTGCAACTGGGCGCGTTGGTGACCGGCAATAC CTACCGCAGCCCGACCCTGCTGGCAAAGATCATCACCACGCTCGACGTGGTTAGCGCCGGTCGAGCGATCCTCGGCATTGGAGCCGGTTGGTTTGAGCTGGAA CACCGCCAGCTCGGCTTCGAGTTCGGCACTTTCAGTGACCGGTTCAACCGGCTCGAANAGGCGCTACAGATCCTCGAGCCAATGGTCAAGGGTGAGCGCCAAC

GTTTTTCGGCGATTGGTACCCACCGA (SEQ ID NO. 112)

::::::::::::Rv155T7.seq::::::::::::
CGGCCACCGGGGCCACTCCGCACAATCTGTACCCGACCAAGATCTACACCATCGAATACGACGGCGTCGCCGACTTTCCGCGGTACCCGCTCAACTTTGTGTC GACCCTCAACGCCATTGCCGGCACCTACTACGTGCACTCCAACTACTTCATCCTGACGCCGGAACAAATTGACGCAGCGGTTCCGCTGACCAATACGGTCGGT CCCACGATGACCCAGTACTACATCATTCGCACGGAGAACCTGCCGCTGCTAGAGCCACTGCGATCGGTGCCGATCGTGGGGAACCCACTGGCGAACCTGGTTC AACCAAACTTGAAGGTGATTGTTAACCTGGGCTACGGCGACCCGGCCTATGGTTATTCGACCTCGCCGCCCAATGTTGCGACTCCGTTCGGGTTGTTCCCAGA GGTCAGCCCGGTCGTCATCGCCGACGCTCTCGTCGCCGGGACCAGCAGGGAATCGGCGATTTCGCCTACA (SEQ ID NO. 113)

Clone Rv156
::::::::::::Rv156SP6.seq::::::::::::
ATACTCAAGCTTGGGGTGGCGCTGTCGGTCGGTGTGCTTGGCGGCGTCGGTATCAACACCGCCCACGAAATGGGGCACAAGAAGGATTCGCTGGAGCGGTGGC TGTCCAAAATCACCCTCGCCCAGACCTGCTACGGGCACTTCTACATCGAGCACAACCGTGGCCATCACNTCCGGGTGTCCACACCGGAGGACCCGGCGTCGGC GCGGTTCGGCGAAACGTTGTGGGAGTTCCTGCCCCGCAGTGTTATCGGCGGCTTGCGCTCGGCCGTTCATTTGGAGGCCCAACGGCTGCGTCGGCTCGGCGTC AGCCCCTGGAATCCCATGACGTATCTGCGCAACGACGTGCNCAACNCGTGGCTGATGTCNGTGGTGTTGTGGGGTGGGC (SEQ ID NO. 114)

::::::::::::Rv156T7.seq::::::::::::
TCGCCACCGCACCGCGGCGAACGCTCAAAGGCACCTACTGGCACCAAGGCCCCACACGTCACCCTGTGACCTCCTGCGCCGACCCCGCCCGAGGTCCTGGCCG TTACCACCGAACGGGCGAGCCGGGAGTCTGGTACGCATCGAACAAAGAGCAAGGTGCATGGGCGGAGTTGTTCCGCCACTTCGTCGATGACGGGGTCGATCCA TTCGAGGTCCGTCGCCGCGTCGGTCGAGTGGCGGTCACACTCCAGGTACTCGACCTCACAGACGAGAGGACTCGATCCCATCTAGGTGTGGACGAAACAGATC TTCTGTCCGACGACTACACCACCACCCAGGCCATCGCCGCCGCCCCGCGATGCCAACTTCGACGCCGTACTGGCCCCGGCGGCGGCGCTCCCCGGTTGTCAAAC

ACTTTGCCGTGTTCGTTCACGCACTGCCCAACATCGAGCCCGA (SEQ ID NO. 115)

Clone Rv157

TABLE 3-continued

End sequences of the polynucleotide inserts cloned in the named recombinant

::::::::::::Rv157SP6.seq:::::::::::
ATGAAATAAGAAGAGCACATCCCTCAGTCGGTTATCATCACTAGCGCTCGCCGCACCCGTGTAACCGATCATAGCGAGCGAACTGGCGAGGAAGCAAAGAATA TCTGTTCTGTCAGATAGCTCTTACGCTCAGCGCAAGAAGAAATATCCCCCGCGGGAACAACTCCAGGTAGAGGTACACACGCGGATAGCCAATTCAGAGTAAT AAACTGTGACACTCACACCCTCATCAATGATGACGAACTACACCCCGATATCCGGTCACATGACGAAGGGAAAGAGAAGGATATCATCTGTGACAAACTGCCC

TCAAATTTGGCTTCCTTAA (SEQ ID NO. 116)

Clone Rv159
::::::::::::Rv159SP6.seq:::::::::::
ATACTCAAGCTTGTCGAACTCCTTCTTGAATACCGGCCGGCCATCCACAGATGCCCGGAAGAACTTCCAGGTACCCATGGCGGCTGGATCAGGGGGCGGCACA GTTGGTCTTGTCCTGCCTCGAGTGGCGTCGTTGTCCGGCTTGGACGGGGCTCCGACGGTACCGGAGGGCAGCGACAAAACACTTATGCACTTGGGCGACCCGC CGAGACGGTGCGACACCCATCCCGACGGCACAAGCTCAGCCGCGGCCGCTCTTGTTCTTCGTCGGATCGACATTCACCCACTTCTGACCGGGCTTGGGCGAAG

GAAGCAGAA (SEQ ID NO. 117)

::::::::::::Rv159T7.seq:::::::::::
GGTATAGTCGCTGACCGGTGCAGGTTTCGACAATGTGGTGCCGGTTCGGCGGCTACGTGCCATCGAGACACTGGCGCAGGCTATCGCACCCGTTATCGGCTAC GAGCAAATCGCGGTATGCGTTCTTGAGCATGAGTCGGCGACCGTCGTCATGGTCGACACCCACGACGGAAAGACGCAGATCGCCGTCAAGCATGTGTGCCGCG GATTATCAGGACTGACCTCCTGGCTGACCGGCATGTTTGGTCGCGATGCCTGGCGCCCGGCCGGCGTGGTCGTGGTCGGCTCGGATAGCGAGGTCAGCGAATT CTCGTGGCAGCTCGAAAGGGTCCTGCCGGTGCCGGTCTTTGCGCAAACGATGGCGCAGGTTACGGTCGCGCGGGGTGCGGCCCTGGCGGCGGCCCA (SEQ ID NO. 118)

Clone Rv15
::::::::::::Rv15SP6D2.seq:::::::::::::
GACACTATATNATACTCAAGCTTCAGGTCAATGTGCGCCAAGCCCTGACGCTGGCCGACCAGGCCACCGCCGCCGGANCCCTNTCTAGA (SEQ ID NO. 119)

::::::::::::Rv15T7.seq::::::::::
CTGTAGCCACCTGTTGCCATCCCCGTCATGCCCGACTCTGGTCATCTCGGATCCGCTGACACCCCGCTAAGGCTGCTCCTCTCGGTGCATTACCTCACCGACG GCGAACNCCCCCAGCTTTACGACTATCCGGATGACGGCACCTGGTTGCCGGCTAACTTCACCGTCAGCTTGGACGGCGGCGCTACCGTCGATGGCGCCAGCGG GGCGATGGCCGGGCCCGGCGACCGATTCGTCNTCANCCTGTCGCGTGAACTTGCCGACGTCATCGTGGTCGGTGTGGGCACCGTGCGCATTGAGGGCTACTCC

GGCGTCCGGATGGGTGTCGTCAAGCGCCCGCACCGGCAGGCCCGA (SEQ ID NO. 120)

Clone Rv160
::::::::::::Rv160SP6.seq:::::::::::
ATACTCAAGCTTCGCACGCTCGGCGCGCGCGGTACCGCCCAGGTCGCCCAACAGATCGTCGATGTTCGCGTCGTCCGCCTCGCGCACGTGGTCTGTCACCAGT CAACGTTAACGCCGCCGCACATGTCCTGCGGCCGGGCAAAAACGTGAAAAACGAGCGGGCGACTGCNATGTCATGACACCGACGGCCGCCGATGGGCCCAGGG TCTGGCAAATTCGATCTGTGCGGCCAGTGCCAGCAGCGTCGCCTCGTCATACGGCCGGCCGACGAGTTGAACCGACATGGGCAGGCCGTCGCCGTCGAAGTCC CACGGCACCACGGGCGCGGGCTGGCCGGTCAGATTCCAAAATTGAAAGTACGGAACCGCTGCACCACCAA (SEQ ID NO. 121)

::::::::::::Rv160T7.seq:::::::::::
ATCGTTTCGACCAGGCGCTCCATCCGGCGAGTGGATACTCCCAGCAGGTAGCAGGTCGCCACCACGCTGGTCAGTGCGCGTTCAGCTCGCTTGCGGCGCTGCA GCAGCCAGTCCGGGAAATAGCTGCCCTGGCGCAGCTTGGGGATCGCGACGTCGATGGTTGCGGCACGGGTGTCGAAATCACGGTGGCGGTAGCCGTTGCGCTG ATTGGACCGCTCATCGCTGCGTTCGCGGTAGCCCGCCCCGCACAGGGCGTCGGCTTCAGCCCCCATCAAGGCGGCGATGAACGTCGAGAGCAGCCCGCGCAGC AGATCCGGGCTCGCCTGTGCGAGTTGGTCAGCCAGAAGCTGCTCGGTGTCGATAAGATGANAAGAAGTCATTGCGTTATTTCCT (SEQ ID NO. 122)

Clone Rv161
::::::::::::Rv161SP6.seq:::::::::::
ATACTCAAGCTTGGGTGTTGCCGATCACCGGAAGCCGCATGATCAGCCACGTTTCGCGCCGCCCGGCATACGGCGGCGTACCGATCTCCGCGTCATACACCCG CGGGTAATCGCCGACGGTGCCGGTTCGCGAGCCGAAGGTGACGACGCTGATTGAATCGAGTTCCAGGTCCAGCGGGTGGCGCAGCAACGGCGCGAGCTCAACN ACGTCAATCACGTTGTCGCTTTCTACGGTCACCGACCCGGTGACCGTAGTCGCCCGGTGCGCTCGGCCGAGAAGTTGCACCGCCACCACCGCGACAACGTCTT

GCACGCGGACGCCACCCCCCGGAT (SEQ ID NO. 123)

::::::::::::Rv161T7.seq:::::::::::
GCGCNAACAGCTCGCGGCAGCCCACGACGTGCTGCGTCGGATTGCCGGCGGCGAGATCAATTCCAGGCAGCTCCCGGACAATGCGGCTCTGCTGGCCCGCAAC TABLE 3-continued End sequences of the polynucleotide inserts cloned in the named recombinant GAAGGACTCGAGGTCACCCCGGTGCCCGGGGTCGTGGTGCACCTGCCGATCGCACAGGTTGGCCCACAACCGGCCGCTTGATGCCCGGTCGGCAAGCCCGGCA GTTGCCAAACCCAGCGTGATCAGGCTCGGCTCGCGAGTTCGGCGAAAAAGTGGCTCGCCTGATCACCTACCATCGGCCAGGATCTGCGTGTCATCACGACGCT CGCCAAGGAGGTTGTTGTGGTGCTATCGACGGCCTTTAGCCAGATGTTCGGAATCGACTATCCGATAGTGTCCGCGCCAATGGACTTGATCGCCGGCGGTGAG

CTGGCTGCCGCNGT (SEQ ID NO. 124)

Clone Rv162
::::::::::::Rv162SP6.seq::::::::::::
ATACTCAAGCTTTCTCCGATACCCGCCATGTCGCGCACATCCAGGACTTCTGGGGGGATCCGCTGACAGCGGCGGGATCCCAAAGTGCGGATGATCGGGCCGC CTACGTCGTGGTGTACCTCGTCGGTAACAACGAAACCGAAGCGTATGACTCGGTCCACGCGGTGCGGCACATGGTGGACACCACACCGCCACCGCACGGGGTG AAGGCCTATGTCACCGGTCCGGCAGCACTCAATGCCGACCAGGCCGAGGCCGGAAACAAAAGTATCGCTAAGGTCACCGCGATCACGAACATGGTGATCGCAG

CAATGTTGCTAGTGATCTATCGCTCCG (SEQ ID NO. 125)

::::::::::::Rv162T7.seq::::::::::::
CCATGAGCACCGCCAGCCGAGCACGAGGCCAAACTCCGCCGACGCAGGCCGGTTGGACTTGTCGTGCTGGACAAGGGGTTTAGCCGCCGAAGCAGTGACGTAC ATCGGCGAAGAGCAGTTCGCCTGTCGACCGACGGCGCAAACCGTGAGGCTAGGGAAGCGAGGAGCACATGGCCGCCGACCCGCAATGTACACGCTGCAAGCAA ACCATCGAACCCGGATGGCTATACATCACCGCCCATCGCCGCGGTCAAGCCGGGATCGTCGATGACGGCGCAGTACTGATTCACGTGCCCGGTGAATGCCGCA

CCCCGGGGAGCACTTTCCGCCAAAACTAACCCGGTTGG (SEQ ID NO. 126)

Clone Rv163
::::::::::::Rv163SP6.seq::::::::::::
CGGGTGTCATTGGCCACCGGCGGCGGCTGTCCGGGAAATGGCGGGTCCCCGGTGGTTTTGCTGAGGAGTGCTGAACCGTAGTCGAAGTGGGCGGCGTCAGACT CCACCCAGCCAGCAGGCAGCGCGAANCTGAATCCTCCAACCGGGTTGTCNATCCGGACAGGTTGGGGTGCGTTTGGGGCAATNACAGGTGGCGGCGGTGCGTT CGGGTCGGCCGGCGGAGGTGCTGCNTTGGGATCCCCGGCTGGGCATTCGGCNTGTTGGCGGCGGCCGGTGGTGGGGGGGCAACACGTGTCNCCGGTGCGGGTG

GCCCT (SEQ ID NO. 127)

::::::::::::Rv163T7.seq::::::::::::
CCAAGATCTACACCATCGAATACGACGGCGTCGCCGACTTTCCGCGGTACCCGCTCAACTTTGTGTCGACCCTCAACGCCATTGCCGGCACCTACTACGTGCA CTCCAACTACTTCATCCTGACGCCGGAACAANTTGACGCAGCGGTTCCGCTGACCAATACGGTCGGTCCCACGATGACCCAGTACTACATCATTCGCACGGAG AACCTGCCGCTGCTAGAGCCACTGCGATCGGTGCCGATCGTGGGGANACCCACTGGCGAACCTGGGTTCAACCAAACTTGAAGGTGATTGTTAACCTGGGCTA

CGGCGACCCGGCCTATGGTTATTCGACCTCGCCGCCCAAATGTTG (SEQ ID NO. 128)

Clone Rv164
::::::::::::Rv164SP6.seq::::::::::::
AGCTTCCCGAGTTCGGCTTTGGATCAAGACCCCAGTCCGCGGGCGCGATCCGGCNGCTCGGTGACTACATCAAGCCACAAATCGACGGCTTTCGGGGTGCCGA TACCGATGACGTGGCGGATGTCGAGTGTTGAGTTCTCGGCGGGGCGGATGCTCACCTGGCGATCACCTGCCTCTCGTTGACGATCGATCGTCTATGCCGCCGT CTCTGCGGGAACAGGCCNCCAGTACATCGCCACAGACGGGATCCACCCGCATTTCGGCTACGGTTGCTCGTTTCGGTGTTCGGACTAGTCGGTCCTGGTGACG

TGCCGGTGATGCGGACCGGTCCTAGCACTGACCAATGGCCAAAATGCGGGC (SEQ ID NO. 129)

::::::::::::Rv164T7.seq::::::::::::
CGGGGGGCCTCTTAATAGTGTAGGAAAGAAGCTCTACATATTCAGGAGGATTCACCATGGCTCGTGCGGTCGGGATCGACCTCGGGACCACCAACTCCGTCGT CTCGGTTCTGGAAGGTGGCGACCCGGTCGTCGTCGCCAACTCCGAGGGCTCCAGGACCACCCCGTCAATTGTCGCGTTCGCCCGCAACGGTGAGGTGCTGGTC TGCCAGCCCGCCAAGAACCAGGCAGTGACCAACGTCGATCGCACCGTGCGCTCGGTCAAGCGACACATGGGCAGCGACTGGTCCATAGAGATTGACGGCAAGA AATACACCGCGCCGGAGATCAGCGCCCGCATTCTGATGAAGCTGAAGCGCGACGCCGAGGCCTACCTCGGTGAGGACATTACCGACGCGGTTATCACGACGCC CGCCTACTTCAATGACGCCCAGCGTCAGGCCACCAAGGACCCGGCCAGATCGCCGGTCTCACGTGCTGCGG (SEQ ID NO. 130)

Clone Rv165
::::::::::::Rv165SP6.seq::::::::::::
ATACTCAAGCTTCATAACAGGCCTGTTGTGGGCGCACCCGGCTCGCCGAGTTCTGCACGCACCGCCTCAAGTGCGGCCCGCACCGCCGGCATCTCCCGGTCAC GCAGGGCCGCGGCCCGCGCCGCAGCGACGGCGTGTTCGCGCAGTTCGCCGTCAATGATGCTGACCTGATCGGCCACCCGGGCGTTCTCGGCGTCTTCGCGTTC ACTAATCGCGGTGCTCAGCAGCGTCTCGACAGCCACCACCCGAGTGGCGACCAGCTGCTCCACCACGGACCGCAGCGATGCCGTCACCTCACCCGTCCAGCGG TCCACCACGACACGGTCGTGCACCAGCGCGCGGGCATTCACCACCCAGGCGGTCACCGCCAGGCCGATCGCCACACCCGCCACCATCCCCGATGCAGCCAGGC TABLE 3-continued

| End sequences of the polynucleotide inserts cloned in the named recombinant |
|---|

CGGGAGTAAGA (SEQ ID NO. 131)

:::::::::::::Rv165T7.seq:::::::::::::
CTGGTGCTGGACGGAGCCTAGTACAACTTCCTCTCCAATGCTCTTGCCCCGATCGCGGCGACCAGGATGACCCAGGACATCCTGCCGCCCGAAGTACTGGAAA AGCTCACACCCGAGTTCGTCGCACCGGTGGTGGCCTACCTGTGCACCGAGGAGTGTGCCGACAACCCATCGGTGTACGTCGTCAGTGGTGGTTAGGTGCAGCG AGTTGCGCTGTTTGGCAACGACGGCGCCAACTTCGACAAACCGCCGTCNGTACAAGATGTTGCGGCGCGGTGGGCCGAGATCNCCGATCTGTCCGGTGCGAAA

ATTGCTGGATTCAAGTTGTAGAACTAAAT (SEQ ID NO. 132)

Clone Rv166
:::::::::::::Rv166SP6.seq:::::::::::::
ATACTCAAGCTTTTCCGGCGTCGTCCACCTGACCCAAAAAGCGCAGGTGCGCCGCCAAACGGCCCGCCTGGCCGCGCAACTGGTCGGCGTCGCCGTGGCCGAC AATCAGTAGCTGGACATCCGGAAACCGCTGCACCACCTTCGGCAGCGCGTCAAGCAAAAACGGCCATTCC (SEQ ID NO. 133)

:::::::::::::Rv166T7.seq:::::::::::::
TTTCAGATCTCATTTTTATGACATGACTGGAGATCTGTCTAGATTGCAGCTCCTGTGAGCGTGGGTACCGGATTCAAGCCGGTCGGTCACGCCGCGGTGGTAC CGGCTTTGCGGCAGTGCTCGGCCTCGAGTTCGGCGATCGCGCGCGAAGTGCGTTTCGCGCACCAAGATCGCGGCCTAATGGCCGGCGATGACCGCGATGACCA

GCGCGATCCAGGAAAAACCGTTCCAACCAGTGCTGGGCGGCCATCCCCG (SEQ ID NO. 134)

Clone Rv167
:::::::::::::Rv167SP6.seq:::::::::::::
ATACTCAAGCTTCCCGACCACAAGTTGAACAGCACCGATTTCGGCGAGCACTTCGTCAACTTCCAGGGTGCCCGCACCAAGTATTTCGACAAGTATTTCCGTC GGGCCGCCGCCGCCGGCGCGCGGCAGGTGGTCATCCTGGCGGCGGGGCTGGACTCCCGCGCGTACCGGCTGCCTTGGCCCGACGGGACCACGGTTTTTGAGCT GGACCGCCCGCAGGTCCTTGATTTCAAGCGCGAGGTGCTCGCCAGCCACGGTGCCCAACCGCGCGCCCTGCGCCCGCGA (SEQ ID NO. 135)

:::::::::::::Rv167T7.seq:::::::::::::
GTGTGCTGTCAATTCAGAGCTGAGCCTGATGCACTCAACTTACTGAGCATGCTAACGCTGGTCGTGCGGGTCTTGTTCCCGCGTGTCGGCAGGGCACACGCTC GGGGCGTAGCTGGGAGAGGCCCCGGTCAAGCCCGGAGAGCAGTGCTCAGTCCGCCAGCTTGACCGACTTTCGATGAGAACGCGCTTCTCGCCGTATTGAACTG GCGTGCTGACGGTCGCTGAGCAGCGCTCGCCGAGTGCGGCCGCTGATTCTTTCATCGAGCCAGGAGGCGCATTCGTGTTCGGCCGCCTGCGGGTCGGCCCCAT CGTCGACGCGATCCGTCACCCACTCCTCGATCAGGTCTGCCTCATCGAACGGGCCAACGGTGCTGTCGGAGTATGTGTGCGTGGGCACGGCGAGCCGGGTGCT GTGGTACACCCACCGTTGCATGACCAAGTTGACGCCTGACTGGCTGAGCACCGCGATCCGCTCACAGGTCGGAACGTTGGTG (SEQ ID NO. 136)

Clone Rv169
:::::::::::::Rv169SP6.seq:::::::::::::
ATACTCAAGCTTTTGGTCTAGCCGGCCGAGCCCGATACAGGTGTCATTGGCCACCGGCGGCGGCTGTCCGGGAAATGGCGGGTCCCCGGTGGTTTTGCTGAGG AGTGCTGAACCGTATGCGAAGTGGGCGGCGTCAGACTCCACCCAGCCAGCAGGCAGCGCGAAACTGAATCCTCCAACCGGGTTGTCGATCCGGACAGGTTGGG GTGCGTTTGGGGCAATGACAGGTGGCGGCGGTGCGTCCGGGTCGGCCGGCGGAAGTGCTGCGTTGGGATCGCCCGGCTGGGCATTCTGCGTGTTGGCGGCGGC

CGGTGGTGGGGGGGCAACAGGTGTCTCCGGTGCGGGTGGCGCTGCACC (SEQ ID NO. 137)

:::::::::::::Rv169T7.seq:::::::::::::
GGGGCCACTCCGCACAATCTGTACCCGACCAAGATCTACACCATCGAATACGACGGCGTCGCCGACTTTCCGCGGTACCCGCTCAACTTTGTGTCGACCCTCA ACGCCATTGCCGGCACCTACTACGTGCACTCCAACTACTTCATCCTGACGCCGGAACAAATTGACGCAGCGGTTCCGCTGACCAATACGGTCGGTCCCACGAT GACCCAGTACTACATCATTCGCACGGAGAACCTGCCGCTGCTAGAGCCACTGCGATCGGTGCCGATCGTGGGGAACCCACTGGCGAACCTGGTTCAACCAAAC TTGAAGGTGATTGTTAACCTGGGCTACGGCGACCCGGCCTATGGTTATTCGACCTCGCCGCCCAATGTTGCGACTCCGTTCGGGTTGTTCCCAGAGGTCAGCC

CGGTCGTCATCGCCGACGCTCTCGTCGCCGGGACCCAGCACGGAAT (SEQ ID NO. 138)

Clone Rv16
:::::::::::::Rv16SP6.seq:::::::::::::
TTCTNTCTTCCCNNATTCGTNNNTCTCNTACTACCNGGGCCNCAAAACACCTTGGCNAACGCTCAAAGGCGNTACNGGCACCAAGGCCCCACACGTCACCCTG TGACCTCCTGCGCCGACCCCGCCCGAGGTCCTGGCCGTTACCACTGAACGGGCGAGCCGGGAGTCTGGTACGCATCGAACAAAGAGCAAGGTGCATGGGCGGA GTTGTTCCGCCNCTTTTTTTATGACGGGGTCGATCCATTCGAGGTCCGTCGCCGCGTCGGTCGAGTGGCGGTCACACTCCAGGTACTCGACCTCNCAGACGAG AGGACTCGATCCCATCTANGTGTGGACNAAACAGATCTTCTGTCCGACGACTACACACCACCCAGGCCATCGCCGCCGCCCGCGATGCCAACTTCNACNCCGT NCTGGCCCCGGCGGCGGCGCTCCCCGGTTGTCAAACACCTGCCGTGTTCGTTCACNCACTGCCCAACATCNAGCCCGANCNATCCNAGGTCCGTCCAACGCCT CCGCGGCTCNCCAACCTNCTCCCNCTGATCNTCCGCACCAAACACATGCCCGACTCCNTGCNCCNATTGCTTGNATCCCT (SEQ ID NO. 139)

TABLE 3-continued

End sequences of the polynucleotide inserts cloned in the named recombinant

::::::::::::Rv16T7.seq:::::::::::
CCGCTATCGGTCGGTGTGCTTGGCGGCGTCGGTATCAACACCGCCCACGAAATGGGGCACAAGAAGGATTCGCTGGAGCGGTGGCTGTCCAAGATCACCCTCG CCCAGACCTGCTACGGGCACTTCTACATCGAGCACAACCGTGGCCATCACGTCCGGGTGTCCACACCGGAGGACCCGGCGTCGGCGCGGTTCGGCGAGACGTT GTGGGAGTTCCTGCCCCGCAGTGTTATCGGCGGCTTGCGCTCGGCCGTTCATTTGGAGGCCCAACGGCTGCGTCGGCTCGGCGTCAGCCCCTGGAATCCCATG ACGTATCTGCGCAACGACGTGCTCAACGCGTGGCTGATGTCGGTGGTGTTGTGGGGTGGGCTGATCGCGGTCTTCGGCCCGGCGCTGATCCCGTTCGTCATCA

TCCAGGCAGTCTTCGGCTTCAG (SEQ ID NO. 140)

Clone Rv170
::::::::::::Rv170SP6.seq::::::::::::
ATACTCATGCTTGCCGAAGTTCCGATGGGTCGCGCCGGCGANCCCAGCGAAGTCGCTAGCGTGGCCGTGTTCTTGGCTTCGGATCTATCCTCGTACATGACCG GCACCGTGTTGGACGTGACTGGCGGCCGGTTCATATGACACCGAGATCATTGCCACGGTACGGCAATTCGTCAAGAAGGAAATCTTTCCCAATGCACCGGCCC TCGAACGTGGCAACAGCTACCCGCAAGAAATCGTCGATCGGCTGGGTGTTATTGGCTTGCTCGGTCGCCGGCTGCAAGGGTATCGACACCACCGAGTTCATTC

TCCGGGCGTGCC (SEQ ID NO. 141)

::::::::::::Rv170T7.seq::::::::::::
GGCGTCAACGGTGTCGGCACCGGCGTCCTGCAGTTGGTAGGCCTGCAGTTTGTGCATCAGGCCGATGCCGCGGCCCTCGTGGCCACGCATGTACAGCACCACG CCGCGCCCCTCACGGGCGACCATCGCCAGCGCGGCGTCCAGCTGAGGCCCGCAATCGCAGCGGCGTGACCCAAACACATCGCCGGTCAAGCACTCCGAATGCA CCCGGACCAGCACGTCGTCACCGTCGGCGTTGGGCCCGGCGATCTCGCCGCGGACCAGCGCGACATGTTCCACGTCCTCGTAGATGCTGGTGTAGCCGATGGC

GCGAATCTCCCATGACGAGTCGGAATCCGCGCCTCGGCG (SEQ ID NO. 142)

Clone Rv171
::::::::::::Rv171SP6.seq::::::::::::
ATACTCAAGCTTCGGCCTCGCTGCAGGAGTGGGAGCCGCAGGGCTGGAAATCCGAAAAACGAGCCGGTGATCGCACTGTCGCCGATCGGGGCCGCACCTGGTT GGTGTTACCGATGAATCCGCACCCAAAATGTGGCTGCGGTGGCGTTTCTTGACTCCTTGGCGTCGACTCTTGTGGCAGCCACCGAGCGGTTGGTCCAGGATCT GGATGGGCAAAGTTGTGCGGCCCGGCCGGTGACGGCCGATGAGCTGACCGAGGTCGACAGCGCCGTGTTGGCTGACTTGGAACCGACATGGATTCGCCCCGGT

TGGCGTCACCTCAAGCATTTCAATGGTTAT (SEQ ID NO. 143)

::::::::::::Rv171T7.seq::::::::::::
ATGCGTCACCCCGATGCGCCCAGATCGGGGCTTCGCAAATAAAGCACGAACAGGCGGGCAAAACGTCTATCTCGGAGCCGGAAGGGCAATCAGCCGACCGTCG ACGAACGACACCGGCGATAACCACTTAGGCGTTGAACGGCCGGCCCAAACATTACGCCTCCGTTGATAAGGCTTTCGGTCTCTTCCCCGGTCATCCCAAGCAC

CTTGCGGCAAATTTGAACGCTTTCCTGTCCGGGCACCGGCCCCGGGCTTTGGGTCCNTCCGA (SEQ ID NO. 144)

Clone Rv172
::::::::::::Rv172SP6.seq::::::::::::
ATACTCAAGCTTCAATCGCGCCGCCACAATCCAAATATGCGTCTAGCGTCTCGATGAGCGTCGGTCCGGCATCGGCTAGGGGCCGCATCACGTCGGTATGCAG GGCCACGATCGCCCAAGGCGTCGCCCATCAAGGGCGCGTTCGGGCAAAAATTCCCCTATCCAGCACGGGCCGCGGCGCTCCGCNCCAGCCGGCGACGGCGTTC ATCCCGGAGATCGCCTCGCTAGCGCTGCGGTGCGCCGCGGTCAGCATGGGCGCCGTGGGGCCGATGACCACCGGGGCGT (SEQ ID NO. 145)

::::::::::::Rv172T7.seq::::::::::::
TTCGGCGGGTCTGTAGATTGCGGTCGGCCACCCCACAGGCACTCATGAACCGCAGCCCACGATCGATCTCGGTGG (SEQ ID NO. 146)

Clone Rv173
::::::::::::Rv173SP6.seq::::::::::::
GCGCACCATCGCCAGTAGGTGCCCGTGGTCGGGCGCGTCGAGCCACCCGAGCGGAAACGCGAGTCCGAACAGCAACAGCAGGACGGGCGCAACCAGGGCGGTG

ACCATGCCCCCGGCGCTGAACATCAACCACAGGAAGGGCTCCGCCGAGCGTCCGCGCGACC (SEQ ID NO. 147)

::::::::::::Rv173T7.seq::::::::::::
CATCGTCGAACTTCGGTCCGGGTTGNTAGNACCGCAGCACCAAACGCACCCACCGACCCCCACGCTTCACGCCAACCCTTTAGTTCATTGGCGTGAACAGCAG CGTAGCCGGTTGCCCCGATATATGTGGAAAAATCGTTCGGACGTACAAAAAAAGTTCCTGACGCTGGCGTCAACTCGAAACTGCCTCGGAAGTCAATGATGAT

CCATCAGTCAATATTAAAGTCG (SEQ ID NO. 148)

Clone Rv174
::::::::::::Rv174SP6.seq::::::::::::
ATACTCAAGCTTGTCTGCTGCCTCAGCGTATGCATCCAACAGCGCATCGCGATCAACGATCAGGCGCGCCGATTTCGGGCCGCGGGCAGTGGCACTGGCCAGA TGGCCGTTTTTTTCGAGAAACTTCAACGCCTGAGCGCTGCTTCCCATCGAGAGACCGGTGGCCTCTACAACCGATGCGACAGTTGGACCGGCGATGTTCGCCA TABLE 3-continued End sequences of the polynucleotide inserts cloned in the named recombinant

GCAGCGCTTCACATACGGCAAGTNTGGCGCGG (SEQ ID NO. 149)

::::::::::::Rv174T7.seq::::::::::::
TTGTCCAGGCGGGGAATCGGGCAGGGAGACGACACCTTCGTTCGGTTCGATCGTCGCGAACGGGTAGTTGGCCGCGACCACGTTGTTTCGGGTCAGCGCGTTG

AAAAGTGTCGACTTGCCGACGTTGGGCAGGCCCACGATCCCCAGGCTCAAGCTCACAGA (SEQ ID NO. 150)

Clone Rv175
::::::::::::Rv175SP6.seq::::::::::::
ATACTCATGCTTGGCGCCTGGGTGGCAGCCCACCTGCCCACCACACGGACCGCGGTGCGGACGCGGCTGACGCGCCTGGTGGTCAGCATCGTGGCCGGTCTGC TGTTGTATGCCAACTTCCCGCCGCGCAACTGCTGGTGGGCGGCGGTGGTTGCGCTCGCATTGCTGGCCTGGGTGCTGACCCNCCGCNCNACAACACCGGTGGG TGGGCTGGGCTACGGCCTGCTATTCGGCCTGGTGTTCTACGTCTCGTTGTTGCCGTGGATCGGCGAGCTGGTGGGCCCCGGGCCCTGGTTGGCACTGGCGACG ACGTNCGCGCTGTTCCCCGGCATCTTCGGTCTGTTCGCCGTCGTGGTACCCTGTTGCCGGGTTGGCCC (SEQ ID NO. 151)

::::::::::::Rv175T7.seq::::::::::::
CGCCAATTCACGATATCGTTAACCGATATCCCGAGCCGATAGCTGGCGGGCTCGGGTGGTGGCCAGCGGCGCTGCGACGAAAGGTGTGACCGTCATGAAACAG ACACCACCGGCGGCCGTCGGCCGTCGTCACCTGCTCGAGATCTCAGCATCCGCAGCCGGTGTGATCGCGCTTTCGGCGTGTAGTGGGTCGCCGCCCGACCCCG GCAAAGGCCGGCCCGACACAACCCCGGAACAGGAAGTCCCGGTCACCGCGCCCGAAGNACTTGATGCGCGAACNCGGAGTGCTCCAAACGCATCCTGCTGAT (SEQ ID NO. 152)

Clone Rv176
::::::::::::Rv176SP6.seq::::::::::::
ATACTCAAGCTTGGGCACTGACTTCGGTACCCCCTCCGCCTTTGGCCAGCAGCAGCCACAGCGCGGTTCGCGGACCGAACGTGGACATCAATAGCCCGGAATC GGTGTGTGCAAGTTGGTAAACGGTGTTGATCCCAAGCTTTGCCAGCCTTTTCGTAGTCTTGGGCCCCACACCCCACAGTGCTTCGACGGTACGGTCACCCATG ATGGCCATCCAGTTGGCATCGGTGAGCTGATAAATGCCAGCTGGTTTCGCCAACCCGGTAGCGATCTTGGCGCGCTGCTTGTTGTCACTGATACCTATCGAGC AAGACAGCCCGGTTTGCGACAAAATGACTTTTCGGATCTCTTCGGCGACTTCGATGGGGTCGTCGGGA (SEQ ID NO. 153)

::::::::::::Rv176T7.seq::::::::::::
AAAGTCCTGTGCCGGTTCGCTAAACACCCGGCGGACACTCAGACGGTGCTGGTGGTGCGGCATGGCACCGCGGGCAGCAAAGCGCACTTCTCCGGGGGACGAC AGCAAGCGACCGCTAGACAAGAGGGGTCGTGCGCAGGCAGAAACGTTGGTACACAGCTGCTGGCGTTCGGCGCCACCGATGTTTATGCCGCCGACCGGGTGCG

CTGCCACCAGACGATGGAGCCACTCGCCGCGGAACTGAACGTGACCATACACA (SEQ ID NO. 154)

Clone Rv177
::::::::::::Rv177SP6.seq::::::::::::
ATACTCAAGCTTGGGTTCCACGCCCGCGCAGCCACGCCGTCACCTTTCCACGAGACCTCACCTGCCGATCCGAAATGGAATCGGCCGTGACGGAATTGGCGCA CCGAACACCCAACGAGGTGGTGGCTTCGTCGCGAACCGTCACCCGAGTCGCGGCCACCGTGCGCACGGCGACGTTCTACACCCGCACCAAGATCCGAAAGCTG CAAGCTCCCAGCACCGATCCCGACGTCATCACCGCTGCCGCCCGGCACGTCCTTGACCTATTCGAGCTGGATCGGCCCGTCCGGTTGCTGGGAGTGCGGTTAG

AACTGGCCTAGAACCGGCGGGCACACCGCNCCTGGGCGGGGCGAATTCTTGACCGCNCCGGCC (SEQ ID NO. 155)

::::::::::::Rv177T7.seq::::::::::::
CGCGGTTGGCGTAGTTGGACGGGTCGCCCTCCGAGGCCAATGATGACGATGACCACGCCGATCACGATGGCCACCGAGAGGGACAACAACAGAAAGCTGACGA ATCCCTCCTTGGCGGCCGGGGCTTTGTGGTCGCCGGTCGCGATGGGCGCGAATTTACGGCCCGCTCCCCCAGGCCGCCGCGAAGCAGGGTCCCCAGCCAGTTG GCGTAGGCGGAATTAACGATCAGCGCCACCGCGATAACCTGCCATGCCTCGGGCATATCGATGTGCGGCCAGAACAGGCCGAAC (SEQ ID NO. 156)

Clone Rv178
::::::::::::Rv178SP6.seq::::::::::::
CCAACAAGAGCATCGGGACATACGGAGTCAACTACCCGGCCAACGGTGATTTCTTGGCCGCCGCTGACGGCGCGAACGACGCCAGCGACCACATTCAGCAGAT GGCCAGCGCGTGCCGGGCCACGAGGTTGGTGCTCGGCGGCTACTCCCAGGGTGCGGCCGTGATCGACATCGTCACCGCCGCACCACTGCCCGGCCTCGGGTTC ACGCAGCCGTTGCCGCCCGCAGCGGACGATCACATCGCCGCGATCGCCCTGTTCGGGAATCCCTCGGGCCGCGCTGGCGGGCTGATGAGCGCCCTGACCCCTC AATTCGGGTCCAAGACCATCANCCTCTGCAACAACGGCGACCCGATTTGTTCNGACGGCAACCGGTGGCGAGCGCACCTAGGCTACGTGCCCGGGATGACCAA

CCAGGCGGCGCGTTTCGTCGCGAGCAGGATCTAACCGCGAGCCGCCCATAGATTCCCG (SEQ ID NO. 157)

::::::::::::Rv178T7.seq::::::::::::
TAANACCCGTGTAATTTGGGATGGGCAAAAAGGCCAAGCACCGCGTGGCCACGAACGCCGGGAGGGACAATCTCGGGCGGCTAGGGCTTCTCGCGGGAAGGCC CGAACGTACGGCGTTTCAACACGTCGCGTCNCCCTCCGACCGCGAACATTCGGGGATGGCAGCAACCTGGTAGCNCCCTGGCCGGGCGATGATCTGCAGCGTC TABLE 3-continued

| End sequences of the polynucleotide inserts cloned in the named recombinant |
| --- |

GCCGCGGGTAGTCGCCGCCCGGGCGGCTACAGTCTGAAACGCGATGACCATCGATGTGTGGATGCAGCATCCGACGCAACGGTTCCTACACGGCGATATGTTC

GCCTCGCTGCGCCGGTGGACCGGTGGGTCTATCCCGGAGACCGACNTCCCGATCGAAGCGACCGTCTCCTCGATGGACGCCGGCGGCGTCACCCTGGGTTTGC

TCACCGCCTGGCGTGGCCCCAA (SEQ ID NO. 158)

Clone Rv179
::::::::::::Rv179SP6.seq::::::::::::
GTCCGCAAAAGACTCAGCGGCCGACTTTGCTCGCAGCTGGCGGTACCGCGCCACCGATTCGATGCCGTGGTCGCGGAAGAATGCCTCCCGAAATCGCACGGCC GACTCCAGTTCGGCGAGCATCCGCGATGCCAGCTGCGGCTGCGCCCTGCCGGCCACGGCACCCACATGCGGCAGTTCGTCCACCTGGGCCAGCGCCCCGCCGC CGAAGTCCAAACAATAGAACTGCACCCGGCCCGCATCGTGGGTAGCAGCCAACGCCATGATCAGCGTCCGCAGCGCGGTTGACTTGCCCGTTTGCGGTGCACC

TACGACCGCGACATTGCCTGCGGCCCCGGACAAGTCGATCGTCAGCGGCACCCN (SEQ ID NO. 159)

::::::::::::Rv179T7.seq::::::::::::
CGTGGCCACGAACGCCGGGAGGGACANTCTCGGGCGGCTAGGGCTTCTCGCGGGAAGGCCCGAACGTACGGCGTTTCAACACGTCGCGTCGCCCTCCGACCGC GAACATTCGGGGATGGCAGCAACCTGGCAGCTACCTGGCCGGGCGATGATCTGCAGCGTCGCCGCGGGTAGTCGCCGCCCGGGCGGCTACAGTCTGAAACGCG ATGACCATCGATGTGTGGATGCATCATCCGACGCAACGGTTCCTACACGGCGATATGTTCNCCTCGCTGCGCCGGTGGACCGGTGGGTCTATCCC (SEQ ID NO. 160)

Clone Rv17
::::::::::::Rv17SP6.seq::::::::::::
ATACTCAAGCTTTGCGGCGGGCGCCGAAATGTGAACGCACCAAACCCGCCCGCTGCGGGTCGGCGGGCCACTCGACCTCGAATTTCGCCGCCGTGACCATCCA GCCCGACGGCAGTTGGGCACCCGGCCCCCCGGTCGCGGCATAACTGTTGGCGTCGCCGTCATAAAGCTCGAACAGCACCGAAACCGACTCCACCACCGGCCGG TGCGCCTCAAAATCCACGCCGATCTCCACATACCGGGAAAACGTCGGTGTCCCATCGGGTTTCGGCTTGCCCGCCAGCTGCACACCACCGGTGGCCTCGGCCA CCTTCGCGGCCTGAGCGCAGCTACNCATCCTGACGATCATCACCCCGCCCCCGGCTCACGCTTGGCCTCCGTGACCGCACGCATCGCCCGGTTGCGCGCACCG

CGACGCCCGTACAGCCGCGCGCAC (SEQ ID NO. 161)

::::::::::::Rv17T7.seq::::::::::::
AGCTTGCCGGGACTGCGGAACAGAAGCGGCGGTTCCTACCGCGGTGTGCGGCCGGCGCGATATCGGCCTTTTTACTAACCGAACCCGATGTGGGCTCCGATCC GGCGCGCATGGCATCGACGGCGACGCCGATCGATGACGGCCAGGCTTACGAGCTTGAGGGTGTGAAGTTGTGGACCACCAACGGTGTGGTAGCGGACCTGCTA GTGGTTATGGCGCGGGTACCGCGCAGTGAAGGGCACCGAGGGGGAATCAGCGCCTTTGTCGTCGAGGCTGATTCGCCCGGGATCACCGTGGAGCGGCGCAACA AGTTCATGGGACTGCGTGGCATCNAAAACGGCGTGACCCGGCTTCATCGCGTCNGGGTGCCCAAAGACAACTTGATCGGCA (SEQ ID NO. 162)

Clone Rv180
::::::::::::Rv180SP6.seq::::::::::::
CTCAAGCTTGGCGATGCGGGCTGGCCAAAACTGGCCGGGCGGGGGTTGCTTGTTCAATCAAGGGTGGGTTGCCG (SEQ ID NO. 163)

::::::::::::Rv180T7.seq::::::::::::
CCGAAGGCCCGTTCCCGGGCGTTCAGCAAGCGATCGTCGGTTGGCCCACTGCGGGTCGAATCTTGCGGCCGCGCCGGTCGTGGAACGCCCAGGTCACCCGGCG

GCGTACC (SEQ ID NO. 164)

Clone Rv181
::::::::::::Rv181SP6.seq::::::::::::
ATACTCAAGCTTTTTCTGCTCATGAAGGTTAGATGCCTGCTGCTTAAGTAATTCCTCTTTATCTGTAAAGGCTTTTTGAAGTGCATCACCTGACCGGGCAAA TAGTTCACCGGGGTGAGAAAAAAGAGCAACAACTGATTTAGGCAATTTGGCGGTGTTGATACAGCGGGTAATAATCTTACGTGAAATATTTTCCGCATCAGCC AGCGCAGAAATATTTCCAGCAAATTCATTCTGCAATCGGCTTGCATAACGCTGACCACGTTCATAAGCACTTGTTGGGCGATAATCGTTACCCAATCTGGATA ATGCAGCCATCTGCTCATCATCCAGCTCGCCAACCAGAACACGATAATCACTTTCGGTAAGTGCAGCAGCTTTACGACGGCGACTCCCATCGGCAATTTCTAT

GACACCAGATACTCTTCGACCGAACGCCGGTGTCTGTTGACCA (SEQ ID NO. 165)

Clone Rv182
::::::::::::Rv182SP6.seq::::::::::::
CTCAAGCTTGGTGCCGACATGGCCGGGCTGGAGCCCGCGTATGGCAAGGTTCCGCTCAATGTGGTTGTGATGCAGCAGGACTACGTTCGCTCAATCAGCTCA AACGTCACCCCCGTGGCGTGCTGCGCAGCATGAAGGTCGGCGCCCGCACGATGTGGGCGAAGGCAACAGGTAAAAACCTGGTCGGCATGGGTCGAGCCCTCAT TGGGCCGTGGCGGATCGGGTTGCACCGCGCCGGAGTGCCGGTCGAACTCAACACCGCCTTCACCGATCTTTTCGTCAAAAATGGCGTCGTGTCCGGGGTATAC (SEQ ID NO. 166)

TABLE 3-continued

End sequences of the polynucleotide inserts cloned in the named recombinant

::::::::::::Rv182T7.seq::::::::::::
CCGAAGCGTGGGAAATCCTGACCGAATACCGCGACGTGCTGGACACTTTGGCCGGCGAGCTGCTGGAAAAGGAGACCCTGCACCGACCCGAGCTGGAAAGCAT CTTCGCTGACGTCTAAAAGCGGCCGCGGCTCACCATGTTCGACGACTTCGGTGGCCGGATCCCGTCGGACAAACCGCCCATCAAGACACCCGGGGGAGATCGC

GATCGAAACGCGGCGAAACTTGGGCC (SEQ ID NO. 167)

::::::::::::Rv183SP6.seq::::::::::::
CGACTCGACAAGCATTCTTGACAGTTGTTTTGGCTCGGCATGGTTAGCCAAGGTTCTGCGGTCCCACCAGATCATCTTGGTCCGGTAGCGCTCGTCCGGGTAT GCTGCCGCCGGGATTCTCGCTGCTATTACTCCCCCGAAAAACGCCACCGGTCCAGCGCGTGGGCCGCCGCGGTCCCCATCACAAACTGAACCCCCAACAGGG GACATGCTTAGCGGTAGGGCGCGCGCCAAGGCGGCAGCAATCGCATCACTGCGCTGCGCGTCACTATTAACCCACCCGGACTTCACTTCCACGACCCCGAATG GCGCCCGGTCATTGATCATCTTGCGCACCGCGGATAATCCGGGATTGCCAGCCCATTCGACTACCGCATGCGAGTCATCGGCTGACCGCAGCGGTCCGATTAC

CCGAGCGCCCCGANTACATCTCCTCCAATATCAATGGGCGCAA (SEQ ID NO. 168)

Clone Rv183
::::::::::::Rv183T7.seq::::::::::::
GCGGTNTAGCTTCCCGTCGTACCGGCGACCGCCAGCCGAGAAGCTCGTTTTCCCAGTGTTGCTGGGGATTCTCACGCTGCTGCTGAGTGCGTGCCAGACCGCT TCCGCTTCGGGTTACAACGAGCCGCGGGGCTACGATCGTGCGACGCTGAAGTTGGTGTTCTCCATGGACTTGGGGATGTGCCTGAACCGGTTCACCTACGACT CCAAGCTGGCGCCGTCTCGTCCGCAGGTCGTTGCTTGCGATAGCCGGGAGGCCCGGATCCGCAATGACGGATTCCATGCCAACGCTCCGAGTTGCATGCGGAT CGACTACGAATTGATCACCCAGAACCATCGGGCGTATTACTGCCTGAAGTACCTGGTGCGGGTCGGATACTGCTATCCGGCGGTGACGACCCCCGGCAAGCCG

CCATCCGTGCTGCTGT (SEQ ID NO. 169)

Clone Rv184
::::::::::::Rv184SP6.seq::::::::::::
CTCAAGCTTGGGCGTGACGGCCACCGGGGCCACTCCGCACAATCTGTACCCGACCAAGATCTACACCATCGAATACGACGGCGTCGCCGACTTTCCGCGGTAC CCGCTCAACTTTGTGTCGACCCTCAACGCCATTGCCGGCACCTACTACGTGCACTCCAACTACTTCATCCTGACGCCGGAACAAATTGACGCAGCGGTTCCGC TGACCAATACGGTCGGTCCCACGATGACCCAGTACTACATCATTCGCACGGAGAACCTGCCGCTGCTAAAGCCACTGCGATCGGTGCCGATCGTGGGGAACCC ACTGGCGAACCTGGTTCAACCAAACTTGAAGGTGATTGTTAACCTGGGCTACGGCGACCCGGCCTATGGTTATTCC (SEQ ID NO. 170)

::::::::::::Rv184T7.seq::::::::::::
CGGGTGTCATTGGCCACCGGCGGCGGCTGTCCGGGAAATGGCGGGTCCCCGGTGGTTTTGCTGAGGAGTGCTGAACCGTAGTCGAAGTGGGCGGCGTCAGACT CCACCCAGCCAGCAGGCAGCGCGAAGCTGAATCCTCCAACCGGGTTGTCGATCCGGACAGGTTGGGGTGCGTTTGGGGCAATGACAGGTGGCGGCGGTGCGTT CGGGTCGGCCGGCGGAGGTGCTGCGTTGGGATCGCCCGGCTGGGCATTCGGCGTGTTGGCGGCGGCCGGTGGTGGGGGGGCAACANGTGTCGCCGGTGCGGGT

GGCGCTGCA (SEQ ID NO. 171)

Clone Rv185
::::::::::::Rv185SP6.seq::::::::::::
NCTTGATATTGGCGTCAACGGTGTCGGCACCGGCGTCCTGCAGTTGGTAGGCCTGCAGTTTGTGCATCAGGCCGATGCCGCGGCCCTCGTGGCCACGCATGTA CAGCACCACGCCGCGCCCCTCACGGGCGACCATCGCCAGCGCGGCGTCCAGCTGAGGCCCGCAATCGCAGCGGCGTGACCCAAACACATCGCCGGTCAAGCAC TCCGAATGCACCCGGACCAGCACGTCGTCACCGTCGGCGTTGGGCCCGGCGATCTCGCCGCGGACCAGCGCGACATGTTCCACGTCCTCGTAGATGCTGGTGT AGCCGATGGCGCGAAACTCCCCATGACGAGTCGGAATCCGCGCCTCGGCGACCCGCTCAATGTGCTTCTCGTGCTTGCGCCGCCATTCGATCAAGTCAGCAAT

GGTGATCAGCGCCAGACCGTGCTCNTCGGCG (SEQ ID NO. 172)

::::::::::::Rv185T7.seq::::::::::::
CATAAGGGCCGGCGTACCCGGTACCGGCCGCGGGCCTACCACGTGCCGGAACTGGAAGCGCAGTAAGCCCTCAACGCGCCACCGCTTTGGCCCGCGCGCCCGG CGTAGGCGCATCGGCGGTGGCCGTGGGGCGGCGCACTGCGACCTCACCAGCGGCTTTCGAGCTTTGTTCGATCAACCGGCCAGCATGGTCGAGGATGCATTCG AGACCATATTCGAAATTGGTTTCATCGGGGGCCCCGATCCGATGCCCCCTCCCAGTTGCGTGAGCAAGCAGCGGAGTCGTCGCGGGATCGATGGCCACGGGGT GTTCAATGGCGGATGGTCCGCTGCCCGCCGACTGGCTCTTGCGGGAGAGCCGATCTAGCACCACCGATCCGCGCACGTGGACCGAAACCGCCGAGTAGATGTC

GAAAGCGT (SEQ ID NO. 173)

Clone Rv186
::::::::::::Rv186SP6.seq::::::::::::
CGTCCTTTTCCCCAAGATAGAAAGGCAGGAGAGTGTCTTCTGCATGAATATGAAGATCTGGTACCCATCCGTGATACATTGAGGCTGTTCCCTGGGGGTCGTT TABLE 3-continued End sequences of the polynucleotide inserts cloned in the named recombinant ACCTTCCACNAGCAAAACACGTAGCCCCTTCAGAGCCNNATCCTGAGCAANATGAACAGAAACTGAGGTTTTGTAAACGCCACCTTTATGGGCAGCAACCCCG ATCACCGGTGGAAATACGTCTTCAGCACGTCGCAATCGCGTACCAAACACATCACGCATATGATTAATTTGTTCAATTGTATAACCAACACGTTGCTCAACCC

GTCCTCGAATTTCCATATCCGGGTGCG (SEQ ID NO. 174)

Clone Rv187
::::::::::::Rv187SP6.seq::::::::::::
CTCAAGCTTCATGTCCGTACGGCTCGGGTACGCTTCCGTCGCAGTGTGCGAGTGATAAATGACGACCGGGACCTCGTCGGCATCTTCCATAGCCCGCCACACC TTCAGTTGCTCACCGGAATCCAACCGGTAGAAGGTCGGCGAGCGCTCGGCATTGGTCATCGGGATATGCCGCTCGGGACGGTCAGAGCCCTCGGGTCCGGCCA

GCACTCCGCAGGCTTCGTCGGGGTGGTCGCGACACGCATGGGCCACCATCGCATTCAC (SEQ ID NO. 175)

::::::::::::Rv187T7.seq::::::::::::
NCGCCGCCAGCCACCACGCGCGGGTCGGGCGCCGGGCCCGGGCCGCCAGGCTGCTCCGCTCGGTGATGGCACGCCACCGCGACACCACCCGGCTGCGCTACGT CGAGCCATACCGGGCGGAGCTACATCGGCTCGGCCGCCCAGTGTTCGGGCCCTCTTTCGAGGTCGAGGTCGATACCGATTTGCGCATCCGCAGCCGCACCCTG GACGACAGAACCGTGCCCTACGANTGCTTGTCGGGCGGGGCCAAAGAACAGCTTGGCATCCTGGCGCGATTGGCCGGCGCGGCGCTGGTCTCCAAAGAAGACG

CCCTTCCGGTGCTGAT (SEQ ID NO. 176)

Clone Rv188
::::::::::::Rv188SP6.seq::::::::::::
CGCCACGTTCATGGGCAACAACCCCGATCACCGGTGGAAATACGTCTTCAGCACGTCGCAATCGCGTACCAAACACATCACGCATATGATTAATTCGTCCAAT TGTATAACCAACACGTTGCTCAACCCGTCCTCGAATTTCCATATCCGGGTGCGGTAGTCGCCCTGCTTTCTCGGCATCTCTGATAGCCTGAGAAGAAACCCCA

ACTAAATCCGCTGCTTCNCCTATTCTCCAGCGCCGGG (SEQ ID NO. 177)

Clone Rv189
::::::::::::Rv18SP6.seq::::::::::::
ATACTCAAGCTTCAACCGATTGACGCATTGTGCGAACTGACGGCGCCCGCGCATGGCCAATCCGGAAGACCATCATTGGCCAGTGGCCGGGCGCTAACAGGTT CCAGCCCCCCACCAGTGCCGCTCGAACATGCGGTGCAACCCATTCGCAGGCCGGCAGGGAAAGCACCGCGGAAGCCGCAAAGGGCTGCAGTTCCGCGCCCAAT AGTGTCGTCCGCAACCAGATGCGCTCGAAAACCGCGCCGGCAGTCAGCGCACCCGACGCGAGGTCGAGAGACGTCGTCAGCGCGCCCACATGGGGTGCCAATC GGCACGGCAGGTAGGCCGCGCGCAACCCGAACGCGTGGTGCATGCCCACGGTCCGCAGGAGGCGCAGCACCCGCCAATGCCGAAGCCCACGAAACATCGGGCG

CATCCACGCTTCAACCTC (SEQ ID NO. 178)

Clone Rv18
::::::::::::Rv18T7.seq::::::::::::
AGCTTTTGGCAGGGTCTCCTTCGAATTCGGCGTGCACCGCTATGGGTTGCAGCAGCGGCTGGCGCCGCACACCCCACTGGCCCGGGTGTTTTCGCCCCGAACC CGGATCATGGTGAGCGAAAAGGAGATTCGCCTGTTCGATGCTGGGATTCGCCACCGCGAGGCCATCGACCGATTACTCGCCACCGGGGTGCGAGAGGTGCCGC AGTCCCGCTCCGTCGACGTCTCCGACGATCCATCCGGCTTCCGCCGTCGGGTGGCGGTAGCCGTCGATGAAATCGCTGCCGGCCGCTACCACAAGGTGATTCT GTCCCGTTGTGTCGAAGTGCCTTTCGCGATCGACTTTCCGTTGACCTACCGGCTGGGGCGTCGGCACAACACCCCGGTGAGGTCGTTTTTGTTGCAGTTGGGC

GGAATCCGTGCTCTGGGTTACAGCCCGAATCGTCAC (SEQ ID NO. 179)

Clone Rv190
::::::::::::Rv190SP6.seq::::::::::::
ATACTCAAGCTTTGTCACACCAACTGTTTCCACCAGGCGCTCCATCCGGCGAGTGGATACTCCCAGCAGGTAGCAGGTCGCCACCACGCTGGTCAGTGCGCGT TCAGCTCGCTTGCGGCGCTGCAGCAGCCAGTCCGGGAAATAGCTGCCCTGGCGCAGCTTGGGGATCGCGACTTCTATGGTTGCGGCACGGGTGTCGAAATCAC GGTGGCGGTAGCCGTTGCGCTGATTGGACCGCTCATCGCTGCGTTCGCGGTAGCCCGCCCCGCACAGGGCGTCGGCTTCAGCCCCCATCAAGGCGGCGATGAA CGTCGAGAGCAGCCCGCGCAGCAGATCCGGGCTCGCCTGTGCGAGTTGGTCAGCCAGAACCTGCTCGGTGT (SEQ ID NO. 180)

::::::::::::Rv190T7.seq::::::::::::
CCTTAAGCCCCGCAGGGCCCGGCACGCGCGGTACCGCCCAGGTCGCCCAACAGATCGTCGATGTTCGCGTCGTCCGCCTCGCGCACGTGGTCTGTCACCAGTC AACGTTAACGCCGCCGCACATGTCCTGCGGCCGGGCAAAAACGTGAAAAACGAGCGGGCGACTGCAATGTCATGACACCGACGGCCGCCGATGGGCCCAGGGT CTGGCAGATTCGATCTGTGCGGCCAGTGCCAGCAGCGTCGCCTCGTCATACGGCCGGCCGACGAGTTGAACCGACATGGGCAGGCCGTCGCCGTCGAAGTCCC ACGGCACCACGGCCGCGGGCTGGCCGGTCAGATTCCAGACTTGAAAGTACGGAACCCGCTGCACCACCAGCAGCAACGTCGAAACTGCACCCCGGCGTTGGTA GGCGCCGATGCGGGACGGGCCGGTCGCGGCGCCTGGCGTCACAACTACGTCGACATCGTCGAAGATCGACTGGATCGGCTGCTCACACCACTCGGCGGCCGCA

GGCCGCCATCCGCCGTC (SEQ ID NO. 181)

TABLE 3-continued

| End sequences of the polynucleotide inserts cloned in the named recombinant |
|---|

Clone Rv191
::::::::::::Rv191SP6.seq::::::::::::
AGCTTTTTGAGCGTCGCGCGGGGCAGCTTCGCCGGCAATTCTACTAGCGAGAAGTCTGGCCCGATACGGATCTGACCGAAGTCGCTGCGGTGCAGCCCACCCT CATTGGCGATGGCGCCGACGATGGCGCCTGGACCGATCTTGTGCCGCTTGCCGACGGCGACGCGGTGGGTGGTCAAGTCCGGTCTACGCTTGGGCCTTTGCGG ACGGTCCCGACGCTGGTCGCGGTTGCGCCGCGAAAGCGGCGGGTCGGGTGCCATCAGGAATGCCTCACCGCCGCGGCACTGCACGGCCAGTGCCGCGGCGATG TCAGCCATCGGGACATCATGCTCGCGTTCATACTCCTCGACCAGTCGGCGGAACAGCTCGATTCCCGGACCGCCCAGCGCATTGGTGATGGAATCGGCGAACT TGGCCACCCGCTGGGTGTTGACATCCTCGACGGTGGGCAATTGCCCCCGGTAACGTTTGCCGCCT (SEQ ID NO. 182)

::::::::::::Rv191T7.seq::::::::::::
CGGTCCGACCCTGTTCGACGGCTACCTGAATCAACCCGATGCCACCGCCGCGGCGTTCGACGCCGACAGCTGGTACCGCACCGGCGACGTCGCGGTGGTCGAC GGCAGTGGGATGCACCGCATCGTGGGACGCGAGTCGGTCGACTTGATCAAGTCGGGTGGATACCGGGTCGGCGCCGGTGAAATTGAAACGGTGCTGCTCGGGC ATCCGGACGTGGCGGAGGCGGCAGTCGTCGGGGTGCCCGACGATGATCTAGGCCAGCGGATCGTTGCCTACGTAGTCGGCTCAGCGAATGTCGATGCGGACGG GCTTATCAACTTTGTTGCCCAACAACTTTCGGTGCACAAGCGCCCGCGCGAGGTGCGTATCGTANATGCGCTGCCGCGCAACGCCTTGGGGAAAGTGCTCCAG

AACATTGCTGTCAGAAGCTGANCTACGCGAATTATCGTGTTACGCTGGA (SEQ ID NO. 183)

Clone Rv192
::::::::::::Rv192SP6.seq::::::::::::
ATACTCAAGCTTGCCGAAGTTCCGATGGGTCGCGCCGGCGAGCCCAGCGAAGTCGCTACCGTGGCCGTGTTCTTGGCTTCGGATCTATCCTCGTTCATGACCG GCACCGTGTTGGACGTGACTGGCGGCCGGTCCATATGACACCGAGATCATTGCCACGGTACGGCAATTCGTCAAGAAGGAAATCTTTCCCAATGCACCGGCCC TCGAACGTGGCAACAGCTACCCGCAAGAAATCGTCGATCGGCTGGGTGTTATTGGCTTGCTCGGTCGCCGGCTGCAAGGGTATCGACACCACCGAGTTCATTC TCGGGCGTGCCGGCGCATTCGAGCTGGCGGTGCGCGCTGCCCAGCACCGTCATAGGTACTTGACGATGGTCCACGTCGGACGAGCGCCTCCACGTCGCTGCCG

AACGGTATGCATGGCGGCTACGATTCTC (SEQ ID NO. 184)

::::::::::::Rv192T7.seq::::::::::::
CGGTGTCGGCACCGGCGTCCTGCAGTTGGTAGGCCTGCAGTTTGTGCATCAGGCCGATGCCGCGGCCCTCGTGGCCACGCATGTACAGCACCACGCCGCGCCC CTCACGGGCGACCATCGCCAGCGCGGCGTCCAGCTGAGGCCCGCAATCGCAGCGGCGTGACCCAAACACATCGCCGGTCAAGCACTCCGAATGCACCCGGACC AGCACGTCGTCACCGTCGGCGTTGGGCCCGGCGATCTCGCCGCGGACCAGCGCGACATGTTCCACGTCCTCGTAGATGCTGGTGTAGCCGATGGCGCGAAACT CCCCATGACGAGTCGGAATCCGCGCCTCGGCGACCCGCTCAATGTGCTTCTCGTGCTTGCGCCGCCATTCGATCAAGTCAGCAATGGTGATCAGCGCCAGACC GTGCTCATCGGCGAACACCGCAATTCATCGGTGTTGCGCCATCGAGCCCTCATCTTTTTGGCTGACGATCTCGCAAATCGCCCCCGCGGGTTGCAGCCGGCAT (SEQ ID NO. 185)

Clone Rv193
::::::::::::Rv193SP6.seq::::::::::::
ATACTCAAGCTTTGGGTGAAAGCCGATCACCGGAAGCCGCATGATCAGCCACGTTTCGCGCCGCCCGGCATACGGCGGCGTACCGATCTCCGCGTCATACACC CGCGGGTAATCGCCGACGGTGCCGGTTCGCGAGCCGAAGGTGACGACGCTGATTGAATCGAGTTCCAGGTCCAGCGGGTGGCGCAGCAACGGCGCGAGCTCAA CGACGTCAATCACGTTGTCGCTTTCTACGGTCACCGACCCGGTGACCGTNCTCGCCCGGTGCGCTCGGCCGATAAGTTGCACCGCCACCACCGCGACACCGTC

TTGCACGCGGACCCACCCCCGGATCCGTTGTTGGCC (SEQ ID NO. 186)

::::::::::::Rv193T7.seq::::::::::::
AGCTTGCTGGCATCCGCTCCAGTAGCGCCCCGCGCGTGGCTTCCAGCGCCCGCAGATGCTCCATGAGCCGGCCGGTCGAGTCGGCGCCGGCGTTCACCGCCAC CCGCCAGGAGCTGGCGGCCAGCATCTCCGCCTTCACGCATTGCGCGATCACAGAGAGAATATACGTCTCATATTCGTTGGAGGTCGTCGCAGGCAATCGGTCG ATGACGGATTTGATGGCATCGAGCTGTGCTTCGGCGTAGCCCTCCAGCACGTCGGTATCGCTGTGGCGGTCCACGACGACCGCACCGGCGCGGCGGACAGCCG

TCGGGTTGGACGNTGTGCGGCGATCAGTCCGGCCAGCTCCGCCTCGGGATCAGCGGC (SEQ ID NO. 187)

Clone Rv194
::::::::::::Rv194SP6.seq::::::::::::
ATACTCAAGCTTGCTGCAGCTTCCTATGACTGCTCCCGAAACCTGGGGGTGTGCCTGCTGTGTATGCACGGCATACGGACATCCTTCCCCTGAGACCCGCGGT CGAACCAGCCACGTGTCCATCATCAGGGGTCAACCCCGGCCAAGGGCGACGGCACGCCAAGTTCGCCGACCGTTAACCTAGTGCTGTTAGCTTCATTTGCTGC GAGCAAAACAGCTGGTCGGCCGTTAGGAACTGAATTGAAACTCAACCGATTTGGTGCCGCCGTAGGTGTCCTGGCTGCGGGTGCGCTGGTGTTGTCCGCGTGT GGTAACNACNACAATGTGACCGGGGGAGGTGCAACCACTGGCCAGGCGTCGGCGAAGGTCGATTGCGGGGGGAAGAAGAACTCAAAGCCAGTGGGTCGACGCG TABLE 3-continued End sequences of the polynucleotide inserts cloned in the named recombinant

CAGGCCAACGC (SEQ ID NO. 188)

::::::::::::Rv194T7.seq::::::::::::
AGCTTGACGCGGAGACGGACACATTGCGAACATTGATGACAAAATAGAAATCATTGATGGTTTGAGTCACCAGGCCGATCAAGCCTTCGCCGAGCCAAATTCC AATCAAGAGGCCCAAGCCCGTACCAATCAGCCCGGCAACGAGGGATTCCGTCATTATCAGCCAAAATAACTGCTCTCGGGTTACACCCAAACAGCGCAATATG GCGAAAAACGGTCGCCGTTGCACGACATTAAATGTCACGGTATTGTAGATTAAAAAGATACCCACCAACAAGGCAATCAAACTGAGAGCGGTTAAATTGACCG TAAAAGCGTCCGTCATCTGTTTGACGGTGTCCCGTTGGGTATCCGACGTTTCCATACGCACACCGGCCGGCAGTCTTTGTTGGATGCGTGTTGCAGTGGCCTC

ATCTTTGATGATCAAATCGATGTGGCTCAGTCTTCCGGGCA (SEQ ID NO. 189)

Clone Rv195
::::::::::::Rv195SP6.seq::::::::::::
ATACTCAAGCTTCGGCTCAGGCGGCGCTGCTGGTAAAGTCGCTGACCGGTGCAGGTTTCGACAATGTGGTGCCGGTTCGGCGGCTACGTGCCATCGAGACACT GGCGCAGGCTATCGCACCCGTTATCGGCTACGAGCAAATCGCGGTATGCGTTCTTGAGCATGAGTCGGCGACCGTCGTCATGGTCGACACCCACGACGGAAAG ACGCAGATCGCCGTCAAGCATGTGTGCCGCGGATTATCAGGACTGACCTCCTGGCTGACCGGCATGTTTGGTCGCGATGCCTGGCGCCCGGCCGGCGTGGTCG TGGTCCGCTCGGATAGCGAGGTCAGCGAATTCNCNTGGCAGCTCCAAAGGGTCCTGCCGGTGCCGGTCTTTGCGCAAACNAAGGCNCAGGTTA (SEQ ID NO. 190)

::::::::::::Rv195T7.seq::::::::::::
TGATCGCGCATCACCTGCTTCATAAACTGGAAGCAGCGCAGCGCTTCCTTTTCGGCCGCAACATGAGCCAGCCTCTCGTCGGCGGTCGGGTGCAGGTGCTCGG GCAGCTCGGCCGCGACAGCCGCCTGACCCTGAAACCAGCTTCCATATCCCGCGACGAACGACGCCAGTCCGCTACGTAACCCCTCCGCGACTGTCCATGGACA ACAGCGCGTTCTCCACCGACCGGGCCCGGGTGTGGGGTGTTTCGGCGACCGGCAGCCAGGTGGTCCACACTGCCGACGGGCGCCGCGAGCCGTTCACCGACCA GGCCGCCGAGCAAGTCCGCCCGATCGCATACTCCAACCGGTTGCGGTACTGCAGGTTCAGCTGGCGTACTCCTCGTCGCGCTCGGCGAGGTCTTGCTCCAGCA

CGTCGCANACGGCAG (SEQ ID NO. 191)

Clone Rv196
::::::::::::Rv196SP6.seq::::::::::::
CAAAGCGCGAACTGCTCGCGGCAGCCCACGACGTGCTGCGTCGGATTGCCGGCGGCGAAATCAATTCCAGGCAGCTCCCGGACAATGCGGCTCTGCTGGCCCG CAACGAAGGACTCGAGGTCACCCCGGTGCCCGGGGTCGTGGTGCACCTGCCGATCGCACAGGTTGGCCCACAACCGGCCGCTTGATGCCCGGTCGGCAAGCCC GGCAGTTGCCAAACCCAGCGTGATCAGGCTCGGCTCGCGAGTTCCGGGAAGAAGTGGCTCCGCCTGATCACCTACCATCCGCCAGGATCTGCGTGTCTTCACC

ACGCCCGCCAAGGAGGTTGTTGTGGTGCTATCGACCGN (SEQ ID NO. 192)

::::::::::::Rv196T7.seq::::::::::::
CCGGAAGCCGCATGATCAGCCAAGTTTCGCGCCGCCCGGCATACGGCGGCGTACCGATCTCCGCGTCATACACCCGCGGGTAATCGCCGACGGTGCCGGTTCG CGAGCCGAAGGTGACGACGCTGATTGAATCGAGTTCCAGGTCCAGCGGGTGGCGCAGCAACGGCGCGAGCTCAACGACGTCAATCACGTTGTCGCTTTCTACG GTCACCGACCCGGTGACCGTNGTCGCCCGGTGCGCTCGGCCGAAAANTTGCACCGCCACCACCGCGAAACCGTCTTGCACNCCGGAAGCCACCCCCGATCCGT

TGTTGGGCCAGGTTATTGGGT (SEQ ID NO. 193)

Clone Rv19
::::::::::::Rv19SP6.seq::::::::::::
CCGGAACCGCCGACGGCACGGTATAACGCCTCCGCATATGGGTCGACAACCAGCGGGTCGGACTTCTGGGCTTCTAGCGTTCGCGCNGTCGCGACAAACAGCG CGGTCGAACCGACACTCGTTGTGATGTCCTAGCTATCACGTTCGGTACGCACCCAATCGAGTCTAGCGCGGGTAGNTCAGCCCCGATCTCCANGCTCCGCCGA

GCCAGGCGC (SEQ ID NO. 194)

::::::::::::Rv19T7.seq::::::::::::
CTGGTTTATGTCCCGTTGAAGTTCCATCACCCGATGTGGCGGGAGCACTGCCAGGTCGATCTCAACTACCACATCCGGCCGTGGCGGTTGCGCGCCCCGGGGG GTCGGCGCGAACTCGACGAGGCGGTCGGAGAAATCGCCAGCACCCCGCTGAACCGCGACCACCCGCTGTGGGAGATGTACTTCGTTGAGGGGCTTGCCAACCA

CCGGATCGCGGTGGTTGCC (SEQ ID NO. 195)

Clone Rv1
::::::::::::Rv1SP6.seq::::::::::::
CCGAGCAGTTGGGAATCGCTCTGCANCAAACCAATATTCTGCGCGACGTCGCGCGACGAGCTGGACCGATTAGGCGTACGCCTCCGNCTGGACGACACCGGGG

CACTCGATGACCCCGACGCCTACGCTCGCAGGATATTGTTCGCCGGACCCCTCTCTAG (SEQ ID NO. 196)

TABLE 3-continued

End sequences of the polynucleotide inserts cloned in the named recombinant

::::::::::::Rv1T7.seq:::::::::::
TATATAATACTCAAGCTTGCCGACGCCAACGCTCGCGCGATGTTGTTAGCCCGACCCGGCTCTTACATGGCACCGGTGCCCCACACGTCAGCCTGTGACGTCC TGCACCGCGACTCTTTACATAGAATGTGGATTGCCGGATTGGGGATGTCCGGCATCGCTCAATCTGTAGTCCGCGTTGTCCCGCGAGGGCCATGTGGATGGGG

GGAAGGATCCGTGGCGTCCGGGATCACCATGGGG (SEQ ID NO. 197)

Clone Rv201
::::::::::::Rv201SP6.seq::::::::::::
ATACTCAAGCTTGCCGAAGTTCCGATGGGTCGCGCCGGCGAGCCCAACGAAATCGCTAGCGTGGCCGTGTTCTTGGCTTCGGATCTATCCTCGTACATGACCG GCACCGTGTTGGACGTGACTGGCGGCCGGTTCATATGACACCGAGATCATTGCCACGGTACGGAAATTCGTCCAGAAGGAAATCTTTCCCAATGCACCGGCCC TCGAACGTGGCAACAGCTACCCGCAAGAAATCGTCAATCGGCTGGGTGTTATTGGCTTGCTCGGTCGCCGGCTGCGAGGGTTTCTACACCACCGAGTTCATTC

TCGGGCGTGCCGGCGCATTCGAACTGGCGGTGCGCGCTG (SEQ ID NO. 198)

::::::::::::Rv201T7.seq::::::::::::
GCACCGGCGTCCTGCAGTTGGTAGGCCTGCAGTTTGTGCATCAGGCCGATGCCGCGGCCCTCGTGGCCACGCATGTACAGCACCACGCCGCGCCCCTCACGGG CGACCATCGCCAGCGCGGCGTCCAGCTGAGGCCCGCAATCGCAGCGGCGTGACCCAAACACATCGCCGGTCAAGCACTCCGAATGCACCCGGACCAGCACGTC TTCACCGTCGGCGTTGGGCCCGGCGATCTCGCCGCGGACCAACGCGACATGTTCCACGTCCTCGTAGATGCTGGTGTAGCCGATGGCGCGAAACTCCCCANGA

CAAGTCGGAATCCGCGCCTCGGCGAACCGCTCAATGTGCCTCTCGTGCTTGCGCCGCCATTC (SEQ ID NO. 199)

Clone Rv204
::::::::::::Rv204SP6.seq::::::::::::
TGGTCCGTGTGCGCATACCAATACAACGCGCCGGGCACCTGACGCGGCGGCCGCAACCAATCGGTGGCCATCGCCATCTTCTGCTACCCGGTCAACGGACGCA

CCTTCTCCTGGCCGACGTAGTGCGCCCACCCGCCGCCGTTGCGTCCCATCGATCCGGTCAAC (SEQ ID NO. 200)

Clone Rv205
::::::::::::Rv205SP6.seq::::::::::::
GGCGTGTTGGCCACCGGGGCCACTCCGCACAATCTGTACCCGACCAAGATCTACACCATCGAATACGACGGCGTCGCCGACTTTCCGCGGTACCCGCTCAACT TTGTGTCGACCCTCAACGCCATTGCCGGCACCTACTACGTGCACTCCAACTACTTCATCCTGACGCCGGAACAAATTGACGCAGCGGTTCCGCTGACCAATAC GGTCGGTCCCACGATGACCCAGTACTACATCATTCGCACGGAGAACCTGCCGCTGCTAAAGCCACTGGCGATCGGTGCCGATCGTGGGGAACCCACTGGCGAA CCTGGTTCAACCAAACTTGAAGGTGATTGTTTACCTGGGCTACGGCGACCCGGCCTATGGTTATTCGACCTCCCCGCCCAA (SEQ ID NO. 201)

::::::::::::Rv205T7.seq::::::::::::
CGTCCGTGNCCCCTCAANCGCGTGNNGCCGAAGCGGCTGGTTACGACTCCCTGTTTGTGATGGACACTTCTACCAACTGCCCATGTTGGGGACGCCCGACCAG CCGATGCTGGAGGCCTACACGGCCCTTGGTGCGCTGGCCACGGCGACCGANCGGCTGCAACTGGGCGCGTTGGTGACCGGCAATACCTACCGCAGCCCGACCC TGCTGGCAAAGATCATCACCACGCTCGACGTGGTTAGCGCCGGTCGAGCGATCCTCGGCATTGGAGCCGGTTGGTTTGAGCTGGAAACACCGCCAGCTCGGCT TCGAGTTCGGCACTTTCAGTGACCGGTTCAACCGGCTCGAAGAGGCGCTACAGATCCTCCAGCCAATGGTCAAGGGTGAGCGCCCAACGTTTTTCGGCGATTG

GTACACCACCGAATC (SEQ ID NO. 202)

Clone Rv207
::::::::::::Rv207SP6.seq::::::::::::
CCGCTTCCGTGTAACCGAGCANNGCGAGCGANCTGGCGAGGAAGCAAAGAAGAACTGTTCTGTCAGATAGCTCTTACGCTCAGCGCAAGAAGAAATATCCACC GTGGGAAAAACTCCAGGTAGAGGTACACACGCGGATAGCCAATTCAGAGTAATAAACTGTGATAATCAACCCTCATCAATGATGACGAACTATCCCCCGATAT CAGGTCACATGACGAAGGGAAAGAGAAGGAAATCAACTGTGACAAACTGCCCTCAAATTTGGCTTCCTTAAAAATTACAGTTCAAAAAGTATGAGAAAATCCA TGCAGGCTGAAGGAAACAGCAAAACTGTGACAAATTACCCTCAGTAGGTCAGAACAAATGTGACGAACCNCCCTCAAATCTGTGACAGATAACCCTCAGACTA TCCTGTCGTCATGGAAGTGATATCGCGGAAGGAAAATACGATNTGAGTCGTCTGGCGGCCTTTCTTTTTCAATGTATGAGAGCG (SEQ ID NO. 203)

Clone Rv209
::::::::::::Rv209SP6.seq::::::::::::
TGACACCCAACAGAGGGCACTTAAGATGGCAATGCGGCCGCCTACCTGCACGTTTTCGCGATGTCAGAGGATGCCGAGGGAGAACAATGCGAGCACGGCCGCT GACNTTGCTCACCGCTTTGGCGGCGGTGACATTGGTGGTGGTTGCGGGCTGCNAGGCCCGANTCNAGGCCGAAGCATATAGCGCGGCCGACCGCATTTCGTCT

CGACCGCAAGCGCGACCTCAGCCGCAGCCGGTGGAGCTACTGCTGCGCGCCATCACGCC (SEQ ID NO. 204)

::::::::::::Rv209T7.seq::::::::::::
ACGGGCGACGCTGAGGTGGGCCCGCGGCTATTCATGCTGTCGTCCACGTCCAGCGACGCACTGCGCCAGACGGCCCGCCAACTAGCCACCTGGGTGGAAGAAC ACCAGGACTGCGTGGCGGCCTCGGATCTGGCCTACACGCTGGCGCGTGGCCGCGCGCACCGGCCGGTGCGCACCGCGGTGGTTGCCGCCAACCTGCCGGAGCT TABLE 3-continued End sequences of the polynucleotide inserts cloned in the named recombinant CGTCGAGGGTTTGCGCGAGGTGGCCGACGGTGACCCCTCTATGACGCGGCGGTGGGACACTGTGATCTAAGACCGGTCTGGGTCTTCTCCGGGCAAGGGTCTC

AGTGGGCGGCGATGGGCACCCAATTGCTCGCCAGCGAACCAGTGTTCGCGGCCACCATCG (SEQ ID NO. 205)

Clone Rv20
::::::::::::Rv20SP6.seq::::::::::::
ATACTCAAGCTTCGCGAGATCCGGATGGCACTCACGCTGGACAAGACCTTCACAAAATCTGAAATCCTGACCCGATACTTGAACCTGGTCTCGTTCGGCAATA ACTCGTTCGGCGTGCAGGACGCGGCGCAAACGTACTTCGGCATCAACGCGTCCGACCTGAATTGGCAGCAAGCGGCGCTGCTGGCCGGCATGGTGCAATCGAC CAGCACGCTCAACCCGTACACCAACCCCGACGGCGCGCTGGCCCGGCGGAACGTGGTCCTCGACACCATGATCNAAAACTTCCCGGGGAGGCGGAGGCGTTGC GTGCCGCCCAGGGCGAACCGCTGGGGGTTCTGCCGCAGCCCAATGATTGCCGCGCGGCTGCATCGCGGGCGGCGACCGCCATTCTTCTGCGAATACGTCCAGG

AGTACTGTCTCGGGGC (SEQ ID NO. 206)

::::::::::::Rv20T7.seq::::::::::::
AGCTTATGTGGCCGCCCACCTACCTTATCTAGCCTAGCTAACTAAATCCAGTGCCGACAGTGCGCGGCTGGCCACCCAGCATGAGGTTATGACCACGGCATAT GCCAGCGCGCTGGCGGCGATGCCGACGCTGACCGAGTTGGCCGCTAATCACACCAGCCATGCGGTGTTGCTGGGAACGAATTTCTTTGGAATCAATACGATCC CGATCGCGCTCAATGAGGCCGACTATGCGCGGATGTGGATTCAGGCGGCCACCACGATGAGTATCTATGAGGGCACCTCCGATGCGGCGCTGGCGTCNGCACC GCAAACCACACCGGCTCCGGTACTGTTCAACGGCGGTGCTGGCGTTTGCCAGCGCCTGCCGGCGATCTC (SEQ ID NO. 207)

Clone Rv214
::::::::::::Rv214SP6.seq::::::::::::
ATACTCAAGCTTGCCACCCATGCCGAGCAAGGTCGACTCAGCGATGACGAATTGTTCTTCTTCGCGGTGTTGCTGCTGGTTGCGGGCTATGAGAGCACTGCTC ATATGATTAGCACNTTGTTTCTGACGCTGGCCGACTATCCAGATCAGCTGACACTCCTTGCGCAGCAACCAGACCTGATCCCGTCGGCGATCGAGGAGCACCT CCGCTTTATATCGCAATCCAAAACATCTGCCGCACAACGCGCGTCGACTATTCGGTCGGTCAAGCGGTCATCCCGGGA (SEQ ID NO. 208)

::::::::::::Rv214T7.seq::::::::::::
CCGGGGTAGAACGATGCGATCTGGGCCATGTCGACATCGGTGGTACAGGTAAACCGCGCCGTGTGCGCGGTCTCGGAGATCAGAACGTGGTCGCAGTTGACAC CGCGGGCTTTCAGCCAGTCGCGATAATCGGCGAAGTCGGCGCCTGCCGCCCCAACTAGCGCGACCTCGCCACCTAGCACACCGATGGCGAAGGCCATGTTTCC

GGCCACGCCGCCGCGGTGCATCATCAACTC (SEQ ID NO. 209)

Clone Rv215
::::::::::::Rv215SP6.seq::::::::::::
ATACTCAAGCTTGGCGGCAACGCCACTACCGGGCTCACCAGGTCCTGTGCCGCCACCGCCGGCGCCGAAAGCACCATCAGGTCGTAGTTGTCTGGACGTTCGA CACCGTAAGCGAACACAATGCCGCCGCCCATGCTGTGCCCGAGCACGATGCGCTTGCACCCGGGATATTCCCGGGTGGCGATCCCAACGAGGGTGTCGAAGTC AGCGGTGTATCTGAGATGTCTCTCACTATCATCCGTTTGGCACCCGAGCGGGCATGCCCGCGGGGGGTCAAC (SEQ ID NO. 210)

::::::::::::Rv215T7.seq::::::::::::
GTCGACGGCATCAAGGTCCGCAGTGATGGTGTTCATCTCACCCAGGAAGGCGTGAAGTGGCTGATACCGTGGCTTGAGGATTCGGTGCGGGTCGCCAGTTAAT CCGCCGTGTGCTCCGGATGAGCGCGACGGTAACCCTGGAATTGTGCTGTGTGCTGGCTGTGTCGTTGTGATGAGCCTGTCTAAGTGGTGCGTAACCGTTTGAC GAGCCGCGGCCTCGCTGCAAACATTGAAGCCCGCACGTCTGGGTTTGTATTTACACAACGAGGGCGCTCCCCGATCTGGCGCGCGCAACGAGGTGCNCACTAT

CCATTCGAGGTGAACTGGACTCCTTGATGCTCATGCCGGTGCGGTTTTGTC (SEQ ID NO. 211)

Clone Rv217
::::::::::::Rv217SP6.seq::::::::::::
ATACTCAAGCTTGCGTTCGATGAAGTAGTCGTCGGTCAGCGCCGCCTCTTCGAGCTCCTTGGCGATGCCCAGCAAGGAGTCATCGCCGCCGAGCTTGGCCAGG ATCTTGTCGGCCTGTTCCTTGACGATGCGGGCCCGCGGATCGTAGTTCTTGTAGACACGATGACCGAAACCCATCAATTTGACCCCGGCCTCGCGGTTCTTGA

CCTTGCGTTACAAACTCGCTGACGTCGTCGCCGCTGTCGCGAATGCCCTC (SEQ ID NO. 212)

::::::::::::Rv217T7.seq::::::::::::
NGTCAAGCCGAGCATGCGCGAGGNAACGACGAACCCAACAAGCCATGGTGGTTGGCGCCGTCGAGAGGTCGGCGGTCGCCACAACGGGAAGATCGCCTTGAGC GTCGCTCGACCGCCGCCTCGAGTTGGGTCATAACGAAGTAGCTGATGCCGATCATGTCGACGTTTCCGTCGCATCAGCGTGCAGCGGCGACCCACTCGACGAG

GTCTCGGTGCCGCCGCGGCCAGGGCACCAGCAGTGACGATTCCAGGCGCCGTCGGG (SEQ ID NO. 213)

Clone Rv218
::::::::::::Rv218SP6.seq::::::::::::
CGATAATCGCTTCCGGTAAGTGCAGCAGCTTTACGACGGCGACTCCCATCGGCAATTTCTATGACACCAGATACTCTTCGACCGAACGCCGGTGTCTGTTGAC TABLE 3-continued End sequences of the polynucleotide inserts cloned in the named recombinant CAGTCAGTAGAAAAGAAGGGATGAGATCTCCCCGTGCGTCCTCAGTAAGCAGCTCCTGGTCGCGTTCATTACCTGACCATACCCGAGAGGTCTTCTCAACACT ATCACCCCGGAGCACTTCTAGAGTAAACTTCCCATCCCGACCACATATAGGCTAAGGTAATGGGCATTACCGCGAGCCATTACTCCTACGCGCGCAATTAACG

AATCCACCATCGGGGCCGCTGGTGTCN (SEQ ID NO. 214)

Clone Rv219
::::::::::::Rv219SP6.seq::::::::::::
NAATACTCAAGCTTTCTCGTGATTACCACCCGTGTAATTTGGGATGGGCAAAAAGGCGAATCACCGCGTGGCCACAAACGCCGGGAGGGACAATCTCGGGCGG CTAGGGCTTCTCGCGGGAAGGCCCGAACGTACGGCGTTTCAACACGTCGCGTCGCCCTCCGACCGCGAACATTCGGGGATGGCAGCAACCTGGTATCACCCTG

GCCGGGCAATGATCTGCAGCGTCGCCGCGGGTAGTGNCCGCCCGGGCGGCTAC (SEQ ID NO. 215)

::::::::::::Rv219T7.seq::::::::::::
CCAACTAGAGCATCGGGACATACGGAGTCAACTACCCGGCCAACGGTGATTTCTTGGCCGCCGCTGACGGCGCGAACGACGCCAGCGACCACATTCAGCAGAT GGCCAGCGCGTGCCGGGCCACGATGTTGGTGCTCGGCGGCTACTCCCAGGGTGCGGCCGTGATCGACATCGTCACCGCCGCACCACTGCCCGGTCTCGGGTTC ACGCAGCCGTTGCCGCCCGCAGCGGACGATCACATCGCCGCGATCGCCCTGTTCGGGAATCCCTCGGGGCCGCGCTGGCGGGCTGATGATCGCCCTCACCCCT

CAATTCGGGTCCAAGA (SEQ ID NO. 216)

Clone Rv21
::::::::::::Rv21SP6.seq::::::::::::
ATACTCAAGCTTGCTGCAGCTTCCTGTGACTGCTCCCGAAACCTGGGGGTGTGCCTGCTGTGTATGCACGGCATACGGACATCCTTCCCCTGAGACCCGCGGT CGAACCAGCCACGTGTCCATCATCAGGGGTCAACCCCGGCCAAGGGCGACGGCACGCCAAGTTCGCCGACCGTTAACCTAGTGCTGTTAGCTTCATTTGCTGC GAGCAAAACAGCTGGTCGGCCGTTAGGAACTGAATTGAAACTCAACCGATTTGGTGCCGCCCGTAAGTGTCCTGGCTGCCGGTGCGCTGGTGTT (SEQ ID NO. 217)

::::::::::::Rv21T7.seq::::::::::::
AGCTTGCGCGGCGTGGCGATCGCGGTTCAAGGCGCGCTCTTCGAGCACAACGAGCGAAGACAGCTCGGCGACGGAGCCTTTATCGACATCCGTTCGGGCTGGC TGACCGGCGGCGAAGAACTGCTGGACGCGTTGTTGTCGACGGTGCCGTGGCGAGCCGAGCGCCGTCAGATGTACGACCGGGTGGTCGATGTGCCGCGGCTGGT

GAGTTTTCACGACCTGACCATCGAAGATCCGCCGCATCCGCAGCTGGCGCGGATGCGCC (SEQ ID NO. 218)

Clone Rv220
::::::::::::Rv220SP6.seq::::::::::::
AATACTCAAGCTTGCGCACGACCAGGACGTCGAGTGGCGCTTGCAGTGACTTGGCGACCTCAAAGGCCACCGGTACCCCGCCGCGCGGCAAGCCAAGGACNAC NACGGCCTTGCCGGATAGCTGCGCCAGGCGTTGCGCCAACTGGCGTCCAGCGTCGCCACGATCGTCAAAGAGCTTCATCTGCCGAGTGTGTCGCCATCTCATG GCTCCAAATATGGAATTAGGTCCCTGGGCCGACTGACGACAGTCCCTCAGCGACCGGATTGCGCATCCCGCCTTGTACGCTGCTCCGCAAATCCCGGGCTTGC

GTCCGCGGAAGCGAACTCGGCGGCGCTACGGTGGTGGCTCACTTCGGCCGTGC (SEQ ID NO. 219)

::::::::::::Rv220T7.seq::::::::::::
GGTTGGTGCGGTCCACCTTCGCGGCGGCGGCGCGATATGCCTTGCTGGTCTTGCTCATTTGATATCCAATCTATGGGTCGTGGTTACTCAGCGGGCCGAAGCT GGCCCTCCCACGGGTAGGGCCCTATTCGACGGTGATGCCCATCGACCGAGCGGTACCGGCGATGATCTTGGCCGCAGCGTCGACGTCGTTGGCGTTGAGGTCC GTCTTCTTGGTCTCGGCGATTTCGCGGACTTGATCCCAGGTGACTTTGGCGACCTTGGTCTTGTGCGGCTCCGCCGAACCCTTCGCCACACCAGCGGCCTTAA GCAGCAGCTTGGCGGCGGGCGGCGTCTTCAGCGTGAAAGTGAAGCTACGGTCTTCATAAACGGTGATCTCCACCGGGATGACGTTGCCGCGCTGGTTCTCCGT CGCGGCGTTGTACGCCTTGCAGAACTCCATGATGTTGACCCGTGCTGACCGAACGCGGGGCCCACTGGCGGGGC (SEQ ID NO. 220)

Clone Rv221
::::::::::::Rv221SP6.seq::::::::::::
ATACTCAAGCTTTTCGACCCGCAAGCCGGCGGTGCCCCTCCTCGTTCCGCTGCCCGGTCTGCTCGATCGGTTCGGGGTCGCCGCGCTAGGCCCAATTGCCCGG CTCCTCCTCGGGCCGTTCCACAACCCGCATCGTCGCCGGGCTAGGTTCAAGCCATGCCGGTAAACCCCAGGACGCCAGTGCTGATCGGCTATGGACAGGTCAA CCACCGAGGCGACATCGACGCCNAAAATCAGTCCATCGAACCCGTCGACCTGATGGCCNCCGCGGCCCGGAAAGCCGCCGAGTCCACCGTGCTCGAAGCGGTG GATTCCATCCGTGTGGTGCACATGCTGTCGGCGCATTACCGGAATTCCCGGGCGTCTCCTCGGC (SEQ ID NO. 221)

::::::::::::Rv221T7.seq::::::::::::
NCCTGGTTCATGAACTGGAAGCAGCGCAGCGCTTCCTTTTCGGCCGCAACATGAGCCAGCCTCTCGTCGGCGGTCGGGTGCAGGTGCTCGGGCAGCTCGGCCG CGACAGCCGCCTGACCCTGAAACCAGCTTCCATATCCCGCGACGAACGACGCCAGTCCGCTACGTAACCCCTCCGCGACTGTCCATGGACAACAGCGCGTTCT CCACCGACCGGGGCCGGGTGTTGGGGTGTTCGGCAACGGCAACCAAGTTGGTCCACACTGCCGACGGGCGCCGCAAATCCGTTCACCGAACCAGGCCGCCNAA TABLE 3-continued End sequences of the polynucleotide inserts cloned in the named recombinant

ACAATTCCGCCCGATCCCATAT (SEQ ID NO. 222)

Clone Rv222
::::::::::::Rv222SP6.seq::::::::::::
ATACTCAAGCTTGTCGGGATCAATCTCGAGGGCATCCACGCACGAAAAGTAAACTCTATCAAGCTTTTTGACGACACCCACGGACGCCCCATATATGTTCGGG TGGGCAAGAACGGTCCCTACCTGGAACGTTTGGTGGCCGGCGACACCGGTGAGCCCACGCCGCAGCGGGCCAACCTCAGCGACTCGATTACCCCGGACGAACT GACTCTACAGGTGGCCGAAGAGCTCTTTGCCACACCGCAACAGGGACGGACTTTGGGCTTGGACCCAGAAACCGGCCACGAAATCTTTGCCAGGGGAAGGCCG GTTTGGGCCTTATGTTACCTATATCCTGCCGGAACCTGCGGCTGATGCGGCCGCGGCCGCTCAGGGAN (SEQ ID NO. 223)

::::::::::::Rv222T7.seq::::::::::::
AGCAGCTAGCCGCGCTCGCCGCGCTGGTCGGTGCGTGCATGCTCGCAGCCGGATGCACCAACGTGGTCGACGGGACCGCCGTGGCTGCCGACAAATCCGGACC ACTGCATCAGGATCCGATACCGGTTTCAGCGCTTGAAGGGCTGCTTCTCGACTTGAGCCAGATCAATGCCGCGCTGGGTGCGACATCGATGAAGGTGTGGTTC AACGCCAAGGCAATGTGGGACTGGAGCAAGAGCGTGGCCGACAAGAATTGCCTGGGCTATCGACGGTCCAGCACAGGAAAAGGTCTATGCCGGCACCGGGTGG ACCGCTATGCGCGGCCAACGGCTGGATGACAGCATCGATGACTCCAAGAAACGCGACCACTACGCCATTCAAGCGGTCGTCGGCTTCCCGACCGCACATGATG

CCGAAGAATTCTACAGCTCCTCCG (SEQ ID NO. 224)

Clone Rv223
::::::::::::Rv223IS1081N1400.seq::::::::::::
CGCGACTGGCTCCCCGGNCGGCTGCTCGGGTCCGCCGATAGAGACCGGGATGTCGCCCGACGACGGGCAGCCGGGTTGCGTGGGACGGGGCGGGGGTCGGGCA GCCCAAGCAACGGGCTAGTCCCCGAATCCTACGGAGCCGTCACCTACGCCTACGTAATAGTAGCTATCAATAACAGTTGACATACGCAACGATCTGTGAGATC AATATTGCCTGACGCATGTCAAGACAGGCGTCAAGACAGGTGTCAATAATTCGCTCCGCTGGTGACGGTAACCGGTCGTGCGGGTGTGTGACGCCTAAGGAAG GAGTGTGGGTGGTGACGCTGAGAGTGGTTCCTGAGGGTTTGGCGGCCGCCAGTGCGGCGGTGGAGGCGTTGACCGCACGGCTGGCCGCCGCACACGCTGGCGC GGCGCCGGCGATTACGGCGGTGGTGGCGCCCGCGGCGGATCCGGTGTCGTTGCAGAATGCGGTGGGGTTTAGCGCCTTAAGTAGCCAGCATGCCGCGATCGCC

GGCGAAAGGGTCCAAGAACTGGGT (SEQ ID NO. 225)

::::::::::::Rv223SP6.seq::::::::::::
ATACTCAAGCTTATTGAACCGCGGGTCGCAGGCAAAGTGGACCTCATAACGACTCGGGTCCAGCGACCGCGCCAACACGAACGGCCGGACGACGTGGGCCAGG GTCGCGGCCTCCCCTACAAACAGGATCCGTTGCCTGCGAACGACAGGCTCCGGTGCGGCGTTGGGCGCCGTGCTCGTCCCAGCGTCCGGTCCCGGGTCGCCGG CGACGCTTGTTTCCTCCATACTCGCCCCCTAATCTCGAGGCAGCCCGTACCCGCAGGCAACCTCCCAAAAATGCAATCCCGCAAAATGCAATGCGTCNAGCTA TTTCTCACACCGACCGCTAGTTGCGGATCAGAAATCCGTTGGGCGCGGAAGTCCAGCCGAATTTGTTCTCCCGCTCCGCATCATGCTTGTAATCGTTTGGAAA TTCATCCTCATATGCCTCGATCGCTTCATAGGGTCCAGGCCCAAACCCGGGCAGGACTGGGTGGCCGTTGATGTTGGAATCCTCCACTACTAGGTATTCACCG

GC (SEQ ID NO. 226)

::::::::::::Rv223T7.seq::::::::::::
GTCTCGATCATGGCCAAAGAGCTCGACGAAGCCGTAGAGGCGTTTCGGACCCGCCCGCTCGATGCCGGCCCGTATACCTTCCTCGCCGCCGACGCCCTGGTGC TCAAGGTGCGCGAGGCAGGCCGCGTCGTCGGGGTGCACACCTTGATCGCCACCGGCGTCAACGCCGAGGGCTACCGAGAGATCCTGGGCATCCAGGTCACCTC CGCCGAGGACGGGGCCGGCTGGCTGGCGTTCTTCCGCGACCTGGTCGCCCGCGGCCTGTCCGGGGTCGCGCTGGTCACCGGCGACGCCCACGCCGGCCTGGTG GCCGCGATCGGCGCCACCCTGCCCGCAGCGGCCTGGCAGCGCTGCAGAACCCACTACGCAGCCAATCTGATGGCAGCCACCCCGAAGCCCTCCTGGCCGTGGG TGCGCACCCTGCTGCACTCCATCTACGACCAGCCCGACGCCGAATCAGTTGTTGCCAATATGATCGGGTTCTCGAC (SEQ ID NO. 227)

Clone Rv224
::::::::::::Rv224SP6.seq::::::::::::
ATACTCAAGCTTTCGTCAGTTCATGGCGCCAGCAGACCAACAAGAGCATCGGGACATACGGAGTCAACTACCCGGCCAACGGTGATTTCTTGGCCGCCGCTGA CGGCGCGAACGACGCCAGCGACCACATTCAGCAAATGGCCAGCGCGTGCCGGGCCACGAGGTTGGTGCTCGGCGGCTACTCCCAGGGTGCGGCCGTGATCAAG

ATCTTCACCGCCGCACCACTGCCCGGCCTCGGGTTCACGCATCCGTTTGGCCGCCGCC (SEQ ID NO. 228)

::::::::::::Rv224T7.seq::::::::::::
GCCCCGTGTAATTTGGGATGGGCAAAAAGCGAAGCACCGCGTGGCCACGAACGCCGGGAGGGACAATCTCGGGCGGCTAGGGCTTCTCGCGGGAAGGCCCGAA CGTACGGCGTTTCAACACGTCGCGTCGCCCTCCGACCGCGAACATTCGGGGATGGCAGCAACCTGGTAGCACCCTGGCCGGGCGATGATCTGCAGCGTCGCCG

CGGGTAGTCTCCGCCCGGGCCGC (SEQ ID NO. 229)

TABLE 3-continued

End sequences of the polynucleotide inserts cloned in the named recombinant

Clone Rv225
::::::::::::Rv225SP6.seq::::::::::::
ATACTCAAGCTTCCTTTGACCGAACGCGTCCACCGCACCGTGAGATTGGTGGCGCCATTCGTCGTGGTGTAGCTGCTGTTGGCGGCGTCGCCGTATTGTGCGG GCCAGCCTTGTGCGGGGGCCGCTTCTACCCACAAGTCGGCACTTCCGCAACCGCCCAGCTCGACCGCGAATTACGGCGGCCGCAACGGCCGCCGGAAGGCGTC

ACGCAATCGCTTATCCTTTCCAGGTTCCCAAATCCTCCGCTTACTTGGGTCCTTCATCGG (SEQ ID NO. 230)

::::::::::::Rv225T7.seq::::::::::::
GGCAGCGGCGACAACCGGAACGTCCGCACGGTGCTCAATCACGGGTGCACGGTGTGCATCAGAATGGCGGGGGTTCGTTGTCGCGGTGAGGCGTTCGGCGAGG AGGTAGTGTCTACCCCTTGCCCGCGGGTTCGTGCGGACTGAAAGGGATTTCATTGGGAACCCACGGCTGCGTATCGCAGGGCCTCGGTGACGTCTGCTTCCTC

NAGCTCAGGAAGTTCGGCGAGAATCTCGGTGGATGTTATTTGGTCCGCCTAC (SEQ ID NO. 231)

Clone Rv226
::::::::::::Rv226SP6.seq::::::::::::
ATACTCAAGCTTTCTCGGCTTCTCTGATAGCCTGAGAAGAAACCCCAAGTTAATCCGCTGCTTCACCTATTCTCCAGCGCCGGGTTATTTTCCTCGCTTCCGG GCTGTCATCATTAAACTGTGCAATGGCGATAGCCTTCGTCATTTCATGACCAGCGTTTATGCACTGGTTAAGTGTTTCCATGAGTTTCATTCTGAACATCCTT

TATTCATTGTTTTGCGTT (SEQ ID NO. 232)

Clone Rv227
::::::::::::Rv227SP6.seq::::::::::::
ATACTCAAGCTTGGTGACCGGCACCGCGATACGTTGCGGCAGGCATCTGGGCTGGCGGTGGTTCGCCGCTCCGAAGCCGTCGAACACCATCGCCAGCGCGGCT TCCACATCAACGACCATTTCGGCCAGCTTGCGGCGCATCAGCGGCTTGTCGATGAGCGCCCCACCGAATGCCCGCCGCTGCCCGGCGTATCACATCGATTCGA CCATCGCGCGGCGCGCGTTGCCGAGGGCGAACGAGGCGGTGCCCAACCGCAATCTGTTTGGTCAGCTCCCTCATGCGGGTTGATTCCTTGCCGTCCGGACGGG

CCCGCGTCATGCGCTCGGTTCGCC (SEQ ID NO. 233)

::::::::::::Rv227T7.seq::::::::::::
CCGTTGCGCAGCGTGAGCCGATAGTTGACATCCGGCTCGGTGAAGGTGAAATCGATGGCCAGGTCGAGGTCCCATGCGCGTGGGCCATTGATGCTGATCGCCA GGACTGCAAAGATTTGGTCCGGCGTCAGCTGGGCGAAAAACGTGGGCGCCGGGACTTGCCCGGAGCTGCCCGGGTTCCCGTCGCGCAGCTCGGCGGCCCCGGT CAGAAAGAAATTGCGCCAGGTCGCACACTCCGCGCCGTAGGCCAGCTGCTCCAGGGTGTCGGCATAGAGCCCGCGGGCCGCAGCGTGCTCGCTGTCGGCGAAC ACCGCATGGTCGAGAAGCGTTGCCGCCCAACGGGAAATCACCTGCGTCGAAAGCTTCGCGGGCCAGCTCCAGCACTCGGTCGATGCCACCCAACGCGT (SEQ ID NO. 234)

Clone Rv228
::::::::::::Rv228SP6.seq::::::::::::
ATACTCAAGCTTGCGGATGTTACCCCTGACAGCGTGAACTATGTCNAAACACACGGCACCGGAACGGTGTTGGGGGACCCCATCGAGTTCGAGTCGCTGGCGG CCACTTATGGCCTGGGTAAAGGCCAGGGCGAGAGCCCGTGCGCATTGGGGTCGGTCAAAACCAACATCGGCCACCTGGAGGCGGCCGCCGGTGTGGCTGGATT CATCAAGGCGGTGCTGGCGGTGCAACGTGGGCACATTCCCCGCAACTTGCACTTCACCCGGTGGAACCCGGCCATCAACACGTCGGCGACGCGGCTGTTCGTG CCGACCGAAAGCGCCCCGTGGCCGGCGGCTGCCGGTCCACGCAGGGCTGCGGTGTCATCGTTCGGCCTCAGCGGGACCAA (SEQ ID NO. 235)

::::::::::::Rv228T7.seq::::::::::::
CCGGTAACCAGATCAGCTCGTCGACCTCACTGCCGGGGGTGAATTCCCCACCGGTGCTGCGCGCTGCCCAGTAGTGCACCTTCTTGACGCCTCGAAAAGGGGA GTCGGTCGGGTAGGTCACCGTCAGGAGCCGCCTACCCAGGTTGGCGCGGTGACCGGTCTCCTCGAGTATCTCCCGCACCGCCCCCACCGGTGCGGTCTCGCCC GGATCCACTTTGCCCTTGGGCAGCGACCAGTCGTCGTAACGGGGGCGGTGAATGACAGCGATCTCGACCGGCCCTTCCGAATCGGCACTGCCGGGTCGCCAGA ACACCGCACCGGCGGCGTACACAATCCGGCCCGCCGAGCGCCGGCGGGCGGACGANTTCTGGATCGACACCTCAACTCCTGCAGGTCAATTCGGCCAAGCTGC

TCGCGGTCGTGGATGTGGTC (SEQ ID NO. 236)

Clone Rv229
::::::::::::Rv229SP6.seq::::::::::::
ATACTCAAGCTTGATGCCGCCGAAACCGAGCGTGAGCACGCCGCCACCCACCACGCGCGGGTCGGGCGCCGGGCCCGGGCCGCCAGGCTGCTCCGCTCGGTGA TGGCACGCCACCGCGACACCACCCGGCTGCGCTACGTCGAGCCATACCGGGCGGAGCTACATCGGCTCGGCCGCCCAGTGTTCGGGCCCTCTTTCGAGGTCGA GGTCTATACCGATTTGCGCATCCGCAGCCGCACCCTGGTCGTCTCGTACCGTGCCCTACCTCTGCTTGTCGGGCGGGGCCA (SEQ ID NO. 237)

::::::::::::Rv229T7.seq::::::::::::
TCCGTACGGCCCGGGTACGCTTCGGTCGCAGTGTGCGAGTGATAGATGACGACCGGGACCTCGTCGGCATCTTCCATAGCCCGCCACACCTTCAGTTGCTCAC CGGAATCCAACCGGTAGAAGGTCGGCGAGCGCTCGGCATTGGTCATCGGGATATGCCGCTCGGGACGGTCAGAGCCCTCGGGTCCGGCCAGCACTCCGCAGGC TABLE 3-continued End sequences of the polynucleotide inserts cloned in the named recombinant TTCGTCGGGGTGGTCGCGACGCGCATGGGCCACCATCCATCCACCAGGTCTGCGCGAATCACCCGC (SEQ ID NO. 238)

Clone Rv22
::::::::::::Rv22SP6.seq::::::::::::
GGACACATTGCGAACATTGATGACAAAATAGAAATCATTGATGGTTTGAGTCACCAGGCCGATCAAGCCTTCGCCGAGCCAAATTCCAATCAAGAGGCCCAAG CCCGTACCAATCAGCCCGGCAACGAGGGATTCCGTCATTATCAGCCAAAATAACTGCTCTCGGGTTACACCCAAACAGCGCAATATGGCGAAAAACGGTCGCC GTTGCACGACATTAAATGTCACGGTATTGTAAATTAAAAAGATACCCACCAACAAGGCAATCAAACTGAGAGCGGTTAAATTGACCGTAAAAGCGTCCGTCAT CTGTTTGACGGTGTCCCGTTGGGTNTCCGACGTTTCCATACGCACACCGGCCGGCAGTCTTTGTTGGATGCGTGTTGCAGTGGCCTCATCTTTGATGATCA (SEQ ID NO. 239)

::::::::::::Rv22T7.seq::::::::::::
GCCTGGCCCAGGTGAAGGCCGACCTCGACGCCAAAGCCGCTGATCCGGCACATGAGTCGGTGGACTGGGACTTGAAGTCGCTGCGATGGGCGTGGAACCGAGC CAAAGATGACGTGGCGCCGTGGTGGGCCGAGAATTCCAAGGAGTGCTACTCGTCGGGGTTGGCCGATCTGGCCCAGGGCCTGGCTAATTGGAAAGCTGGCAAG AACGGGACCCGCAAAGGCCGGCGGGTGGGCTTCCCGCGATTCAAATCCGGGCGGCGTGATCCTGGCAGGGTGCGGTTCACCACCGGCACCATGCGCATAGAGG ATGACCGGCGCACGATCACGGTCCCGGTGATCGGGCCGCTGCGGGCCAAGGAGAACACCCGCCGGGTGCAACGCCACCTCGTGAGCGGGCGCGCGCAGATCCT

GAACATGACCTTGTCGCAGCGGTGGGG (SEQ ID NO. 240)

Clone Rv230
::::::::::::Rv230SP6.seq::::::::::::
TAACTCAAGCTTCAAGTCCGCNGTCCGACCCTGTTCGACGGCTACCTGAATCAACCCGATGCCCCGCCGCGGCGTTCGACCCGACAGCTGGTACCGCACCGGC GACGTCGCGGTGGTCGACGGCAGTGGGATGCACCGCATCGTGGGACGCGAGTCGGTCGACTTGATCAAGTCGGGTGGATACCGGGTCGGCGCCGGTGAAATTG AAACGGTGCTGCTCGGGCATCCGGACGTGGCGGANGCGGCAGTCGTCGGGGTGCTCGACTATTATCTAGGCCAGCGGATCGTTGCCTACGTAGTCGGCTCAGC

GAATGTCGATGCGGACGGGCTTATCAACTTTGTTGCCCAACAACTTT (SEQ ID NO. 241)

::::::::::::Rv230T7.seq::::::::::::
CCATGTCGCCCACATATCGTCGATGTTCGCGTCGTCCCGCCTCGCGCACGTGGTCTGTCACCAGTCAACGTTAACGCCGCCGCACATGTCCTGCGGCCGGGCA AAAACGTGAAAAACGAGCGGGCGACTGCAATGTCATGACACCGACGCCGCCGATGGGCCCAGGGTCTGGCAGATTCGATCTGTGCGGCCAGTGCCAGCAGCGT CGCCTCGTCATACGGCCGGCCGACGAGTTGAACCGACATGGGCATGCCGTCGCCGTCGAAGTCCCACGGCACCACGGCCGCGGGCTGGCCGGTCAGATTCCAN

ACTTGAAAGTACTGAAGCCGCTGCACCACCAG (SEQ ID NO. 242)

Clone Rv231
::::::::::::Rv231SP6.seq::::::::::::
CGAAAGCGTGAAACAGCTCGCGGCAGCCCCCGACGTGCTGCGTCGGATAGCCGGCGGGCGAAGATCAATTCCAGGCAGCTCCCGGACAATGCGGCTCTGCTGG CCCGCAACGAAGGACTCGAGGTCACCCCGGTGCCCGGGGTCGTGGTGCACCTGCCGATCGCACAGGTTGGCCCACAACCGGCCGCTTGATGCCCGGTCGGCAA GCCCGGCAGTTGCCAAACCCAGCGTGATCNTGCTCNGCTCTNTANTTCGGCGAAGAAGTGGCTCGCCTGATCACCTACCATCGGCCAGGATCTGCGTGTCATC

ACAACGCTCGCCAAGGAGGTTGTTGTG (SEQ ID NO. 243)

::::::::::::Rv231T7.seq::::::::::::
TCCGCCACGCTTCGCGCCGCCCGGCATACGGCGCGTACCGATCTCCGCGTCATACACCGCGGGTAATCGCCGACGGTGCCGGTTCGCGAGCCGAAGGTGACGA CGCTGATTGAATCGAGTTCCAGGTCCAGCGGGTGGCGCAGCAACGGCGCGAGCTCAACGACGTCAATCACGTTGTCGCTTTCTACGGTCACCGACCCGGTGAC CGTAGTCGCCCGGTGCGCTCGGCCGAGAAGCTGCACCGCCACCACCGCGACACCGTCTTGCACGCGGACCCACCCCGGATCGGTTGTTGGCCAAGGTAATTGG

GTCATTCCATTTGACGGGACGCCGACCC (SEQ ID NO. 244)

Clone Rv232
::::::::::::Rv232SP6.seq::::::::::::
CATTCTTTAACAGTTGTTTTGGGCTCGGCATGGTTAGCCAACGTTCTGCGGTCCACCATATCATCTTGGTCCGGTAGCGCTCGTCCGGGGTATGCTGCCGCCG GGATTCTCGCTGCTATTACTCCCCCCGAAGAACCGCCACCGGTCCAGCGCGTGGGCCGNCGCGGTCCCATCACAAACTGAACCCCCAACAGGGACATGCTTAT CGGTAGGGCGCGCGCCAAGGCGGCAGCAATCGCATCACTGCGCTCTGCGCGTCACTATTAACCCACCCGGACTTCACTTCCACCACCCCGAATGGCGCCCGGT

CATTGATCATCTGGCGCACCGCGGATAA (SEQ ID NO. 245)

::::::::::::Rv232T7.seq::::::::::::
CGGTGTCCTGCAGTTGGTAGGCCTGCAGTTTGTGCATCATGCCGATGCCGCGGCCTCGTGGCCACGCATGTACAGCACCACGCCGCGCCCCTCACGGGCGAAC TABLE 3-continued End sequences of the polynucleotide inserts cloned in the named recombinant ATCGCCAGCGCGGCGTCCAGCTGAAGCCCGCAATCGCAGCGGCGTGACCAAACACATCGCCGGTCAAGCACTCCGAATGCACCGGACCAGCACGTCGTCACCG TCGGCGTTGGGCCCGGCGATCTCGCCGCGGACCATGCGCGACATGTTCCACGTCCTCGTANATGCTGGTGTAGCCGATGGCGCGAAACTCCCCATGACGAGTC

GGAATCCGCGCCTCGGCGACCCGCTCAATGTGCT (SEQ ID NO. 246)

Clone Rv233
::::::::::::Rv233SP6.seq::::::::::::
CGGCATCTGGCGGCTGAACCTGTTCTTGGGCAACATGCCGAGGATCGCCTCTTCCACCACGCGGTCGGGGTGGCGTTGCATTACCTCACCGATGGTGCGCTTG TGCAGGCCGCCGGGATACCCCGAGTGCCGGTAAACCATCTTGTGCTGCAGTTTGTCGCCGCTGATGGCGACCTTGTCGGCGTTGATCACGATNACNAATCACC GCCANCGACATTGGGGGCGAACGTCGGCTCGTGCTTGCCGCGCAGCAGGCTGGCCGCCGCGACGCAAGGCGCCAACCACCACGTCCGTGGCGTCGATGACGTA

CCACCATCGCGTGGTGTCACCCGCCTTGGGC (SEQ ID NO. 247)

::::::::::::Rv233T7.seq::::::::::::
GCGGCAAAAATTGAAGCACTCNTGGCCACTNCCGCCGGGAGGGACAATCTCGGGCGGCTAGGGCTTCTCGCGGGAAGGCCCGAACGTACTGCGTTTCAACACG TCGCGTCGCCCTCCGACCGCGAACATTCTGGGATGGCAGCAACCTGTTAGCACCCTGGCCGGGCGATGATCTGCAGCGTCGCCGCGGGTAGTCGCCCCCGGGC GGCTACAGTCTGAAACGCGATGACCATCGATGTGTGGACGCCGCATCCGACNCAACGGTTCCTACACTGTGATATGTTCGCCTCGCTGCGCCGGTGGACGGTG

GGTCTATCCCGGA (SEQ ID NO. 248)

Clone Rv234
::::::::::::Rv234SP6.seq::::::::::::
CGCGTTGAACTGAAGGGGTGCCGCCCGGCTCGAGCAGGCAAGCCATTTGTTCGATGCGGTTACCGAAGATCTCTTCGGTGACTGCCCGCCGCCGGCCAGCTCG GCTCAGTGTCCGGCGTTGGTCGCCGCGGCGACAATCTTGGCGTCCACGGTGGTCGGGGTCATGCCCGCGAGCAGGATTGGCGAGCGGNCGGTCAGCCGGGTGA ACTTCGTCAAGAGCTGACGCTGCGGTTGGGGAGGCGAATCATGGTCGGTGCGTAGCCTCGACTAGGCCCGGG (SEQ ID NO. 249)

::::::::::::Rv234T7.seq::::::::::::
TGACAACGCGGCGGCGATTACCCCGCTACCGCAGCAGCATGACGCGGTAGCGAACACCGCCGGATGCAGCGCAGGTGCGTCGATGTGCTCACGGAATCGCCCC GGCACCGCGATCTCGAGGATCACCAGTGCCACCCCCTGCAGCGCGACACCGACGATTCCGTACACCGCCACGCCGATCAGGCCCTGGGCCAGCTGATTGGAGC TGGCGTATATGGCGGCGATGGTGACGATGGTCATCGCCTCTTACATTGTGGCGGCCAGAACCACGGCGTTGGGGCGGCGGTCGATGAACACTAGGCGACCANA

TCCCCGGGGTCAACAGGTTGACCATCC (SEQ ID NO. 250)

Clone Rv235
::::::::::::Rv235SP6.seq::::::::::::
CGCGGACATCCCGAACGAGGACACGCGACCGCTTCGGTGTGTGATCTATCAGGGCTCGCACCACGCGCAACCGCTTCCGGCTACCTAGACGCGGT (SEQ ID NO. 251)

::::::::::::Rv235T7.seq::::::::::::
GCATGCGGGTGATGCCGTTCTCAGTGCGCAACAGCGTTCGACGCGGCATACCCAGCCGCACATGCCGTGCACGCCGGNGCCGGGGCGGGAATCT (SEQ ID NO. 252)

Clone Rv237
::::::::::::Rv237SP6.seq::::::::::::
CTCAAGCTTCAGNCCNTCTAAGCGGTCTGCGCGGCGATCGCAAAGATCGCCCTTTGCCGGCGTTGGGGGCTTCTGCTCGGGGGTGTTGTACACCTTCTCGAAC ACCTCGGCACCGACACCACCACCGTCGGCTTGAACACCGCCAACATCGGCAGCANATCTTGATGTCCTGGTGAATCCACGGTGACTTTGGAGTGGAAGGCGGC CATACTGATCGCGCGCGCCACCACATGAGCTAGCGGCAGGAAAACCAGCAGCCGCTCACCCTTGCGCAGCAGCGTCGGGTGATATGCCTGGCGCCC (SEQ ID NO. 253)

::::::::::::Rv237T7.seq::::::::::::
AGTCGAANGTCAGTCCGGTCTCCTCTCCGACTACGGCCAAGAACTGGGGCGACGGTGTCAGTGCAGAACAGCGGAAACTGGTGGCGCCCTAGGCGAGCGAACG CTCACAAACGGCGGTGACCGCTTCTGGTCGTGCACCATCGAGCCGTGCCCAGCCCGGCCGCGTGCCGTCAGCCGCATCCACTGGATGCCCTTCTCGGCGGTTT CAATCANGTACAGGCGACGTTCGCCACCATCGTGCCGGGGCACGGTTAGCGAGAAACGCCGACTTCACCGATTGCCTCGGTGATGxxxxx (SEQ ID NO. 254)

Clone Rv23
::::::::::::Rv23SP6.seq::::::::::::
AGCTTCGCGGCGTGGCGATCGCGGTTCAAGGCGCGCTCTTCGAGCACAACGAGCGAAGACAGCTCGGCGACGGAGCCTTTATCGACATCCGTTCGGGCTGGCT GACCGGCGGCGAAGAACTGCTGGACGCGTTGTTGTCGACGGTGCCGTGGCGAGCCGAGCGCCGTCAGATGTNCGACCGGGTGGTCGATGTGCCGCGGCTGGTG TABLE 3-continued End sequences of the polynucleotide inserts cloned in the named recombinant AGTTTTCACGACCTGACCATCGAAGATCCGCCGCATCCGCAGCTGGCGCGGATGCGCCGGCGGCTCAACGACATCTACGGCGGCGAACTGGGTGAGCCCTTCA CCACCGCCGGGCTGTGCTACTACCGCGACGGCTCTGACAGCGTCGCCTGGCATGGCGACACCATTGGTCGCGGCAGCACTGAGGACACTATGGTGGCGATCGT

CAGCCTCGGCGCCACCCGCGTCTTCGCGCTGCGGCCGCGTGG (SEQ ID NO. 255)

Clone Rv240
::::::::::::Rv240SP6.seq::::::::::::
AGCTTCAGCTGATACTCGACCAGCCCCACTCGGGCCAATACGTGAATGTCTAGCATCTTCACCCGTTCACGGGCTANTCGAGTAGTAGACATTGATTAGCCTG AACGTACCTCCGACGCCAGCTGACGAACGGGTATGACGGATGGATTTCGTGGTGTCGCGCCCGAGGTCAATTCGTTACGGATGTATCTCGGGGCCGGATCGGG GCCGATGTTGGCGGCCGCGGCGGCCTGGGACGGACTATCCGACGAACTGGCGGTGGCGGCGTCGTGGTTTGGGTCGGTGACCTCGGGCCTGGCGGATGCGGCG

TGGCGCGGCCCGCGGCGGTTGCGATGGCNCGCGCGGT (SEQ ID NO. 256)

::::::::::::Rv241T7.seq::::::::::::
CTGGTCATGGACGTTGCTCCGGTAGTGGCTCACTGCCGATCCTCCTCGTTGAGAGTGCCACCTCAGGGTTGGGTAGGGTTGGGTACTCGAAACCAAGTTACCC ACCAGTAACACCGTCAAAATATATCCGTTGCATAGGTCAATGCAAGTTGATGTGAGCTACATTGCACCAACTAACTAACCAACCGGTTGGGTTAGCGGTGATC CTGGCCGTGTCGGTCCTCTCACCTGCGGTGATAGCGATCAAATGAAGAATATGCGGAGTCTAGGGCGGCAGCGCCTGGCANCGTAGATCATCGGCTCACGCGG

ATGCGGCCTCTTGGTACGGACATGCGCGCG (SEQ ID NO. 257)

Clone Rv241
::::::::::::Rv241SP6.seq::::::::::::
CTCGTGAGTAGCACCCCTGTAATTTGGGATCGGCAAAAAGGCGAATCACCGCGTGGCCACGACACGCCGGGAGGGACNATCTCGGGCGGCTAGGGCTTCTCGC GGGAAGGCCCGAACGTACGGCGTTTCAACACGTCGCGTCGCCCTCCGACCGCGAACATTCGGGGATGGCAGCAACCTGG (SEQ ID NO. 258)

::::::::::::Rv241T7.seq::::::::::::
GGATCAACTACCGGCCAACGGTGATTCTTGGGCGCCGCTGACGCGCGAACGACCCAGCGACACATTCAGCAGATGGCCAGCGCGTGCCGGGCCACGATGTTGG TGCTCGGCGGCTACTCCCATGGTGCGGCNCGTGATCGACATCGTCACCGCCGCACCACTGCCGGCCTCGGGTTCACGCAGCCGTTGCCGCCCGCAGCGGACGA

TCACATC (SEQ ID NO. 259)

Clone Rv243
::::::::::::Rv243SP6.seq::::::::::::
AGGACCGTCAGCACGGCGACGTGCTACTCGCCGAGCAGTGGGAATCGCTCTGCAGCAAACCATTACTCTGCGCGACGTTCGAGATGACCTTCTGAATGGACGG ATCTACCTGCCGCGCGACGACCTGGACCGCGTATGCGTCCGCCTCCGCCTGGACGACACCGGGGCACTCTATGACCCCGACGGACGGCTCGCGGTACTGCTGC GGTTCACCGCCGACGCCCGCACGGTACGCGTCGGGACTGCGCTGAGTCCANCCTCGACGCCGTAGCGCTGCTGCTGTGCGGCCATGTCTGGCATCTACCGCCG

TCGCTCCCTTGA (SEQ ID NO. 260)

::::::::::::Rv243T7.seq::::::::::::
CGACTCTGTTGGCCACTGCGGGTCGATCTTGCGGCCGCCCCGGTCGTGGAACGCCCAGGTCACCCGGCGGCGCACCGCGGTCAGCGCGTCGTTGGCCAGCGTG GTCACATGGAAGTGGTCGACGACGAGCTTGGCGTTGGGCAGCAGCCCGGGCGTGCGGATCGCCGAGGCGTATGCAGCGGCGGGGTCGATGGCCACCGTACTGG ATGCTCTCCCGGAACTGCGGTGTGCGCGCTTGCAGCCATGCCAGCACCGCCGCGCCGCCGCGGCCTTCATGCTGCCCATAAACCCTGATACCGGCCAGGTCGA

CNAACCNGTATCCCACGGTCAACCC (SEQ ID NO. 261)

Clone Rv244
::::::::::::Rv244SP6.seq::::::::::::
CACACGGACGGCGGTGCGGACGCAGCTGACGCGCATGGTGGTCAGCATCGCGGCCGGTCTGCTGTTGTATGCCTACTTCGCGCCGCGCAAATGCTGGTGGGCG GCGGTGGTGGCGCTCGCATGGCTGGGCTGGGTGCTGACCCAACTCTCGAACCACACCGGTGGGTGGGCTGGGCTATGGCCTGCCATATCGGCCTGGTGTTCTA

CN (SEQ ID NO. 262)

::::::::::::Rv244T7.seq::::::::::::
CCGATATCCGAGCCGATAGCTGGCGGGCTCGGGTGGTNGCCAGCGGCGCTGCGACGAAAGTGTGACCGTCATGAAACAGACACCACCGGCGGCCGTCGGCCGT CGTCACCTGCTCGAGATCTCAGCATCCGCAGCCGGTGTGATCGCGCTTTCGGCGTGTAGTGGGTCGCCGCCCGAGCCCGGCAAACGCCGGCCCGACACAACCC

CGGAACAGGAAGTCCGGTCACCGCGCC (SEQ ID NO. 263)

Clone Rv245
::::::::::::Rv245SP6.seq::::::::::::
GCTTCAGGACAAATTGNATCCCTATGCACCCGTTGTCACGCCGATGAGTGAAGACTGCACGCAATCGCCGGAATCCGGCAAAACCCTGCACAAGCGAAATCAA TABLE 3-continued End sequences of the polynucleotide inserts cloned in the named recombinant CCGGAGGCTGACAAGGCAACGTCGGTGATCCGTACCGCCTGGTTGGACAAACGGCAGAAGGCGCCTCGTCCGGTCCATCTACGCCGAGCACACTGGTGATAGC GCCATCGGCATCGGTGCGGCCACGGTGGAGACGAACGTCCGCNGGCGTCTGGGTCAGTAACCCGCCGACCAGTTCTCGGGCAAGCTGGTCAACATCGGGCGCC

ACGTCTCCAAC (SEQ ID NO. 264)

::::::::::::Rv245T7.seq::::::::::::
GTTTGGCGGCCTTATTGCACTGAGGTCGTCAATTGACCCACAGCGGAAATGCCGACTATTCGCAGGCCTCCTTCGCCTTGGCTGCCGGAGATGGGCTCCGCGG GAACCGCATGCAGGTATATGACCTCGGTTTCTCGGGTGCTACCGCGTGCCTTGTCGAGGATGAACTCGGCGTTGGAATTGTCCAGCCGGCCCAATTCATCGAG CGCAGATTCGTACACATGGCCGGCGGCGACATACCTTCACCGTGGATCTGCTCCACACGGACCGCCCTGTCGGGATCTGCTCACGGGTAAAGGAATTA (SEQ ID NO. 265)

Clone Rv246
::::::::::::Rv246SP6.seq::::::::::::
GCGCACTCCTCCTTATCGCTCCGCTCTGCATCGTCGCGGCGCGGTCAGGTGCAAACGCCTTCGGGGGTGGGGGTCCTGCGGAGCACACCGGATACGGAGCGCA ACGCGTCGCGTTGTGCGGGCAAACAAGTGTGCAGGNNCCAATGCCATGTCCAGCAGCTTATCAGTGTCGAACGTGCGAACGTCGCGCCTTCGCCGGTGCCTGA

ATCTCTACAAG (SEQ ID NO. 266)

::::::::::::Rv246T7.seq::::::::::::
CGCTGAAAGCCACCATTCGCGGGTCGGCGCCGGGCTCGGGCCGCCAGGCTGCTCCGCTCGGTGATGGCACGCCACCGCGACACCACCCGGCTGCGCTACGTC GAGCCATACCGGGCGGAGCTACATCGGCTCGGCCGCCTAGTGTTCGGGNCCTCTTTCGAGGTCGAGGTCGA (SEQ ID NO. 267)

Clone Rv247
::::::::::::Rv247SP6.seq::::::::::::
TGTAATTTGGGATGGGCAAAAAGCAAANCACCGCGTGGCCACAAACGCGGGGAGGGACAATCTCGGGCGGCTAGGGCTTCTCGCGGGAAGCCCGAAACGTACG

GCGTTTCAACACGTCGCGTCGCCTCCGACGCGAAATTCGGG (SEQ ID NO. 268)

::::::::::::Rv247T7.seq::::::::::::
CTTGGGCAACATGCTGAGGATCGCCTTTTCACCACGCGGTCGGGGTGGCGTTGCATTAGCTCACCGATGGTGCGCTTGTTGCAGGCCGCCGGGATACCCGAGT GCCGGTAAACCATCTTGTGCTGCAGTTTGTCCCGCTGATGGCGACCTTGTCGCGTTGATCACGATGACGAAGTCACCGCCATCGACATTGGGGGCGAACTCGG

CTTGTGCTTG (SEQ ID NO. 269)

Clone Rv249
::::::::::::Rv249SP6.seq::::::::::::
GCATGCTTCATTATCTAATCTCCAGCCGTGGTTTAATCAGACGATCGAAAATTCATGCAGACGGTCCCAAATAGAAAGACATTCTCCAGGCACCAGTTGAAGA GGTTGATCAATGGTCTGTTCAAAAACAAGTTCTCATCCGGATTGAACTTTACCAACTTCATCCGTTTCATGTACAACATTTTTAGAANCATGCTTC (SEQ ID NO. 270)

Clone Rv24
::::::::::::Rv24SP6.seq::::::::::::
ATACTCAAGCTTGATGCCGCCGAAACCGAGCGTGAGCACGCCGCCAGCCACCACGCGCGGGTCGGGCGCCGGGCCCGGGCCGCCAGGCTGCTCCGCTCGGTGA TGGCACGCCACCGCGACACCACCCGGCTGCGCTACGTCTATCCATACCGGGCGGAGCTACATCGGCTCGGCCGCCCATTGTTCNGGCCCTCTTTCGAGGTCGA

GGTCTATACCGATTTGCGCATCCG (SEQ ID NO. 271)

::::::::::::Rv24T7.seq::::::::::::
TCCGTACTGGTCGGGTACGCTTCGGTCGCAGTGTGCGAGTGATAGATGACGACCGGGACCTCGTCGGCATCTTCCATAGCCCGCCACACCTTCAGTTGCTCAC CGGAATCCAACCGGTAGAAGGTCGGCGAGCGCTCGGCATTGGTCATCGGGATATGCCGCTCGGGACGGTCAGAACCTCGGGTCCG (SEQ ID NO. 272)

Clone Rv251
::::::::::::Rv251SP6.seq::::::::::::
GTTCTCGCACGATTTCGGATTAGCGGGATGGTCTCAATTGGGTATGCGGGGAAGGCGCTGACATTCGCCCGCGATTAGCTGTTTGATGGACCGGGGGTGATTTT

TGATCACGGAAATGGGTGTTTATNCAGGTCGCACGCTTTCATCCGGGGCGGAACG (SEQ ID NO. 273)

::::::::::::Rv251T7.seq::::::::::::
GGGTGTGCCTGCTGTGTATGCACGGCATACGGACATCCTTCCCCTGAAGACCCGCGGTCGAACAGCCACGTGTCCATCATCANGGGGTCAACCCCGGCCAAGG GCGACGGCACGCCAAGTTCGCCGACCGTTAACCTAGTGCTGTTAGCTTCATTTGCTGCGAGCAAAACAGCTGGTCGGNCGTTAGGAATGAATTGAAACTCAAC

CGATTTGGTGCCGCCGTAGGTGTCCTGGCTG (SEQ ID NO. 274)

Clone Rv252
::::::::::::Rv252SP6.seq::::::::::::

TABLE 3-continued

End sequences of the polynucleotide inserts cloned in the named recombinant

ACTACCCGGCCAACGGTGATNTCTTGGCCGCCGCTGACNGCGCGAACGACGCCAGCGACCACATTCAGCAGATGGCCAGCGCGTGCCGGGCCACGANGTTGGT

GCTCGGCGGCTACTCCCANGGTGCGGNCGTGATCGACATCNTCACCGCCGCACCACTGCCCGGCCTCGGGTTCACCAGCCGTTGCCGCCCGCAGCGGACGATC

ACATCGCTTTTATTTNNTNTTCNGGAATCCCTCGGGCCGCGCTGGCGGGCTGATGA (SEQ ID NO. 275)

Clone Rv253
:::::::::::::Rv253SP6.seq:::::::::::::
ACGTCGGGANACTGTTCGCGTTCATCCTCGTCTCGGCGGATTGGTCTGCTGCGCCGGACCGACCGATCTTCAGCGGGGGGTCACGCTCCGTGGGGTGCCGTTA CTTCCGATCGCCCAGTGTGCGCGTGCTGTGGCTGATGCTGAACCTCACCGCGTTGANTTGGATCGGTTCGGGATCTGGCTGGTGGCCGGAACGCNATTTATGT

CGCTACGGGCGCCGGC (SEQ ID NO. 276)

:::::::::::::Rv253T7.seq:::::::::::::
GCTCAAAGGCACTACTGGCACCAAGGCCCACACGTCACCTGTGACTCCTGCGCCGACCCGCCCGAGGTCTGGCCGTTACACCGAACGGGCGAGCCGGGAGTTG

GTACCATCGAACAAGACAAGGTGCATGGGCGGAGTTGTTCCGCCACTTCGTCGATGACGGGTC (SEQ ID NO. 277)

Clone Rv254
:::::::::::::Rv254SP6.seq:::::::::::::
CGATACCGGCTGCTTACCGAGACATCCACCATGCCACCCGAATCACCGCACGCGCCGAAATCGCACAACAGCTTGACGCCTTGCAGGTTCCGCGATTGGAATT GCCGACGGTCTCTGACGGCGTCGACCTTGGCAGCCTCTACGAGCTCTCGGAATCACTTGCCCAGCAGGGGGTTCGATGAGTGTCACACCGAAGACCTCGATAT GGGCGCAATCCTGGCCGACACATCCAACCGGGTGGTTGTGTGCTGCGGCGCCGGTGGGGTCNGCAANACACTACCGCGGCCGCGCTGGCGTTGCGCGCGGCCG

AATATGGCCGCACTGTGGTCG (SEQ ID NO. 278)

:::::::::::::Rv254T7.seq:::::::::::::
CGTCGTCGTCGTGGTATGCGATAGCCATCCCGTCGGGCTACTCGCCATCACCGATCAGCTTCGCCCCGAAGCCGCCGCGGCGATTTCCGCTGCGACCAAACTG ACCGGGGCCAAACCGGTATTGCTTACCGGCGACAACCGGGCCACCGCCGATCGGCTCGGTGTACANGTTGGCATCGACGACGTACGGGCCGGGCTACTGCCGA CGACAANGTCGCAGCCGTGCNGCNGCTGCAAGCTGGAGGTGCCAGATTGACCGTGGTCGGTGACGGTATCAACGACCTCCGGCCTTAGCGGCCGCGCATGTCG

CATCGCCATGGGCAGCGCCCGAC (SEQ ID NO. 279)

Clone Rv255
:::::::::::::Rv255SP6.seq:::::::::::::
GCACGCAATCGAAGTCACCCAAACCGGGCGGGCCAGGCGTCTNACGCCACGTCNACCAGCCGCAACCTCAACCCGGCCACGGCGAGCTCCTGATCAAGGCCGA GGCCATCGGTGTCTACTTCATCGACACCTACTTCCGCTCCGGGCAATATCCGCGCGAACTCCCGTTCGTCATCTGCTCCGAAGTATGCGGCACGGTGGANGCC

GTCGGCCAGGGGTTAC (SEQ ID NO. 280)

:::::::::::::Rv255T7.seq:::::::::::::
TCGACTGTGTGGCCACAGATCACGCCCCGCATGCCGAGCACGAGAAATGCGTCGAATTCGCCGCGGGCCGGCCGGCATGCTCGGGTTGCAGACGGCATTGTCG GTGGTGGTGCATACAATGGTGGCGCCGGCTTGTTGANTTNGGCGCGATATCGCGCGGGTGATGAGTGANAACCGGCGTGCA (SEQ ID NO. 281)

Clone Rv257
:::::::::::::Rv257SP6.seq:::::::::::::
GAACCTGACACCCTGGTCACGGGTGAGCACGGACTTGATTTCTTCNCTATTGGTCGGCGCTGTTGAGCACACCACGCCGCTGACGGCCGTCGCGTCCTCGCTG TGCTCGGTCTGGTGGAGCGCGCTGCCCGCGGCCNAACATCNTAAATCAAGCGTATTCGTCAACAGATATCATCAATGTCGGCGCTGGACTATTCAAATCATCG ATATACTGGTGACCTGGTCCTTCGCCATCGATCAATGGCGATAGTCACGCAAATCGTCACGGACATCGTCGGCGTCCCAGCTGGCCCGTGCCAACAGATGCTG CAACCCATCGGGGTGGTATCACCGCGGTGCTCGGCGATGGTCCACAATTCTTGCGGTCCAAGCCCNAAACATCCCGGGCATGAATTCACCGGCATGCGCN (SEQ ID NO. 282)

:::::::::::::Rv257T7.seq:::::::::::::
CTATCGTACCCGCGCCGGTCACCTTCTGGATATCGCCGGCCTGGTCAAGGGGGCGTCCGAGGGAGCCGGGCTGGGTNACAAGTTCCTGGCTCATATCCGCGAA TGCGACGCCATTTGTCAGGTGGTGCGGGTGTTCGTCGACGACGACGTGACTCATGTCACCGGACGGGTCGATCCCCAGTCCGACATTGAGGTCGTCGAGACCG AGCTGATCCTGGCAGATCTGCAAACCCTGGAGCGGGCCACGGGCCGGCTGGAGAATGAAGCGCGCACCAACAAGGCGCGCAAGCCGGTCTACGAAGCGGCACT GCGTGCCCAGCANGTGCTCGACGCCGGGCAAGACGCTGTTCGCCGCGGGGGTGGATGCCGCCGCGTTGCGCGACTGAAACTGCTGACCACCAAGCCCTTCCTG

T (SEQ ID NO. 283)

Clone Rv258
:::::::::::::Rv258SP6.seq:::::::::::::
TACTCAAGCTTCAGGCCGCCACGTCCGCCGTCCGTCGGCGACGTGACCTCGAGCGCCGAGTTCGACTCGACATCGCCGCCGGCGCATGCCGACATGAACGCGG TABLE 3-continued End sequences of the polynucleotide inserts cloned in the named recombinant CACTCACCGCAAGCCCGTCGGACGTCAGGTCGATCGACTCCGCTTCAAGCACCGGATCGTCCGGGCAACTCGCGGCCTCGGCCTGTGCGAACGGCACACCCGT CGTGGCGGCNCCCCGCGCGGAACTGGGCTCATCACGGTCGTTGCGAGCCGGTCGCGTCACCGCGTACCGACGCCGTC (SEQ ID NO. 284)

::::::::::::Rv258T7.seq::::::::::::
CCGACATCGAGTGGGCTCGCAGTGACTTGGCGACCTCCAAGCCACCGGTACCCGCCGCGCGGCAAGCCAAGGACGACGACGGCCTTGCCGGATAGCTGCGCCA GGCGTTGCGCCAACTGGCGTCCAGCGTCGCCACGATCGTCAAAGAGCTTCATCTGCCGAGTGTGTCGCCATCTCATGGCTCCAAATATGGAATTAGGTCCCTG GGCCGACTGACGACAGTCCCTCAGCGACCGGATTGCGCATCCCGCCTTGTACGCTACTCCGCAAATCCCGGGCTTGCGTCCGCGGAAGCGAACTCGGCGGCGC TACGTGGTGGTTCACTTCGGCCGTGCGCACTCGGATCGACGGGCCGATGGTGGCCGGGCCCGCGCGCTTCTTGGTCATCCGATTGAGT (SEQ ID NO. 285)

Clone Rv259
::::::::::::Rv259SP6.seq::::::::::::
ATACTCAAGCTTGTCGCGGTAAACCGCACGCAGGGCGGTGGGTGCGGTGTCAAAGACACCCACACTTCTTTGCGGTTCGGTGATCTCGACACCGGCCGCGAGC CGACCACCATGCGCGCGTAGATCGGCGATCAGCGCGTCGGCTATCGCCTGGGTGCCGCCCACCGGAATCGGCCAGCCGACCGAATGGGCCAGCGTTGCCAGCA TCAGTCCGGCGCCGGCCGACACCAGTGACGGCAACGGTGAAATCGCGTGGGCGGCAACGCCGGTGAACAACGCGCGGGCATCCTCGCCCGCCAACGACCGCCA

GGCAGGGTGCCTGGGCCATCATCCGCAGCCCGA (SEQ ID NO. 286)

::::::::::::Rv259T7.seq::::::::::::
TGGACTCATAACGATCGGGTCAGCGACGCGCCAACACGAACGGCCGGACGAGTGGGCCAGGGTCGCGCCTCCCCTACAAACAGGATCCGTTGCCTGCGAGCGA CAGGCTCCGGTGCGGCGTTGGGCGCCGTGCTCGTCCCAGCGTCCGGTCCCGGGTCGCCGGCGACGCTTGTTTCCTCCATACTCGCCCCCTAATCTCGAGGCAG CCCGTACCCGCAGGCAACCTCCCAAAAATGCAATCCCCCAAAATGCAATGCGTCGAGCTATTTCTCACACCGACCGCTAGTTGCGGATCAGAAATCCGTTGGG CGCGGAAGTCCAGCCGAATTTGTTCTCCCGCTCCGCATCATGCTTGTAATCGTTTGGAAATCATCCTCATATGCCTCGATCGCTTCATAGGTCAAGCCCAAAC

CCGGCAGGATGGGTGGCC (SEQ ID NO. 287)

Clone Rv25
::::::::::::Rv25SP6.seq::::::::::::
CTTTACACTTTATGCTTCCGGCTCGTATGTTGTGTGGAATTGTGAGCGGATAACAATTTCACACAGGAAACAGCTATGACCATGATTACGCCAAGCTATTTAG GTGACACTATAGAATACTCAAGCTTAGTGGTTGCGCACGTAAATTCGTCAGGTGACCGATCCCCTGCTGTCTCACTCGCCTCACAGCGACCACCACGGCTGGC GCTCAAGGCGGGCACGTGCGGAGCAGATGAGGAATTGTGCGACGTCTTGATGCAGCCTGCAGAACACCGAGACCCTCGACGAACTTACGATCGAAACCGCTTA GGCCAACCGGTGACGGGGGTGTCTTTCCGCGGCTAGGGCGCCTTATCGTCCGAAGGCCGTGGGTGGTGATCGCCTTCTGGGTCGCGCTTGCGGGTCTGCTTGC

GCCGACGGTGCCGTCCCTGGACCGATCTCCCAGCGGCATCCAGTGGCGATTCTGCCATCGG (SEQ ID NO. 288)

::::::::::::Rv25T7.seq::::::::::::
CAGGCATGCAAGCTTGCGATGTATCAACACGCCGTTGCGCAGCGTGAGCCGATAGTTGACATCCGGCTCGGTGAAGGTGAAATCGATGGCCAGGTCGAGGTCC CATGCGCGTGGGCCATTGATGCTGATCGCCAGGACGTCAAAGATTTGGTCCGGCGTCAGCTGGGCGAAAAACGTGGGCGCCGGGACTTGCCCGGAGCTGCCCG GGTTCCCGTCGCGCAGCTCGGCGGCCCCGGTCAGAAAGAAATTGCGCCAGGTCGCACACTCCGCGCCGTAGGCCAGCTGCTCCACGGTGTCGGCATATAGCCC GCGGGCCGCAGCGTGCTCGCTGTCGGCGAACACCGCATGGTCGAGAAGCGTTGCCGCCCAACGGAAATCACTGCGTCAAAGCTTCGCCGGGCCACTCCAGCAC

TCCGTC (SEQ ID NO. 289)

Clone Rv260
::::::::::::Rv260SP6.seq::::::::::::
ATACTCAAGCTTGACCGACGCTGATCGCACCGCACGCGGGAACCTCAAGGGCACTACTGGCACAAGGGCCCACACGTCAACCTGTTAACTCCTGCGCCGACCC CGGCCGAAGTCCTTGGCGTTAACACCGAACGGGCCAACCCGGGAATTTGGGTTCCATCAAAACAAATAGCAGGTGCCTGGGCGGAGTGTTC (SEQ ID NO. 290)

::::::::::::Rv260T7.seq::::::::::::
GTCGTCGTGTGCTGGGGCGTCCGTATCAGCACGCCCACGAAATGGGGCACAAGAAGGATTCCTGGAACGGTGGCTGTCCAAGATCACCCTCGCCCAAAACTGC

TACGGGCACTTCTACATCGAGCACAACCGTGGCCATCACGTCCGCGGTGTCCACACCGGGAGG (SEQ ID NO. 291)

Clone Rv261
::::::::::::Rv261SP6w.seq::::::::::::
ATATGCCTTGCTGAGCTTTTCGGATCGCAGCGAGTCGTACCCGCGCCGGTCACCTTCGTGGATATCGCCGGCCTGGTCAAGGGGGCGTCCGAGGGAGCCGGGC TABLE 3-continued End sequences of the polynucleotide inserts cloned in the named recombinant TGGGTAACAGGTTCCTGGCTCATATCCGCGAATGCGACGCCATTTGTCAGGTGGTGCGGGTGTTCGTCGACAACGACGTGACTCATGTCACCGGACGGGTCGA TCCCCAGTCCGACATTGAGGTCGTCGAGACCGAGCTGATCCTGGCAGATCTGCAAGCCCTGGAGCGGGCCACGGGGCGGCTNGAA (SEQ ID NO. 292)

::::::::::::Rv261T7.seq::::::::::::
GACACCCTGGTCACGGGTGAGCAGGACTCGATTTCTTCGCTATTGGTCGGCGCTGTTGAGGCACAGCACGCCGCTGAGGCCGTCGCGTCCTCGCTGTGCTCGG TCTGGTGGAGCGCGCTGCCCGCGGCCGAACATCGTAAATCAAGCGTATTCGTCAACAGATATCATCAATGTCGGCGCTGGACTATTCAAATCATCGATATACT GGTGACCTGGTCCTTCGCCATCGATCAATGGCGATAGTCACGCAGATCGTCACGGACATCGTCTGCGTCCCAGCTGGCCCGTGCCAACAGATGCTGCAACCCA TCGGGGTGGTATCNCCGCGGTGCTCGGCGATGGTCCAACAATTCTTGCGGTCCAAGCCCGAAACCATCCGGCCATGAGTTCACCGGCATGGCGCAACGGCTGG

TGCCGGGCAAAACGCGGCGCGATCGAATTC (SEQ ID NO. 293)

Clone Rv262
::::::::::::Rv262SP6.seq::::::::::::
TGTAGAAGGTGGGTCCCGTCCAACTTCGCGGCGGCGGCGCGATATGCCTTGCTGGTCTTGCTCATTTGATATCCAATCTATGGGTCGTGGTTACTCAACGGGC

CGAAGCTGGCCCTCCCACGGGTAGGGTCCTATTCGACGGTGATGTCC (SEQ ID NO. 294)

::::::::::::Rv262T7.seq::::::::::::
CCCGAATCCGGTGGCCGGCAGGGGGCCTGGCGACGTGGACACCTTCTAACTTGTCTTTACCGGTCACTGTTGCACCCCAACACCTTTAACGACGTGGACGGAC GTTACATCGGATTCGACGGTGTCATCCACAGCGTTGCCATTGGGCACACCCACTACGCCAATTTCTCCGACTGGGACACCTACCGCAGCCTCGCCCCACTGCA GGGACTGTTGTTCCCGCAACGGGCCATCGACATGATCCAGTCGTTGGTGACCGACGCGGAGCAGACTGGTGCGTATCCGCGTTGGGCGCTGGCGAAATTCCGC

CACCGGCATGAT (SEQ ID NO. 295)

Clone Rv263
::::::::::::Rv263SP6.seq::::::::::::
TTGAGATGCTGGTCGGGATGCCGATGGTTGGAACATGGTCCCCTGGCGTCGAATACGCGCGAGCGCATGAGCTCACCGGTTCGGAACAACGTATCGAAGAACT CGCACTGCTGGCAGATGGTATCTCCGATGTGGTTGTAATTTGTATCCCAACTCTAACTGTGCTATCGGATCTGCGTGAATA (SEQ ID NO. 296)

::::::::::::Rv263T7.seq::::::::::::
CGTAATCACGATCCCGCTGAGACACTTGACCTTACGGCCGAAGTGACTTCGCTGCTGCTATGCCGACACCCGATTTCCATACGCTGCTGTACACGACGGCCGG GCCGGTGGCCTCCATCACGCTCAACCGCCCGGAACAGCTCAACACCATCGTCCCGCCCATGCCCGACGAGATCGAGGCCGCTATCGGGTTGGTCGAACGCGAC

CAGGACATCAAGGTCATCNTNCTGCGCGGTGGCGGGCGCGCCTTCTCCGGCGG (SEQ ID NO. 297)

Clone Rv264
::::::::::::Rv264SP6.seq::::::::::::
CAAGCTTAAGCTGGTTCCGGCCACTCCATGAGCCGTAGTGCAATGGTTCGTGCACGGCGAGGCCGAACTTGCCATAAACATCCCTGACGAAAGTCTCCGGCAA GCCGATTGCTTCTTCGGGCCGCTTCTTGTGGATTGTCCGATAACCCGGTCCCTCATGCTGGAAGTTGTGCGCACTCTTTCCTTCCGCGATGTGGGCTAACGAC TCGTCATTGAGCAAGAAGTACGTGCACAGGCATCGTCCGCCGGGCTTCAGCACGCGGGAGATCTCGTCCAGATAGTGCTCCACGTCCGGNGGGAAACATGTGG

GTGAACACCGAGGTNAGAAACACCNCATCCAACGACGCATCCGGGATATGGAAAGCGAAA (SEQ ID NO. 298)

::::::::::::Rv264T7.seq::::::::::::
TATGGTCTTCGTCGACCAGTACGTCGTAGGCGCCATGAGCCAGCGACTGAAGCCGCGCCATGCCTGCACGGCCCGCTCATCCAGCGAGGCGGCCATCTCCCGC AGATAGCCTGCCGCCTCGGCGCGCACGCTGTCCGGATCGCGTCCGAGCTCGTCGGCCAGCGCACGCAGCCGCTCGTCATACCATCGGGCATCCAGCAGTTGGG TAACCTCAACGGGGTCGGTCGCTAGCGGCGTCATTGATTCAGCAACAATACCGATGCGCTGCAGCAACTTTCGCAGTCCGATGCGGCCCACCTCCCGTGCAGT CACTGGCTAGCCCCCGTCATGCCGGTTGTGTCGATGGCACGGCAGCGGGCTCGTAAACCTGCGGTCTCAGCTCGCTGG (SEQ ID NO. 299)

Clone Rv265
::::::::::::Rv265SP6.seq::::::::::::
GCTTAGCGGTCTTGCTCGAACCGACATTGCGTGCCACTCATGAGCGGGTGGCGGTCGCGGTGCTTACACATCT (SEQ ID NO. 300)

::::::::::::Rv265T7.seq::::::::::::
GTATCTGGCGCCTCTCGAATATCCTTGAACGTCCCGCGGTGCCACCCAGATAGATCGCAGCGCCCTGCAATGGAGTTCCCTTTATGGCCTCTCTAGCCTCCCG

CTTGATCGGCTCGACCCGAGAGATGCCCTCGGGCGTTGCGGGATCTCCCTCCA (SEQ ID NO. 301)

Clone Rv266
::::::::::::Rv266SP6.seq::::::::::::
CTTCACGCCGATCCGCGACCGCGAACGCGACGGTGACGGTGGGCGACAAGGTTCGGTTGGTCGCCGCGGCGCTGGGCGATATCAGCTCACCCGGTTTCGAGGT GTTCGGCGACCGGACGGTGCTGCAGACATTCTTGAGCGTCCTCGACCGGCCCGATTCGGCCTTCAACATCGTGACGCCGTATTTCGGCGGTACCGCTCGGCGC TABLE 3-continued End sequences of the polynucleotide inserts cloned in the named recombinant CGAGTCGAAGGCGGCCTGAGCTAAAGCCGGGCATTGCGCGAGTGGTAAACAAGTTCGGTGACTTCGGTTGACCGACTCGACGGGCTCGATCTGGGCGCGCTGG ACCGGTATCTGCGTTCGCTGGGGATCGGGCCNACCGCNANTTGCGTTGCGANCTGATTCCGGTGGAGCTCCAATCTGACTTCCGG (SEQ ID NO. 302)

::::::::::::Rv266T7.seq::::::::::::
GCAGCTACCGACCCTAGCGACGAGTGTGTTCGCAGCGTCGAATGTGAACGTTCGGCGTGATTCGGCGCGCGGGTTCCCGCTCTCAGCGCACGTTCGGCGCCGA GGNGGCTAGTCCCTGGTTAAGCAATGTCTCGGTCGCCGCCAGCAGCGCGCATGTCGCCAACCCGTCNACCGCGTTGCGCATGTCCGGTACCGACGGAAACGAC GGCGCGATCCGGATGTTCTTGTCGTCCGGATCCTTTCGATACGGGAACGACCCCCCGCCTCGGTCACCGCGATACCAACGTCCTTAGCCAANGCTACNGTCCG GCGCGCGGTCCCGGGCAACACGTCGAAGCTGATGAANTAACCACCCTTGGGCTCGGTCCAAGANGCGATCTTGGACTCCTTAACCGCTGATNCAA (SEQ ID NO. 303)

Clone Rv267
::::::::::::Rv267IS1081N60.seq::::::::::::
TCCCCATCGGCGCCGGACCGTTTGAAAGTCCAAGCACGGGTGGGATGGAATCGACGACAGTTGAGCGCCGTCGGTGGCCGTGGTCAGCAGCTGTTCGCGAACG CACCAGGTCACATCCCTTCGACATCTCACCGACGTGGCACGGGCGACATCAACAGGAAGATTGACGAATCCCTCGCAGGCGCGGCACGTCCGCAGGCCAACGC CAACTACGGGGCCACCAGCGATCCTCCGCTCACGCACCAGCCCAAGCCAGGCTCANCCACCCAAGTCGGCCCGCGCTCTCCCTCGCCCCCTGGTCTCCGGGGC CTTGTTAAACAACTACCGGAAGTCCACCAATCCTCGCTGCATCTCGACACCGTCCGCCTCACTCCCTTCCTCCCGCCCCTCTCCACACNACACACCTCTTGCA TTAAGGTCACGGAGCGGTCACTTTTCGTCGGACGAAATTCGCAATCCGGCCGCTCGCCGCCAGAGAT (SEQ ID NO. 304)

::::::::::::Rv267SP6.seq::::::::::::
CGGAAAGTGGATACTCCCAGCAGGTAGCAGGTCGCCACCACGCTGGTCAGTGCGCGTTCAGCTCGCTTGCGGCGCTGCAGCAGCCAGTCCGGGAAATAGCTGC CCTGGCGCAGCTTGGGGATCGCGACGTCGATGGTTGCGGCACGGGTGTCGCAAATCACGGTGGCGGTAGCCGTTGCGCTGATTGGACCGCTCATCGCTGCGTT

CGCGGTAGCCCGCCCCGCACAGGGCGTCGGCTTCAGCCCCCATCAAGGCGGCGA (SEQ ID NO. 305)

::::::::::::Rv267T7.seq::::::::::::
GGCCGAGTCCAGCACTTCGCACTATGTGCAGACCAAANACCCGGTGGTCGCCGCGCTGCGGCAGCGGCTGGCAACGGCGCCGGTGATCACCGAGTGGTGCGNA GTTGCCGACCGGCAGTTCGCCGCGGGCTTACTACGAGAAGGGCCTGCGCGACGTCATCAGGTATCACGTGTCGATGACGTCGAGCGTTAACTTCCCCGACCAG ACGGCGACCTCGCCGATGGACCCCGCGTTGTACCTGGTGTGGGCGCAAGCTAACGCCGCCGCANGCTATCGGTACTCGGTCGAAGCGCAGCCGGGGTCGCAAG CGCTAGCGGGCAAGGTCGCGACGATCTCGGTCACCTGGACCAACTACGGCGCTGCTGCCGCCACCGAATAGTGNGTGCCCGGCTACCGGCTGGTGGATTCCAC

GGGACATGTGGTTCGGACCTGCCGGCAGCGGTGGAACTGAAGANGCTGGTCT (SEQ ID NO. 306)

Clone Rv268
::::::::::::Rv268SP6.seq::::::::::::
AGCTTCAAGGACATCGTCATCGCGACCAAAACCGCGAGCTAGGTCGGCATCCGGGAAGCATCGCGACACCGTGGCGCCGAGCGCCGCTGCCGGCAGGCCGATT AGGCGGGCAGATTAGCCCGCCGCGGCTCCCGGCTCCGATTACGGCGCCCCGAATGGCGTCACCGGCTGGTAACCACGCTTGCGCGCCTGGGCGGCGGCCTGCC GGATCAGGTGGTATATGCCGACAAAGCCTGCGTGATCGGTCATCACCAACGGTGACAGCAGCCGGTTGTGCACCATCGCNAACGCCACCCCGGTCTCCGGGTC

TGTCAN (SEQ ID NO. 307)

::::::::::::Rv268T7.seq::::::::::::
GCTCGCGGTCCAGCAGCAGACGTGTCTGACCCCGACGCCCGGCCGCCGGTACCGAAACCGGATCGGCCCGCCGATGGCCGCGGCCACGGCGTCTGCCTTACCC GGCCCGGATACCAGCAGCCACACCTCGCGGGAACGCTGAATCGCCGGCAGGGTCAAGGTGATTCGGCGTGGCGGCGGTTTCGCGAATCGTCCACCGCCACCAC CATGCGGGTGCTCTCGAAGACGCGGGGCTGTGCGGGAACAGCGAGTTAATGTGGCCCTCGGGCCCCATGCCCAGCAGGTGGACGTCGAAATTCGGCCCGGGTC

ACCTGGTGCGGCACTGGCGGCC (SEQ ID NO. 308)

Clone Rv269
::::::::::::Rv269SP6.seq::::::::::::
AGCTTGTCGATCGTCCGGCAGCGTCCGGCGAGTCAAGTCGAAGCCAGTCCGGTCTCCTCTCCGACTACGGCCAAGAACTGGGCGACGGTGTCAGTGCATACCA GCGGANACTGGTGGCGCCCTAGGCGAGCGACCGCCTCACAAACGGCGGTGACCGCGTTCTGGTCGTGCACCATCGAGCCGTGCCCATCCCGGCCGCGTGCCGT CAGCCGCATCCACTGGATGCCCTTCTCGGCGGTTTCAATCAGGTACAGGCGACGTTCGCCANCATCGTGCCGGGGCANGG (SEQ ID NO. 309)

::::::::::::Rv269T7.seq::::::::::::
TTGGTGATCATCGNCCCAACGACCCCGAGGCGATGTTCTTGCACACCGAGGAGTGTCGCAAGCTGGGGCTGGCCTTCGCCGCCGATCCGTCTCAGCAGCTGGC GAAGCTGTCGGGGTGAGGAAATTCGCAGGCTCGTCAACGGTGCTGCTTACTTGTTCACCAACGACTACTAATGGGATCTGCTGCTGTCCAAGACCGGCTGGTC TABLE 3-continued End sequences of the polynucleotide inserts cloned in the named recombinant AGANGCCGATGTGATGGCGCAGATCGACCTGCGGGTGACCACATTGGGTCCTAAGGGTGTCGATTTGGTAGAACCTGACGCACCACCATCCACGTCGGCGTTG

GTCCCCGAAACAGCCAGACCGA (SEQ ID NO. 310)

Clone Rv26
::::::::::::Rv26SP6.seq::::::::::::
GGCTCGTATGTTGTGTGGAATTGTGAGCGGATAACAATTTCACACAGGAAACAGCTATGACCATGATTACGCCAAGCTATTTAGGTGACACTATAGAATACTC AAGCTTGATTTTGATCATCATGATGATCATCACCCGAAGTGTGGTAGCCGCAGTGGTTATCGTGGGTACCGTCGTGCTTTCCATGGGCGCCTCTTTCGGGCTT TCCGTATTGGTCTGGCAGGACATTCTGGGTATCGAGTTGTACTGGATGGTGTTGGCGATGTCGGTGATCCTGCTCCTGGCGGTGGGATCCGACTACAATCTGC TGCTGATTTCCCGGTTGAAAGAGGAAATTGGGGCCGGATTGAACACCGGAATTATCCGTGCCATGGCTGGTACCGGGGGAGTGGTGACGGCTGCCGGCATGGT

GTTCGCCGTTACCATGTCGTTGTTTGTGTTCAGCGATTTGCGAATT (SEQ ID NO. 311)

::::::::::::Rv26T7.seq::::::::::::
CAGGCATGCAAGCTTGGCGTGCCGTTCCAACCCGAATTGGCTTTCGGCGCCATCGGTGAGGACGGCGTGCGGGTGCTCAACGACGACGTCGTCCGCGGGACAC ACCTCGATGCTGCCGCCATGGACGCGGTCGAACGCAAGCAGCTGATCGAGCTACAACGCCGCGCGGAACGCTTCCGCCGCGGGCGTGACCGCATCCCGTTGAC CGGGCGGATCGCGGTGATCGTCGATGACGGCATCGCCACCGGAGCGACGGCCAAGGCGGCGTGCCAGGTCNCCCGGGCGCACG (SEQ ID NO. 312)

Clone Rv270
::::::::::::Rv270SP6.seq::::::::::::
GGCATCTTGGCCGCCATGTTAGCCACACTGCCACCGGCTATAGAAGCGATGCGCACCGTCCTGCCAGCACATTGCGGCGCTCCTCCCTGGAAAGCAAGATAAC

CAAGCTCATGCCGTGGTTGTGGGTGGCGTGGTTTGGTTTGGGTAACTTTGG (SEQ ID NO. 313)

::::::::::::Rv270T7.seq::::::::::::
TCGGCTAATAATCGTCGACGCCGGCCTCCTCTGCAATCGCCTTGGCGGTCGCCGGGTTGTCACCGGTGATCATCACGGTGCGGATGCTCATTCGGCGCATTTC GTCGAATCGTTCCCGTATGCCCACCTTGACGATGTCCTTCAGATGGACGACGCCGATGGCCCGCGCGCTGCTGTTATCGGTCCATTCCGCAACGACTAGGGGT GTCCCCCGCCGGAGCTGATGCCGTCGACAATGGCACCCACCTCCTCGGTGGGGTGGGCACCGTGATCGCGAACCCACTTCATCACCGCAGCCGCGGCACCTTG

CGGATTCGACGGATG (SEQ ID NO. 314)

Clone Rv271
::::::::::::Rv271SP6.seq::::::::::::
CTCAAGCTTGGAGGCGTGGCGATCGCGGTCCAAGGCGCGCTCTCCGAGCACAACGAGCGAAGACNGCTCGGCGACGGAGCCTTTATCGACNTCCGTTCGGGCT GGCTGACGGCGGCNAAATAATGCTGGACTCGTTGTTGTCGACGGTGCCGTGGCGAGCCGAGCGCCGTCAGATGTACGACCGGGTGGTCTATGTGCCGCGGTTG GTGAGTTTCCACGACCTGACCATCGAAGATCCGCCGCATCCGCTGCTGGCGCGGATGCGCCGGTGGCTCAACTAATTCTACGGCGGCGAACTGGGTNATCCCT

TCNCCACCGTCGG (SEQ ID NO. 315)

::::::::::::Rv271T7.seq::::::::::::
CCTAGGTCAACCGTACCGTCATCGGATCGGGGTCGACCGCACAGATGGACTGGAGCTTCGGCGAGGTCATCGCCTATGCCTCGCGGGGGGTGACGCTGACCCC GGGTGACGTGTTCGGCTCGGGCACGGTGCCCACCTGCACGCTCGTCGAAGCACCTCAGGCCACCGGAAATCATTCCCGGGCTGGCTGCACGACTGCGACGTGG TCACCCTCCAGGTCGAAGGGCTGGGCGAGACGATGCAGACCGTCCGGACGAGCGGCACTCCTTTTCCGTTGGCTCTTCGGCCGAATCCGGACGCCGAACCCGA CCGGCGCGGGGTCAACCCGGCACCGACGCGGGTGCCGTTTACCCGCGGGCTGCACAAATCCCGACGGGTATGGGCTTTGACCTGCCGACGGGGGA (SEQ ID NO. 316)

Clone Rv272
::::::::::::Rv272SP6.seq::::::::::::
AGCTTGGCGTGACACCAACACAGGGCACTTAAGATGGCAATGCGCCGCCTACCTGCACGTTTTCGCGATGTCAGAGGATGCCGAGGGGAGAACAATGCGAGCA CGGCCGCTGACGTTGCTCACCGCTTTGGCGGCGGTGACATTGGTGGTGGTTGCGGGCTGCGAGGCCCGAGTCTAGGCCGAAGCATATAGCGCGGCCGACCGCA TTTCGTCTCGACCGCAAGCGCGACCTCAGCCGCAGCCGGTGGAGCTACTGCTGCGCGCCATCACGCCGCCTAGGGCTCCGGCGGCGTCGCCGAACGTCGGGTT

TGGCGAACTGCCTACCCGGGTCCGGCAGGCAACCGAT (SEQ ID NO. 317)

::::::::::::Rv272T7.seq::::::::::::
TCATGCCGTTGGACCGACCATCGGAGTTAGTTGCCGAACCGCGGGACCACCGCAAGCACCCGGTCCTGGTCGCGCACCGCGTCGGCCAACCGCTTGAGCACCA CCACGCCGCAGCCCTCGCCGCGCACGAATCCATCCGCGTTGGCGTCGAAGCTGTTGCATCGGCCGGTCGGTGACAGCGCCGACCACTTGGACAGCGCGATGGC GGTGAACGGTGACAAGGTGAGCTGCACCCCGCCCGCCAATGCCACGTCGGTTTCACGCAGGCGAAGCTCTGACACGCCAAGTGAATTGCCACCAGCGACGACG

AACAAGCGGTATCTACGGCGATGG (SEQ ID NO. 318)

TABLE 3-continued

End sequences of the polynucleotide inserts cloned in the named recombinant

Clone Rv273
::::::::::::Rv273SP6.seq::::::::::::
GGGTCGACTTTCTGCAAGGCGAGGCTACACCGTCGTCGTCGTGGTATGCGATAGCCATCCCGTCGGGCTACTCGCCATCACCGATCAGCTTCGCCCCGAAGCC GCCGTGGTGATTTCCGCTGCGACCAAACTGAACGGGGCCAAACCGGTATTGCTTACCGGCGACAACCGGGCCACCGCCGATCGGCTCGGTGTTCAGGTTGGCA

T (SEQ ID NO. 319)

::::::::::::Rv273T7.seq::::::::::::
AATCCGAAATCCTGACCGATACTTGAACCTGGTCTCGTTCGGCAATAACTCGTCGGCGTGCAGGACGCGGCGCAAACGTACTTCGGCATCAACGCGTCCGACC TGAATTGGCAGCAAGCGGCGCTGCTGGCCGGCATGGTGCAATCTAACAGCACGCTCTTCCCGTACACCAACCCCGACGGCGCGCTGGCCCGGGCGGAACGTGG

TCCTCGACACCATGATCGAAAAACCTTCCCGGGGAGGCGGATGC (SEQ ID NO. 320)

Clone Rv274
::::::::::::Rv274SP6.seq::::::::::::
TTCCGAATTTCGGGTCCNGGTCATATGACCCTCATGGAAGAAGAAGCGGCCGCCCCGCGCCCGTGCGACGGCGAATGAAAACCCTCACCCAGGCCGCATTGAA CGCCGACAAGACGGTGGAGCAGGTCGAAGACGTCCTGGACGGTCTGGGTAAGACCATGGCCGAGCTGAACAGCTCGCTGTCACAGCTGAACAGCACCGTGGAG CGCTTGGAGGACGGTCTGGACCATCTCGAAGGTACCCTGCACAGCCTGGACGATCTCGCGAAACGGCTCATCGTGTTGGTCGAGCCGGTGGAAGCCATCGTCG

ATCGGATCGACTACATCGTGAGCCTCGGCGAAACGGTGATGTCACCGCTGTCGGTC (SEQ ID NO. 321)

::::::::::::Rv274T7.seq::::::::::::
NCTCGATCTTGGGGTACGTTCGATGAGGCTGCTGACCAACAACCCGGCCAAGCGGGTGGGACTGGATGGATACGGATTGCACATCATCGAGCGCGTGCCGCTG CCGGTGCGGGCCAACGCGGAAGAACATCCGTTACCTGATGACCAAGCGTGACAAATTGGGGCACGACTTGGCTGGGTTGGACGATTTTCACGAATCCGTGCAT CTGCCCGGAGAATTCGGCGGTGCCTTGTGAAGGTGGCGCCGGGGTGCCGGATCTGCCGTCGCTGGATCGTCTGGTGTGCGGCTGGCGATTGTCGCCAGCAGCT GGCACGGAAAGATCTGCGACGCGCTGTTGGACGGCGCCCGCAAGTGGCCGCCGGGTGTGGCCTCGATGACCGACTGTGGTTCGGGTGCTCCGCGCGATCGATA

T (SEQ ID NO. 322)

Clone Rv275
::::::::::::Rv275SP6.seq::::::::::::
TCATCCCGACCAAAACGCGAGCTAGGTCGGCATCCGGGAAGCATCGCGACACCGTGGCGCCGAGCGCGCTGCCGGCAGGCCGATTAGGCGGGCATATTATCCC GCCGCGGCTCCCGGCTCCGAGTACGGCGCCCCGAATGGCGTCACCGGCTGGTAACCGCTCTTGCGCGCCTGGGCGGCGGCCTGCCGGATCAGGTGGTAGATGC CNACAAAGCCTGCGTGATCGGTCATCACCAACGGTGACAGCAGCCGGTTGTGCACCAAGCGCGAACGCCACCCCGGTCTCCGGGTCTGTCCAACCGATCGACC

GCCCAAGCCCACATGAACAAACCCCGGCATCACGTTGCCGATCGGCATACCGTGA (SEQ ID NO. 323)

::::::::::::Rv275T7.seq::::::::::::
TTGGCGGGTTGGCCCAGCAGCCCGCCGGTGACGGCGACGATGCTGGGCTGGTTGCGGCCCTGCGCCACCGCGGCTTGCATGCTGGTTGGCTGTCTTGGGACGA TCCCGAAATAGTCCACGCGGATCTGGTGATTTTGCGGGCTACCCGCGATTACCCCGCGCGGCTCGACGAGTTTTTGGCCTGGACTACCCGCGTGGCCAATCTG CTGAACTCGCGGCCGGTGGTGGCCTGGAATGTCGAGCGCCGTTACCTACGTGACCTGATGGATCGGGGGGTGCCGACCGTGCCCGGCGATGTGTATGTGCCGG GANAGCCGGTCCGGTTGCCACGCAAAGGCCATGTCTTCGTCGGTCCGACCATCGGTACCGGGACACGGCGCTGTATTGCCCGGTTCGCTGCCGAGTTCGTCGC GCAACTGCACGCNGGCGGGCCAGCGGTGCTCGTTCANCCCGGAGGTTCCGGTGACGATGATCGTGTTGGTCTCCCT (SEQ ID NO. 324)

Clone Rv276
::::::::::::Rv276SP6.seq::::::::::::
GATGGAGAGAACAAAGACCGTCGATAGGACACGTGTTACGCCGGTAGCTGTCATTGGTATGGGGTGCCGCTGCCGGGGGGCATCTACTCACCCGATCGGTTGT GGGAGGCGTTGCTGCGGGGCGACAATCTGGTCACCGAGATCCCCGCCGACCGCTGGGACATCTACGAGTACTACGACCCCGAACCCGGCGTGCCCGGACGCAC CGACTGCAAATGGGGCGCGTACCTCGATAACGTCGGCGACTTTGATCCCGAGTTCTTCGGGATCGGGGAGAAAGAAACGATAGCGATCGATCCGCAGCACCGC TTGTTGCTGGAAACCTCCTGGGAAGCCATGGAACACGGCGGGCTAACACCGAACCATATGCCTCCCGACANGGGTTTTCGTGGGGTT (SEQ ID NO. 325)

::::::::::::Rv276T7.seq::::::::::::
CGAACTGAGCCCATAGAAAGGCAGCGACTAATTCGCTGGGCAAATAGGAAGACCCTTTGTCCTGCCACGTATATTTGTCGACCTCGTTGCGAAGGAAGCGGCT GCGATTGGTGCCCTTTTCCCTGGAGAATCTCTGCCCGGAGCAGGAAGTCTTATGAGTTGACAAGCAGGGGCGCCGCCTTCGCCGGAAATCACATTCTTGGTCT CGTGAAATGAGAGCGCTCCCAGGTCGCCGATGCTGCCGAGCGCCCGCCCACGATACGACGCCATCGCGCCTTGGGCCGCGTCTTCGACCACCGCCAGGTTGTG TABLE 3-continued End sequences of the polynucleotide inserts cloned in the named recombinant GTGCGTGGCGATCTTCATGATCGCGTCCATCTCGCAGGCCACCCGGCATAGTGAACGGGGACCATGGCCTCGGTTCGCGGGTGAA (SEQ ID NO. 326)

Clone Rv277
::::::::::::Rv277SP6.seq::::::::::::
CTTAGACGCCACCTCCGGGCCGAGCTCCACGGGGTGGATAAGTACGGCCGGATGTGGCCGCAATGGGAAGTTGTTGCCCGCTTGACTGTCCGGGTTAACGCCG

GATTCCACCACATCCCCTTGCGAAAGGCCGTTGGGTT (SEQ ID NO. 327)

::::::::::::Rv277T7.seq::::::::::::
GATCGCGATCGTCGATGTGGCCATCCGGCTTGGCGTCGACCCGCGTAAGGCAGACCAGATGGTTCGCGGCACGGTCAACCTGCCACACGCACTGGTAAGACTG CCCGCGTCGCGGTATTCGCGGTTGGTGAAAAGGCCGATGCTGCCGTTGCCGCGGGGGCTGATGCTGTCGGATCGACGATCTGATCGAGAGGATCAGGGCGGCT

GGCTGGAATTCGATGCCGCGATCGCGATACCGGATT (SEQ ID NO. 328)

Clone Rv278
::::::::::::Rv278SP6.seq::::::::::::
AGCTTACGCCGCTTTCGCTTCNGATTTGGGACGCCGCATCGAAAGCGCAGTTGGAAGCGCGGCGCCCGGCTGGTCGAGCTGCTCAAGCAGCCGCAATCCCAGC CCATGCCCGTTGAGGAGCAAGTGGTTTCGATCTTCCTGGGCACCGGCGGTCACCTGGACTCGGTGCCCGTCAAGGATGTCGGCGGTTCGAAACCGAATTACTG

GACCACATGCGGGC (SEQ ID NO. 329)

::::::::::::Rv278T7.seq::::::::::::
CGACGGGACCTCGTCGCATCTTCCATAGCCCGCCACACCTTCAGTTGCTCACCGGAATCCAACCGGTATAAGGTCGGCGAAGCGCTCGGCATTGGTCATCGGG ATATGCCGCTCGGGACGGTCAGATGCCCTCGGGTCCNGCCAGCACTCCTCAGGCTTCGTCGGGGTGGTCGCGACCGCATGGGCCACATCGCATTCACCAGGTC TGCGCGAATCACCAGCACGTANACGGTTCCTTTCCTAAGCAACACCGAAATTTCAGGACCCGAATGCTCCGGGAAAACATGTCACGGTAAGTCCGGTATTCCG

GGTACCGGTTGAGCATTGA (SEQ ID NO. 330)

Clone Rv279
::::::::::::Rv279SP6.seq::::::::::::
CGGCATCGGTTTGGGCTGTCACCAGCAGTTGGTAGTTCTTCACTACTGTTGTTCGAGCGTCGAGCCGCCGCGCGTGTCGAGGTCGCCGGACGCGTACCCGCCA GGCCGGTCAGGGTGCCCTTCCAGTCCACGCNGCTGTGGTCGGCTAACCGCTTATCTTCAATCGAGACNATCGCCAGCTTCATCGTGTTGGCGATCTTGTCCGA GGGCACCTCGAACCGGCGCTGCGANTACAGCCACGCGATCGTGTTGCCCTTCGCGTCGACCATCGTCGATACCGCAGGCACTTGCCCCTCGAGCAGCTGGGCC

GATCCGTTGGCAACGACCTCAGAGGCACGATTGGACATCAGCCCTAGCCCGCCTGCG (SEQ ID NO. 331)

::::::::::::Rv279T7.seq::::::::::::
CCGTCGANGCCGCCGACTTGGCTTGACCGACACCAACATGGCCTGAGGGTGTTCAACAAGACCGTGGCCGACGGGCTGAACATCACCATGAGCGGCATGAGCC ACGCCACCGAGTTCATCATGTTGATCGCCGAAAACCATTGGCGGGTAGCGGAAGAACGGTCGAGGTGCTCTACACCGAGTATTCGAAGTCGAAAGGCCAACCG CTGCTCAACGGCGTCAACATCATTTTCGACGGGTTTCTGCGAGGGAGGATGCCACGATGAACTGGATCCAGGTGCTGTTGATCGCGTCGATCATCGGGTTGCT GTTCTACCTGTTGCGGTCGCGCCGAAGCGCGCGGTCCGTGCCTGGGTCAAGGTGGGCTATGTCTTGTTCGTGCTCCCGGCATCTATGCCGTGCTGAGA (SEQ ID NO. 332)

Clone Rv27
::::::::::::Rv27SP6.seq::::::::::::
TTACACGNCCTGCTTCCGGCTCGTATGTTGTGTGGAATTGTGAGCGGATAACAATTTCACACAGGAAACAGCTATGACCATGATTACGCCAAGCTATTTAGGT GACACTATAGAATACTCAAGCTTTTTGAGCGTCGCGCGGGGCAGCTTCGCCGGCAATTCTACTAGCGAGAAGTCTGGCCCGATNCGGATCTGACCGAAGTCGC TGCGGTGCAGCCCACCCTCATTGGCGATGGCGCCGACNATGGCGCCTGGACCGATCTTGTGCCGCTTGCCGACGGNGACGCGGTANGTGGTCAAGTCCGGTCT ACNCTTGGGCCTTTGCGGACGGTCCCGACGCTGGTCGCGGTTGCGCCGCGGAAAGCGGCGGGTCGGTGCCATCAGGAATGCCTCACCGCCGCGGCACTGNAC

GGCCAGTGCCGCGGCGATGTCNGCCATCGGGACATCATGCTCGCGTTCATACTCCTCGACC (SEQ ID NO. 333)

::::::::::::Rv27T7.seq::::::::::::
CAGGCATGCAAGCTTTGTCACACCAAGTGTTTCGACCAGGCGCTCCATCCGGCGAGTGGATACTCCCAGCAGGTAGCAGGTCGCCACCACGCTGGTCAGTGCG CGTTCAGCTCGCTTGCGGCGCTGCAGCAGCCAGTCCGGGAAATAGCTGCCCTGGCGCAGCTTGGGGATCGCGACGTCGATGGTTGCGGCACGGGTGTCGAAAT CACGGTGGCGGTAGCCGTTGCGCTGATTGGACCGCTCATCGCTGCGTTCGCGGTAGCCCGCCCCGCACAGGGCGTCGGCTTCAGCCCCCATCAAGGCGG (SEQ ID NO. 334)

Clone Rv280
::::::::::::Rv280SP6.seq::::::::::::
AGCTTAGCCAGTTTTTCTACTCTTGGGCCCACACCCACAGTGCTTCGACGGTACGGTCACCCATGATGGCCATCCAGTTGGCATCGGTGAGCTGATAAATGCC TABLE 3-continued End sequences of the polynucleotide inserts cloned in the named recombinant AGCTGGTTTCGCCAACCCGGTAGCGATCTTGGCGCGCTGCTTGTTGTCACTGATACCTATCGAGCAAGACAGCCCGGTTTGCGACAAGATGACTTTTCGGATC TCTTCGGCGACTTCGATGGGGTCGTCGGGAGTCCCGGGCGCCACCGCGAGGTAAGCCTCGTCCCAGCCCCATACCTCGACCGGGTATCCCAGGTCGCGCAATA ACGCCACCACCTCCTCGGACGCCGCGTTGTAGGCGGCTGGGTTCGACGGCAAGAAGTGGCCTCAGGGCATCGTCGGCGCGGTCCCAACGGCNTGCCGGCGCGC

ACACCGTAGGCGCGGGGCTC (SEQ ID NO. 335)

::::::::::::Rv280T7.seq::::::::::::
CCGGCGGAACTCAGACGTGCTGGTGGTGCGGCATGGCACCGCGGGCAGCAAAGCGCACTTCTCCGGGGACGACAGCAAGCGACCGCTAGACAAGAGGGGTCGT GCGCAGGCAGAAGCGTTGGTACCACAGCTGCTGGCGTTCGGCGCCACCGATGTTTATGCCGCCGACCGGGTGCGCTGCCACCAGACGATGGAGCCACTCGCCG CGGAACTGAACGTGACCATACACAACGAGCCCACCCTGACCGAAGAGTCCTACGCCAACAACCCCAAACGCGGCCGACACCGAGTGCTGCAGATCGTCGAGCA AGTAGGCACACCCGTGATCTGCACGCAGGGCAAGGTCATTCCCGATCTGATCACGTGGTGGTGCGAGCGCGACCGTGTGCCCCCGACAGTCCCGCAATCGCAA

AGGCAGCACGTTGGTGT (SEQ ID NO. 336)

Clone Rv281
::::::::::::Rv281SP6.seq::::::::::::
GTATGGTCAGCTGTCCATCCGGCGCTGTCGGCCGAGCTGCCAGATCTCGTCAGCCGTAACCGGGTTGCGGGATCCACGCGTGCGGGTTGTCTAC (SEQ ID NO. 337)

::::::::::::Rv281T7.seq::::::::::::
CCGACTTTCCGCGGGTACCCGCTCAACTTTGTGTCNACCTCAACGCCATTGCCGGCACCTACTACGTGCACTCCAACTACTTCATCCTGACGCCGGAACAAAT TGACGCAGCGGTTCCGCTGACCAATACGGTCGGTCCCACGATGACCCAGTACTACATCATTCGCACGGAGAACCTGCCGCTGCTAGAGCCACTGCGATCGGTG CCGATCGTGGGGAACCCACTGGCGAACCTGGTTCAACCAAACTTGAAGGTGATTGTTAACCTGGGCTACGCGACCCGGCCTATGGTTATTCGACCTCGCCGCC

CAATGTTGCGACTCCGTTCGGTTGTTCCAGAANGTCAGCCCG (SEQ ID NO. 338)

Clone Rv282
::::::::::::Rv282SP6.seq::::::::::::
GCACCGATGTCGGCGAGCACTTCGTCAACTTCCAGGGGTGCCCGCACCAAGTATTTCGACGAGTATTTCCGTCGGGCCGCCGCCGCCGGTGCGCGGCAGGTGG

TCATCCTGGCGGCGGGGCTGGGACTCGCGCGCGTACCGGCTGCCTCGGC (SEQ ID NO. 339)

::::::::::::Rv282T7.seq::::::::::::
TGCACCCAACTTACTGAGCATGCTAACGCTGGTCGTGCGGGTCTTGTTCCCGCGTGTCGGCAGGGCACACGCTCGGGGCGTAGCTGGGAGAGGCCCCGGTCAA GCCCGGAGAGCAGTGCTCAGTCCGCCAGCTTGACCGACTTTCGATGAGAACGCGCTTCTCGCCGTATTGAACTGGCGTGCTGACGGTCGCTGAGCAGCGCTCG

CCGAGTGCGGCCGCTGATTCTTTCATCGAGCCAGGACGCGCATTCGTGTTCGGCCGC (SEQ ID NO. 340)

Clone Rv283
::::::::::::Rv283SP6.seq::::::::::::
AGCTTACGGCCGGTCGACGCGACGAGTGGTTCATGACACCACAAACCGTCAACGCCTACTACAACCCGGGGATGAACGAAATCGTCTTCCCGCAGCGATTTTA CAGCCACCATTTTTCGATCCGCAGGCCGACGAGGCCGCCAACTACGGCGGGATCGGGGCGCGTGATCGGGCACGATGATCGGGCACGGTTTCGACGATAGGGC

GCCAAATACGANGGCGACGCAATCTGGTCNATTGGTGGATCGA (SEQ ID NO. 341)

::::::::::::Rv283T7.seq::::::::::::
ATGTCGTCACGTCACCACAATCGCGAGGACCCAATCATGCCGCCCAGGGCGGCCAACCCAATGGTGGCCGCGAAGCGGCAGCTCGATCGCAGCGCGGAGGTGC CGGCCGCCAGTTGATTCACGAACAGGGTGAGGTCATAGGCGGGCAGGATAGTGACGAACGCAAGACCTATATCTGCCGTCGGAGTAAGAATCGAGTAGCCGGT

CGACCAACGGAAGCGAAAGTGTCCGCGATGTTGATGAGCGTCGCCGGTTGTGGCGGCGGTGGC (SEQ ID NO. 342)

Clone Rv284
::::::::::::Rv284SP6.seq::::::::::::
AGCTTCACCAGCGTGCCGATGCTGTTCGCNACACCTCCCTACTATGCGCAATTCGCCGACACGGGTGGCATCAACACGGGCGATAAGGTGGACATCGCTGGGG TGAACGTCGGGCTGGTGCGCTCGCTGGCAATCCGCGGCAACCGCGTGTTGATCGGATTCTCGTTGCCCGGCAAGACAATCGGGATGCAAAGCCGGGCAGCAAT TCGCACCGACACCATTCTTGGCCGTAAGAACCTGGAAATCGAACCCCGCGGTTCGGAGCCGTTGAAACCCAACGGTTTCCTGCCGTTGGCGCAGAACACTACG

CCATACCAAATCTATGACGCGTTCGTC (SEQ ID NO. 343)

::::::::::::Rv284T7.seq::::::::::::
CTGCCGCGGTGGCGGTCAGCGCCTGGCAAGTCACCGCACCGCCGTCCGGTTCATCGGCAGGCTCCCCCGAAAAGGGCCCTGGCAACAGAAGGTGATCAATGAG CTCCCGCAGACCTTCGCCGATCTGGGACCGACATACGTGAAGTTCGGCCAGATCATCGCGTCCAGCCCGGGAGCATTCGGTGAGTCGCTGTCGCGGGGAATTC TABLE 3-continued End sequences of the polynucleotide inserts cloned in the named recombinant CGCGGCCTGCTCGACCGGGTGCCGCCCGCAAAAACCGACGAGGTGCACAAGCTCTTCGTCGAGGAACTCGGCGACGAGCCGGCCCGGCTGTTCGCCTCCTTCG AGGAAGAACCGTTCGCGTCTGCGTCCATCGCCCAAGTGCACTACGCGACCTGCGCAGCGGCGAAGAAGTGTGGTCAAGATCCACGGCCGGGCATCCGCCGCCG

CGTTT (SEQ ID NO. 344)

Clone Rv285
::::::::::::Rv285SP6.seq::::::::::::
GATCGTGCCGGCCCCCCGGCGGCAGTAGCAGATCAGCTCGTCGAAATCGCGGCAACCAGTCCAGTCGATTTCCATACGGGCGCCGTCAATCAACTCTGCGAAC ATCGCGATCGGCACCGGAAACCGGCGAGCCGCGTCAGCCAGCGCAACCAGCACCGGGATCGGATGAATCATCAATATTATCAAGTGATTTCCTGATGGCATCG AGCTCGGTGATCTTGGTCTCGGGGGCCAGCTCGCCGTCGGCGACGTCGTCGATCCGGCGGCGAGCGCATATGACCGCAAATAGTGCCGCTCGCTTTTCGCGCG GCAAGAGTCGGATGCCGTAATATANGTTTCTGGCGGCCGTGCGCGTGATCNACTCGGTGATTCGATACGCCTGTTCATCTCGGTCATGCCGTCCTC (SEQ ID NO. 345)

::::::::::::Rv285T7.seq::::::::::::
GGTGGCGCAATGACCGAAACCACCCCAGCCCCGCAAACCCCGGCGGCCCCGGCCGGGCCCGCACAATCGTTCGTGTTGGAGCGGCCCATCCAGACCGTTGGGC GCCGTAAGGAGGCCGTGGTACGAGTGCGGCTGGTGCCCGGCACCGGCAAGTTCGACCTCAACGGCCGCAGCTTGGAGGACTACTTCCCAAACAAGGTGCACCA GCAGTTGATCAAGGCACCCCTGGTCACCGTGGATCGGGTGGAAAGTTTCGACATCTTTGCCCACCTGGGCGGCGGCGGCCCGTCGGGTCATGGCCGGCGCGCT GCGCCTGGGTATCGCCCGGGCATTGATTCTNGTATCGCCGGATGACCGGCCCGCGCTGAATAANGCCGGCTTCTTGACCGTGATCCACGCGCCACCGAACGCA

AA (SEQ ID NO. 346)

Clone Rv286
::::::::::::Rv286SP6.seq::::::::::::
CACAATAGATTACTCAAGCTTCGAACCAGCGGCCTTATCACGTATCCCCGCTGAGACCTTGACCCTTAGGGCCGAAGTGACTTCGCTGCTGCTATGCCGACAC CCGATTTCCAGACGCTGCTGTTACACGACGGCCGGGCCGGTGGCCACCATCACGCTCAACCGCCCGGAACAGCTCAACACCATCGTCCCGCCCATGCCCGACG AGATCGAGGCCGCTATCGGGTTGGCCGAGCGCGACCAGGACATCAAGGTCATCGTGCTGCGCGGTGCCGGCCGCGCCTTCTCCGGCGGTTACAACTTCGGCGG

CGGGTTCCAACATTGGGGGCAT (SEQ ID NO. 347)

::::::::::::Rv286T7.seq::::::::::::
TCAGGACGCTTATGGTTGGCAGATGGTCGCCCTGGCGTCGAATACGCGCGAGCGCATGAGCTCACCGGTTCGGAACAACGTATCGAAGAACGTCGCACTGCTG GCAGATGGTATCTCCGATGTGGTTGTAATTTGTATCCCAACTCTAACTGTGCTATCGGATCAGCGTGAATATCGAGATATTGCGAATGCGATGACAGGCCGCC ATTCGGTTTATTCGCTTACGCTTCCCGGGTTCGATTCGTCTGATGCACTGCCGCAAAACGCGGATATGATTGTTGAAACCGTATCTAACGCAATTATTGATGT GGTAGGCGGCAGCTGCCGTTTTGTGCTGTCGGGCTATTCATCGGGTGGGGGTGTTTGGCTATGCCCTCTGCTCCCAT (SEQ ID NO. 348)

Clone Rv287
::::::::::::Rv287SP6.seq::::::::::::
CGCAGCTGTCGCCGATCTGGTCCGGAATACCTAGCTCCAGGTTCTGAGTGGAGATGAGTGCGGCCATCGAAGTGTTGTCAATGTACTCCAGGATGTCAGGTGC CAGGCCGCTGGCGAGGATCTTGGGCACCGCCGCCATGACTTGGTCGAAGTCGGCGAACGGGGCGAGCACGCTGGCGTCGTGGTC (SEQ ID NO. 349)

::::::::::::Rv287T7.seq::::::::::::
GTAGTTCGTTCATCCAAACACAGTGCGGTACCGGCTCAAGCGGATCACCGACTTCACCGGGCGCGATCCCACCCAGCCACGCGATGCCTATGTCCTTCGGGTG GCGGCCACCGTGGGTCAACTCAACTATCCGACGCCGCACTGAAGCATCGACAGCAATGCCGTGTCATAGATTCCCTCGCCGGTCAGAGGGGGTCCAGCAGGGG

CCCCGGAAAAGATACCAGGGGCGCCGTCGGACCGA (SEQ ID NO. 350)

Clone Rv288
::::::::::::Rv288SP6.seq::::::::::::
TCCGCTCGCTTCTCCGAGAGGTTGAGTGCCAACGCTCTGCCGATGCCCGAAGCCGGCCCCGGTGATGACGGCGACCTTGCCTTCGAATGAGCTCATTTGACTA CTCCCCGTGGTTGTCCCTGCGATTGGTGGAGGTGGCCGCGCAGCCTTGCCCCGAGGTCGGCGATCGCGTCTCGGGCTTCGGGGAGCAGACTGACCTGCAGATG GAAGTCGTGCCACATGCCCGCGAACCGGCGATGCTCGATGCTTGTTTTCGAAGCGGCGCAGGCGGTTTCGATCTTGTCCGCGTCAACACNGATCGGATCGTCG

CCCGCGGTCTGCATGACGAATGGGCG (SEQ ID NO. 351)

::::::::::::Rv288T7.seq::::::::::::
ATGGGAGGCCACCGATTACCATCTTGCACACACCGATTCCGGGCTATTGATGTCCACGTTCGGTCCGCGAACCGCGCTGTGGCTGCTGCTGGCCAAAGGCGGA GGCGATACCGAAGTCAGTGCCCAAGCTTGGGTTCCACGCTCGCGCAGCCACGCCGTCACCTTTCCACGAGACCTCACCTGCCGATCCGAAATGGAATCGGCCG TABLE 3-continued End sequences of the polynucleotide inserts cloned in the named recombinant TGACGGAATTGGCGCAGCGAACACTCAACGAGGTGGTGGCTTCGTCGCGAACCGTCACCCGAGTCGCGGTCACCGTGCGCACGGCGACGTTCTACACCCGCAC CAAGATCCGAAAGCTGCAAGCTCCCAGCACCGATCCCGACGTCATCACCGCTGCCGCCCGGCACGTTCTTGAACCTATTCGAGCTGGAATCGGCCGTCCGGTT

GCTGGGAATTGCNGTTAAGAACTGGGCCT (SEQ ID NO. 352)

Clone Rv289
::::::::::::Rv289SP6.seq::::::::::::
GCTTTGCGCGCTTCTCCGAGAGGTTGGAGTGCCAACGCTCTGCCGATGCCCGAGCCGGCCCCGGTGATGACGGCGACCTTGCCTTCGAATGAGCTCATTTGAC TACTCCCCGTGGTTGTCCCTGCGATTGGTGGAGGTGGCCGCGCAGCCTTGCCCCGAGGTCGGCGATCGCGTCGCGGGCTTCGGGGAGCAAACTGACCTGCAGA TGGAAGTCGTGCCACATGCCCGCGAACCGGCGATGCTCGATGCTTGTTTTCGAAGCGGCGCAGGCGGTTCGATCTTGTCCGCGTCAACGCAGATCGGATCGTC

GCCCGCGGGTCTGCATGAAGAAT (SEQ ID NO. 353)

::::::::::::Rv289T7.seq::::::::::::
CTCACGCAGCCACGCCGTCACCTTTCCACGAAGACCTCACCTGCCGATCCGAAATGGAATCGGCCGTGACGGAAATTGGCGCAGCGAAACACTCAACGAGGTG GTGGCTTCGTCGCGAACCGTCACCCGAGTCGCGGTCACCGTGCGCACGGCGACGTTCTACACCCGCACCAACATCCGAAAGCTGCAAGCTCCCAGCACCGATC CCGACGTCATCACCGCTGCCGCCCGGCACGTTCTTGACCTATTCGAGCTGGATCGGCCCGTCCGGTTGCTGGGAGTGCGGTTAGAAACTGGCCTAGAAACCGG

CGGGCACACCGCACCTGGGCGGGGN (SEQ ID NO. 354)

Clone Rv28
::::::::::::Rv28SP6.seq::::::::::::
TGCTTCCGGCTCGTATGTTGTGTGGAATTGTGAGCGGATAACAATTTCACACAGGAAACAGCTATGACCATGATTACGCCAAGCTATTTAGGTGACACTATAG AATACTCAAGCTTGATGCCGCCGAAACCGAGCGTGAGCACGCCGCCAGCCACCACNCGCGGGTCGGCGCCGGGCCCGGGTCGCCANGCTGCTCCGCTCGGTG ATGGCACGCCACCGCGACACCACCCGGCTGCGCTACGTCGAGCCATACCGGGCGGAGCTACATCGGCTCGGCCGCCCAGTGTTCGGGCCCTCTTTCGAAGTCG

AAGTCGATACCGATTGCGCATCCGCNGCCGCA (SEQ ID NO. 355)

::::::::::::Rv28T7.seq::::::::::::
CAGGCATGCAAGCTTCACGTCCGTACGGCTCGGGTACGCTTCGGTCGCAGTGTGCGAGTGATAGATGACGACCGGGACCTCGTCTGCATCTTCCATAGCCCGC CACACCTTCAGTTGCTCACCGGAATCCAACCGGTAGAAGGTCGGCGAGCGCTCGGCATTGGTCATCGGGATATGCCGCTCGGGACGGTCAGAACCCTCGGGTC

CGGCCAGCACTCCGCAGGCTTCGTCGGGGTGGTCGCGACGCGCATGGGCCACC (SEQ ID NO. 356)

Clone Rv290
::::::::::::Rv290SP6.seq::::::::::::
GCTTGTCTATCGTCCCGGCCAGGTCCGGCCAGTCAAGGTCGAAGGCCAGTCCGGTCTCCTCTCCGACTACGGCCAAGAACTGGGCGACGGTGTCAGTGCAGAC CAGCGGAAACTGGTGGCGCCCTAGGCGAGCGACCGCCTCACAAACGGCGGTGACCGCGTTCTGGTCGTGCACCATCGAGCCGTGCCCAGCCCGGCCGCGTGCC GTCAGCCGCATCCACTGGATGCCCTTCTCGGCGGTTTCAATCAGGTACAGGCGACGTTCGCCACCATCGTGCCGGGGCACGGTTAGCGAGAAACCGCCGACTT

CACGATTGCCTCGGTGATGCCGTCGAAACAGATCGGGCCT (SEQ ID NO. 357)

::::::::::::Rv290T7.seq::::::::::::
GCGCGCCATGTTGAGGTTGTCCGACGGTGACGACGGTGAACCACAACTGTTTGACCTGTCCGCACACACCGTGTGGATCGGCGAGCGGACCCGACAAATCGAT GGCGCGCACATCGCGTTTGCCCAGGTGATTGCTAATCCGGTCGGGGTCAAGTTGGGCCCCAACATGACCCCGGAACTGGCCGTGGAGTACGTCGAGCGGCTCG ACCCGCACAATAAGCCGGGCCGGCTGACTTGGTGAGCAGGATGGGCAACCACAAGGTCCGCGATCTGTTGCCACCGATCGTGGAGAACGTCCATGCCACCGGG

CATCAGGTCATCTGGC (SEQ ID NO. 358)

Clone Rv291
::::::::::::Rv291SP6.seq::::::::::::
TTGCCTTCCATGCCGAGCAAGGTCGACTCAGCGATGACGAATTGTTCTTCTTCGCGGGTGTTGCTGCTGGTTGCGGGCTATGAGAGCACTGCTCATATGATTA GCACATTGTTTCTGACGCTGGCCGACTATCCAGATCAGCTGACACTCCTTGCGCAGCAACCAGACCTGATCCCGCCGGCGATCGAGGA (SEQ ID NO. 359)

::::::::::::Rv291T7.seq::::::::::::
CGACGCTGGGCCCAACTGCGACCACCAGGTCCTGGTATGGCAGGACATGGCCGGGTTCAGCGGCGCCAATACCG (SEQ ID NO. 360)

Clone Rv292
::::::::::::Rv292SP6.seq::::::::::::
TAACGACTCGGGTCCAGCGACCGCGCCAACACNAACGGCCGGACNACGTGGGCCAGGGTCGCGGCCTCCCCTACAAACAGGATCCGTTGCCTGCGAACGACAG GCTCCGGTGCGGCGTTGGGCGCCGTGCTCGTCCCAGCGTCCGGTCCCGGGTCGCCGGCGACGCTTGTTTCCTCCATACTCGCCCCCTAATCTCGAGGCAGCCC TABLE 3-continued End sequences of the polynucleotide inserts cloned in the named recombinant GTACCCGCAGGCAACCTCCCAAAAATGCAATCCCCCAAAATGCAATGCGTCNAGCTATTTCTCACACCGACCGCTAGTTGCGGATCANAAATCCGTTGGGCGC

GGA (SEQ ID NO. 361)

::::::::::::Rv292T7.seq::::::::::::
CNTGGCGGTGGGTGCGGTGTCGAACACGACCACACTTCTTTGCGGTTCGGTGATCTCGACACCGGCCGCGAGCCGACCACCATGCGCGCGTAGATCGGCGATC AGCGCGTCGGCTATCGCCTGGGTGCCGCCCACCGGAATCGGCCAGCCGACCGAATGGGCCAGCGTTGCCATCATCAGTCCGGCGCCGGCCGACACCAGTGACG GCAACGGTGAAATCNCGTGGGCGGCAACGCCGGTGAACAACGCGCGGGCATCCTCGCCCGCCAGCGACCGCCAGGCAGGGGTGCCCTGGGCCAGCATCCGCAG

CCCGAGACNCAGGACCGANCCCAGTG (SEQ ID NO. 362)

Clone Rv293
:::::::::::::Rv293SP6.seq:::::::::::::
GCTTTTCNGATCGCAGCGAGTCGTACCCGCGCCGGTCACCTTCGTGGATATCGCCGGCCTGGTCAAGGGGGCGTCCGAGGGAGCCGGGCTGGGTAACAAGTTC CTGGCTCATATCCGCGAATGCNACGCCATTTGTCAGGTGGTGCGGGTGTTCGTCAACAACNACTTGACTCATGTCACCGGACGGGTCGATCCCCANTCCGACA TTGAGGTCGTCGANACCGAGCTGATCCTGGCANATCTGCAAACCCTGGAGCGGGCCACGGGCCGGCTGGAGAAGGAANCGCGCACCAACAAGGCGCGCAAGCC GGTCTACGACGCGGCACTGCGTGCCCAGCAGGTGCTCGACGCCGGCAANACGCTGTTCGCCGCGGGGGTGGATGCCG (SEQ ID NO. 363)

:::::::::::::Rv293T7.seq::::::::::::
GTCGTACGCCATTNGTCGGTGTGCGCATACCAGTACGACGCGCCGGGCACCTGACGCGGCGGCCGCGACCAGTCGGTGGCCATCGCCATCGTCTGCCACCCGG TCAACGGACGCACCTTCTCCTGGCCGACGTAGTGCGCCCACCCGCCGCCGTTGCGTCCCATCNATCCGGTCAACATGAGCAGCGCCAACACCGAGCGGTACAT GACATCGCTGTGGAACCAGTGACAGATTCCGCCGCCCATGATGATCATCGACCGTCCTCCGGATTCGGTCGCGTTGCGGGCGAAATTCCTTGGCAAACCGGAT TGCCTGCGCGGCCGGCACACCGGTGATCGACTCCTGCCAGGCCGGGGTGTTCTGCTGGGTTCGGTCGTGGTACCGGT (SEQ ID NO. 364)

Clone Rv294
::::::::::::Rv294SP6.seq::::::::::::
GCGAGGCGGTATCGCTTCCCGTCGTACCGGCGACCGCCAGCCGAGAAGCTCGTTTTCCCAGTGTTGCTGGGGATTCTCACGCTGCTGCTGANTGCGTGCCANA CCGCTTCCGCTTCGGGTTACAACGAGCCGCGGGGCTACGATCGTGCGACGCTGAANTTGGTGTTCTCCATGGACTTGGGGATGTGCCTGAACCGGTTCACCTA CNACTCCAAGCTGGCGCCGTCTCGTCCGCAGGTCGTTGCTTGCGATAGCCGGGAGGCCCGGATCCGCAATGACGGATTCCATGCCAACGCTCCGAGTTGCATG

CGGATCGAATACNAATTGATCACCCA (SEQ ID NO. 365)

:::::::::::::Rv294T7.seq::::::::::::
TGGGTCTTGCCGGCGAGCCCAGCGAAGTCGCTAGCGTGGCCGTGTTTCTTGGCTTCGGATCTATCCTCGTTACATGACCGGCACCGTGTTGGACGTGACTGGC GGCCGGTTCATATGACACCGAGATCATTGCCACGGTACGGCAATTCGTCAAGAAGGAAATCTTTCCCNATGCACCGGCCCTCGAACGTGGCAACAGCTACCCG CAAGAAATCGTCGATCGGCTGGGTGTTATTGGCTTGCTCGGTCGCCGGCTGCAAGGGTATCGACACCACCGAGTTCATTCTCGGGCGTGCCGGCGCATTCGAG CTGGCGGTGCGCGCTGCCCAGCACCGTCATAAGTACTTGANGATGGTCAAACGTCGGACGAACCGCCACCACGTCGCTGCCGAACGG (SEQ ID NO. 366)

Clone Rv295
::::::::::::Rv295SP6.seq::::::::::::
TAGATGCCCAAGCTTGCCNTTANAGACCTCGTCGACCAAGCACGGACGCGACCGTCGAAGGTGGCGAATCCGGGCTTGGCGTCNACCCGCGTAAGGCAGACCA GATGGTTCGCGGCACGGTCAACCTGCCACACGGCACTGGTAAGACTGCCCGCGTCGCGGTATTCGCGGTTGGTGAAAAGGCCGATGCTGCCGTTGCCGCGGGG

GCGGATGTTGTCGGGAGTGACGATCTGATCGAGAGGATTCAGGGCGGCTGGCTGGA (SEQ ID NO. 367)

:::::::::::::Rv295T7.seq::::::::::::
TCTCCACGGCGTGGATCAAGGTACCGGCCGGGATGTTGCGCAATGGCAGGTTGTTGCCCGGCTTGATGTCTGCGTTAGCGCCGGATTCCACCACATCCCCTTG CGAAAAGTCCGTTGGGTGCAATGATGTAGCGCTTCTCCCCATCGAGATAGTGGAGCAACGCAATCCGTGCGGTACGGTTCGGGTCGTACTCGATGTGCGCGAC CTTGGCGTTGACACCATCTTTGTCATTGCGGCGAAAGTCGATCATCCGGTAAGCGCGCTTATGACCGCCGCCTTTGTGCCGGGTNGGTAATCCGGCC (SEQ ID NO. 368)

Clone Rv296
::::::::::::Rv296SP6.seq::::::::::::
GCCCGGTTCGATCGGGCATGTCCGCAGTCGTCGTTACCGGAGGCGGTCGTGGCCGCGCTAATCGGCGTCGGCGCCGACAAGATGTGGGATATCCGCAATCGGG GCGTCATCCCTGCGGGCGCGCTCCCCCGCGTCCGAGCCTTCGTCGACGCAATCGAGGCAAGTCACGACGCGGATGAGGGGCAGCAGTGAATTACAGCGAGGTC TABLE 3-continued End sequences of the polynucleotide inserts cloned in the named recombinant GAGCTGTTGAGTCGCGCTCATCAACTGTTCGCCGGAAACAGTCGGCGACCGGGGTTGGATGCGGGCACCACACCCTACGGGGGATCTGCTGTCTCGGGCTGCC

GACCTGAATGTNGGTGCGGGCANCGCCGGTATCNACTCCCGTGGAACACAGCCGGGGC (SEQ ID NO. 369)

:::::::::::::Rv296T7.seq::::::::::::
CTCGGCGTGGATATCGGTGTAGCCGGCGCCGGTGAANGTCGGCTCCTTACGTCCACTCGACAACAGCTCATAGCGATCCAACCAGTANGCAACCGCCTTCAGC AGTACAACCGCGCCGGCGAACACTGCGAGTTGAACGCGAGCTGCCTGGGTCAGCATGCCTCTGCCGGTTGTCAGCCGAAGGCCGCCGAACAGGTAATGCGTCA ACAGGCTCGCTAGAAACGCCAGAACCACGGCCACGAACAGCCAGTTCAGCACCGACCGGTAGAACGGCAGATCGAAGACGAAAAAACCCAATGTCATAGCCGA

ATTCGGGGTCCACGATGCCAAAGGTGCCCCCGTGTACAACAACTGAACCTTCACCCA (SEQ ID NO. 370)

Clone Rv29
:::::::::::::Rv29SP6.seq::::::::::::
TCCGGCTCGTATGTTGTGTGGAATTGTGAGCGGATAACAATTTCACACAGGAAACAGCTATGACCATGATTACGCCAAGCTATTTAGGTGACACTATAGAATA CTCAAGCTTCACGTCCGTACGGCTCGGGTACGCTTCGGTCGCAGTGTGCGAGTGATAGATGACGACCGGGACCTCGTCGGCATCTTCCATAGCCCGCCACACC TTCAGTTGCTCACCGGAATCCAACCGGTAGAAGGTCGGCGAGCGCTCGGCATTGGTCATCGGGATATGCCGCTCGGGACGGTCAGAGCCCTCGGGTCCGGCCA GCACTCCGCAGGCTTCGTCGGGGTGGTCGCGACGCGCATGGGCCACCATCGCATTCACCAGGTCTGCGCGAATCACCAGCACGTAGACGGTTCCTTTCCTAAG

CAACACCGAAGTTTCAGGACCGAATGCTCCGGGAAACATGTCA (SEQ ID NO. 371)

:::::::::::::Rv29T7.seq::::::::::::
CAGGCATGCAAGCTTGATGCCGCCGAAACCGAGCGTGAGCACGCCGCCAGCCACCACGCCCGGGTCGGGCGCCGGGCCCGGGCCGCCAGGCTGCTCCGCTCGG TGATGGCACGCCACCGCGACACCACCCGGCTGCGCTACGTCGAGCCATACCGGGCGGAGCTCCATCCGCTCGGCCGCCAGTGTCCGGGCCCTC (SEQ ID NO. 372)

Clone Rv2
:::::::::::::Rv2SP6.seq::::::::::::
CCTGCATCCGGCTCGTATGTTGTGTGGAATTGTGANCGGATAACAATTTCACACAGGAAACAGCTATGACCATGATTACGCCAAGCTATTTAGGTGACACTAT AGAATACTCAAGCTTCCAATCCCCCTGCCCTGATACGCGTCGGCAACCGTGAACGCGATCTCGGCGACCGTCGGATCGGTTTCATCCCGCACAAAACGCGCGT CGGCTACGGGGTCGCTTCCGTCGGTCACCACCCAGACGAAGTGGTCGACGTAGTCGACTTCCGACAGGTAGTGCATCAACGCCGGACTGGGAACACNAGCCGA CATGAACCGTCGATACAGCGTCTCNCCGGAGAACTGGATGTGTCCGTGCACGGTCCGCTCGCGGTCACCGGGCAGCACGGGGCGTAACATCAGTTGAGTCCCG

TCGGCAAGCCGTACCGGAATCGGGGAGACGA (SEQ ID NO. 373)

:::::::::::::Rv2T7.seq::::::::::::
CAAGATGATCGCCGGTGCCACCCCGATCCGTGCCTCGGTCAGCGCGAACGTGCTTTCCGGTCCGGCGACCACCATGTCGCACGCACCGACCAGGCCGAACCCG CCGGCCCGCACATGCCCGTTGATGGCGCCGACCACCGGCAGCGGCGACTCGACGATGGCGCGCAACAGCGCCGTCATTTCCCGCGCCCGCGCCACCGCCATCC GGTACGGATCACCACCACCACCGCCGGCCTCGCTGAGGTCCGCGCCGGCGCAGAACGTTCCGCCGGTATGCCCCAGCACGACCAGCCGCACCGCCGGATCTGC TTCGGCCGCACTCAGCCCTTGATGTAGTTGGCTGACCAGCGTGCTCGACAGCGCGTTGCGGTTGTGCGGAGAGTTCAGTGTCAGCCTGGCGAAGGGGCCGCCG

CAGGCGGCCGGGCCAGCGTAGTCGACGGGGCTG (SEQ ID NO. 374)

Clone Rv301
:::::::::::::Rv301SP6.seq::::::::::::
CTCAAGCTTCGATCGACAGTACTCCCGCCTTGGGTCTGGTCTTCGAGCTGGTCGGTCATGGTCGGACCTGCTGGTAGTGGGGATCTAACGCAACATGGTCGGG ATTCATCATGGTGTACCCGTGATACCCATTCGCAGCTGCCGGTGAAACCCCGCGATGCCGGGATTTCCAGCCGCACTAGGATGTCTAGCCGGCCAGCCGCTGC CGCCGGACTTCGGGATGTTCGGTATACCACCGATCGGCAATCTTGCNTATCCGCCGATGCTCGAACGCTAGCCACCCCAAACCAACCACTGTGACNACAATC (SEQ ID NO. 375)

:::::::::::::Rv301T7.seq::::::::::::
TGAATTTCCCGATCCCACAATCTCGGTTCAGATACAGGTCGCCATACCCCTTACTTCGGCAACGCTGGGCGGATTGGCCCTGCCGCTGCAGCAGACCATCGAC GCCATCGAATTGCCGGCAATCTCGTTCAGCCAATCCATACCCATCGACATTCCGCCGATCGACATCCCGGCCTCCACTATCAACGGAATTTCGATGTCGGAGG

TCGTGCCGATCGATGTGTCCGTCGACATTCCGG (SEQ ID NO. 376)

Clone Rv302
:::::::::::::Rv302SP6.seq::::::::::::
TACTCAAGCTTGAACGCTGCGAGCGAGCCCATGTAGAGCGTTTGGTACCAAACCGATCGGTGGGCCAACTTGCCATGGGCTCACAGCGGCTATCGCGAGCGTG TAGCCGATCATCGGCCAGGCGACGGTGGCCTGAGCGGCAGGGGTTGCCTTATCCATCCTCTTGCGGCATGGTTGCCGCAGGGAGTGCCGGTAGGTCTGGTCGG TABLE 3-continued End sequences of the polynucleotide inserts cloned in the named recombinant CAACCTGGCCCGCTGCGGGTTGGGTTCGGATTCCCTCGGCTAGTAAGGTGCTCGCCTGGTGTTACAACGAATCGCTAGACAGCTCTTATCGGGAGTGGCCGTC GCGATCGTTGCGCTGCCGCTGGCGATCGCGTTCGGCNTTACCGCCACCGGAACGTCCCAAGGTGCGCTCATCGGGCTCTACGGCGCCATCTTCGCCGGATTCT

TCCCNGCCGTGTTCGGTGG (SEQ ID NO. 377)

::::::::::::Rv302T7.seq::::::::::::
GCGGTGTCTGAACTTCGCCCGTTCCCTCCAGCGCATTGAGCTTCAGCCCGACCGGCAGGTAGGGAGTCGGCATGCGGTCCTTCGCCCCGACCCCGCTGGCTAA ATAGCCACCCCCGAGCGCGGTCACGGTCTTTGCACCGGGACGACGGCATACCGGCAGCGCGAACATCGCCGCGGGCTGCAGCGTGAACGTCGAATACGAGTCG AACAGTGTCGGCGCGTAAAAACCCGAGCCGGCGGTCGCTTCGGTAATCAACGGCTCCTGCGCAACCAGCTGCAANTCNCCGGTGCCACCGGCGTTGACAATCT

TGATNTCGGCGACCTCGCGCACCAN (SEQ ID NO. 378)

Clone Rv303
::::::::::::Rv303SP6.seq::::::::::::
TACTCAGCTTCGGCTCAGGTGGTGCTGCTGGTAAAGTTCNCTGAACGGTGCAGGTTTCGACAATGTGGTGCCGGTTCGGCGGGTACTGCCATCGAGACACTGG CGCAGGCTATCGCACCCGTTATCGGCTACAAACAAATCGCGGTATGCGTTCTTGAGCATGAGTCGGCGACCGTCGTCATGGTCGACACCCACGACGGAAAGAC GCAGATCGCCGTCAAGCNTGTGTGCCGCGGATTATCAGGACTGACCTCCTGGCTGACCGGCNTGTTTGGTCNCGATGCCTGGCGCCCGGCCGGCGT (SEQ ID NO. 379)

::::::::::::Rv303T7.seq::::::::::::
CATCACCTGGTTCATGAAACTGGAAGCAGCGCAGCGCTTCCTTTTCGGCCGCAACATGAGCCAGCCTCTCGTCGGCGGTCGGGTGCAGGTGCTCGGGCAGCTC GGCCGCGACAGCCGCCTGACCCTGAAACCAGCTTCCATATCCCGCGACGAACGACGCCAGTCCGCTACGTAACCCCTCCGCGACTGTCCATGGACAACANCGC

GTTCTCCACCGACCGGGCCCGGGTGTGGGGTGTT (SEQ ID NO. 380)

Clone Rv304
::::::::::::Rv304SP6.seq::::::::::::
CTCAAGCTTCCCGGCGGCCAGTACCGAAAGCGCGAACAGCTCGCGGCAGCCCACAACNTGCTGCGTCGGATTGCCGGCGGCGANATCAATTCCAGGCAGCTCC CGGACATTGCGGCTCTGCTGGCCCGCAACGAAGGACTCGAGGTCACCCCGGTGCCCGGGGTCGTGGTGCACCTGCCGATCGCACAGGTTGGCCCACAACCGGC CGCTTGATGCCCGGTCGGCAAGCCCGGCAGTTGCCAAACCCAGCGTGATCAGGCTCGGCTCGCGAGTTCGGCGAAGAAGTGGCTCGCCTGATCACCTACCATC

GGCCAGGATCTGCGTGTCATCACNACGCTCGCCAAGGAGGTTGTTGTGGTGCT (SEQ ID NO. 381)

::::::::::::Rv304T7.seq::::::::::::
GCCACGTTTCGCGCCGCCCGGCATACGGCGGCGTACCGATCTCCGCGTCATACACCCGCGGGTAATCGCCGACGGTGCCGGTTCGCGAGCCGAAGGTGACGAC GCTGATTGAATCGAGTTCCAGGTCCAGCGGGTGGCGCAGCAACGGCGCGAGCTCAACGACGTCAATCACGTTGTCGCTTTCTACGGTCACCGACCCGGTGACC GTAGTCGCCCGGTGCGCTCGGCCGAGAAGTTGCACCGCCACCACCGCGACACCGTCTTGCACGCGGACGCCACCCCCGGATCGGTTGTTGGCCAAGGTAATTG GGTCATTCCATTTGACGGGACGCCGACCCCGCAGCCCCAGTACCGCCCACGACCACGCCGGCTGACCCCACCACTGTACGAACACCAAGGCGACGCCGACCA (SEQ ID NO. 382)

Clone Rv306
::::::::::::Rv306SP6.seq::::::::::::
CTCAAGCTTGATGCCGCCTAAACCGAAGCGTGAGCACGCCGCCACCCACCACGCGCGGGTCGGGCGCCGGGCCCGGGCCGCCAGGCTGCTCCGCTCGGTGATG GCACGCCACCGCGACACCACCCGGCTGCGCTACGTCAAGCCATACCGGGCGGAGCTACATCGGCTCGGCCGCCCAGTGTTCGGGCCCTCTTTCGAGGTCNAGG TCNATACCGATTTGCGCATCCGCAGCCGCACCCTGGACGACAGAACGGTGCCCTACGAGTGCTTGTCGGGCGGGGCCAAAGAACANCTTGGCATCCTGGCGCG

ATTGGCCGGCGCGGTCCTGGTC (SEQ ID NO. 383)

::::::::::::Rv306T7.seq::::::::::::
CTCGGGTACGCTTCGGTCGCAGTGTGCGAGTGATAGATGACGACCGGGACCTCGTCGGCATCTTCCATAGCCCGCCACACCTTCAGTTGCTCACCGGAATCCA ACCGGTANAANGTCGGCGAGCGCTCGGCATTGGTCATCGGGATATGCCGCTCGGGACGGTCAGAGCCCTCGGGTCCGGCCAGCACTCCGCAGGCTTCGTCGGG

GTGGTCGCGACNCGCATGGGCCACCATCGCATTCACCAGGTCTGCGCG (SEQ ID NO. 384)

Clone Rv307
::::::::::::Rv307SP6.seq::::::::::::
CTCAAGCTTCAATTCCTCCACGACGCGTTCCCAAATGAATTTCCCGATCCCACAATCTCGGTTCAGATACAGGTCGCCATACCCCTTACTTCGGCAACGCTGG GCGGATTGGCCCTGCCGCTGCAGCAAACCATCGACGCCATCGAATTGCCGGCAATCTCGTTCAGCCAATCCATACCCATCGACATTCCGCCGATCGACATCCC TABLE 3-continued End sequences of the polynucleotide inserts cloned in the named recombinant GGCCTCCACTATCAACGGAATTTCGATGTCGGAGGTCGTGCCGATCGATNTNTCCGTCNACATTCCGGNGGTCACCATCACCGGCACCAGNATCGACCCGATT

CCGCTGAACTTCGACGTTCTCAGCAGCGCCGGAACCA (SEQ ID NO. 385)

::::::::::::Rv307T7.seq::::::::::::
TTAACCCCCGTGGCCTCTACGCCGCCTNCGGGTCGAACATGCATCCCGAGCANATGCTCGAGCGCGCACCCCACTCGCCGATGGCCGGAACCGGCTGGTTACC CGGGTGGCGGCTGACGTTCGGCGGCGAGGACATCGGCTGGGAAGGGGCGCTTGCCACCGTCGTCGAAGACCCAGATTCGAAGGTGTTCGTCGTGCTCTACGAC ATGACCCCGGCGGACGAGAAGAACCTTGACCGGTGGGAAGGCTCCGAGTTCGGCATCCACCANAAGATCCGATGCCGCGTT (SEQ ID NO. 386)

Clone Rv308
::::::::::::Rv308SP6.seq::::::::::::
CTCAAGCTTGATTTTGATCATCATGGATGATCATCACCCGAAGTGTGGTAGCCGCAGTGGTTATCGTGGGTACCGTCGTGCTTTCCATGGGCGCCTCTTTCGG GCTTTCCGTATTGGTCTGGCAGGACATTCTGGGTATCGAGTTGTACTGGATGGTGTTGGCGATGTCGGTGATCCTGCTCCTGGCGGTGGGATCCGACTACAAT CTGCTGCTGATTTCCCGGTTGAAAAANGAAATTGGGGCCGGATTGAACACCGGAATTATCCGTGCCATGGCTGGTACCGGGGGAGTGGTGACGGCTGCCGGCA

TGGTGTTCGCCGTTACCATGTCGTTGTTTGTGTTCAGCGATTTGCGAATTATTGGTCAGAT (SEQ ID NO. 387)

::::::::::::Rv308T7.seq::::::::::::
CGNCCAACCCGAATTGGTTTTCGGCGCCNTCGGTGAGGACGGCGTGCGGGTGCTCAACGACGACGTCGTCCGCGGGACACACCTCGATGCTGCCGCCATGGAC GCGGTCGAACGCAAGCAGCTGATCGAGCTACAACGCCGCGCGGAACGCTTCCGCCNCNGGCGTTACCGCATCCCGTTGACCGGGCGGATCGCGGTGATCGTCG ATGACGGCATCGCCACCGGAGCGACGGCCAAGGCGGCGTGCCAGGTCGCCCGGGCGCACGGTGCGGACAAGGTGGTGCTGGCGGTCCCGATCGGCCCANACGA

CATCGTGGCGAGATTCGCCGG (SEQ ID NO. 388)

Clone Rv309
::::::::::::Rv309SP6.seq::::::::::::
CGTGACTGCCACCGGGGCCACTCCGCAGAATCTGTACCCGACCAAGATCTACACCATCGAATACGACGGCGTCGCCGACTTTCCGCGGTACCCGCTCAACTTT GTGTCNACCCTCAACGCCATTGCCGGCACCTACTACGTGCACTCCAACTACTTCATCCTGACGCCGGAACAAATTGACNCAGCGGTTCCNCTGACCAATACGG TCGGTCCCACGATGACCCANTACTACNTCATTCGCACGGANAACCTGCCGCTGCTAGAGCCACTGCGATCGGTGCCGATCGTGGGGAACCCACTGGCGAACCT

GGTTCAACCAAACTTGAAGGTGATTGTTAACCTGGGG (SEQ ID NO. 389)

::::::::::::Rv309T7.seq::::::::::::
TCGCTCAAGCGCNTGAGGCCGAANCGGCTGGTTACGACTCCCTGTTTGTGATGGACCACTTCTACCAACTGCCCATGTTGGGGACGCCCGACCAGCCGATGCT GGAGGCCTACACGGCCCTTGGTGCGCTGGCCACGGCGACCGAGCGGCTGCAACTGGGCGCGTTGGTGACCGGCAATACCTACCGCAGCCCGACCCTGCTGGCA AAGATCATCACCACGCTCGACGTGGTTAGCGCCGGTCGAGCGATCCTCGGCATTGGAGCCGGTTGGTTTGAGCTGGAACACCGCCAGCTCGGCTTCGAGTTCG

GCACTTTCAGTGACCGGTTCAACCGGCTCGAAAAGGCGCTACANAT (SEQ ID NO. 390)

Clone Rv30
::::::::::::Rv30SP6.seq::::::::::::
ATACTCAAGCTTCCGCTGGGGCCTGTTCAACCATGGCGATCCCGTTGGTCCCGGACATCCCGAACGAGGACACCGCGACCCNCTTCGGTGTGTGATCATTACC GTTGGGCCACTGCGTAACCGCTTGCGGCACAAAGAGCCCGGTCTCGACGTCGGAAAGCTCATCGGGCACCCGATTGAAATGCAGCAGCGGCGGCACCACCCCG TGCCGCAGTGACAGAATTGCCTTGATCAGCCCGACGGTCCCCGCCGATGCCGTGCTGTGCCCCATGTTGCTCTTGGCCGATCCAAGCGCGCAGGGGGTGCCCG CGCCATACACCCGCGCCAGGCTGCGGTACTCAATCGGGTCGCCGATTGGCGTACCGGTGCCGTGCGCCTCCACCACACCGACCGTTTCGGGCTG (SEQ ID NO. 391)

::::::::::::Rv30T7PEG.seq::::::::::::
CACCAGCGTTCCAGCGGCATACCACCGCACATGCCGTGCACCCGGCGCCGGGCGGAGTCGCCGCATAACACANGTACACCTTGGGAATCGGTGTGCGCCAGGG ATTCNACCGCGGGGTGGGGCCGGCGATCGCGCGCCAGGTCGAGTTGGCGCCGACCGTGATNTCACCGCCGACGTAGTTGGCGTTGTGGTCCGCCATCCGCGCG GCGGGCACGGCGCGGGCCGCCACCACGATGTCACGGAAGCCGGGGGCGAACGCTCGACGACCTGGTTACCGTCTCNGTCGCNTCNANCGTGGACCCGACNGCA CGTGGGCATATGTCCANAACGGACGNGGCCGGTTTCNTCGATGCNGCCGGGGTCCGCGACNTGCGGACNCNCNGNCACACCATCCGCCAGTCCGCGTGGCGTC

CCGCCGCGACTCTGCCTCGGCCGCGCCA (SEQ ID NO. 392)

Clone Rv310
::::::::::::Rv310SP6.seq::::::::::::
CTCAAGCTTTGNCGACGATCGGGCGATGTCGATGANAGGAAACCCCAGCGCACAACCGACNATTTTGGCGTAGCCGGCGGACNTCTGCTCGATTCCGATCACG TCGGCGCTCGCATCGAGCATGGCGCCGGCGACGGCTAGCAGCGATCCGCCGTCGTCGAGGAACACGACACGAGCCGTACGCCCGGCCGTAAGCCGCGCCCAGG TABLE 3-continued End sequences of the polynucleotide inserts cloned in the named recombinant ATTCGGCGAAAAACCGTTCTACGTGGCGGGTGTACTGGGTGTCCAATGATTCGTGGGGTGCGTAGGCGTCGCTGCAATCGTCGACATAAATGCCGTCGGCCCG

CATCGCGTCAACAACTCCCGGGTGAGTGGAATANCACTTGCCGA (SEQ ID NO. 393)

::::::::::::Rv310T7.seq::::::::::::
TCCAACGCGGTGACAGATTTGTCTATCCTGGACCTGACGGTGAGGTCGAAGTTTTCCAGGAATTCGGCAAAATCGGTAAGAGCCTGAAGAATTCGGTATCGCC GGACGAAATCTGCGACGCATACGGGGCAGATACGCTTCGGGTTTACGAGATGTCGATGGGGCCGCTGGAGGCTTCACGTCCATGGGCCACAAAGGATGTTGTC GGCGCGTACCGTTTTCTGCAGCGGGTGTGGCGCTTGGTCGTCGACGAGCACACCGGCGAAACTCGGGTGGCTGACGGCGTGGAACTCGACATCGATACGCTAC

GGGCGTTGCACCGCACCATCGTCGGCGTGTC (SEQ ID NO. 394)

Clone Rv311
::::::::::::Rv311SP6.seq::::::::::::
CTCGTCCTTGACTACGCCCAGTATCGAAANCCTCCTGTGCCGGTNCGCTAAACACCCGGCGGACACTCANACGGTGCTGGTGGTGCGGCATGGCACCGCGGGC AGCAAAGCGCACTTCTCCGGGGACGACAGCAAGCGACCGCTAGACAAGAGGGGTCGTGCGCAGGCAGAAGCGTTGGTACCACAGCTGCTGGCGTTCGGCGCCA CCGATGTTTATGCCGCCGACCGGGTGCGCTGCCACCANACNATGGAGCCACTCGCCGCGGAACTGAACGTGACCATACACAACGAGCCCNCCCTGACCGAAGA

GTCCTACGCCAACAACCCCAAACGCGGCCGACACCGAGTGCTGCAGATCTTCG (SEQ ID NO. 395)

::::::::::::Rv311T7.seq::::::::::::
GTATCGCCTCCNCCTTTGGCCACCAGCAGCCACAGCGCGGTTCGCGGACCGAACGTGGACATCAATAGCCCGGAATCGGTGTGTGCAAGTTGGTAAACGGTGT TGATCCCAAGCTTTGCCAGCCTTTTCGTAGTCTTGGGCCCCACACCCCACAGTGCTTCGACGGTACGGTCACCCATGATGGCCATCCAGTTGGCATCGGTGAG CTGATAGATGCCAGCTGGTTTCGCCAACCCGGTAGCGATCTTGGCGCGCTGCTTGTTGTCACTGATACCTATCGAGCAAGACAGCCCGGTTTGCGACAAGATG

ACTTTTCGGATCTCTTCNGCGAACTTCCAATGGGGGTCTCCGGGANT (SEQ ID NO. 396)

Clone Rv312
::::::::::::Rv312SP6.seq::::::::::::
CTCAAGCTTTTGGTCTAGCCGGCCGAGCACGATACGGGTGTCCTTGGCCACCGGCGGCGGCTGTCCGGGAAATGGCGGGTCCCCGGTGGTTTTGCTGANGANT GCTGAACCGTAGTCGAAGTGGGCGGCGTCAGACTCCACCCAGCCAGCAGGCAGCGCGAAGCTGAATCCTCCAACCGGGTTGTCGATCCGGACAGGTTGGGGTG CGTTTGGGGCAATGACAGGTGGCGGCGGTGCGTTCGGGTCGGCCGGCGGAGGTGCTGCGTTGGGATCNCCCGGCTGGGCATTCGGCNTNTTGGCGGCGGCCGG

TGGTGGGGGGGCAACANGTGTCCCGGTGCGGGTGGCGCTGC (SEQ ID NO. 397)

::::::::::::Rv312T7.seq::::::::::::
ATCTGTACCCGACCAAGATCTACACCATCGAATACGACGGCGTCGCCGACTTTCCGCGGTACCCGCTCAACTTTGTGTCGACCCTCAACGCCATTGCCGGCAC CTACTACGTGCACTCCAACTACTTCATCCTGACGCCGGAACAAATTGACGCAGCGGTTCCGCTGACCAATACGGTCGGTCCCACGATGACCCAGTACTACATC ATTCGCACGGAGAACCTGCCGCTGCTAGAGCCACTGCGATCGGTGCCGATCGTGGGGAACCCACTGGCGAACCTGGTTCAACCAAACTTGAAGGTGATTGTTA

ACCTGGGCTACGGCGACCCGGCCTATGGTTATTCGACCTCGCCGCC (SEQ ID NO. 398)

Clone Rv313
::::::::::::Rv313SP6.seq::::::::::::
CTCAAGCTTGCAATGCGGGTCGGGATGCCCATGGTTGGAANATGGTCGCCCTGGCGTCNAATACGCGCGAGCGCATGAGCTCACCGGTTCGGAACAACGTATC GAAAAACGTCGCACTGCTGGCAGATGGTATCTCCGATGTGGTTGTAATTTGTATCCCAACTCTAACTGTGCTATCGGATCAGCGTGAATATCGANATATTGCG AATGCGATGACAGGCCGCCATTCGGTTTATTCGCTTACGCTTCCCGGGTTCGATTCGTCTGATGCACTGCCGCAAAACGCGGATATGATTGTTGAAACCGTAT

CTAACGCAATTATTGATGTGGTAGGCGGCAGCTGCCGTTTTGTGCTGTCGG (SEQ ID NO. 399)

::::::::::::Rv313T7.seq::::::::::::
CAAATACACGCCGGACGCACAGGCGGACATCGCCATCCCGAGCACACCCAAAACGGGATACAGGATGGAGGCCAACGCCACGGCCGCGCCCAGGATCACCAAC CACACCGGCTTGGTCAGCTTGTCGGCGGCGGTATAGGCATCGGGCCGCTGCAACGCAGCATGCACAAACGCGTACACCGCTGTCACCAAGACGGCGACCAGCA ATACCAGCATGACGGTACCCACGAGGTGGCTCACGCATTCAGACTATGCGGTTTGCATCCAACACG (SEQ ID NO. 400)

Clone Rv314
::::::::::::Rv314SP6.seq::::::::::::
CTCGTCCTTCGGCCTCGCTGCAGGAGTGGGAGCCGCAGGGCTGGAAATCCGAAAAACGAGCCGGTGATCGCACTGTCGCCGATCGGCGCCGCACCTGGTTGGT GTTACGGATGAATCCGCAGCGAAATGTGGCTGCGGTGGCGTGTCGTGACTCGTTGGCGTCGACGCTGGTGGCAGCCACCGAGCGGTTGGTCCAGGATCTGGAT GGGCAAAGTTGTGCGGCCCGGCCGGTGACGGCCGATGAGCTGACCGAGGTCGACAGCGCCGTGTTGGCTGACTTGGAACCGACATGGAGTCGCCCCGGTT TABLE 3-continued End sequences of the polynucleotide inserts cloned in the named recombinant (SEQ ID NO. 401)

::::::::::::Rv314T7.seq::::::::::::
GTCTAGNCCGCCGAACACGATACGGGTGTCATTGGCCACCGGCGGCGGCTGTCCGGGAAATGGCGGGTCCCCGGTGGTTTTGCTGAAGANTGCTGAACCGTAG TCGAAGTGGGCGGCGTCAGACTCCACCCAGCCAGCAGGCAGCGCGAAGCTGAATCCTCCAACCGGGTTGTCGATCCGGACAGGTTGGGGTGCGTTTGGGGCAA TGACAGGTGGCGGCGGTGCGTTCGGGTCGGCCGGCGGAAGTGCTGCGTTGGGATCGCCCGGCTGGGCATTCGGCGTGTTGGCGGCGGCCGGTGG (SEQ ID NO. 402)

Clone Rv315
::::::::::::Rv315SP6.seq::::::::::::
ACTCAAGCTTGAGATTGGCGTCAACGGGTGTCGGCACCGGCGTCCTGCAGTTGGTAGGCCTGCAGTTTGTGCATCAGGCCGATGCCGCGGCCCTCGTGGCCAC GCATGTACANCACCACGCCGCGCCCCTCACGGGCGACCATCGCCAGCGCGGCGTCCAGCTGAGGCCCGCAATCGCAGCGGCGTGACCCAAACACATCGCCGGT

CAAGCACTCCGAATGCACCCGGACCAGCACGTCG

TCACCGTCGGCGTTGGGCCCGGCGATCTCGCCGCGGACCAGCGCGACATGTTCCACGTCCTCGTAAATGCTGGTGTANCCGATGGCGCGAAACTCCCCATGAC

AANTCGGAATCCCGCGCCTCGGCGACCCCGCTCAATGTTGCTTCTCNTGCTTG (SEQ ID NO. 403)

::::::::::::Rv315T7.seq::::::::::::
TCGACNAGCATTCTTGACNGTTGTTTTGGCTCGGCATGGTTAGCCAAGGTTCTGCGGTCCCACCAGATCATCTTGGTCCGGTAGCGCTCGTCCGGGTATGCTG CCGCCGGGATTCTCGCTGCTATTACTCCCCCCGAAGAACGCCACCGGTCCAGCGCGTGGGCCGCCGCGGTCCCCATCACAAACTGAACCCCCAACAGGGGACA TGCTTAGCGGTAGGGCGCGCGCCAAGGCGGCAGCAATCGCATCACTGCGCTGCGCGTCACTATTAACCCACCCGGACTTCACTTCCACGACCCCGAATGGCGC

CCGGTCATTGATCATCTTGCGCACCGCGGATAATCCGGGAT

TG (SEQ ID NO. 404)

Clone Rv316
:::::::::::::Rv316SP6.seq:::::::::::::
ACCGGGGCCACTCCGCACAATCTGTACCCGACCAANATCTACACCATCGAATACGACGGCGTCGCCGACTTTCCGCGGTACCCGCTCAACTTTGTGTCNACCC TCAACGCCATTGCCGGCACCTACTACGTGCACTCCAACTACTTCATCCTGACGCCGGAACAAATTGACGCNGCGGTTCCGCTGACCAATACGGTCGGTCCCAC NATGACCCANTACTACATCATTCGCACGGANAACCTGCCGCTGCTAAAGCCACTGCGATCGGTGCCGATCGTGGGGAACCCACTGGCGAACCTGGTTCAACCA AACTTGAAGGTNATTGTTNACCTGGGCTACGGCGANCCGGCCTNTGGTTATTCCACCTCNCCGCCCAATGTTTGCNACTCCCGTTCGGGGTTGTTCCCNNAAG

GTCAACCC (SEQ ID NO. 405)

:::::::::::::Rv316T7.seq:::::::::::::
CGCTCAAGCGCNTGAGGCCGAANCGGCTGGTTACGACTCCCTGTTTGTGATGGACCACTTCTACCAACTGCCCATGTTGGGGACGCCCGACCAGCCGATGCTG GAGGCCTACACGGCCCTTGGTGCGCTGGCCACGGCGACCGAGCGGCTGCAACTGGGCGCGTTGGTGACCGGCAATACCTACCGCAGCCCGACCCTGCTGGCAA AGATCATCACCACGCTCGACGTGGTTAGCGCCGGTCGAGCGATCCTCGGCATTGGAGCCGGTTGGTTTGANCTGGAACACCGCCAGCTCGGCTTCGAGTTCGG

CACTTTCAGTGACCGGTTC (SEQ ID NO. 406)

Clone Rv317
::::::::::::Rv317SP6.seq::::::::::::
CTCAAGCTTGCGTTCGATGAAGTAGTCGTCGGTCAGCGCCGCCTCTTCGAGCTCCTTGGCGATGCCCAGCAAGGAGTCATCGCCGCCGAGCTTGGCCAGGATC TTGTCGGCCTGTTCCTTGACGATGCGGGCCCGCGGATCGTAGTTCTTGTAGACACGATGACCGAAACCCATCAATTTGACCCCGGCCTCGCGGTTCTTGACCT TGCGTACAAACTCGCTGACGTCGTCGCCGCTGTCGCGAATGCCCTCGAGCATCTCCAGGACAGCCTGATTGGCGCCGCCATGAAGCGGACCCCATAGTGCGTT

GATGCC (SEQ ID NO. 407)

::::::::::::Rv317T7.seq::::::::::::
GGTCAGGCCGAGCAGGCGCGAGGAACGACGAACCCAACAAGCCATGGTGGTTGGCGCCGTCGAGAGGTCGGCGGTCGCCACAACGGGAAGATCGCCTTGAGCG TCGCTCGACCGCCGCCTCGAGTTGGGTCATAACGAAGTAGCTGATGCCGATCATGTCGACGTTTCCGTCGCATCAGCGTGCAGCGGCGACCCACTCNACGAGG TCTCGGTGCCGCCGCGGCCAGGGCACCAGCAGTGACGAGTCCAGGCGCCGTCGGGCCAAGCAGTCGCGGTGCCANCCGTGGTGGGTCGGGCGATGGTTGGGTG

TGCTCATTTCGGGAACGCCA (SEQ ID NO. 408)

Clone Rv318
::::::::::::Rv318SP6.seq::::::::::::
CTCGAAGCTTTAACAGCATCAACCCCGCCCCGCACCAGCACCGACACNATGTCGATGCCATCGAGGTGAATGTCGAACTGGCGCAAACCATCGGCGACCGCGA TABLE 3-continued End sequences of the polynucleotide inserts cloned in the named recombinant CCACCGGCAACATGGGTACCGGCGATTTCCGGTGCCAATGCCGACCCGACGGGCCGCTCTCACCGCAGGTGACCTCGATCACCGAGACCANCCGGCCGTTNTN NTCACGCACCCCTACCGTGTCACGCCCAAAACGGCGCTGGTGGTCGATTGCCGGAGTGCACCCCNCACCCAGTGTCGTGCCCGGATCC (SEQ ID NO. 409)

::::::::::::Rv318T7.seq::::::::::::
TGATGCCGCACCCGATCGACGGTCGTTGGTCGGGGTTGACTGGCCGCCCGGCGAAGCAGGGCGTCGACCGCGGCCCGGACGTCGGCGGCCGTCACCGGTCGGC CATTGCCCGGGCGGGAGTCGTCGAGCTGACCACGGTAGACAAGTCGGCGCTGGCCGTCGAAGACNAACGTGTCGGGTGTGCAGGCCGCGGAGAAGGCGCGGGC GACNTCTTGGGTTTCGTCGTANAGATACGGGAACGTCCAGCCGTGGCGGCGGGCCTCGGCGACCATCTGATCGGGCCCGTCC (SEQ ID NO. 410)

Clone Rv319
::::::::::::Rv319SP6.seq::::::::::::
TTTCGGGCGAGGCGGTATANCTTCCCNTCGTACCGGCGACCGCCAGCCGANAAGCTCGTTTTCCCAGTGTTGCTGGGGATTCTCACGCTGCTGCTGANTGCGT GCCAAACCGCTTCCGCTTCGGGTTACAACGAGCCGCGGGGCTACNATCGTGCGACGCTGAAGTTGGTGTTCTCCATGGACTTGGGGATGTGCCTGAACCGGTT CACCTACNACTCCAAGCTGGCGCCGTCTCGTCCGCAGGTCGTTGCTTGCGATAGCCGGGAGGCCCGGATCCGCAATGACGGATTCCNTGCCANCGCTCCGAGT TGCNTGCGGATCGACTACNAATTGATCACCCANAACCATCGGGCGTNTTACTGCCTGAAGTACCTGGTGCGGGTCGGATACTGCTATCCGGCGGTGACAACCC

CGGCAAGC (SEQ ID NO. 411)

::::::::::::Rv319T7.seq::::::::::::
GTTTTGGCTCGGCATGGTTAGCCAAGGTTCTGCGGTCCCACCAGATCATCTTGGTCCGGTAGCGCTCGTCCGGGTATGCTGCCGCCGGGATTCTCGCTGCTAT TACTCCCCCCGAAGAACGCCACCGGTCCAGCGCGTGGGCCGCCGCGGTCCCCATCACAAACTGAACCCCCAACAGGGACATGCTTAGCGGTAGGGCGCGCGCC AAGGCGGCAGCAATCGCATCACTGCGCTGCGCGTCACTATTAACCCACCCGGACTTCACTTCCACGACCCCGAATGGCGCCCGGTCATTGATCATCTTGCGCA CCGCGGATAATCCGGGATTGCCAGCCCATTCNACTACCGCATGCGAGTCATCGGCTGACCGCAGCGGTC (SEQ ID NO. 412)

Clone Rv31
::::::::::::Rv31SP6.seq::::::::::::
TCGCCTAGGCGGGCTTCCCCTTCCGTCCGAGCNGTCAGAAGCTCCTATGACAATGCACTACCCGAGACNATCAACGGCCTATGCAATACCNAGCTGATCAAAC CCGGCAAGCCCTGGCGGTCCATCGAGGATGTCGAGTTGGCCACCGCGCGCTGGGTCGACTGGTTCAACCATCGCCGCCTCTACCGGTACTGCGGCGACATCCC GCCGGTCTAACTCGACGCCGCCTCACTACGCTCAACGCCAGAGACCANCCGCCGGCTGACGTCTCAGATCAGAGAGTCTCCGGACTCACCGGGGCGGTTCATC

CCCACTGTCGATAGCGTCTGTGGATAACTTTGTCTGCA (SEQ ID NO. 413)

::::::::::::Rv31T7.seq::::::::::::
GCGCGTNGAACTGATAGGTGCGGCCCGGCTCGAGCANGCCGGCCATTTGTTCGATGCGGTTACCGAAGATCTCTTCGGTGACCTGCCCGCCGCCGGCCAGCTC

GGCCCAGTGCCCGGCGTTGGCCGCCGCGGCGACAATCTTGGCGTCCACGGTGGTCTGGGTCA (SEQ ID NO. 414)

Clone Rv321
::::::::::::Rv321SP6.seq::::::::::::
CTCAAGCTTCAATACAGAGTTATAAACTGTGATAATCAACCCTCATCAATGATGACNAACTAACCCCCGATATCAGGTCACATGACGAAGGGAAAGAGAAGGA AATCAACTGTGACAAACTGCCCTCAAATTTGGCTTCCTTAAAAATTACAGTTCAAAAAGTATGAGAAAATCCATGCAGGCTGAAGGAAACAGCAATAACTGTG ACAAATTACCCTCAGTAGGTCAGAACAAATGTGACGAACCACCCTCAAATCTGTGACAGATAACCCTCAGACTATCCTGTCGTCATGGAAGTGATATCGCGGA

AGGAAAAT (SEQ ID NO. 415)

Clone Rv322
::::::::::::Rv322SP6.seq::::::::::::
CTCAAGCTTCGATCGACATTACTCCCGCCTTGGGTCTGGTCTCCGAGCTGGTCGGTCATGGTCGGACCTGCTGGTAGTGGGGATCTAACGCAACATGGTCGGG ATTCATCATGGTGTACCCGTGATACCCATTCGCAGCTGCCGGTGAAACCCCGCGATGCCGGGATTTCCAGCCGCACTAGGATGTCTAGCCGGCCAGCCGCTGC CGCCGGACTTCGGGATGTTCGGTATACCANCGATCGGCAATCTTGCGTATCCGCCGATGCTCGAACGCTANCCACGCCAAACCAACCACTGTGACNACAATCG CCACCACACCAAAGGTCATGCCCTCGGCGTGATGTCCGGTGCCGAAAGCCGCAAGAGCTCCGACGCCGCC (SEQ ID NO. 416)

::::::::::::Rv322T7.seq::::::::::::
CATTCCCAATTGAATTTCCCNATCCCACAATCTCGGTTCAGATACAGGTCGCCATACCCCTTACTTCGGCAACGCTGGGCGGATTGGCCCTGCCGCTGCAGCA NACCATCGACGCCATCGAATTGCCGGCAATCTCGTTCAGCCAATCCATACCCATCGACATTCCGCCGATCGACATCCCGGCCTCCACTATCAACGGAATTTCG ATGTCGGAGGTCGTGCCGATCGATGTGTCCGTCGACATTCCGGCGGTCACCATCACCGGCACCAGGATCGACCCGATTCCGCTGAACTTCGACGTTCTCAGCA TABLE 3-continued End sequences of the polynucleotide inserts cloned in the named recombinant GCGCCGGACCCATCAACATCTCGATCATCGACATTCCGGCGCTGCCGGGCTTTGGCAACTCGACCGAGCTGCCGTCGTCGGGCTTCTTCAACACCGGCGGCGG

TGGCGGCT (SEQ ID NO. 417)

Clone Rv327
::::::::::::Rv327SP6.seq::::::::::::
CTCAAGCTTTCGGCGGAGACGGACANNTTGCGAACATTGATGACAAAATAGAAATCATTGATGGTTTGAGTCACCAGGCCGATCAAGCCTTCGCCGAGCCAAA TTCCAATCAAGAGGCCCAAGCCCGTACCAATCAGCCCGGCAACGAGGGATTCCGTCATTATCAGCCAAAATAACTGCTCTCGGGTTACACCCAAACAGCGCAA

TATGGCGAAAAACGGTCGCCGTTGCACGACATTAAATGTCACGGTATTG (SEQ ID NO. 418)

::::::::::::Rv327T7.seq::::::::::::
AGCTTAACTGCTCCCTAATACCTGGGGCTGTGCCTGCGGTGTATGCACGGCATACGGACATCCNTCCCCTGAGACCCNCGGTCTAATCAGCCACGTGTCCACC ATCAGGGGTCAACCCCGGCCAAGGGCGACGGCACCCCAAGTTCGCCGACCGTTAACCTATTGCTGTGAGCTTCATTTGCTGCGAGCAAAACAGTTGGTCGGCC GTTAGGAACTGAATTGACACTCAACCGATTTGGTGCCNCCGTAGGTGTCCTGGCTGCGGGTGCGCTGGTGTTGTCCGCGTGTGGTAACGACCACAATGTGACC

GGGGGAGGTGCAACCACTGGCCACGCGTCCGCGAATGTCTATTGCGGGGG (SEQ ID NO. 419)

Clone Rv328
::::::::::::Rv328SP6.seq::::::::::::
CTCAAGCTTGGGGTGGCGCTGTCGGTCGGTGTGCTTGGCGGCGTCGGTATCAACACCGCCCACGAAATGGGGCACAAGAAGGATTCGCTGGAGCGGTGGCTGT CCAAAATCACCCTCGCCCAGACCTGCTACGGGCACTTCTACATCGAGCACAACCGTGGCCATCACGTCCGGGTGTCCACACCGGAGGACCCGGCGTCGGCGCG GTTCGGCGAAACGTTGTGGGAGTTCCTGCCCCGCAGTGTTATCGGCGGCTTGCGCTCGGCCGTTCATTTGGAGGCCCAACGGCTGCGTCGGCTCGGCGTCAGC

CCCCT (SEQ ID NO. 420)

::::::::::::Rv328T7.seq::::::::::::
GCACCAAGGCCCCACACGTCACCCTGTGACCTCCTGCGCCGACCCCGCCCGAGGTCCTGGCCGTTACCACCTGAACGGGCGAGCCGGGAGTCTGGTACGCATC GAACAAAGAGCAAGGTGCATGGGCGGAGTTGTTCCGCCACTTCGTCGATGACGGGGTCNATCCATTCGAGGTCCGTCGCCGCGTCGGTCGAGTGGCGGTCACA CTCCAGGTACTCGACCTCACAGACGAGAGGACTCGATCCCATCTAGGTGTGGACGAAACAGATCTTCTGTCCGA (SEQ ID NO. 421)

Clone Rv329
::::::::::::Rv329SP6.seq::::::::::::
TCGCCTCCGCATATGGGTCGACGCCAAGCGGGTCCGGATTTCTGGGCTTCATCGCTCGCGCCGTCGCGACAAACAGCGCGGTCGAACCGACACTCGTTGTGAT GTCCCAGCTATCACCTTCGGTACGCACCCAATCGACCCTACNCGGCTATCTCAGCCGCGATCTCCAGGCTCCGCCGAGCCAGGTGCATCCCGGTCCGGATCCC

ACTAACCCGGCACCATTGGCGTCN (SEQ ID NO. 422)

::::::::::::Rv329T7.seq::::::::::::
GTCCTCGAGTGCCGCCGTCGNCACNCCCAGCGCCCGCGCGGCCACTTGGATGCGACCCGTTTCAAGTCCCTTCATCATCTGCGAAAAGCCTTGACCCATGGCT CCGCCCAGGATCGCCGAGACCGGCACCCGGAGGTTGTCGAACGACAGCTCGCAGGATTCGACGCCCTTGTAACCCAACTTCGGCAAGTCCCGCGACACCGTGA GTCCCGGCCCGGGTTCGACGAGCACGATCGACATGCCTTGGTGCCGCGGTGTGGCGTTCGGGTCGG (SEQ ID NO. 423)

Clone Rv32
::::::::::::Rv32SP6.seq::::::::::::
GGCATACCAATGTGGACTTCTGCTCACCCACGATATCCGTGGTCTGATCCGCTGCTGCGGCGGGCTGCNACCTGCNTCTCNGCGGCACCCGTNACTACATGGC NCGCGCCGCACGCATACGTCGCGGCGGGACCCACTCCNACTGGTCGACGGTGCTGGCCGCGTGTCCGCANGTCCCNAACCCGGCCGCACCGACGAAACCGGCC GCCGTCCGTTCTGGACCAACGCTCATGTGCCGTCGGGGTCCATGCTCGACGCCATCGAGACCGTAACCAGCGTCCTCGAGCGGTTCGCCTCCGGCTTCCGTGA CATCTTCGTGGCTGCTCGCGCCGTGCCGCCGCGCGGATGGTCGACCACAACGCCAACCACCTCGGCGGTGACATCACCGTCCGCGCCACTCGACCTGGCGCGC

GATCGCGGCCC (SEQ ID NO. 424)

::::::::::::Rv32T7.seq::::::::::::
GTGAGCAGACCTACGCCNCCTGGTTGCGCCAACTCGGTACCGATCATGGCGCGCNGCCTGTCGTCACCGATACCCAGCGAACAAGACAGCCCGGTCCGCGACA AGATGACTTTCCCGATCTCTTCGGCGACTTCCATGGGGTCGTCCGGAGTCCCGGGCGCCACCGCGAGGTAACCCTCGTCTCAGTCCCATACGCGACCGGGTAT CCACGTCGCGCAACAACGCCACCACCTCCCCAGACGCCNCGTTGTACGCGGCTGGGTTCCACNGCAATAAGTGGCCTCANGGCATCGTCCGGCGGCGGTCCNC

AACGCA (SEQ ID NO. 425)

Clone Rv330
::::::::::::Rv330SP6.seq::::::::::::
CTCAAGCTTGAGGTTAACTTTGAACGGATCGAGCTGGACGTTCGAGACGGTGATCGGGCCGAACCTGAATTGTCCGGTAATGCCCAACGCAAAAAGCAGGGTG TABLE 3-continued End sequences of the polynucleotide inserts cloned in the named recombinant GTGGCCGGGGCGGTGAAACCGGCGTCGGCGGCACCGTCGAAATCTATGTGGATTGCCGGAATGGGGATGTCCGGCACGGCGAAACCGTAGTTCGCTTGTCCCG TGAGGCCCAGGTGGATGGGGGGAAAGATCCTGGTGTCCGGGATAATAATGGGGCCGATGCCGCCGGTTGAAGTCCACTGGATCGGGAATTCCGGAATCTTGAT

CCGACGTTCAGGCCGAACAGGCCCTC (SEQ ID NO. 426)

::::::::::::Rv330T7.seq::::::::::::
CGGCGACGTCGCGATACGCCGAGCAGTTGGGAATCGCTCTGCAGCAAACCAATATTCTGCGCGACGTTCGAGAGGACTTTTTGAATGGACGGATCTACCTGCC GCGCGACGAGCTGGACCGATTAGGCGTACGCCTCCGCCTGGACGACACCGGGGCACTCGATGACCCCGACGGACGGCTCGCGGCNCTGCTGCGGTTCAGTGCC GACCGCGCCGCAGACTGGTNTTCGCTGGGACTGCGGCTGATTCCACACCTCGACCGCCGCAGCGCTGCCTGCTGTGCGGCCATGTCTGGCATCTACCGCCGTC

AGCTCGCCTTGATCAGAGCATCGCCGGCGGTCGTCTA (SEQ ID NO. 427)

Clone Rv331
::::::::::::Rv331SP6.seq::::::::::::
CTATAAAATACTCAAGCTTGATGCCGCCGAAACCGAGCGTGAGCACGCCGCCAGCCACCACGCGCGGGTCGGGCGCCGGGCCCGGGCCGCCAGGCTGCTCCGC TCGGTGATGGCACGCCACCGCGACACCACCCGGNTGCGCTACGTCNAGCCATACCGGGCGGAGCTACATCGGCTCGGCCGCCCAGTGTTCGGGCCCTCTTTCG AGGTCNAGGTCNATACCGATTTGCGCATCCGCAGCCGCACCCTGAACNACANAACCGTGCCCTACTATTGCTTGTCNGGCGGGGCCAAAAAACAGCTTGGCAT

CCTGGCCCNATTGGCCGGCGCGG (SEQ ID NO. 428)

::::::::::::Rv331T7.seq::::::::::::
CTTCGGTCGCAGTGTGCGAGTGATAGATGACGACCGGGACCTCGTCGGCATCTTCCATAGCCCGCCACACCTTCAGTTGCTCACCGGAATCCAACCGGTAGAA GGTCGGCGAGCGCTCGGCATTGGTCATCGGGATATGCCGCTCGGGACGGTCAGAGCCCTCGGGTCCGGCCAGCACTCCGCAGGCTTCGTCGGGGTGGTCGCGA CGCGCATGGGCCACCATCGCATTCACCAGGTCTGCGCGAATCNCCANCACGTANACNGTTCCTTTCCTAA (SEQ ID NO. 429)

Clone Rv333
::::::::::::Rv333SP6.seq::::::::::::
CTGGCACCAAGGCCCCACACGTCACCCTGTGACCTCCTGCGCCGACCCCGCCCGAGGTCCTGGCCGTTACCACCGAACGGGCGAGCCGGGAGTCTGGTNCGCA TCGAACAAANAGCAAGGTGCATGGGCGGAGTTGTTCCGCCACTTCGTCGATGACGGGGTCNATCCATTCGAGGTCCGTCGCCGCGTCGGTCNAGTGGCGGTCA CACTCCAGGTACTCGACCTCACAGACNAAAGGACTCNATCCCATCTAGGTGTGGACNAAACAGATCTTCTGTCCGACNACTACACCACCACCCAGGCCATCGC CGCCGCCCGCGATGCCAACTTCGACGCCGTACTGGCCCCGGCGGGGGGCGCTCCCCGGTTGTCAACACTTGCCGTGTTCNTTCACGCNCTGCCCCACATCCAA

CCCCAACG (SEQ ID NO. 430)

Clone Rv334
::::::::::::Rv334SP6.seq::::::::::::
GTTCTTGGGCCCATGCGGAGGTATCGCCGTTTCCACCACGCGGTCGGGGTGGCGTTGCATTAGCTCACCGATGGTGCGCTTGTGCAGGCCGCCGGGATACCCC

GAGTGCCGGTAAACCATCTTGTGCTGC (SEQ ID NO. 431)

Clone Rv335
::::::::::::Rv335SP6.seq::::::::::::
CAATACTCAAGCTTGGCGTGCGGTTCCAACCCGAATTGGCTTTCGGCGCCATCGGTGAGGACGGCGTGCGGGTGCTCAACNACNACGTCGTCCGCGGGACACA CCTCGATGCTGCCGCCATGGACGCGGTCGAACGCAAGCAGCTGATCGAGCTACAACGCCGCGCGGAACGCTTCCGCCGCGGGCGTGACCGCATCCCGTTGACC

GGGCGGATC (SEQ ID NO. 432)

::::::::::::Rv335T7.seq::::::::::::
CNTCATGATGATCATCACCCGAAGTGTGGTAGCCGCAGTGGTTATCGTGGGTACCGTCGTGCTTTCCATGGGCGCCTCTTTCGGGCTTTCCGTATTGGTCTGG CAGGACATTCTGGGTATCGAGTTGTACTGGATGGTGTTGGCGATGTCGGTGATCCTGCTCCTGGCGGTGGGATCCGACTACAATCTGCTGCTGATTTCCCGGT TGAAAGAGAAATTGGGGCCGGGATTGAACACCGGAATTATCCGTGCCATGGCTGGTACCGGGGGAGTGGTGACGGCTGCCGGCATGGTGTTCGCCGTTACCAT

GTCGTTGTTTGTGTTCAGCGATTTGCGAATTATTGGTCAGATCGGTACCAC (SEQ ID NO. 433)

Clone Rv336
::::::::::::Rv336SP6.seq::::::::::::
ATACTCAAGCTTTTACGGTGATCGCNCATCACCTGGTTCATGAACTGGAAGCAGCGCAGCGCTTCCTTTTCGGCCGCAACATGAGCCAGCCTCTCGTCGGCGG TCGGGTGCAGGTGCTCGGGCAGCTCGGCCGCNACAGCCGCCTGACCCTGAAACCAGCTTCCATATCCCGCGANNAACGACGCCAGTCCGCTACGTNACCCCTC

CGCGACTGTCCATGGACAACAGCGCGTTCTCCACCGACCGGGCCCGGGTGTGGGGTNTT (SEQ ID NO. 434)

::::::::::::Rv336T7.seq::::::::::::

TABLE 3-continued

End sequences of the polynucleotide inserts cloned in the named recombinant

GCTGGTAGAGTCGCTGACCGGTGCAGGTTTCGACAATGTGGTGCCGGTTCGGCGGCTACGTGCCATCGAGACACTGGCGCAGGCTATCGCACCCGTTATCGGC

TACGAGCAAATCGCGGTATGCGTTCTTGAGCATGAGTCGGCGACCGTCGTCATGGTCGACACCCACGACGGAAAGACGCAGATCGCCGTCAAGCATGTGTGCC

GCGGATTATCAGGACTGACCTCCTGGCTGACCGGCATGTTTGGTCGCGATGCCTGGCG (SEQ ID NO. 435)

Clone Rv337
::::::::::::Rv337SP6.seq::::::::::::
GCTTTCCGCCGATACCCGCCATGTCNCGCACATCCAGGACTTCTGGGGGGATCCGCTGACAGCGGCGGGATCCCAAAGTGCGGATGATCGGGCCGCCTACGTC GTGGTGTACCTCGTCGGTAACAACGAAACCGAAGCGTATGACTCGGTCCACGCGGTGCGGCACATGGTGGACACCACACCGCCACCGCACGGGGTGAAGGCCT ATGTCACCGGTCCGGCANCACTCAATGCCGACCAGGCCGAGGCCGGANACAAAANTATCGCTAAGGTCACCGCGATCACNAGCATGGTGATCGCAGCAATGTT

GCTAGTGATCTATCGCTCCGTAATTA (SEQ ID NO. 436)

::::::::::::Rv337T7.seq::::::::::::
CTTCCAACCCGAATTGGCTTTCGGCGCCATCGGTGAGGACGGCGTGCGGGTGCTCAACGACGACGTCGTCCGCGGGACACACCTCGATGCTGCCGCCATGGAC GCGGTCGAACGCAAGCAGCTGATCGAGCTACAACGCCGCGCGGAACGCTTCCGCCGCGGGCGTGACCGCATCCCGTTGACCGGGCGGATCGCGGTGATCGTCG ATGACGGCATCGCCACCGGAGCGACGGCCAAGGCGGCGTGCCANGTCGCCCGGGCGCACGGTGCGGACAAGGTGGTGCTGGCGGTCCCGATCGGCCCA (SEQ ID NO. 437)

Clone Rv338
::::::::::::Rv338SP6.seq::::::::::::
TACTCAAGCTTCGCGAGATCCGGATGGCACTCACGCTGGACAAGACCTTCACAAAATCTGAAATCCTGACCCGATACTTGAACCTGGTCTCGTTCGGCAATAA CTCGTTCGGCGTGCAGGACGCGGCGCAAACGTNCTTCGGCATCAACGCGTCCGANCTGAATTGGCAGCAAGCGGCGCTGCTGGCCGGCATGGTGCAATCNACC

AGCACGCTCAACCCGTA (SEQ ID NO. 438)

::::::::::::Rv338T7.seq::::::::::::
CCCACGACTTTCTCCTCGATCAGTTGGATTTGTACGAAGAGGCAACGAAAGCAGTGATCCTCGGGATGGTCGACGCCTACATCGACCCGCCGTTCACGCCGCA CAGCCTGCTAGATGCGCTGGGCGAGCAGGTCCCACAGTTCGCCGCTAAGGCACGGCGTCTGTTCCCGTCCGGATCGCCATTCGGCCTCGGCGTCCTGCTCCCA

TTCGATCAATAGGGCTGGCAGCTCCGTCGGCAGGGGCCTACGCCTCACCCCGTCACG (SEQ ID NO. 439)

Clone Rv339
::::::::::::Rv339SP6.seq::::::::::::
CTCAAGCTTATGCGCGCCGGCCGAGGTCTGCTCACGGCAACCCCTGAAGTTTAGGGGACNACCTACTCAGCGCAAAATTTCGCTAATGTGAGTCCGCCCCACC AGGGGNANATCAACCCATGTCGATCATGATCTACCCGGATACCGGATTGGCGGTAGCGCCCACGATCGTCNAAATNTCCGCCTGAATCATCGGATAGCTGATC CGGCGTCAACGCGTTTTGANTTCACCGCGCAACAGCCGCCAGGCCGGCCCGCANCGANCCGATCTCNTCGGGCCGCATGGGCCCCAATCTTNTCG (SEQ ID NO. 440)

::::::::::::Rv339T7.seq::::::::::::
GTGTGTGGTGGAACCCATCTGAGCAGTGTGCCAAACCGGGGCAGACAGCTCCCAATTGACGTGAGCCCGCTCACTTGCTGGGTAAGCGTC (SEQ ID NO. 441)

Clone Rv33
::::::::::::Rv33SP6.seq::::::::::::
CTTTACACTTCCTGCATCCGGCTCGTATGTTGTGTGGAATTGTGAGCGGATAACAATTTCACACAGGAAACAGCTATGACCATGATTACGCCAAGCTATTTAG GTGACACTATAGAATACTCAAGCTTGGGCGTGACGGCCACCGGGGCCACTCCGCACCATCTGTACCCGACCAAGATCTAC (SEQ ID NO. 442)

::::::::::::Rv33T7.seq::::::::::::
CAGGCATGCAAGCTTTAGCTGCCCGAATGCGTCACCCCGATGCGCCCAGATCGGGGCTTCGCAGATAAAGCACGAACAGGCGGGCAAAACGTCNATCTCGGAG CCGGAAGGGCAATCAGCCGACCGTCGACGAACGACACCGGCGAGACCACTTAGGCAGTGACGGCCGGCCCGAACATTACGCGCTCGTTGATTAGGCGTTCGGT CTCGTCCGCGGTCATGCCGAGCAGCTTGCGGCAGATCTGAACGCTGTCCTGTCCGGGCAGCGGCGCCGGGCGTTGGGGTGCCTGCCCGAATGTGACGAAACGG

AGCCGGACCCGTCTCGGCGGGCCGCGGACGGCGATCCGC (SEQ ID NO. 443)

Clone Rv340
::::::::::::Rv340SP6.seq::::::::::::
CNCAAGCTTGCGGATGTTACCCCTGACAGCCTGAACTATGTCNAAACACACGGCACCGGAACGGTGTTGGGGGACCCCATCGANTTCGAGTCGCTGGCGGCCA CTTATGGCCTGGGTAAAGGCCAGGGCNANAGCCCGTGCGCATTGGGGTCGGTCAAAACCAACATCGGCCACCTGGAGGCGGCCGCCGGTGTGGCTGGATNCAT CAAGGCGGTGCTGGCGGTGCAACGTGGGCACATTCCCCGCAACTTGCACTTCACCCGGTGGAACCCGGCCATCNACGCGTCGGCNACGCGGCTGTTCGTGCCN TABLE 3-continued End sequences of the polynucleotide inserts cloned in the named recombinant

ACCNAAAACCCCCCGTGGCCGGCGGC (SEQ ID NO. 444)

::::::::::::Rv340T7.seq::::::::::::
GGAACCGGTAACCAGATCAGCTCGTCGACCTCACTGCCGGGGGTGAATTCCCCACCGGTGCTGCGCGCTGCCCAGTAGTGCACCTTCTTGACGCCTCGAAAAG GGGAGTCGGTCGGGTAGGTCACCGTCAGGAGCCGCCTACCCAGGTTGGCGCNATAGCCGGTCTCCTCGAGTATCTCCCGCACCGCCCCCACCGGTGCGGTCTC ACCCANATCCACTTTGCCCTTGGGCAGCGACCAGTCGTCGTANCNGGGGCGGTGAATGACAACGATCTCGACCGGCCCTTCCN (SEQ ID NO. 445)

Clone Rv341
::::::::::::Rv341SP6.seq::::::::::::
TACTCAAGCTTCAGAACAGGCCTGTTGTGGGCNCACCCGGCTCGCCGAGTTCTGCACGCACCGCCTCAAGTGCGGCCCGCACCGCCGGCATCTCCCGGTCACG CAGGGCCGCGGCCCGCGCCGCAGCGACGGCGTGTTCGCGCAGTTCGCCGTCAATGATGCTGACCTGATCGGCCACCCGGGCGTTCTCGGCGTCGTCGCGTTCA

CTAATCGCGGTGCTCAGCAGCGTCTCGACAGCCACCACCCGAGTGGCGACCAGCTGC (SEQ ID NO. 446)

::::::::::::Rv341T7.seq::::::::::::
TAATGTCTTGCCAACGTCACCACAATCGCGATGAATTCAATCATGCCGCCCAGGGCGGCCAACCCAATGGTGGCCGCGAGCGGCAGCTCGATCGCAGCGCGGA GGTTGCCGGCCGCCAGTTGATTCACGAACAGGGTGAGGTCATAGGCGGGCAGGATAGTGACGAAGGCAAGACCTATATCTGCCGTCGGAAGAAGAATCGAGTA GCCGGTCGACACAACGGAAGCGAAAGTGTCCGCGATGTTGATGAGCGTCGCCGGTTGTGGCGGCGGTGGCGGC (SEQ ID NO. 447)

Clone Rv343
::::::::::::Rv343SP6.seq::::::::::::
TACTCAAGCTTTCGTCAGTTCATCGCGCCAGCAGACCAACAAGAGCATCGGGACATACGGAGTCAACTACCCGGCCAACGGTGATTTCTTGGCCGCCGCTGAC GGCGCGAACGACGCCAGCGACCACATTCAGCANATGGCCAGCGCGTGCCGGGCCACGAGGTTGGTGCTCGGCGGCTACTCCCAGGGTGCGGCCGTGATCGACA TCGTCACCGCCGCACCACTGCCCGGCCTCGGGTTCACGCAGCCGTTGCCGCCCGCAGCGGANNATCACATCGCCGCGATCGCCCTGTTC (SEQ ID NO. 448)

::::::::::::Rv341T7.seq::::::::::::
CCACCCGTGTAATTTGGGATGGGCNAAAAGGCNAAGCACCGCGTGGCCACGAACGCCGGGAGGGACAATCTCGGGCGGCTAGGGCTTCTCGCGGGAAGGCCCG AACGTACGGCGTTTCAACACGTCGCGTCGCCCTCCGACCGCGAACATTCGGGGATGGCAGCAACCTGGTAGCACCCTGGCCGGGCGATGATCTGCAGCGTCGC CGCGGGTAGTCGCCGCCCGGGCGGCTACAGTCTGAAACGCGATGACCATCGATGTGTGGATGCAGCATCCGACG (SEQ ID NO. 449)

Clone Rv344
::::::::::::Rv344SP6.seq::::::::::::
TCAAGCTTTAGCTGCCCGAATCCGTCANCCCGATGCNCCCAGATCGGGGCTTCGCANATAAAGCACNAACAGGCGGGCAAAACGTCNATCTCGGAGCCGGAAG GGCAATCANCCGACCGTCNACAAACGACACCGGCGANACCACTTAGGCAGTGACGGCCGGCCCGAACATTACNCGCTCGTTGATTAGGCGTTCGGTCTCGTCC GCGGTCATGCCGAGCAGCTTGCGGCANATCTGAACGCTGTCCTGTCCGGGCAGCGGCGCCGGGCGTTGGGGTGCCTGCGGAATGTGACNAAACGGAGCCGGAC

CCNTCTCGGCG (SEQ ID NO. 450)

::::::::::::Rv344T7.seq::::::::::::
CCGGGGCCACTCCGCACAATCNGTACCNNACCAANATCTACACCATCGAATACGACGGCGTCGCCGANTTTCCGCGGTACCCGCTCAACTTTGTGTCGACCCT CAACGCCATTGCCGGCACCTACTACGTGCACTCCAACTACTTCATCCTGACGCCGGAACAAATNGACGCNTCGGTTCCGCTGACCAATACGGTCGGTCCC (SEQ ID NO. 451)

Clone Rv346
::::::::::::Rv346SP6.seq::::::::::::
NCTGGCCTTTGGTCCACACTAANACAATACTCAAGCTTCCGGCCGCAGAGCCGCCAACTCACGATATCGTTAACCGATATCCCGAGCCGATAGCTGGCGGGCT CGGGTGGTGGCCAGCGGCGCTGCGACNAAAGGTGTGACCGTCATGAAACAGACACCACCGGCGGCCGTCGGCCGTCGTCACCTGCTCGANATCTCAGCATCCG CAGCCGGTGTGATCGCGCTTTCGGCGTGTNGTGGGTCNCCGCCCGAGCCCGGCAAAGGCCGGCCCGACACAACCCCGGAAC (SEQ ID NO. 452)

::::::::::::Rv346T7.seq::::::::::::
CATCTGCCCACCACACGGACCGCGGTGCGGACGCGGCTGACGCGCCTGGTGGTCAGCATCGTGGCCGGTCTGCTGTTGTATGCCAGCTTCCCGCCGCGCAACT GCTGGTGGGCGGCGGTGGTTGCGCTCGCATTGCTGGCCTGGGTGCTGACCCACCGCGCGACGACACCGGTGGGTGGGCTGGGCTACGGCCTGCTATTCGGCCT GGTGTTCTACGTCTCGTTGTTGCCGTGGATCGGCGAGCTGGTGGGCCCCGGGCCCTGGTTGGCACT (SEQ ID NO. 453)

Clone Rv347
::::::::::::Rv347SP6.seq::::::::::::
GACAATACTCAAGCTTGACTGGCCACCCACCGGCATGACCACCGACAGGCCCGACTGGTCGTACCACTCGAACGCCGGGGTGTTGATGTCCCAGCCGCTGAAN TABLE 3-continued End sequences of the polynucleotide inserts cloned in the named recombinant TCGTCCTGCGCGCGCAGGCCGTCNAACAGGTACAGGGCGGGCGAATTGGCACCACCACTTTGGAATTGGACCTTGATGTCACGGCCCATCGACGGCGACGGCA CCTGCAGGTACTCCACCGGCAAGCCCGGCCGGGAAAATGCCCCCGCGGTCNCCGTGCCACCGACGGCGCCGANCAAACCCGACACTAGGGCCGCGCCNACGGC

CCCGACCACNANTCNACGCGACATACCCGTGACGGCGCCACNAACCCTGTCAACA (SEQ ID NO. 454)

::::::::::::Rv347T7.seq::::::::::::
CCTCCAACTCGGCGGGGAAGCGACNCCAGCCTACCGAGCTTGGAGTCCANGACGCCAGCGGCGGCGTCGGTCTGCGTCGTGGTGCCGCCGGGGTGGCGTTGGC TGGCAACGATCTCCACCCAGCCGGTCGGGTTACCCACGATCTCGGCATANACGCGGGCCGAGGCCGGTGCGATACCGTATTGCGTCAATTGGGACGCGGTTGT GCATTCGGCTAGCTCGGTTGCCACACCCGTCAGGGGTTCGACGTTGGCGGGTTCGGCGGGCCCCANCACCGCTGTCACCATGCCCGCCAAGCCGACCTGCGGC

GCCACCAACTGCAGCACCANCATGTCGCCGTCGCGCGCCGCGATCACATGG (SEQ ID NO. 455)

Clone Rv348
::::::::::::Rv348SP6.seq::::::::::::
CTCAAGCTTTTTGAGCGTCGCGCGGGGCANCTTCGCCGGCAATTCTACTANCGAGAANTCTGGCCCGATACGGATCTGACCGAANTCGCTGCGGTGCANCCCA CCCTCATTGGCGATGGCGCCGACNATGGCGCCTGGACCGATCTTGTGCCGCTTGCCGACGGCGACGCGGTAGGTGGTCAAGTCCGGTCTACGCTTGGGCCTTT GCGGACGGTCCCGACGCTGGTCGCGGTTGCGCCGCNAAAGCGGCGGGTCGGGTGCCATCAGGAATGCCTCNCCGCCGCGGCACTGCACGGCCAGTGCCGCGGC

GA (SEQ ID NO. 456)

::::::::::::Rv348T7.seq::::::::::::
CNCCAGCTTGATTGGTCTGGTTGCATTGGCCAGCTGCGCGAGCCTGGCTCACTTCAACTACGACGACCGCAAACAATTGCCGCCTTCGGATCCGAGTTCGGTT GGGTACGCGGCAATGGAGCACCATTTCTCGGTGAATCAGACTATTCCTGAGTACTTGATCATCCACTCTGCACACGACCTGCGAACCCCGCGCGGCCTTGCCG ACCTGGAGCAGCTGGCGCAACGTGTGAGCCAGATCCCAGGCGTTGCCATGGTTCGCGGTGTGACCCGGCCAAACGGGGAAAC (SEQ ID NO. 457)

Clone Rv349
::::::::::::Rv349SP6.seq::::::::::::
CAATACTCAAGCTTGACTGGCCCGCACCTTCGGCGCCACCCACACCGTCAACGCCCGCGAAGTCNACGTCGTCCAGGCCATCGGCGGCCTCACGGATGGATT CGGCGCGGACGTGGTGATCGACGCCGTCGGCCGACCGGAAACCTACCAGCAGGCCTTCTACGCCCGCGATCTCGCCGGAACCGTTGTGCTGGTGGGTGTTCCN

ACGCCCGACATGCGCCTGGACATGCCGCTGGTCNACTTCTTCTCTCACGG (SEQ ID NO. 458)

::::::::::::Rv349T7.seq::::::::::::
TCGACGGTTTGGCGGCCTTAAATGCACTGAGGTCGTCAATTGACCCCACAGCGGAAATGCCGACTATTCGCAGGCCTCCTTCGCCTTGGCTGCCGGAGAGGGG CTCCGCGGGAACCGCATGCAGGTATATGACCTCGGTTTCTCGGGTGCTACCGCGTGCCTTGTNTANGATNANCTCGGCGTTGGAATTGTCCAGCCGGCCCAAT TCATCGAGCGCANATTCGTACACNTGGCCGGCGGCGACATACGCTTCACCGTGGATCTGCTCCACACGGACCGCCCTGTCGGGATCCTGCTCACGGGTAANGG

AACTTACGTGGCACTCGG (SEQ ID NO. 459)

Clone Rv34
::::::::::::Rv34SP6.seq::::::::::::
GACCACGCCAGGCTAATCACGTGACGCTACCGAATACCCTNCCTAGTGGTGCAGGCTCCCGCTGGAAATGGCCCTGTACCAACTCGCGCACCGGTGCCAG (SEQ ID NO. 460)

::::::::::::Rv34T7.seq::::::::::::
CGGCACCCGACCCCTTTGAGCCGTCCGCCGTGGCCGCGGTGGAACTGGCCGACGAGGGACTGATCGTGCTGGGCAAATTGGTCGATGGCACGCTGGCCGCCGA

TCTGAAGGTCN (SEQ ID NO. 461)

Clone Rv350
::::::::::::Rv350SP6.seq::::::::::::
CTCAAGCTTGCCGTTACCCCGACTTCCGGAGGGACACCATGAGCACCGCCAGCCGAGCACGAGGCCAAACTCCGCCGACGCAGGCCGGTTGGACTTGTCGTGC TGGACAAGGGGTTTAGCCGCCGAAGCAGTGACGTACATCGGCGAAAAGCAGTTCGCCTGTCGACCGACGGNGCNNACCGTGAGGCTAGGGAAGCGAGGAGCAC ATGGCCGCCGACCCGCAATGTACACGCTGCAAGCAAACCATCGAACCCGGATGGCTATNCNTCACCGCCCATCGCCGCGGT (SEQ ID NO. 462)

::::::::::::Rv350T7.seq::::::::::::
CATGTCGCGCACATCCAGGACTTCTGGGGGGATCCGCTGACAGCGGCGGGATCCCAAAGTGCGGATGATCGGGCCGCCTACGTCGTGGTGTACCTCGTCGGTA ACAACGAAACCGAAGCGTATGACTCGGTCCACGCGGTGCGGCACATGGTGGACACCACACCGCCACCGCACGGGGTGAAGGCCTATGTCACCGGTCCGGCAGC ACTCAATGCCGACCAGGCCGAGGCCGGAGACAAAAGTATCGCTAAGGTCACCGCGATCACGAGCATGGTGATCGCAGCAATG (SEQ ID NO. 463)

Clone Rv351

TABLE 3-continued

End sequences of the polynucleotide inserts cloned in the named recombinant

::::::::::::Rv351SP6.seq::::::::::::
ATACTCAAGCTTCGGTACGGTGGCGGGCCGTGCTGCTGGCCGCGGTCGCGGCGTGCGCGGCCTGCGGTCTCGTTTACNAGCTCGCGCTGCTGACACTGGCGGC NAGCCTGAACGGCGGCGGGATCGTGGCCACCTCCCTGATCGTCGCGGGCTACATAGCCGCGCTGGGAGCAGGCGCCTTGCTGATCAAGCCGCTACTTGCACAC

GCGGCCATCGCGTTCATCGCCGTGGAGGCGGTGCTGGGCATCATCGGCG (SEQ ID NO. 464)

::::::::::::Rv351T7.seq::::::::::::
TGTCAAGTCCTTTCAGATCTCNTTTTTATGACATGACTGGAGATCTGTCTAGATTGCAGCTCCTGTGAGCGTGGGTACCGGATTCAAGCCGGTCGGTCACGCC GCGGTGGTACCGGCTTTGCGGCAGTGCTCGGCCTCGAGTTCGGCGATCGCGCGCGAAGTGCGTTCGCGCAGCAAGATCGCGGCCGTAATGCCGGCGATGACCG CGATGACCAGCGCGATCCAGGAGAACCGTTCCAACCAGTGCTGGGCGGCCATCCCGGCGAAGTAGACCAGTGCAGTGGTGCC (SEQ ID NO. 465)

Clone Rv352
::::::::::::Rv352SP6.seq::::::::::::
CAATACTCAAGCTTCAAAACAGGCCTGTTGTGGGCGCACCCGGCTCGCCGAGTTCTGCACGCACCGCCTCAANTGCGGCCCGCACCGCCGGCATCTCCCGGTC ACGCAGGGCCGCGGCCCGCGCCGCANCGACGGNGTGTTCGCGCAGTTCGCCGTCAATGATGCTGACCTGATCGGCCACCCGGGCGTTCTCGGCGTCGTCNCGT

TCACTAATCGCGGTGCTC (SEQ ID NO. 466)

::::::::::::Rv352T7.seq::::::::::::
TACGCTGGCGCTGGAGGGAGCCANNTACAACATCCACGCCAATGCTCTTGCCCCGATCGCGGCGACCAGGATGACCCAGGACATCCTGCCGCCCGAAGTACTG GAAAAGCTCACACCCGAGTTCGTCGCACCGGTGGTGGCCTACCTGTGCACCGAGGAGTGTGCCGACAACGCATCGGTGTACGTCGTCGGTGGTGGCAAGGTGC AGCGAGTTGCGCTGTTTGGCAACGACGGCGCCAACTTCGACAAACCGCCGTCGGTACAAGATGTTGCGGCGCGGTGGGCCGAGATCACCGATCTGTCCGGTGC

GAAAATTGCTG (SEQ ID NO. 467)

Clone Rv353
::::::::::::Rv353SP6.seq::::::::::::
GCTTTTCCCGTCCGTCNNCGCTCAACCGCGTGAGGCCGAAGCCGNTGGTTACGACTCCCTGTTTGTGATGGACCACTTCTACCAACTGCCCATGTTGGGGACN CCCGACCAGCCGATGCTGGAGGCCTACACGGCCCTTGGTGCGCTGGCCACGGCGACCGANCGGCTGCNNNTGGGCGCGTTGGTGACCGGCAATACCTACCGCA GCCCGACCCTGCTGGCAAANATCATCACCACGCTCGACGTGGTTAGCGCCGGTCGAGCGATCCTCGGCATTGGAGCCGGTTGGTTTGANCTGGAACA (SEQ ID NO. 468)

::::::::::::Rv353T7.seq::::::::::::
CNGCTTTTTAATGGCCTTGACNTGGGCGNGCCGGCCACCGGGGCCACTCCGCACAATCTGTACCCGACCAAGATCTACACCATCGAATACGACGGCGTCGCCG ACTTTCCGCGGTACCCGCTCAACTTTGTGTCGACCCTCAACGCCATTGCCGGCACCTACTACGTGCACTCCAACTACTTCATCCTGACGCCGGAACAAATTGA CGCAGCGGTTCCGCTGACCAATACGGTCGGTCCCACGATGACCCAGTACTACATCATTCGCACGGAGAACCTGCCGCTGCTAGAGCCACTGCGATCGGTGCCG ATCGTGGGGAACCCACTGGCGAACCTGGTTCAACCAAACTTGAAGGTGATTGTTAACCTGGGCTACGGCGACCCGGCCTATG (SEQ ID NO. 469)

Clone Rv354
::::::::::::Rv354SP6.seq::::::::::::
CTCAAGCTTGCCGGGAGGGTGCATGGCCGACTCGGATTTACCCACCANGGGGCGCCAACGCGGTGTCCGCGCCGTCNAGCTGAACGTTGCTGCCCGCCTGGAG AACCTGGCGCTGCTGCGCACCCTGGTCGGCGCCATCGGCACCTTCGAGGACCTGGATTTCGACGCCGTGGCCGACCTGAGGTTGGCGGTGGACGAGGTGTGCA CCCGGTTGATTCGCTCGGCCTTGCCGGATGCCACCCTGCGCCTGGTGGTCGATCCGCGAAAANACGAANTTGTGGTGGAGGCTTCTGCTGCCTGCGACACCCA

CNACGTGGTGGCACCGGGCAGCTTTAGCTGGCAT (SEQ ID NO. 470)

::::::::::::Rv354T7.seq::::::::::::
CCGACGCCGTCGTGGCCACCAACACCGCGACCAGCACCGTGACCCGGACCGGGGTGCCGCGCGAACCGGTCTTGGCCAATTGCCGCGGCACCAAGCCGTCGCG CGCCATGGCGAACAGCACGCGGCATTGCCCGAGCATCAACACCATCACCACCGTGGTAAGCCCGGCCAGCGCGCCGACGGAGATGATGCCGCTGGCCCAGTAC ACCCCGTTGGCCTGGAACGCGGTGGCCAGATTTGCCGGCCCGCGGCCCGGTACGGTCCGCAGTTGGGTGTATGGAACCATGCCCGACAGCACCACCG (SEQ ID NO. 471)

Clone Rv355
::::::::::::Rv355SP6.seq::::::::::::
TTNACTGGCCTTTGGTCCACACTAGACAATACTCAAGCTTCCAGGACATCGTCATCGCGACCAAAACCGCGAGCTAGGTCGGCATCCGGGAAGCATCGCGACA CCGTGGCGCCGAGCGCCGCTGCCGGCAGGCCGATTAGGCGGGCAAATTAGCCCGCCGCGGCTCCCGGCTCCGANTACGGCGCCCCGAATGGCGTCACCGGCTG

GTAACCACGCTTGCGCGCCTGGGCGGCGGCCTGCCGGATCAGGTGGTAAATGCCGACA (SEQ ID NO. 472)

TABLE 3-continued

End sequences of the polynucleotide inserts cloned in the named recombinant

::::::::::::Rv355T7.seq::::::::::::
NGACGTCTTCCATCCGCGCGTCGTTTTGGCGGGTTGGCCACAGCAGCCCGCCGGTGACGGCGACGATGCTGGGCTGGTTGCGGCCCTGCGCCACCGCGGCTTG CATGCTGGTTGGCTGTCTTGGGACGATCCCGAAATAGTCCACGCGGATCTGGTGATTTTGCGGGCTACCCGCGATTACCCCGCGCGGCTCGACGAGTTTTTGG CCTGGACTACCCGCGTGGCCAATCTGCTGAACTCGCGGCCGGTGGTGGCCTGGAATGTCGAGCGCCGTTACCTA (SEQ ID NO. 473)

Clone Rv356
::::::::::::Rv356SP6.seq::::::::::::
CTTCCTCCTGAGTACCNCCCGTNTACTTTGGGATGGGTAAAAAGGCGAATCNCCGTTTGGTCACGAACGCCGGGAGGGACAATCTCGGGCGGCTGGGGCCTCT

CGCGGGAANGCCCGAATGTACGGTGTCTCGACACTTCCCNTCCCCCTCCG (SEQ ID NO. 474)

::::::::::::Rv356T7.seq::::::::::::
GAGCATCGGGACNTACGGAGTCAACTACCCGGCCAACGGTGATTTCTTGGCCGCCGCTGACGGCGCGAACGACGCCNGCGACCACATTCAGCAGATGGCCAGC GCGTGCCGGGCCACGAGGTTGGTGCTCGGCGGCTACTCCCAGGGTGCGGCCNTGATCNACATCGTCACCGCCGCACCACTGCCCGGCCTCGGGTTCACGCAGC

CGTTGCCGCCCNCAGCGGACGATCACNTCGCCGCGATCGCC (SEQ ID NO. 475)

Clone Rv357
::::::::::::Rv357SP6.seq::::::::::::
TACTCATGANCATCCTTTAATCANNGCTTTGCGTTTTTTTATTAAATCTTGCAATTTACTGCAAAGCAACAACAAAATCGCAAAGTCATCAAAAAAACCGCAAA GTTGTTTAAAATAAGAGCANCACTACAAAAGGAGATAAGAAGAGCACATACCTCAGTCACTTATTATCACTAGCGCTCGCCGCAGCCGTGTAACCGAGCATAG

CGAGCGAACTGGCGAGGAAGCAAAGAAGAACTGTTCTGTCAGATAGCTCTTACGCNCA (SEQ ID NO. 476)

Clone Rv358
::::::::::::Rv358SP6.seq::::::::::::
CTCAAGCTTCAGGTCAATGTGCNCCAAGCCCTGACGCTGGCCGACCAGGCCACCGCCGCCGGANACNCTGCCAAGGCCACCGAATACAACAACGCCGCCGAGG CGTTCGCANCCCAGCTGGTGACCGCCGAGCANANCGTCAAAAACCTCAAGACGCTGCATGACCAGGCGCTTANCNCCGCANCTCAGGCCAAGAAGGCCGTCNA

ACGAAATGCGATGGTGCTGCACCANAAGATCGCCGAGCGAACCAAGCTGCTCAGCCNG (SEQ ID NO. 477)

::::::::::::Rv358T7.seq::::::::::::
CATGGTGGCACTGTAGCGACGTGCTGCAATCAAGGTCATGCCCGACTCTGGTCAGCTCGGANCCGCTGACACCCCGCTAAGGCTGCTCAGCTCGGTGCATTAC CTCACCGACGGCGAACTCCCCCAGCTTTACGCATATCCGGATGACGGCACCTGGTTGCGGGCGAACTTCATCATCAGCTTGGACGGCGGCGCTACCGTCGATG GCACCAGCGGGGCGATGGCCGGGCCCGGCGACCGATTCGTCTTCAACCTGTTGCGTGAACTTGCCGACGTCATCGTGGTCGGCGTGGGCACCGTGCGCATTGA

GGGCTACTCCGGCGTCCGGATGGGTGTCGTCCAGCGCCAGCAC (SEQ ID NO. 478)

Clone Rv359
::::::::::::Rv359SP6.seq::::::::::::
TACTCAAGCTTGCGGGTGATCGCCTTGGTCAACGGCACCGTGATCGGATCGGGGTCNACCGCACAAATGGACTGGAGCTTCGGCGAANTCATCGCCTATGCCT CGCGGGGGGTGACGCTGACCCCGGGTGACNTGTTCGGCTCGGGCACGGTGCCCACCTGCACGCTCGTCTATCACCTCNGGCCACCGGAATCATTCCCGGGCTG

G (SEQ ID NO. 479)

::::::::::::Rv359T7.seq::::::::::::
GTTGGNGCCTCGTCGGCGAACAGTTCTCGCACGATTTCCGGATTAGCGGGACTGGTCACCAGTTGGGTATGCGGGAAGGCGCTGACGTTCGCCCGCGATTAGCT GTTTGATGGACGCGGTGGTGATGTTCTGATCACGGAACTGGCTGTAATAGCCCAGGGTCGCCACGCTTTCATCCGGGCCCGGACCCGGCGCACCGAGCGTGTC

GCGCAGGTATGCGACGTGATTTTCGCTGAAGTCCCCGTACCCGGAGAACT (SEQ ID NO. 480)

Clone Rv35
::::::::::::Rv35SP6.seq::::::::::::
TGCTTCCGGCTCGTATGTTGTGTGGAATTGTGANCGGATAACAATTTCACACAGGAAACAGCTATGACCATGATTACGCCAAGCTATTTAGGTGACACTATAG AATACTCAAGCTCCAGGTCAATGTGCGCCAAGCCCTGACGCTGGCCGACCAGGCCACCGCCGCCGGAGACGCTGCCTTTGTCACCGAATACAACAACGCCGCC GAGGCGTTCGCAGCCCAGCTGGTGACCGCCGAGCAGAGCGTCGAAGACCTCAAGACGCTGCATGACCAGGCGCTTAGCGCCGCAGCTCAGGCCAAGAATGCCG TCGAACGAAATGCGATGGTGCTGCGGCATAAGATCGCCGAGCGAACCAAGCTGCTCAGCCAGCTCGAGCAGGCGAAGATGCACGAGCA (SEQ ID NO. 481)

::::::::::::Rv35T7.seq::::::::::::
CAGGCATGCAAGCTTCGGAGGCAGACCCGTGCATGGTGGCACTGTAGCGACGTGCTGCAATCAAGGTCATGCCCGACTCTGGTCAGCTCGGAGCCGCTGACAC CCCGCTAAGGCTGCTCAGCTCGGTGCATTACCTCACCGACGGCGAACTCCCCCAGCTTTACGACTATCCGGATGACGGCACCTGGTTGCGGGCGAACTTCATC TABLE 3-continued End sequences of the polynucleotide inserts cloned in the named recombinant AGCAGCTTGGACGGCGGCGCTACCGTCGATGGCACCAGCGGGGCGATGGCCGGGCCCGGCGACCGATTCGTCTTCAACCTGTTGCGTGAACTTGCCGACGTCA TCGTGGTCGGCGTGGGCACCGTGCGCATTGAAGGCTACTCCGGCGTCCGGATGGGTGTCGTCCATCGCCA (SEQ ID NO. 482)

Clone Rv360
::::::::::::Rv360SP6.seq::::::::::::
TACTCAAGCTTGGGGTGGCGCTGTCGGTCGGTGTGCTTGGCGGCGTCGGTATCAACACCGCCCACGAAATGGGGCACAAGAAGGATTCGCTGGAGCGGTGGCT GTCCAAAATCACCCTCGCCCANACCTGCTACGGGCACTTCTACATCGAGCACAACCGTGGCCATCACGTCCGGGTGTCCACACCGGAGGACCCGGCGTCGGCG

CGGTTCGGCNAAACGTTGTGGGANTTCCTGCCCCGCANTGTTATCGGCGGCTTGCGCT (SEQ ID NO. 483)

::::::::::::Rv360T7.seq::::::::::::
GGCCATCGCCACCGCNCCGCGGCGAACGCTCAAAGGCACCTACTGGCACCAAGGCCCCACACGTCACCCTGTGACCTCCTGCGCCGACCCCGCCCGAGGTCCT GGCCGTTACCACCGAACGGGCGAGCCGGGAGTCTGGTACGCATCGAACAAAGAGCAAGGTGCATGGGCGGAGTTGTTCCGCCACTTCGTCGATGACGGGGTCG ATCCATTCGAGGTCCGTCGCCGCGTCGGTCGAGTGGCGGTCACACTCCANGTACTCGACCTCACAGACGAGAGGACTCGATCCCATCTAGGTGTGGACGAAAC

AGATCTTCTGTCCGACGACTACACCACCACCCAGGCCATCGC (SEQ ID NO. 484)

Clone Rv361
::::::::::::Rv361SP6.seq::::::::::::
GCTTGCGGGTGATCGCCTTGGTCAACGGCACCGTGATCGGATCGGGGTCNACCGCNCAGATGGACTGGANCTTCGGCGAANTCNTCGCCTATGCCTCGCGGGG GGTGACCCTGACCCCGGGTGACNTGTTCGGCTCGGGCACGGTGCCCACCTGCACGCTCGTCAAGCACCTCNGGCCACCGGAATCATTCCCGGGCTGGCTGCAC NACGGCGACNTGGTCNCCCTCCAGGTCGAAGGGCTGGGCNAAACAANGCAGACCGTCCGGACAANCGGCACTCCTTTTCCGTTGGCTCTTCGGCCGAATCCGG

ACGCCNAACCCGACCGGCG (SEQ ID NO. 485)

::::::::::::Rv361T7.seq::::::::::::
GTTCTCGCACGATTTCCGGATTAGCGGGACTGGTCACCAGTTGGGTATGCGGGAAGGCGCTGACGTTCGCCGCGATTAGCTGTTTGATGGACGCGGTGGTGAT GTNCTGATCACGGAACTGGCTGTAATANCCCAGGGTCGCCNCGCTTTCATCCGGGCCCGGACCCGGCGCACCGAGCGTGTCGCGCAGGTATGCGACGTGATTT TCGCTGAAGTCCCCGTACCCGGAGAACTCGAACACGCTGAGGCGCTCGTCACCGTCGTNNCGGCGACCAAGCGCGGCGAGCAACTGCGCAAAATCGTTAAGAN

AGGTCGAATCGTTGAAATTCGGCACCACCTGCACC (SEQ ID NO. 486)

Clone Rv363
::::::::::::Rv363SP6.seq::::::::::::
CACAAGACAATACTCAAGCTTCAGGTCAATGTGCNCCAAGCCCTGACGCTGGCCGACCAGGCCACCGCCGCCGGANACGCTGCCAAGGCCACCGAATACAACA ACGCCGCCGAGGCGTTCGCAGCCCAGCTGGTGACCGCCGAGCANANCGTCNAAAACCTCAAGACGCTGCATGACCAGGCGCTTANCGCCNCAGCTCAGGCCAA GAAGGCCGTCGAACGAAATGCGATGGTGCTGCAGCANAANATCGCCGANCGAACCAAGCTGCTCAGCCAGCTCGAGCAG (SEQ ID NO. 487)

::::::::::::Rv363T7.seq::::::::::::
CCACCCGTGCATGGTGGCACTGTAGCGACGTGCTGCAATCAAGGTCATGCCCGACTCTGGTCAGCTCGGAGCCGCTGACACCCCGCTAAGGCTGCTCAGCTCG GTGCATTACCTCACCGACGGCGAACTCCCCCAGCTTTACGACTATCCGGATGACGGCACCTGGTTGCGGGCGAACTTCATCAGCAGCTTGGACGGCGGCGCTA CCGTCGATGGCACCAGCGGGGCGATGGCCGGGCCCGGCGACCGATTCGTCTTCAACCTGTTGCGTGAACTTGCC (SEQ ID NO. 488)

Clone Rv364
::::::::::::Rv364SP6.seq::::::::::::
GCTTTCCGCCGATACCCNCCATGTCCCGCACATCCAGGACTTCTGGGGGGATCCGCTGACAGCGGCGGGATCCCAAAGTGCGGATGATCGGGCCGCCTACGTC

GTGGTGTACCTCGNCGGTAACAACGAAACCGAANCGTATGACTCNGTCCACGCGGTG (SEQ ID NO. 489)

::::::::::::Rv364T7.seq::::::::::::
CAACCCGANTTGGCTTTCGGCGCCNTCGGTGAGGACGGCGTGCGGGTGCTCAACGACGACGTCGTCCGCGGGACACACCTCGATGCTGCCGCCATGGACGCGG TCGAACGCAAGCAGCTGATCGATCTACNACGCCGNGNGGAACGCTTCNGCCGCGGGCGTGACCGCNTCCCGTT (SEQ ID NO. 490)

Clone Rv365
::::::::::::Rv365SP6.seq::::::::::::
GGGATGGGCAAAAAGGCGAAGCACCGCGTGGCCACGAACGCCGGGAGGGACAATCTCGGGCGGCTAGGGCTTCTCGCGGGAAGGCCCGAACGTACGGCGTTTC AACACGTCGCGTCGCCCTCCGACCGCGAACATTCGGGGATGGCAGCAACCTGGTAGCACCCTGGCCGGGCGATGATCTGCCAGCGTCCCCGCGGGTAGTCGCC

GCCCGGGCGG (SEQ ID NO. 491)

::::::::::::Rv365T7.seq::::::::::::
CAGCAGACCAACAAGAGCATCGGGACATACGGAGTCAACTACCCGGCCAACGGTGATTTCTTGGCCGCCGCTGACGGCGCGAACGACGCCAGCGACCACATTC TABLE 3-continued

| End sequences of the polynucleotide inserts cloned in the named recombinant |
|---|

AGCAGATGGCCAGCGCGTGCCGGGCCACGAGGTTGGTGCTCGGCGGCTACTCCCACGGTT (SEQ ID NO. 492)

Clone Rv366
::::::::::::Rv366SP6.seq::::::::::::
CTCAAGCTTGACTGGCCACCCACCGGCATGACCACCGACAGGCCCGACTGGTCGTACCACTCGAACGCCGGGGTGTTTGA (SEQ ID NO. 493)

::::::::::::Rv366T7.seq::::::::::::
TTGGTGCCCGGAATGGCGAGTCCCATTTANTCGCTGATTTGTTTGAACAGCGACGAAACCGGTGTTGAAAATGTCGCCTGGGTCGGGGATTCCCTCTCCAAGC AAGAGTAACTGGCCCCAAATAAAGTTACTCGTCGTCTTGCAAAGACCGCTACCCGATGCCATTTATGTGTTTCCTTACGCTCNNNNTTCCGGTGCGCCATCAT

TATCTGCACCTTTGCACTGCACATTGAGCTTAGCAGCGCTCG (SEQ ID NO. 494)

Clone Rv367
::::::::::::Rv367SP6.seq::::::::::::
GAATTNGCTTTCGGCGCCATCGGCCCAGGACCGCGTGCGGGTGCTCAACGACGACGTCGTCCGCGGGACACACCTCGATGCTGCCGCCATGGACGCGGTCGAA CGCAAGCAGCTGATCGAGCTACAACGCCGCGCGGAACGCTTCCGCCGCGGGCGTGACCGCATCCCGTTGACCGGGCGGATCGCNGTGATCGTCGATGACGGCA TCGCCACCGGAGCGACGGCCAAGGCGGCGTGCCAGGTCGCCCGGGCGCACGGTGCGGACAAGGTGGTGCTGGCGGTCCCGATCGGCCCAGACGACATCGTGGC

GAGATTCGCCGGGTACGCCGATGAAGTGGTGT (SEQ ID NO. 495)

Clone Rv368
::::::::::::Rv368SP6.seq::::::::::::
TAAAGCTTTCGTCAGTTCATNGNGCCCCCGGACCAACAAAAGCATCGGGACATACGGAGTCAACTACCCGGCCAACGGTGATTTCTTGGCCGCCGCTGACGGC GCNAACGACGCCAGCGACCACATTCAGCAGATGGCCAGCGCGTGCCGGGCCACGAGGTTGGTGCTCGGCGGCTACTCCCAGGGTGCGGCCGTGATCNACATCG TCACCGCCGCACCACTGCCCGGCCTCGGGTTCACGCAGCCGTTGCCGCCCGCAGCGGACGATCACNTCGCCGCGATCGCCCTGTTCGGGAATCCCTCGGGCCG CGCTGGCGGGCTGATGAGCGCCCTGACCCCTCAATTCGGGTCCAANACCATCNACCTCTGCAACAACGGCGACCCGATTTGTTCGGACGGCAACCGGTGGCGA

NCGCACCT (SEQ ID NO. 496)

::::::::::::Rv368T7.seq::::::::::::
CCGGGAGGGACCATCNCGGGCGGCTNCGGCTTCTCTCCGGAAGGTTCTANNGTNNNGCGTTTCNACNCTTCCCGTCGCCCTGCGACCGCCGAACATTCGGGGT

ATGGNNGCANCCTGTNAGCATCCNGGCCGGGC (SEQ ID NO. 497)

Clone Rv369
::::::::::::Rv369SP6.seq::::::::::::
CTCAAGCTTCCGCATCAGATCGCTATAGAACCGGTGCGCGTCCCCACCGAGTGGCTGGTCGCCTTCCAGCACGATCGTTACCGCGTTATCGGAATCAAACTCN CCGAACACCTGACCAACGCGCTTGATCGCCTGAATCGATGCGGCGTCGCTGGGGCTCATCGATACCGAGTGTGCTTTTCCGACCACTTCCAGTTGCGGTACGG CGAGATTGACAAAGGCGGTGAAGCCCAGCCAGAGCAGGACGATCACCNCCGCAAACCGGCGGATTTGCCCG (SEQ ID NO. 498)

::::::::::::Rv369T7.seq::::::::::::
GCTTGGCAGCCTGCGGCTGGGCGCCCTNGAGCTCTTCGATCTGGATCTCCGGACTCGAGATGCTCACTTGCCCGGCCGTGGACGTACCCATTGCGGCCGGGAC CCCAGCGCCCCAGGTGACCAGCGAGTTGGGCTGCACGCTGACCGGCCCGTCGGGGTCGACGCCGGTAACGGTCAGCAGCTCCGANGTCCNNCTGATCCCGACC GCAGCTGCCAATGCGCGGCTGGCAGCCGACGTGGATGTGCCGGGGCCTAGATCGCGGGGCAGCAGCGAGACCGCGTCACCGACGGTCATCACCTTGCCGAGTT

TNGGCCTGCCGCAN (SEQ ID NO. 499)

Clone Rv36
::::::::::::Rv36SP6.seq::::::::::::
GCTTCCGGCTCGTATGTTGTGTGGAATTGTGAGCGGATAACAATTNCACACAGGAAACAGCTATGACCATGATTACGCCAAGCTATCTAGGTGACACTATAGA

ATACTCAAGCTTGAGCCATCGGGCTATCAGCTGGTTGATGTCCCG (SEQ ID NO. 500)

::::::::::::Rv36T7.seq::::::::::::
CAGGCATGCAAGCTTGTCGTCTATCACATCCGACCACCAACCGCCCGACGGCTCGGCAGAACGCCTCCGCATATGGGTCGACGACCAGCGGGTCGGACTTCTG GGCTGCCAGCGCTCGCGCCGTCGCGACAAACAGCGCGGTCGAACCGACACTCCTTGTGATGTCCCACCTATCACCTTCGGTACGCACCCAATCGACCCTACGC

GGCTAGCTCAGCCCCGATCTTCCAGAGCTCCGCCCG (SEQ ID NO. 501)

Clone Rv370
::::::::::::Rv370SP6.seq::::::::::::
GCTTTTTGAGCGTCGCGCGGGGCGGCTTCCCCGGCAATTCTACTAGCGAGAAGTCTGGCCCGATACGGATCTGACCGAAGTCGCTGCGGTGCAGCCCACCCTC ATTGGCGATGGCGCCGACNATGGCGCCTGGACCGATCTTGTGCCGCTTGCCGACGGCGACGCGGTAGGTGGTCAATTCCGGTCTACGCTTGGGCCTTTGCGGA

CGGTCCCGACGCTGGTCGCGGTTG (SEQ ID NO. 502)

TABLE 3-continued

End sequences of the polynucleotide inserts cloned in the named recombinant

::::::::::::Rv370T7.seq::::::::::::
CGANCCTGTTCGACGGCTACCTGAATCACCCCGATNCCACCGCCGCGGCGTTCGACGCCGACAGCTGGTACCGCACCGGCGACGTCGCGGTGGTCGACGGCAG TGGGATGCACCGCATCGTGGGACGCGAGTCGGTCGACTTGATCAAGTCGGGTGGATACCGGGTCGGCGCCGGTGAAATTGAAACGGTGCTGCTCGGGCATCCG

GACGTGGCGGAGGCGGCAGTCGTCGGGGT (SEQ ID NO. 503)

Clone Rv371
::::::::::::Rv371SP6.seq::::::::::::
NAAGCTTTGTCACACCAAGTGTTTCNACCAGNCGCTCCATCCGGCGAAGTGGATACTCCCAGCAGGTAGCAGGTCGCCACCACGCTGGTCAGTGCGCGTTCAG

CTCGCTTGCGGCGCTGCAGCAGCCAGTCCGGGAAATAGCTGCCCTGGCG (SEQ ID NO. 504)

::::::::::::Rv371T7.seq::::::::::::
CGCTGGNCGCCGGCGCTGGGCTGCGGTAACCAATTACCACAACACTTTTCGGTAGCCGAACAGCGGCGCGTACCAGCGAAATGGCACAGCCACCGCAGTCGCC GACATCCCGCGAAGATGTGGCAGATTTTCGTGCGGTCGAGCCGGCGAAGGCCTAGCGTCATTGTTGCCTGGCAAGGTTGCTGGGCCCGG (SEQ ID NO. 505)

Clone Rv373
::::::::::::Rv373SP6.seq::::::::::::
CTCAAGCTTCTTCTGCCCCTTGCCGTTNCGGATNACATCCCGCAGCGACTCGGCTTCGGCGTCGATGTCGAAGTTCTCGATCAGCTTCTGGATCGACTCCGCG CCCATGGCACCGGTGAAGTACTCGCCGTAGCGGTCGACNAGTTCGCGGTAGAGGTTTTCGTCNACNATCAGCTGCTTGGGCGCCANCTTGGTGAAAGTGCTCC AAATGTCCTCCAACCGGTCCAGCTCACGCTGCGCGCGGTCACGGATCTGGCGCATCTCGCGCTCGCCGCCGTCGCGAACTTGCGCCGCGCATCGGCCTTGGGG

CCC (SEQ ID NO. 506)

::::::::::::Rv373T7.seq::::::::::::
GTTCACACCTACCTACTATGCCNCAATTCNCCGACACGGGTGGCATCAACACGGGCGATAAGGTGGAAATCGCTGGGGTGAACGTCGGGCTGGTGCGCTCGCT GGCAATCCGCGGCAACCGCGTGTTGATCGGATTCTCGTTGCCCGGCAAGACAATCGGGATGCAAAGCCGGGCAGCAATTCNCNCCNACACCATTCTTGGCCGT AAGAACCTGGAGATCGAACCCCGCGGTTCGGAGCCGTTGAAACCCAACGGTTTCCTGCCGTTGGCGCANACCACTACGCCATACCAAATC (SEQ ID NO. 507)

Clone Rv374
::::::::::::Rv374SP6.seq::::::::::::
CTCAAGCTTTACGCCGACGCCGGCCTACACAACACCAAGGAAACGATTGCCTACTGCCGAATCGGGGAACGGTCCTCGCACACCTGGTTCGTGTTGCGGGAAT TACTCGGACACCAAAACGTCAAGAACTACGACGGCAGTTGGACAGAATACGGCTCCCTGGTGGGCGCCCCGATCGAGTTGGGAAGCTGATATGTGCTCTGGAC

CC (SEQ ID NO. 508)

::::::::::::Rv374T7.seq::::::::::::
TCCCNCATGGGATAACGGGTTTAGATTTCNACAACGGCACCGTGTTTCTCAACAAGCCGGTCATCAGCTGGGCCGGCGACAACGGTATCTACTTCACCCGCTT TCGCCCGTACAAGAAAAACCACTAGGCCACCATCGAGTCCAAGAACAACCACCTGGTCCGCAAGTACGCGTTCTACTACCGCTATGACACCGCCGAGGAACGC GCCGTGCTCAACCGGATGTGGAAGCTGGTCAACGACCGCCTCAACTACCTCACCCCGACCATCAAACCGATC (SEQ ID NO. 509)

Clone Rv375
::::::::::::Rv375SP6.seq::::::::::::
CTCAAGCTTGGGTGTTGCCGATCACCGGAAGCCNCATGATCAGCCACGTTTCGCGCCGCCCGGCATACGGCGGCGTACCGATCTCCGCGTCATACACCCGCGG GTAATCGCCGACGGTGCCGGTTCGCGAGCCGAAGGTGACAACGCTGATTGAATCNAGTTCCANGTCCAGCGGGT (SEQ ID NO. 510)

::::::::::::Rv375T7.seq::::::::::::
TNAACAGCTCGCGGCAGCCCACGACCTGCTGCGTCGGATTGCCGGCGGCGAGATCAATTCCAGGCAGCTCCCGGACAATGCGGCTCTGCTGGCCCGCAACGAA NGACTCGAGGTCACCCCGGTGCCCGGGGTCGTGGTGCACCTGCCGATCGCACAGGTTGGCCCACAACCGGCCGCTTGATGNNNNGTCGGCAAGCCCGGCAGTN GCCAAACCCAGCGTGATCANGCTCGGCTCGCGAGTTCGGCGAANAAGTGGCTCGCCTGATCACCTACCATCGGCCANGATCTGCGTGTCA (SEQ ID NO. 511)

Clone Rv376
::::::::::::Rv376SP6.seq::::::::::::
GCCANCCGGCTTGGCGTCGACTCCCGTTCNGCACATCATACGGTCCCCGGTACTGTCCAACTGCGCCGGTGCGCTAGCCAAACGTCACGACTCTCAGTGATCC CAGTTCGTGATCCGGCCGGTGGCGCCGCTGCGGCGGGGGCTNATNTACTTCGGACTNATTATCTCATCCAAAGGACACCGGGCCGGTGGCTGGAATCCCATGG

TGCGATCGGCCACACAN (SEQ ID NO. 512)

TABLE 3-continued

End sequences of the polynucleotide inserts cloned in the named recombinant

::::::::::::Rv376T7.seq:::::::::::
CCGACCTGGTATCTTCCGATAGCGCGCGTTGATATCCGGTCTGATCTCCTGCCCTTAACGCCGGATCTCAGCAGGTCCCCATGCAAAGATCCGAGGTGTCCCN

GATCTAGGGGTCCTCGTCCTCCAGATGATGGAGCAAGTCGGCCC (SEQ ID NO. 513)

Clone Rv377
::::::::::::Rv377SP6.seq::::::::::::
CTCAAGCTTCGGCTCAGGCGGCGCTGCCGGTAACGTCGCTGACCGGTGCAGGTTTCGACAATGTGGTGCCGGTTCGGCGGCTACGTGCCATCAAGACACTGGC

GCAGGCTATCGCACCCGTTATCGGCTACAAACAAATCGCGGTATGC (SEQ ID NO. 514)

::::::::::::Rv377T7.seq:::::::::::
CATCACCTGNTTCATGAACTGGAAGCACCGCAGCGCTTCCTTTTCGGCCGCAACATGAGCCAGCCTCTCGTCGGCGGTCGGGTGCAGGTGCTCGGGCAGCTCG GCCGCGACAGCCGCCTGACCCTGAAACCAGCTTCCATATCCCGCGACGAACGACGCCAGTCCGCTACGTAACCCCTCCGCGACTGTCCATGGACAACAGCGCG

TTCTCCACCGACCGGGCCCGGGTGTGGGGTGT (SEQ ID NO. 515)

Clone Rv378
::::::::::::Rv378SP6.seq::::::::::::
AGCTTAGCTTCCCGCCCCGGCAATAGGGCTCCAGCTCATCCGGTGTGACCAGATAGGGGCCCAGGGTGATACCGCTGTCTTTGCCCTTGGCCTGTCCGATGCG CAGCTGGCCCTCCAGCATCTGCAGGTCCCGTGCGGACCAGTCGTTGAAAATGGTATAGCCGATGATCGACCG (SEQ ID NO. 516)

::::::::::::Rv378T7.seq:::::::::::
CCNGAACAGAAGCGGNGGTTCCTACCGCGGTGTGCGGCCGGCGCGATATCGGCCTTTTTACTAACCGAACCCGATGTGGGCTCCGATCCGGCGCGCATGGCAT

CGACGGCGACGCCGATCGATGACCGCCAGGCTTACCACCTT (SEQ ID NO. 517)

Clone Rv379
::::::::::::Rv379SP6.seq::::::::::::
CTCAAGCTTGCGCGACTCGACAAGCATTCTTGACAGTTGTTTTGGCTCGGCATGGTTAGCCAAGGTTCTGCGGTCCCACCAGATCATCTTGGTCCGGTAGCGC TCGTCCGGGTATGCTGCCGCCGGGATTCTCGCTGCTATTACTCCCCCCGAAGAACGCCACCGGTCCAGCGC (SEQ ID NO. 518)

::::::::::::Rv379T7.seq:::::::::::
GCNAGGCGGTATAGCTTCCCGTCGTACCGGCGACCGCCAGCCGAGAAGCTCGTTTTCCCAGTGTTGCTGGGGATTCTCACGCTGCTGCTGAGTGCGTGCCAGA CCGCTTCCGCTTCGGGTTACAACGAGCCGCGGGGCTACGATCGTGCGACGCTGAAGTTGGTGTTCTCCATGGACTTGGGGATGT (SEQ ID NO. 519)

Clone Rv37
::::::::::::Rv37SP6.seq:::::::::::
GTGTGGAACCGTGAGCGGATAACAATTTCACACAGGAAACAGCTNTGACCTTGATTACGCCAAGCTATTTAGGTGAGGCTATATTAATACTCAAGATTGCGGT CGAGCACATCGGCCCAAGAACCGCCGAAGGCACGGCGGAACGCCTGCGGCACATGGGGCGACGACCAGCGGGTCGGACTTCTGGGCTGTCCAGCCGGATCGCG

CCGTCGCGA (SEQ ID NO. 520)

::::::::::::Rv37T7.seq::::::::::
CACTGTCAGTACATATGCGCCGCTCCTCCTCATCGCTGCGCTCGGCATCGTCGCCGGCGGTCATGGCGTCACCCTACCCAAGCCGAACGCGAAACGAGAACGT GTTCCATTATTAGGGTGTGAGCACCAATACCAGATTGCTCACCAGGAACTCACGCAGCACCGGGACGGATGTCAGCCACCACGCCCATCTGGGGTGGTAGCGG GGAAATACGGCTAACGCGGCTCCGGTGCCGGCAGCCCAGCGCAGACCCTCGGCGGCGGACACGGCAAACAACGACGACCCATAGTTGTTCTTTGCCGGATGGC CGTGTTTGCGGACATATCGGGCGGCGGCGCGGGCGCCGCCGAGGTAGTGGCTGAGGCCCATCTCGTGCCCGCCGAATGGCCCCAGCCAAACCGTGTA (SEQ ID NO. 521)

Clone Rv381
::::::::::::Rv381SP6.seq::::::::::::
CTCAAGCTTTTACGGTGATCGCGCATCACCTGGTTCATGAACTGGAAGCAGCGCAGCGCTTCCTTTTCGGCCGCAACATGAGCCANCCTCTCGTCGGCGGTCG GGTGCAGGTGCTCGGGCAGCTCGGCCGCGACAGCCGCCTGACCCTGAAACCAGCTTCCATATCCCGCGACNAACGAC (SEQ ID NO. 522)

::::::::::::Rv381T7.seq:::::::::::
CTCAGAAGCCGCTAGCTGGTAGAGTCGCTGACCGGTGCACGTGGCGNCAATGTGCGCTGCCGGTTCGCG (SEQ ID NO. 523)

Clone Rv382
::::::::::::Rv382SP6.seq::::::::::::
CTCAAGCTTGCGCTCATCAAGCGCGAACAGCAGGGCGGTCGGCTGGTCGCCATGACGGGTGACGGGACCAATGACGCACCCGCGCTCGCGCAAGCCGATGTCG GGGTGGCNATNAATACCGGCACCCAGGCGGCCCGGGAAGCCGGCAACATGGTCNATCTCCACTCC (SEQ ID NO. 524)

::::::::::::Rv382T7.seq:::::::::::
ACTTCTATTTCGACTGGTGTGCTGTGGCGCGATCCGACTGCCGGCGTGGTCAAGGCCGGCCAGTTGTGGGATNCCACAGGCAC (SEQ ID NO. 525)

TABLE 3-continued

End sequences of the polynucleotide inserts cloned in the named recombinant

Clone Rv383
:::::::::::::Rv383SP6.seq::::::::::::
GCTTGTCGTATTCCGTGGCACTGTCAGACATATGCGCCGCTCCTCCTCATCGCTGCGCTCGGCATCGTCGCCGGCGGTCATGGCGTCACCCTACCCAAGCCGA ACGCGAAACGAGAACGTGTTCCATTATTAGGGTGTGAGCACCAATACCAGATTGCTCACCAGGAACTCAC (SEQ ID NO. 526)

:::::::::::::Rv383T7.seq::::::::::::
CGATATTCGTCGGCCGCGTTGTCTCGACTGGGTCGCGT (SEQ ID NO. 527)

Clone Rv384
:::::::::::::Rv384SP6.seq::::::::::::
GACCTCGGCCACCAAGCCGGACGCGACCGTCGAGGTGGCGATCCGGCTTGGCGTCGACCCGCGTAAGGCAGACCACATGGTCCGCGGCACGGCCANCCTGCCA

CACGGCACTGGTAAGACTGCCCGCGTCGCGGCN (SEQ ID NO. 528)

:::::::::::::Rv384T7.seq::::::::::::
CCGGAAGTCTAGGGGACGACCTACTCAGCGCAAAATGTCGCTAATGTGAGTCCGCCCCACCAGGGCAGATCAACCCATGTCGATGATGACCTACCCGGATACC

GGATTGGCGGT (SEQ ID NO. 529)

Clone Rv385
:::::::::::::Rv385SP6.seq::::::::::::
AGCTTCAGTTCCTCCACGACGCGTTCCCAAATGAATTTCCCGATCCCACAATCTCGGTTCAGATACAGGTCGCCATACCCCTTACTTCGGNAACGCTGGGCGG

ATTGGCCCTGCCGCTG (SEQ ID NO. 530)

:::::::::::::Rv385T7.seq::::::::::::
CCGCCTACGGGTCGAACATGCATCCCGAGACCGATGCTCGAGCGCGCACCCCACTCGCCGATGGCCGGAACCGGCTGGTTACCCGGGTGGCGGCTGACC (SEQ ID NO. 531)

Clone Rv386
:::::::::::::Rv386SP6.seq::::::::::::
GCGGCTGGTTACGACTCCCTGTTTGTGATGGACCACTTCTACCAACTGCCCATGTTGGGGACGCCCGACCAGCCGATGCTGGAGGCCTACACGGCCCTTGGTG CGCTGGCCACGGCGACCGAGCGGCTGCAACTGGGCGCNTTGGTNACCGGCAATACCTACCGCAGCCCGACCCTGCTGGCAAAGATCATCACCACGCTCGACGT GGTTAGCGCCGGTCGAGCGATCCTCGGCATTGGAGCCGGTTGGTTTGAGCTGGAACACCGCCAGCTCGGCTTCGAGTTCGGCACTTTCAGTGACCGGTTCAN (SEQ ID NO. 532)

:::::::::::::Rv386T7.seq::::::::::::
GCCTTTCCGCACAATCTGTACCCCAGGACCNTCTAAAAAATCGAATACGACGGCGTCGCCGACTTTCCGCGGTACCCGCTCAACTTTGTGTCGACCCTCAACG CCATTGCCGGCACCTACTACGTGCACTCCAACTACTTCATCCTGACGCCGGAACAAATTGACGCAGCGGTTCCGCTGACCANTNNTGTCGGTCCCACGATGAC CCAGTACTACATCATTCGCACGGAGAACCTGCCGCTGCTAGAGCCACTGCGATCGGTGCCGATCGTGGGGAACCCACTGGCGAACCTGGTTCAACCAAACTTG

AAGGTGATTGTTAACCTGG (SEQ ID NO. 533)

Clone Rv387
:::::::::::::Rv387SP6.seq::::::::::::
GCAGACCAACAAGATGCATCGGGATCATACGCCGTCAACTACCCGGCCAACGGTGATTTCTTGGCCGCCGCCCAC (SEQ ID NO. 534)

Clone Rv388
:::::::::::::Rv388SP6.seq::::::::::::
CTCAAGCTTGCCAAAGAGACCTCGTCCACCAAGCNGGACGCGACCGTCNAGGTGGCGATCCGGCTTGGCGTCCACCCGCGTAAGGCANACCANATGGTTCGCG GCACGGTCAACCTGCCACACGGCACTGGTAANACTGCCCGCGTCGCGGTATTCGCGGTTGGTGAAAAGGCCGATGCTGCCGTTGCCGCGGGGGCGGATGTTGT CGGGAGTGACAATCTGATCGANAGGATTCAGGGCGGCTGGCTGGAATTCGATGCCGCGATCGCGACACCGGATCAGATGGCCAAAGTCGGTCNCATCGCTCGG

GTGCTGGGTC (SEQ ID NO. 535)

:::::::::::::Rv388T7.seq::::::::::::
CCACGGCGTGGATCAAGGTACCGGCCGGGATGTTGCGCAATGGCAGGTTGTTGCCCGGCTTGATGTCGGCGTTAGCGCCGGATTCCACCACATCCCCTTGCGA AAGTCCGTTGGGTGCAATGATGTAGCGCTTCTCCCCATCGAGATAGTGGAGCAACGCAATCCGTGCGGTACGGTTCGGGTCNTACTCGATGTGCGCGACCTTG GCGTTGACACCATCTTTGTCATTGCGGCGAAAGTCGATCATCCGGTAAGCGCGCTTATGACCGCCGCCTTTGTGCCGGGTGGTAATCCGGCCATGCGCGTTGC

GTC (SEQ ID NO. 536)

Clone Rv389
:::::::::::::Rv389SP6.seq::::::::::::
GGCGGCTGCGTCGGCGAGATGATCGCCCGGTGCCACCCCGATCCGTGCCTCGGTCAGCGCCAACGTGCTTTCCGGTCCGGCGACCACCATGTCGCATGCGCCG TABLE 3-continued End sequences of the polynucleotide inserts cloned in the named recombinant

AC (SEQ ID NO. 537)

::::::::::::Rv389T7.seq::::::::::::
GCAATCGCCTTGGCGGTCGCCGGGTTGTCACCGGTGATCATCNCGGNGCGGATGCTCATNCGGCGCATTTCGTCNAATCGTTCCCGTATGCCCACCTTGACGA

TGTCCTTCATATGGACCACGCCGATGGCCCNCGCGCTNCTG (SEQ ID NO. 538)

Clone Rv38
::::::::::::Rv38SP6.seq::::::::::::
CCGGCTCGTATGTTGTGTGGAATTGTGAGCGGATAACAATTTCACACAGGAAACAGCTATGACCATGATTACGCCAAGCTATTTAGGTGACACTATAGAATAC TCAAGCTTCCACATCGGTATGCCAAAGCATTGCGCCGCTATCGATTTCGCGCTGGCATCGCCAAGGTGGACTTCTTGCTCAGCGACGAGATCCCGTGGTCGGA TCCGCGGCTGCGGCGGGCTGCGACCCTGCATCTCGGCGGCACCCGTGACCAGATGGCGCGCGCCGAGGCAGACGTCGCGGCGGGACGCCACGCCGACTGGCCG ATGGTGCTGGCCGCGTGTCCGCACGTCGCCGACCCCGGCCGCATCGACGAAACCGGCCGCCGTCCGTTCTGGACCTATGCCCACGTGCCGTCGGGGTCCACGC

TCGACGCGACCGAGACCGT (SEQ ID NO. 539)

::::::::::::Rv38T7.seq::::::::::::
CGCGTCCACCGCAGCGTGAGATTGGTGGCGCCATTCGTCGTGGTGTAGCTGCTGTTGGCGGCGTCGCCGTATTGTGCGGGCCAGCCTTGTGCGGGGGCCGCTT CTACCCACGAGTCGGCACTTCCGCAACCGCCCAGCTCGACCGCGATTACGGCGGCCGCAACGGCCGCCGGAAGGCGTCTCGCAAGCGCCTTATCCTTTCGCAG GTTCCCAGATCCTTCCGCTACGTGGGTCGCTCATCGGCGGGCCCGGCCGAATGAGTACAGGTGAGGGTAACCGCTACAAATGAAGTTGGTCAGTGCTGGCCAA CTGTGTAATGGTTGCCCGGCTCGGGTCACCACGTACATTCTGGCAAGGCGGGCGAGATTCGGTTCCTCGCGTCCTTGGCCGGTGGCGGTTCCCGGTTGTCCGT

GGGCGTGTCGTGTACGTGGTGTAAGTGTCGTGAACTCCTCAGTTTGGGCT (SEQ ID NO. 540)

Clone Rv390
::::::::::::Rv390SP6.seq::::::::::::
CTCAAGCTTGCGCTGGATCTGGCGGCTGAGCCTGTTCTTGGGCAACATGCCGAGGGATCGCCTTTTCCACCACGCGGTCGGGGTGGCGTTGCATTAGCTCACC GATGGTGCGCTTGTGCAGGCCGCCGGGATACCCCGAGTGCCGGTAAACCATCTTGTGCTGCAGTTTGTCGCCGCTGATGGCGACCTTGTCGGCGTTGATCACN ATGACNAAGTCACCGCCATCGACATTGGGGGCGAACGTCGGCTTGTGCTTGCCGCGCAGCAGGTTGGCCGCCGCGACGGCAAGGCGGCCAANCACCACGTC (SEQ ID NO. 541)

::::::::::::Rv390T7.seq::::::::::::
TTTGGGATGGGCAAAAAGGCGAAGCNCCGCGTGGCCACGAACGCCGGGAGGGACAATCTCGGGCGGCTAGGGCTTCTCGCGGGAAGGCCCGAACGTACGGCGT TTCAACACGTCGCGTCGCCCTCCGACCGCGAACATTCGGGGATGGCAGCAACCTGGTAGCACCCTGGCCGGGCGATGATCTGCAGCGTCGCCGCGGGTAGTCG CCGCCCGGGCGGCTACAGTCTGAAACGCGATGACCATCGATGTGTGGATGCAGCATCCGACGCAACGGTTCCTACACGGCGATATGTTCGCCTCGCTGCGCCG

GTGGACCGGTGGGTCTATCCCGGA (SEQ ID NO. 542)

Clone Rv391
::::::::::::Rv391SP6.seq::::::::::::
CTCAAGCTTCGTCATAAGACCATGGTGCGCTTTCTTTCACCCGTCCANAGTCGGGGGCATCCGCACCGGCTCGCATCGCATCATCCTCCCACGACGGGCCGCT CATCAGCTTGGGCCATTTCAATGTACTTGATACCCCGCGCTGCGGGTAGGCCACTGCNACAATTCAAACACGGTGTCACACGGTGAATANTGTCNANATGGGC

TCTGATCAACCGTCNCAAACCCGGTTTC (SEQ ID NO. 543)

::::::::::::Rv391T7.seq::::::::::::
GAATTCTGCGTGCACCGCTATGGGTTGCAGCAGCGGCTGGCGCCGCACTACCCCACTGGCCCGGGTGTTTCGCCCCGAACCCGGATCATGGTGAGCGAAAAGG AGATTCGCCTGTTCGATGCTGGGATTCGCCACCGCGAGGCCATCGACCGATTACTCGCCACCGGGGTGCGAGAGGTGCCGCAGTCCCGCTCCGTCGACGTCTC CGACGATCCATCCGGCTTCCGCCGTCGGGTGGCGGTAGCCGTCGATGAAATCGCTGCCGGCCGCTACCACAAGGTGATTCTGTCCCGTTGTGTCGAAGTGCCT TTCGCGATCGACTTTCCGTTGACCTACCGGCTGGGGCGTCTGCACAACACCCCGGTGAGGTCGTTTTTGTTGCAGTTGGGCGGAATCCGTGCTCTGGGTTACA

GCCCCGAACTCGTCNCGGCGGTGCGCGC (SEQ ID NO. 544)

Clone Rv392
::::::::::::Rv392SP6.seq::::::::::::
GCAGTTGGGAATCGCTCTGCAGCAAACCANTATTCTGCGCGACGTTCGAGAGGACTNTTTGAATGGACGGATCTACCTGCCGCGCGACGAGCTGGACCGATTA GGCGTACNCCTCCGCCTGGACGACTCCGGGGCACTCGATGACCCCGACGGACGGCTCGCGGCACTGCTGCGGTTCANTGCCNACCGCGCCGCANACTGGTATT CGCTGGGACTGCGGCTGATTCCACACCTCGACCGCCGCAGCGCTGCCTGCTGTGCGGCCATGTCTGGCATCTACCGCCGTCNGCTCGCCTTGATCAGACCATC TABLE 3-continued End sequences of the polynucleotide inserts cloned in the named recombinant GCCGGCGGTCGTCTACCATCGGCGAATCTCTCTGTTCGGGACTGAANAANGCCCAAGTGGCGGCGGCAGCACTGGNCTCTTCGGTAACCTGCNGACCGCCCAT

TGGACCGCTACCG (SEQ ID NO. 545)

::::::::::::Rv392T7.seq::::::::::::
TTGATCTGGACGTCTGAGACGGTGATCGGNCCGAACCTGAATTGTCCGGTAATGCCCAGCGCAGAAAGCANGGTGGTGGCCGGGGCGGTGAANCCGGCGTCGG CGGCACCGTCGAAGTCGATGTGGATTGCCGGAATGGGGATGTCCGGCACGGCGAAGCCGTAGTTCGCTTGTCCCGTGAGGCCCANGTGGATGGGGGGAAGGAT CGTGGTGTCCGGGATGATAATGGGGCCGATGCCGCCGGTTGAAGTCCAGTGGATCGGGAATTCGGGAATCGTGATGCCGACGTTCAGGCCGAACAGGCCCTCC AAGTTGCCTCGCCACNAGATGCCGTTGCTGAAGTTGCCCGACATGAGGGCGCCGGTGTCCACATTGCCCGAATTGGCGACGCCGGTGTTGGC (SEQ ID NO. 546)

Clone Rv393
::::::::::::Rv393SP6.seq::::::::::::
CACGTAGGCGCCGTCCATAAATNACTCCGCCGCGCTTCGCACATCCTCGTANCGATCCTTGGCGAGCAGGTCAACCGGGCGCTGCCCGTCNAGGAGCCGGTTT TTGGCGTGCAGCCACTGGCCGACACCTCGGGGGGTAAGCGAATCCGAGAGCAGGAGGACNAGGTCACGAANCTGCGCCAGCCGGTCGTACCGCTCAGGGCGGA TGTCGCCGGTCCGCCACCCGCGTACCGCCCGATCGGACACCTGTATGACCGCGGCGACNTCGACCTGGGTGACGCCGAAGGGTTTCAGGGCATCNACNATCTC GCTGGCCTCGACCGCCCGGTCCAGGGTGACCGCCATCGTGGTTCCTCCGCAACTTCCGGTTCTACTACCGTAAACGCTACCG (SEQ ID NO. 547)

::::::::::::Rv393T7.seq::::::::::::
CGGGGAACGGTCCTCGCACACCTGGTTCGTGTTGCGGGAATTACTCGGACANCAAAACGTCAAGAACTACGACGGCAGTNGGACAGAANACGGCTCCCTGGTG GGCGCCCCGATCGAGTTGGGAAGCTGATATGTGCTCTGGACCCAAGCAAGGACTGACATTGCCGGCCAGCGTCGACCTGGAAAAAGAAACGGTGATCACCGGC CGCGTAGTGGACGGTGACGGCCAGGCCGTGGGCGGCGCGTTTCGTGCGGCTGCTGGGACNCCTCCGACGAGTTCACCGCCGGGAGGTCGTCGCGTCGGCCACC

GGGCGAATTTCCGGTTCTTCGCCGCGCCCCGGGATCCTGGGACCGCNGGCGCGCGCTGTT (SEQ ID NO. 548)

Clone Rv396
::::::::::::Rv396SP6.seq::::::::::::
CTCAAGCTTTGTCCGACAAGCGTTCCCGGGCGGTCAGCAAGCGAACGTCGGTTGGCCCACTGCGGGTCGATATTGCCGCCAGGGA (SEQ ID NO. 549)

::::::::::::Rv396T7.seq::::::::::::
CGTCAGCACGGCGACGTCGCGNTACGCCGAGCAGTTACACAATCGCTCTGCAGCAAACCAATATTCTGCGCGACGTTCGAGAGGACTTCTTGATTGGACTG (SEQ ID NO. 550)

Clone Rv39
::::::::::::Rv39SP6.seq::::::::::::
CTGCATCCGGCTCGTATGTTGTGTGGAATTGTGAGCGGATAACAATTTCACACAGGAAACAGCTATGACCATGATTACGCCAAGCTATTTAGGTGACACTATA GAATACTCAAGCTTCGCGCAGCGGCGGGTTGACCCGGTTCACGCCGTCATAGCTGGCCAATCTGGCATCGTCGATCANCATGTGGTGGGGGGTGACCTCGGCG GTGATCGAAATACCCTGGTCCTTATCCCATTTCAGGATTTCGACGGTGCCCGCGGCCGACGCGTGACAGATGTGCACCCGGGCGCCGGCGTCACGGGCCAGCA AGGCGTCGCGGGCGACGATCGATTCCTCGGCGGCCCGCGGCCATCCCGCCAGGCCCAGCCGCGCCGCCATGGGTCCCTCGTGCGCGACGGCGCCGACCGTCAG

CCGGGGCTCCTCGGCGTGCTGGGCGATCAGCACGCCCAAACCGGTG (SEQ ID NO. 551)

::::::::::::Rv39T7.seq::::::::::::
CCGACGCGCACTACGTGCTGGTGTCCACCCGCGACCCGCACCGGCACGAGCTACGCAGCTACCGCATCGTCGATGGCGCTGTCACCGAGGAACCTGTCAATGT CGTCGAGCAGTACTGAACCGTTCCGAGAAAGGCCAGCATGAACGTCACCGTATCCATTCCGACCATCCTGCGGCCCCACACCGGCGGCCAGAAGAGTGTCTCG GCCAGCGGCGATACCTTGGGTGCCGTCATCAGCGACCTGGAGGCCAGCTATTCGGGCATTTCCGAGCGCCTGATGGACCCGTCTTCCCCAGGTAAGTTGCACC GCTTCGTGAACATCTACGTCAACGACGAAGACGTGCGGTTCTCCGGCGGCTTGGCCACCGCGATCGCTGACGGTGACTCGGTCACCATCCTCCCCGCCGTGGC

CGGTGGGTGAGCGGACACATGACACGATACGACTCACTGTTGCATGCCTTG (SEQ ID NO. 552)

Clone Rv3
::::::::::::Rv3SP6.seq::::::::::::
TGCTTCCGGCTCGTATGTTGTGTGGAATTGTGAGCGGATAACAATTTCACACAGGAAACAGCTATGACCATGATTACGCCAAGCTATTTAGGTGACACTATAG AATACTCAAGCTTGCCGGGAGGGTGCATGGCCGACTCGGATTTACCCACCAAGGGGCGCCAACGCGGTGTCCGCGCCGTCGAGCTGAACGTTGCTGCCCGCCT GGAGAACCTGGCGCTGCTGCGCACCCTGGTCGGCGCCATCGGCACCTTCGAGGACCTGGATTTCGACGCCGTGGCCGACCTGAGGTTGGCGGTGGACGANGTG TGCACCCGGTTGATTCGCTCGGCCTTGCCGGATGCCACCCTGCGCCTGGTGGTCGATCCGCGAAAAGACGAAGTTGTGGTGGAGGCTTCTGCTGCCTGCGACA

CCCACGACGTGGTGGCACGGGCAGCTTTAGCTGGCATTCCT (SEQ ID NO. 553)

TABLE 3-continued

End sequences of the polynucleotide inserts cloned in the named recombinant

::::::::::::Rv3T7.seq:::::::::::
GGAAACACCGNCGCCGTCGTGGCCACCAACACCGCGACCAGCACCGTGACCCGGACCGGGGTGCCGCGCGAACCGGTCTTGGCCAATTGCCGCGGCACCAAGC CGTCGCGCGCCATGGCGAACAGCACGCGGCATTGCCCGAGCATCAACACCATCACCACCGTGGTAAGCCCGGCCAGCGCGCCGACGGAGATGATGCCGCTGGC CCAGTACACCCCGTTGGCCTGGAACGCGGTGGCCAGATTTGCCGGCCCGCGGCCCGGTACGGTCCGCAGTTGGGTGTATGGAACCATGCCCGACAGCACCACC GATACCGCGACGTAGAGAAGGGTCACGACCCCCAGCGACGCGAGAATCCCTCGAGGGACGTCTCGTTGAGGACGCTTGGTCTCCTCGGCCATGGTGGCCACGA

TGTCAAACCCGATAAACGCGAAGAACACGATCGATGCCCGGCCAGCACGCCGTA (SEQ ID NO. 554)

Clone Rv40
::::::::::::Rv40SP6.seq::::::::::::
CCTGCTTCCGGCTCGTATGTTGTGTGGAATTGTGAGCGGATAACAATTTCACACAGGAAACAGCTATGACCATGATTACGCCAAGCTATTTAGGTGACACTAT AGAATACTCAAGCTTGTCCTCGGGCGTGGCCTCGGCCAAGAAATCGTCGACGCCGGCCTCCTGTGCAATCGCCTTGGCGGTCGCCGGGTTGTCACCGGTGATC ATCACGGTGCGGATGCTCATTCGGCGCATTTCGTCGAAGCGTTCCCGTATGCCCACCTTGACGATGTCCTTCAGATGGACGACGCCGATGGCCCGCGCGCTGC TGTTATCGGTCCATTCCGCAACGACTAGGGGTGTCCCCCCGCCGGAGCTGATGCCGTCGACAATGGCACCCACCTCCTCAGTGGGGTGGCCACCGTGATCGCA

AAACCACTTCATCACCGCAGCCGCGGCACCTTGCGGATCCGAACGGATGCGCTC (SEQ ID NO. 555)

::::::::::::Rv40T7.seq:::::::::::
TTCGTTCGATGGCGCCGCCCCGGCTACGGTTTGACCTGTGGGTGTCGAATTGGGGTCAAATTCCGAGGTCGGCGCGCTAAGAGTGGTCATCCTGCACCGCCCG GGGGCCGAACTGCGCCGGCTCACACCGCGCAACACCGACCAGCTGCTGTTCGACGGCCTGCCCTGGGTATCCCGCGCGCATGACGAGCACGACGAATTCGCCG AGCTGCTGGCTTCCCGCGGTGCGGAAGTGCTGTTGCTGTCGGACCTGTTGACTGAGGCACTACATCACAGCGGGGCCGCCCGCATGCAGGGGATCGCCGCTGC CGTCGACGCACCGCGGCTGGGACTGCCGCTGGCGCAAGAACTTTCGGCCTACCTGCGTATCTCGACCCAAGCANGTTGGCGCATGTGCTGACGCCGGCATGAC

TTCAACGAACTCCCNTCCGACACGCCGAACGAAGTGTCGTTGGTGTTGCGTATGC (SEQ ID NO. 556)

Clone Rv412
::::::::::::Rv412SP6.seq::::::::::::
GCGGCGAGTGTGGTGGGTGCCGAACACGAATCCAACGACGCACTGGCGGAGAGATACCACTTGCTGTACTGGAAGCACGTGCTGATGATCTCCCGTGGAATGT

GCCTCGCCGCCGTCTATCGAAAACAGTGAGCATGCTGCG (SEQ ID NO. 557)

::::::::::::Rv412T7.seq::::::::::::
CAACCGCGCTCGGCGCGTCTGGGCCTTCCGCCGGCTCCGCCGACAATTCTATCTCTGGATCAGCGGGGCTCTCCGGGCCGGCCTCCGCGAACTCAACAGGCCG CGCCTTCCGGCCGAAACATTCCCTAGCCATATATGATCGCACCTCGATACACGATCTGGCGGCAACACCGCAAAGCGTCCGACGGGCCCAACCTCCGCAATTC

AGGTATCCGGG (SEQ ID NO. 558)

Clone Rv413
::::::::::::Rv413SP6.seq::::::::::::
GAAGGTCGGCGAAGGTGTGGCTGGNTGCCGATCACGAATCCAATGATGCAGTGGTCGGAAGATATTAGCCACTTGCTGTTCTGGAGACAGGTGCTGATGATCT

CCCGTGGAATGTCCCTCGACTCCGTCTATCGAAATCTGTGAACA (SEQ ID NO. 559)

::::::::::::Rv413T7.seq::::::::::::
TCCTGCGCTCTGGGCCATTCTCGGGTCTGCCGACAATTCTATCTCTGGATCTGTGGGGCTCTCTTGGCCGGCCTCNGCGATCTCTTCANGGCGCGCCTTCCGG CCGAAACATTCCCTATCCATATATGATCGCACCTCTATACACCGTTTGGCGGCAACACCGCAAAGTGTCTGTCG (SEQ ID NO. 560)

Clone Rv414
::::::::::::Rv414SP6.seq::::::::::::
AGCTTTACGCTGGCGTATCAGCGTTGGGGCCGCTGCCATTTCGGTCGCCCAACGCGTTGCCAGCTCCCTGCGCTGTCAGGGCTTGCGCGCCAAACTGGCCACC

GCAACAAACTTGGCTGAGCTTGATC (SEQ ID NO. 561)

::::::::::::Rv414T7.seq::::::::::::
CTCTATCTGGCGTCACATTCGCAATCTTTAGATTGCAGATATCGATAAAATCACCCGCGCGACAAGACCGCCATGTCATCCTTTCGATGTTATTTCGCCGGCC

TGGGGAAAGCGCAACGACGTTGCCTACACGTTCCGCCGT (SEQ ID NO. 562)

Clone Rv415
::::::::::::Rv415SP6.seq::::::::::::
AGCTTTNCCTTGCATCTGCACCCCGATCCACGTCAGCCACGTCGGCGTTCTCCACCAAGAAGTTGCGGGCATTCTCCTTGCCCTGGCCGAGCTGCTCGCCCTC GTAGGTGAACCAGGCACCCGACTTGCGGATGAGGCCCTGATCCACACCCATGTCGATCAGCGAGCCCTCCCTGCTGATTCCCTTGCCGTAGAGGATGTCGAAC TCGGCCTGCTTGAAGGGGGGCGAACAGTTGTGCACGACAACCCCTTCGGCGACGAGGGTGTGCAGTTCCTCGACCTCGAGGTCGAACGTTCGTGCCCGCCGCG TABLE 3-continued End sequences of the polynucleotide inserts cloned in the named recombinant TTGGCAGCACTTCTCGGATCACGGAATAGCGGANTTCTTCCGCCAGCATGTCGTGCAGGAATTTGTCATCCAGGGCATCCGCGAGCGCCTGCACGCG (SEQ ID NO. 563)

::::::::::::Rv415T7.seq::::::::::::
ACTGTCNAGGGAATGCTTCGCAGCATCTACCTGCAGTCGCTTGTGCATAAGCGGACGGCCCNACCTGTTCGTGTTCCGGGACACCAGACGCGGGAGCACCGGC AGTACGGCGAAAGGTTTGAGCGGAAGGAGTTGCGCAAATCGGGGCGCCCCAACACCCGTCCGCAAGACGCGGTCAACGACCTGTTTCAGGCGATCAGGGTCAC CGACTCACCTGCACTGAGAACAAGCGATCTGCTGATCTGCCAGAAGATGGACATGAATGTCCACGGCAAGCCTGATGGCCTGCCGCTCTTCCGGGAATGTTTG

GC (SEQ ID NO. 564)

Clone Rv416
::::::::::::Rv416SP6.seq::::::::::::
TGAATTATGATCCCGACACAACTGCATCANTTTAGCCGCGTCGNGATGCTATCCGCCGACGGTTTGGANCNGGTCCGTGTCGTTCGTGTTGATCTCACCCGAA GTTGTGTCCGCCGCCGCCGGGGATCTAGCGAACGTGGGATCGACAATCAGCGCCGCCAACAAGGCGGCAGCGGCTGCGACCACGCAGGTGCTGGCCGCGGGCG CCGATNAGGTGTCAGCGCGCATCGCGGCGCTGTTTGGTATGTACGGCCTGNAATATCCGGCGATCAGTGCGCAAGTTGCCGCGTATCACCANCAGTCCGTGCA

G (SEQ ID NO. 565)

::::::::::::Rv416T7.seq::::::::::::
AACGGGGACCNCAAGAAACCATTCAANAACGAGGGGTCGTCACCAACGTCGAAACCGACGGTTGCCAGCCGGCCCACGATATTGCGTGCTCGAGGGTCCGCTG TACCCTCACCGAACGTGAGTCCCACACCGCGGAGGCGGGCGACTCTGGCGTCGTTAGCAGCCGAGCTCAAGGTGTCCCGCACCACTGTCTCGAATGCTTTTAA CCGACCGGATCAGCTCTCCGCCGATCTACGTGAACGAGTGCTTGCCACGGCCAAGCGACTGGGCTATGCCGGACCGGATCCGGTGGCGCGATCGTTGCGGACC

CGCAAAGCCGGTGCGGT (SEQ ID NO. 566)

Clone Rv417
::::::::::::Rv417SP6.seq::::::::::::
AGCTTTGGAGCCNCNCCGANCCNCCGGTACGCCCCGCCACCGCCGTACCCGGCACCCGACCCCTTTGAGCCGTTCGCCGTGGCCGCGGTGGANCTGGCCGACG AGGGACTGATCGTGCTGGGCAAAGTGGTCGATGGCACGCTGGCCGCCGATCTGAAGGTCGGCATGGAGATGGAGCTGACGACCATGCCGCTGTTCGCCGACNA CGACGGTGTGCAGCGCATCGTCTACGCGTGGCGGATCCCATCGCGCGCCGGCGACNATGCANAGCGCANCGATGCTGAGGAGCGGCGCCGATGAGGATGAGCG CGCCGGAACCCGTTTACNTCCTGGGTGCCGGTATGCACCCGTGGGGGAAATGGGGTAATGACTTC (SEQ ID NO. 567)

::::::::::::Rv417T7.seq::::::::::::
TTCTCNCATCGTTCGTACTNNGATGGGACGCTGCTGCCCGAGGCGATCCTGGCCAACCGGCTCTCGCCGGCGCTGACCTTCGGCGGGGCGAACCTGAACTTCT TTCCGATGGGCGCTTGGGCCAAACGTACCGGGGCTATCTTCATTCGGCGTCAGACGAAAGATATTCCCGTCTACCGCTTCGTATTACGTGCTTACGCCGCGCA GCTGGTGCAAAACCATGTCAACCTCACCTGGTCGATCGAAGGGGGTCGGACCAGAACGGGCAAGCTACGGCCACCGGTGTTCGGGATCCTGCGTTACATCACC GATGCGGTCGACGAAATCGACGGTCCCGAAGTGTATTTGGTGCCGACCTCGATCGTGTACGAACAGCTGCACGAAGTGGAAGCCATGACCACCGAAGCCTATG

GCGCCGTGAA (SEQ ID NO. 568)

Clone Rv418
::::::::::::Rv418SP6.seq::::::::::::
TTCTTCCGGGTACCGCTGATCGGCGGCACCATCACGCACCCGGTGCAGGGCGAGGCGGCCGCCGGTGTGGTGTTGCTACGGCCGGCCAGCCCGGGTACCGGTG TGATCGCCGGTGGTGCGGCCCGCGCGGTGCTGGAATGTGCGGGGGTGCACGACATCTTGGCCAAGTCGCTGGGCAGTGACAACGCGATCAATGTGGTGCACGC CACCGTGGCCGCGCTCAAGCTGCTGCACCGTCCGGAGGAGGTGGCGGCGCGCCGCGGTTTGCCAATAGAAGACGTCCCCCCGGCCGGGATGCTG (SEQ ID NO. 569)

::::::::::::Rv418T7.seq::::::::::::
GTCGAAAGTGACCATCTCTACCTTGAGTGCCATACCGCCCGACCCTATGCCTCGGATAGCTCGGCGGAAAGAAACGCTTGCAGTGCCGCCGAATAGGCGGCTA CGTCGTGAGCGCCCATCAACTCTCGCGCGGAGTGCATCGCCAGCTGGGCGGCGCCGACGTCGACCGTGGGGATTCCGGTGCGCGCCGCGGCCAACGGCCCGAT CGTCGACCCGCACGGCAGATCGGCGCGATGTTCGTAACGCTGCATAGGCACTCCCGCGCGCTGGCAGGCCAGTTGCGAAACGCCCCCGCCGGGTGCCTTCCGT

CGGTTGGCTTTACCGCAAATTTGGGGTTGCCCCT (SEQ ID NO. 570)

Clone Rv419
::::::::::::Rv419SP6.seq::::::::::::
AAAGCCACGGAAACGATTGCCTACTGCCGAATCGGGGAACGGTCCTCGCACACCTGGTTCGTGTTGCGGGAATTACTCGGACACCAAAACGTCAAGAACTACG TABLE 3-continued End sequences of the polynucleotide inserts cloned in the named recombinant ACGGCAGTTGGACAGAATACGGCTCCCTGGTGGGCGCCCCGATCGAGTTGGGAAACTGATATGTGCTCTGGACCCAAGCAAGGACTGACATTGCCGGCCAGCG

TCTACCTGGAAAAA (SEQ ID NO. 571)

::::::::::::Rv419T7.seq::::::::::::
TTTCGCCACCGCNAGGTCGTGCGCGTTCCAGAAAAGCGTGGTTTCGCCGGGCGCGAGGATTCGACGGTCCAACTGACCAGCCGGTCCCGCCACCCGTTAGGCA GGATCGCGGTGTCTATATGTTCGCCCTCGGCATAAACGCCATTGCTGCGGTGAAAATCGGACATCTCGCCGATTGCCACGTCTACATGATCCGCTTTGTCCCG

CGCCGGGTCGTTGACAAACGCGATGTCNGCCTCCTGGGAAGCGGTGGC (SEQ ID NO. 572)

Clone Rv41
::::::::::::Rv41SP6.seq::::::::::::
TCGCCAAGTGGATTCGTGCTCACCNACGAGATCCGTGGTCGGATCCGCNGCTGCGGCGGGCTGCGACCCTGCATCTCGGCGGCACCCGTGACCAAATGGCGCG CGCCGAAGCAGACGTCTCGGCGGGACGCCACGCCGACTGGCCGATGGTGCTGGCCGCGTGTCCGCNCGTCNCCGACCCCGGCCGCATCNACCAAACCGGCCGC CGTCCGTTCTGGACCTATCCCACGTGCCNTCGGGGTCCACGCTCGACGCGACCGANAACGTAACCAGCGTCCTCGANCGGTTCGCCCCCGGCTTCCGTGACAT

CGTGGTGGCGGCCGCGCCGT (SEQ ID NO. 573)

::::::::::::Rv41T7.seq::::::::::::
GTACCGTCACCATGATCGCCCCCATCGGCATCGGTGAGCTGATAGATCCCAGCCGGTTTCGCCAACCCCGGAGCGATCTTGGCGCGCTGCTNGTNGTCNCTGA NACNTAGCCACCAACAGAGCCCGGTGTGCGACAAGANGACTGATCGGATCTCTCCGGACACNTCGAGGGGGTCNTCAGGAGNCCGGGCGCCACCCCGAGGTAA GCCTCCGCCCAGCCTCACACCGCGACCGGGTATCNCAAGTCGCGCAATAANCCCACCACCTCCTCGGACCCCACGTTGTATGCGGCTGGGT (SEQ ID NO. 574)

Clone Rv42
::::::::::::Rv42SP6.seq::::::::::::
ATACTCAAGCTTAGACCTCACTGATGTGGCGGGACGCGGGAGATAACCGCGGTTCGAGCCGTTCAACAGTGGTGGTTCCCACACCAGTTGTTTGCCTTTGCGA AGTAAAGCGATTCGATTTGCTCGAAAAGAGGGCTGGCTGCTCGTGAGGGACATCCATGGCCGATACCTCAGCGATCTCAACGGTCAAGCGACTGCATGTTTGG CGCAAGGTATCGCTAAGCATAGGTTCGTGACGGATTTGACAGCAAGAGCTTTCCAAAGATTGCTGTCCACATANTGATTCGCATCTCTACACCTCTTCGCCGG TGCTGTCAAGAGCCATTCGAATCAGTTATCTCGCTCGTGCTTGGAANAAATTTTCCCAGCCTGCGTTGGACAAACCGCGTCGCCAAAGCGGT (SEQ ID NO. 575)

::::::::::::Rv42T7.seq::::::::::::
AGCTTCCCGAGAAACAGTGCATTCCCTAAGCAGCCCGTTGTCACGCCGATGAGTGAAGAGTGCACGCAATCGCCGGAATCCGGCAAAGCCCTGCACAAGCGAA ATCAACCCGGAGGCTGACAAGGCAACGTCGGTGATCCGTACCGCCTGGTTGGACAAACGGCAGAAGGCGGCCTCGTCCGGTCCATCTACGCCGAGCACACTGG TGATAGCGCGCATCGGCATCGGTGCGGCCACGGTGGAGACGACGTCCGCGGGCGTCTGGGTCAGTAACCCGCCGACCAGTTCTCGGGCAAGCTGGTCGACCAT CGGGCGCCACGTCTCCAACGCGCCACGCGCCATACCTGGTGCCAGTTGCTTGCGCATCCGGGTGTGCGCCGGCGGATCGGACGTCGCAGAAACGCAGCCACCC

CGTGAGAAGTGACCCACGGCGCTGGACACGTGTCTGGTTAC (SEQ ID NO. 576)

Clone Rv43
::::::::::::Rv43SP6.seq::::::::::::
CGGCCGGGATGTGCGCAATGGCAGGTTGTCGCCCGGCTTGATGTCGGCGTTAGCGCCGGATTCCACCACATCCCCTTGCGAAAGTCCGTTGGGTGCAATGATG TANCGCTTCTCCCCATCGAGATAGTGGAGCAACGCAATCCGTGCGGTACGGTTCGGGTCGTACTCGATGTGCGCGACCTTGGCGTTGACACCATCTTTGTCAT GGCGGCGAAAGTCGATCATCCGGTAAGCGCGCTTATGACCGCCGCCTTTGTGCCNGGTGGTAATCCGGCCATGCGCGTTGCGTCCACCGCGACCGTGCAGCGG GCGCACCAGCGACNTCTCCGGGGTTGACCGGGTGATCTCGGCGAAATCAGATACGCTGGCGCCGCGACGACCAGGCGTCGTGGGCTTGTACTTGCGAATTGCC

ATGGTCTAATCAGGTCTTTCTCTCACCTCTCGTCGCCGGGCTAGGGCGCATTGCCTGCTCCT (SEQ ID NO. 577)

::::::::::::Rv43T7.seq::::::::::::
TAGCGGTGTAACCAACTCCCGGGTCACCACCCGCAAACCTCTTGCGGCAACAGCACCGTCGACGCGTCAACCGGGCTGCCCGGAATCCTGTGGATGGGCATCG AGTGCATGGTCACGACGTCCCCGACGCGGCCGGTGGCAACGACAAGTGGCCCGGATGCACCACAAATGACGGCCGCACACCGGTGGGGACGGCCAGCACGAGA GCCGTGTCGCCGAAGTCGACGCTAATGCCGTAGGCATTGGCCGTCACAACAGGCGACGCCCCGCGTACCACCGAGTCCACGGNGGTTGGGCGGTCTCCTCGGC

CAACCAGGCGTGAACCCGGCGGATCCGAATGCAGCAAGACCCGTGGGC (SEQ ID NO. 578)

Clone Rv44
::::::::::::Rv44-2ndSP6.seq::::::::::::
CCATTGGTCGGTGTGCGCATACCANTACNACGCGCCGGGCACCTGACGCGGCGGCCGCAACCATTCGGTGGCCATCGCCATCGTCTGCCACCCGGTCAACGGA TABLE 3-continued End sequences of the polynucleotide inserts cloned in the named recombinant CGCACCTTCTCCTGGCCGACCTAGTGCGCCCACCCGCCGCCGTTGCGTCCCATCGATCCGGTCAACATGAGCAGCGCCAACACCGAGCGGTACATGACATCTG

CTGTGGAACCAGTGACANATTCCGCCGCCCATGATGATCNTCGACCGTCCTCCGGATTCGGTC (SEQ ID NO. 579)

::::::::::::Rv44-2ndSP7.seq::::::::::::
GCCGGCCTGGTCAAAGGGGCGTCCGAAGGANCCGGGCTGGGTAACAAGTTCCTGGCTCATATCCGCGAATGCGACGCCATTTGTCAGGTGGTGCGGGTGTTCG TCGACGACNACGTGACTCATGTCACCGGACGGGTCGATCCCCAGTCCGACATTGAGGTCGTCGAGACCGAGCTGATCCTGGCAGATCTGCAAACCCTGGAGCG GGCCACGGGCCGGCTGGAGAANGAAGCNCGCACCAACAAGGCGCGCAAGCCGGTCTACGACCCGGC (SEQ ID NO. 580)

Clone Rv45
::::::::::::Rv45SP6.seq::::::::::::
GATCCACTGACCACGATGACATATCGAAATGCTCGACGATTCCGATGGCGATCAAGGCCACGATGCCCTGGCCGTTGGGCGGTATCTGGTGGATGGTGTACCC GCGGTAGGTTCCCGTGATCGTGTCGACCCAGTCCACGCGATGGGCGGCGAGGTCGTCGGCACGCATCACCCCGCCGTNTGCCGCCGAGTGCGCCTCGAGTTTG GCGGCCAGCTCTCCCCGGTAGAACTCTCACCGTTGGTCGCCGCGATCTTCTCTANCGTCGCCGCGTGGTCAGGAAAGGTAAACAGCTCACCGGGTTTCGGCGC TCGTCCGCCGGGCATGAACGCATCTGCGAATCCGGGCTGGGATGCGAACAACGGACCTGTGCCG (SEQ ID NO. 581)

::::::::::::Rv45T7.seq::::::::::::
TCTACTGCCGAATCGGGGAACGGTCCTCGCCCACCNGGTTCGTGTTGCCGGAATTACTCAGGACACCGAAACGTCGAGAACTACGAGCGGAGTTGGACANAAT ACCGCTCCCNGGTGGGCGCCCCCATCGANTTGGGAAGCNGAAATGTGCTCTGGACCCCACCCAAGAATGACATTGCCGGCCGCCCTCCAACTGGAAATAGAAA CNGTGATCACCCGCCGCGTTCTTGGAAGGAATGGCATGCCCTGGGCCGGGCGTTCCTTCCGCTGCCGGACTCCTCCCACCAATTCACCGCCGAAGGCGTCCCG

TCTGC (SEQ ID NO. 582)

Clone Rv46
::::::::::::Rv46SP6.seq::::::::::::
ATACTCAAGCTTCTGTCACCGAAATCCCGCATGGGATAACGGGTTTAGATTTCGACAACGGGACCGTGTTTCTCAACAAGCCGGTCATCAGCTGGGCCGGCGA

CAACGGTATCTACTTCACCCGCTTTCGCCCGT (SEQ ID NO. 583)

::::::::::::Rv46T7.seq::::::::::::
CTGGCTCAAGCGCTCGGCGCGCAGGTGAACTCGGACCGGCTCGACGTCGCCGAACGCGAGGCGGTGCTGGCCCACGCCGACGCCGTCGTCGCACATATCGGCA CCGTGCACAAGTCTACAACAACGCCGGCATCGCGTACAACGGCAACGTCGACAAGTCGGAGTTCAAGGACATCGAGCGCATCATCGACGTCGACTTCTGGGGC

GTCCTCCACGGGCCC (SEQ ID NO. 584)

Clone Rv47
::::::::::::Rv47SP6.seq::::::::::::
CCGCCCTCCGCATTATGGGTCAAGAACCATCGGGTCGGACTTCTGGGCTTCCAACGCTCGCGCCGTCCCN (SEQ ID NO. 585)

::::::::::::Rv47T7.seq::::::::::::
CCGTGGCACTGTCAGACATATGCGCCGCTCCTCCTCATCGCTGCGCTCGGCATCGTCGCCGGCGGTCATGGCGTCACCCTACCCAAGCCGAACGCGAAACGAG AACGTGTTCCATTATTAGGGTGTGAGCACCAATACCAGATTGCTCACCAGGAACTCACGCAGCACCGGGACGGATGTCGGCCACCACGCCCATCTGGGGTGGT

AGCGGGGAAATACCGCTAACGCGGCTCCGGTGCCG (SEQ ID NO. 586)

Clone Rv48
::::::::::::Rv48SP6.seq::::::::::::
TACTCAAGCTTGTCCAAATATCGAAGCGTCGGGTCGCGAGGCTCGGTCGGCAGCTCCAGCAAAACCCGCTCCACCCCTAGATGCCGGTATCCCTCAAGGTCTT TATCCGCCGCTTCACCCCACTGGCACACGGTCACCGGCACGTCGCCCCCGGCCATGGCGCGCAACCGCTGAAGCGGACCCGACAGCCGCTGCGGTGATGGACT GATCGCGATCCACCCGGCATTGAGCCGGGCTATCCGCGGGAAGTTCGCCGGTCCCCCGCCCACATACAGCGGAGGATAGGGCTTTGTCACCGGCTTCGGCCAG CAGTAGATCGGATCGAAGTCCACATATGTCCCATGGAATTCCGCCTGCTCCTGCGTTCAGATCTCGATTATCGCGCGCAACCGCTCATCGATCACACGTCCGC GCACCGCAGGGTCCACACCATGGTTGGCGACTTCTTCGCGCAACCAGCCACACCCACGCCGAAACGAAACCGTCCCTGCG (SEQ ID NO. 587)

::::::::::::Rv48T7.seq::::::::::::
CAGGCATGCAAGCTTGGCCAACTCCTCATCGGACTTGAAGGTGCCGTCCTCGTTGGCGGCCCTGCTCCACGGCACGTTGATGGCACCAGGAATGTGTCCGGGC CGCTGGCTTTGTTCCTGCGGCAGGTGCGCGGGGGCCAGGATCTTGCCGGAGAACTCGTCGGGAGAGCGCACGTCGATGAGGTTCTTGACGTTGATGGCCGCCA GGACCTCGTCGCGGAATGCCCGAATCGTGTTATCCGGCGGGGANGCGGTGTAGGAAGTCACCGGCCGGCTGACCGGGTCGCTGGACAGCGGGCGTCCGTCGAG

CTCC (SEQ ID NO. 588)

Clone Rv49

TABLE 3-continued

End sequences of the polynucleotide inserts cloned in the named recombinant

::::::::::::::Rv49SP6.seq::::::::::::::
ATACTCAAGCTTCAAAACAGGCCTGTTGTGGGCGCACCCGGCTCGCCGAGTTCTGCACGCACCGCCTCAAGTGCGGCCCGCACCGCCGGCATCTCCCGGTCAC GCAGGGCCGCGGCCCGCGCCGCAGCGACGGCGTGTTCGCGCAGTTCGCCGTCAATGATGCTGACCTGATCGGCCACCCGGGCGGTCTCGGCGTCGTCCCGTTC ACTAATCGCGGTGCTCAGCAGCGTCTCGACAGCCACCACCCGAGTGGAGACCAGATGCNCCACCACGGACCGCAGCGATGCCAGTCACCTCACCCGTCC (SEQ ID NO. 589)

::::::::::::::Rv49T7.seq::::::::::::::
CAGGCATGCAAGCTTTGCAGTTGCTGAGTAATGTCGGCCAACGTCACCACAATCGCGATGAATTCAATCATGCCGCCCAGGGCGGCCAACCCAATGGTGGCCG CGAGCGGCAGCTCGATCGCAGCGCGGAGGTTGCCGGCCGCCAGTTGATTCACGAACAGGGTGAGGTCATAGGCGGGCAGGATAGTGACGAAGGCAAGACCTAG ATCTGCCGTCGGAAGAAGAATCGAGTATCCGGTCGACACAACGGAAGCGAAAGTGTCCGCGATGTTGATGAGCGTCGCCGGTTGTGGCGGCGGTGGCGGCGGT AGCACCGTCCGCACATACCGCGGGAACGCGGGCATCCGAATTTGGGGCAGGGTGTTCAAGGCGGCTGGCAACTCACCATGAATCT (SEQ ID NO. 590)

Clone Rv4

::::::::::::::Rv4SP6.seq::::::::::::::
CCGGCTCGTATGTTGTGTGGAATTGTGACCGGATAACAATTTCACACAGGAAACAGCTATGACCATGATTACGCCAAGCTATTTAGGTGACACTATAGAATAC TCAAGCTTGGCCGCAGGGCCGAGTCGATTGGTCGCGGTCGCCTCGACAGTTAGCTTATGCAATGCTAACTTCGGGGCAAAGTTCAGGCGGATCGGCCGATGGC GGGCGTAGGTGAAGGAGACAGCGGAGGCGTGGAGCGTGATGACATTGGCATGGTGGCCGCTTCCCCCGTCGCGTCTCGGGTAAATGGCAAGGTAGACGCTGAC GTCGTCGGTCGATTTGCCACCTGCTGCCGTGCCCTGGGCATCGCGGTTTACCAGCGTAAACGTCCGCCGGACCTGGCTGCCGCCCGGTCTGGTTTCGCCGCGC

TGACCCGCGTCGCCATGACAGTGCGACCCTGNACCCGGGCTGGCC (SEQ ID NO. 591)

::::::::::::::Rv4T7.seq::::::::::::::
GTGTGCTGTCAATTCAGAGCTGAGCCTGATGCACTCAACTTACTGAGCATGCTAACGCTGGTCGTGCGGGTCTTGTTCCCGCGTGTCGGCAGGGCACACGCTC GGGGCGTAGCTGGGAGAGGCCCCGGTCAAGCCCGGAGAGCAGTGCTCAGTCCGCCAGCTTGACCGACTTTCGATGAGAACGCGCTTCTCGCCGTATTGAACTG GCGTGCTGACGGTCGCTGAGCAGCGCTCGCCGAGTGCGGCCGCTGATTCTTTCATCGAGCCAGGAGGCGCATTCGTGTTCGGCCGCCTGCGGGTCGGCCCCAT CGTCGACGCGATCCGTCACCCACTCCTCGATCAGGTCTGCCTCATCGAACGGGCCAACGGTGCTGTCGGAGTAAGTGTGCGTGGGCACGCGAGCCGGGTGCTG

TGGTACACCCACCGTTGCATGAACAA (SEQ ID NO. 592)

Clone Rv50
::::::::::::::Rv50SP6.seq::::::::::::::
ATACTCAAGCTTCACCAGGCGCCGGCGGGCCGCGGCGCCAAGCCAGGCAGCCGCGCTCGGCGCGTCGGGGCCTTCCGCCGGCTCGGCCGACAGTTCGATCTCT GGATCGGCGGGGCTCTCCGGGCCGGCCTCGGCGACCTCAGCGGGCCGCGCCTTCCGGCCGAACCATTCCCTAGCCATAGATAACCGCACCTCAATGCACGGTT

TGGCGGCAACCCGG (SEQ ID NO. 593)

::::::::::::::Rv50T7.seq::::::::::::::
AGCTTCCGTCACGACCCGCCCTCGCCGGTGCCGGCGCCATCGGTCATCGGATCTCATGACGACGTCACGTAGGCCCGCTAGCCGCGAGCGGGCGCGGTCAACT GGCGAGGCGGCGGCGACGTGACTGAGCTGGCCGAGCTGGACCGGTTCACCGCGGAACTACCGTTCTCGCTCGACGACTTTCAGCAGCGGGCTTGCAGCGCGCT

GGAACGCGGCCACGGTGTTGCTGGTGTGCGCGCCGACCGGCGCTGGCAAGACGGTGGTCG (SEQ ID NO. 594)

Clone Rv51
::::::::::::::Rv51SP6.seq::::::::::::::
ATACTCAAGCTTGCCGGGACCGCGGAACAGAACCGGCGGTTCCTACCGCGGTGTGCGGCCGGCGCGATATCGGCCTCCCGACTAACCCGAACCCGATGTGGGC

TCC (SEQ ID NO. 595)

::::::::::::::Rv51T7.seq::::::::::::::
ACGTTGGCTCTGCCGGAACGTATTTCCAGCGGCACGCATTCGGCGTGGGTGCCGGGCGCCGAGTTGCGTCGCTGGGATCACGCAGCAGTCGCCGGCGGCTGCC

GTCGGGCTATGAATTGCACCGAGCCGGAAAATCCNCAC (SEQ ID NO. 596)

Clone Rv52
::::::::::::::Rv52SP6.seq::::::::::::::
ATACTCAAGCTTGTCGTATTCCGTGGCACTGTCAGACATATGCGCCGCTCCTCCTCATCGCTGCGCTCGGCATCGTCGCCGGCGGTCATGGCGTCACCCTACC CAAGCCGAACGCGAAACGAGAACGTGTTCCATTATTAGGGTGTGAGCACCAATACCAGATTGCTCACCAGGAACTCACGCAGCACCGGGACGGATGTCAGCCA

CCACCCCCATCTGGGGTGGTAGCGGGGA (SEQ ID NO. 597)

::::::::::::::Rv52T7.seq::::::::::::::
CGTTGGTAGCCCGATATGCATAGTGTATCTTACTGAACATGATTTCCATTATGGAGCCCGGGGTGCCGGCAGCGCGAACGGTGCGCCGTCAGACGCGGGCGGC TABLE 3-continued End sequences of the polynucleotide inserts cloned in the named recombinant ACTGACCAGGGTGTTGCGGGCGAACATCGGCCCGGCTTCGGATTCCGGTCCGGGTACCGGGCGACCCACCGCTTCGAGGTA (SEQ ID NO. 598)

Clone Rv53
::::::::::::Rv53SP6.seq::::::::::::
ATACTCAAGCTTGGCCAACTCCTCATCGGACTTGAAGGTGCCGTCCTCGTTGGCGGCCCTGCTCCACGGCACGTTGATGGCACCAGGAATGTGTCCGGGCCGC TGGCTTTGTTCCTGCGGCAGGTGCGCGGGGGCCATGATCTTGCCGGAAAACTCGTCGGGAGAGCGCACGTCGATGAGGTTCTTGACGTTGATGGCCGCCAGGA CCTCGTCGCGGAATGCCCGAATCGTGTTATCCGGCGGGGAGGCGGTGTATGAGGTCACCGGCCGGCTGACCGGGTCGCTGGACAGCGGGCGTCCGTCCAGCTC

CCACTTCTTGCGGGCGCCGTCCAACNACTTGACTTCTCCTGG (SEQ ID NO. 599)

::::::::::::Rv53T7.seq::::::::::::
ATATCTTAAGCGTCGGGTCCCGAGGCTCGGTCGGCAGCTCCAGCAAAACCCGCTCCACCCCTAGATGCCGGTATCCCTCAAGGTCTTTAGCCGCCGCTTCACC CCACTGGCACACGGTCACCGGCACGTCGCCCCCGGCCATGGCGCGCAACCGCTGAAGCGGACCCGACAGCCGCTGCGGTGATGGACTGATCGCGATCCACCCG GCATTGAGCCGGGCTATCCGCGGGAAGTTCGCCGGTCCCCCGCCCACATACAGCGGAGGATAGGGCTTTGTCACCGGCTTCGGCCAGCAGTAGATCGGATCGA AGTCCACATATGTCCCATGGAATTCCGCCTGCTCCTGCGTCCAGATCTCGATTATCGCGCGCAACCGCTCATCGATCACACGTCCGCGCACCGCAGGGTCCAC

ACCATGGTTGGCGACTTCTTCGCGCA (SEQ ID NO. 600)

Clone Rv54
::::::::::::Rv54SP6.seq::::::::::::
ATACTCAAGCTTGTCGCGGTAAACCCGCAGCAGGGCGGTGGGTGCGGTGTCAAAAACAACCACACTTCTTTGCGGTTCGGTGATCTCGACACCGGCCGCGAGC CGACCACCATGCGCGCGTAAATCGGCGATCAGCGCGTCGGCTATCGCCTGGGTGCCGCCCACCGGAATCGGCCAGCCGACCGAATGGGCCAGCGTTGCCAGCA TCAGTCCGGCGCCGGCCGACACCAGTGACGGCAACGGTGAAATCGCGTGGGCGGCAACGCCGGTGAACAACGCGCGGGCATCCTCGCCCGCCAGCGACCGCCA GGCAGGGGTGCCCTGGGCCAGCATCCGCAGCCCGAGACGCAGGACCGAGCCCAGTGCAGTAGGCAAAGACCGCTTGTCGGAGACATGAACTCCACGACCGT (SEQ ID NO. 601)

::::::::::::Rv54T7.seq::::::::::::
AGCTTATTGAACCGCGGGTCGCAGGCAAAGTGGACCTCATAACGACTCGGGTCCAGCGACCGCGCCAACACGAACGGCCGGACGACGTGGGCCAGGGTCGCGG CCTCCCCTACAAACAGGATCCGTTGCCTGCGAGCGACAGGCTCCGGTGCGGCGTTGGGCGCCGTGCTCGTCCCAGCGTCCGGTCCCGGGTCGCCGGCGACGCT TGTTTCCTCCATACTCGCCCCCTAATCTCGAGGCAGCCCGTACCCGCAGGCAACCTCCCAAAAATGCAATCCCCCAAAATGCAATGCGTCGAGCTATTTCTCA CACCGACCGCTAGTTGCGGATCAGAAATCCGTTGGGCGCGGAAGTCCAGCCGAATTTGTTCTCCCGCTCCGCATCATGCTTGTAATCGTTTGGAAATTCATCC

TCATATGCCTCGATCGCTTCATAGGGTCCAGGCCAAACCGGGCA (SEQ ID NO. 602)

Clone Rv55
::::::::::::Rv55SP6.seq::::::::::::
CTTCCGGCTCGTATGTTGTGTGGAATTGTGAGCGGATAACAATTTCACACAGGAAACAGCTATGACCATGATTACGCCAAGCTATTTAGGTGACACTATAGAA TACTCAAGCTTGGCCACCTCGCGGTGTGTGGTGGAACCCATCTGAGCAGTGTGCCAAACCGGGGCAGACAGCTCCCAATTGACGTGAGCCCGCTCACTTGCTG

GGTAAGCGTCG (SEQ ID NO. 603)

::::::::::::Rv55T7.seq::::::::::::
TAGCGCCCCCTCCCGGGCGGAGCTCCACGGCGTGGATCAAGGTACCGGCCGGGATGTTGCGCAATGGCAGGTTGTTGCCCGGCTTGATGTCGGCGTTAGCGCC GGATTCCACCACATCCCCTTGCGAAAGTCCGTTGGGTGCAATGATGTAGCGCTTCTCCCCATCGAGATAGTGGAGCAACGCAATCCGTGCGGTACGGTTCGGG TCGTACTCGATGTGCGCGACCTTGGCGTTGACACCATCTTTGTCATTGCGGCGAAAGTCGATCATCCGGTAAGCGCGCTTATGACCGCCGCCTTTGTGCCGGG TGGTAATCCGGCCATGCGCGTTGCGTCCACCGCGACCGTGCAGCGGGCGCACCAGCGACTTCTCCGGGGTTGACCGGGTGATCTCGGCGAAATCAGATACGCT GGCGCCGCGACGACCAAGCGTCGTGGGCTTGTTCTTGCGAATTGCATGTCTAATCAGGTCTTTCTC (SEQ ID NO. 604)

Clone Rv56
::::::::::::Rv56SP6.seq::::::::::::
TGAAACTATATAATACTCAAGCTTGCCAAAGAAGACCTCGTCGACCAAGCAGGACGCGACCGTCGAGGTGGCGATCCGGCTTGGCGTCGACCCGCGTAAGGCA AACCAGATGGTTCGCGGCACGGTCAACCTGCCACACGGCACTGGTAAGACTGCCCGCGTCGCGGTATTCGCGGTTGGTGAAAAGGCCGATGCTGCCGTTGCCG CGGGGGCGGATGTTGTCGGGAGTGACGATCTGATCGAAAGGATTCAGGGCGGCTGGCTGGAATTCGATGCCGCGATCGCGACACCGGATCAGATGGCCAAAGT CGGTCGCATCGCTCGGGTGCTGGGTCCGCGCGGCCTGATGCCCAACCCGAAAACCGGCACCGTCACCGCCGACGTCGCCAAGGCCGTCGCGGACATCAAGGGC

GGCAAGATCAACTTCCGGGTTGACAAGCAGGCCAACCTGCACTTCTC (SEQ ID NO. 605)

TABLE 3-continued

End sequences of the polynucleotide inserts cloned in the named recombinant

::::::::::::Rv56T7.seq::::::::::::
GCTGAGCTCCACGGCGTGGATCAAGGTACCGGCCGGGATGTTGCGCAATGGCAGGTTGTTGCCCGGCTTGATGTCGGCGTTAGCGCCGGATTCCACCACATCC CCTTGCGAAAGTCCGTTGGGTGCAATGATGTAGCGCTTCTCCCCATCGAGATAGTGGAGCAACGCAATCCGTGCGGTACGGTTCGGGTCGTACTCGATGTGCG CGACCTTGGCGTTGACACCATCTTTGTCATTGCGGCGAAAGTCGATCATCCGGTAAGCGCGCTTATGACCGCCGCCTTTGTGCCGGGTGGTAATCCGGCCATG CGCGTTGCGTCCACCGCGACCGTGCAGCGGGCGCACCAGCGACTTCTCCGGGGTTGACCGGGTGATCTCGGCGAAATCAGATACGCTGGCGCCGCGACGACCA

GGCGTCGTGGGCTTGTACTTGCGAATTGCCATGTCTAATCAGGTCTTTCTCT (SEQ ID NO. 606)

Clone Rv57
::::::::::::Rv57SP6.seq::::::::::::
ATACTCAAGCTTGTTGGTGACCTCGCCGGCGAACAGTTCTCGCACGATTTCCGGATTAGCGGGACTGGTCACCAGTTGGGTATGCGGGAAGGCGCTGACGTTC GCCGCGATTAGCTGTTTGATGGACGCGGCGGTGATGTCCTGATCACGGAACTGGCTGTAATAGCCCAGGGTCGCCACGCTTCCATCCGGGCCCGGACCCGGC (SEQ ID NO. 607)

::::::::::::Rv57T7.seq::::::::::::
GATGATCGCCGGTGCCACCCCGATCCGTGCCTCGGTCAGCGCGAACGTGCTTTCCGGTCCGGCGACCACCATGTCGCACGCACCGACCAGGCCGAACCCGCCG GCCCGCACATGCCCGTTGATGGCGCCGACCACCGGCAGCGGCGACTCGACGATGGCGCGCAACAGCGCCGTCATTTCCCGCGCCCGCGCCACCGCCATCCGGT

ACGGATCACCACCACCTCCGCCGGCCTCGCTGAGGTCC (SEQ ID NO. 608)

Clone Rv58
::::::::::::Rv58SP6.seq::::::::::::
ATACTCAAGCTTGCCGCAATCGAAACCAACCTGTTTGTGCCGCAAGAAATTACGCCGTGGCCCGGCGCCGATCAAGAAACGCCCCGGCGCGCGGCGGTGTCGT CGTATGGCATGACGGGCACCAATGTGCACGCCATTGTCGAGCAGGCACCGGTGCCAGCCCCCGAATCCGGTGCACCAGGCGACACCCCGGCCACACCCGGTAT CGACGGCGCGCTGCTGTTCGCGCTGTCGGCCAGCTCGCAGGACGCGCTGCGGCAAACCGCCGCGCGGCTGGCCGATTGGGTCT (SEQ ID NO. 609)

::::::::::::Rv58T7.seq::::::::::::
TTGGCGGGTTGGCCACANCANCCCGCCGGTGACGGCGACGATGCTGGGCTGGTTGCGGCCCTGCGCCACCGCGGCTTGCATGCTGGTTGGCTGTCTTGGGACG ATCCCGAAATAGTCCACGCGGATCTGGTGATTTTGCGGGCTACCCGCGATTACCCCGCGCGGCTCGACGAGTTTTTGGCCTGGACTACCCGCGTGGCCAATCT GCTGAACTCGCGGCCGGTGGTGGCCTGGAATGTCCANCGCCGTTCACCTACGTGACCTTGATGGGATCCGGGGGNT (SEQ ID NO. 610)

Clone Rv59
::::::::::::Rv59SP6.seq::::::::::::
NCGTGGACACCGGTGTCGANCGCCACCAGCCGCATGTCTGCANGTCNATTCCGTCCTCGGCAACATCTTGAATGCCGAGCAGCGCCTGGGCGTGATCGGCAAC CGGGGATGACCGCTCGCCGATCCGCTCGACAATCCCGGCGGCACGTGACATGCCGGCGGACGGCTCGACGAGCTGGAACTTCAGCGACGACGATCCGGAATTG ATCACCAGCACGGTGCTACTCATGGACCCCTGCGCCTGAATCCCGTGATGGCCACGGTGTTGACTATTCGTCGACAGTGCACCCGAGATAGTCTTCACGGCTG

CGT (SEQ ID NO. 611)

::::::::::::Rv59T7.seq::::::::::::
CATGTATTGCCGTGCTCACGGCGCCACGCTCGATGGTTTCTCGAAGTCTCCGGGCTGGTGTACAGCTTCTCGTTGATCTCGTTCGCCACGCCGTCCTCTTCCC GCCGACGACCCGATCTCGATCTCCANAATGATCTTGGCGGCCGCCGCCGCCTTGAGCAGCTCCTGGGCGATGGCCAGGTTCTCATCGATGGGCACTGCCGACC GTCCCACATGTGCGACGGAACAAAGATGTCACCTTGCTCACGCGTGCGCNAGATCNCANAAGGGCCGGACATACTGTCNACTTGTCCTTGGGCAGTGGTCCGT

GTCAGCCCACGTGACGGGTACTTGGCGCGATAACGTGGTG (SEQ ID NO. 612)

Clone Rv5
::::::::::::Rv5SP6.seq::::::::::::
GCCACCACGACCCGGCCGTAACTCTGCTCACGGAAATGCGGCCAGGCCGCGCGTAGCACGTGGTATCCGCCATAAAGGTGCACCTTAAGCACGGCGTCCCAAT TCTCGAACGACATCTTGTGGAAGGTGCCGTCGCGCAAGATCCCGGCGTTGCTCACCACACCGTGCACGGCGCCGAATTCGTCAAGCGCGGTCTTGATGATGTT CGCTGCGCCGTCCTCGGTGGCGACGCTGTCCTTAGTTGGCGACCGCCCGGCCCCCCTTGTCGCGAATCTCGGCGACGACCTCATCGGCCATCGCCGAACGGCG

CCCGTGCCCGTCGCGGGCGCCACCGAGGTCGTTGACCACGA (SEQ ID NO. 613)

::::::::::::Rv5T7.seq::::::::::::
CAGGCATGCAACCTTTGTCCACACGGCGTCTACTCCGTGCAAGGTCCGACCGCTTCCACGTCCCGCCGTGACGGTGCTCCATCTCCCTCAGCAACGCGTGAAG

TGGTCCGATCCCGCGGCTTCAGG (SEQ ID NO. 614)

Clone Rv60

TABLE 3-continued

End sequences of the polynucleotide inserts cloned in the named recombinant

::::::::::::Rv60SP6.seq::::::::::::
GTTGAGACGCAACCAGCGCACAACGACGATTTGGCGTAGCGGCGGACGTCTGCTCGATTCGATCACGTCGCGCTCGCATCGAGCATGGCCCGCGACGCTACAC GATCGCCGTCGTCGATGACACGACCGAGCCGTACGCCGGCCGTAAGCCGCGCCAGGATTCGGCGAAAAACGTCTACGTGGCGGGTGTACTGGGTGTCGAATGA TTCGTGGGGTGCGTATGCGTCCTGCAATCGTCGACATAGATCCGTCGCCGCATCGCGTCGACAACTCCGGGTGAGTGGAATACACTTGCCGATCACGCGACGT GCGCGGATCGATGCCGACCGAAATACGACCACATGGCTCTTGTTGCNCAGTGTTGGCGGCATCAAATACCCTCAGTGCCGTCCGAC (SEQ ID NO. 615)

::::::::::::Rv60T7.seq::::::::::::
TTNCCGCCTTNACGCCTACTCCNAGACGATGCTCGACGCGTGTGAGCACACGGCGCTGCTGTAGACGGCACGGCGCAGCTGGATCGCGCTTGGTGCACCCAAG CCTCTACGCGCGTCGCTGCGTCGTCATCGGGTACCGAACATATTCCGGTCGTTGCGCAGAGTGTGCATGTGCGGCTCTTGTGAACGAACATAGCAAAGCGTAT ATGTCTGTGGCGGCTCTGCAGATATCGCGATAATACGTATATACATAAGGTGGCGCGCGATCTATCGGTATATCCGTTATGGCGGACGTGCGTGAGCGTGAGT

CGCGGCGCATCGCGCACTTCGCGATCGCGTGACTGGTCCTCGCGACTGCGCGCATGCGTAGC (SEQ ID NO. 616)

Clone Rv61
::::::::::::Rv61SP6.seq::::::::::::
GGTGATGACGCACTTGCTTCGAATGAGTCATTGACTACTCCCGTGGTTGTCCTGCGATGGTGGAGTGCCGCGCAGCCTTGCCCGANGTCGCGATCGCGTCGCG GGCTTCGGGGAGCAGACTGACCTGCAGATGGAAGTCGTGCCACATGCCCGCGAACGGCGAGCTCGATGCTTGTTTTCGAAGNGCGCANGCGGTTTCGATCTTG TCCGCGTCAACGCAGATCGGATCTCGCCGCGGTCTGCATGACGATGGGCGCAGGCCCGCTCATGTCCCGTAGACGGGGAGATACGGGCAGCCGCGGATCGAGA CCTACGTAGCGCGGCGCCCATCGTGCCATCGACGAAGAATGACGGATCGCGCAGCGCCGTCGCGTCGCTTCGATGTCACGCGAGATCGCCACGGCAGATCAGC

GATGCGCGGGC (SEQ ID NO. 617)

::::::::::::Rv61T7.seq::::::::::::
CGGTACGCCGGCAACAAACGCCTTGTGACGAGCGCGTCCGAGCGGTCATCGGCCTCCACCGTCATGCACAGCTCCTTCTCCAGGTCTACGCCGACGTCGCGGT CCACATTGGTGAGCTTGGCGAATGCCTCGGCAACCTCGTCGAAATGCGCCTCCGCGTCCGCATCGAAGGTCGCCATGTCAAAGATCAACTCGACGTAGTAGCT AGTTACCGCATCAGGTCAGTGTTTGCTGGCCTCGGAGTCCGGCCGAACAATGGCCATTTCCCGCGACTCTAGAATCCAGTCATCGTCTCGGTGACGACGCCTT

GCCGATCACATAGCTCGACCGGATCGGAGAGAATCTGGTTCTCGT (SEQ ID NO. 618)

Clone Rv62
::::::::::::Rv62SP6.seq::::::::::::
ATACTCAAGCTTAAGCGCAGCAGTACCGGCGGTGCCTGGGCATCCCAGCAAAACGGGGAGCTCAACGAACGATTCCTGAACGAAGGGTCGTCCACCAACCTCC

AAACCGAACGGTTGCCAGCCCCGGC (SEQ ID NO. 619)

::::::::::::Rv62T7.seq::::::::::::
GCAAGTCCGCTCAATGTGGTTGTGATCACANGACTACGTCGCCTCAATCAGCTCAAACGTCACCCCGTGGCGTGCTGCGCAGCATGAAGGTCGGCGCCCGCAC GATGTGGGCGAAGCAACAGGTAATAACTGGTCGGCATGGGTCAACCCTCATTGGGCCGTTGCGGATCGGGTGCACGCCCGGAGTGCCGGTCGAACTCAACACC GCCTTCACCGATCTTTTCGTCGAAAATGGCGGTCGTGTCGGGGTATACGTCCGCGATCCCACGAGGCGGAATCCGCTGAGCCGCACTGA (SEQ ID NO. 620)

Clone Rv63
::::::::::::Rv63SP6.seq::::::::::::
ATACTCAAGCTTCGCGCCCTCAAGCGGCTGAAGGTGGTTCCGGCGTNCCAACNGTCGGGCAACTCGCCGATGGGCATGGTGCTCGACNCCGTCCCGGTGATCC CGCCGGAGCTGCGCCCGATGGTGCAGCTCGACGGCGGCCGGTTCGCCNCGTCCGACTTGAACGACCTGTACCGCAGGGTGATCAACCGCNACNNCNNGNTGAA AAGGCTGATCGATCTGGGTGCGCCGGAAATCATCGTCAACAACNAGAANCGGATGCTGCNGGAATCCGTGGACGCGCTGTTCGACAATGGCCGCCGCGGCCGG

CCCGTCACCGGGCCGGGCAACCGTCCGCTCAAGTCGCTTTCCGATCTGCTCA (SEQ ID NO. 621)

::::::::::::Rv63T7.seq::::::::::::
TGCGCATGGCAGTTGTTGCCGGCTTGAGTCGCGTTAGCGCGGATTCCACCACATCCCTTGCGAAGTCGTGGGTGCAATGATGTAGCGCTTCTCCCATCGAGAT AGTGGAGCAACGCAATCCGTGCGTACGTTGGGTCGTACTCGAGTGCGCANCTTGGCGTTGACACCATCTTTGTCATTGCGGCGAAGTCGATCATCCGGTAAGC GCGCTTATCGACGCCGCCTCTGTGCCGGGTGGTAATCCGGCCATGCGCTTGCGTCCACCGCGACGTGCAGCGGGCGCACACCGACTTCTCCGGGTGACGGGTG

ATCTCGGCGAATCAGAACCTGGCGCGCGACACAGCGTCGTGGCTGTACTTGC (SEQ ID NO. 622)

Clone Rv64
::::::::::::Rv64SP6.seq::::::::::::
TGGGTGATCAGATACTGGCTAGTTGGTCGGGTGGGGTGATCGAAGATCGCGGTGGCCGGCAGCGTTACTGCGGTGACGCTGTTAAGCGGTTACGTACTCCACG TABLE 3-continued End sequences of the polynucleotide inserts cloned in the named recombinant GCACTCAANGAATTANATCCCGAATCGGCAAACCCTGGCCAGCGTCGAGTCCGCAGCGCCGTCGCGCCCCCCACCGCTGCGGCATGCTCACATACCACCTCGA TCGCTGCGGGAGTTGCTCGTCGGCCGACCGACCGGCCAGCCGGGCGGCAAACCGGAGGACCCAAGATTCAGCACCACCATCGCTAGCCCGATCTGGCCGCGCG

TGG (SEQ ID NO. 623)

::::::::::::Rv64T7.seq:::::::::::
TCGTAGCGGTTGCGACCANTCCGCGGACAGCTCCGCCACGCGACGGGTCGGGATCACCGCGGTCAAACCACCGAGCGGCGAGGATCTCTGGCCGTCGACGTGA CCGCGCACGGCCGCGGTGATGGCCAGTCCCGACCGCCGTTCCACTTGGCGTACGCGCTGGATGTGTTGTGCCGCAACGGAATCCCACCTCAATTATGACCTCG TTGTGGGCGAGCGCGGTATCGTACGCCCGACCAGGAATCGTCGATGCTATCTCACGTCACCGAAGGCCTCTCCCAGCACACCGCATCCAGAACGTGCACACNG TCGACATGTCTCGGCGGATCCGCCTGCAGAACGAACGCCANGTGCGCTGTGCGACACGGGTCGCGATCACCGCTCGCACGCGGAGATCGGCACACGCGCAGCG

CATCGATCATAATCTCTCGATGCGGTCTCCACCACCGAACAG (SEQ ID NO. 624)

Clone Rv65
::::::::::::Rv65SP6.seq::::::::::::
ATACTCAAGCTTCGCTGAGGTGGTGGGGCACGATCACGTCACCGCACCGCTGTCGGTGGCGCTGGATGCCGGCCGGATCAACCACGCGTACCTGTTCTCTGGG CCGCGTGGCTGCGGAAAGACGTCGTCAGCGCGTATCCTGGCNCGGTCGTTGAACTGTGCGCAGGGCCCTACCGCCAACCCGTGCGGGGTCTGCGAATCCTGCG TTTCGTTGGCGCCCAACGCCCCCGGCAGCATCGACGTGGTAGAGCTGGATGCCGCCAGCCACGGCGGCGTGGACGACACCCGCGAGCTGCGGGACCGCGCGTT

CTATGCGCCGGTCCACTCACGGTACCGGGTATTTATCGTCGACGAGGCGCACATGGT (SEQ ID NO. 625)

::::::::::::Rv65T7.seq:::::::::::
GCACTCACGCTGGTACAAGACCTTCACAAAATCTGAAATCCTGACCCGATACTTGAACCTGGTCTCGTTCGGCAATAACTCGTTCGGCGTGCAGGACGCGGCG CAAACGTACTTCGGCATCAACGCGTCCGACCTGAATTGGCAGCAAGCGGCGCTGCTGGCCGGCATGGTGCAATCGACCAGCACGCTCAACCCGTACACCAACC CCGACGGCGCGCTGGCCCGGCGGAACGTGGTCCTCGACACCATGATCGAGAACCTTCCCGGGGAGGCGGAGGCGTTGCGTGCCGCCAAGGCCGATCCGCTGGG

GGTACTGCCGCAGCCCAATGAGTTGCCGCGCGGCTGCATCGCGGCCGGCGACCG (SEQ ID NO. 626)

Clone Rv66
::::::::::::Rv66SP6.seq::::::::::::
ATACTCAAGCTTGTATAAAAAGATCGGTGAGCGCATCGATTCGCTCCGCCGGGTTTGCCGCTGCGGCGGCGGAGCTGCCGTGACCGTCTATTTGGGTGATCAG ATACTGGGCTAGTTCGGTCGGGGTGGGGTGATCGAAGATCGCGGTGGCCGGCAGCGTTACTGCGGTGACGGCTGTTAAGCGGTTACGTACCTCCACGGCACTC AAGGAATTAAATCCCGAATCGGCAAACGCCTGGCCAGCGTCGAATCCGGCAGCGCCGTCGCGCCCCAGCACCGCTGCGGCATGCTCACATACCACCTCCATCG

CTGCGGCGAATTGCTCGTCGGCCGACCGACCGGCCAGCCGGGCGGCAAACCCGGAAGA (SEQ ID NO. 627)

::::::::::::Rv66T7.seq:::::::::::
CCTCATCATATGCCGATAGAGCTCTACATATTCAGGAGATCACCATGGCTCGTGCGGTCGGGATCGACTCGGGACCACCAACTCCGTCGTCTCGGTTCTGGAA NGTGGCGACCNGGTCGTCGTCGCCAACTCCGGAGGGCTCCAGGACCACCCGTCAATTGTCGCGTTCGCCCGCAACGGTGAGGTGCTGGTCNGCCAGCCCGCCA AGAACAGGCAGTGACCAACGTCGATCGCACCGTGCGCTCGGTCAAGCGACCATGGGCAGCGACTGGTCCATAGAGATTGACGCAAGAAATACACGCCCGGAGA TCTCGCCGCATTCTGATGAACTGAACGCGACCCGAGGCTACTCGGTGANGACATNACGACGCGTTATCACACCCCGCCTNCTTCAATGACCCCACGTCNGGCA CCAAGGACCCGGCAATCGCGGCTCACTTGNGCGATNGTCNACAACCAACGCGNCGCCTGGCTACGGGCTCAACAAGGCANAAGACACAATCCGCTCTCGATTG

GTG (SEQ ID NO. 628)

Clone Rv67
::::::::::::Rv67SP6.seq::::::::::::
ATACTCAAGCTTATCGAGGCGGCGCATACCGAAGCGTGGGAAATCCAGACCGAATACCGCGACGTGCTGGACACTTTGGCCGGCGAGCTGCTGGAAAAGGAGA CCCTGCACCGACCCGAGCTGGAAAGCATCTTCGCTGACGTCGAAAAGCGGCCGCGGCTCACCATGTTCGACAACTTCGGTGGCCGGATCCCGTCGGACAAACC GCCCATCAAGACACCCGGCGAGCTCGCGATCGAACGCGGCGAACCTTGGCCCCAGCCGGTCCCCGAGCCGGCGTTCAAGGCGGCGATTGCGCATGCTACCCAA GCCGCTGAGGCCGCCCGGTCCGACCCGGCCAAACCGGGCACGGCGCCAACGGTTCGCCCGCCGGCACCACCGGTCCGGTGACCGCAGTACGGTCCCCCCAGCC

TGACTACCGTGCCCCGGCGGGCT (SEQ ID NO. 629)

::::::::::::Rv67T7.seq:::::::::::
TGGCCGGGCTGGTAGCCCGCGTATGGCAAGGTTCCGCTCAATGTGGTTGTGATGCAGCAGGACTACGTTCGCCTCAATCAGCTCAAACGTCACCCCCGTGGCG TGCTGCGCAGCATGAAGGTCGGCGCCCGCACGATGTGGGCGAAGGCAACAGGTAAGAACCTGGTCGGCATGGGTCGAGCCCTCATTGGGCCGTTGCGGATCGG GTTGCAGCGCGCCGGAGTGCCGGTCGAACTCAACACCGCCTTCACCGATCTTTTCGTCGAAAATGGCGTCGTGTCCGGGGTATACGTCCGCGATTCCCACGAG TABLE 3-continued End sequences of the polynucleotide inserts cloned in the named recombinant GCGGAATCCGCTGAGCCGCAGCTGATCCGGGCTCGCCGCGGCGTGATCCTGGCCTGTGGTGGTTTCGAGCATAACGAGCAGATGCGAAT (SEQ ID NO. 630)

Clone Rv68
::::::::::::Rv68SP6.seq::::::::::::
GTCCAGTCAAGCATCGGTCCTCTCCGACTACGCCAAGANTGGCGACGTGTCAGTGCANACAGCGGANATGGTGGCGCCTATGCGTCGACGCTCACAAACNGCG GTGANCGCGTTCTGGTCGTGCACCATCGAGCCGTGCCAGCCCGGCCGCGTGCCGTCAGCCGCATCCACTGGATGCCTTCTCGGNGTTTCAATCANGTACANGC GACGTTCGCCACCATCGTGCCGGGGCACGGTTAGCGAGAAACCGCCGACTTCACCGATTGCCTCGGTGATGCCGTCGAACAGATCGGGCCTATTGTCGACAGC CAGTGTGATNCGTATTTGCCGCCGTGCTCCTCGTCGCAACGATGCGAACACAGATCCGTGGNGGACGATAGCGGCTGACAANGTGGGGGCAACACAATCACAT

GCCACATTTCTTCATTTCACGCCCACAACCCAGACTTCGTCTCGATGNGCCG (SEQ ID NO. 631)

::::::::::::Rv68T7.seq::::::::::::
CACGCGGTCTGGCCCGATCCGAAGATCCCTTTGCCGGCGTGGCGGCTCTGCTCGGCGGTGTTGTACACTTCTCGAACACCTCGGCACCGACACCACCACCGTN GCTTGAACACCGCCAACATCGGCAGCAGATCTTGATGGTCCTGGTGAATCCCACGGTGACTTTGGAGTGGAAGGCGCCATACTGATCGCCGCGCCAGCACATG AGCTAGCGGCAGGAAAACCAGCAGCCGCTCACCTTGCGCAGCAGCGTCNGGTGATATGCCTGGCGCCCTTAATCTCGTGAACCAGTTGGATTGGGTCAACTGG CAGCCTTGGGTCTCCGGTGGTGCCGANGTGTANATAAGCTCCCGGGTCCGTCAACGTANTGCGCAGGCGGCGGTTACTCGGCGGGTCAACGAGCCCCGCTCGT GAGCNATCAGCCTTTGGACCGAACGGGATTCATACTCCGCAGGCGGCCCTCCGAAATCGGCACATGTCCTTTGATCGTTCGCAACAN (SEQ ID NO. 632)

Clone Rv69
::::::::::::Rv69SP6.seq::::::::::::
GGCCATGTCACATCGGTGGTACAGGTAAACCGCGCCGTGTGCGCGGTCTCGGAGATCAGAACGTGGTCGCAGTTGAACCGCGGGCTTTCAGCCAGTCGCGATA ATCGGCGGAAGTCGGCGCCTGCCGCCCCAACTAGCGCGACTCGCCACCTAGCACACCGATGGCGAAGGCCATGTNTCCGGCCACGCCGCCGCGGTGCATCACC AAGTCATCGACTAGGAAGCTAAGCGACANCTTGTGCAGGTGTTCGGGCAGTAGCTGCTCGGAAAATCGGCTGGAAACCGCATCAAATGGTCGGTCCAATCGAA

CCGGTTACCCGATCGTCACAAAAATCTCCGTCCT (SEQ ID NO. 633)

Clone Rv6
::::::::::::Rv6SP6.seq::::::::::::
GGGTCTACAACCACCGGGTCTGACTTCTGGGCTTCCACCGCTCGCGCCGTCGCGACAAACAGCGCGGTCGAACCGACACTCGTTGTGATGTCCCAGCTATCAC CTCCGGTAGGCACCCAATCGACCCTACCCGGCTATCTCACCCCCGATCTCCAGGCTCCGCCGATCCATGCGCATCCCGGTCCGGATCCC (SEQ ID NO. 634)

::::::::::::Rv6T7.seq::::::::::::
CAGGCATGCAAGCTTGTCGTATTCCGTGGCACTGTCAGACATATGCGCCGCTCCTCCTCATCGCTGCGCTCGGCATCGTCGCCGGCGGTCATGGCGTCACCCT ACCCAAGCCGAACGCGAAACGAGAACGTGTTCCATTATTAGGGTGTGAGCACCAATACCAGATTGCTCACCAGGAACTCACGCAGCACCGGGACGGATGTCAG CCACCACGCCCATCTGGGGTGGTAGCGGGGAAATACGGCTAACGCGGCTCCGGTGCCGGCAGCCCAGCGCAGACCCTCGGCGGCGGACACGGCTAACAACGAC GACCCATAGTTGTTCTTTGCCGGATGGCCGTGTTTGCTGACATATCGGGCGCGGCGCCGGCGCCGCC (SEQ ID NO. 635)

Clone Rv70
::::::::::::Rv70SP6.seq::::::::::::
NCTACGCTGCTGAATGTTGTGCGCCGGAGGANCTCAAGACCCACGCGGTTGTACGCGGACNTGCGACATGTTCAACCGCCGGA (SEQ ID NO. 636)

::::::::::::Rv70T7D3.seq::::::::::::
CTAACCAACAAGCCATGGTGGTTGGCGCCGTCGAGAGGTCGGCGGTCGCCACAACGGGAAGATCGCCTTGAGCGTCGCTCGACCGCCGCCTCGAGTTGGGTCA TAACGAAGTACTGATGCCGATCATGTCGACGTGTCCGTCGCATCAGCGTGCAGCGGCGACCCCTCGACGAGCCTCGGTGCCGCCGCGGCCAGGGCACCAGCTG TTTTAGCGCATTGTGCTCCGCCGGTAATAAAGGANGTCGGTCGCCTCCGCTGCTGTGGTTGCGGAATAACATCTTCCCTTCCTGCAACAGGATGAGAATGGTT

TTAATTGCTC (SEQ ID NO. 637)

Clone Rv71
::::::::::::Rv71SP6.seq::::::::::::
CTAAGCTTTCGGGTCCGCCGCCACTAGTACCGCGTTGCCGGCCCCGCCGACCTAGAATGTTCCGCCCATTGCCGTTTCCTCCCGCCGCCGGGTT (SEQ ID NO. 638)

::::::::::::Rv71T7.seq::::::::::::

TABLE 3-continued

End sequences of the polynucleotide inserts cloned in the named recombinant

TCTGGTGCCGGGTGTGCCGACGGGTCCGTCCGCCTCTGCTTCAGTGATTCTGTGATGCGACCGGCAACGTCCTCGTTGTTCGGTGTCTATGTGGTCCGTCTCT

CCTTGTTCCGCATACGATT (SEQ ID NO. 639)

Clone Rv72
::::::::::::Rv72SP6D2.seq::::::::::::
GCGATCGNTNACCACAAGGGCGCAACCGTTCGCGCGTCGACTGAACGTGCTGCCGCCTGGAGAACTGGCGCTGCTGCCACCTGGTCGGCGCATCGGCACTTCG AGGACTGGATTTCGACGCGTGGCCCGACCTGANGTNGGCGGTGGACNNGTGTGCACCCGGTTGATTCCTCGGCCTTGCCGGGATGCCACCTGCGCCTGGTGGT

CGAT (SEQ ID NO. 640)

::::::::::::Rv72T7D3.seq::::::::::::
CGTGACCGGACGGGGTGCCGCGCGAACCGGTCTTGGCCAATTGCCGGGGACTGGGGCTGGAGTATAAAGCGGGCCTGTTGCCGGAAGATAAAGTCAAAGCGGT GACCGAGCTGAATCAACATGCGCCGCTGGCGATGGTCGGTGACGGTATTAACGACCGCCAGCGATGAAAGCTGCCGCCATCGGGATTGCAATGGGTAGCGGCA CAGACTGGCGCTGGAAACCGCCGACGCACATTAACCATAACCACCTGCGCGGCTGGTGCAAATGATTGAACTGGCACGNCCACTCACGCCAATATCCGCCAGA

ACATCACTATTGCGCTGGG (SEQ ID NO. 641)

Clone Rv73
::::::::::::Rv73SP6.seq::::::::::::
ATACTCAAGCTTCTTACCCANAGCATGAACCCCGCCGTCCAATGCCGCCACCGTGGTGCTGTCGGCCGGCCGGGTGCGGGCACAATCGCCGAGTTCGGCGAAC AGATCCTCGAAGGTCTTCACGGCCAGCGATTGTTGCACGTGTCAGCCAGCCAAGTCACGGTGGTTTGACGCCACACGTTCGCCACCGCCGCGCCGCGCATTAG GGCATCCTAATATAGGTTAGGCTACCCTANTTATTCCTGTGGTCNAAGGAGGCAGCCGAACGTGACCTTCCCGATGTGGTTCGCAGTTCCGCCGGAAGTGCCG TCAGCATGGCTGTCCACCGGCATGGGCCCCGGTCCGCTGCTGGCCGCGGCCAGGGCGTGGCACGCGCTGGCCGCGCAATACACCGAAATTGCAACGGAACTCG CAAGCGTGCTCGCTGCGGTGCAGGCAACTCGTGGCAGGGGCCCAGCGCCGACGGTTCGTCNTCCCCATCAACCGTTCCGTATTGGCTAACCACCTGCACGGTG

GCACCGCACAACGCCGCCACAAACGCGCCCCGGTATAC (SEQ ID NO. 642)

::::::::::::Rv73T7.seq::::::::::::
GGCCGAACTTAATCGGTTGTTGGCGGCTGCCGAGTTGGGTCACTCGGGGGGTGTGCACTGGCACATGGTGGGCCGGATTCAACGCAACAAAGCCGGGTCGCTG GCTCGCTGGGCGCACACCGCTCACTCGGTGGACAGCTCGCGGTTGGTGACCGCGCTGGATCGGGCGGTTGTTGCGGCGCTGGCCGAACACCGTCGTGGCGAGC GGCTGCGGGTTTACGTCCAGGTCAGCCTCGACGGTGACGGATCCCGGGGCGGCGTCGACAGCACGACGCCCGGCGCCGTAGACCGGATTTGCGCGCAGGTGCA GGAGTCAGAGGGCCTCGAACTGGTCGGGTTGATGGGCATTCCGCCGCTGGATTGGGACCCGACGAAGCCTTTGACCGGCTGCAATCGGAGCACAACCGGGTGC GTGCGATGTTCCCGCACGCGATCGGTCTGTCGCGGGCATGTCCAACAACTTGAAATCCCGTCAACATGGTCGAC (SEQ ID NO. 643)

Clone Rv74
::::::::::::Rv74SP6.seq::::::::::::
GCTTCCCCTGATACTCGACCAGCCCCACTCGGGCCAATACGTGAATGTCCTAGCATTTTTCACCCGTTCACGGGCTAGTCGAGTAGTAGACGATTGATTAGCC

TGAACGTACCTCCGACGGCCAGCTGACGAACGGGTTTGACGGA (SEQ ID NO. 644)

::::::::::::Rv74T7D3.seq::::::::::::
TCAGCTGTCTGTAGAAGGGCTGGCGATACTGTGCACTGTCTGATATCGCNNCGTNGTGGGACTATNCAGNCCATNANGATGCGGTTCNGNNNNTGCAGAGNAT CCTGGNACACATNCGGTTCACGTTAATCANCATCGCGANTTNCTNCGTNTTCGATTANTTCTGCTAACGNNTCTNNNAGTGCCTGCGGGTCGACTCTAGAG (SEQ ID NO. 645)

Clone Rv75
::::::::::::Rv75SP6.seq::::::::::::
NCTCTGCCGGGCNAGAGCGCAGAGTCGGACGGCTTCGTCGATCGTGAAGCGACCNTGCGATGANCAGATATCGNTNACACTGCTCANAAACTTCGGATCATCG NTGATACACAGGCCAACGGGTAGCGGTTGTCCAACCGCTTCGTCAACGANATGGGATCGTGACGANCCTACGCTCGCAGGATATGTCGCNGACCNGNTCTAGA

NAN (SEQ ID NO. 646)

::::::::::::Rv75T7D3.seq::::::::::::
CACTTCATGCTCGTGCGTTGGCNTCGATTTGCNCGAGNGGTTAGCTCCTCGAGTGNGTGACGTATCACTCCGGCNGACTANCCGTATCNGCGTCCCGCACCGG TCAACTGGTCTAGCCACACCGGGGAGAATNCNCGACCGGNGCTATCGACCNATCACGGCTTGTCGNNAAGATAGNCAGCC (SEQ ID NO. 647)

Clone Rv76
::::::::::::Rv76SP6.seq::::::::::::
ATACTCAAGCTTGCCAACCGCCACCCTGCATCCGGGGGGCGAGCACTGCTCCGCCGACCAGTACGAACCAACCTGCGGTGCCCAGGCCATTGACAATGTGCTG

GTCGGCGCCCGCGAGTTCTAGCACAGCAACGCCGCGGCCACCACAGGGGCG (SEQ ID NO. 648)

TABLE 3-continued

End sequences of the polynucleotide inserts cloned in the named recombinant

:::::::::::::Rv76T7.seq::::::::::::
CGGTCGGTGTGCTTGGCGGCGTCGGTATCAACACCGCCCACGAAATGGGGCACAAGAAGGATTCGCTGGAGCGGTGGCTGTCCAAGATCACCCTCGCCCAGAC CTGCTACGGGCACTTCTACATCGAGCACAACCGTGGCCATCACGTCCGGGTGTCCACACCGGAAGACCCGGCGTCGGCGCGGTTCGGCAAAACTTTGTGGGAT

TTCCCGCCCCCCC (SEQ ID NO. 649)

Clone Rv77
:::::::::::::Rv77SP6.seq::::::::::::
AATACTCAAGCTTCGCGGAGGTGGTGGGGCAGGAGCACGTCACCGCGCCGCTGTCGGTGGCGCTGGATGCCGGCCGGATCAACCACGCGTACCTGTTCTCTGG GCCGCGTGGCTGCGGAAAGACGTCGTCAGCGCGTATCCTGGCGCGGTCGTTGAACTGTGCGCAGGGCCCTACCGCCAACCCGTGCGGGGTCTGCGAATCCTGC GTTTCGTTGGCGCCCAACGCCCCCGGCAGCATCGACGTGGTAGAGCTGGATGCCGCCAGCCACGGCGGCGTGGAGCAACCCCGCGAGCTGCGGGACCGCCC (SEQ ID NO. 650)

:::::::::::::Rv77T7.seq::::::::::::
GATGGCACTCACGCTGGACAAGACCTTCACAAAATCTGAAATCCTGACCCGATACTTGAACCTGGTCTCGTTCGGCAATAACTCGTTCGGCGTGCAGGACGCG GCGCAAACGTACTTCGGCATCAACGCGTCCGACCTGAAATTGGCAGCAAACCGGCGCTGCTGGGCCGGGCATGGTGCAATCCGAACAAGCACGCTCAACCCGT

ACACCAACCCCGAAGGGCCGCTGGCCCGGCGGAACCTTGTCCTCCA (SEQ ID NO. 651)

Clone Rv78
:::::::::::::Rv78SP6.seq::::::::::::
AACAGCTATGACCATGATTACGCCAAGCTATTTAGGTGACACTATAGAATACTCAAGCTTCTGGGCGTCGTGGTGCCCGGCCTGCCGGTGCAGGAACTGGATT TTACTGCCATCTCTCGCGACCCTGAGGTGGTCCAGGCTTACAACACCGACCCACTCGTGCACCACGGACGGGTTCCGGCCGGGATTGGCCGCGCGCTGCTGCA NGTGGGCGAGACCATGCCGCGGCGANCACCGGCATTGACCGCGCCGCTGCTAGTGCTGCACGGCACCGATGACCGGCTGATCCCCATCGAAGGCAGCCGTCGC CTGGTCNAATGTNTNGGATCNGCCGACGTGCANCTGAANGANTATCCCCGGCTGTNCCACNAGGTGTTCAACGAACCGGANCGCAACCAAGTG (SEQ ID NO. 652)

:::::::::::::Rv78T7.seq::::::::::::
CAAGGCATACGCCAAGACCCAAGGGATCGCAGTCACCTCCGTCAACGGCCTGGTCGCCGGCCACGGGTCCGTGCAGGAGACGTGGCTGGCCATGCAAAGCGCC GCCGCCTTATCAGGAACGCCCCGGCTTGTCGGCTTTTCCTGCATCGACACATTTCCGGAGGTGTTGTGGTTGGCGCANCGCGCGAGACAGGCCTGGGATGGCG TGCGCATCGTCATCGGGAATGCGATGGCAACACTGAACTACGAGCGCATCCTGCGCCAGCATGACTGTTTCGACTACGTCGTCGTTGGCGACGGGGANGTAGC GTTCACCAAGCTGGCCTTGGCCCTGGCGAATGACCTGCGGTTGACGACTCCCGGGACTAACCCGCCGTANTGAGCAAGGACAGATTCTGCGCACACCCTCCTC

GCTGGTCGACCTTGACA (SEQ ID NO. 653)

Clone Rv79
:::::::::::::Rv79SP6.seq::::::::::::
AACAGCTATGACCATGATTACGCCAAGCTATTTAGGTGACACTATAGAATACTCAAGCTTGCCGGTGATCTGGGTGGCCAACTCGGCGGGCACCATCTCCATC ACGACNGCAAACGCTCCGGCTTCGGCGACAGCGATCGCGTCTGCGATNGTTTGTTCGGCGGCGTCTCCGCGGCCCTGCACCCGGAAGCCGCCCAAGGTGTTGA CNCTTTGCGGGGTGAAGCCGATGTGTGCCATCACCGGGATNCCCGCCGCGGTCAGACANGCGATTTGCTCGGCCACCCGCTCACCGCCCTCGANCTTGACNGC

ATGTGCGCCGCCGTCCTTGAAGAAACCGGTGGCGGNGGCAACCC (SEQ ID NO. 654)

:::::::::::::Rv79T7.seq::::::::::::
CGTTGAGATCCAGCTGCGCACTGTGCAGCGCCTCGGTGGTCTGCTCGGCCTGCCGGGATAACTCGTTGAGCTTGGCCAGCGCGTCGTCGGCCGGATCAGCCAG CACATTCGCGGCCAGGACGCCGGAGGAGACGGTGAAGCTCGCAAAGAAACCTATGGCGGACCGCATGATTACACGCGCGATCAACCACCTCTGGTCGAGCCTC AAAATTTGCTTCCTTAAACGGGCCATCGACGGATGACGTCGAGCTGGTTTAGGTCTCAAACAGGTTACGAAACGATCTCGGAATTGTCCAAAAGGGGAAGTTA AGAAAATGGATAGATTTCTACCATTTCGCTGTGGACGATCGTACTTCTGCTATAGGGCTCCAGGGGCATCGACACGCAACGACCTTACGCGACACCGGATCCG

CGCTGGCGGCGGAACGGCACCANGCGCAACCGAAGGGCCAATCCGACATCGG (SEQ ID NO. 655)

Clone Rv7
:::::::::::::Rv7SP6.seq::::::::::::
ATACTCAAGCTTATCTAGGCGCCAGCTTGATTGGTCTGGTTGCATTGGCCAGCTGCGCGAGCCTGGCTCACTTCAACTACAACAACCGCAAACAATTGCCGCC TTCGGATCCGAGTTCGGTTGGGTACGCGGCAATGGANCACCATTTCTCGGTGAATCAGACTATTCCTGAGTACTTGATCATCCACTCTGCACACGACCTGCGA ACCCCGCGCGGCCTTGCCGACCTGGAGCAGCTGGCGCAACGTGTGAGCCANATCCCAGGCGTTGCCATGGTTCGCGGTGTGACCCGGCCAAACGGGGAAACCC TABLE 3-continued End sequences of the polynucleotide inserts cloned in the named recombinant TTGAACAGGCCCGGGCGACATACCAAGCCGGCCAAGTTGGCAACCGGCTGGGCGGCGCGTCGCGAATGATCGATGAGCGCACCGGCGACCTGAATCGGCTGGC ATCGGGTGCCAACCTGTTGGCCGACAATCTCGGTGACTTCGCGGTCAAGTCAGCCGGGCCGTTGCGGGTGTCCGCAGCCTTGTCCAGCCCCTCGCTTACTCCA (SEQ ID NO. 656)

::::::::::::Rv7T7.seq:::::::::::
CAGGCATGCAAGCTTTTTGAGCGTCGCGCGGGGCAGCTTCGCCGGCAATTCTACTAGCGAGAAGTCTGGCCCGATACGGATCTGACCGAAGTCGCTGCGGTGC AGCCCACCCTCATTGGCGATGGCGCCGACGATGGCGCCTGGACCGATCTTGTGCCGCTTGCCGACGGCGACGCGGTAGGTGGTCAAGTCCGGTCTACGCTTGG GCCTTTGCGGACGGTCCCGACGCTGGTCGCGGTTGCGCCGCGAAAGCGGCGGGTCGGGTGCCATCAGGAATGCCTCACCGCCGCGGCACTGCACGGCCAGTGC CCGCGGCGATTCAGCCATCGGGACATCATGCTCGCTTCATACTCCTCGACCAGTCGGCGGAACAGCTCGATTCCCGGAACGCCCACGCATGGTG (SEQ ID NO. 657)

Clone Rv80
::::::::::::Rv80SP6.seq::::::::::::
AACAGCTATGACCATGATTACGCCAAGCTATTTAGGTGACACTATAGAATACTCAAGCTTGTAGAAAAAGATCGGTGAGCGCATCGATTCGCTCCGCCGGGTT TGCCGCTGCGGCGGCGGAGCTGCCGTGACCGTCTATTTGGGTGATCAGATACTGGGCTAGTTCGGTCGGGGTGGGGTGATCGAAGATCGCGGTGGCCGGCAGC GTTACTGCGGTGACAGCTGTTAAGCGGTTACGTATCTCCACGGCACTCAAGGAATTAAATCCCGAATCGGCAAACGCCTGGCCAGCGTCNAGTCCGGCAGCGC CGTCNCGCCCCAGCACCGCTGCGGCATGCTCACATACCACCTCGATCGCTGCGGCGANTTGCTCGTCNGCCGACCGACCGGCCANCCGGGCGGCAAACCCNGA

AGACCCAAGAATTCATCACCACCATCGCTAGC (SEQ ID NO. 658)

::::::::::::Rv80T7.seq::::::::::::
CCTTCTTGACACCCACCTCGCCATCGACCTTGAGCACTCCGTCGTAGTTGGTGAACATGTGACCGGCGATCGGGCGGGTGAACGCGTACTGGGTGTCGGTGTC GACGTTCATCTTCACCACGCCGTAGCGCAGCGCCTCCTCGATCTCCGACTTAAGCGAACCCGAGCCGCCGTGGAACACGAAATCNAACGGCTTGGCGTCNGCC GGCAGTCCGAGCTTGGCCGCCGCCACCTGTTGCCCTTGCGCAAGGATGTCNGGGCGAANCTTGACGTTGCCGGGCTTGTANACGCCATGCACGTTGCCGAACG TCNCGGCCAGCANGTATTTGCCGTGCTCACCGGCGCCCANCGCCTCGATGGTTTTCTCGAAGTCCTCCGGGCTGGTGTACAGCTTCTCGTTGATCTCGTTCGC

CACGCCGTCCTCTTCGCCGCCGACG (SEQ ID NO. 659)

Clone Rv81
::::::::::::Rv81SP6.seq::::::::::::
AACAGCTATGACCATGATTACGCCAAGCTATTTAGGTGACACTATAGGATACTCAAGCTTGGAAAGGAGATCCCCGGGAACCTGGTGGCAACCCCGCCATTGG GGTTGTTGGGATTGCCGATCAGCGTGAANGAAAGCTCGTCTGGAGACAGCGGGTCGGCCGAAGCCGCAAGATTGGCCATCACTAGTGACGANATCGTGGCGCT CTGCGAGTANCCNAAGACAGTGACGTTGTTNCCGGCGGCAATTTGCTGCCGAATCGCACTTTCGAGAATGACNGCACCCTGCGCCACCGANGAATCNAAAGTG AGGTTCTTGATCACGACCACCGGGTNGAGCCCTTGGGGCGTGAAGANCGCCTGCGCNATAACACCCGGGACGCTGCCACTCATGTNCAGCGCGTTCGCGANCT

CNACATATCT (SEQ ID NO. 660)

::::::::::::Rv81T7.seq::::::::::::
TCCTGGTGATCGANGGCCGCGGTTCCGGCCGAAAATCCGGTTCGGGTTCGGGTCGCGGTTCCAACTTGANCGCGGTCCGCAGCTGATTCACCGTGGCAACGCC GGCCAACTGCGCATAATGCGCATCCGAACCCTCACCCGCCCGCCCCGCGATCACCCCAACCTGATCCAACGACAACCGCCCCTCCCGCATACCCCGGGCGCAG CGCGGAAACTCCGGCAACCGCCGCGCCACCGTGGCGATCGTGTGGGCGTTGCCTGACGAACANCCCATCTTCCAGGCCACCAACCCCGCCACCGACCGCGCCC CCGTCACACCCCACAACCCGTCGCGATCCAGCTCAGCCACGATCTCCACAATGCGCCCATCAATCGCATTGCGCTGAACGGGCAACTCCGCCAACTCCTCCAA (SEQ ID NO. 661)

Clone Rv82
::::::::::::Rv82SP6.seq::::::::::::
AACAGCTATGACCATGATTACGCCAAGCTATTTAGGTGACACTATAGAATACTCAAGATCTGGTACCCATCCGTGATACATTGAGGCTGTTCCCTGGGGGTCG TTACCTTCCACGAGCAAAACACGTAGCCCCTTCAGAGCCAGATCCTGAGCAAGATGAACAGAAACTGAGGTTTTGTAAACGCCACCTTTATGGGCAGCAACCC CGATCACCGGTGGAAATACGTCTTCAGCACGTCGCAATCGCGTACCAAACACATCACGCATATGATTAATTTGTTCAATTGTATAACCAACACGTTGCTCAAC CCGTCCTCGAATTTCCATATCCGGGTGCGGTAGTCGCCCTGCTTTCTCGGCATCTCTGATAGCCTGAGAAGAAACCCCAACTAAATCCGCTGCTTCACCTATT

CTCCAGCGCCGGGTTATTTTCCTCGCTTCCGGGCTGTCATCATTAAACTGTGCAA (SEQ ID NO. 662)

Clone Rv83
::::::::::::Rv83SP6.seq::::::::::::

TABLE 3-continued

End sequences of the polynucleotide inserts cloned in the named recombinant

AACAGCTATGACCATGATTACGCCAAGCTATTTAGGTGACACTATAGAATACTCAAGCTTANCGCCACCTCCCGGGCGGAACTCCACGGCGTGGATNAAGGTA

CCGGCCGGGATGTTGCGCAATGGCAGGTTGTTGCCCGGCTTGANGTCCGCGTTAGCGCCGGATTCCACCACATCCCCTTGCGAAANTCCGTTGGGTNCNATGA

TGTNNCGCTTCTCCCCNTCNANATAATGGANCAACGCNATCCGTGCGGTACGGTTCGGGTCNTACTCCATGTNCGCGACCTTGGCGTTGANACCATCTTTGTC

ATTGCGGCGAAAGTCNATCATCCGGTNAGCNCGCNTATGANCGCCGCCTTTGTGCCGGGTGGTAATCCGGCCATGCGCNTTGCGTCCACCGCGAACGTGCAAC

GGGGGCNCCAACGANTTCTCCNGGGTTGAACCGGTNATCT (SEQ ID NO. 663)

::::::::::::Rv83T7.seq::::::::::::
TGTGTGTGGTGGTAACCCATCTGAGCAGTGTGCCAAACCGGGGCAGCCAGCTCCCAATTGACGTGAGCCCGCTCACTTGCTGGGTAAGCGTCG (SEQ ID NO. 664)

Clone Rv84
::::::::::::Rv84SP6.seq::::::::::::
AACAGCTATGACCATGATTACGCCAAGCTATTTAGGTGACACTATANAATACTCAAGCTTGCGGGTNATNGCCTTGGTCAACGGCACCGTGATCGGATCNGGG TCTACCGCACACATNGACTGGAGCTTCGGCGAANTCATCGCCTATGCCTCGCGGGGGGTGACGCTGANCCCNGGTGACNTGTTCNGCTCNGGCACGGTGCCCA CCTGCACGCTCNTCNAACACCTCANGCCACCGGAATCATTCCCNGGCTGGCTGCACGANAGCGANNTTGTCNCCCTCCAAGTCTAAAGGCTGGGCGANANAAG

CANAACGTCCCGACNAACGGCACTCCTTTTCCNTTTGCTCTTC (SEQ ID NO. 665)

::::::::::::Rv84T7.seq::::::::::::
GAAATCATTGATGGTTTGAGTCACCAGGCCGATCAAGCCTTCGCCGAGCCAAATTCCAATCAAGAGGCCCAAGCCCGTACCAATCAGCCCGGCAACGAGGGAT TCCGTCATTATCAGCCAAAATAACTGCTCTCGGGTTACACCCAAACAGCGCAATATGGCGAAAAACGGTCGCCGTTGCACGACATTAAATGTCACGGTATTGT AGATTAAAAAGATACCCACCAACAANGCAATCAAACTGAGAGCGGTTAAATTGACCGTAAAAGCGTCCGTCATCTGTTTGACNGTGTCCCGTTGGGTATCCGA CGTTTCCATACGCACACCGGCCGGCAGTCTTTGTTGGATGCGTNTTGCAATGGCCTCATCTTTGATGATCAAATCGATGTNGCTCAGTCTTCCGGGCATATGG

AACAACTCTTGGGCCGTGGAAATATCAGCAATGATA (SEQ ID NO. 666)

Clone Rv85
::::::::::::Rv85SP6.seq::::::::::::
CTTTCGCCCAGGCCGGCGCGGATGTCCTCATCGCTTCACGAACATCATCCGAGCTTGACGCTGTCGCCGAACAGATCCGCGCTGCCGGCCGCCGCGCCCACAC CGTTGCCGCCGATCTGGCCCATCCCGAGGTGACCGCGCAGCTGGCTGGTCAGGCCGTCGGAGCTTTCGGGAAGCTCGACATCGTCGTCAACAACGTTGGCGGC ACCATGCCCAACACGCTGCTAAGCACCTCGACCAANGACCTCGCGGACGCCTTCGCCTTCAACGTGGGCACCGCCCACGCGCTGACCGTCGCGGCGGTGCCGT TGATGCTGGAACACTCCGGCGGCGGCAGCGTGATCAACATCAGCTCCACCATGGGCCGGCTGGCGGCGCGGGGTTTC (SEQ ID NO. 667)

::::::::::::Rv85T7.seq::::::::::::
TGTGGGCTCCGATCCGGCGCGCATGGCATCGACGGCGACGCCGATCGATGACGGCCAGGCTTACGAGCTTGAGGGTGTGAAGTTGTGGACCACCAACGGTGTG GTAGCGGACCTGCTAGTGGTTATGGCGCGGGTACCGCGCAGTGAAGGGCNCCGAGGGGGAATCANCGCCTTTGTCGTCGAGGCTGATTCGCCCGGGATCACCG TGGAGCGGCGCAACAAGTTCATGGGACTGCGTGGCATCGAAAACGGCGTGACCCGGCTTCNTCGCGTCAGGGTGCCCAAAGACAACTTGATCGCANGGAAGCG ACGGTCTGAAGATCGCGCTGACCACACTCAACGCCGGACGGCTGTCCCTACCGGCGATCCAACCGGAGT (SEQ ID NO. 668)

Clone Rv86
::::::::::::Rv86SP6.seq::::::::::::
GAGCTGGCCGAGCTGGACCGGTTCACCGCGGAACTACCGTTCTCGCTCGACGACTTTCAGCAGCGGGCTTGCAGCGCGCTGGAACGCGGCCACGGTGTGCTGG TGTGCGCGCCGACCGGCGCTGGCAAGACAGTGGTCGGCGAGTTCGCCGTGCACCTGGCGCTGGCGGCCGGCAGTAAATGTTTCTACACCACGCCGCTGAAAGC CCTGAGCAACCAAAAGCACACCGATCTCACAGCACGCTACGGCCGTGACCAGATCTGGCTGCTGACCGGTGACCTGTCNGTCAACGGCAACCGCCGGTGGTGG

TGATGACCACCGAAATGCTGCGCAACATGCTCTAC (SEQ ID NO. 669)

::::::::::::Rv86T7.seq::::::::::::
CATCTCTGGATCGGCGGGGCTCTCCGGGCCGGCCTCGGCGACCTCAGCGGGCCGCGCCTTCCGGCCGAACCATTCCCTAGCCATAGATGACCGCACCTCGATG CACGGTTTGGCGGCAACGCGGCAAGGCGTCNGTCGGGCCCAGCCGCGGCAATGCGGGTACCCGGGAGCGCGGGTCNGTANACCANCGCTGGACTGCGTCGCGC GGTGCGTCNACNTCAAAGTCCCCGGCGTCCCATATCGCGTATGACGCGGGCGCGCCCGGCACCANGGGTGCCGATCCGGCCGTCTCGAACACCACCGGCCCGC CAGCCGCCGCGGGTCCGGCAGCNAACCCGCCCGCGCCGATACCCGCTGCCCGCGTGCGTGATTGACCGCCGCGCGCACGCTGGCCANGGATCAAAGCCCGTG (SEQ ID NO. 670)

Clone Rv87

TABLE 3-continued

End sequences of the polynucleotide inserts cloned in the named recombinant

::::::::::::Rv87SP6.seq:::::::::::
GGACGCGTAGCCCGCCAGGCCGGTCAGGGTGCCCTTCCAGTCCACGCCGCTGTGGTCGGCGAACCGCTTATCTTCAATCGAGACGATCGCCAGCTTCATCGTG TTGGCGATCTTGTCCGAGGGCACCTCGAACCGGCGCTGCGAGTNCAGCCACGCGATCGTGTTGCCCTTCGCGTCGACCATCGTCGATACCGCAGGCACTTGCC CCTCGAGCAGCTGGGCCGAGCCGTTGGCAACGACCTCAGANGCACGATTGGACATCAGCCCTAGCCCGCCTGCGAACGGGAACGTCAGCGCAGTGGCGACGAC ACTGGCCAACAGACAGCACCCAGCCAGCTTCAGAACGGTGATCGCGGCCGGGAAGCGCTCGGGCATGCGTNCTACAGTAGCGACCTCCTGTCACTCCACGTGC

CGCTCGGTCCAATAGAATCTTTCCGCGGGCGGGTGAATCTCTGCNGGATCGGGGCNGGCGC (SEQ ID NO. 671)

::::::::::::Rv87T7.seq:::::::::::
GCTCGTTGCCGGCGGCGATCTCGTCGAGCTCGTCTTCCATCGCCGCGGTGAAGTCGTAGTCGACGAGCCGACCGAAATGCTGCTCGAGCAGACCGGTTACCGC GAACGCCACCCATGACGGCACCAGTGCACTGCCCTTCTTGTGCACGTNGCCGCGATCCTGGATGGTCTTGATGATCGACGANTAGGTCGACGGGCGGCCGATG CCCAGCTCCTCGAGCGCTTTGACCAGCGACGCCTCNGTGTNNCGGGCCGGCGGGTTGGTGGCATGGCCGTCTGGGGTCAACTCGACNATGTCCAACCGTTGAC

CCGGGGTCAGATGGGGCAGTCGCCGCTCGGCATCGTCAGCCTCGCCGC (SEQ ID NO. 672)

Clone Rv88
::::::::::::Rv88SP6.seq:::::::::::
GTCTTTCGATGGCTGCTTCTTCGGCGCTGACGCTGGCGATCTATCACCCCCAGCAGTTCGTCTACGCGGGAGCGATGTCGGGCCTGTTGGACCCCTCCCAGGC GATGGGTCCCACCCTGATCGGCCTGGCGATGGGTGACGCTGGCGGCTACAAGGCCTCCGACATGTGGGGCCCGAAGGAGGACCCGGCGTGGCAGCGCAACGAC CCGCTGTTGAACGTCNGGAANCTGATCGCCAACNACACCCNCGTCTGGGTGTACTGCGGCAACNGCAAGCCGTCGGATCTGGGTGGCAACAACCTGCCGGCCA AGTTCCTCGAGGGCTTCGTGCGGACCATCAACATCAAGTTCCAAGACGCCTACAACGCCNGTGGCGGCCACAACCGCGTGTTCGACTTCCCGG (SEQ ID NO. 673)

::::::::::::Rv88T7.seq:::::::::::
GCCAGGTCGAGGTCCCATGCGCGTGGGCCATTGATGCTGATCGCCAGGACGTCAAANATTTGGTCCGGCGTCAGCTGGGCGAAAAACGTGGGCCCCAGGACTT GCCCGGAGCTGCCCGGGTTCCCGTCGCGCAGCTCGGCGGCCCCGGTCAGAAANAAATTGCGCCAGGTCGCACACTCCGCGCCGTANGCCAGCTGCTCCAGGGT GTCGGCATAGAGCCCGCGGGCCGCAGCGTGCTCGCTGTCGGCGAACACCGCATGGTCGAGAAGCGTTGCCGCCCAACGGAAATCACCTGCGTCNAANGCTTCG

CGGGCCAACTCCAGCACTCGGTCGATG (SEQ ID NO. 674)

Clone Rv89
::::::::::::Rv89SP6.seq:::::::::::
NAAACGTTCCGGCTTNGGTGCCGGGCGCTTATTTGCGTCTCTGGGATCACNCTCAGTCGCCGGCGGCTGCCGTTGGGCTATNANTTGCACCGANCCGGAAAAT CCGCACNANAACTGCNAGTAGCGGCCTGCAGAANTGCATCCTCGGCGAANCNGACTACCGGTGGACANCNACAAGCGCCGCCGAACAACGCACTGGCCCGAGG GATNGGCGTCTATCGGCCCCGCCCGTCGAACTNGGAACAGACNGTGCGGTTCTACCGTGATCTGGTGGGAATGCTCNACCANACCTTCCCNANNGCTACGGAA CNACGGCGCGATATTCNGCCNTCCCANCTCGAGCCTGACNCTNGATATCGTCGANNCTCACCATCNCGATCNGCTGTGCGGGTNTTGCTCGGACTN (SEQ ID NO. 675)

::::::::::::Rv89T7.seq:::::::::::
CGAACGACGAACNCCNCAAGCCATGGTGGTTGGCGCCGTCAAAAGGTCCGCGGTCGCCACTACTGGAAAATCGCCTTGAGCGTCNCTCGACCNCCGCCTCGAG TTGGGTCNTAACGAAATACCTGATGCCGATCANGTCNACGTCTCCGTCGCNNCAACGTGCAGCGGCGACCCACTCTACNANGTCTCGGTNCCGCCNCGGCCAG NGCACCACCAGTGACNAATCCNTGCGCCNTCGGGCCNAGCANTCCCGGTGCNACCGNGGTGGGTCCGGCGATGGTNGGGTGTNCTCNNTACNGGAACGCCAGC GCNATCANCATCGGCANACTCNCGTCGATGTGCCGCGGCGCAACCATCCCCCACAATGATCNGGTGCGTCTGATCAGGCN (SEQ ID NO. 676)

Clone Rv8
::::::::::::Rv8SP6D.seq:::::::::::
TTAGGCGTGACGGCCACCGGGGCCACTCCGCACAATCTGTACCCGACCAAGATCTACACCATCGAATACGACGGCGTCGCCGACTTTCCGCGGTACCCGCTCA

ACTTTGTGTCGACCCTCAACGCCATTGCCGGC (SEQ ID NO. 677)

::::::::::::Rv8T7D4.seq:::::::::::
CGTCACCCCGATGCGCCCAGATCGGGGCTTCGCAGATAAAGCACGAACTGGCGGGCAAAACGTCGATCTCGGAGCCGGAAGGGCAATCAGCCGACCGTCGACG

AACGACACCGGCGAGACCACTTAGGCAGTGACGGCCT (SEQ ID NO. 678)

Clone Rv90
::::::::::::Rv90SP6.seq:::::::::::
CTTTTCNCGATGTCTCATGATNCCNANGGAGAACNNTGCNANCNCNGCCGCTGACNTNGCNCACCGCTNTGGCNGNGGTGACATTGGTGGTGGTTGCGGGCTG TABLE 3-continued End sequences of the polynucleotide inserts cloned in the named recombinant CNACGCCCGACTCGANGCCGANCCATNTNTTGCGGCCGACCGCNTNTCGTCTCNACCGCANNCCCNATCTCNGCCGCNCCCGGTGGANCTACNGCTNCTTCGC CATCTCTCGCCNATGGCTCCNGCGNNTCGCNCAACGTNTGGTTTGGTNANCTGCCTACCTGGTCNT (SEQ ID NO. 679)

::::::::::::Rv90T7.seq::::::::::::
GCTGCGCCAGTCGTTCGGTGCGGTCATGCCGTTGGACCNACCATCGGAGTTAGTTGCCGAACCGCGGACCACCGCAAGCACCCGGTCCTGGTCGCGCACCGCG TCGGCCAACCGCTTGAGCACCACCACGCCGCAGCCCTCGCCGCGCACGAATCCATCCGCGTTGGCGTCNAANCTGTNGCATCGGTCGGTCGGTGACAGCGCCG ACCACTTGGACAGCGCGATGGCGGTGAACGGTNANTAGGTGACCTGCCNCCNCGCCCGCCAATGCCCACCTCCGCTTCACNCATGCGAATGGTCTGACACGCC NAGTGAATTGCCACCAGCGACAACAAAAATCGGTATCTNCNGCGACGGCGGACACGCNATCCCNACTGATACTCGATCCGCCCCACCGCTTGNANCTCCGGGT TCCNGTGCTCATGTACCNTCATGTCGGTCTGCGCNCGATATTGACGATCGTGTTTCCCACGANNANAGANCCTCATCACGCCGGTTCGAGTGCCG (SEQ ID NO. 680)

Clone Rv91
::::::::::::Rv91SP6.seq::::::::::::
CTGTGTGCGGNCGGCGCGATATCGGCCTTTTTACTAACCGAACCCGATGTGGGCTCCGATCCGGCGCGCATGGCATCTACNGCGACGCCGATCGATGACGGCC AGGCTTACGAGCTTGAGGGTGTGAANTTGTGGACCNCCAACGGTGTGGTAGCGGACCTGCTANTGGTTATGGCGCGGGTACCGCGCAGTGAANGGCACCGAGG GGGAATCANCGCCTTTGTCGTCTANGCTGATTCTCCCGGGATCACCNTGGAGCGCNCCNCNANTTCATGGGACTGCGTGGCATCCAANACGGCGTGACCGGCT TCATCCNTCNGGGTGCCCAAAGACAACTTGATCNGCNNGGAAGCGACGTCTGAANATCGCGCTGATCNCACTCAACGCCGGACGCTGTCCTACCGGCGATCGC

ACCGGANTTGCCAANCCGCGCTNANNATNCGCGNGAATGNCCGTCCACNANTGCATGG (SEQ ID NO. 681)

::::::::::::Rv91T7.seq::::::::::::
TGGGGTGCCGGGCGCCGAGTTGCGTCCCTGGGATCACGCAGAGTCGCCGGCGGCTGCCGTTGGGCTATGAATTGCACCGAGCCGGAAAATCCGCANCAAAACT GCGAGTAGCGGCCTGCAGAAGTGCANCCTCGGCGAAACGGAGTACGGTGGACAACGAAAAGCGCCGCCGAACNACGCACTGGCCCGAGGGATTGGCGTCAATC GGCCCCGCCCGTCGAACTTGGAAGANACANTGCGGTTCTACCGTGATCTGGTGGGAATGCTCCAACNNACCTTCNCCGAAAGCTACGGAAGCNACGGCGCGAT

NTTCGGCCTTCCCAGCTCGACCTGACGCTGGAAATCG (SEQ ID NO. 682)

Clone Rv92
::::::::::::Rv92SP6.seq::::::::::::
NGGCNGGGAAGTTAATGCCCTACTGGTTCNATGCTCNCACNTCNCCNGTGACNNCCTGCNCCGACCCGCCGAGGTCCTGNCCGTNACCACCGANCNGGCGATC CGGGACTCTNGTACGCATCCAACANNGANCAACGTGCACGGGCGGAGTNGTNCCGCCACTTCGNCNATGACGGGGTCGATCCNTTCGACGTCCGTCGCCGCGT CGGTCGAGTGGCGGTCACNCTCCNNGTACTCGACCNCACNGACGAGAGGACTCGANCCCATCTACGTGTGGACGAAACANATCTTCTGTCCNACGACTACACC ACCACCCAGGCCATCGCCGNCGCCCGCGANGCCCCTTCGACGCCNTACTGGTCCNGNGGNGGCGCTCTCCGGTTGTCTNNCNCNTGNCGTGTTCCTTCACNCA

CTGCCCNACATCGANCCCGAGCNATNCNANGTCCGTCAATC (SEQ ID NO. 683)

::::::::::::Rv92T7.seq::::::::::::
GGACACTGTTCGCGTGCCCCTCGTCAAAGCCGGAGTGGTCGTGCTGCGCCGGACCCGACCCGACCTTCAGCGGGGGTTCACAGCTCCGTGGGTGCCGTTACTT CCGATCGCCGCAGTGTGCGCGTGCCTGTGGCTGATGCTGAACCTCACCGCGTTGACTTGGATCCGGTTCGGGATCTGGCTGGTGGCCGGAACCGCGATTTATG TCNGCTACGGGCGCCGGCACTCGGCGCATGGCCTTCGGCAAGCNCNANANAACGCGACCCGGAGGTGTTGAACTAGCTTCGCCGCGTATTTACAAATTGCNTT ATATGTCTACACATAAGACGCAAACTGCTCTATTGTCAANTCCCANCGTGGTGTGGCNCATGAAGATGTTTGG (SEQ ID NO. 684)

Clone Rv94
::::::::::::Rv94SP6.seq::::::::::::
TCCTTCTCGGTATCGGTTTGGGCTGTCACCANCAGTTGGTAGTTCTTCACGTNCTGTTGTTCGAGCGTCNAGCCGTCGCGCGTGTCNANGTCNCCGGACGCGT ATCCCGCCAGGCCGGTCANGGTGCCCTTCCANTCCACGCCGCTGTGGTCGGCGAACGCTNATCTTCAATCGAGACCATCGCCAGCTTCATCNTGTTGGCGATC TTGTCNNACGGCACCTCNAACCGGCGCTNCTAGTACNCCACNCNATCNTGTTNCCTTCNCGTCNACATCCTCGATNCCNCNTGCACTTTCCCTCGANCNCCTG GGCCGAGCCGTTGGCANTNACCTCNGAGCCCCATTGGACATCANCCCANCCCGCCTGCGAACGGGAACGTCAGCNCNCTGGCGACAACCTGGCCAACAN (SEQ ID NO. 685)

::::::::::::Rv94T7.seq::::::::::::
CACNCCGTGATCGCNAGCCCCNGTAGAAATNGTTGAGCCAGTTGGTGCGGCGCTCGTTGCCGGCGGTNATCTCGTCGAGCTCNTCTTCCATCGCCGCGGTGAA GTCGTACTCGACNAGCCGACCNAAATGCTGCTCNAGCAGACCGGTTACCNNNAACNCCNCCTCNTGACNGCACCAGTGCNCTGCCCTTCTTGTGCACGTACCC GCNATCCTGGATGGTCTTGATGATCNACTANTNTGTCGACGGGCGGCCGATGCCCATCTCCTCNAGCGCTTTGACCAGCGACNCCTCGGTGTATCGGGCCGGC TABLE 3-continued End sequences of the polynucleotide inserts cloned in the named recombinant

GGGTTNGTGGCATGGCCGTCTGGGGTCANCTCNACNATNTTCANCCGTTGACCCGGGGTCACA (SEQ ID NO. 686)

Clone Rv95
::::::::::::Rv95SP6.seq::::::::::::
TGGCCTTCTTGNCANGGGCNNACATNNGCTATNGCGAGCGTGTAACCGATCATCNTCCNGGCGACTGTGGCCTGANCGGCAAGGGTNGCCTNATTCNTCCTCC TGNGGCATGGTTNCCACACGGAATGNCGGTAAGTCTGGTCGGCAACCTGGCCCGCTGCGGGTTGGGTTCGGATTCGCTCGGCTANTAAGGTGCTCGCCTGGTG TNACNACTAATCNCNATATACNCTTANCGGGAGTNGNCGTCCCGATCCTNGCCCTGCCGCNGGCGATCNCGTTCGCANCACCGCCACCGGAACTCNCAANGTG CGCTCATCGGGCTCTACGCGCCATCTTCCCCGGATTCTTCGCGGCNGNGTNCCGNGGGACCCCGGACTGTGACNGGCCCAACGGCTCATCATCG (SEQ ID NO. 687)

::::::::::::Rv95T7.seq::::::::::::
CCGGATAGCGGTGTCTGAACTTCGCCCGTTCCCTCCANCGCATTGAGCTTCAGCCCGACCGGCAGGTNNGGAGTCGGCATGCGGTCCTTCGCCCCGACCCCGC TGGCTAAATANCCACCCCCGAGCGCGGTCACGGTCTTTGCACCGGGACGACGCATACCGGCAGCGCGAACATCNCCGCGGGCTGCAGCNTGAACGTCCAATAC CANTCNAACAGTGTCCGCGCGTNAAAACCCGANCCGGCGGTCGCTTCNGTAATCAACGGCTCCTGCGCAACCAGCTGCAAGTCGCCGGTGCCACCGGCGTTGA

CGATCTTGATGTCTGCGANCTCGCGCACCAGCTCGACGGCCCGGGCA (SEQ ID NO. 688)

Clone Rv96
::::::::::::Rv96SP6.seq::::::::::::
CCTCCCGACCACATACAGGCAAAGTAATGGCATTACCGCGAGCCATTACTCCTACGCGCGCAATTAACGAATCCACCATCGGGGCAGCTGGTGTCGATAACGA AGTATCTTCAACCGGTTGAGTATTGAGCGTATGTTTTGGAATAACAGGCGCACGCTTCATTATCTAATCTCCCAGCGTGGTTTAATCAGACGATCGAAAATTT CATTGCAGACAGGTTCCCAAATAGAAAGAGCATTTCTCCAGGCACCAGTTGAAGAGCGTTGATCAATGGCCTGTTCAAAAACAGTTCTCATCCGGATCTGACC TTTACCAACTTCATCCGTTTCACGTACAACATTTTTTAGAACCATGCTTCCCCAGGCATCCCGAATTTGCTCCTCCATCCACGGGGACTGAGAGCCATTACTA

TTGCTGTATTTGGTAAGCAAAATACGT (SEQ ID NO. 689)

Clone Rv9
::::::::::::Rv9SP6.seq::::::::::::
CTTCACNTCCGTACGGCTCGGGTACGCTTCGGTCNCATTGTGCGAGTGATAGATGACGACCGGGACCTCGTCGGCATCTTCCATAGCCCGCCACACCTTCAGT TGCTCACCGGAATCCAACCGGTANAAGGTCGGCGANCGCTCNGCATTGGTCATCGGGATATGCCGCTCGGGACGGTCANAGCCCTCGGGTCCGGCCAGCACTC CGCAGGCTTCGTCGGGGTGGTCGCGACGCGCATGGGCCACCATCGCATTCACCAGGTCTGCGCGAATCACCAGCACGTANACGGTTCCTTTCCTAAGCAACAC CGAANTTTCAGGACCCGAATGCTCCGGGAAACATGTCACGGTAGGTCGGTATTCCGGCTACCGGCTGANCATTGAGCACGCCGGCCAGCACCGCACGAACCAG

GCAATCAGCCGCCGCCGCACCCGACCGCGG (SEQ ID NO. 690)

::::::::::::Rv9T7.seq::::::::::::
CAGGCATGCAAGCTTGATGCCGCCGAAACCGAGCGTGAGCACGCCGCCAGCCACCACGCGCGGGTCGGGCGCCGGGCCCGGGCCGCCAGGCTGCTCCGCTCGG TGATGGCACGCCACCGCGACACCACCCGGCTGCGCTACGTCGAGCCATACCGGGCGGAGCTACATCGGCTCGGCCGCCCAGTGTTCGGGCCCTCTTTCGAGGT CGAGGTCGATACCGATTTGCGCATCCGCAGCCGCACCCTGGACGACAGAACCGTGCCCTACGAATTGCTTGTCGGGCGGGGCCAAAGAACAGCTTGGCATCCT

GGCGCGATTGGCCGGCGCGGCGCTGGTCGCCAAGGAAGACCCGTTCCGGTGCTGAT (SEQ ID NO. 691)

BAC vectors contained in the 1-1945 *M. tuberculosis* H37Rv genornic DNA library.
RvXXXSP6 corresponds to the SF6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

TABLE 4

End sequences of the polynucleotide inserts cloned in the named recombinant BAC vectors contained in the I-2049 *M. bovis* strain Pasteur genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

Clone X0001
::::::::::::::X0001SP6.seq:::::::::::::
AAG-

TCGGGTTTCCACACGCGCGGTTTGACCCTAGTCATATGTAATCATGTGTACCATGTGCGGGCGCTTTTCGACGGC

CGCGAACCACCGGA-ATTTCCTGTGATTTCACTGCATGCGTACCATCTGGCACAATTGAGCA-TTGTCT-TCGCGG

TGGTCGG-CGGGTTGCGTGCCGCCTGCTGCGA-ATGCACCA-TAAGCCCGAACCCACCGGCTTGGTGACCACCGC

ACGCTGCGTGTGGGGGGTAACCACTCCGCGACCCCAAGGATGGTCATTTCCAATGAACCGGCTGGACTTCGTCC

A-A (SEQ ID NO. 692)

:::::::::::::X0001T7.seq:::::::::::::
GTCGCGGTTCGATCGACCCGATCTTCACCTCGTAACCTCGATGCTTAGCAGGATCCAGCTTGACCGCGTTTGGCT

CTACCCACTCTTTGAGTGGCGCCGTCGCCTGTGCCCCATCGGTGTTCATGACGAACGCTTCGAAAGACTTCCTCT

TGTGAGCCGGAATGTCTGCGTAAAGAAGTTCCATGTCCGGGAAGTAGACCCGGTCGCCCTCCACGTGGTACTCC

TTCGAGGTCCGCTTCTCGCCGGATCCGATAAACACCGGCCCCAGGCACCGCAGCGTGAGTTCGAACGGCTTCAG

GTAGGTGTTCATGCGGCGGACTCCGGGAGTGCGAGAAATAGCGGTCGCGCGTAGCTGTAGACCGGATGGTTTCC

GCCCAGGCTGACGTCGAAGATGCCTCCTTGGAAGGGGCGCGA (SEQ ID NO. 693)

Clone X0002
:::::::::::::X0002SP6.seq:::::::::::::
AACTCAAGTTTTTACGGTGATCGCGCATCACCTGGTTCATGAACTGGAAGCAGCGCAGCGCTTCCTTTTCGGCCG

CAACATGAGCCAGCCTCTCGTCGGCGGTCGGGTGCAGGTGCTCGGGCAGCTCGGCCGCGACAGCCGCCTGACC

CTGAAACCAGCTTCCATATCCCGCGAC-

AACGACGCCAGTCCGCTACGTAACCCCTCCGCGACTGTCCATGGACAACAGCGCGTTCTCCACCGACCGGGCCC

GGGTGT (SEQ ID NO. 694)

:::::::::::::X0002T7 seq:::::::::::::
GTGCAGGTTTCGACAATGTGGTGCCGGTTCGGCGGCTACGTGCCATCGAGACACTGGCGCA-GCTATCGCACCC

GTTATCGGCTGCGAGCAAATCGCGGTATGCGTTCTTGAGCATGAGTCGGCGACCGTCGTCATGGTCGACACCCA

CGACGGAAAGACGCAGATCGCCGTCAAGCATGTGTGCCGCGGATTATCAGGACTGACCTCCTGGCTGACCGGCA

TGTTTGGTCGCGATGCCTGGCGCCCGGCCGGCGTGGTCGTGGTCGGCTCGGATAGCGAGGTCAGCGAATTCTCG

TGGCAGCTCGAAAGGGTCCTGCCGGTGCCGGT (SEQ ID NO. 695)

Clone X0003
:::::::::::::X0003SP6.seq:::::::::::::
TTCGAGTCATGCGCCCGCCTCGACCACGAA-ATGCACGTCG-GGTTCGATCGACCCGATCTTCACCTCGTAACCTC

GATGCTTAGCAGGATCCAGCTTGACCGCGTTTGGCTCTACCCACTCTTTGAGTGGCGCCGTCGCCTGTGCCCCAT

CGGTGTTCATGACGAACGCTTCGAAAGACTTCCTCTTGTGAGCCGGAATGTCTGCGTAAAGAAGTTCCATGTCC

GGGAAGTAGACCCGGTCGCCCTCCACGTGGTACTCCTTCGAGGTCCGCTTCTC (SEQ ID NO. 696)

:::::::::::::X0003T7.seq:::::::::::::
GTCATGTGTACCATTTGCGGGCGCTTTTCGACGGCCGCGAAACACCGGAGATTTCCTGTGATTTCACTGCATGCG

TACCGTCTGGCACAATTGAGCAGTTGTCTGTCGCGGTGGTCGGCCGGGTTGCGTGCCGCCTGCTGCGAGATGCA

CCAATAAGCCCGAACCCACCGGCTTGGTGACCACCGCACGCTGCGTGTGGGGGGTAACCACGCCGCGACCCCA

AGGATGGTCATTTCCAATGAACCGGCTGGACTTC-TCAACAA (SEQ ID NO. 697)

Clone X0004

TABLE 4-continued

:::::::::::::X0004T7.seq:::::::::::::
AACAGCGCGGTTGAACTGATAGGTGCGGCCCGGCTCGAGCAGGCCGGGCCATTTGTTCGATGCGGTTACCGAAA

GATCTCTTCGGTGACCTGCCCGCCGCCGGCCAGCTCGGCCCAGTGCCCGGCGTTGGCCGCCGCGGCGACGATCT

TGGCGTCCACGGTGGTCGGGG (SEQ ID NO. 698)

Clone X0006
:::::::::::::X0006T7.seq:::::::::::::
GCATCTGGGCTGGCGGTGGTTCGCCGCTCCGAAGCCGTCGAACACCATCGCCAGCGCGGCTTCCACATCAACGA

CCATTTCGGCCAGCTTGCGGCGCATCAGCGGCTTGTCGATGAGCGCCCCACCGAATGCCCGCCGCTGCCCGGCG

TA-CACAGCGATTCGACCAGCGCGCGGCGCGCGTTGCCGAGGGCGAACGAAGCGGTGCCCAACCGCAATCTGTT

GGTCAGCTCCATCATGCGGGTGAGTCCCTTGCCG (SEQ ID NO. 699)

Clone X0007
:::::::::::::X0007SP6.seq:::::::::::::
ATCGGTTTCCAGCAACAGCCGATCGACGGCTTCGCCCA-GGCCGCTCCCGGGCGACCCGACCATTGCTGTCGCC

GCGTAACGCCATCACGGATGACGCGCAGTTCGTCGCTGTCTAGCTCCACCATCGCCTGCACACCGGCGGCCAG-

ACCCATTGGCCGTCGCACTCGTA-

AGCAGGTAATCCTCGTCGACGGACTCGGTAACCACCGCCGCCAGCTCCGCTGCCAGGTCGGCGGGGTTGACACC

GGCGGGCATCGGGATGGACGACGACGCGGTGCTGACGGCGCCTGTC (SEQ ID NO. 700)

:::::::::::::X0007T7.seq:::::::::::::
AGCGGTTTCCCA-GCGGGATGTGCTGTGAGCGCCGCACCACCAGCGCCGACGCTAAGGATGGAACGCACGGCAT

CTTCTGACGCGTAACCGCGTTGTGATCGCGAGCTGAGGAGACGGTATGGGGGAGGGTTCTCGGAGGCCATCTGG

GATGTTGATGTCTGTCGATCTTGAGCCGGTGCAACTCGTCGGCCCGGACGGTACGCCGACGGCCGAACGCCGCT

ACCACCGTGACCTTCCTGAGGAAACGCTGCGTTGGCTCTACGAGATGATGGTGGTCACCCGCGAGCTGGATACC

GAATTCGTCAATCTGCACG (SEQ ID NO. 701)

Clone X0008
:::::::::::::X0008SP6.seq:::::::::::::
CAAGCTTCCACAGGTAGGGATCGAGGAACAGCGCGTTGAACTGATAGGTGCGGCCCGGCTCGAGCAGGCCGGC

CATTTGTTCGATGCGGTTACCGAAAATCTCTTCGGTGACCTGCCCGCCGCCGGCCAGCTCGGCCCAGTGCCCGG

CGTTGGCCGCCGCGGCAACGATCTTGGCGTCCACGGTGGTCGGGGTCATGCCCGCGAGCAGGATCGGCGAGCG

GCCGGTCAGCCGGGTGAACTTCGTCGAAAGCTTGACCCTGCCGTCGGGGAGGCGAACCACGGTCGGTGCGTAN

CTCCACCAAGCCCGGGCAACCTCGGGGGTGGCGCC (SEQ ID NO. 702)

:::::::::::::X0008T7.seq:::::::::::::
TGGACCTCATGACAACGCGGCGGCGATTACCCCCGCTACCGCCAGCAGCATGACGGCGGTAGCGAACACCGCC

GGATGCAGCGCAGGTGCGTCGATGTGCTCACGGAATCGCCCCGGCACCGCGATCTCGAGGATCACCAGTGCCAC

CCCCTGCAGCGCGACACCGACGATTCCGTACACCGCCACGCCGATCAGGCCCTGGGCCAGCTGGCGTATATGGC

GGCGATGGTGACGATGGCCAGCGCCACATACATTGTGGCGGCCAGAACCACGGCGTTGGGGCGGCGGTCGATG

AACACTAGGCGACGCAGATCGCCCGGGGTCAACAGGTTGACCATCAGAAAGCCTGCGA (SEQ ID NO. 703)

Clone X0009
:::::::::::::X0009SP6.seq:::::::::::::
TTTGGTGCGGCCGGCAATCAACTTC-

GCTC-CAGCGGTTTCCCAGGCGGGATGTGCTGTGAGCGCCGCACCACCAGCGCCGACGCTAAGGATGGAACGCA

CGGCATCTTCTGACGCGTAACCGCGTTGTGATCGCGAGCTGAGGAGACGGTATGGGGGAGGGTTCTCGGAGGC

CATCTGGGATGTTGATGTCTGTCGATCTTGAGCCGGTGCAACTCGTCGGCCCGGACGGTACGCCGACGGCCGAA

CGCCGCTACCACCGTGACCTTCCTGAGGAAACGCTGCGTTGGCTCTACGATATGATGGTGGTCACCCG (SEQ ID NO. 704)

TABLE 4-continued

:::::::::::::X0009T7.seq:::::::::::::
CGCCCAGGGCCGCTCCCGGGCGACCCGACCATTGCTGTCGCCGCGTAACGCCATCACGGATGACGCGCAGTTCG

TCGCTGTCTAGCTCCACCATCGCCTGCACACCGGCGGCCAGGACCCATTGGCCGTCGCACTCGTAGAGCAGGTA

ATCCTCGTCGACGGACTCGGTAACCACCGCCGCCAGCTCCGCTGCCAGGTCGGCGGGGTTGACACCGGCGGGC

ATCGGGATGGACGACGACGCGGTGCTGACGGCGCCTGTCGCGACGCTGAGCTCGGACACAGCTAGTAAATGTA

GCCTAACCTACTTAATGGGTCGCAGCCCCCCGGGGTCGTCGCATGTCCAACGTTGCTCGACTGGAAGAAAATGC

TCGTCGGGGAGCAAATGGCACC (SEQ ID NO. 705)

Clone X0010
:::::::::::::X0010SP6.seq:::::::::::::
AATACTCAATCTTGATCGGTTTCCAGCAACAGCCGATCGACGGCTTCGCCCAGGGCCGCTCCCGGGCGACCCGA

CCATTGCTGTCGCCGCGTAACGCCATCACGGATGACGCGCAGTTCGTCGCTGTCTAGCTCCACCATCGCCTGCA

CACCGGCGGCCAGGACCCATTGGCCGTCGCACTCGTAGAGCAGGTAATCCTCGTCGACGGACTCGGTAACCACC

GCCGCCAGCTCCGCTGCCAGGTCGGCGGGGTTGACACCGGCGGGCATCGGGATGGACGACGACGCGGTGCTGA

CGGCGCCTGTCGCGACTCTGAGCTCGG (SEQ ID NO. 706)

:::::::::::::X0010T7.seq:::::::::::::
GGATGTGCTGTGAGCGCCGCACCACCAGCGCCGACGCTAAGGATGGAACGCACGGCATCTTCTGACGCGTAACC

GCGTTGTGATCGCGAGCTGAGGAGACGGTATGGGGGAGGGTTCTCGGAGGCCATCTGGGATGTTGATGTCTGTC

GATCTTGAGCCGGTGCAACTCGTCGGCCCGGACGGTACGCCGACGGCCGAACGCCGCTACCACCGTGACCTTCC

TGAGGAAACGCTGCGTTGGCTCTACGAGATGATGGTGGTCACCCGCGAGCTGGATACCGAATTCGTCAATCTGC

AGCGCCAGGGGGAAGCTGGCGTTGTACACGCCCTGTCGCGGGCAGGAAGCCGCGCAGGTGGGTGCGGCGGCTT

GCCTACGCAAAACCGACTGGTTGTTCCCC (SEQ ID NO. 707)

Clone X0012
:::::::::::::X0012SP6.seq:::::::::::::
ATCACGACAACAGCGACGGTGTGTCGGATCAGCGGCCCCCGTTGCCGGGCAATGTTGAGGCGTTTCTGCGTCTG

GTTGAGGCCGGCTGGGAC-

CCGAGGTGGCTCGTCGGCCACATGGGCAGCACACCACCGTGGTGATGCATCTAGACGTGCAGGACCGTGCCGCT

GGCCTGCA (SEQ ID NO. 708)

:::::::::::::X0012T7.seq:::::::::::::
GCGGCTACGTGCCATCGAGACACTGGCGCAGGCTATCGCACCCGTTATCGGCTGCGAGCAAATCGCGGTATGCG

TTCTTGAGCATGAGTCGGCGACCGTCGTCATGGTCGACACCCACGACGGAAAGACGCAGATCGCCGTCAAGCAT

GTGTGCCGCGGATTATCAGGACTGACCTCCTGGCTGACCGGCATGTTTGGTCGCGATGCCTG:

(SEQ ID NO. 709)

Clone X00013
:::::::::::::X0013T7.seq:::::::::::::
TACAAGCGGCACCTCGCCGGTGAACTGACCGTTCGCACGCTGCGCACCGCCGCCGGGCGCGTGCTCGGCGCGC

CGGCGGCCCCCGAGGCCTGAGAGGGGAACCAACCATGCAGGTGAACATGACGGTAAACGGCGAGCCCGTCACC

GCCGAGGTCGAACCCCGGATGCTGCTGGTCCATTTTCTCCGTGATCAGCTGCGGCTCACCGGAACTCACTGGGG

CTGTGATACCAGCAACTGCGGGACATGCGTGGTGGAGGTCGACGGCGTGCCGGTGAAATCCTGCACGATGCTCG

CCGTGATGGCCTCCGGGC (SEQ ID NO. 710)

Clone X0014
:::::::::::::X0014T7.seq:::::::::::::
AGCGGCTGGTTACGACTCCCTGTTTGTGATGGACCACTTCTACCAACTGCCCATGTTGGGGACGCCCG-

CC-TCCGATGCTGGAAGCCTACACTGCCCTTGGTGCGCTGGCC-C-GCGACCGAGCGGCTGCAACTGGGCGC-

TTGGTGACC-GCAATACCTACCGCACCCC-ACCCTGCTGG-CAAA-

ATCATCACCACGCTCGACTTGGTTAGCGCCGGTCGA-CGATCCTCGGCATTGGAACCGGTTGGTTT-

TABLE 4-continued (SEQ ID NO. 711)

Clone X0015
:::::::::::::X0015SP6.seq:::::::::::::
ACGCGCGCCGATCATATCTGCTATGGATGTACAATTCAGCTCTTGCTGTTATACCAGTATATGGTGTACTATTTG

ATCTATGCTGACGTGTGAGATGCGGGAATCGGCCCTGGCTCGACTCGGCCGGGCTCTGGCTGATCCGACGCGGT

GCCGGATTCTGGTGGCGTTGCTGGATGGCGTTTGCTATCCCGGCCAGCTAGCTGCGCACCTCGGGTTGACCCGA

TCGAATGTGTCCAACCATCTGTCGTGTTTGCGGGGCTGCGGGCTGGTA-

TCCCAACCTATGAGGGCCGGCAGGTTCGGTAT (SEQ ID NO. 712)

:::::::::::::X0015T7.seq:::::::::::::
CCGCGCTGCTGCTGACGTCGGTCGAACGTGCGACACGTCTGCGAATACCGGCCGAACGCTGGGTTTATCCACAG

GCTGGCACCGACGCCCACGACACACCGGCCGTCGCCGACCGCCACCGACTGCATCGGTCGACGGCCATTCGGAT

CGCCGGTGCCCGGGCGCTGGAACTGGCTGGGCTGGGGCTCGATGACATCGAATACGTCGACCTGTATTCGTGCT

TTCCCTCCGCTGTCCAAGTCGCCGCAATCGAACTCGGCCTGGACACCGACGATCCTGCCCGCCCGCTGACCGTC

ACCGGGGGCCTGACCTTCGCCGGCGGGCCGTGGAGCAATTACGTCACGCACTCCAT (SEQ ID NO. 713)

Clone X0016
:::::::::::::X0016SP6.seq:::::::::::::
CAGGCGTGCAATGACCTGCACTGCGCCGGA-A-TCCCTAACCCACTAAACCGGGGCCGCTCACAAGCCGTGCAGC

TCGGTCAGCGTCAGGTGCGCGACCAGGAA-

TAATGAGCAGACCCGTGCCGTCAACGATGGTGGCGATCATCGGCCCCGAAACGAATGGCCGGGTC-

ATGCGCAACTTCTTCAGCAGCGGCGGAAGGACGGCA-CCACCAGCGAC-ACCACACCACGAT (SEQ ID NO. 714)

:::::::::::::X0016T7.seq:::::::::::::
GCGAA-CACTTCGTCAACTTCCAGGGCTGCCCGCACCAAGTATTTCGACGAGTATTTCCGTCGGGCCGCCGCCGC

CGGCGCGCGGCAGGTGGTCATCCTGGCGGCGGGGCTGGACTCGCGCGCGTACCGGCTGCCTTGGCCCGACGGG

ACCACGGTTTTTGAGCTGGACCGCCCGCAGGTCCTTGATTTCAAGCGCGAGGTGCTCGCCAGCCACGGTGCCCA

ACCGCGCGCCCTGCGCCGCGAGATCGCCGTCGACCTGCGTGACGATTGGCCACAAGCCTTGCGGGACAGTGGGTT

TCGATGCGGCTGCACCGTCGGCATGGATTGCCGAAGGGCT (SEQ ID NO. 715)

Clone X0017
:::::::::::::X0017SP6.seq:::::::::::::
TTGGGC-TTGCCC-CAATA-GGCCCCAATCAAAAGCCGAGCAGGTGGAACCTA-CGCATTCGCCTC-TCGT-TGTGC

ACCCGAGCCATCGCACGCGCGGGAATTCCCGGAT-TC-CCGTATTCTCCGGCGGCCGGGCTAACCCATCCCA-GCC

GAACGGTTGGCTC-TGCCGTGGGTCCCGTGTTGGCCGATCGGGGCGTCACCGGGGGTGCTCGGGTGCGG-

TGACCATGGC-AACTGCCCC-ATGGGCCGACCCTGGTGCAGATAAACCTG (SEQ ID NO. 716)

:::::::::::::X0017T7.seq:::::::::::::
TGGTGGAGGTCCCCACCAA-ACCCGGCCGTAACTCTGCTCACGGAAATGCGG-CAGGCCGCGCGTAGCACGTGGT

ATCCGCCATAAAGGTGCACCTTAAGCACGGCGTCCCAATTCTCGAACGACATCTTGTGGAAGGTGCCGTCGCGC

AAGATCCCGGCGTTGCTCACCACACCGTGCACGGCGCCGAATTCGTCAAGCGCGGTCTTGATGATGTTCGCTGC

GCCGTCCTCGGTGGCGACGCTGTCGGTA-TTGGCGACCGCCCGGCCCCCCTTGTCGCGAAATCTCGGCGACGAC

CTCATCGGCCATCGCCGAACCGGGCGCCCG (SEQ ID NO. 717)

Clone X0018
:::::::::::::X0018SP6.seq:::::::::::::
GCCGGCCAAACTGGCCGGCGGGGTTGCTGTC-TCAAGGTGGGTTCCGCCACCAA-ACC-

CACTCAAGGATCGCAAGGAAAGC-

TCAAGGATGCGGTCGCGGCCGCCAAGGCCGCGGTCAAGGAGGGCATCGTCCCTGGTGGGGA-CCTCCCTCATC

CACCAGGCCCGCAAGGCGCTGACCGAACTGC-TGCGTC-C-GACCGGTGACAA-GTCCTCGGTGTCCACGTGT-CTC

TABLE 4-continued

CGAAGCCCTTGCCGCTCCGTTGTTCTGGATC-CC-CCAAC-CTGGCTTGGACGGCTC-

GTGGTGGTCAACAAGGTCAGCGAGCTACCCGCCGGGCATGGGCTGAACGTGA (SEQ ID NO. 718)

Clone X0018
:::::::::::::X0018T7.seq:::::::::::::
CGAACCT-

AATTGTCCTGTAATGCCCAGCTCACCAA-GCATGGCTGGTGGCCGGGGCGGTGAAGCCGGCGTCTGCGGCACCG

TCCAACTC-ATGTGGAT-GCCGGAATGGGGATGTCCGG-ACGGCGAATCCGTA-

TTCGCTTGTCCCGTGAGGCCCAGGTGGATGGGGGGAAGGATC-TGGTGTCCGGGATGAT-

ATGGGGCCGATGCCGCCGGTTGAAGTCCACTGGATCGGGAATTCGGGAATCGTGAT-

CCGACGTTCAGGCCGAAC (SEQ ID NO. 719)

Clone X0019
:::::::::::::X0019SP6.seq:::::::::::::
CTAACGGAATGAAAGCCCTGGTGGCCGT-TCGGCGGTGGCCGTCGTCGCACTGCTCGGTGTATCTTCCGCCCAAG

CTGATCCCGAGGCGGATCCCGGCGCAGGTGAGGCCAACTATGGTGGCCCCCCAAGTTCCCCACGTCTTGTCGAT

CACACCGAATGGGCGCA-

TGGGGAATTCTGCCCAGCCTCCGGGTCTACCCGTCCCAAGTTGGGCGTACA-CCTCCCGCCGCCTCGGGATGGCC

GCTGCCGACCCGGCCTGGGCC-AGGTTCTCGCGCTGTCACCGGAAGCCGACACTGCCGGC (SEQ ID NO. 720)

:::::::::::::X0019T7.seq:::::::::::::
CCGCGGGACAC-CCTC-ATGCTGCCGCCATGGACGCGGTCGAACGCAAGCAGCTGATCGAGCTACAACGCCGCG

CGGAACGCTTCCGCCGCGGGCGTGACCGCATCCCGTTGACCGGGCGGATCGCGGTGATCGTCGATGACGGCATC

GCCACCGGAGCGACGGCCAAGGCGGCGTGCCAGGTCGCCCGGGCGCACGGTGCGGACAAGGTGGTGCTGGCG

GTCCCGATCGGCCCA-ACGACATCGTGGCGAAGATTCGCCGGGTACGCCGATGATGTGGTGTGTTTGGCGACGC

CGGCGTTGT (SEQ ID NO. 721)

Clone X0020
:::::::::::::X0020T7.seq:::::::::::::
CTCTGGGACCGGCCACGGTGCC-CCGGCGTTCCCGGACGTGCTGCGCCAGGTGTCCGGCGGCCGCGTGCATGGT

GTTCCCGGATCGGCCGCTGGCCAGAGCCCACCGGTGAATCTGGCGCCTGGCCGACCACCGTGCGCCGTAGGCTT

GCGATCGTGCAGCGCTGGCGTGGCCAGGACGAGATCCCGACGGATTGGGGCAGATGCGTGCTCACCATCGGGG

TATTTGACGGCGTGCACCGCGGGCACGCCGAACTGATCGCGCACGCGGTCAAAGGCGGC (SEQ ID NO. 722)

Clone X0021
:::::::::::::X0021SP6.seq:::::::::::::
AATACTCAAGCTTTCGTCAGTTCATTGCGCCAGCAGACCAACAA-AGCATCGGGACATACGGA-TCAACTACCCG

GCCAACGGTGATTTCTTGGCCGCCGCTGACGGCGCGAACGACGCCAGCGACCAC-TTCAGCAAATGGCCA-CGCG

TGCCGGGCCACGAGGTTGGTGCTCGGCGGCTACTCCCAGGGTGCGGCCGTGATC-ACATC-TCACCGCCGCACCA

CTGCCCGGCCTCGGGTTCACGCAGCCGTTGCCGCCCGCAGCGGAC-

ATCACATCGCCGCGATCGCCCTGTTCGGGAATCCCTC-GGCCGCGCTGGCGGGCTGATTAAC (SEQ ID NO. 723)

:::::::::::::X0021T7.seq:::::::::::::
TGCCGCGGATTTGGCTGGCTGCCCAATATTCAGAATCGGGCCTTTCTTTTTGCGCGACAATAAGGTCACAGTAAA

CCCTCGTTTTGTGAGATGCGGGGCGGGCCGGGCGAA-TCGACCTCGAGTGAATGGATCTCGAGTGAATGGACAG

GGCATCGCCTACGAGTCGCATCCCCATCCAACAGACCGGTGCTCTTGCATCGGACCCTGAAGGTCCCGCACGGA

GGGTGTGGTTGCCGGCGCGGGGTCACGGTGCGGTAGCGACGTAGTGTTTGAACGAATTTCTTGATGCTCCAACC

TGTTTGGTGTTCAATCCAGTTCT (SEQ ID NO. 724)

TABLE 4-continued

Clone X0175
.....X0175SP6.....
AA-CTTGCGCGCTCGGCCGGGTC-AGCATCCAGCTGCTCGGCAAGGAGGCCAGCTAC-C-TCGCTGCGTATGCCCA

GCGGTGAGATCCGCCGGGTC-ACGTCCGCTGCCGCGCGACCGTCGGCGAAGTGGGCAATGCCGAGCAGGCAAAC

ATCAACTGGGGCAAGGCCGGTCGGATGCGGTGGAAGGGCAAGCGCCCGTCGGTCCGGGGCGTGGTGAT-AACC

CGGTC-ACCACCCGCACGGCGGTGGTGAGGGTAAAACCTCCGGCGGCCGTCACCCGGTTAGCCCGTGGGGCAA (SEQ ID NO. 725)

.....X0175T7.....
A-TCGAAAGTGACCATCTCTACCTTGAGTGCCATACCGCCCGACCCTATGCCTCGGATAGCTCGGCGGAAAGAAA

CGCTTGCAGTGCCGCCGAATAGGCGGCTACGTCGTGAGCGCCCATCAACTCTCGCGCGGAGTGCATCGCCAGCT

GGGCGGCGCCGACGTCGACCGTGGGGATTCCGGTGCGCGCCGCGGCCAACGGCCCGATCGTCGACCCGCACGG

CAGATCGGCGCGATGTTCGTAACGCTGCATAGGCACTCCCGCGCGCTGGCAGGCCAGTGCGAACGCCGCCGCG

GTGCGTCCG (SEQ ID NO. 726)

What is claimed is:

1. A method of detecting *Mycobacterium tuberculosis* in a sample, comprising:

(a) contacting the sample with a first nucleic acid, wherein the first nucleic acid is a polynucleotide having a sequence comprising SEQ ID NO:1, or a polynucleotide whose sequence is complementary to SEQ ID NO:1; and (b) detecting hybridization between the first nucleic acid and a second nucleic acid in the sample;

wherein detecting hybridization between the first and second nucleic acids indicates the presence of *Mycobacterium tuberculosis* in the sample.

2. The method of claim 1, wherein the first nucleic acid hybridizes to the genome of *Mycobacterium tuberculosis* but not to the genome of *Mycobacterium bovis* under stringent hybridization conditions.

3. The method of claim 2, wherein the stringent hybridization conditions comprise hybridizing at 65° C. in 6X SSC, followed by washing at 65° C. in 2X SSC.

4. The method of claim 3, wherein the hybridization conditions further comprise washing at 65° C. in 0.1X SSC.

5. The method of claim 2, further comprising amplifying the second nucleic acid in the sample before detecting hybridization.

6. The method of claim 5, wherein the second nucleic acid in the sample is amplified with at least one polynucleotide selected from SEQ ID NO:742 or SEQ ID NO:743.

7. The method of claim 2, wherein the first nucleic acid comprises a recombinant BAC vector, Rv58, which belongs to the BAC DNA library I-1945.

8. A method of detecting *Mycobacterium tuberculosis* in a sample, comprising:

(a) contacting the sample with a pair of primers under conditions sufficient to permit nucleic acid amplification, wherein the pair of primers is capable of amplifying a nucleic acid, wherein the nucleic acid comprises SEQ ID NO:1;

(b) amplifying the nucleic acid; and (c) determining the size of the amplified nucleic acid, wherein the size of the amplified nucleic acid indicates the presence of *Mycobacterium tuberculosis* but not *Mycobacterium bovis* in the sample.

9. A method of detecting specifically bovine strains of Mycobacterium in a biological sample, comprising:

(a) contacting the sample with a pair of primers wherein the pair of primers comprise SEQ ID NO: 742 and SEQ ID NO: 743;

(b) amplifying a nucleic acid;

(c) detecting whether an amplified nucleic acid is formed; and (d) determining the size of the amplified nucleic acid wherein the size of the amplified nucleic acid indicates the presence of a bovine strain of Mycobacterium.

* * * * *